US012503432B2

(12) United States Patent
Jain et al.

(10) Patent No.: US 12,503,432 B2
(45) Date of Patent: Dec. 23, 2025

(54) IONIZABLE LIPIDS FOR NUCLEIC ACID DELIVERY

(71) Applicant: Global Life Sciences Solutions Canada ULC, Vancouver (CA)

(72) Inventors: Nikita Jain, Vancouver (CA); Anitha Thomas, New Westminster (CA); Andrew William Brown, Vancouver (CA)

(73) Assignee: Global Life Sciences Solutions Canada ULC, Vancouver (CA)

( * ) Notice: Subject to any disclaimer, the term of this patent is extended or adjusted under 35 U.S.C. 154(b) by 892 days.

(21) Appl. No.: 17/620,575

(22) PCT Filed: Jun. 19, 2020

(86) PCT No.: PCT/CA2020/050854

§ 371 (c)(1), (2) Date: Dec. 17, 2021

(87) PCT Pub. No.: WO2020/252589

PCT Pub. Date: Dec. 24, 2020

(65) Prior Publication Data

US 2022/0396548 A1 Dec. 15, 2022

Related U.S. Application Data

(60) Provisional application No. 63/009,104, filed on Apr. 13, 2020, provisional application No. 62/877,536, filed on Jul. 23, 2019, provisional application No. 62/864,064, filed on Jun. 20, 2019.

(51) Int. Cl.

| | |
|---|---|
| ***C07C 309/69*** | (2006.01) |
| ***A61K 39/00*** | (2006.01) |
| ***A61K 40/11*** | (2025.01) |
| ***A61K 40/31*** | (2025.01) |
| ***A61K 40/42*** | (2025.01) |
| ***C07C 219/20*** | (2006.01) |
| ***C07D 205/04*** | (2006.01) |
| ***C07D 207/08*** | (2006.01) |
| ***C07D 453/02*** | (2006.01) |

(52) U.S. Cl.

CPC ............ *C07C 309/69* (2013.01); *A61K 39/00* (2013.01); *A61K 39/001112* (2018.08); *A61K 40/11* (2025.01); *A61K 40/31* (2025.01); *A61K 40/4211* (2025.01); *C07C 219/20* (2013.01); *C07D 205/04* (2013.01); *C07D 207/08* (2013.01); *C07D 453/02* (2013.01)

(58) Field of Classification Search

CPC ... C07C 309/69; C07C 219/20; C07D 205/04; C07D 207/08; C07D 453/02; A61K 39/001112; A61K 39/00; A61K 40/4211; A61K 40/31; A61K 40/11

See application file for complete search history.

(56) References Cited

U.S. PATENT DOCUMENTS

| | | | |
|---|---|---|---|
| 5,753,613 | A | 5/1998 | Ansell et al. |
| 6,734,171 | B1 | 5/2004 | Saeravolac et al. |
| 8,158,601 | B2 | 4/2012 | Chen et al. |
| 9,758,795 | B2 | 9/2017 | Cullis et al. |
| 9,943,846 | B2 | 4/2018 | Cullis et al. |
| 10,076,730 | B2 | 9/2018 | Wild et al. |
| 2004/0262223 | A1 | 12/2004 | Strook et al. |
| 2011/0117125 | A1 | 5/2011 | Hope et al. |
| 2016/0022580 | A1 | 1/2016 | Ramsay et al. |

FOREIGN PATENT DOCUMENTS

| | | | |
|---|---|---|---|
| CA | 3 044 134 | A1 | 7/2009 |
| CA | 2 743 135 | A1 | 5/2010 |
| CA | 3 067 452 | A1 | 12/2018 |
| CN | 102281899 | A | 12/2011 |
| EP | 3 202 760 | A1 | 8/2017 |
| GB | 1 539 268 | A | 1/1979 |
| JP | S53-84943 | A | 7/1978 |
| JP | H2-108647 | A | 4/1990 |

(Continued)

OTHER PUBLICATIONS

Japanese Patent Office, Office Action issued in counterpart Japanese Patent Application No. 2021-574974, mailed on Aug. 8, 2023.

Asamitsu et al., "Synthesis and Odor Description of Both Enantiomers of Methyl 4,5-Didehydrojasmonate, a Component of Jasmin Absolute", *Chemistry & Biodiversity,* 3:654-659 (2006).

Eustache et al., "Conformationally Constrained No Synthase Inhibitors: Rigid Analogs of L-N-Iminoethylornithine", *Bioorganic & Medicinal Chemistry Letters,* 8:2961-2966 (1998).

Nakamura et al., "Enantio-differential approach to identify the target cell for glucosyl jasmonate-type leaf-closing factor, by using fluorescence-labeled probe compounds", *Tetrahedron,* 62(37):8805-8813 (2006)—Abstract only.

European Patent Office, Office Action issued in counterpart European Patent Application No. 20826513.2, mailed on Aug. 2, 2022.

Chinese National Intellectual Property Administration, Office Action issued in counterpart Chinese Patent Application No. 202080045008.3, mailed on Dec. 21, 2022.

(Continued)

*Primary Examiner* — D Margaret M Seaman

(74) *Attorney, Agent, or Firm* — MCANDREWS HELD & MALLOY, LTD

(57) ABSTRACT

The present document describes compounds, or pharmaceutically acceptable salt thereof, of a core formula (I) where $R_1$ features an amine group, particularly useful in the formulation of lipid particles including nucleic acid therapeutic agents, or proteins, or both, and for delivery of nucleic acid and protein therapeutics to cells in vivo or ex vivo, including anticancer and vaccine applications.

(I)

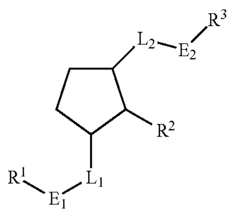

16 Claims, 10 Drawing Sheets

(56) References Cited

FOREIGN PATENT DOCUMENTS

| | | | |
|---|---|---|---|
| JP | H3-112939 | A | 5/1991 |
| JP | 2011-509258 | A | 3/2011 |
| JP | 2014-1142 | A | 1/2014 |
| WO | WO 2009/086558 | A1 | 7/2009 |
| WO | WO 2010/054405 | A1 | 5/2010 |
| WO | WO 2012/108397 | A1 | 8/2012 |
| WO | WO 2017/117647 | A1 | 7/2017 |
| WO | WO 2018/006166 | | 1/2018 |
| WO | WO 2018/232502 | A1 | 12/2018 |

OTHER PUBLICATIONS

Canadian Intellectual Property Office; International Search Report and Written Opinion in counterpart International Application No. PCT/CA2020/050854, mailed on Sep. 11, 2020.

Leung, Alex K.K. et al., "Chapter Four—Lipid Nanoparticles for Short Interfering RNA Delivery", *Advances in Genetics,* vol. 88, 2014, pp. 71-110.

Zhi, Defu et al., "Historic perspective. A review on cationic lipids with different links for gene delivery", *Advances in Colloids and Interface Science,* 2018, vol. 253, pp. 117-140.

Jubeli et al., "Next generation macrocyclic and acyclic cationic lipids for gene transfer: Synthesis and in vitro evaluation", *Bioorganic & Medicinal Chemistry,* vol. 23, No. 19, pp. 6364-6378 (2015).

IONIZABLE LIPIDS FOR NUCLEIC ACID DELIVERY

CROSS-REFERENCE TO RELATED APPLICATIONS

This patent application is the U.S. National Stage of International Patent Application No. PCT/CA2020/050854, filed Jun. 19, 2020, which claims priority under 35USC§ 119(e) of U.S. provisional patent application 62/864,064 filed on Jun. 20, 2019, and 62/877,536 filed on Jul. 23, 2019, and 63/009,104 filed on Apr. 13, 2020, which are each incorporated by reference.

BACKGROUND

(a) Field

The subject matter disclosed generally relates to ionizable lipids, specifically those ionizable lipids capable of transfecting living cells with genetic material.

(b) Related Prior Art

The number of nucleic acid treatment strategies for disease, even those diseases that do not have an initial genetic cause, is growing. Each nucleic acid therapeutic has a different form, chemistry, and charge, and typically requires a different delivery modality.

Lipofection has been used as a means of altering the genetics of cells through lipid mediated gene delivery since at least 1987. Over years, refinements have been made to such lipids to adapt them to more situations. Cationic lipids like DODAC, DOTMA, DDAB, and DOTAP were used in the 1990s, but proved too toxic to contemplate for clinical applications.

A clinically relevant approach has been the development of ionizable lipids for human use. Examples of ionizable lipids include, 1,2-dilinoleyloxy-3-dimethylaminopropane (DLin-DMA), dilinoleylmethyl-4-dimethylaminobutyrate (DLin-MC3-DMA, (see e.g., U.S. Pat. No. 8,158,601), and 2-dilinoleyl-4-dimethylaminoethyl-[1,3]-dioxolane (DLin-KC2-DMA). DLin-MC3-DMA is employed in Onpattro™ patisiran. The need for more options for clinically relevant transfection lipids continues to exist.

SUMMARY

According to embodiments of the invention, there is provided a compound, or a pharmaceutically acceptable salt thereof, of formula (I):

(I)

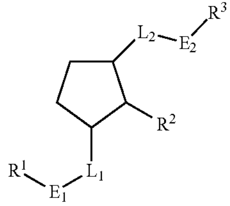

wherein:

$L_1$ is a direct bond or $C_1$-$C_5$ alkylene;

$E_1$ is selected from —O—, —OC(O)O—, —OC(O)-$\delta^1$, —OC(O)N(Q)-$\delta^1$, —OC(O)S-$\delta^1$, —N(Q)C(O)-$\delta^1$, —N(Q)C(O)O-$\delta^1$, —C(O)O-$\delta^1$, and —C(O)N(Q)-$\delta^1$; Q is H or $C_1$-$C_5$ alkyl; $\delta^1$ designates the bond linked to the $R^1$ group;

$R^1$ is selected from:

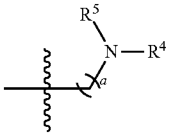
,
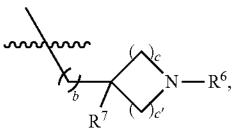

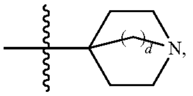
and
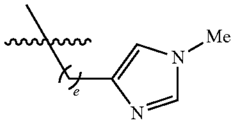
;

wherein:

$R^4$ and $R^5$ are each independently selected from group consisting of $C_1$-$C_6$ alkyl, $C_2$-$C_6$ alkenyl and $C_2$-$C_6$ alkynyl; alternatively $R^4$ and $R^5$ may join to form 4-6 membered heterocyclic ring containing oxygen (O) or up to 2 nitrogen (N), optionally substituted with 1-2 substituents each independently selected from a $C_1$-$C_6$ alkyl, cyclopropyl, OH, and a $C_1$-$C_3$ alkoxy group;

$R^6$ is selected from $C_1$-$C_6$ alkyl, $C_2$-$C_6$ alkenyl, $C_2$-$C_6$ alkynyl, $C_3$-$C_6$ cycloalkyl and a 2-hydroxyethyl group;

$R^7$ is selected from H, $C_1$-$C_6$ alkyl, $C_2$-$C_6$ alkenyl, and a $C_2$-$C_6$ alkynyl group;

a and c' are independently 1, 2, 3, 4, or 5;

b, c and e are independently 0, 1, or 2;

d is 1, or 2;

$R^2$ is selected from H, $C_1$-$C_{12}$ alkyl, $C_2$-$C_{12}$ alkenyl, $C_2$-$C_{12}$ alkynyl, and

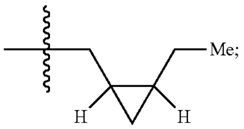 [SMILES: *CC1CC1CC]

$L_2$ is a direct bond or $\delta^2$—$(CR^8R^{8'})_k$-$\delta^3$ wherein $R^8$ and $R^{8'}$ are each independently H, $C_1$-$C_{12}$ alkyl, $C_2$-$C_{12}$ alkenyl or $C_2$-$C_{12}$ alkynyl; $\delta^2$ designates the bond linked to $E_2$ group and $\delta^3$ designates the bond linked to cyclopentyl scaffold described in formula (I);

k is 1, 2, 3, 4, or 5;

$E_2$ is selected from —O—, —OC(O)O—, —OC(O)-$\delta^4$, —OC(O)N(Q)-$\delta^4$, —N(Q)C(O)-$\delta^4$, —N(Q)C(O)O-$\delta^4$, —C(O)N(Q)-$\delta^4$ or —C(O)O-$\delta^4$; Q is H or $C_1$-$C_5$ alkyl; where $\delta^4$ designates the bond linked to $R^3$ group;

$R^3$ is selected from $C_8$-$C_{20}$ alkyl, $C_8$-$C_{20}$ alkenyl, $C_8$-$C_{20}$ alkynyl,

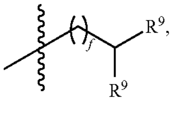

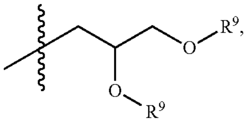

-continued

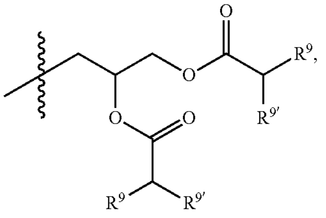

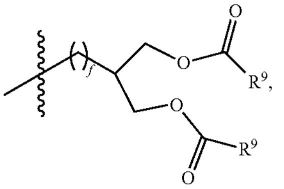

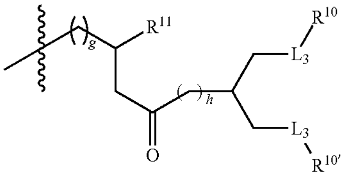

or

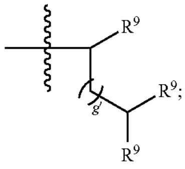

wherein:

f is 0, or 1;

g is 1, or 2;

g' is 1, 2, 3, 4, or 5;

h is 0, 1, 2, 3 or 4;

$R^9$ is a $C_6$-$C_{20}$ chain having the formula —$(CH_2)_i$-[$L_4$-$(CH_2)$]$_j$—$R^{12}$, wherein:

$L_4$ is selected from

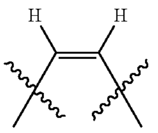

,

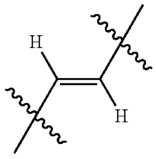

,

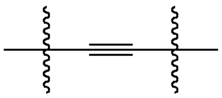

and

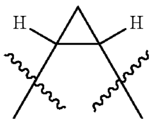

;

i is an integer in the range 6-20;

j is 0, 1, 2, or 3;

$R^{12}$ is selected from H and $C_4$-$C_8$ alkyl;

$R^{9'}$ is selected from H, $C_4$-$C_{10}$ alkyl, $C_4$-$C_{10}$ alkenyl, and $C_4$-$C_{10}$ alkynyl;

$R^{10}$ and $R^{10'}$ are each, independently selected from $C_4$-$C_{10}$ alkyl, $C_4$-$C_{10}$ alkenyl, and $C_4$-$C_{10}$ alkynyl;

$L_3$ is —OC(O)-$\delta^5$, —O-$\delta^5$, or a direct bond; $\delta^5$ designates the bond linked to $R^{10}$ and $R^{10'}$;

$R^1$=$R^9$, or has the formula:

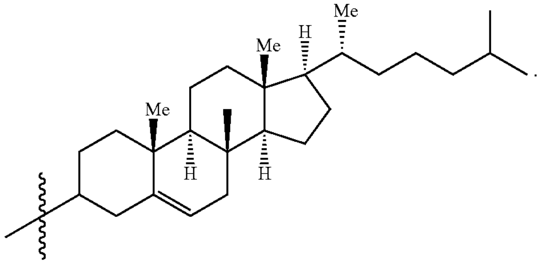

According to other embodiments of the invention, there is provided a compound, or a pharmaceutically acceptable salt thereof, of formula (I):

(I)

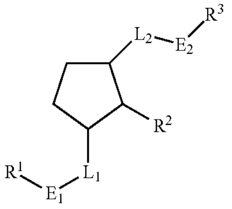

wherein:

$L_1$ is a direct bond or $C_1$-$C_5$ alkylene;

$E_1$ is selected from —OC(O)O—, —OC(O)-$\delta^1$, —OC(O)N(Q)-$\delta^1$, —OC(O)S-$\delta^1$; Q is H or $C_1$-$C_5$ alkyl; $\delta^1$ designates the bond linked to the $R^1$ group;

$R^1$ is selected from: IDC-29 $C_1$

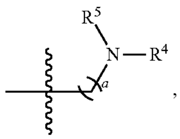

,

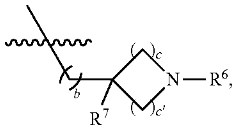

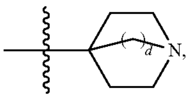

and

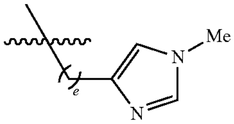

;

wherein:

$R^4$ and $R^5$ are each, independently selected from $C_1$-$C_6$ alkyl, $C_2$-$C_6$ alkenyl and $C_2$-$C_6$ alkynyl; alternatively $R^4$ and $R^5$ may join to form 5-6 membered heterocyclic ring containing up to 2 nitrogen (N), optionally substituted with 1-2 substituents each independently selected from a $C_1$-$C_6$ alkyl, and a cyclopropyl group;

$R^6$ is selected from $C_1$-$C_6$ alkyl, and $C_3$-$C_6$ cycloalkyl group;

$R^7$ is selected from H, and $C_1$-$C_6$ alkyl group;

a is 1, 2, or 3;

b and c are independently 0, 1, or 2;

c' is 2, 3, or 4;

d is 1, or 2;

e is 0, or 1;

$R^2$ is selected from H, $C_1$-$C_5$ alkyl, $C_2$-$C_5$ alkenyl, $C_2$-$C_5$ alkynyl, and

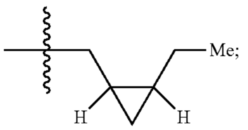

$L_2$ is a direct bond or $\delta^2$—$(CR^8R^{8'})_k$-$\delta^3$ wherein $R^8$ and $R^{8'}$ are each independently H, $C_1$-$C_{12}$ alkyl, $C_2$-$C_{12}$ alkenyl or $C_2$-$C_{12}$ alkynyl; $\delta^2$ designates the bond linked to $E_2$ group and $\delta^3$ designates the bond linked to cyclopentyl scaffold described in formula (I);

k is 1;

$E_2$ is selected from —O—, —OC(O)O, —OC(O)-$\delta^4$, —OC(O)N(Q)-$\delta^4$, —C(O)N(Q)-$\delta^4$ or —C(O)O-$\delta^4$; Q is H or $C_1$-$C_5$ alkyl; where $\delta^4$ designates the bond linked to $R^3$ group;

$R^3$ is selected from $C_8$-$C_{20}$ alkyl, $C_8$-$C_{20}$ alkenyl, $C_8$-$C_{20}$ alkynyl,

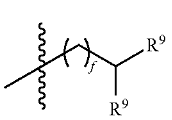 ; 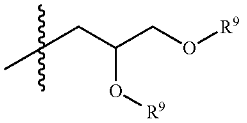 ;

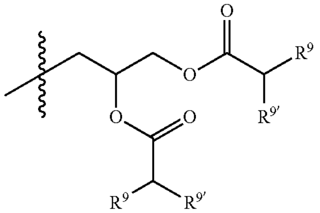 ,

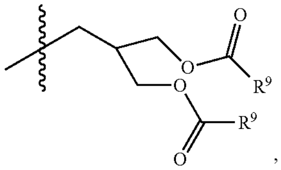 , and

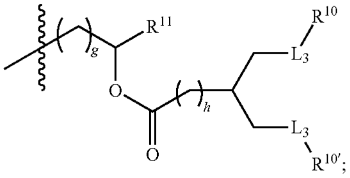

wherein:

f and h are each 0;

g is 1, or 2;

$R^9$ is a $C_6$-$C_{20}$ chain having the formula —$(CH_2)_i$-[$L_4$-$(CH_2)$]; $R^{12}$, wherein:

$L_4$ is selected from

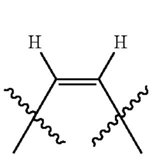 , 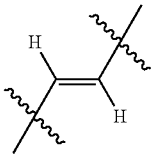 ,

-continued

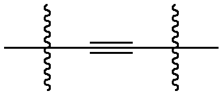 and 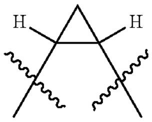 ;

i is an integer in the range 6-20;

j is 0, 1, or 2;

$R^{12}$ is selected from H, and $C_4$-$C_8$ alkyl group;

$R^{9'}$ is selected from H, and $C_4$-$C_{10}$ alkyl;

$R^{10}$ and $R^{10'}$ are each, independently selected from $C_4$-$C_{10}$ alkyl, $C_4$-$C_{10}$ alkenyl, and $C_4$-$C_{10}$ alkynyl;

$L_3$ is —OC(O)-$\delta^5$, or a direct bond; 65 designates the bond linked to $R^{10}$ and $R^{10'}$;

$R^{11}$ is the same as $R^9$.

According to other embodiments of the invention, there is provided a Compound, or a pharmaceutically acceptable salt thereof, of formula (II):

(II)

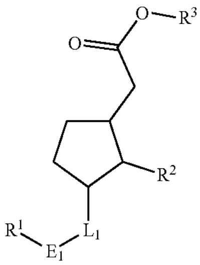

wherein:

$L_1$ is a direct bond;

$E_1$ is selected from —OC(O)O, —OC(O)-$\delta^1$, —OC(O)N(Q)-$\delta^1$, —OC(O)S-$\delta^1$; Q is H or $C_1$-$C_5$ alkyl; 51 designates the bond linked to the $R^1$ group;

$R^1$ is selected from

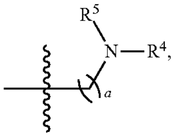 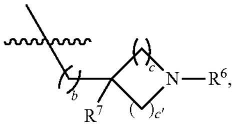

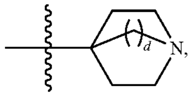 and 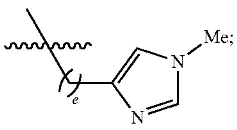

wherein:

$R^4$ and $R^5$ are each, independently selected from $C_1$-$C_6$ alkyl; alternatively $R^4$ and $R^5$ may join to form 5-6 membered heterocyclic ring containing up to 2 nitrogen (N), optionally substituted with 1-2 substituents each independently selected from a $C_1$-$C_6$ alkyl;

$R^6$ is selected from $C_1$-$C_6$ alkyl, and cyclopropyl group;

$R^7$ is selected from H, and $C_1$-$C_6$ alkyl group;

a is 1, 2, or 3;

b is 0, or 1;

c is 0, 1, or 2;

c' is 2, 3, or 4;

d is 2;

e is 1;

$R^2$ is selected from H, $C_1$-$C_5$ alkyl, $C_2$-$C_5$ alkenyl, and

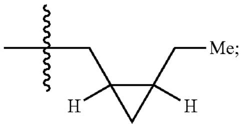 [SMILES: *CC1CC1CC]

$R^3$ is selected from:

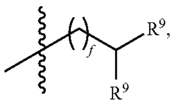

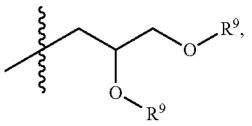

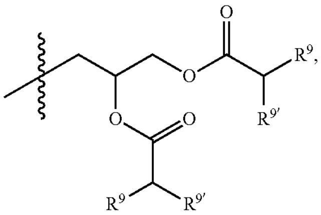

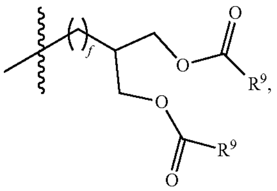 and

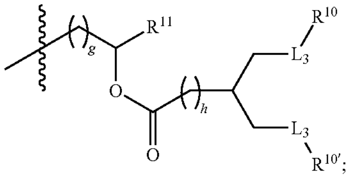

wherein:

f and h are each 0;

g is 1, or 2;

$R^9$ is a $C_6$-$C_{20}$ chain having the formula $-(CH_2)_i$-[$L_4$-($CH_2$)]; $R^{12}$, wherein:

$L_4$ is selected from

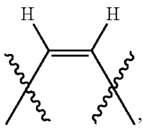 and 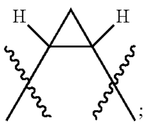

i is an integer in the range 6-20;

j is 0, 1, or 2;

$R^{12}$ is selected from H and $C_4$-$C_8$ alkyl group;

$R^9$ is selected from H, and $C_4$-$C_{10}$ alkyl;

$R^{10}$ and $R^{10'}$ are each, independently selected from $C_4$-$C_{10}$ alkyl;

$L_3$ is a direct bond;

$R^{13}$ is the same as $R^{11}$.

According to other embodiments of the invention, there is provided a compound, or a pharmaceutically acceptable salt thereof, of formula (III):

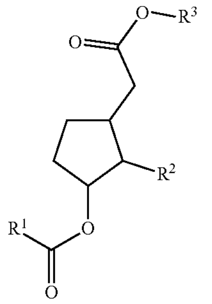

(III)

wherein:

$R^1$ is selected from:

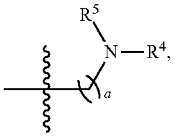

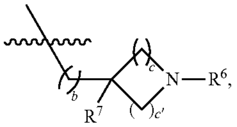

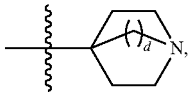 and

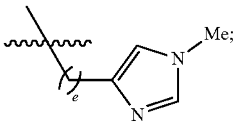

wherein:

$R^4$ and $R^5$ are each, independently selected from $C_1$-$C_6$ alkyl; alternatively, $R^4$ and $R^5$ may join to form 5-6 membered heterocyclic ring containing up to 2 nitrogen (N), optionally substituted with 1-2 substituents each independently selected from a $C_1$-$C_6$ alkyl;

$R^6$ is selected from $C_1$-$C_6$ alkyl, and cyclopropyl group;

$R^7$ is selected from H, and $C_1$-$C_6$ alkyl group;

a is 1, 2, or 3;

b is 0, or 1;

c is 0, 1, or 2;

c' is 2, 3, or 4;

d is 2;

e is 1;

$R^2$ is selected from H, $C_1$-$C_5$ alkyl, $C_2$-$C_5$ alkenyl, and

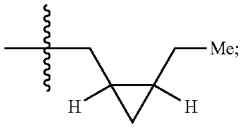 [SMILES: *CC1CC1CC]

$R^3$ is selected from:

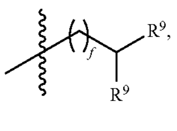

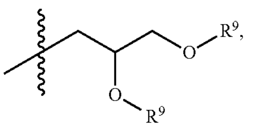

-continued

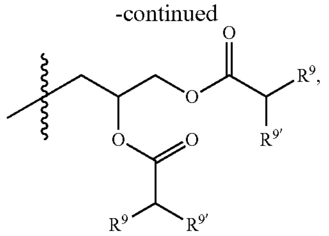

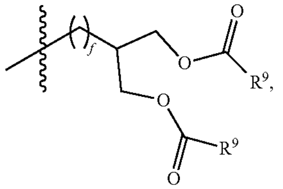

and

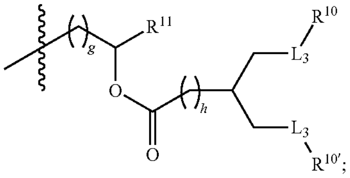

wherein:

f and h are 0;

g is 1, or 2;

$R^9$ is a $C_6$-$C_{20}$ chain having the formula —$(CH_2)_i$-[$L_4$-$(CH_2)$]— $R^{12}$, wherein:

$L_4$ is selected from

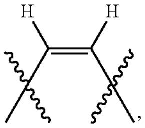

, and

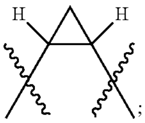

;

i is an integer in the range 6-20;

j is 0, 1, or 2;

$R^{12}$ is selected from H and $C_4$-$C_5$ alkyl group;

$R^{9'}$ is selected from H, and $C_4$-$C_{10}$ alkyl;

$R^{10}$ and $R^{10'}$ are each, independently selected from $C_4$-$C_{10}$ alkyl;

$L_3$ is a direct bond;

$R^{11}$ is the same as $R^9$.

According to embodiments of the invention, $R^1$ is one of:

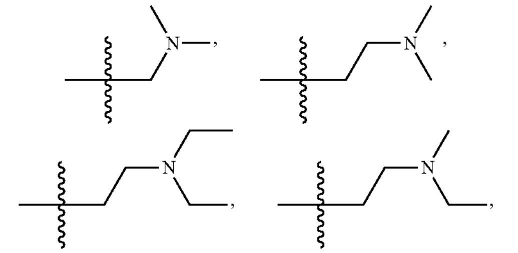

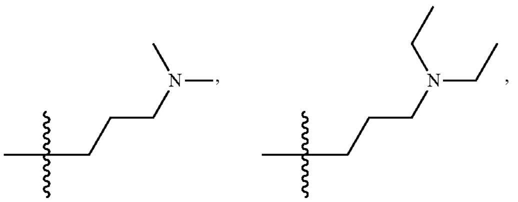

-continued

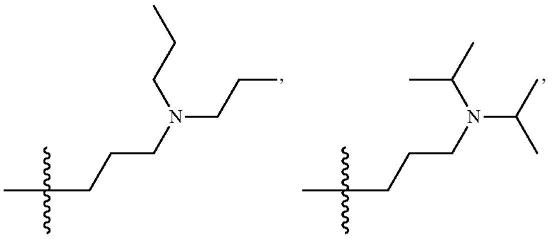

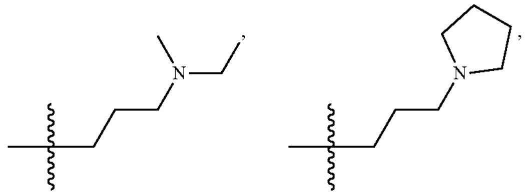

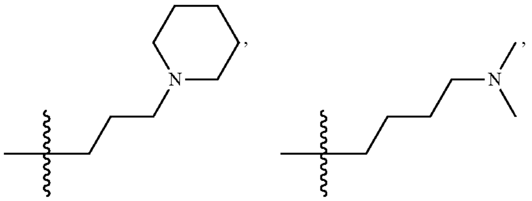

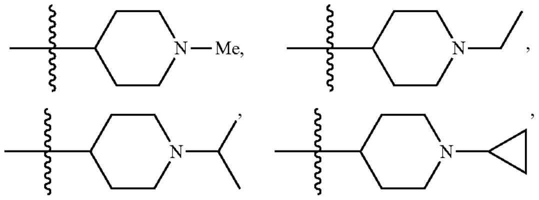

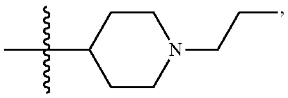

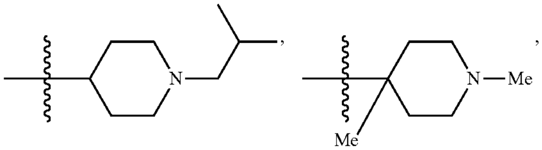

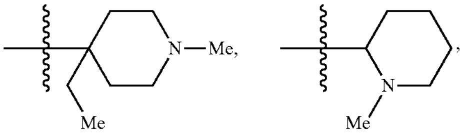

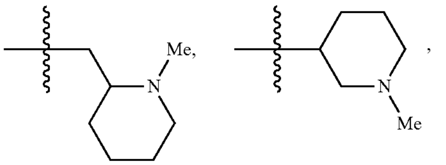

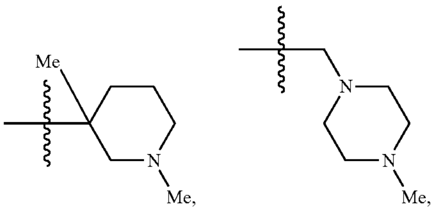

-continued
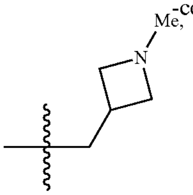
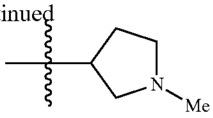
,
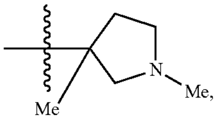
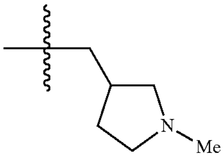
,
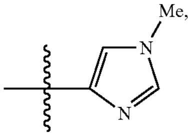
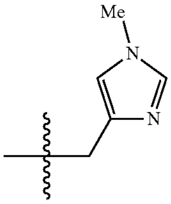
,
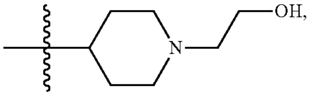
-continued
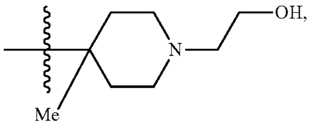
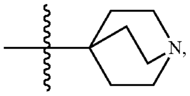
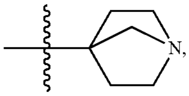
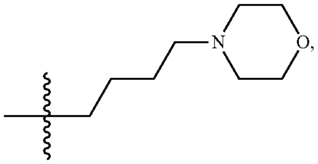
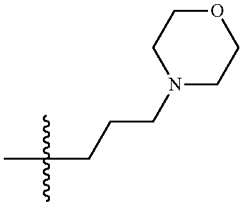
, or
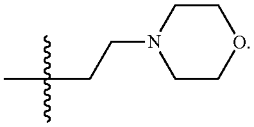
In further embodiments, each $R^3$ is independently:
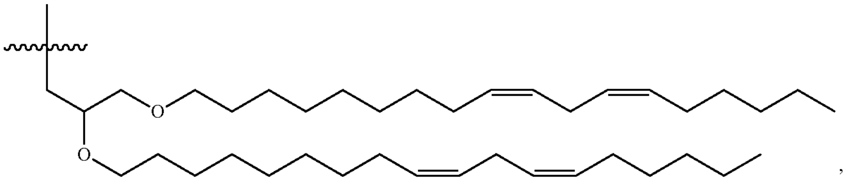
,
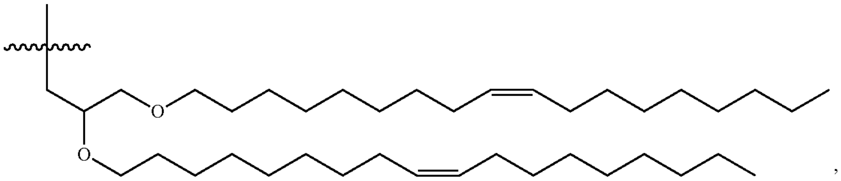
,
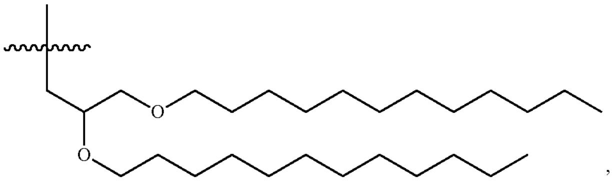
,
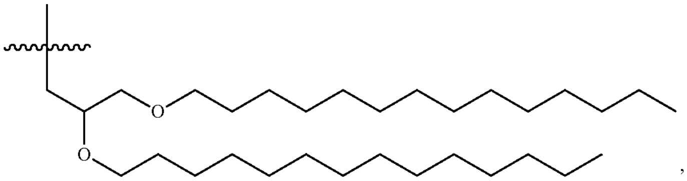
,
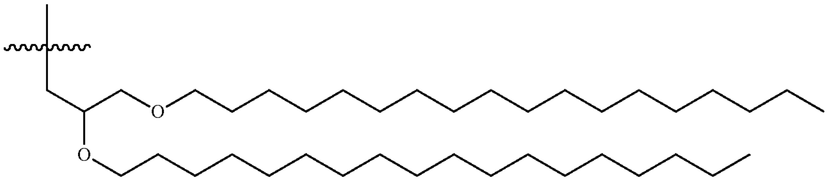
, -continued
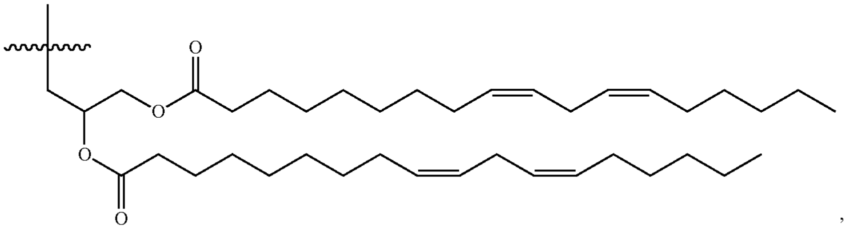
,
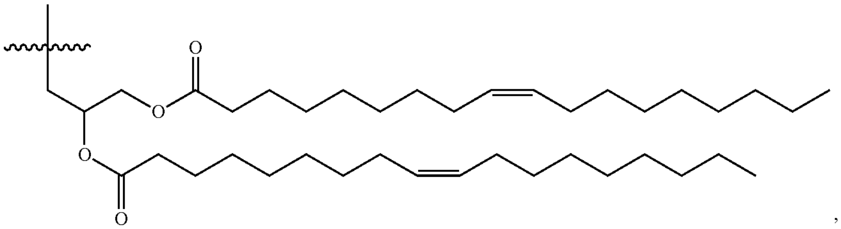
,
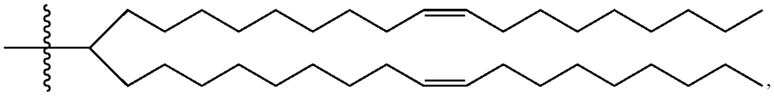
,
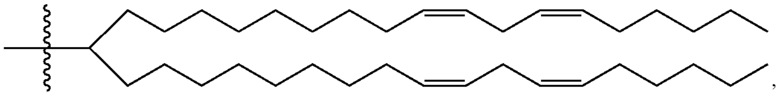
,
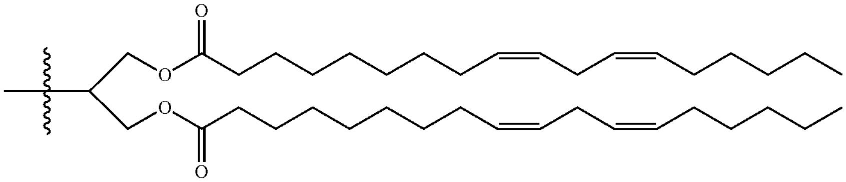
,
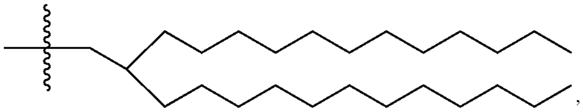
,
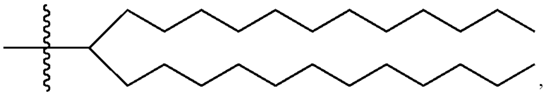
,
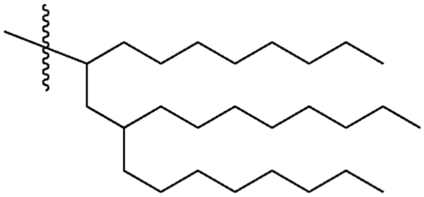
,
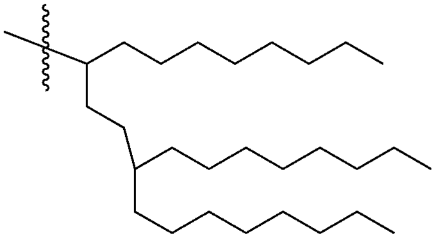
,
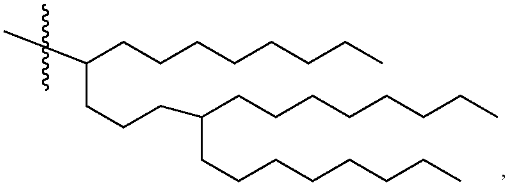
,
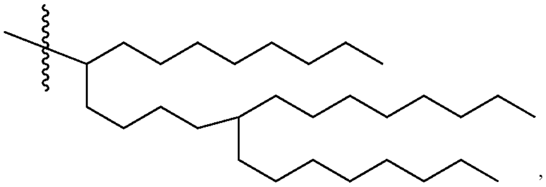
,
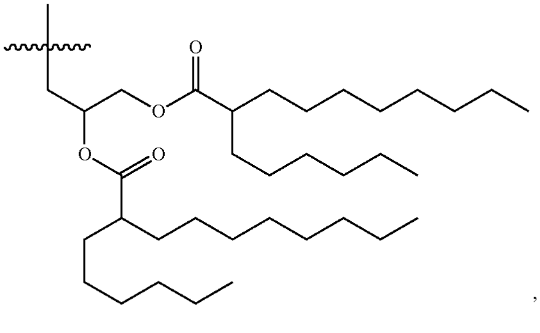
, -continued
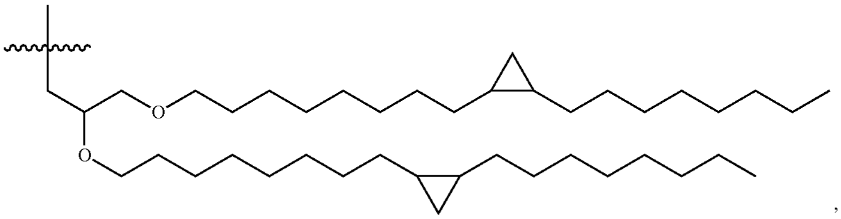
,
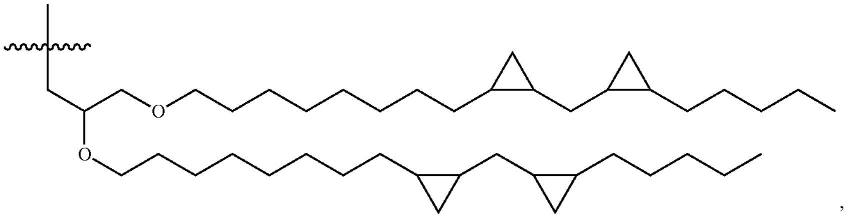
,
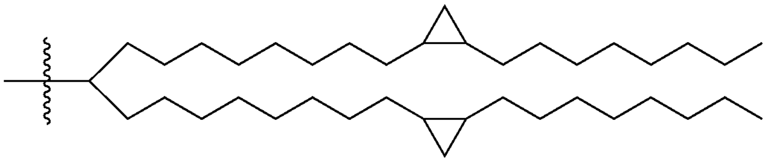
,
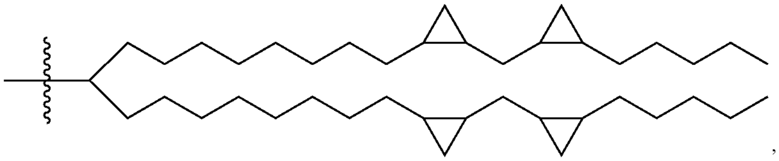
,
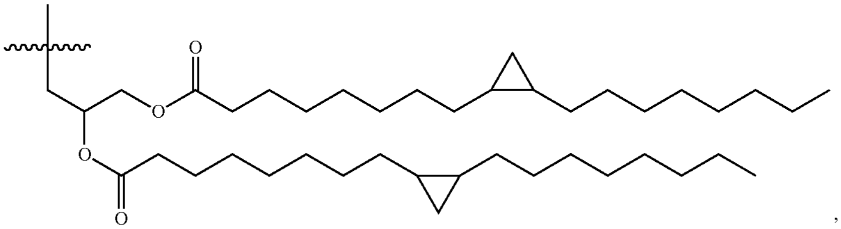
,
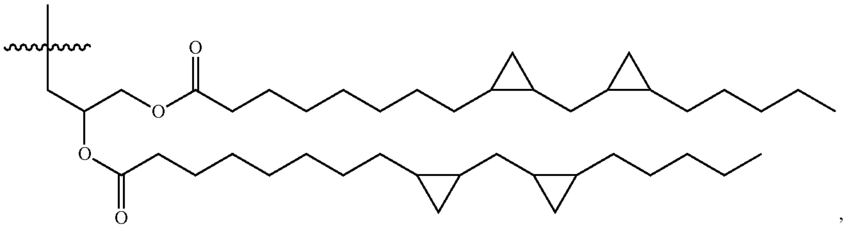
,
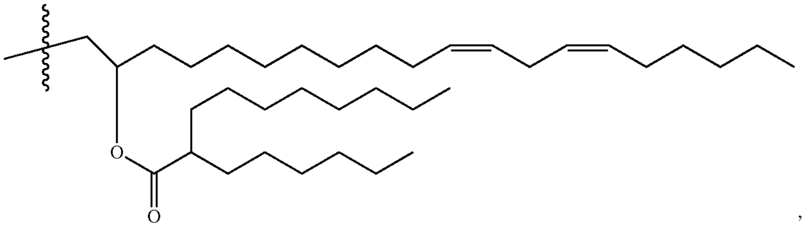
,
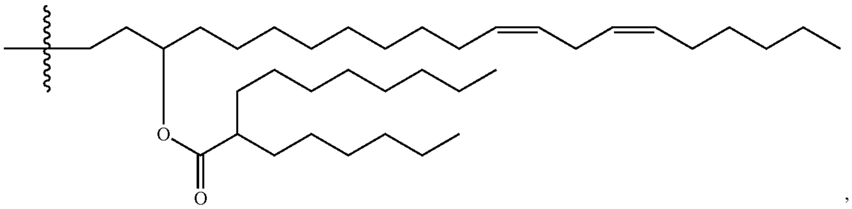
, -continued
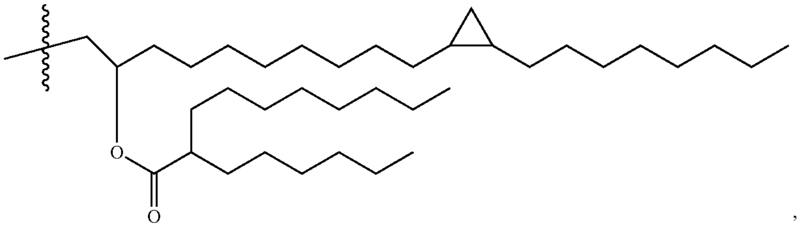
,
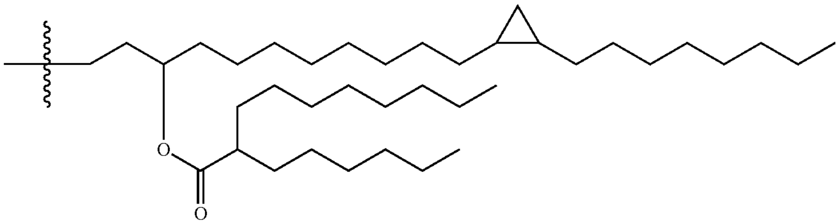
,
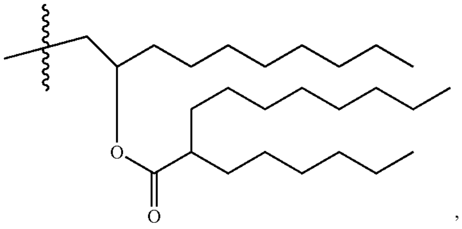
,
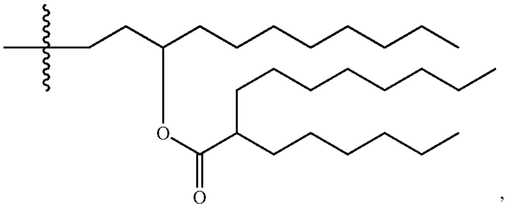
,
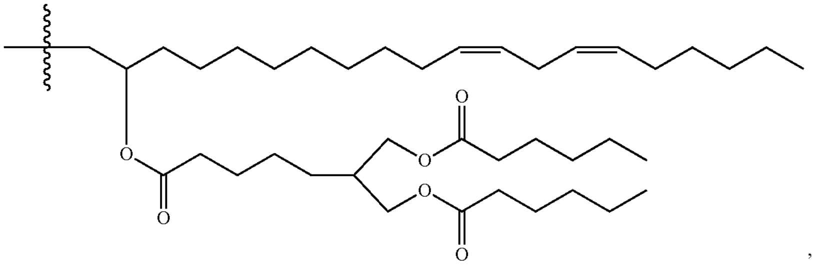
,
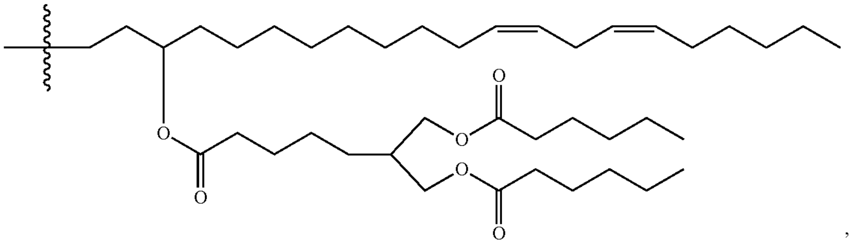
,
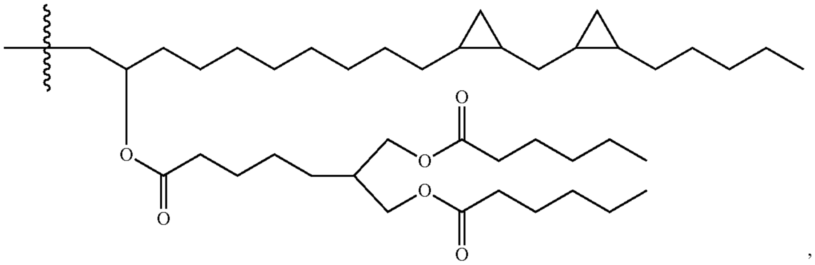
,
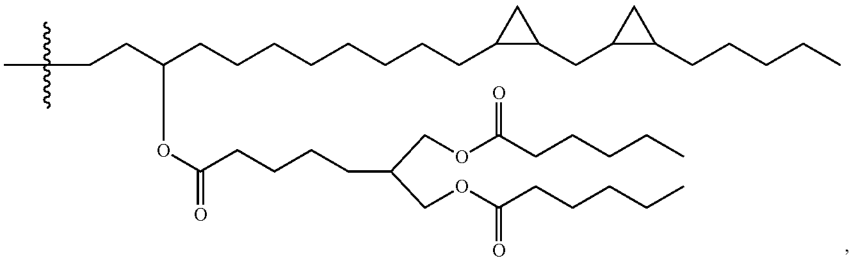
, -continued
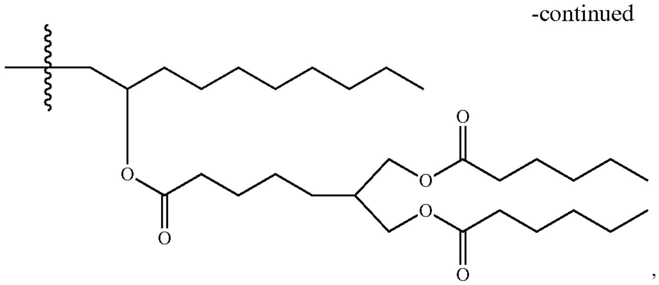
,
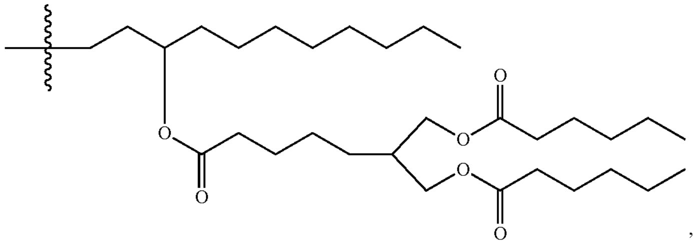
,
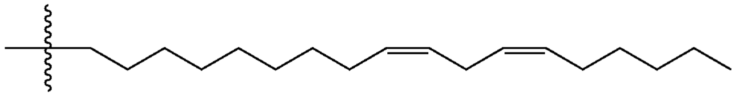
,
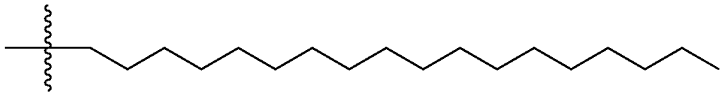
,
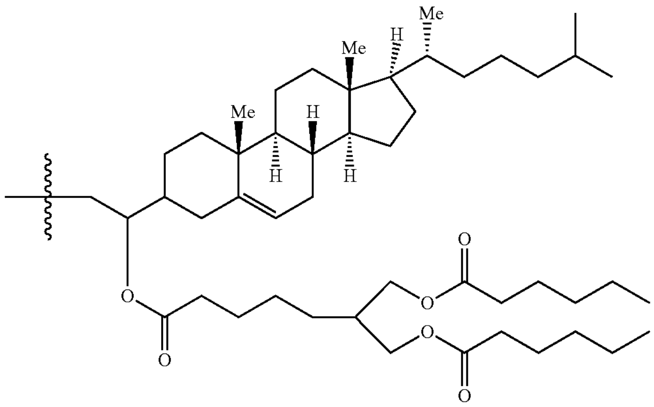
or
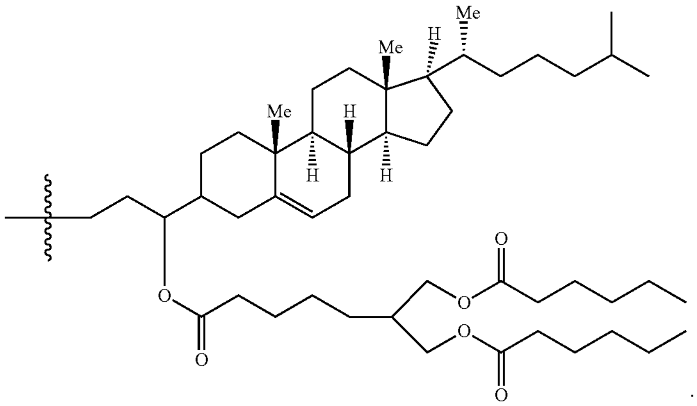
.

In other embodiments of the invention, $R^2$ is selected from:

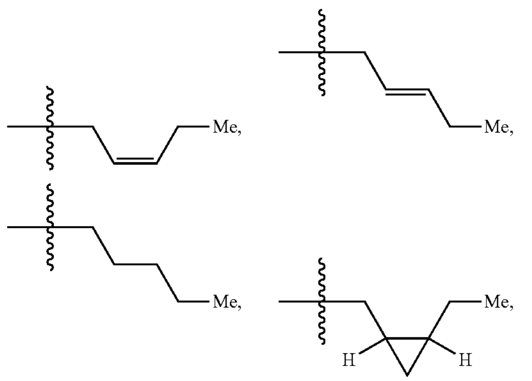

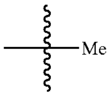

and

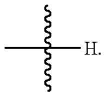

In still other embodiments of the invention, $E_1$ is selected from:

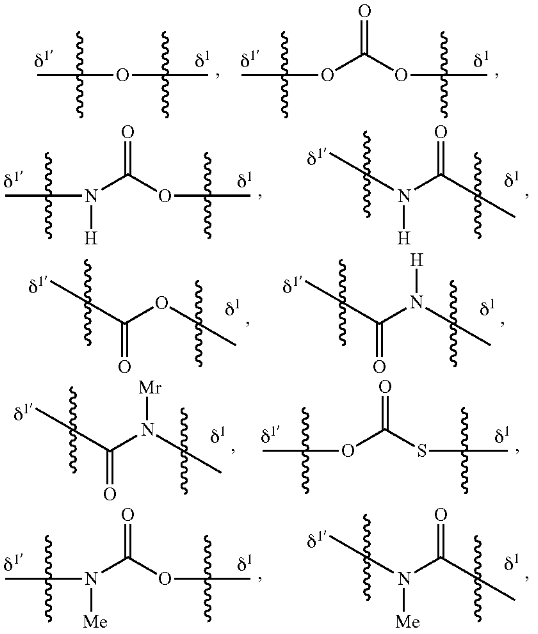

-continued

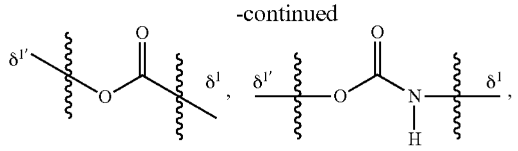

and

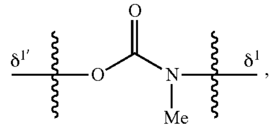

wherein $\delta^1$ designates the bond linked to the $R^1$ group; $\delta^{1'}$ designates the bond linked to the $L_1$ group.

In still other embodiments of the invention, $E_2$ is selected from:

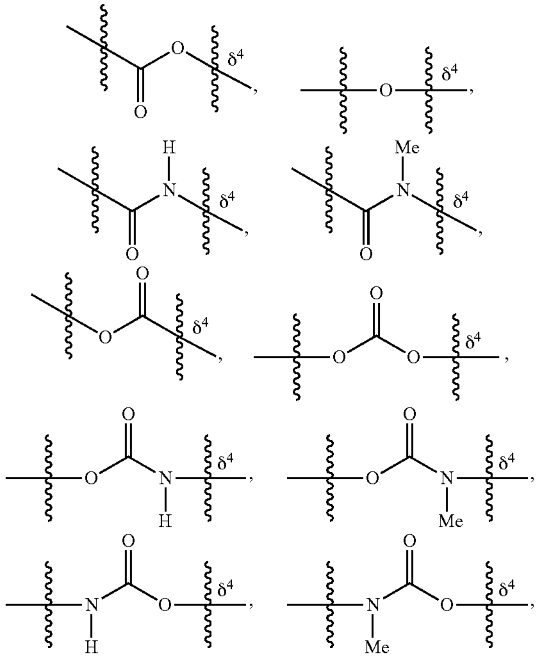

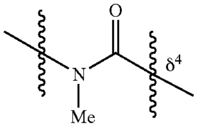

and

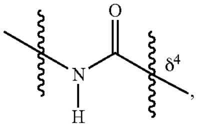

wherein $\delta^4$ designates the bond linked to the $R^3$ group.

According to embodiments of the invention there is provided a compound selected from the group consisting of:

TABLE 1

| Ref. | Structure |
|---|---|
| PNI 101 | 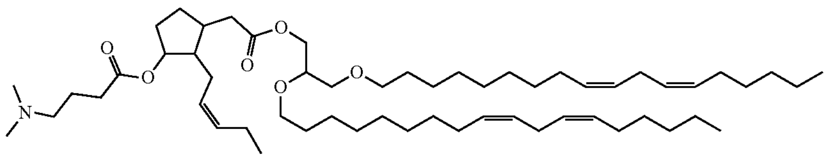 , |

TABLE 1-continued
| Ref. | Structure |
|---|---|
| PNI 123 | 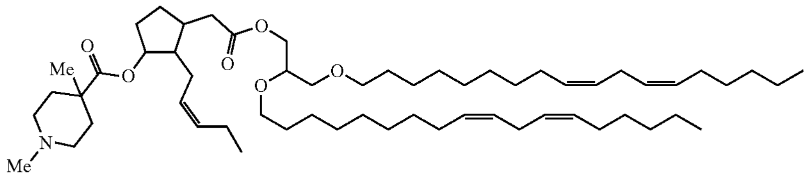 [SMILES: CC/C=C\CC1C(CC(=O)OCC(COCCCCCCCC/C=C\C/C=C\CCCCC)OCCCCCCCC/C=C\C/C=C\CCCCC)CCC1OC(=O)C1(C)CCN(C)CC1], |
| PNI 128 | 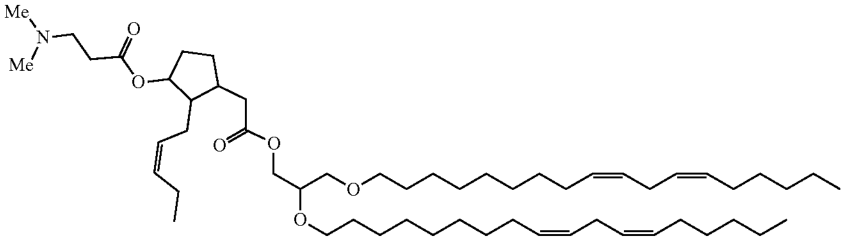 [SMILES: CC/C=C\CC1C(CC(=O)OCC(COCCCCCCCC/C=C\C/C=C\CCCCC)OCCCCCCCC/C=C\C/C=C\CCCCC)CCC1OC(=O)CCN(C)C], |
| PNI 132 | 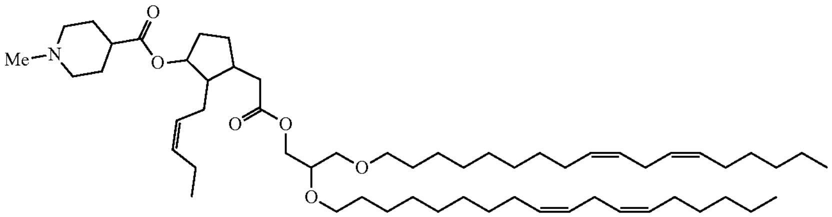 [SMILES: CC/C=C\CC1C(CC(=O)OCC(COCCCCCCCC/C=C\C/C=C\CCCCC)OCCCCCCCC/C=C\C/C=C\CCCCC)CCC1OC(=O)C1CCN(C)CC1], |
| PNI 135 | 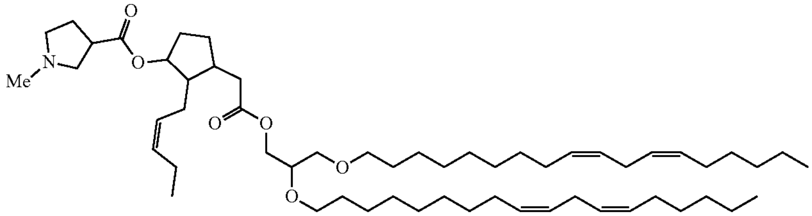 [SMILES: CC/C=C\CC1C(CC(=O)OCC(COCCCCCCCC/C=C\C/C=C\CCCCC)OCCCCCCCC/C=C\C/C=C\CCCCC)CCC1OC(=O)C1CCN(C)C1], |
| PNI 143 | 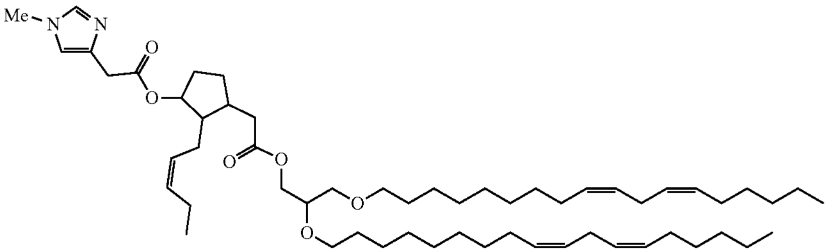 [SMILES: CC/C=C\CC1C(CC(=O)OCC(COCCCCCCCC/C=C\C/C=C\CCCCC)OCCCCCCCC/C=C\C/C=C\CCCCC)CCC1OC(=O)Cc1cn(C)cn1], |
| PNI 542 | 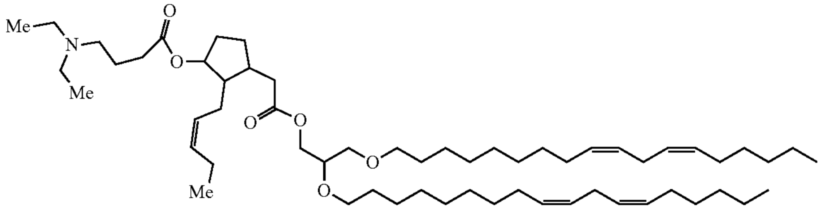 [SMILES: CC/C=C\CC1C(CC(=O)OCC(COCCCCCCCC/C=C\C/C=C\CCCCC)OCCCCCCCC/C=C\C/C=C\CCCCC)CCC1OC(=O)CCCN(CC)CC], |

TABLE 1-continued
| Ref. | Structure |
| --- | --- |
| PNI 557 | 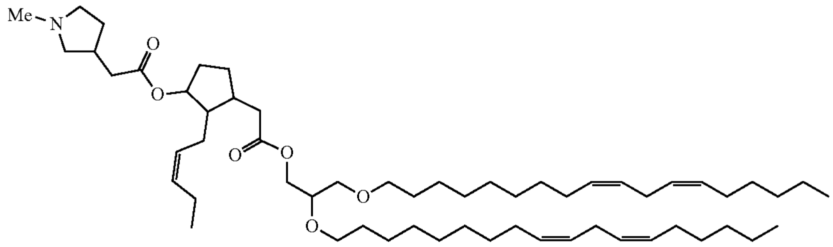 [SMILES: CC/C=C\CC1C(CC(=O)OCC(COCCCCCCCC/C=C\C/C=C\CCCCC)OCCCCCCCC/C=C\C/C=C\CCCCC)CCC1OC(=O)CC1CCN(C)C1] , |
| PNI 558 | 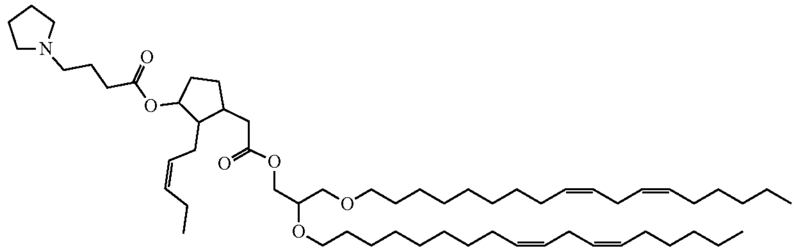 [SMILES: CC/C=C\CC1C(CC(=O)OCC(COCCCCCCCC/C=C\C/C=C\CCCCC)OCCCCCCCC/C=C\C/C=C\CCCCC)CCC1OC(=O)CCCN1CCCC1] , |
| PNI 559 | 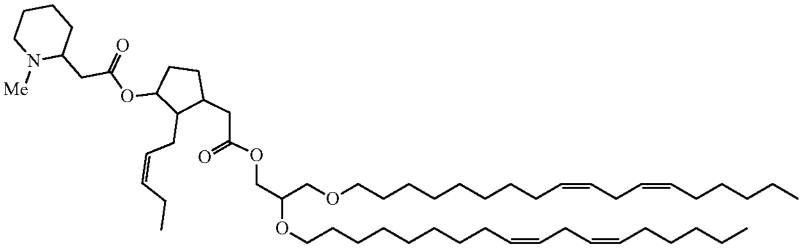 [SMILES: CC/C=C\CC1C(CC(=O)OCC(COCCCCCCCC/C=C\C/C=C\CCCCC)OCCCCCCCC/C=C\C/C=C\CCCCC)CCC1OC(=O)CC1CCCCN1C] , |
| PNI 148 | 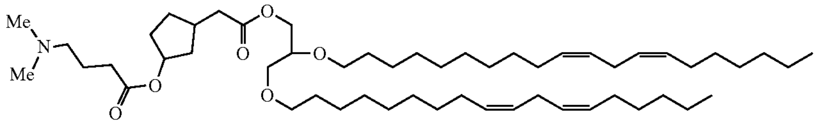 , |
| PNI 516 | 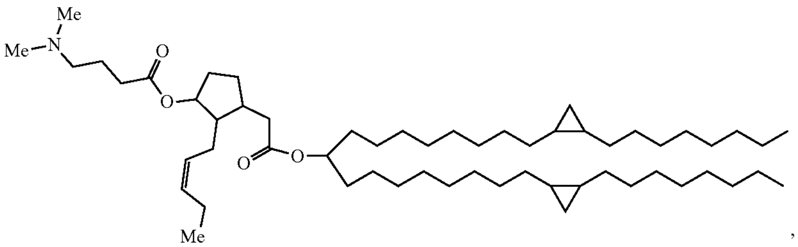 [SMILES: CC/C=C\CC1C(CC(=O)OC(CCCCCCCCC2CC2CCCCCCCC)CCCCCCCCC2CC2CCCCCCCC)CCC1OC(=O)CCCN(C)C] , |
| PNI 549 | 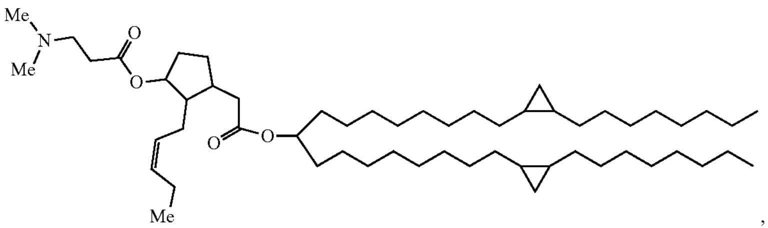 [SMILES: CC/C=C\CC1C(CC(=O)OC(CCCCCCCCC2CC2CCCCCCCC)CCCCCCCCC2CC2CCCCCCCC)CCC1OC(=O)CCN(C)C] , |

TABLE 1-continued
| Ref. | Structure |
| --- | --- |
| PNI 560 | 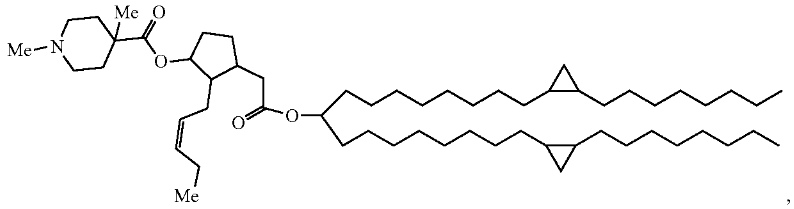 [SMILES: CC/C=C\CC1C(CC(=O)OC(CCCCCCCCC2CC2CCCCCCCC)CCCCCCCCC2CC2CCCCCCCC)CCC1OC(=O)C1(C)CCN(C)CC1] , |
| PNI 543 | 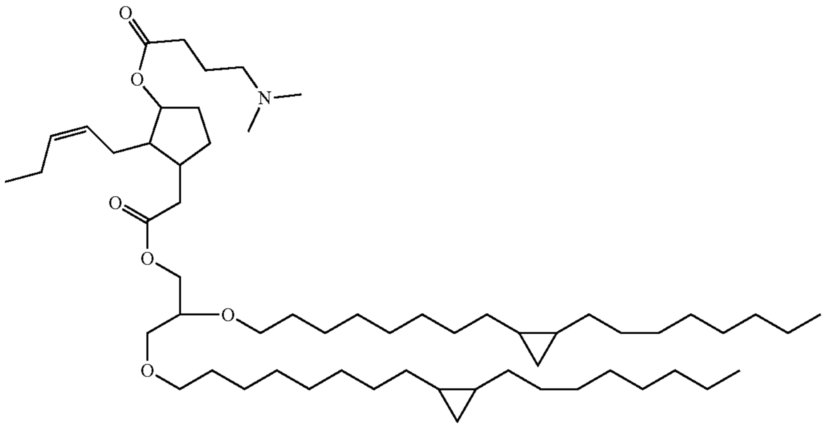 [SMILES: CC/C=C\CC1C(CC(=O)OCC(COCCCCCCCCC2CC2CCCCCCCC)OCCCCCCCCC2CC2CCCCCCCC)CCC1OC(=O)CCCN(C)C] , |
| PNI 544 | 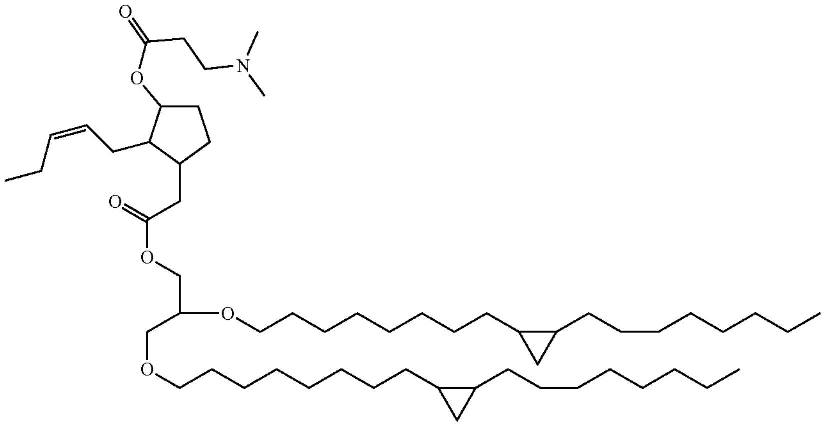 [SMILES: CC/C=C\CC1C(CC(=O)OCC(COCCCCCCCCC2CC2CCCCCCCC)OCCCCCCCCC2CC2CCCCCCCC)CCC1OC(=O)CCN(C)C] , |
| PNI 545 | 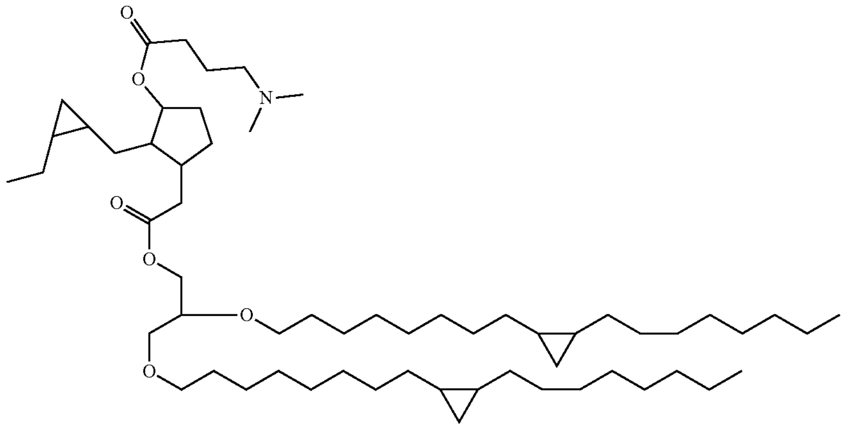 , |

TABLE 1-continued
| Ref. | Structure |
|---|---|
| PNI 546 | 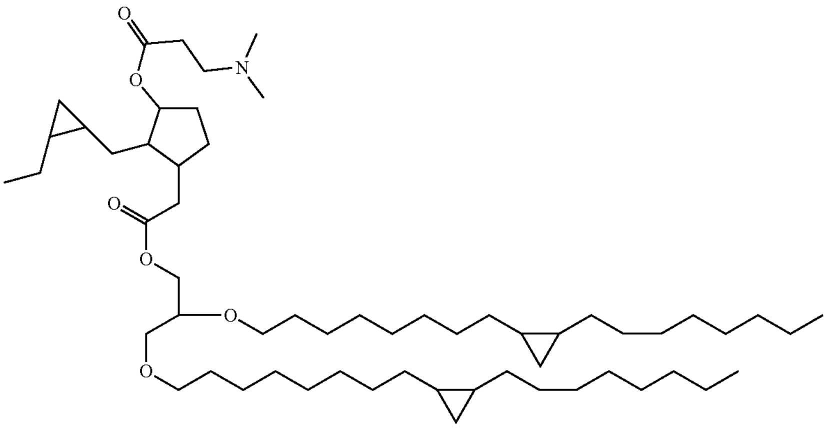 [SMILES: CCCCCCCCC1CC1CCCCCCCCOCC(COC(=O)CC1CCC(OC(=O)CCN(C)C)C1CC1CC1CC)OCCCCCCCCC1CC1CCCCCCCC] , |
| PNI 547 | 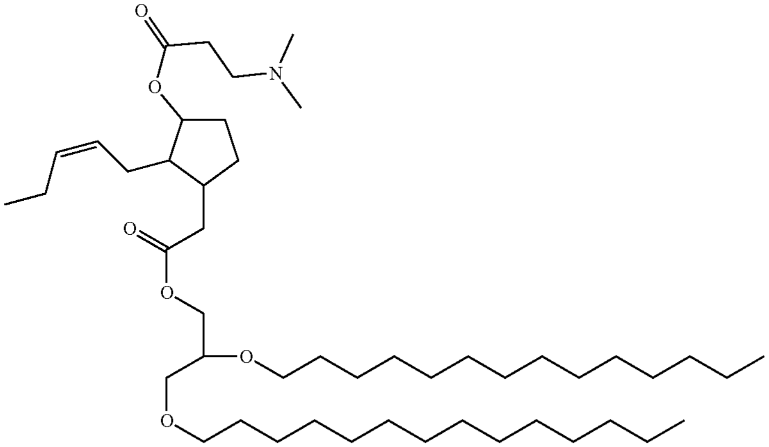 , |
| PNI 548 | 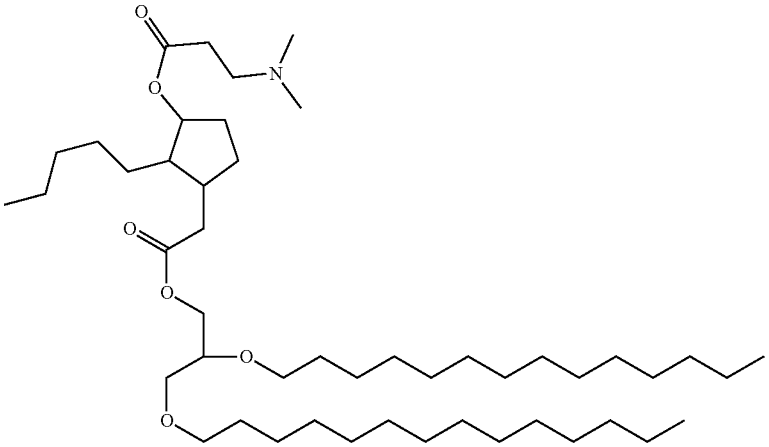 , |

TABLE 1-continued
| Ref. | Structure |
| --- | --- |
| PNI 554 | 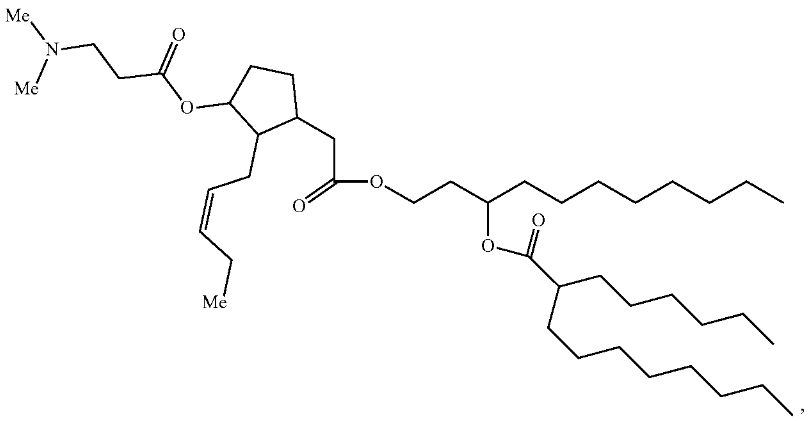 [SMILES: CC/C=C\CC1C(CC(=O)OCCC(CCCCCCCC)OC(=O)C(CCCCCC)CCCCCCCC)CCC1OC(=O)CCN(C)C], |
| PNI 562 | 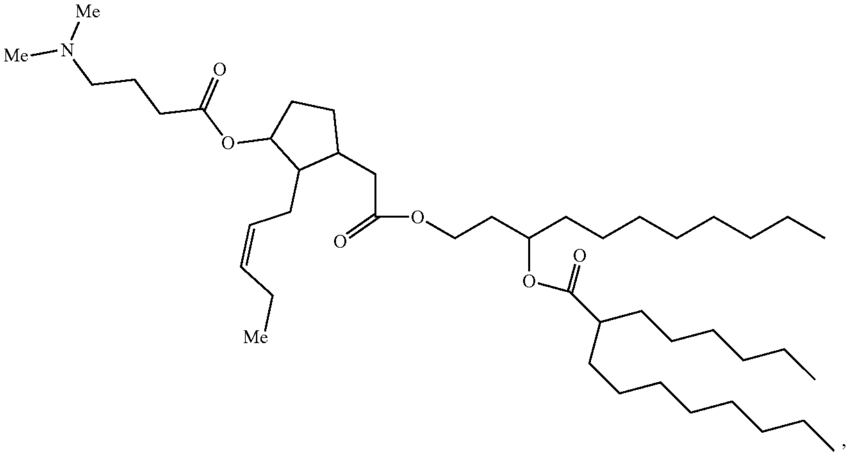 [SMILES: CC/C=C\CC1C(CC(=O)OCCC(CCCCCCCC)OC(=O)C(CCCCCC)CCCCCCCC)CCC1OC(=O)CCCN(C)C], |
| PNI 565 | 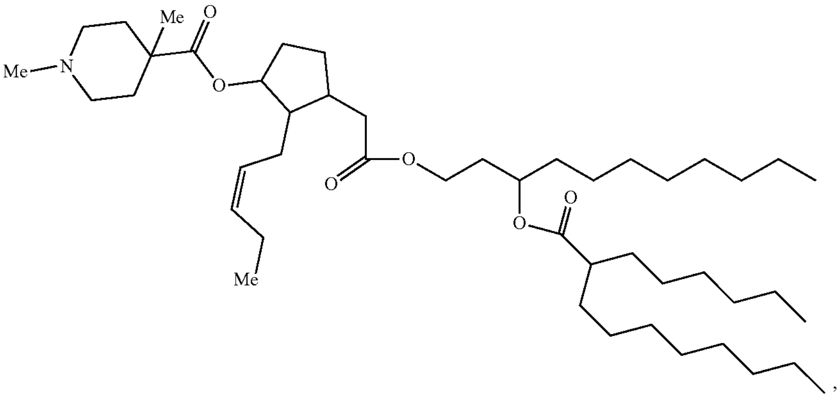 [SMILES: CC/C=C\CC1C(CC(=O)OCCC(CCCCCCCC)OC(=O)C(CCCCCC)CCCCCCCC)CCC1OC(=O)C1(C)CCN(C)CC1], |

TABLE 1-continued
| Ref. | Structure |
|---|---|
| PNI 510 | 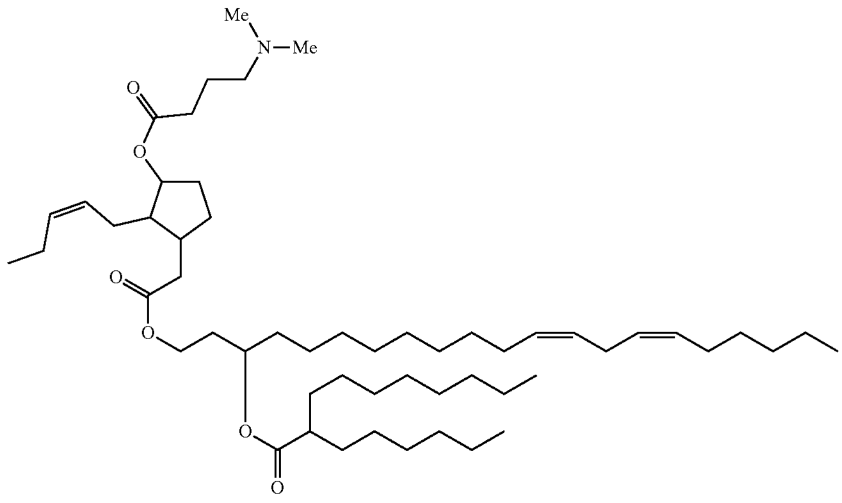, |
| PNI 552 | 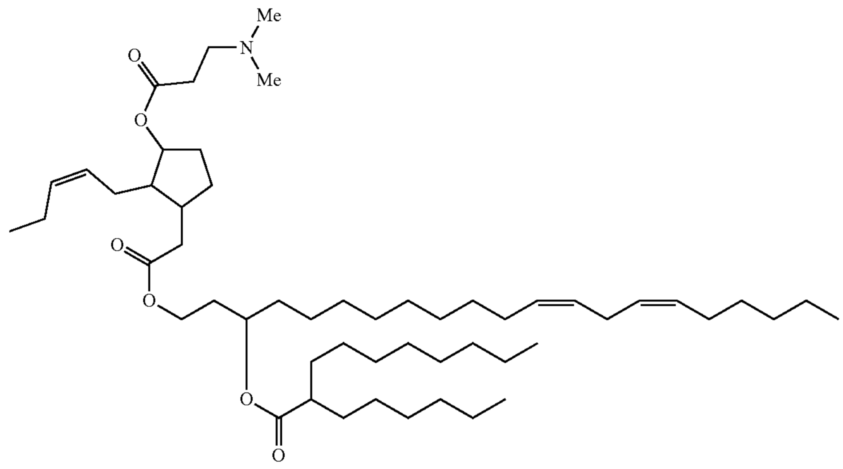 [SMILES: CC/C=C\CC1C(CC(=O)OCCC(CCCCCCCC/C=C\C/C=C\CCCCC)OC(=O)C(CCCCCC)CCCCCCCC)CCC1OC(=O)CCN(C)C], |
| PNI 563 | 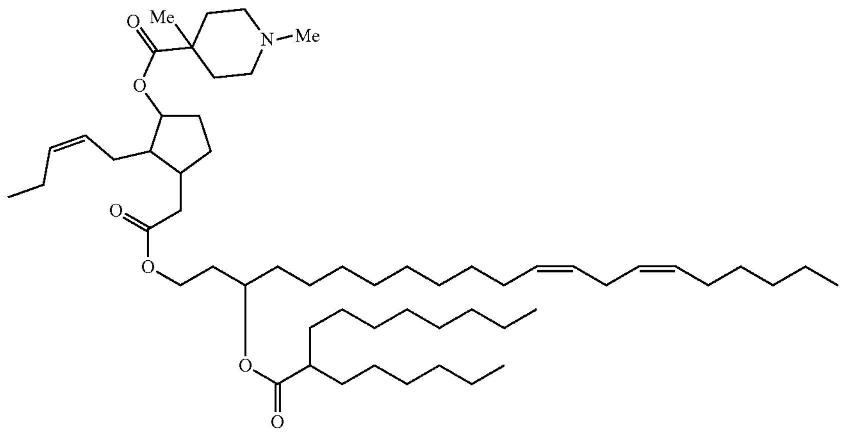 [SMILES: CC/C=C\CC1C(CC(=O)OCCC(CCCCCCCC/C=C\C/C=C\CCCCC)OC(=O)C(CCCCCC)CCCCCCCC)CCC1OC(=O)C1(C)CCN(C)CC1], |

TABLE 1-continued
| Ref. | Structure |
| --- | --- |
| PNI 584 | 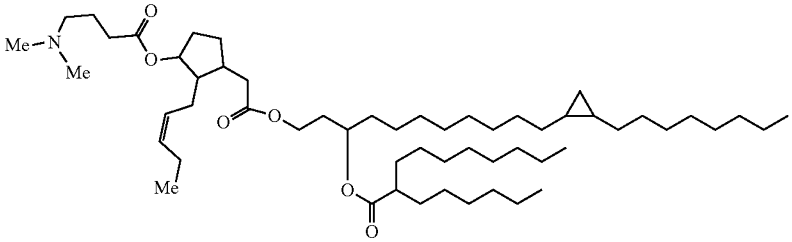 [SMILES: CC/C=C\CC1C(CC(=O)OCCC(CCCCCCCCC2CC2CCCCCCCC)OC(=O)C(CCCCCC)CCCCCCCC)CCC1OC(=O)CCCN(C)C], |
| PNI 585 | 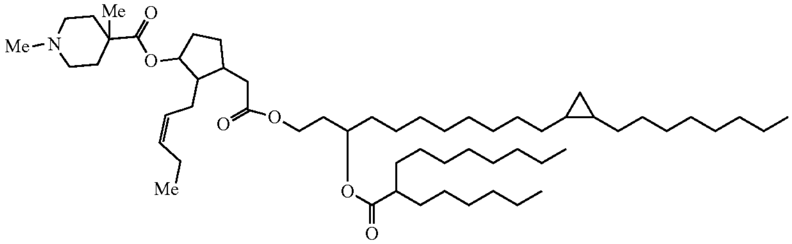 [SMILES: CC/C=C\CC1C(CC(=O)OCCC(CCCCCCCCC2CC2CCCCCCCC)OC(=O)C(CCCCCC)CCCCCCCC)CCC1OC(=O)C1(C)CCN(C)CC1], |
| PNI 586 | 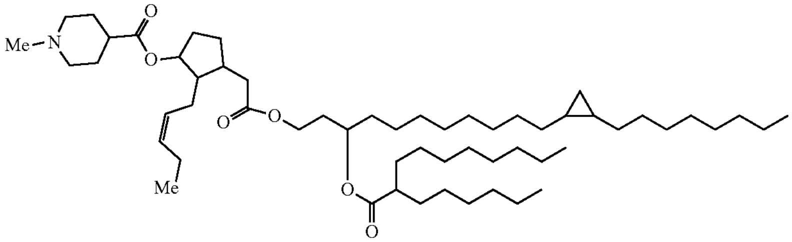 [SMILES: CC/C=C\CC1C(CC(=O)OCCC(CCCCCCCCC2CC2CCCCCCCC)OC(=O)C(CCCCCC)CCCCCCCC)CCC1OC(=O)C1CCN(C)CC1], |
| PNI 515 | 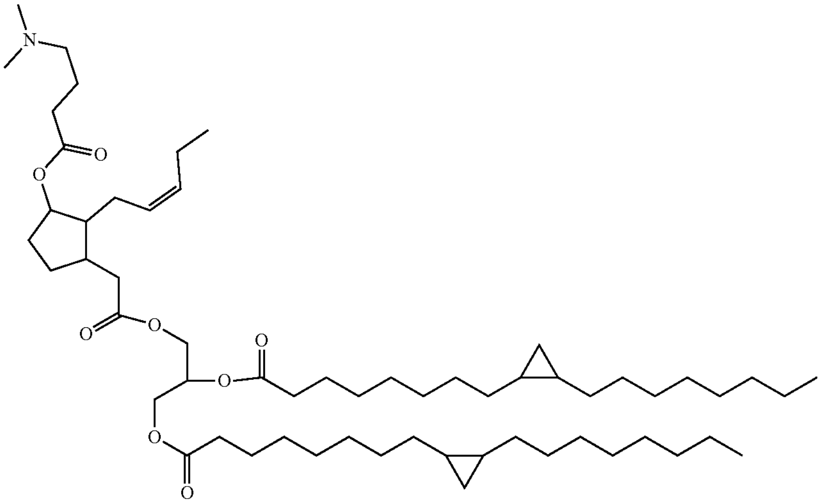 [SMILES: CC/C=C\CC1C(CC(=O)OCC(COC(=O)CCCCCCCC2CC2CCCCCCCC)OC(=O)CCCCCCCC2CC2CCCCCCCC)CCC1OC(=O)CCCN(C)C], |
| PNI 551 | 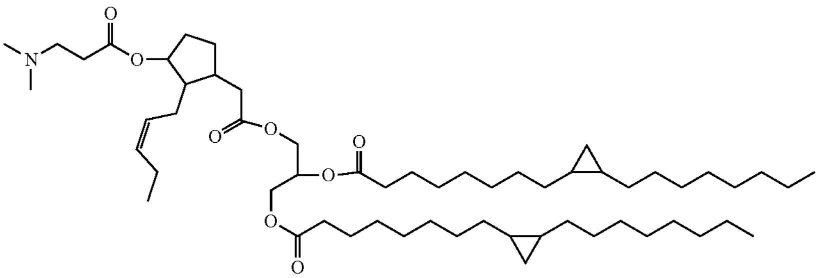, |

TABLE 1-continued
| Ref. | Structure |
| --- | --- |
| PNI 269 | 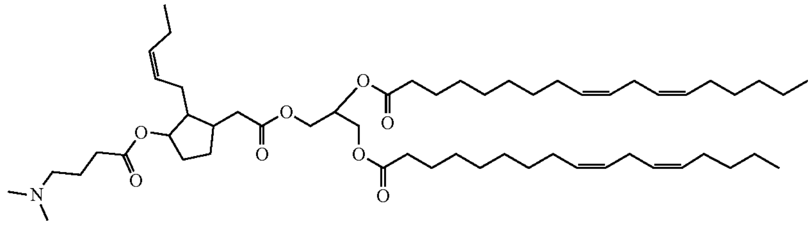 , |
| PNI 550 | 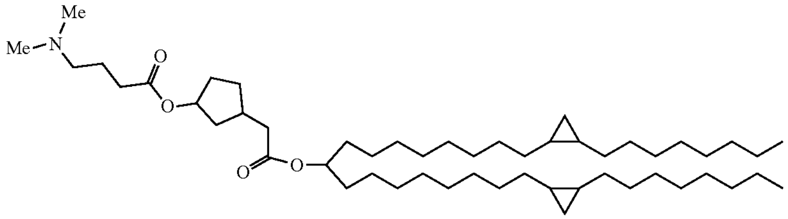 , |
| PNI 147 | 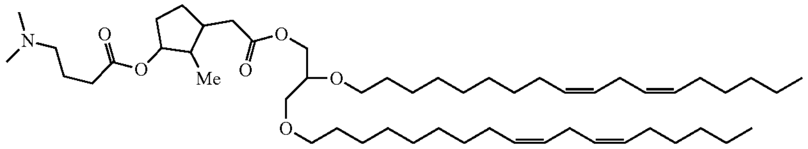 , |
| PNI 567 | 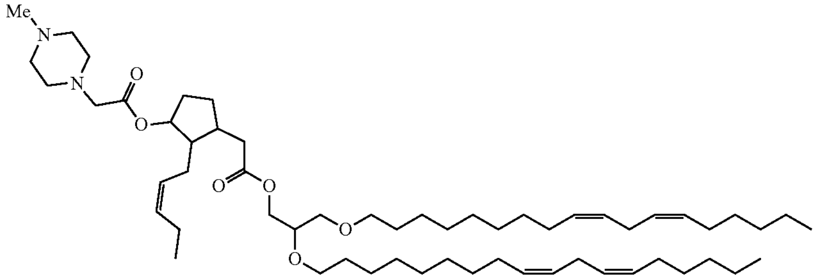 [SMILES: CC/C=C\CC1C(CC(=O)OCC(COCCCCCCCC/C=C\C/C=C\CCCCC)OCCCCCCCC/C=C\C/C=C\CCCCC)CCC1OC(=O)CN1CCN(C)CC1] , |
| PNI 568 | 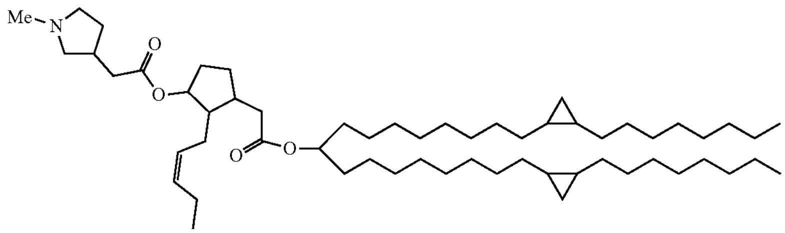 [SMILES: CC/C=C\CC1C(CC(=O)OC(CCCCCCCCC2CC2CCCCCCCC)CCCCCCCCC2CC2CCCCCCCC)CCC1OC(=O)CC1CCN(C)C1] , |
| PNI 569 | 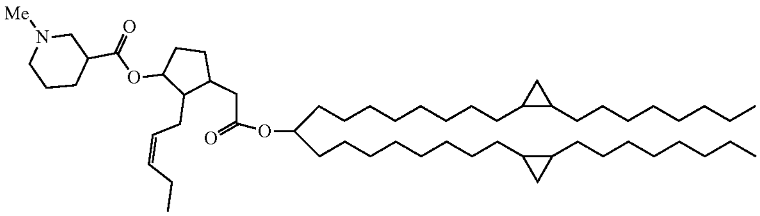 , |
| PNI 570 | 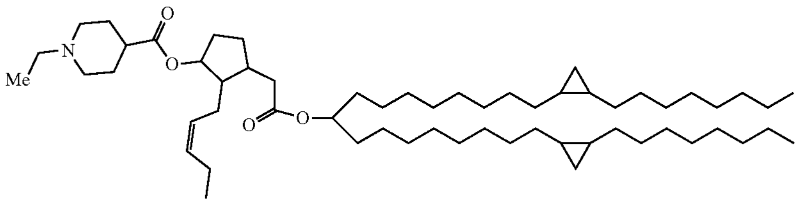 , |

TABLE 1-continued
| Ref. | Structure |
| --- | --- |
| PNI 571 | 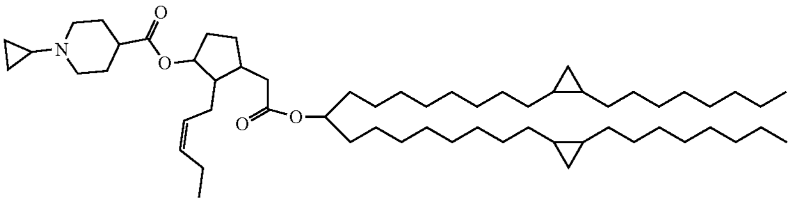 , |
| PNI 572 | 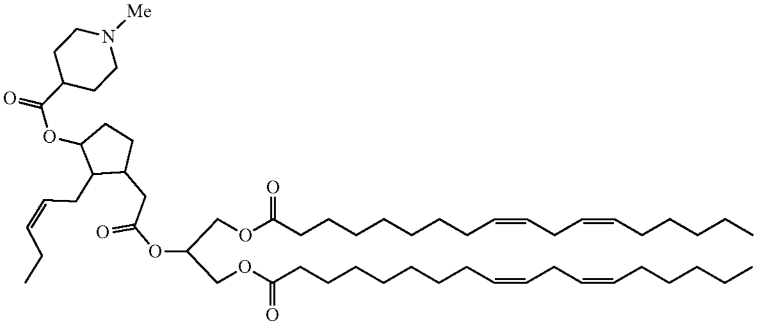 , and |
| PNI 573 | 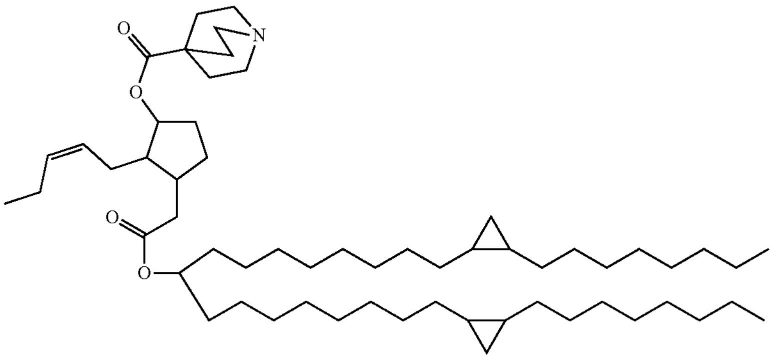 [SMILES: CC/C=C\CC1C(CC(=O)OC(CCCCCCCCC2CC2CCCCCCCC)CCCCCCCCC2CC2CCCCCCCC)CCC1OC(=O)C12CCN(CC1)CC2] , |
or a pharmaceutically acceptable salt thereof.
According to embodiments of the invention, there are also provided the compounds listed in Table 2.
TABLE 2
| ID | Representative Compounds | Theoretical $pKa_1$ |
| --- | --- | --- |
| PNI 587 | 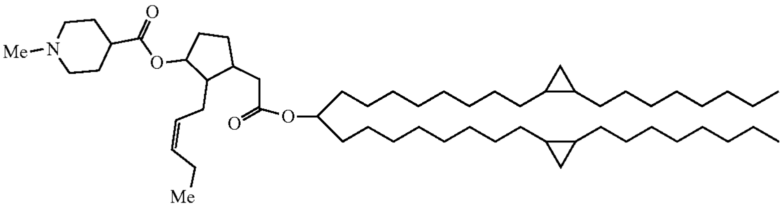 [SMILES: CC/C=C\CC1C(CC(=O)OC(CCCCCCCCC2CC2CCCCCCCC)CCCCCCCCC2CC2CCCCCCCC)CCC1OC(=O)C1CCN(C)CC1] | 9.17 |

TABLE 2-continued
| ID | Representative Compounds | Theoretical $pKa_1$ |
|---|---|---|
| PNI 588 | 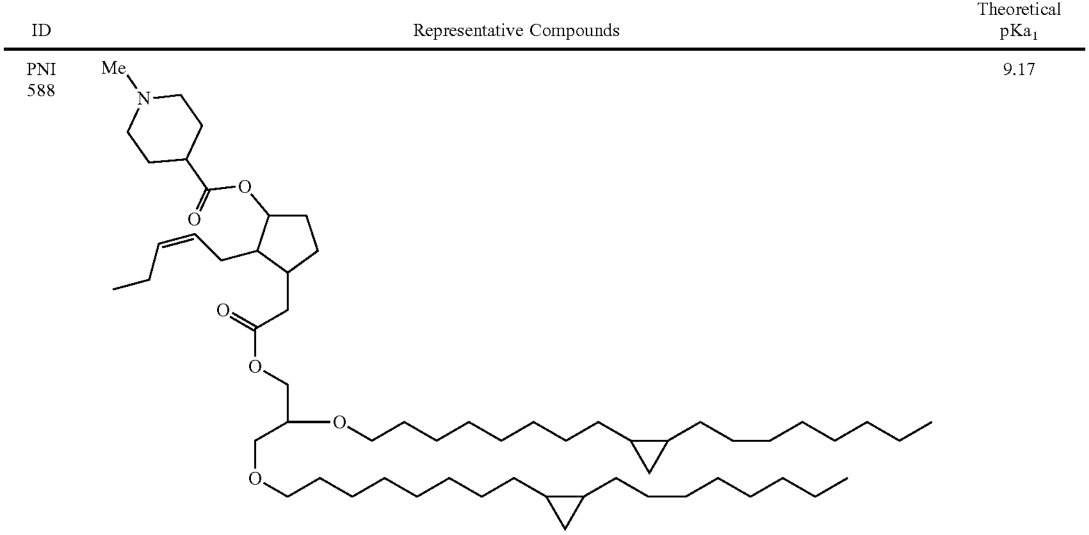 | 9.17 |
| PNI 589 | 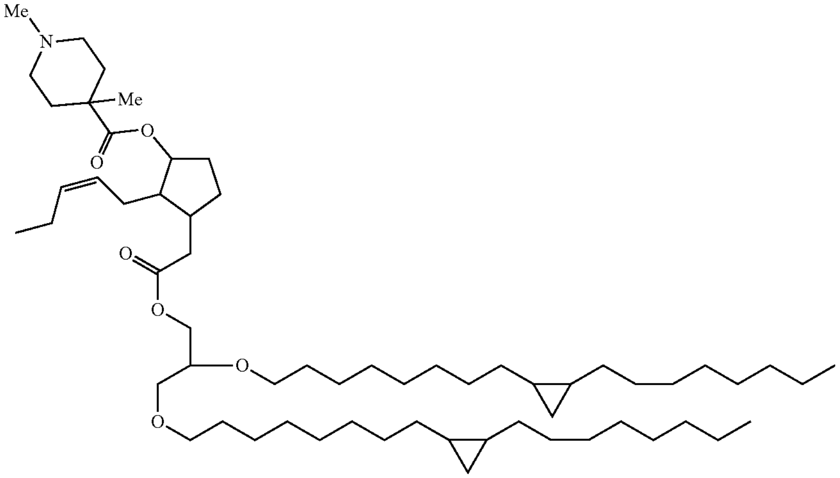 [SMILES: CC/C=C\CC1C(CC(=O)OCC(COCCCCCCCCC2CC2CCCCCCCC)OCCCCCCCCC2CC2CCCCCCCC)CCC1OC(=O)C1(C)CCN(C)CC1] | 9.14 |
| PNI 590 | 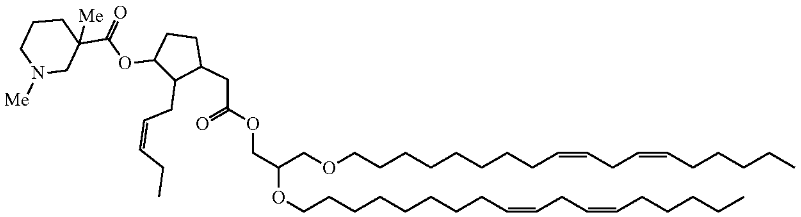 [SMILES: CC/C=C\CC1C(CC(=O)OCC(COCCCCCCCC/C=C\C/C=C\CCCCC)OCCCCCCCC/C=C\C/C=C\CCCCC)CCC1OC(=O)C1(C)CCCN(C)C1] | 8.45 |
| PNI 591 | 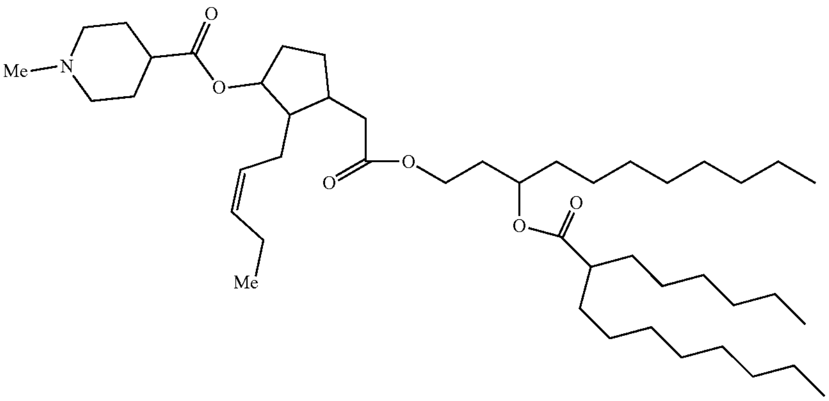 [SMILES: CC/C=C\CC1C(CC(=O)OCCC(CCCCCCCC)OC(=O)C(CCCCCC)CCCCCCCC)CCC1OC(=O)C1CCN(C)CC1] | 9.17 |

TABLE 2-continued
| ID | Representative Compounds | Theoretical $pKa_1$ |
|---|---|---|
| PNI 592 | 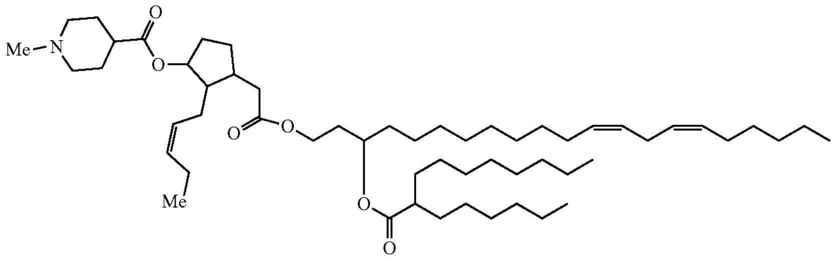 [SMILES: CC/C=C\CC1C(CC(=O)OCCC(CCCCCCCC/C=C\C/C=C\CCCCC)OC(=O)C(CCCCCC)CCCCCCCC)CCC1OC(=O)C1CCN(C)CC1] | 9.17 |
| PNI 271 | 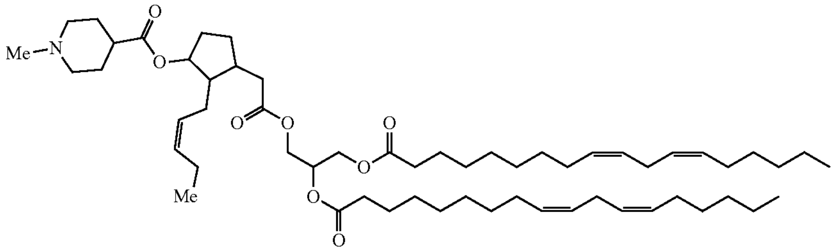 [SMILES: CC/C=C\CC1C(CC(=O)OCC(COC(=O)CCCCCCC/C=C\C/C=C\CCCCC)OC(=O)CCCCCCC/C=C\C/C=C\CCCCC)CCC1OC(=O)C1CCN(C)CC1] | 9.17 |
| PNI 272 | 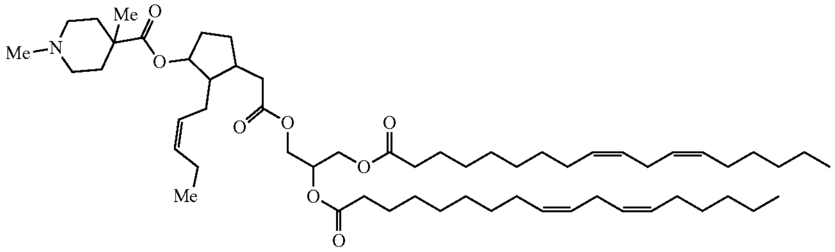 [SMILES: CC/C=C\CC1C(CC(=O)OCC(COC(=O)CCCCCCC/C=C\C/C=C\CCCCC)OC(=O)CCCCCCC/C=C\C/C=C\CCCCC)CCC1OC(=O)C1(C)CCN(C)CC1] | 9.14 |
| PNI 593 | 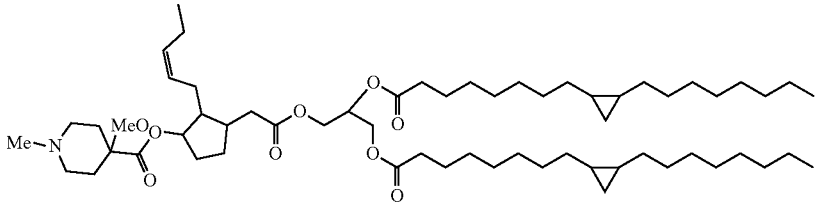 [SMILES: CC/C=C\CC1C(CC(=O)OCC(COC(=O)CCCCCCCC2CC2CCCCCCCC)OC(=O)CCCCCCCC2CC2CCCCCCCC)CCC1OC(=O)C1(OC)CCN(C)CC1] | 9.14 |
| PNI 594 | 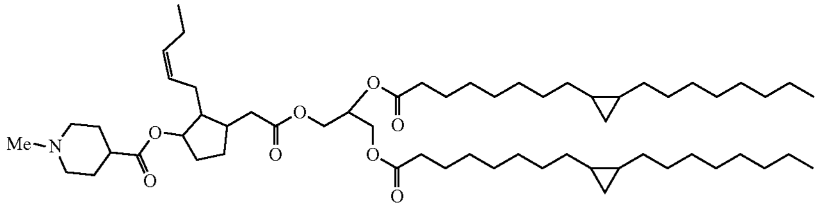 [SMILES: CC/C=C\CC1C(CC(=O)OCC(COC(=O)CCCCCCCC2CC2CCCCCCCC)OC(=O)CCCCCCCC2CC2CCCCCCCC)CCC1OC(=O)C1CCN(C)CC1] | 9.17 |
| PNI 595 | 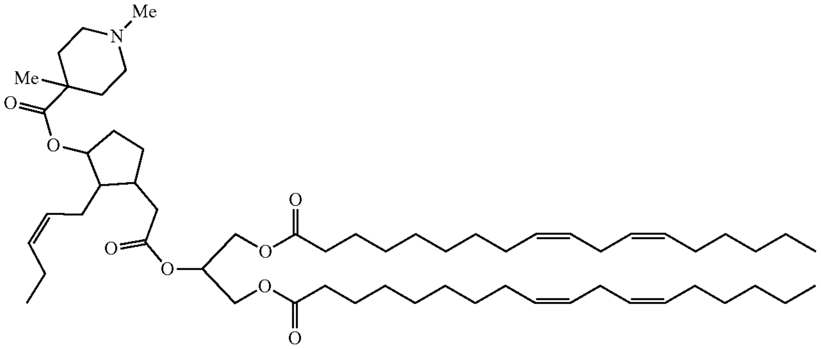 [SMILES: CC/C=C\CC1C(CC(=O)OC(COC(=O)CCCCCCC/C=C\C/C=C\CCCCC)COC(=O)CCCCCCC/C=C\C/C=C\CCCCC)CCC1OC(=O)C1(C)CCN(C)CC1] | 9.14 |

TABLE 2-continued
| ID | Representative Compounds | Theoretical pKa$_1$ |
|---|---|---|
| PNI 596 | 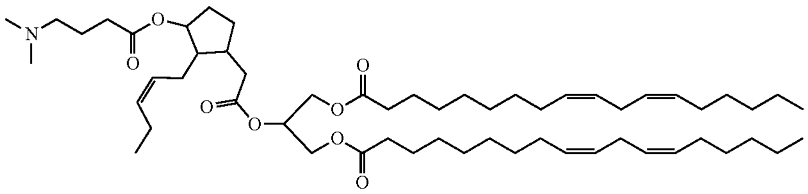 [SMILES: CC/C=C\CC1C(CC(=O)OC(COC(=O)CCCCCCC/C=C\C/C=C\CCCCC)COC(=O)CCCCCCC/C=C\C/C=C\CCCCC)CCC1OC(=O)CCCN(C)C] | 9.43 |
| PNI 597 | 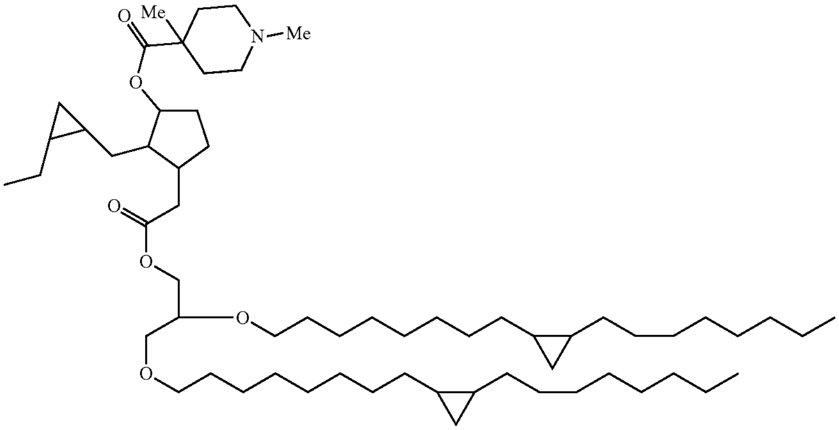 [SMILES: CCCCCCCCC1CC1CCCCCCCCOCC(COC(=O)CC1CCC(OC(=O)C2(C)CCN(C)CC2)C1CC1CC1CC)OCCCCCCCCC1CC1CCCCCCCC] | 9.14 |
| PNI 598 | 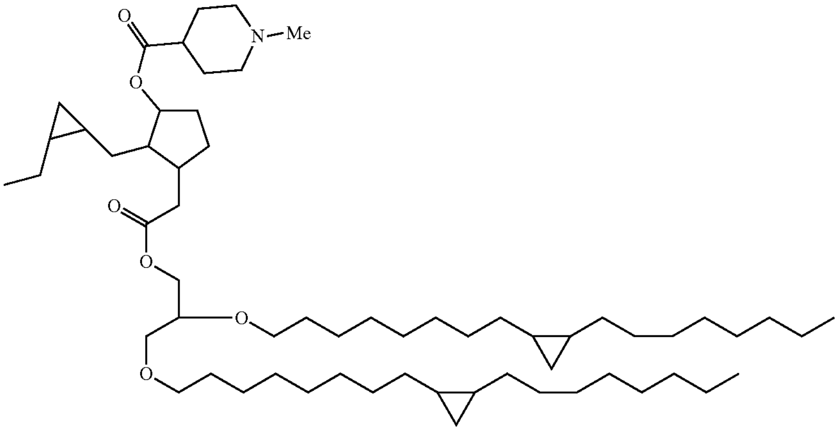 [SMILES: CCCCCCCCC1CC1CCCCCCCCOCC(COC(=O)CC1CCC(OC(=O)C2CCN(C)CC2)C1CC1CC1CC)OCCCCCCCCC1CC1CCCCCCCC] | 9.17 |
| PNI 566 | 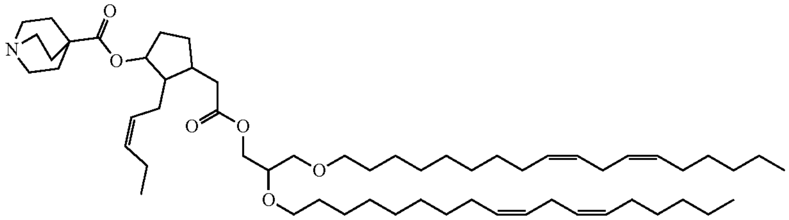 [SMILES: CC/C=C\CC1C(CC(=O)OCC(COCCCCCCCC/C=C\C/C=C\CCCCC)OCCCCCCCC/C=C\C/C=C\CCCCC)CCC1OC(=O)C12CCN(CC1)CC2] | 8.85 |
| PNI 599 | 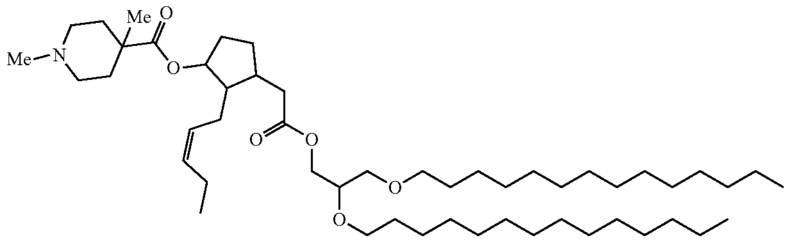 [SMILES: CC/C=C\CC1C(CC(=O)OCC(COCCCCCCCCCCCCCC)OCCCCCCCCCCCCCC)CCC1OC(=O)C1(C)CCN(C)CC1] | 9.14 |

TABLE 2-continued
| ID | Representative Compounds | Theoretical pKa$_1$ |
|---|---|---|
| PNI 600 | 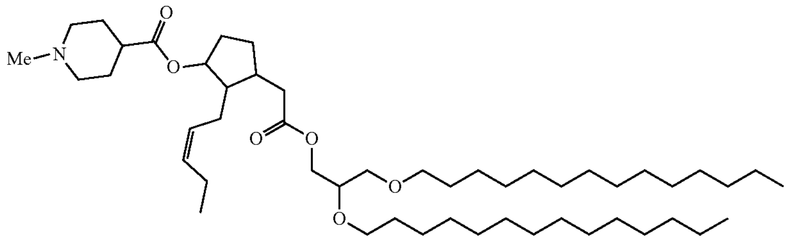 [SMILES: CC/C=C\CC1C(CC(=O)OCC(COCCCCCCCCCCCCCC)OCCCCCCCCCCCCCC)CCC1OC(=O)C1CCN(C)CC1] | 9.17 |
| PNI 150 | 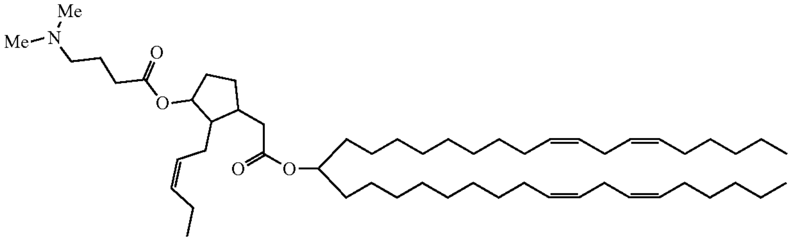 [SMILES: CC/C=C\CC1C(CC(=O)OC(CCCCCCCC/C=C\C/C=C\CCCCC)CCCCCCCC/C=C\C/C=C\CCCCC)CCC1OC(=O)CCCN(C)C] | 9.44 |
| PNI 154 | 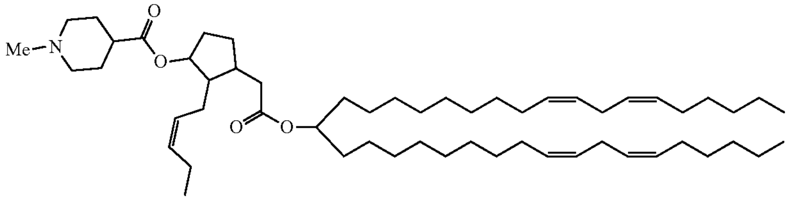 [SMILES: CC/C=C\CC1C(CC(=O)OC(CCCCCCCC/C=C\C/C=C\CCCCC)CCCCCCCC/C=C\C/C=C\CCCCC)CCC1OC(=O)C1CCN(C)CC1] | 9.17 |
| PNI 155 | 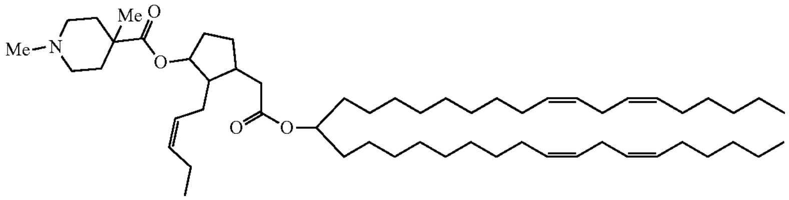 [SMILES: CC/C=C\CC1C(CC(=O)OC(CCCCCCCC/C=C\C/C=C\CCCCC)CCCCCCCC/C=C\C/C=C\CCCCC)CCC1OC(=O)C1(C)CCN(C)CC1] | 9.14 |
| PNI 308 | 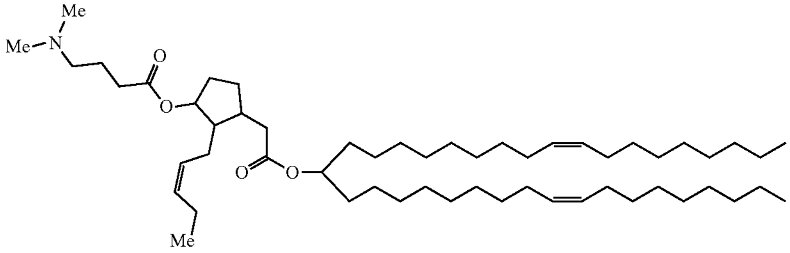 [SMILES: CC/C=C\CC1C(CC(=O)OC(CCCCCCCC/C=C\CCCCCCCC)CCCCCCCC/C=C\CCCCCCCC)CCC1OC(=O)CCCN(C)C] | 9.44 |
| PNI 309 | 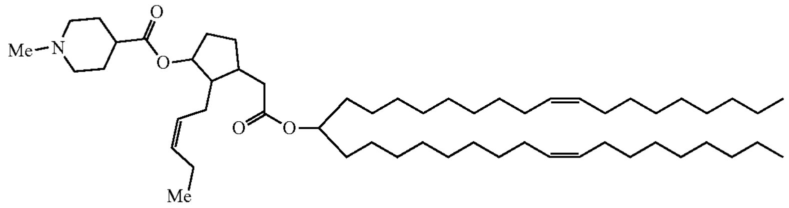 [SMILES: CC/C=C\CC1C(CC(=O)OC(CCCCCCCC/C=C\CCCCCCCC)CCCCCCCC/C=C\CCCCCCCC)CCC1OC(=O)C1CCN(C)CC1] | 9.17 |

TABLE 2-continued
| ID | Representative Compounds | Theoretical pKa$_1$ |
|---|---|---|
| PNI 310 | 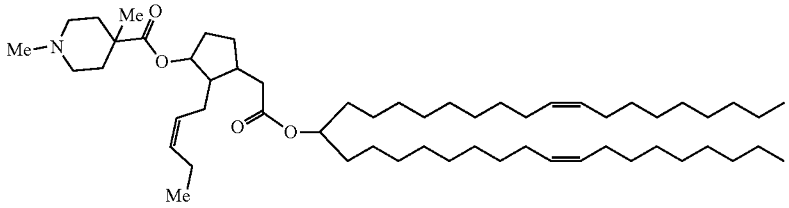 [SMILES: CC/C=C\CC1C(CC(=O)OC(CCCCCCCC/C=C\CCCCCCCC)CCCCCCCC/C=C\CCCCCCCC)CCC1OC(=O)C1(C)CCN(C)CC1] | 9.14 |
| PNI 173 | 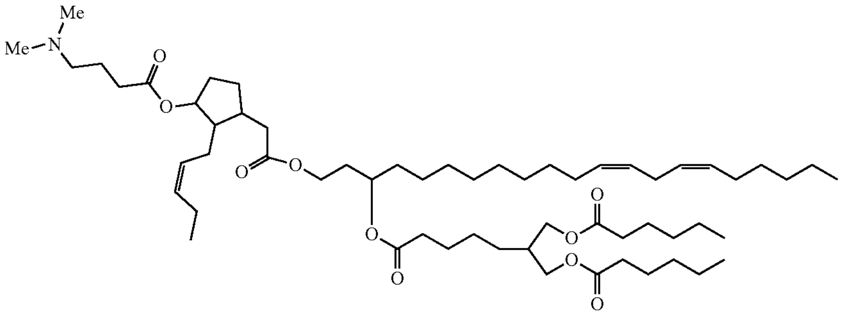 [SMILES: CC/C=C\CC1C(CC(=O)OCCC(CCCCCCCC/C=C\C/C=C\CCCCC)OC(=O)CCCCC(COC(=O)CCCCC)COC(=O)CCCCC)CCC1OC(=O)CCCN(C)C] | 9.44 |
| PNI 176 | 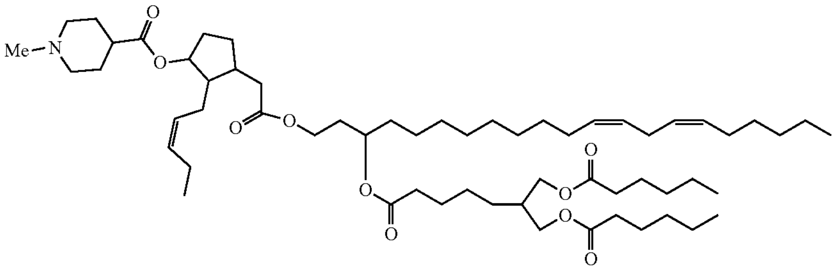 [SMILES: CC/C=C\CC1C(CC(=O)OCCC(CCCCCCCC/C=C\C/C=C\CCCCC)OC(=O)CCCCC(COC(=O)CCCCC)COC(=O)CCCCC)CCC1OC(=O)C1CCN(C)CC1] | 9.17 |
| PNI 177 | 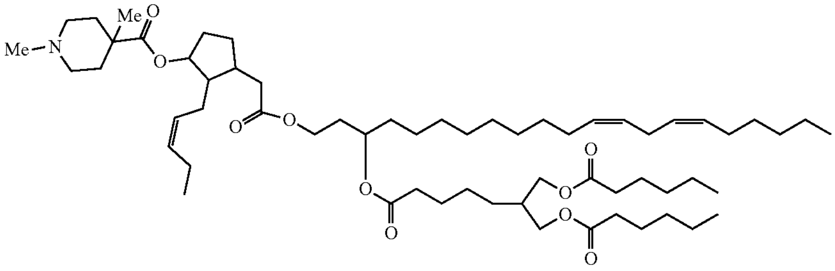 [SMILES: CC/C=C\CC1C(CC(=O)OCCC(CCCCCCCC/C=C\C/C=C\CCCCC)OC(=O)CCCCC(COC(=O)CCCCC)COC(=O)CCCCC)CCC1OC(=O)C1(C)CCN(C)CC1] | 9.14 |
| PNI 189 | 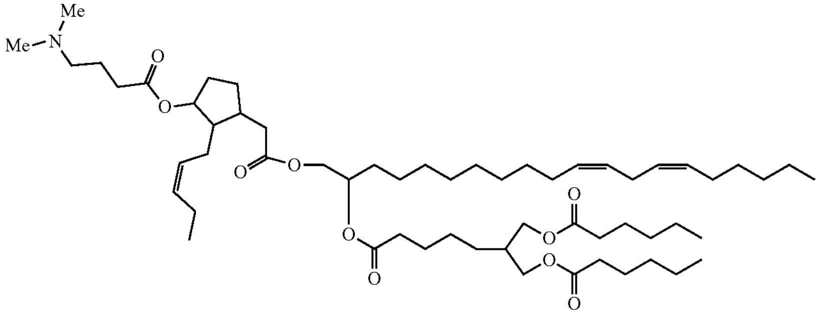 [SMILES: CC/C=C\CC1C(CC(=O)OCC(CCCCCCCC/C=C\C/C=C\CCCCC)OC(=O)CCCCC(COC(=O)CCCCC)COC(=O)CCCCC)CCC1OC(=O)CCCN(C)C] | 9.44 |

TABLE 2-continued
| ID | Representative Compounds | Theoretical $pKa_1$ |
|---|---|---|
| PNI 190 | 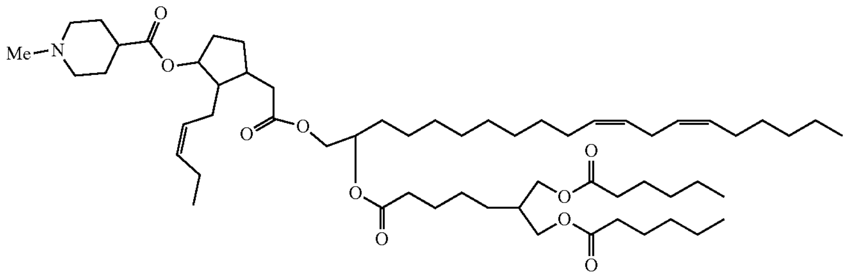 [SMILES: CC/C=C\CC1C(CC(=O)OCC(CCCCCCCC/C=C\C/C=C\CCCCC)OC(=O)CCCCC(COC(=O)CCCCC)COC(=O)CCCCC)CCC1OC(=O)C1CCN(C)CC1] | 9.17 |
| PNI 191 | 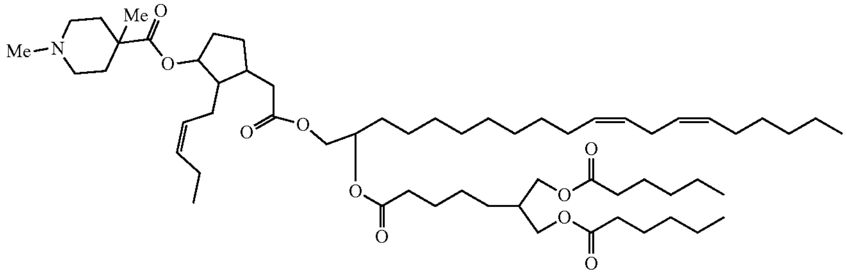 [SMILES: CC/C=C\CC1C(CC(=O)OCC(CCCCCCCC/C=C\C/C=C\CCCCC)OC(=O)CCCCC(COC(=O)CCCCC)COC(=O)CCCCC)CCC1OC(=O)C1(C)CCN(C)CC1] | 9.14 |
| PNI 199 | 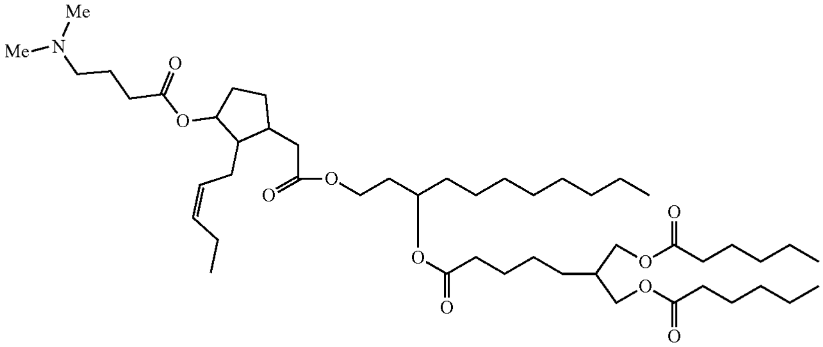 [SMILES: CC/C=C\CC1C(CC(=O)OCCC(CCCCCCCC)OC(=O)CCCCC(COC(=O)CCCCC)COC(=O)CCCCC)CCC1OC(=O)CCCN(C)C] | 9.44 |
| PNI 201 | 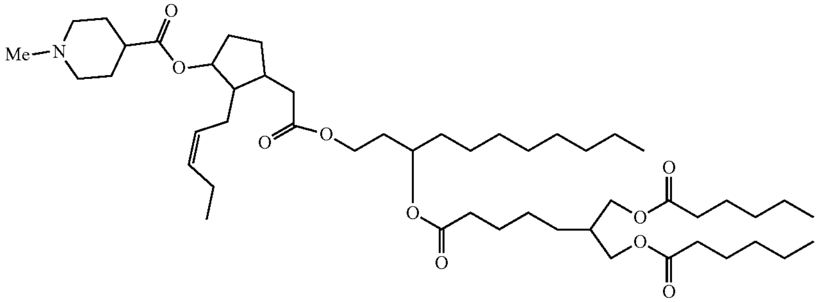 [SMILES: CC/C=C\CC1C(CC(=O)OCCC(CCCCCCCC)OC(=O)CCCCC(COC(=O)CCCCC)COC(=O)CCCCC)CCC1OC(=O)C1CCN(C)CC1] | 9.17 |
| PNI 202 | 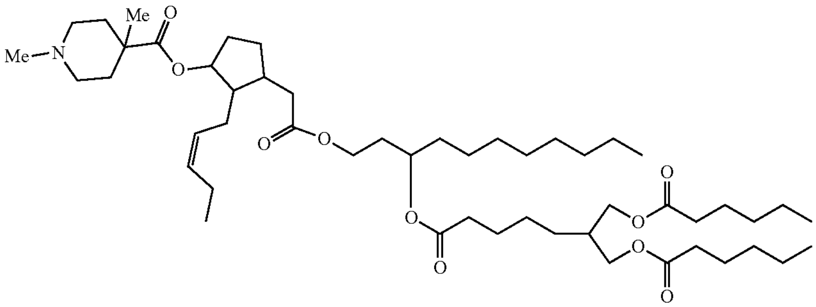 [SMILES: CC/C=C\CC1C(CC(=O)OCCC(CCCCCCCC)OC(=O)CCCCC(COC(=O)CCCCC)COC(=O)CCCCC)CCC1OC(=O)C1(C)CCN(C)CC1] | 9.14 |

TABLE 2-continued
| ID | Representative Compounds | Theoretical $pKa_1$ |
|---|---|---|
| PNI 213 | 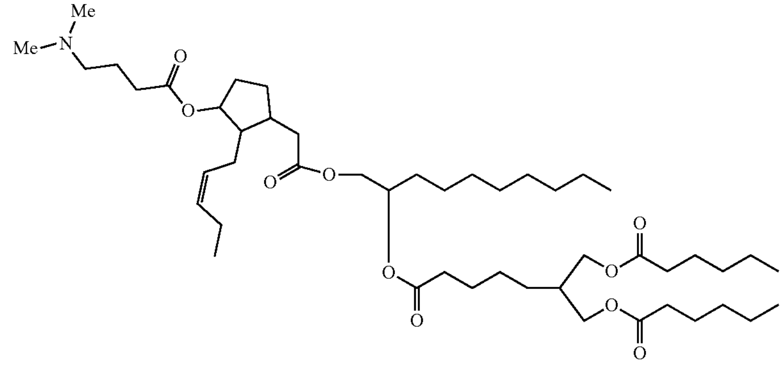 [SMILES: CC/C=C\CC1C(CC(=O)OCC(CCCCCCCC)OC(=O)CCCCC(COC(=O)CCCCC)COC(=O)CCCCC)CCC1OC(=O)CCCN(C)C] | 9.44 |
| PNI 214 | 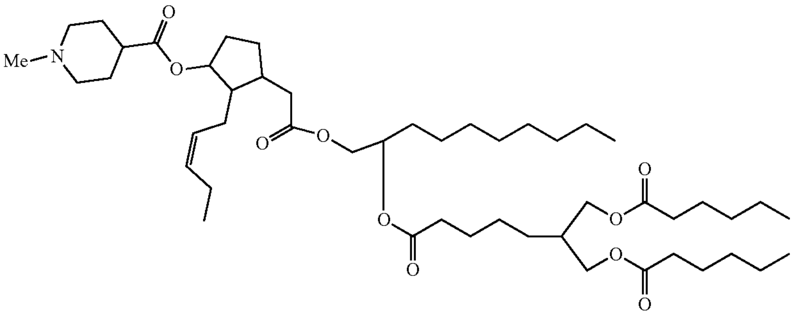 [SMILES: CC/C=C\CC1C(CC(=O)OCC(CCCCCCCC)OC(=O)CCCCC(COC(=O)CCCCC)COC(=O)CCCCC)CCC1OC(=O)C1CCN(C)CC1] | 9.17 |
| PNI 215 | 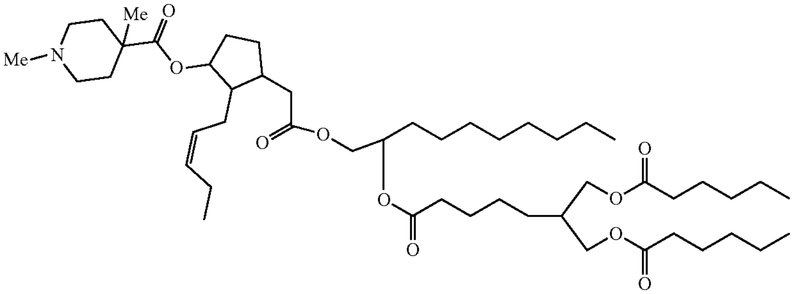 [SMILES: CC/C=C\CC1C(CC(=O)OCC(CCCCCCCC)OC(=O)CCCCC(COC(=O)CCCCC)COC(=O)CCCCC)CCC1OC(=O)C1(C)CCN(C)CC1] | 9.14 |
| PNI 223 | 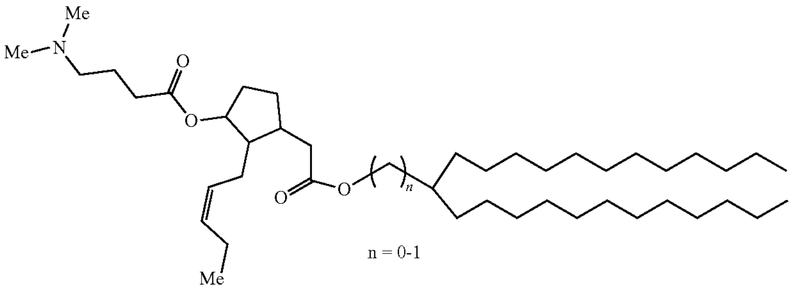 n = 0-1 | 9.44 |
| PNI 225 | 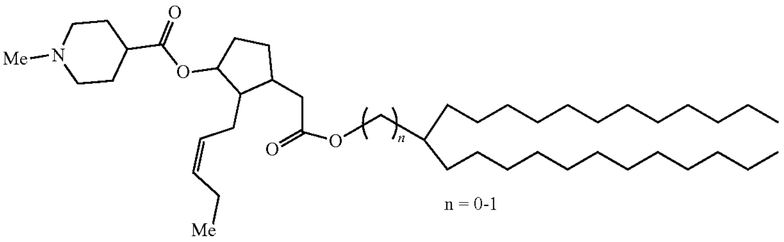 n = 0-1 | 9.17 |

TABLE 2-continued
| ID | Representative Compounds | Theoretical $pKa_1$ |
|---|---|---|
| PNI 226 | 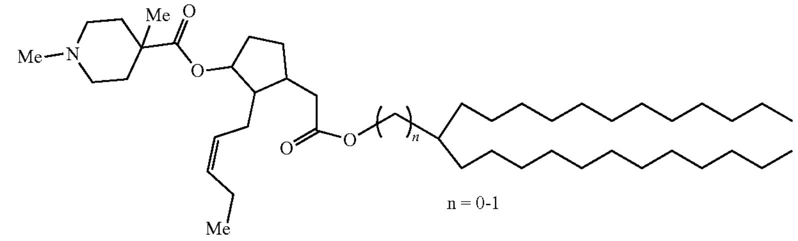 n = 0-1 | 9.14 |
| PNI 238 | 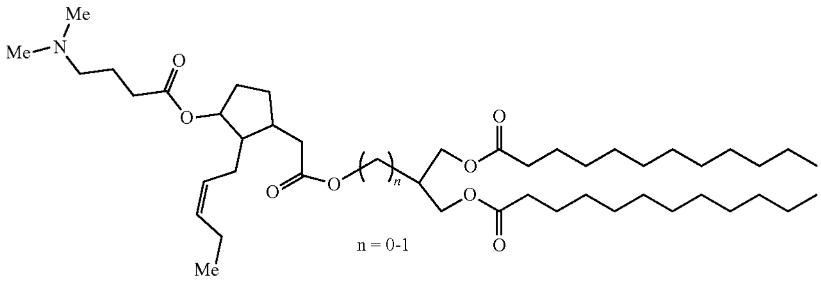 n = 0-1 | 9.44 |
| PNI 241 | 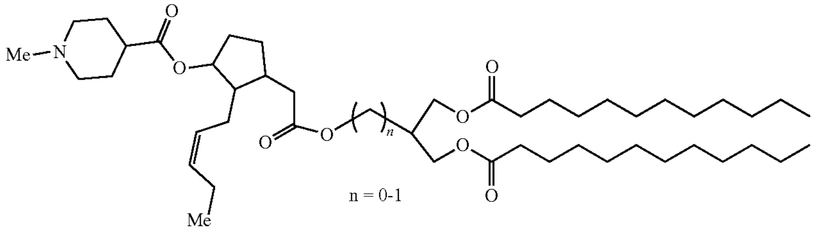 n = 0-1 | 9.17 |
| PNI 242 | 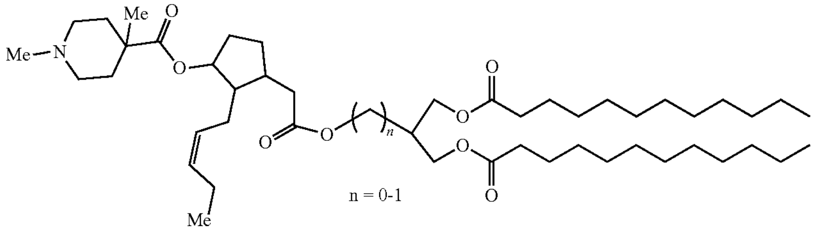 n = 0-1 | 9.14 |
| PNI 254 | 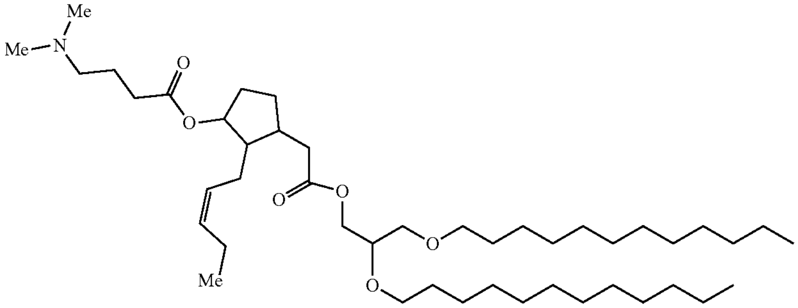 [SMILES: CC/C=C\CC1C(CC(=O)OCC(COCCCCCCCCCCCC)OCCCCCCCCCCCC)CCC1OC(=O)CCCN(C)C] | 9.44 |

TABLE 2-continued
| ID | Representative Compounds | Theoretical $pKa_1$ |
|---|---|---|
| PNI 256 | 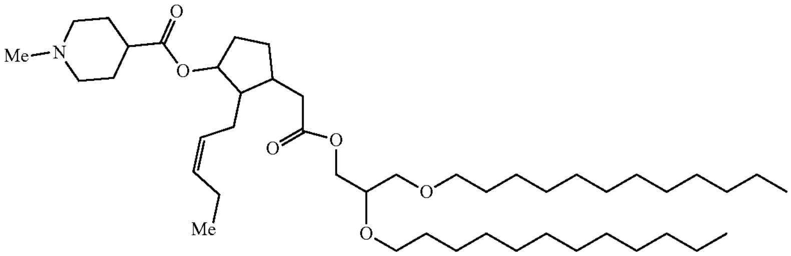 [SMILES: CC/C=C\CC1C(CC(=O)OCC(COCCCCCCCCCCCC)OCCCCCCCCCCCC)CCC1OC(=O)C1CCN(C)CC1] | 9.17 |
| PNI 257 | 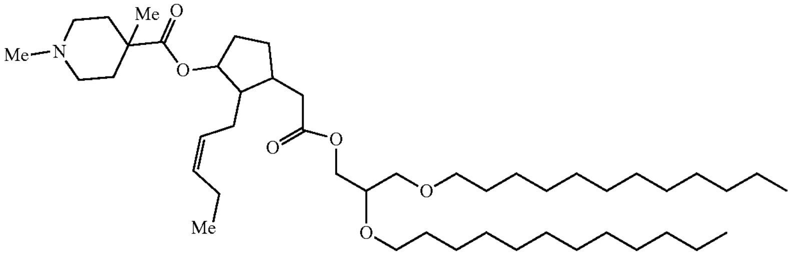 [SMILES: CC/C=C\CC1C(CC(=O)OCC(COCCCCCCCCCCCC)OCCCCCCCCCCCC)CCC1OC(=O)C1(C)CCN(C)CC1] | 9.14 |
| PNI 283 | 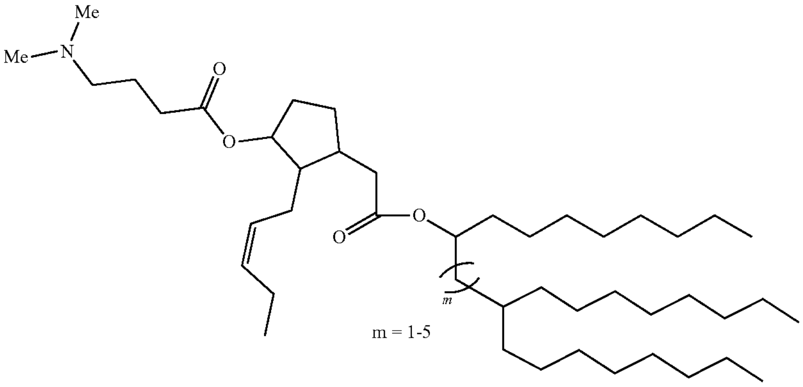 m = 1-5 | 9.44 |
| PNI 285 | 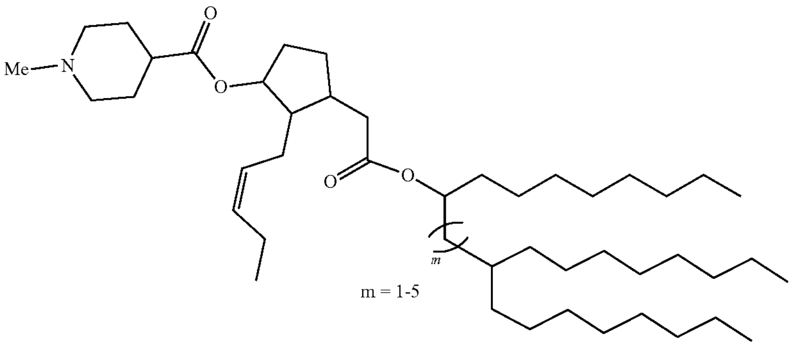 m = 1-5 | 9.17 |

TABLE 2-continued
| ID | Representative Compounds | Theoretical pKa$_1$ |
|---|---|---|
| PNI 286 | 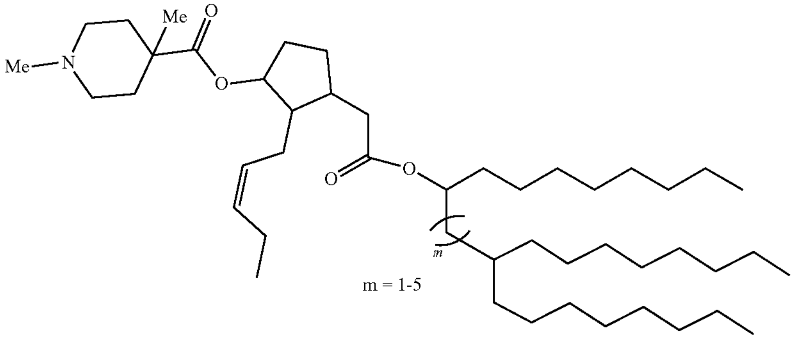 m = 1-5 | 9.14 |
| PNI 297 | 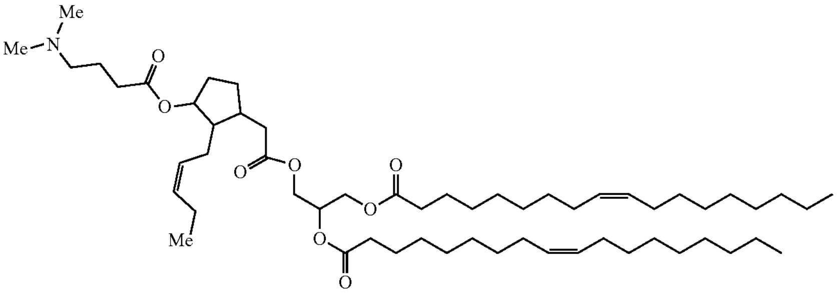 [SMILES: CC/C=C\CC1C(CC(=O)OCC(COC(=O)CCCCCCC/C=C\CCCCCCCC)OC(=O)CCCCCCC/C=C\CCCCCCCC)CCC1OC(=O)CCCN(C)C] | 9.44 |
| PNI 299 | 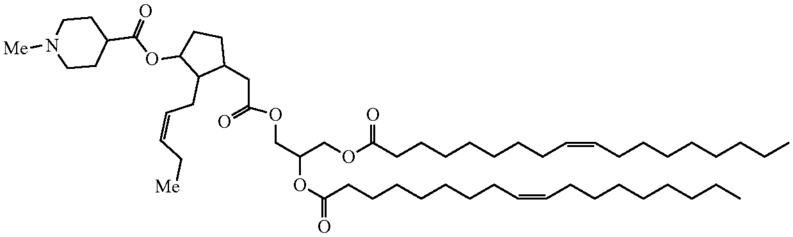 [SMILES: CC/C=C\CC1C(CC(=O)OCC(COC(=O)CCCCCCC/C=C\CCCCCCCC)OC(=O)CCCCCCC/C=C\CCCCCCCC)CCC1OC(=O)C1CCN(C)CC1] | 9.17 |
| PNI 300 | 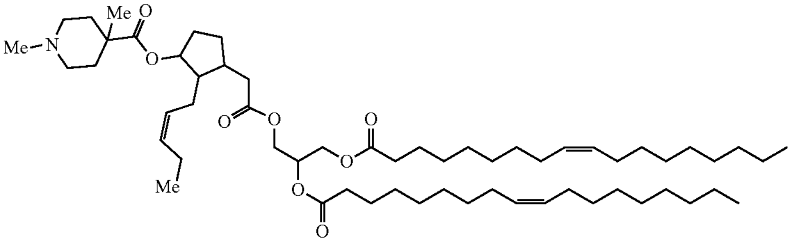 [SMILES: CC/C=C\CC1C(CC(=O)OCC(COC(=O)CCCCCCC/C=C\CCCCCCCC)OC(=O)CCCCCCC/C=C\CCCCCCCC)CCC1OC(=O)C1(C)CCN(C)CC1] | 9.14 |
| PNI 512 | 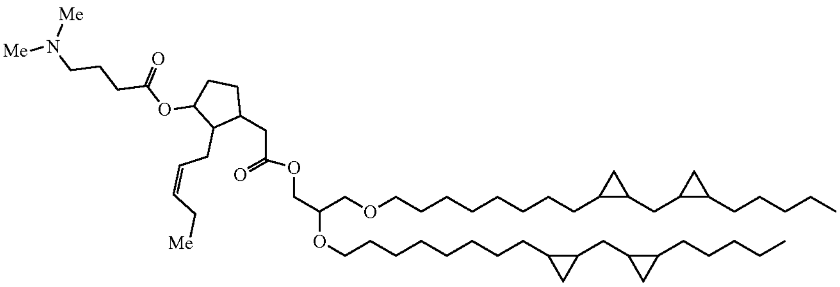 [SMILES: CC/C=C\CC1C(CC(=O)OCC(COCCCCCCCCC2CC2CC2CC2CCCCC)OCCCCCCCCC2CC2CC2CC2CCCCC)CCC1OC(=O)CCCN(C)C] | 9.44 |

TABLE 2-continued
| ID | Representative Compounds | Theoretical pKa1 |
|---|---|---|
| PNI 601 | 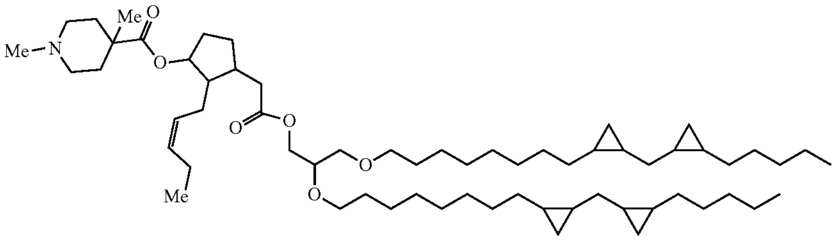 [SMILES: CC/C=C\CC1C(CC(=O)OCC(COCCCCCCCCC2CC2CC2CC2CCCCC)OCCCCCCCCC2CC2CC2CC2CCCCC)CCC1OC(=O)C1(C)CCN(C)CC1] | 9.14 |
| PNI 602 | 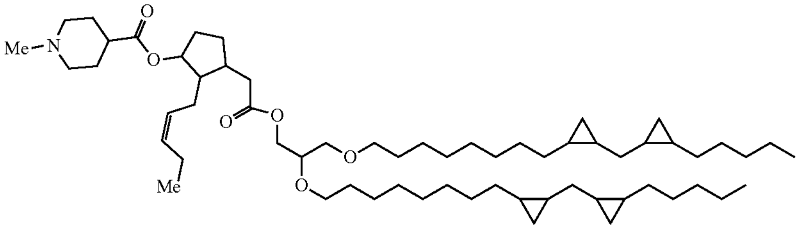 [SMILES: CC/C=C\CC1C(CC(=O)OCC(COCCCCCCCCC2CC2CC2CC2CCCCC)OCCCCCCCCC2CC2CC2CC2CCCCC)CCC1OC(=O)C1CCN(C)CC1] | 9.17 |
| PNI 513 | 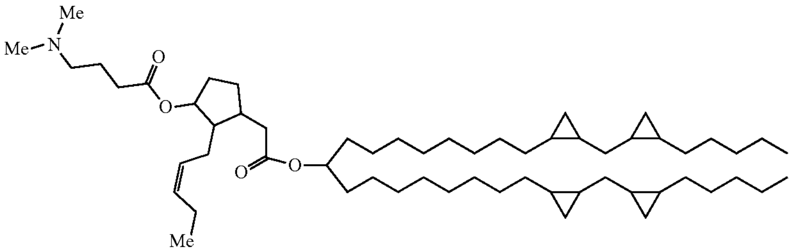 [SMILES: CC/C=C\CC1C(CC(=O)OC(CCCCCCCCC2CC2CC2CC2CCCCC)CCCCCCCCC2CC2CC2CC2CCCCC)CCC1OC(=O)CCCN(C)C] | 9.44 |
| PNI 603 | 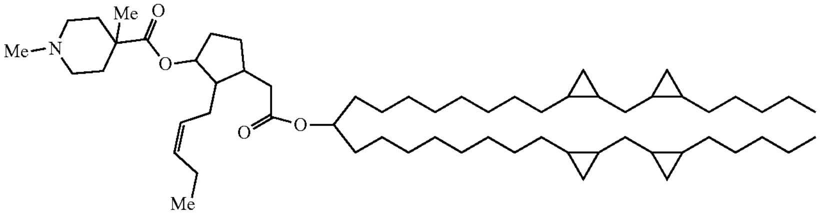 [SMILES: CC/C=C\CC1C(CC(=O)OC(CCCCCCCCC2CC2CC2CC2CCCCC)CCCCCCCCC2CC2CC2CC2CCCCC)CCC1OC(=O)C1(C)CCN(C)CC1] | 9.14 |
| PNI 604 | 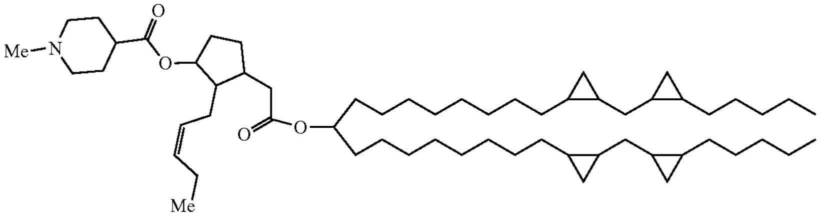 [SMILES: CC/C=C\CC1C(CC(=O)OC(CCCCCCCCC2CC2CC2CC2CCCCC)CCCCCCCCC2CC2CC2CC2CCCCC)CCC1OC(=O)C1CCN(C)CC1] | 9.17 |
| PNI 605 | 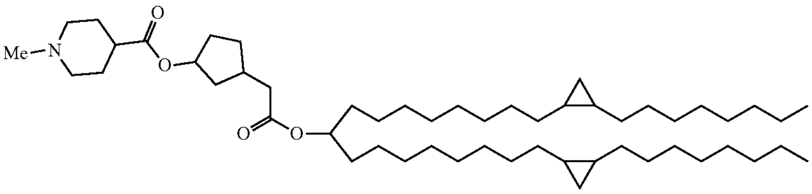 [SMILES: CCCCCCCCC1CC1CCCCCCCCC(CCCCCCCCC1CC1CCCCCCCC)OC(=O)CC1CCC(OC(=O)C2CCN(C)CC2)C1] | 9.18 |

TABLE 2-continued
| ID | Representative Compounds | Theoretical $pKa_1$ |
| --- | --- | --- |
| PNI 606 | 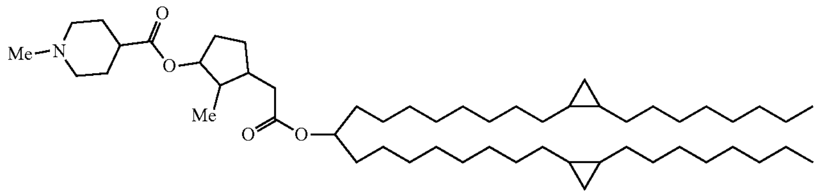 [SMILES: CCCCCCCCC1CC1CCCCCCCCC(CCCCCCCCC1CC1CCCCCCCC)OC(=O)CC1CCC(OC(=O)C2CCN(C)CC2)C1C] | 9.17 |
| PNI 607 | 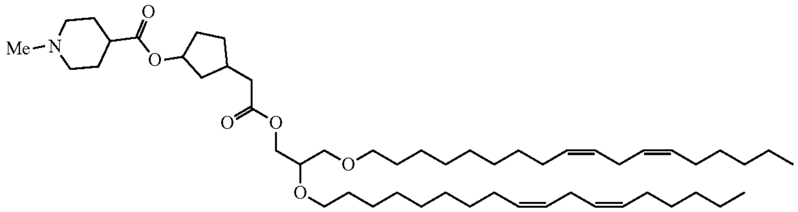 [SMILES: CCCCC/C=C\C/C=C\CCCCCCCCOCC(COC(=O)CC1CCC(OC(=O)C2CCN(C)CC2)C1)OCCCCCCCC/C=C\C/C=C\CCCCC] | 9.18 |
| PNI 608 | 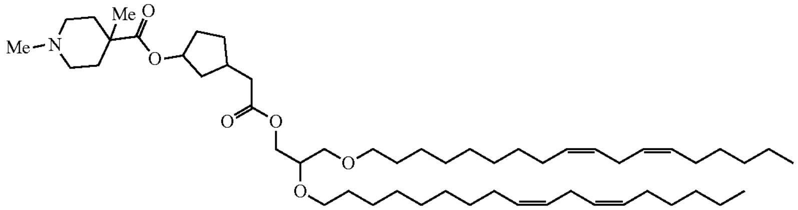 [SMILES: CCCCC/C=C\C/C=C\CCCCCCCCOCC(COC(=O)CC1CCC(OC(=O)C2(C)CCN(C)CC2)C1)OCCCCCCCC/C=C\C/C=C\CCCCC] | 9.15 |
| PNI 609 | 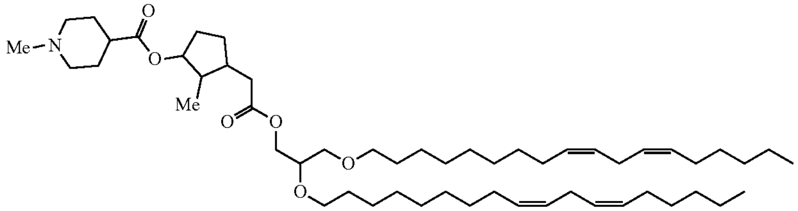 [SMILES: CCCCC/C=C\C/C=C\CCCCCCCCOCC(COC(=O)CC1CCC(OC(=O)C2CCN(C)CC2)C1C)OCCCCCCCC/C=C\C/C=C\CCCCC] | 9.17 |
| PNI 610 | 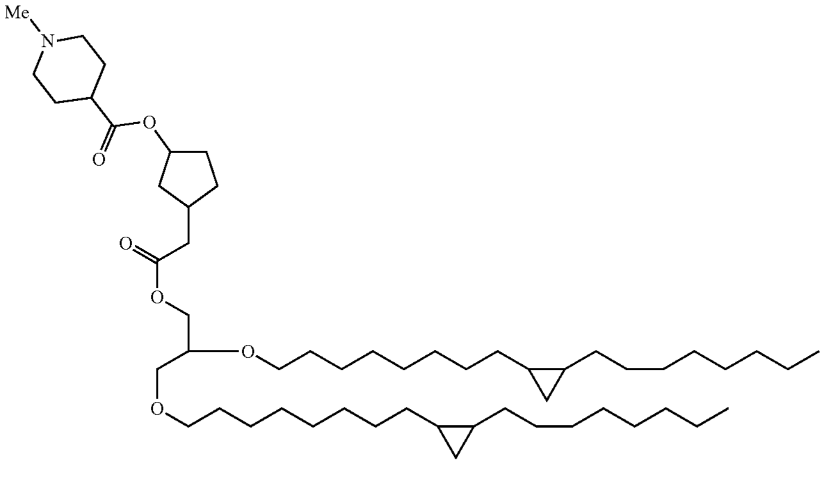 [SMILES: CCCCCCCCC1CC1CCCCCCCCOCC(COC(=O)CC1CCC(OC(=O)C2CCN(C)CC2)C1)OCCCCCCCCC1CC1CCCCCCCC] | 9.18 |

TABLE 2-continued
| ID | Representative Compounds | Theoretical $pKa_1$ |
| --- | --- | --- |
| PNI 611 | 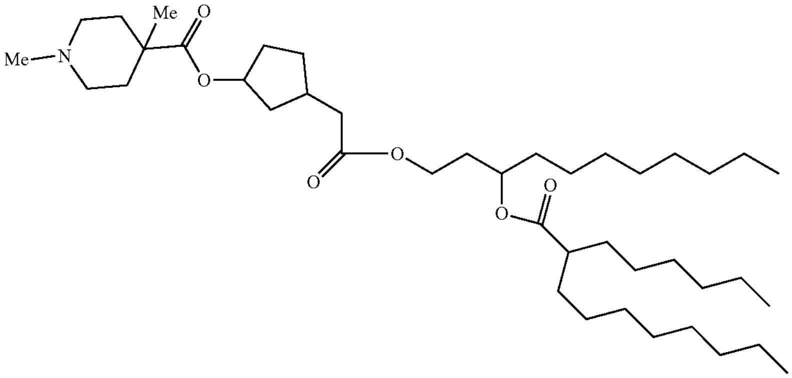 [SMILES: CCCCCCCCC(CCOC(=O)CC1CCC(OC(=O)C2(C)CCN(C)CC2)C1)OC(=O)C(CCCCCC)CCCCCCCC] | 9.15 |
| PNI 612 | 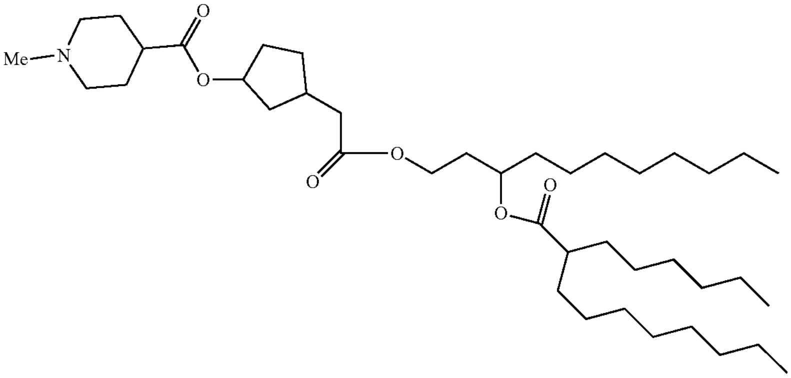 [SMILES: CCCCCCCCC(CCOC(=O)CC1CCC(OC(=O)C2CCN(C)CC2)C1)OC(=O)C(CCCCCC)CCCCCCCC] | 9.18 |
| PNI 613 | 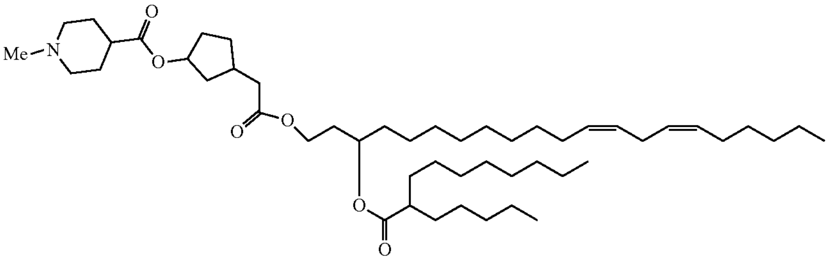 [SMILES: CCCCC/C=C\C/C=C\CCCCCCCCC(CCOC(=O)CC1CCC(OC(=O)C2CCN(C)CC2)C1)OC(=O)C(CCCCC)CCCCCCCC] | 9.18 |
| PNI 614 | 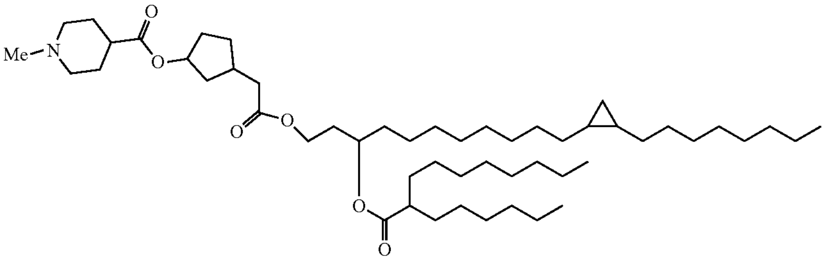 [SMILES: CCCCCCCCC(CCCCCC)C(=O)OC(CCCCCCCCC1CC1CCCCCCCC)CCOC(=O)CC1CCC(OC(=O)C2CCN(C)CC2)C1] | 9.18 |
| PNI 171 | 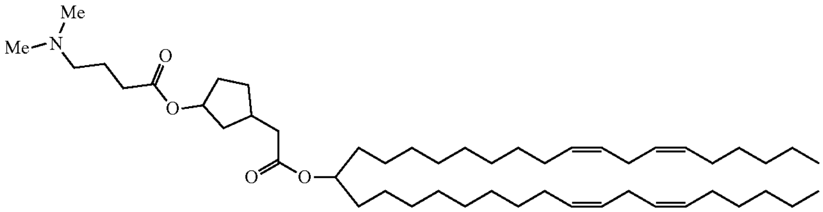 [SMILES: CCCCC/C=C\C/C=C\CCCCCCCCC(CCCCCCCC/C=C\C/C=C\CCCCC)OC(=O)CC1CCC(OC(=O)CCCN(C)C)C1] | 9.45 |

TABLE 2-continued
| ID | Representative Compounds | Theoretical $pKa_1$ |
| --- | --- | --- |
| PNI 615 | 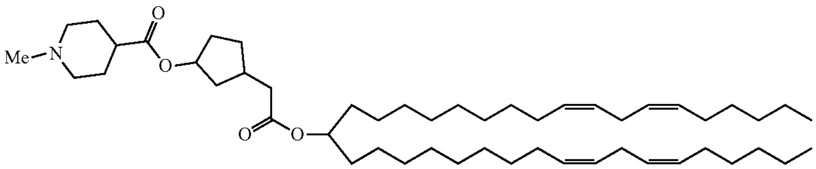 [SMILES: CCCCC/C=C\C/C=C\CCCCCCCCC(CCCCCCCC/C=C\C/C=C\CCCCC)OC(=O)CC1CCC(OC(=O)C2CCN(C)CC2)C1] | 9.18 |
| PNI 616 | 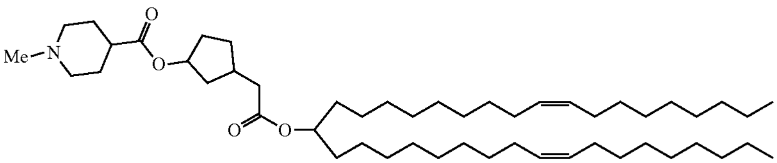 [SMILES: CCCCCCCC/C=C\CCCCCCCCC(CCCCCCCC/C=C\CCCCCCCC)OC(=O)CC1CCC(OC(=O)C2CCN(C)CC2)C1] | 9.18 |
| PNI 617 | 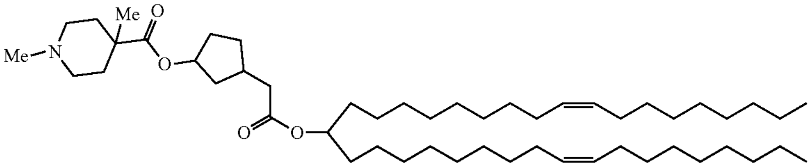 [SMILES: CCCCCCCC/C=C\CCCCCCCCC(CCCCCCCC/C=C\CCCCCCCC)OC(=O)CC1CCC(OC(=O)C2(C)CCN(C)CC2)C1] | 9.15 |
| PNI 187 | 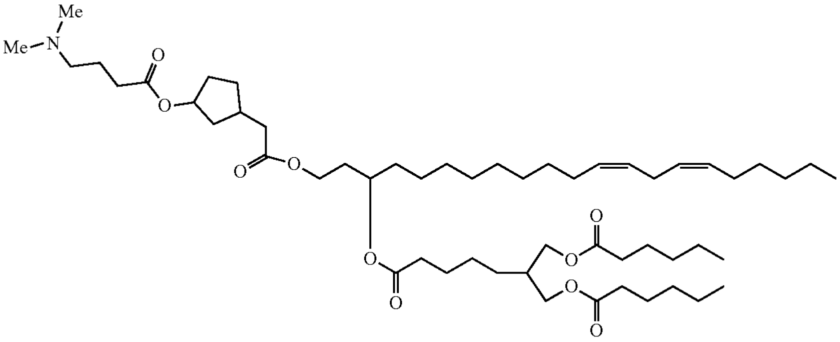 [SMILES: CCCCC/C=C\C/C=C\CCCCCCCCC(CCOC(=O)CC1CCC(OC(=O)CCCN(C)C)C1)OC(=O)CCCCC(COC(=O)CCCCC)COC(=O)CCCCC] | 9.45 |
| PNI 618 | 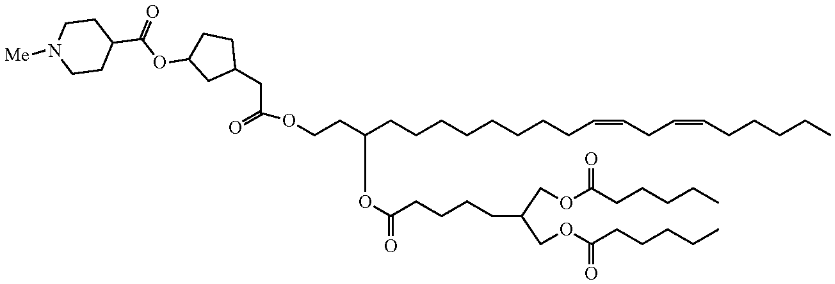 [SMILES: CCCCC/C=C\C/C=C\CCCCCCCCC(CCOC(=O)CC1CCC(OC(=O)C2CCN(C)CC2)C1)OC(=O)CCCCC(COC(=O)CCCCC)COC(=O)CCCCC] | 9.18 |
| PNI 212 | 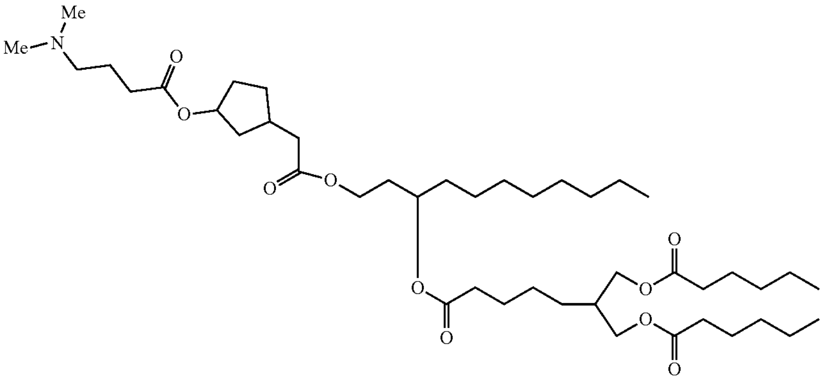 [SMILES: CCCCCCCCC(CCOC(=O)CC1CCC(OC(=O)CCCN(C)C)C1)OC(=O)CCCCC(COC(=O)CCCCC)COC(=O)CCCCC] | 9.45 |

TABLE 2-continued
| ID | Representative Compounds | Theoretical $pKa_1$ |
|---|---|---|
| PNI 619 | 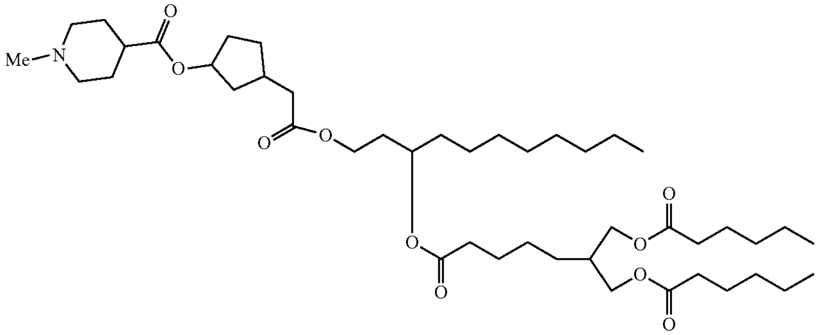 [SMILES: CCCCCCCCC(CCOC(=O)CC1CCC(OC(=O)C2CCN(C)CC2)C1)OC(=O)CCCCC(COC(=O)CCCCC)COC(=O)CCCCC] | 9.18 |
| PNI 620 | 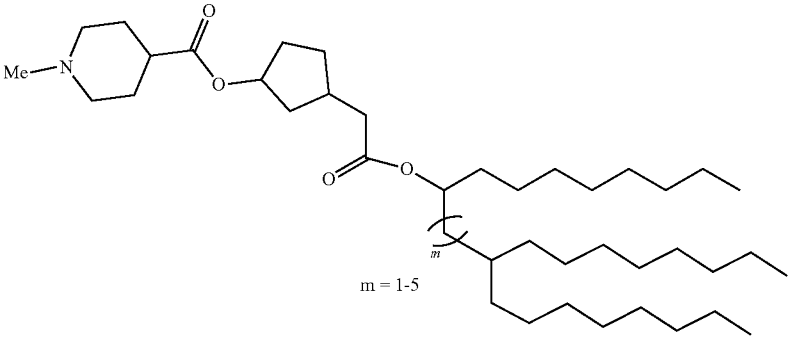 m = 1-5 | 9.18 |
| PNI 621 | 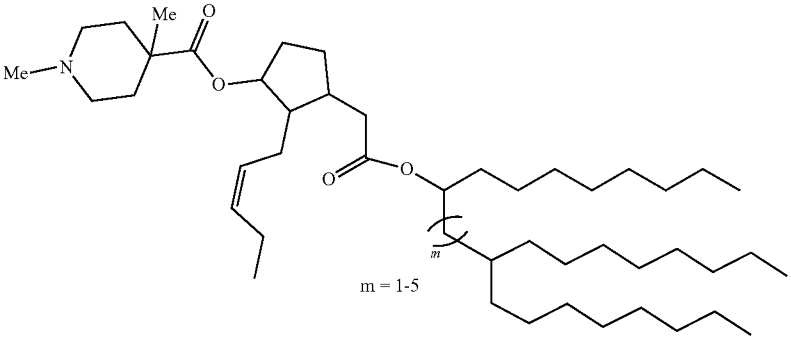 m = 1-5 | 9.14 |
| PNI 622 | 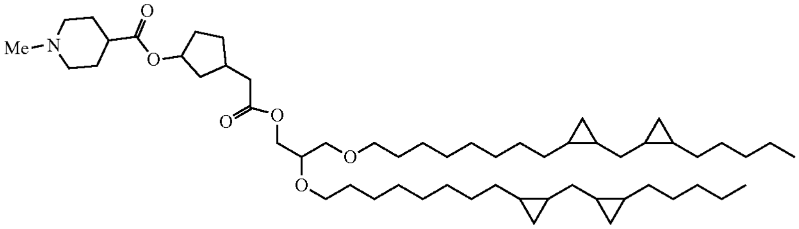 [SMILES: CCCCCC1CC1CC1CC1CCCCCCCCOCC(COC(=O)CC1CCC(OC(=O)C2CCN(C)CC2)C1)OCCCCCCCCC1CC1CC1CC1CCCCC] | 9.18 |
| PNI 623 | 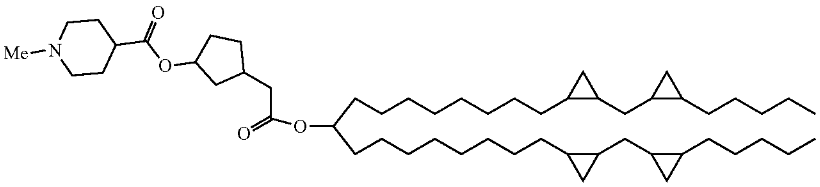 [SMILES: CCCCCC1CC1CC1CC1CCCCCCCCC(CCCCCCCCC1CC1CC1CC1CCCCC)OC(=O)CC1CCC(OC(=O)C2CCN(C)CC2)C1] | 9.18 |

TABLE 2-continued
| ID | Representative Compounds | Theoretical $pKa_1$ |
| --- | --- | --- |
| PNI 146 | 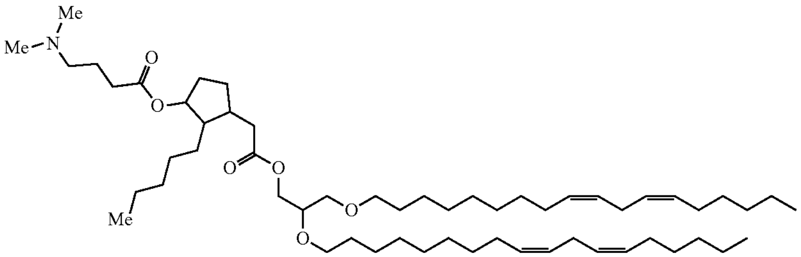 [SMILES: CCCCC/C=C\C/C=C\CCCCCCCCOCC(COC(=O)CC1CCC(OC(=O)CCCN(C)C)C1CCCCC)OCCCCCCCC/C=C\C/C=C\CCCCC] | 9.44 |
| PNI 145 | 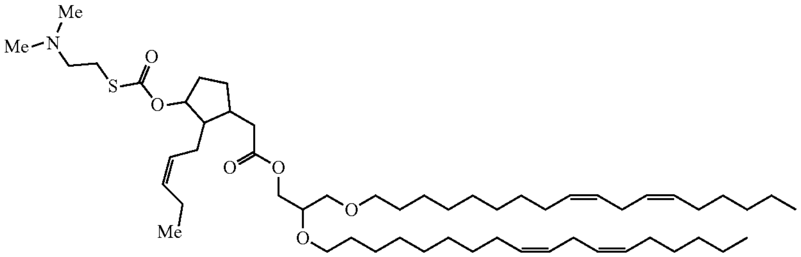 [SMILES: CC/C=C\CC1C(CC(=O)OCC(COCCCCCCCC/C=C\C/C=C\CCCCC)OCCCCCCCC/C=C\C/C=C\CCCCC)CCC1OC(=O)SCCN(C)C] | 9.02 |
| PNI 129 | 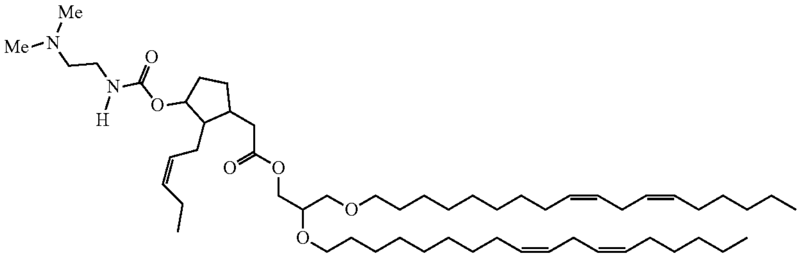 [SMILES: CC/C=C\CC1C(CC(=O)OCC(COCCCCCCCC/C=C\C/C=C\CCCCC)OCCCCCCCC/C=C\C/C=C\CCCCC)CCC1OC(=O)NCCN(C)C] | 8.87 |
| PNI 130 | 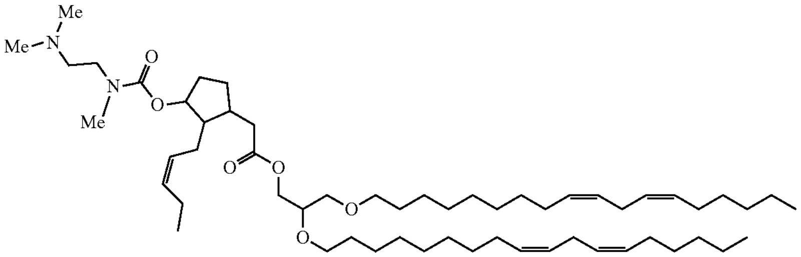 [SMILES: CC/C=C\CC1C(CC(=O)OCC(COCCCCCCCC/C=C\C/C=C\CCCCC)OCCCCCCCC/C=C\C/C=C\CCCCC)CCC1OC(=O)N(C)CCN(C)C] | 8.94 |
| PNI 131 | 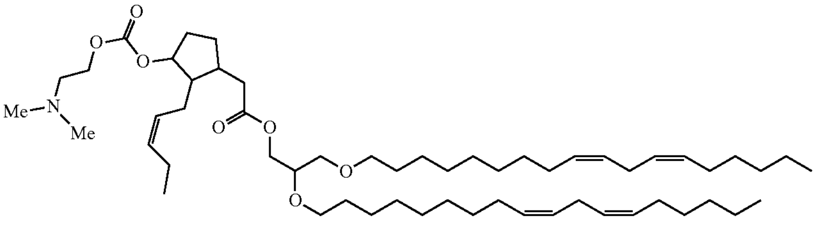 [SMILES: CC/C=C\CC1C(CC(=O)OCC(COCCCCCCCC/C=C\C/C=C\CCCCC)OCCCCCCCC/C=C\C/C=C\CCCCC)CCC1OC(=O)OCCN(C)C] | 8.68 |
| PNI 133 | 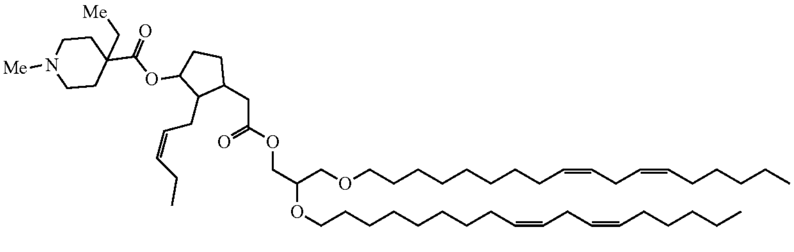 [SMILES: CC/C=C\CC1C(CC(=O)OCC(COCCCCCCCC/C=C\C/C=C\CCCCC)OCCCCCCCC/C=C\C/C=C\CCCCC)CCC1OC(=O)C1(CC)CCN(C)CC1] | 9.15 |

TABLE 2-continued
| ID | Representative Compounds | Theoretical $pKa_1$ |
|---|---|---|
| PNI 134 | 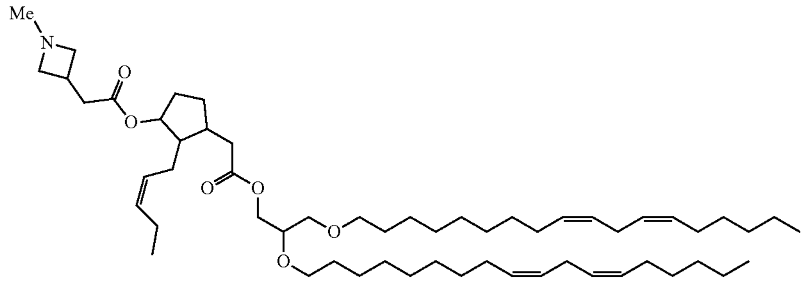 [SMILES: CC/C=C\CC1C(CC(=O)OCC(COCCCCCCCC/C=C\C/C=C\CCCCC)OCCCCCCCC/C=C\C/C=C\CCCCC)CCC1OC(=O)CC1CN(C)C1] | 9.20 |
| PNI 136 | 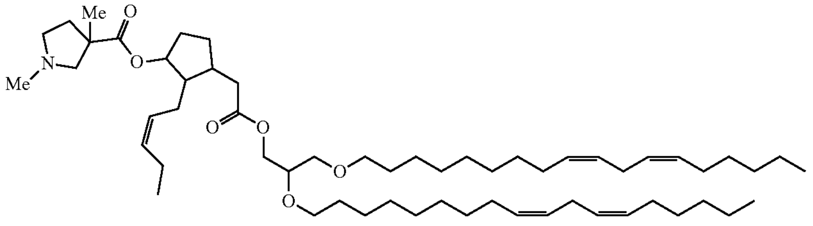 [SMILES: CC/C=C\CC1C(CC(=O)OCC(COCCCCCCCC/C=C\C/C=C\CCCCC)OCCCCCCCC/C=C\C/C=C\CCCCC)CCC1OC(=O)C1(C)CCN(C)C1] | 8.29 |
| PNI 138 | 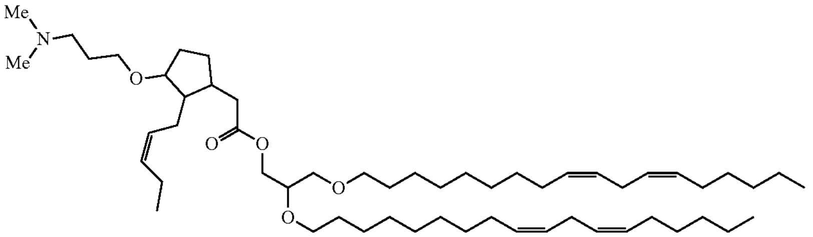 [SMILES: CC/C=C\CC1C(CC(=O)OCC(COCCCCCCCC/C=C\C/C=C\CCCCC)OCCCCCCCC/C=C\C/C=C\CCCCC)CCC1OCCCN(C)C] | 9.88 |
| PNI 139 | 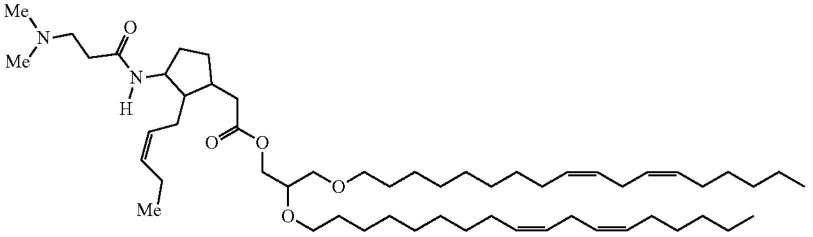 [SMILES: CC/C=C\CC1C(CC(=O)OCC(COCCCCCCCC/C=C\C/C=C\CCCCC)OCCCCCCCC/C=C\C/C=C\CCCCC)CCC1NC(=O)CCN(C)C] | 8.83 |
| PNI 140 | 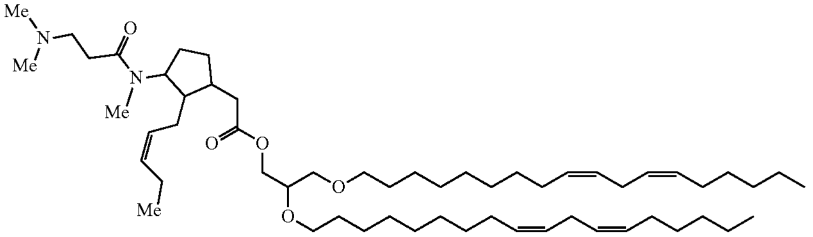 [SMILES: CC/C=C\CC1C(CC(=O)OCC(COCCCCCCCC/C=C\C/C=C\CCCCC)OCCCCCCCC/C=C\C/C=C\CCCCC)CCC1N(C)C(=O)CCN(C)C] | 8.87 |
| PNI 141 | 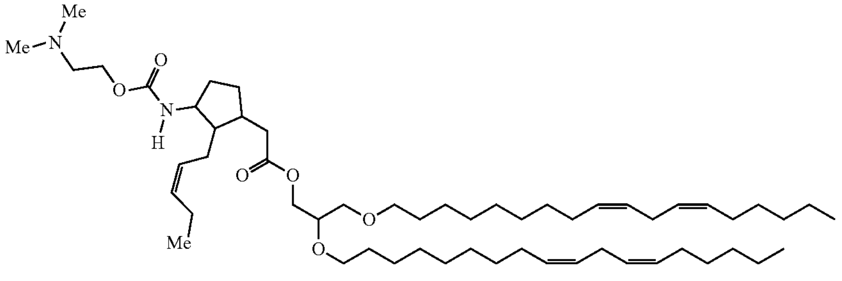 [SMILES: CC/C=C\CC1C(CC(=O)OCC(COCCCCCCCC/C=C\C/C=C\CCCCC)OCCCCCCCC/C=C\C/C=C\CCCCC)CCC1NC(=O)OCCN(C)C] | 8.76 |

TABLE 2-continued
| ID | Representative Compounds | Theoretical pKa1 |
|---|---|---|
| PNI 142 | 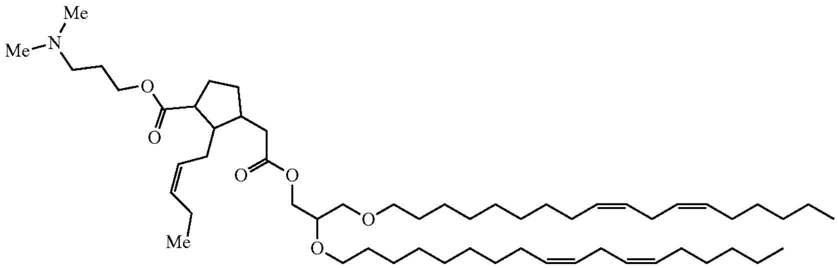 [SMILES: CC/C=C\CC1C(CC(=O)OCC(COCCCCCCCC/C=C\C/C=C\CCCCC)OCCCCCCCC/C=C\C/C=C\CCCCC)CCC1C(=O)OCCCN(C)C] | 9.54 |
| PNI 149 | 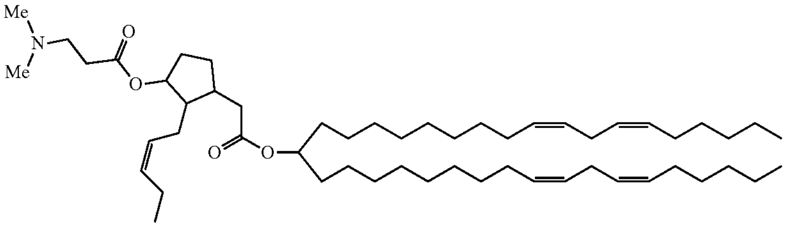 [SMILES: CC/C=C\CC1C(CC(=O)OC(CCCCCCCC/C=C\C/C=C\CCCCC)CCCCCCCC/C=C\C/C=C\CCCCC)CCC1OC(=O)CCN(C)C] | 8.67 |
| PNI 151 | 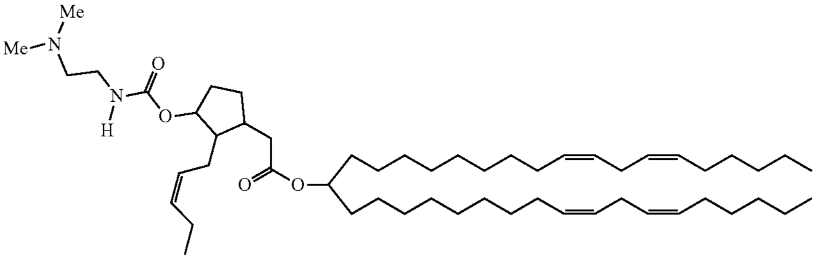 [SMILES: CC/C=C\CC1C(CC(=O)OC(CCCCCCCC/C=C\C/C=C\CCCCC)CCCCCCCC/C=C\C/C=C\CCCCC)CCC1OC(=O)NCCN(C)C] | 8.87 |
| PNI 152 | 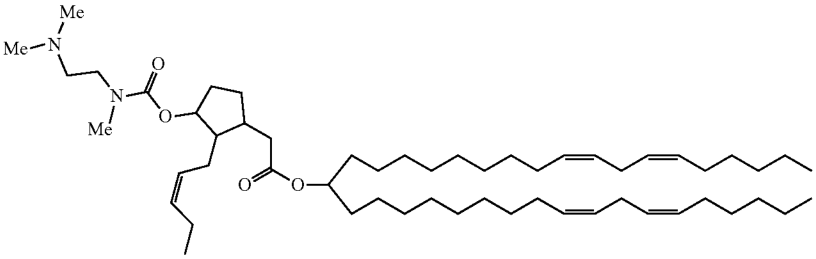 [SMILES: CC/C=C\CC1C(CC(=O)OC(CCCCCCCC/C=C\C/C=C\CCCCC)CCCCCCCC/C=C\C/C=C\CCCCC)CCC1OC(=O)N(C)CCN(C)C] | 8.94 |
| PNI 153 | 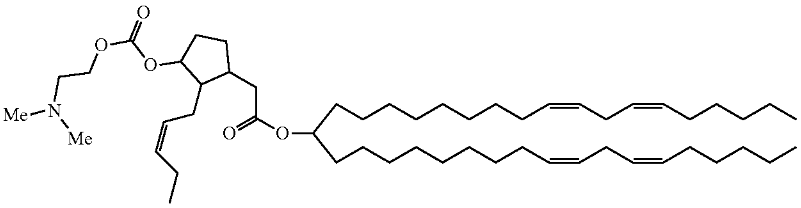 [SMILES: CC/C=C\CC1C(CC(=O)OC(CCCCCCCC/C=C\C/C=C\CCCCC)CCCCCCCC/C=C\C/C=C\CCCCC)CCC1OC(=O)OCCN(C)C] | 8.68 |
| PNI 156 | 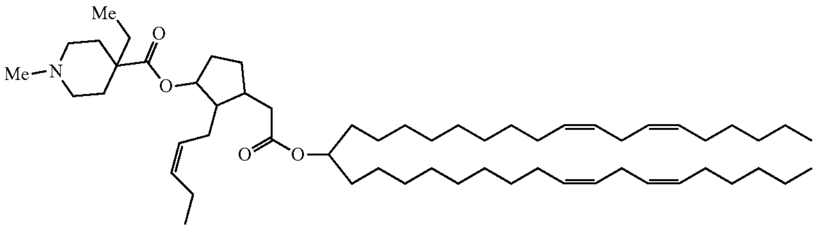 [SMILES: CC/C=C\CC1C(CC(=O)OC(CCCCCCCC/C=C\C/C=C\CCCCC)CCCCCCCC/C=C\C/C=C\CCCCC)CCC1OC(=O)C1(CC)CCN(C)CC1] | 9.15 |

TABLE 2-continued
| ID | Representative Compounds | Theoretical pKa$_1$ |
|---|---|---|
| PNI 158 | 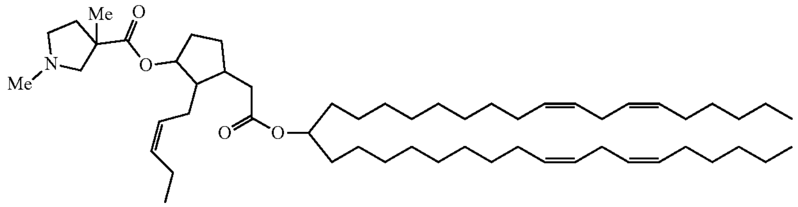 [SMILES: CC/C=C\CC1C(CC(=O)OC(CCCCCCCC/C=C\C/C=C\CCCCC)CCCCCCCC/C=C\C/C=C\CCCCC)CCC1OC(=O)C1(C)CCN(C)C1] | 8.29 |
| PNI 159 | 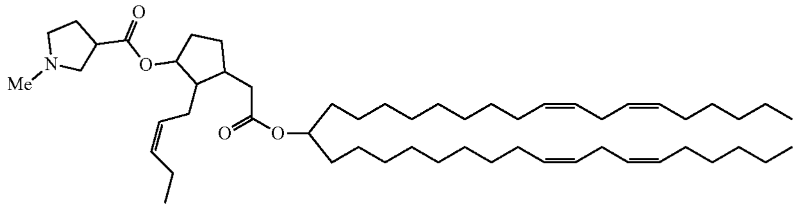 [SMILES: CC/C=C\CC1C(CC(=O)OC(CCCCCCCC/C=C\C/C=C\CCCCC)CCCCCCCC/C=C\C/C=C\CCCCC)CCC1OC(=O)C1CCN(C)C1] | 8.33 |
| PNI 161 | 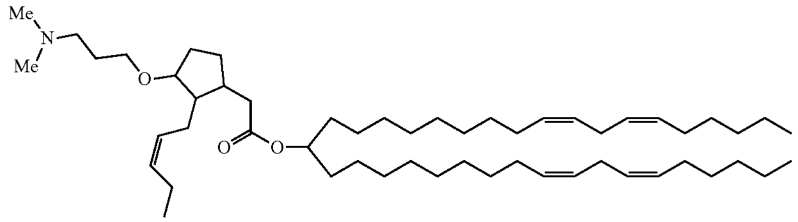 [SMILES: CC/C=C\CC1C(CC(=O)OC(CCCCCCCC/C=C\C/C=C\CCCCC)CCCCCCCC/C=C\C/C=C\CCCCC)CCC1OCCCN(C)C] | 9.88 |
| PNI 162 | 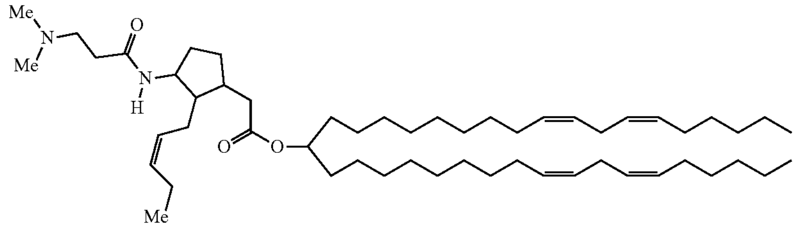 [SMILES: CC/C=C\CC1C(CC(=O)OC(CCCCCCCC/C=C\C/C=C\CCCCC)CCCCCCCC/C=C\C/C=C\CCCCC)CCC1NC(=O)CCN(C)C] | 8.83 |
| PNI 163 | 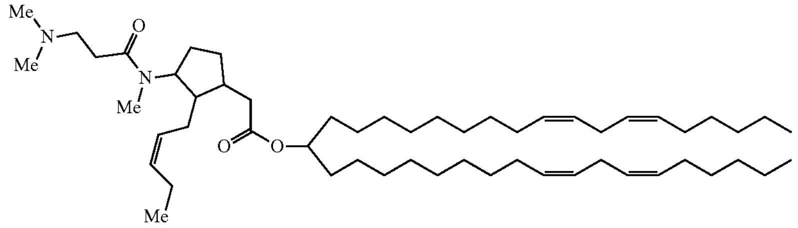 [SMILES: CC/C=C\CC1C(CC(=O)OC(CCCCCCCC/C=C\C/C=C\CCCCC)CCCCCCCC/C=C\C/C=C\CCCCC)CCC1N(C)C(=O)CCN(C)C] | 8.87 |
| PNI 164 | 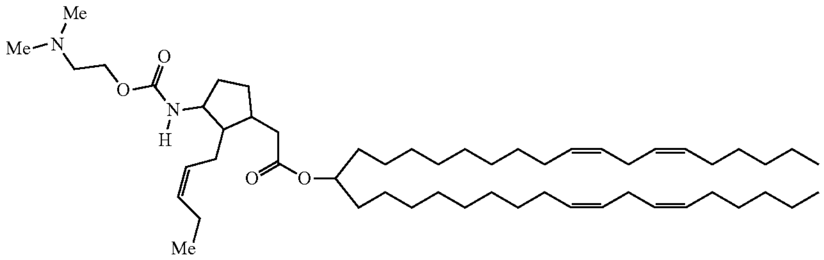 [SMILES: CC/C=C\CC1C(CC(=O)OC(CCCCCCCC/C=C\C/C=C\CCCCC)CCCCCCCC/C=C\C/C=C\CCCCC)CCC1NC(=O)OCCN(C)C] | 8.77 |

TABLE 2-continued
| ID | Representative Compounds | Theoretical $pKa_1$ |
| --- | --- | --- |
| PNI 165 | 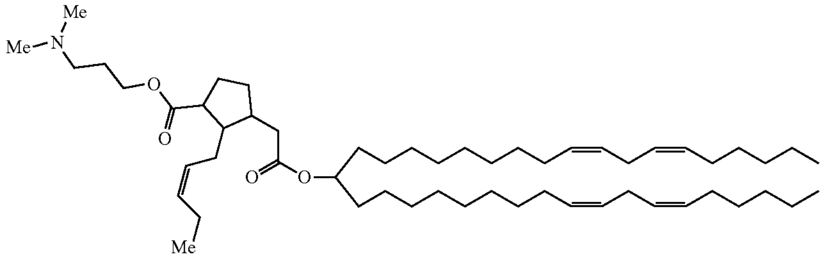 [SMILES: CC/C=C\CC1C(CC(=O)OC(CCCCCCCC/C=C\C/C=C\CCCCC)CCCCCCCC/C=C\C/C=C\CCCCC)CCC1C(=O)OCCCN(C)C] | 9.54 |
| PNI 166 | 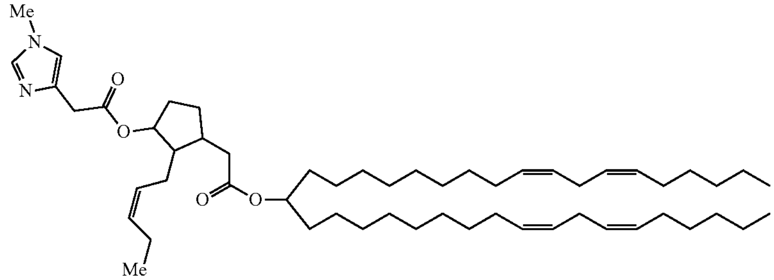 [SMILES: CC/C=C\CC1C(CC(=O)OC(CCCCCCCC/C=C\C/C=C\CCCCC)CCCCCCCC/C=C\C/C=C\CCCCC)CCC1OC(=O)Cc1cn(C)cn1] | |
| PNI 168 | 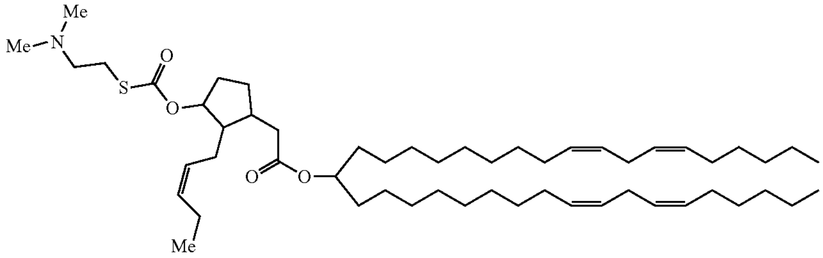 [SMILES: CC/C=C\CC1C(CC(=O)OC(CCCCCCCC/C=C\C/C=C\CCCCC)CCCCCCCC/C=C\C/C=C\CCCCC)CCC1OC(=O)SCCN(C)C] | 9.02 |
| PNI 169 | 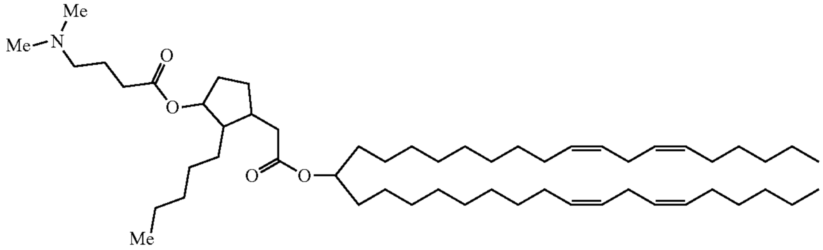 [SMILES: CCCCC/C=C\C/C=C\CCCCCCCCC(CCCCCCCC/C=C\C/C=C\CCCCC)OC(=O)CC1CCC(OC(=O)CCCN(C)C)C1CCCCC] | 9.44 |
| PNI 170 | 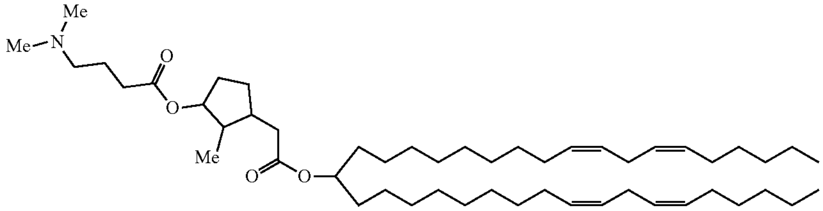 | 9.44 |
| PNI 172 | 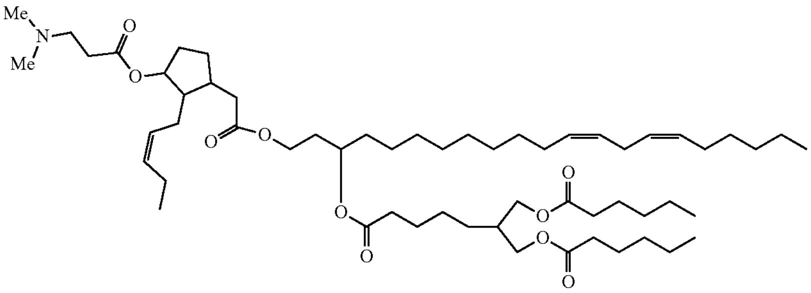 [SMILES: CC/C=C\CC1C(CC(=O)OCCC(CCCCCCCC/C=C\C/C=C\CCCCC)OC(=O)CCCCC(COC(=O)CCCCC)COC(=O)CCCCC)CCC1OC(=O)CCN(C)C] | 8.67 |

TABLE 2-continued
| ID | Representative Compounds | Theoretical $pKa_1$ |
|---|---|---|
| PNI 174 | 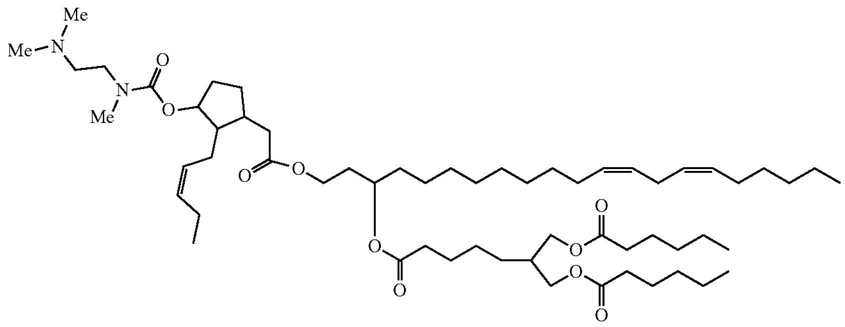 [SMILES: CC/C=C\CC1C(CC(=O)OCCC(CCCCCCCC/C=C\C/C=C\CCCCC)OC(=O)CCCCC(COC(=O)CCCCC)COC(=O)CCCCC)CCC1OC(=O)N(C)CCN(C)C] | 8.94 |
| PNI 175 | 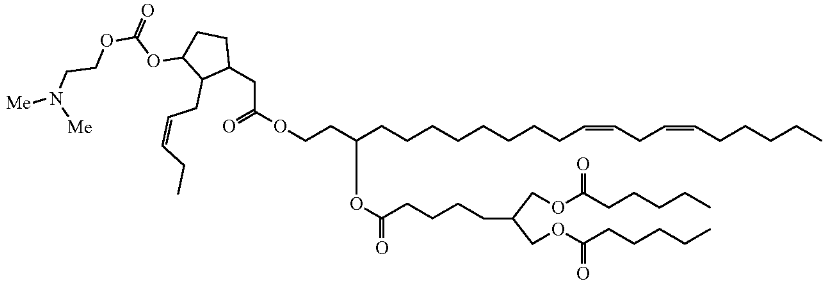 [SMILES: CC/C=C\CC1C(CC(=O)OCCC(CCCCCCCC/C=C\C/C=C\CCCCC)OC(=O)CCCCC(COC(=O)CCCCC)COC(=O)CCCCC)CCC1OC(=O)OCCN(C)C] | 8.68 |
| PNI 180 | 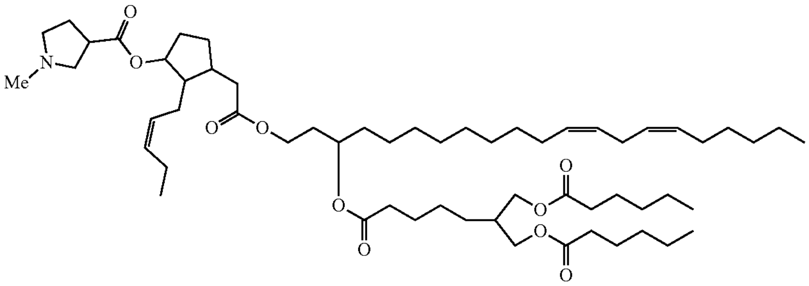 [SMILES: CC/C=C\CC1C(CC(=O)OCCC(CCCCCCCC/C=C\C/C=C\CCCCC)OC(=O)CCCCC(COC(=O)CCCCC)COC(=O)CCCCC)CCC1OC(=O)C1CCN(C)C1] | 8.33 |
| PNI 181 | 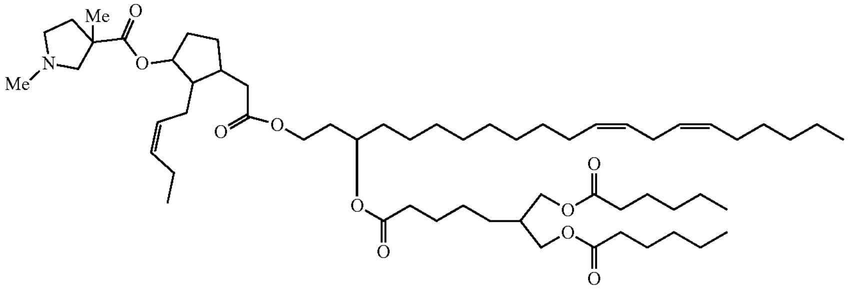 [SMILES: CC/C=C\CC1C(CC(=O)OCCC(CCCCCCCC/C=C\C/C=C\CCCCC)OC(=O)CCCCC(COC(=O)CCCCC)COC(=O)CCCCC)CCC1OC(=O)C1(C)CCN(C)C1] | 8.29 |
| PNI 185 | 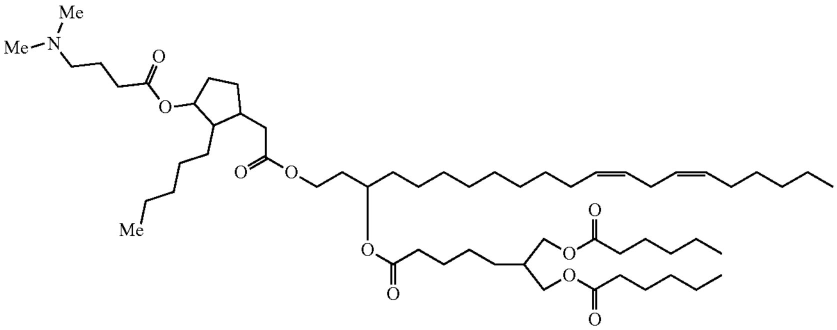 [SMILES: CCCCC/C=C\C/C=C\CCCCCCCCC(CCOC(=O)CC1CCC(OC(=O)CCCN(C)C)C1CCCCC)OC(=O)CCCCC(COC(=O)CCCCC)COC(=O)CCCCC] | 9.44 |

TABLE 2-continued
| ID | Representative Compounds | Theoretical $pKa_1$ |
| --- | --- | --- |
| PNI 186 | 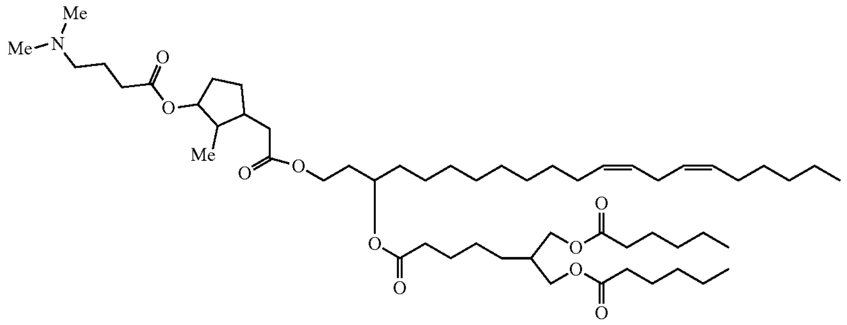 [SMILES: CCCCC/C=C\C/C=C\CCCCCCCCC(CCOC(=O)CC1CCC(OC(=O)CCCN(C)C)C1C)OC(=O)CCCCC(COC(=O)CCCCC)COC(=O)CCCCC] | 9.44 |
| PNI 188 | 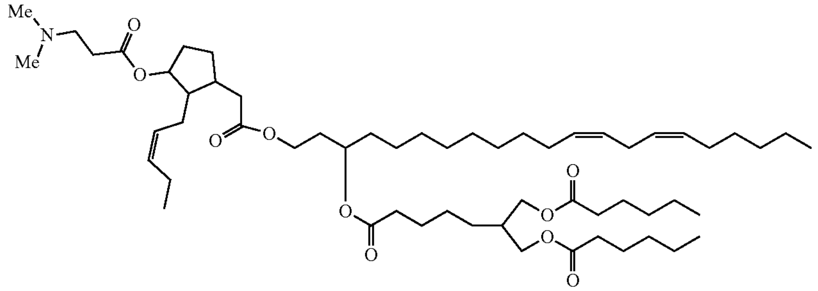 [SMILES: CC/C=C\CC1C(CC(=O)OCCC(CCCCCCCC/C=C\C/C=C\CCCCC)OC(=O)CCCCC(COC(=O)CCCCC)COC(=O)CCCCC)CCC1OC(=O)CCN(C)C] | 8.67 |
| PNI 193 | 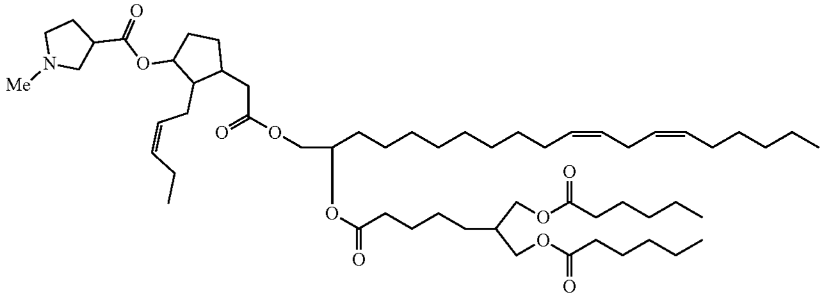 [SMILES: CC/C=C\CC1C(CC(=O)OCC(CCCCCCCC/C=C\C/C=C\CCCCC)OC(=O)CCCCC(COC(=O)CCCCC)COC(=O)CCCCC)CCC1OC(=O)C1CCN(C)C1] | 8.33 |
| PNI 194 | 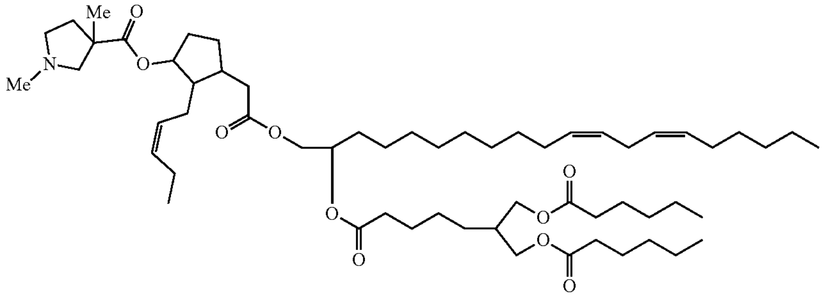 [SMILES: CC/C=C\CC1C(CC(=O)OCC(CCCCCCCC/C=C\C/C=C\CCCCC)OC(=O)CCCCC(COC(=O)CCCCC)COC(=O)CCCCC)CCC1OC(=O)C1(C)CCN(C)C1] | 8.29 |
| PNI 195 | 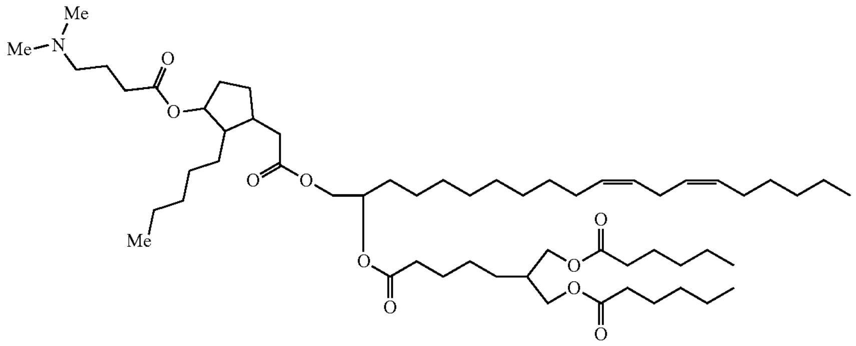 [SMILES: CCCCC/C=C\C/C=C\CCCCCCCCC(COC(=O)CC1CCC(OC(=O)CCCN(C)C)C1CCCCC)OC(=O)CCCCC(COC(=O)CCCCC)COC(=O)CCCCC] | 9.44 |

TABLE 2-continued
| ID | Representative Compounds | Theoretical pKa1 |
|---|---|---|
| PNI 196 | 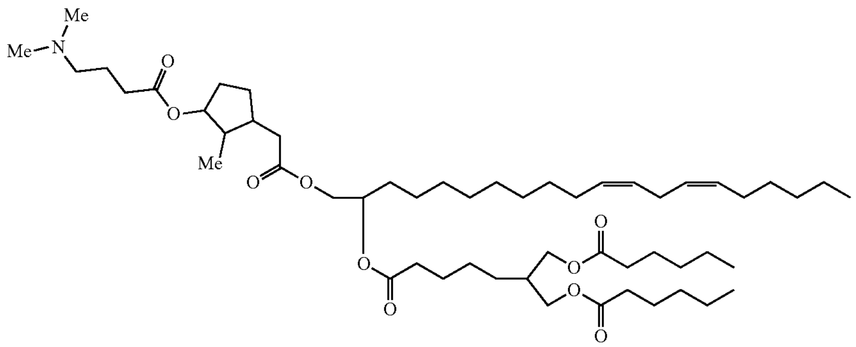 [SMILES: CCCCC/C=C\C/C=C\CCCCCCCCC(COC(=O)CC1CCC(OC(=O)CCCN(C)C)C1C)OC(=O)CCCCC(COC(=O)CCCCC)COC(=O)CCCCC] | 9.44 |
| PNI 198 | 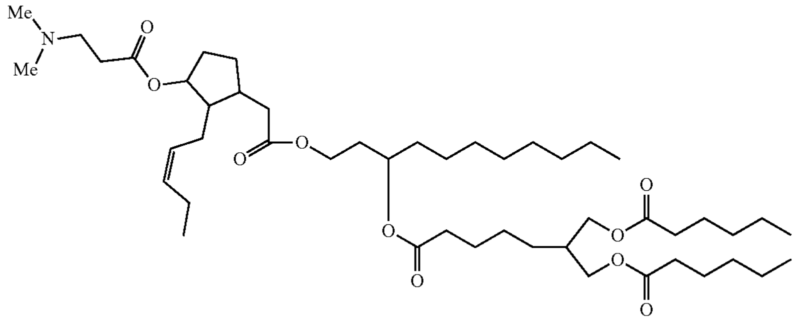 [SMILES: CC/C=C\CC1C(CC(=O)OCCC(CCCCCCCC)OC(=O)CCCCC(COC(=O)CCCCC)COC(=O)CCCCC)CCC1OC(=O)CCN(C)C] | 8.67 |
| PNI 200 | 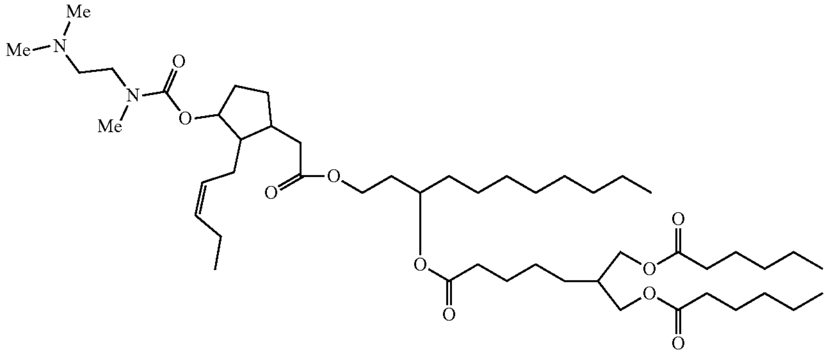 [SMILES: CC/C=C\CC1C(CC(=O)OCCC(CCCCCCCC)OC(=O)CCCCC(COC(=O)CCCCC)COC(=O)CCCCC)CCC1OC(=O)N(C)CCN(C)C] | 8.94 |
| PNI 205 | 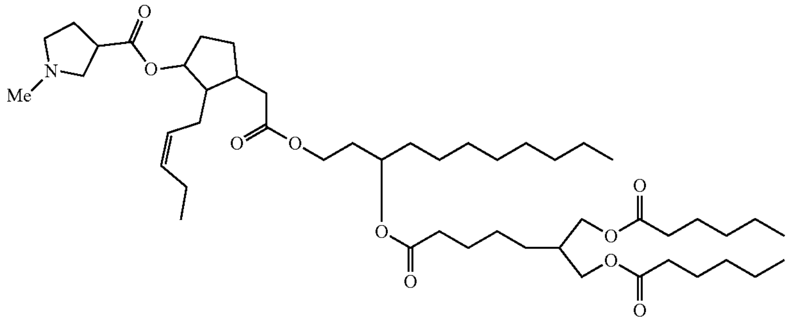 [SMILES: CC/C=C\CC1C(CC(=O)OCCC(CCCCCCCC)OC(=O)CCCCC(COC(=O)CCCCC)COC(=O)CCCCC)CCC1OC(=O)C1CCN(C)C1] | 8.33 |

TABLE 2-continued
| ID | Representative Compounds | Theoretical $pKa_1$ |
|---|---|---|
| PNI 206 | 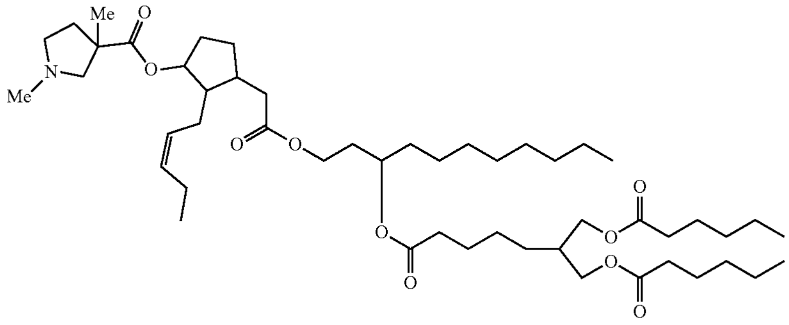 [SMILES: CC/C=C\CC1C(CC(=O)OCCC(CCCCCCCC)OC(=O)CCCCC(COC(=O)CCCCC)COC(=O)CCCCC)CCC1OC(=O)C1(C)CCN(C)C1] | 8.29 |
| PNI 210 | 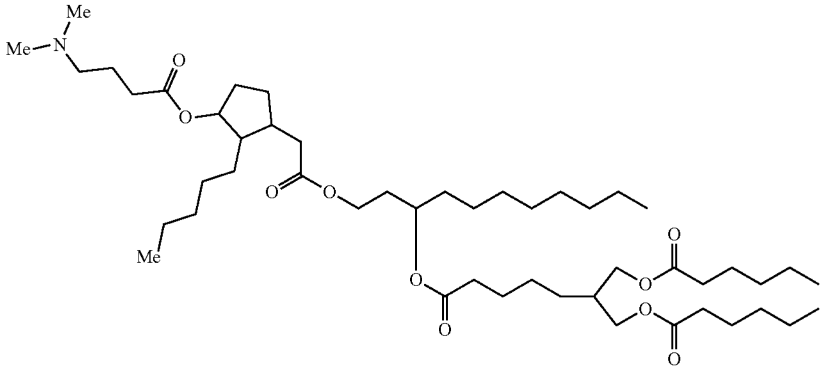 [SMILES: CCCCCCCCC(CCOC(=O)CC1CCC(OC(=O)CCCN(C)C)C1CCCCC)OC(=O)CCCCC(COC(=O)CCCCC)COC(=O)CCCCC] | 9.44 |
| PNI 211 | 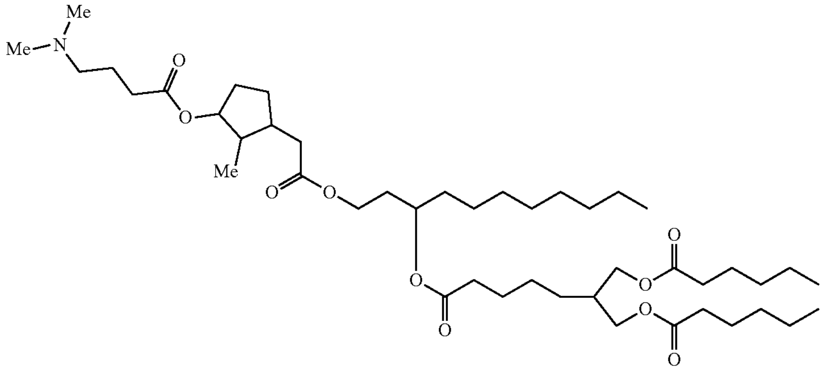 [SMILES: CCCCCCCCC(CCOC(=O)CC1CCC(OC(=O)CCCN(C)C)C1C)OC(=O)CCCCC(COC(=O)CCCCC)COC(=O)CCCCC] | 9.44 |
| PNI 217 | 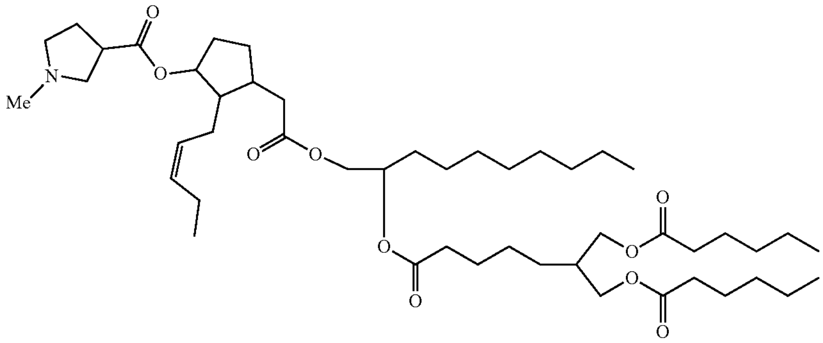 [SMILES: CC/C=C\CC1C(CC(=O)OCC(CCCCCCCC)OC(=O)CCCCC(COC(=O)CCCCC)COC(=O)CCCCC)CCC1OC(=O)C1CCN(C)C1] | 8.33 |

TABLE 2-continued
| ID | Representative Compounds | Theoretical pKa1 |
|---|---|---|
| PNI 218 | 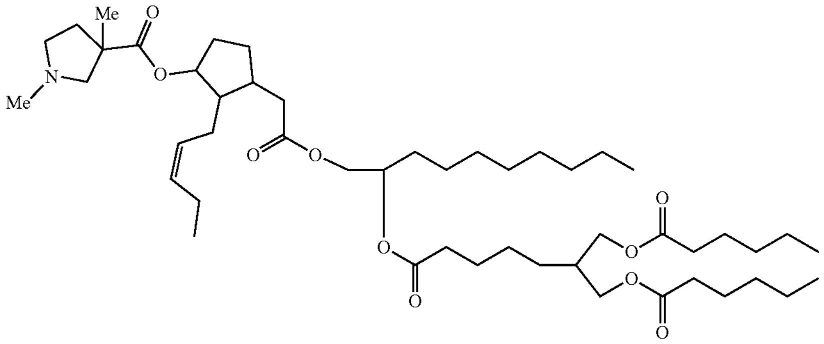 [SMILES: CC/C=C\CC1C(CC(=O)OCC(CCCCCCCC)OC(=O)CCCCC(COC(=O)CCCCC)COC(=O)CCCCC)CCC1OC(=O)C1(C)CCN(C)C1] | 8.29 |
| PNI 219 | 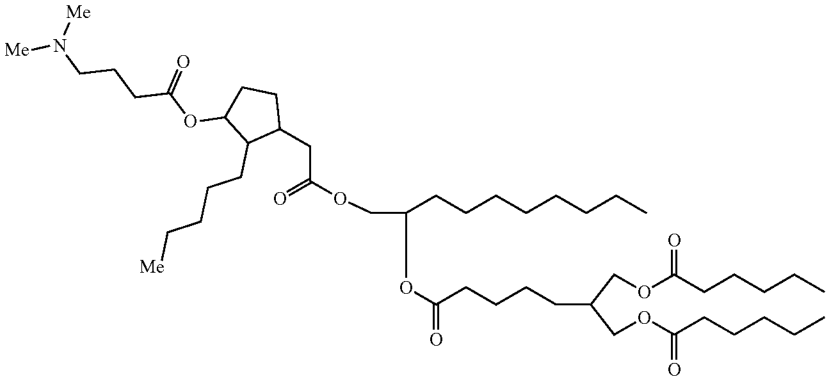 [SMILES: CCCCCCCCC(COC(=O)CC1CCC(OC(=O)CCCN(C)C)C1CCCCC)OC(=O)CCCCC(COC(=O)CCCCC)COC(=O)CCCCC] | 9.44 |
| PNI 220 | 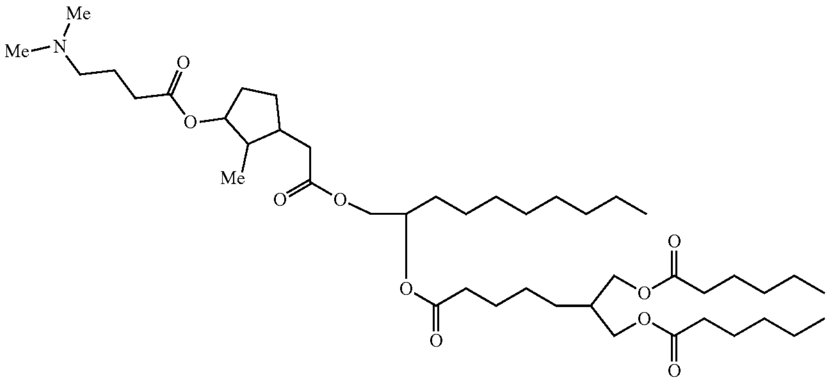 [SMILES: CCCCCCCCC(COC(=O)CC1CCC(OC(=O)CCCN(C)C)C1C)OC(=O)CCCCC(COC(=O)CCCCC)COC(=O)CCCCC] | 9.44 |
| PNI 229 | 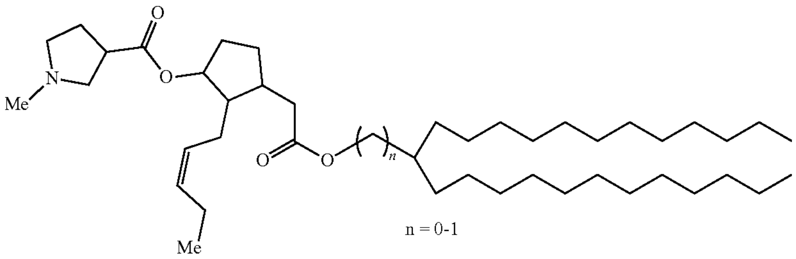<br>n = 0-1 | 8.33 |

TABLE 2-continued
| ID | Representative Compounds | Theoretical $pKa_1$ |
|---|---|---|
| PNI 230 | 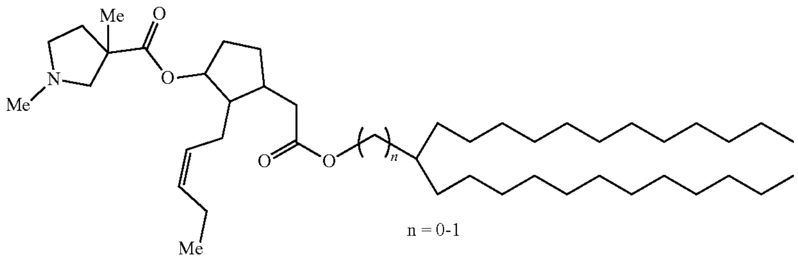 n = 0-1 | 8.29 |
| PNI 234 | 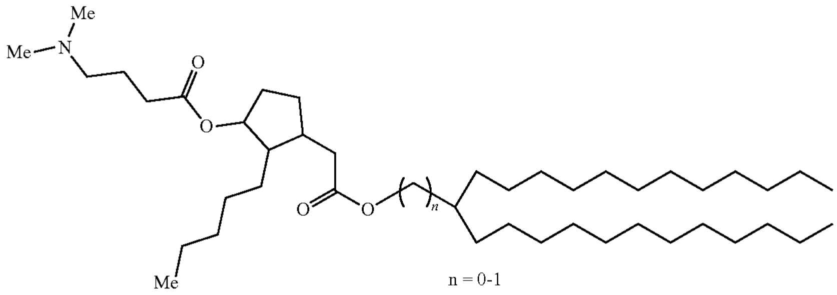 n = 0-1 | 9.44 |
| PNI 235 | 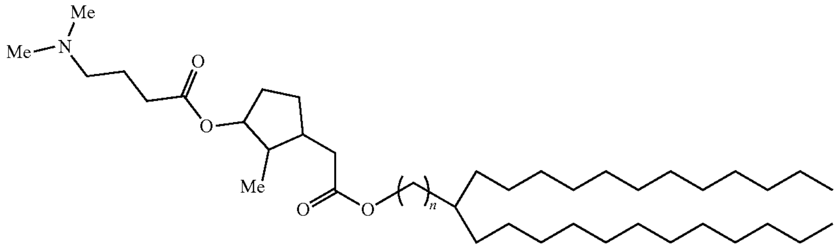 n = 0-1 | 9.44 |
| PNI 236 | 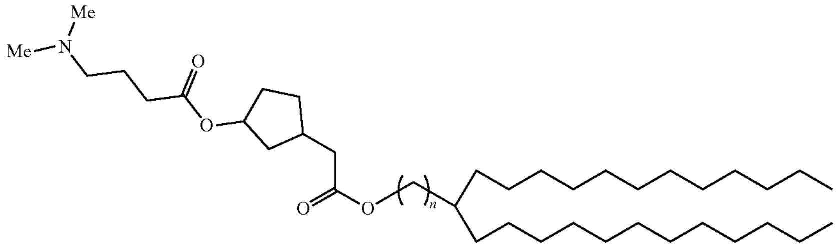 n = 0-1 | 9.45 |
| PNI 239 | 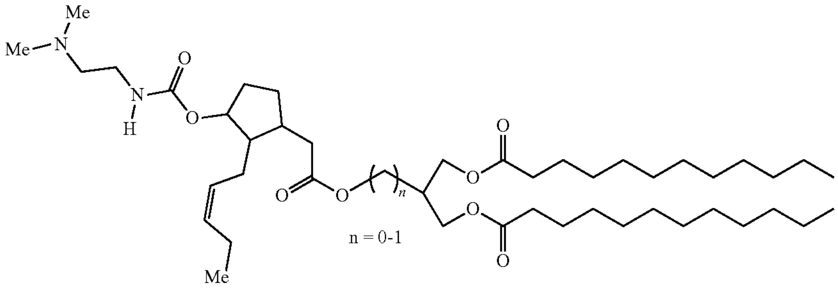 n = 0-1 | 8.87 |

TABLE 2-continued
| ID | Representative Compounds | Theoretical $pKa_1$ |
| --- | --- | --- |
| PNI 240 | 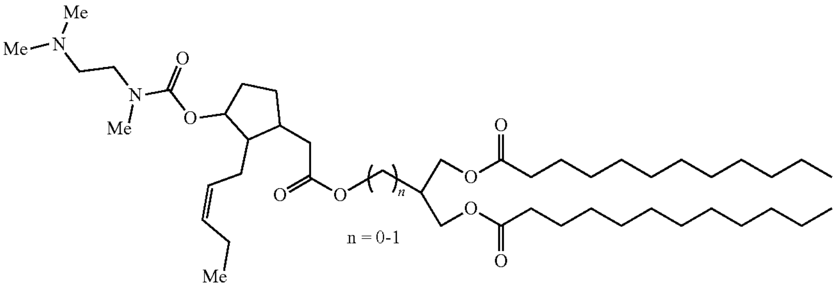 n = 0-1 | 8.94 |
| PNI 245 | 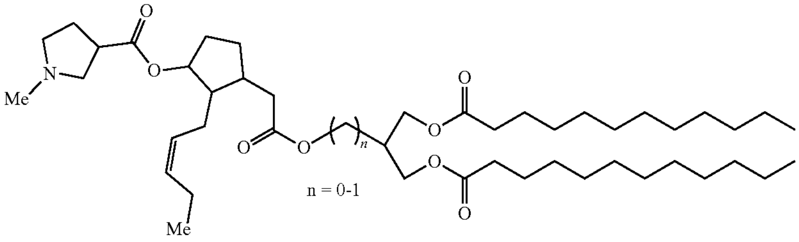 n = 0-1 | 8.33 |
| PNI 246 | 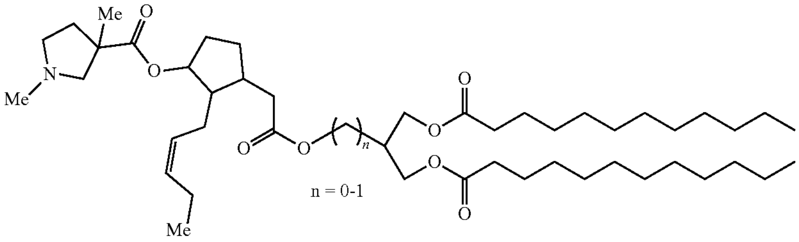 n = 0-1 | 8.29 |
| PNI 250 | 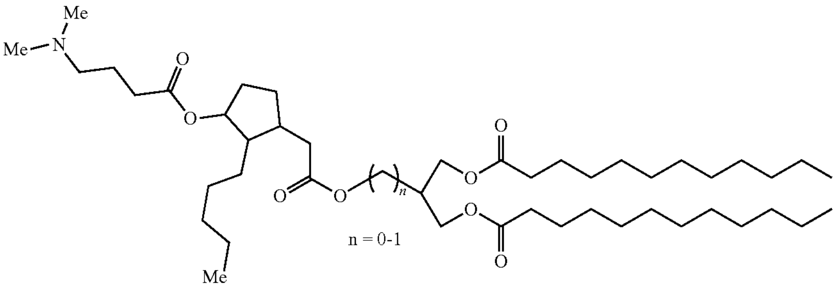 n = 0-1 | 9.44 |
| PNI 251 | 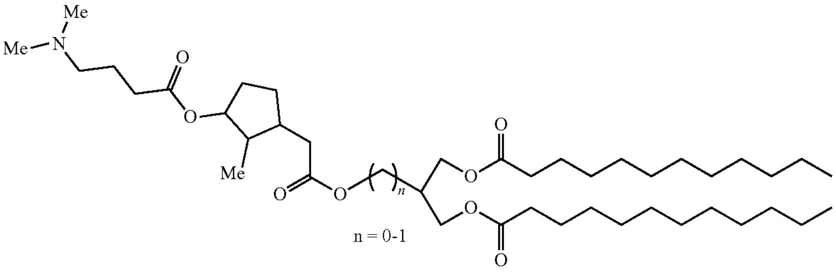 n = 0-1 | 9.44 |

TABLE 2-continued
| ID | Representative Compounds | Theoretical $pKa_1$ |
|---|---|---|
| PNI 252 | 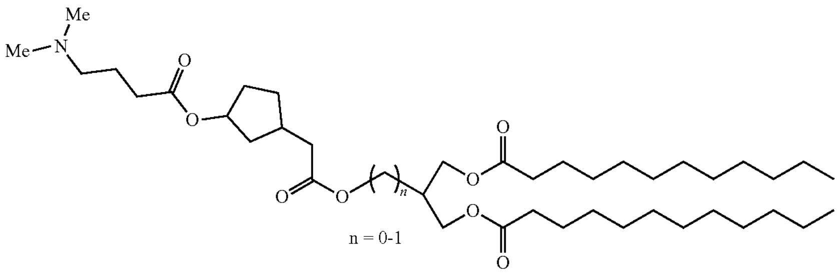 n = 0-1 | 9.45 |
| PNI 255 | 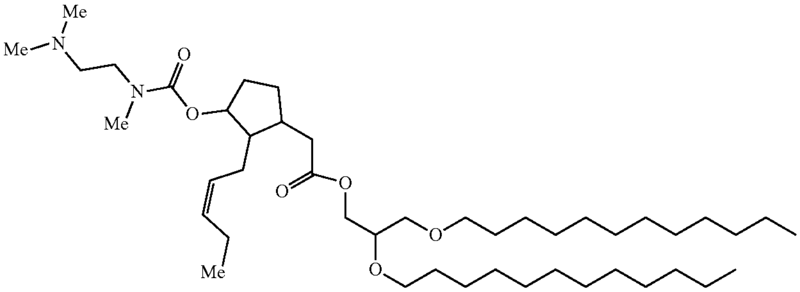 [SMILES: CC/C=C\CC1C(CC(=O)OCC(COCCCCCCCCCCCC)OCCCCCCCCCCCC)CCC1OC(=O)N(C)CCN(C)C] | 8.94 |
| PNI 260 | 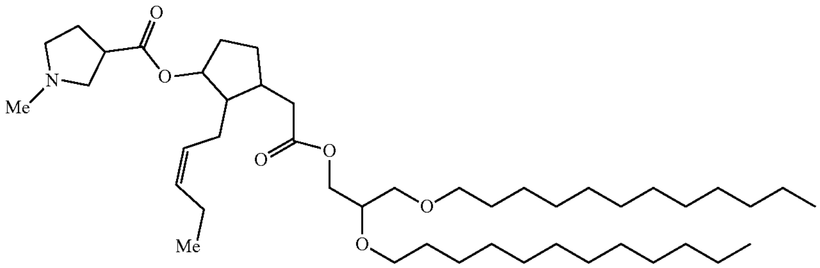 [SMILES: CC/C=C\CC1C(CC(=O)OCC(COCCCCCCCCCCCC)OCCCCCCCCCCCC)CCC1OC(=O)C1CCN(C)C1] | 8.33 |
| PNI 261 | 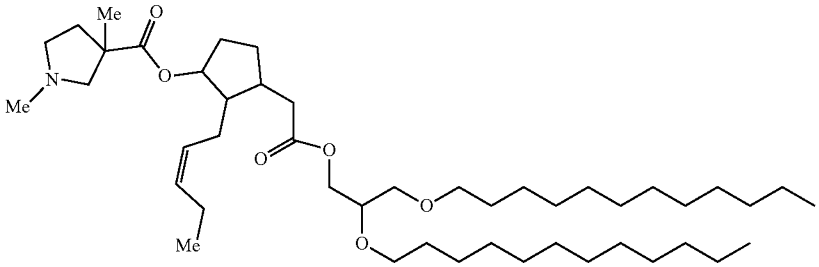 [SMILES: CC/C=C\CC1C(CC(=O)OCC(COCCCCCCCCCCCC)OCCCCCCCCCCCC)CCC1OC(=O)C1(C)CCN(C)C1] | 8.29 |
| PNI 265 | 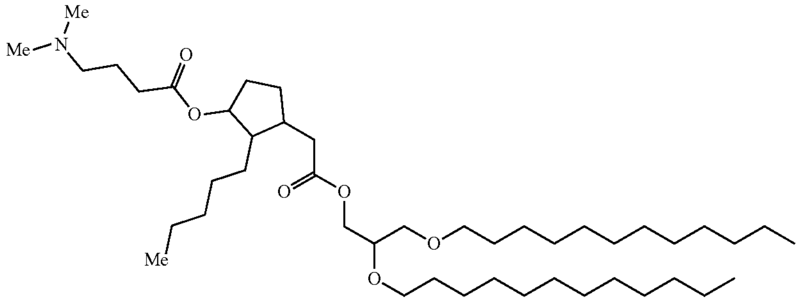 [SMILES: CCCCCCCCCCCCOCC(COC(=O)CC1CCC(OC(=O)CCCN(C)C)C1CCCCC)OCCCCCCCCCCCC] | 9.44 |

TABLE 2-continued
| ID | Representative Compounds | Theoretical pKa$_1$ |
| --- | --- | --- |
| PNI 266 | 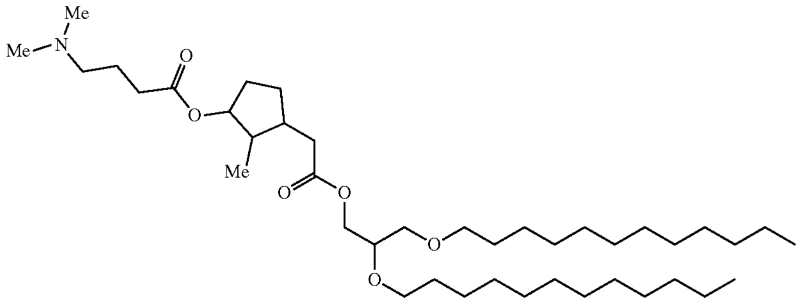 [SMILES: CCCCCCCCCCCCOCC(COC(=O)CC1CCC(OC(=O)CCCN(C)C)C1C)OCCCCCCCCCCCC] | 9.44 |
| PNI 267 | 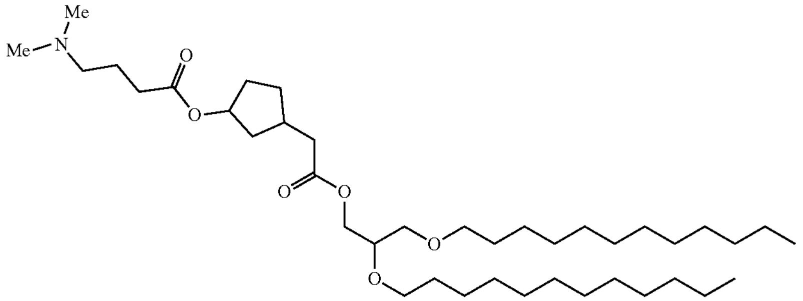 [SMILES: CCCCCCCCCCCCOCC(COC(=O)CC1CCC(OC(=O)CCCN(C)C)C1)OCCCCCCCCCCCC] | 9.45 |
| PNI 268 | 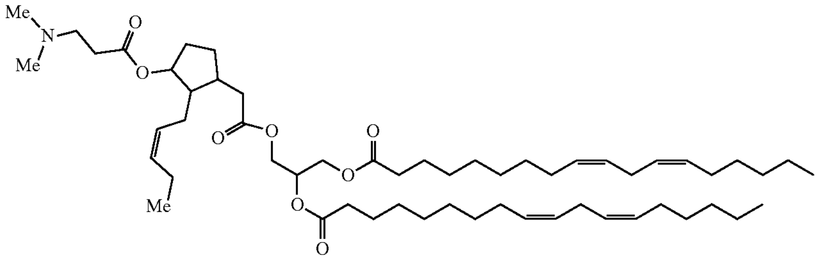 [SMILES: CC/C=C\CC1C(CC(=O)OCC(COC(=O)CCCCCCC/C=C\C/C=C\CCCCC)OC(=O)CCCCCCC/C=C\C/C=C\CCCCC)CCC1OC(=O)CCN(C)C] | 8.67 |
| PNI 274 | 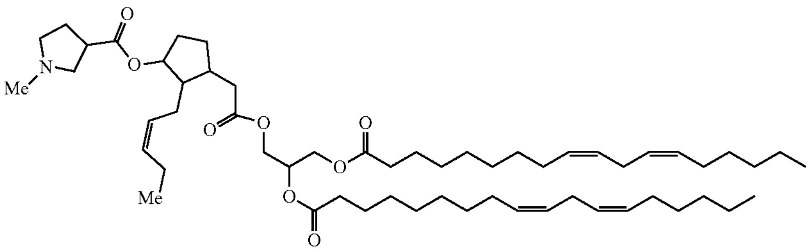 [SMILES: CC/C=C\CC1C(CC(=O)OCC(COC(=O)CCCCCCC/C=C\C/C=C\CCCCC)OC(=O)CCCCCCC/C=C\C/C=C\CCCCC)CCC1OC(=O)C1CCN(C)C1] | 8.33 |
| PNI 275 | 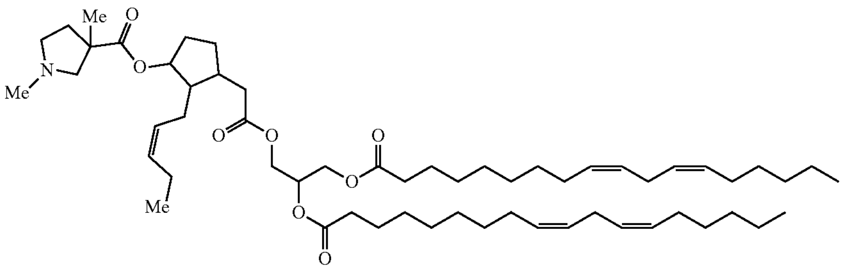 [SMILES: CC/C=C\CC1C(CC(=O)OCC(COC(=O)CCCCCCC/C=C\C/C=C\CCCCC)OC(=O)CCCCCCC/C=C\C/C=C\CCCCC)CCC1OC(=O)C1(C)CCN(C)C1] | 8.29 |

TABLE 2-continued
| ID | Representative Compounds | Theoretical pKa$_1$ |
|---|---|---|
| PNI 279 | 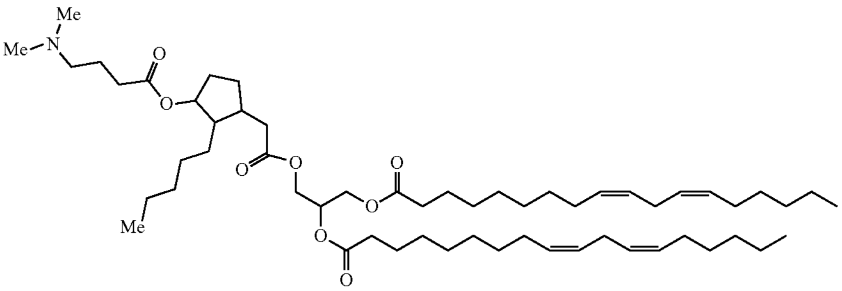 [SMILES: CCCCC/C=C\C/C=C\CCCCCCCC(=O)OCC(COC(=O)CC1CCC(OC(=O)CCCN(C)C)C1CCCCC)OC(=O)CCCCCCC/C=C\C/C=C\CCCCC] | 9.44 |
| PNI 280 | 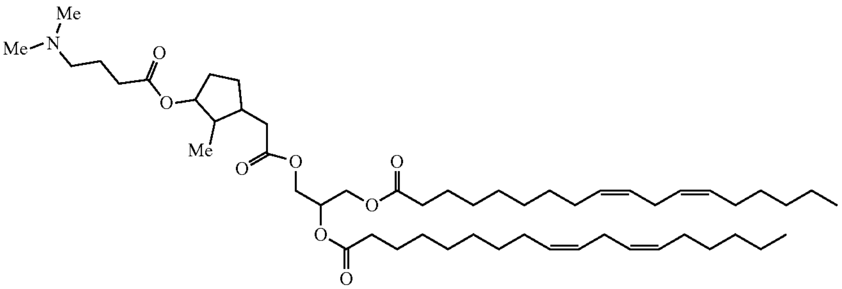 [SMILES: CCCCC/C=C\C/C=C\CCCCCCCC(=O)OCC(COC(=O)CC1CCC(OC(=O)CCCN(C)C)C1C)OC(=O)CCCCCCC/C=C\C/C=C\CCCCC] | 9.44 |
| PNI 281 | 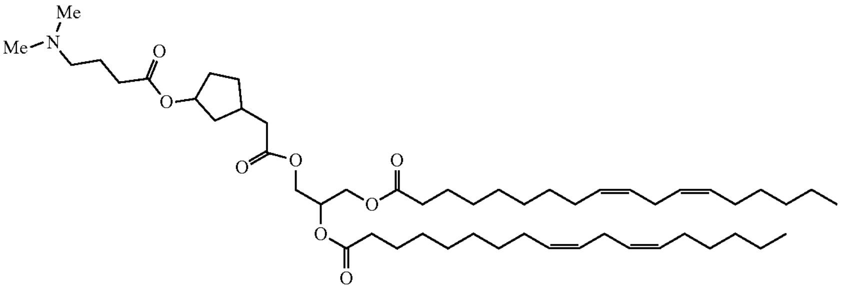 [SMILES: CCCCC/C=C\C/C=C\CCCCCCCC(=O)OCC(COC(=O)CC1CCC(OC(=O)CCCN(C)C)C1)OC(=O)CCCCCCC/C=C\C/C=C\CCCCC] | 9.45 |
| PNI 282 | 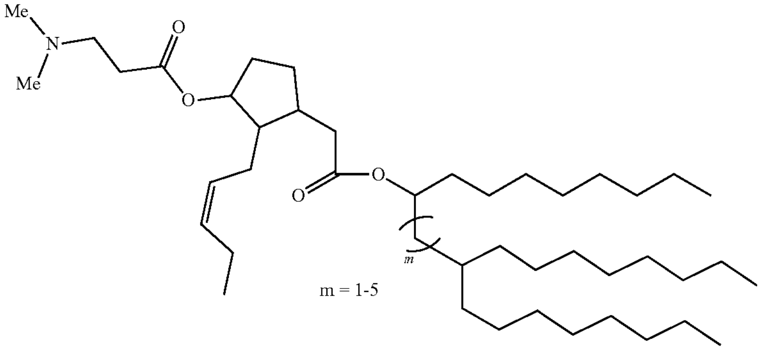 m = 1-5 | 8.67 |

TABLE 2-continued
| ID | Representative Compounds | Theoretical $pKa_1$ |
|---|---|---|
| PNI 284 | 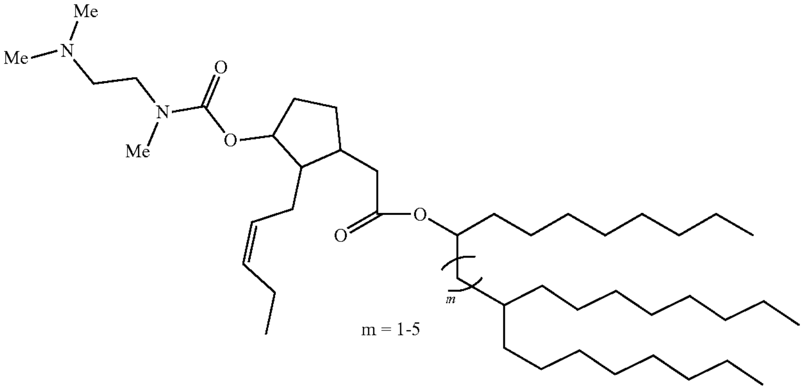 m = 1-5 | 8.94 |
| PNI 288 | 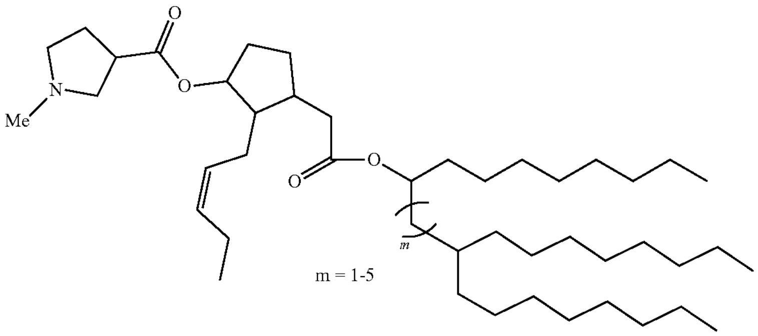 m = 1-5 | 8.33 |
| PNI 289 | 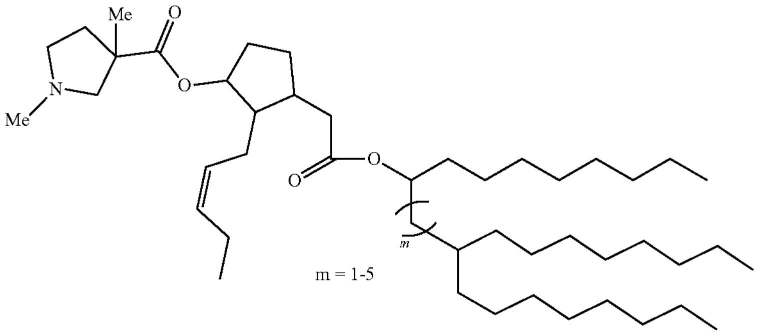 m = 1-5 | 8.29 |
| PNI 293 | 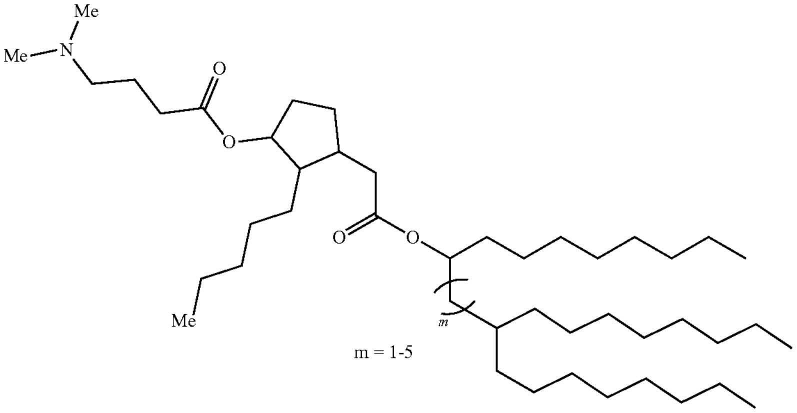 m = 1-5 | 9.44 |

TABLE 2-continued
| ID | Representative Compounds | Theoretical $pKa_1$ |
|---|---|---|
| PNI 294 | 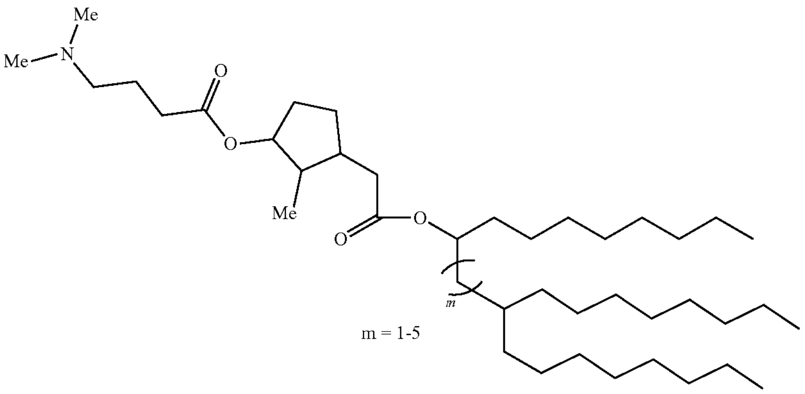 m = 1-5 | 9.44 |
| PNI 295 | 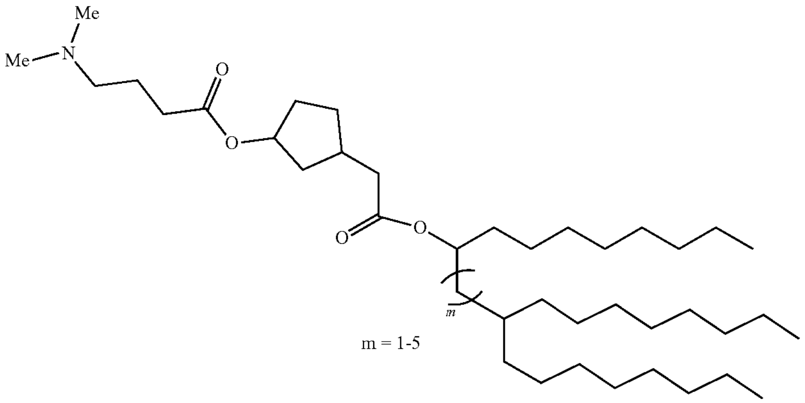 m = 1-5 | 9.45 |
| PNI 296 | 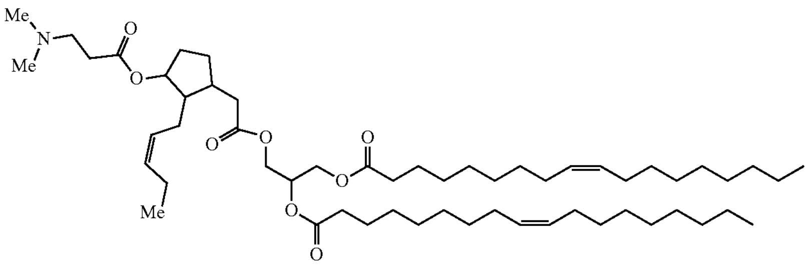 [SMILES: CC/C=C\CC1C(CC(=O)OCC(COC(=O)CCCCCCC/C=C\CCCCCCCC)OC(=O)CCCCCCC/C=C\CCCCCCCC)CCC1OC(=O)CCN(C)C] | 8.67 |
| PNI 302 | 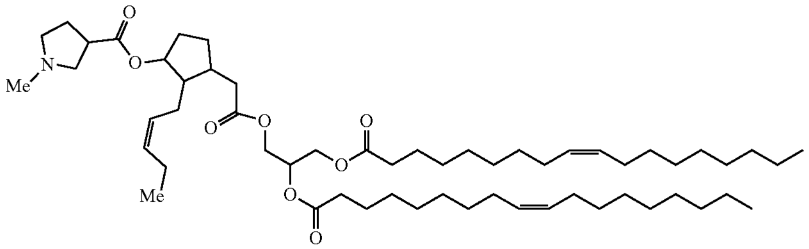 [SMILES: CC/C=C\CC1C(CC(=O)OCC(COC(=O)CCCCCCC/C=C\CCCCCCCC)OC(=O)CCCCCCC/C=C\CCCCCCCC)CCC1OC(=O)C1CCN(C)C1] | 8.33 |
| PNI 303 | 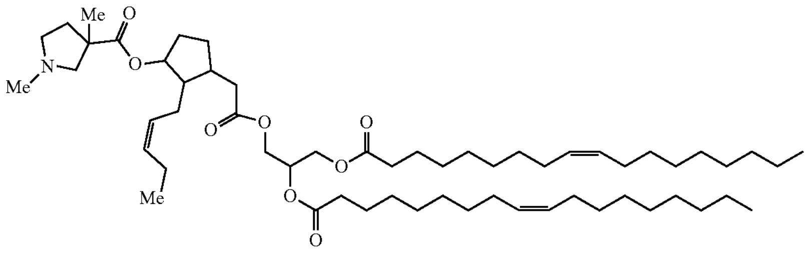 [SMILES: CC/C=C\CC1C(CC(=O)OCC(COC(=O)CCCCCCC/C=C\CCCCCCCC)OC(=O)CCCCCCC/C=C\CCCCCCCC)CCC1OC(=O)C1(C)CCN(C)C1] | 8.29 |

TABLE 2-continued
| ID | Representative Compounds | Theoretical pKa$_1$ |
|---|---|---|
| PNI 304 | 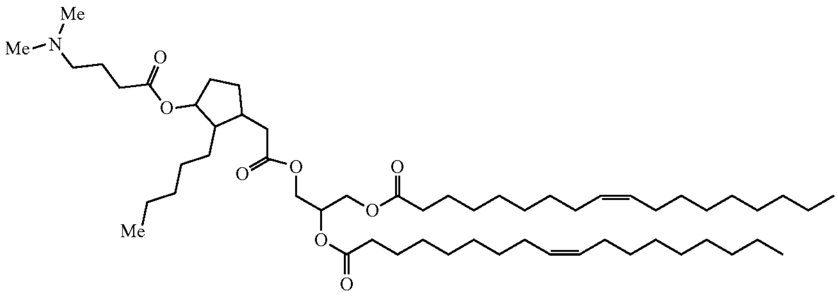 [SMILES: CCCCCCCC/C=C\CCCCCCCC(=O)OCC(COC(=O)CC1CCC(OC(=O)CCCN(C)C)C1CCCCC)OC(=O)CCCCCCC/C=C\CCCCCCCC] | 9.44 |
| PNI 307 | 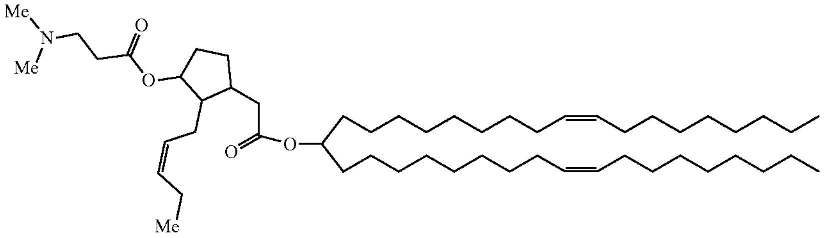 [SMILES: CC/C=C\CC1C(CC(=O)OC(CCCCCCCC/C=C\CCCCCCCC)CCCCCCCC/C=C\CCCCCCCC)CCC1OC(=O)CCN(C)C] | 8.67 |
| PNI 312 | 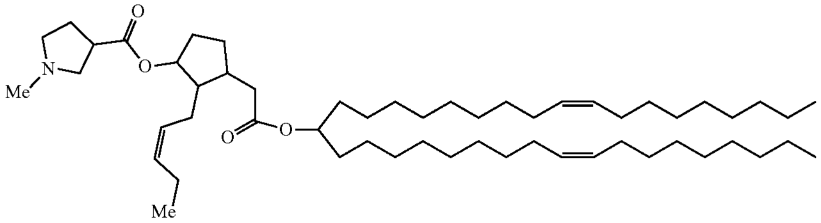 [SMILES: CC/C=C\CC1C(CC(=O)OC(CCCCCCCC/C=C\CCCCCCCC)CCCCCCCC/C=C\CCCCCCCC)CCC1OC(=O)C1CCN(C)C1] | 8.33 |
| PNI 313 | 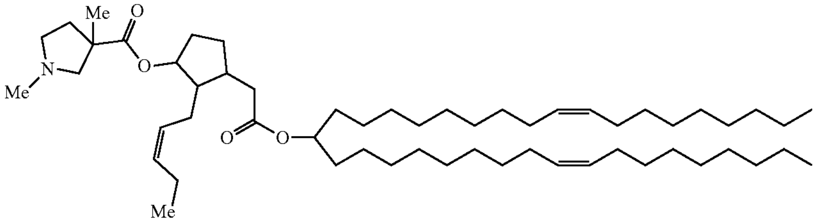 [SMILES: CC/C=C\CC1C(CC(=O)OC(CCCCCCCC/C=C\CCCCCCCC)CCCCCCCC/C=C\CCCCCCCC)CCC1OC(=O)C1(C)CCN(C)C1] | 8.29 |
| PNI 314 | 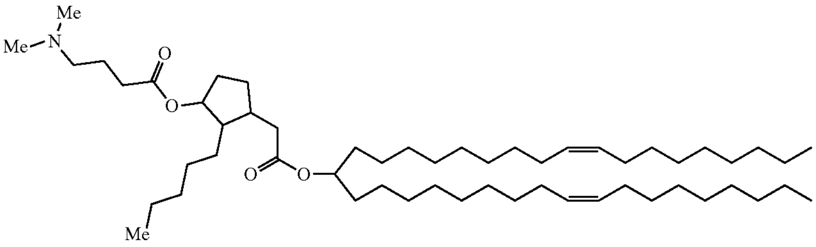 [SMILES: CCCCCCCC/C=C\CCCCCCCCC(CCCCCCCC/C=C\CCCCCCCC)OC(=O)CC1CCC(OC(=O)CCCN(C)C)C1CCCCC] | 9.44 |
| PNI 508 | 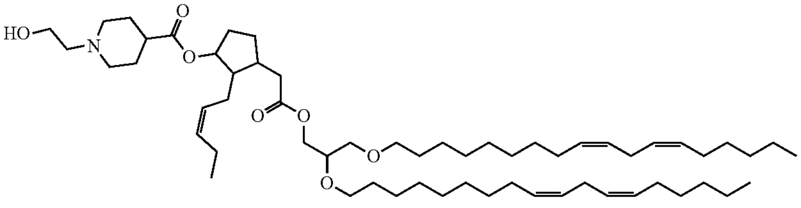 [SMILES: CC/C=C\CC1C(CC(=O)OCC(COCCCCCCCC/C=C\C/C=C\CCCCC)OCCCCCCCC/C=C\C/C=C\CCCCC)CCC1OC(=O)C1CCN(CCO)CC1] | 8.36 |

TABLE 2-continued
| ID | Representative Compounds | Theoretical $pKa_1$ |
|---|---|---|
| PNI 509 | 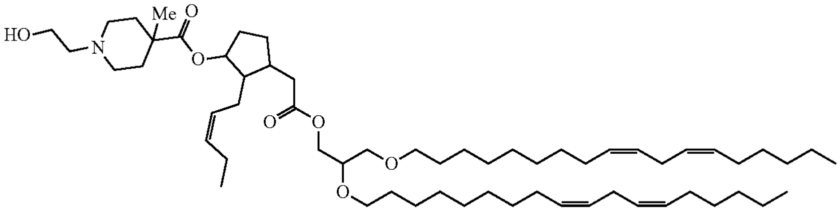 | 8.34 |
| PNI 511 | 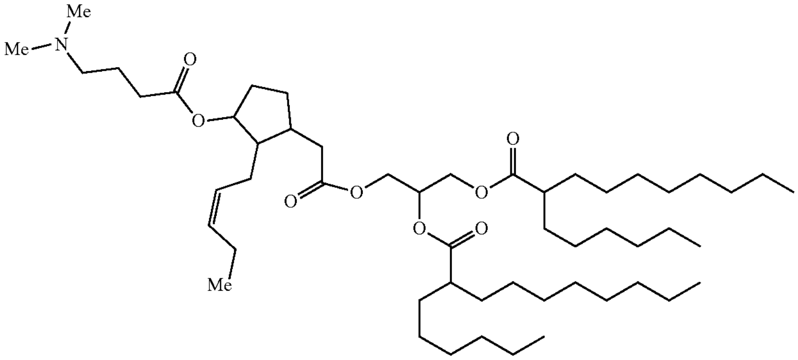 [SMILES: CC/C=C\CC1C(CC(=O)OCC(COC(=O)C(CCCCCC)CCCCCCCC)OC(=O)C(CCCCCC)CCCCCCCC)CCC1OC(=O)CCCN(C)C] | 9.44 |
| PNI 514 | 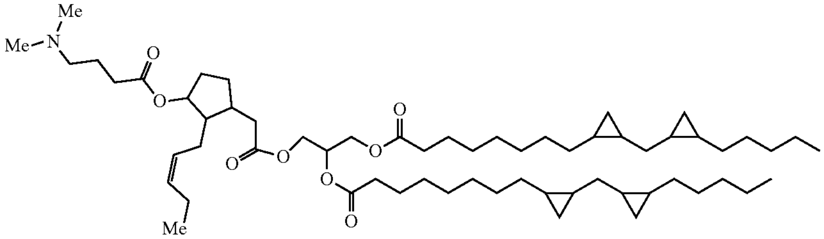 [SMILES: CC/C=C\CC1C(CC(=O)OCC(COC(=O)CCCCCCCC2CC2CC2CC2CCCCC)OC(=O)CCCCCCCC2CC2CC2CC2CCCCC)CCC1OC(=O)CCCN(C)C] | 9.44 |
| PNI 517 | 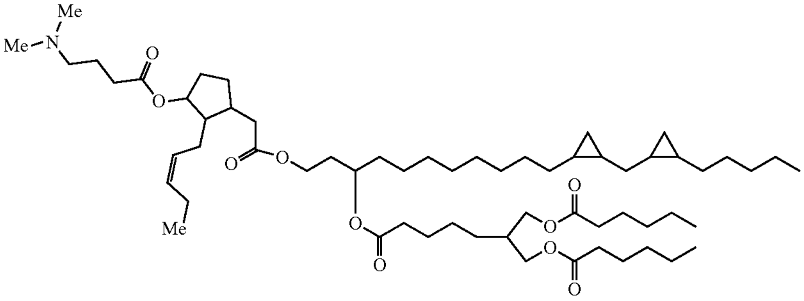 [SMILES: CC/C=C\CC1C(CC(=O)OCCC(CCCCCCCCC2CC2CC2CC2CCCCC)OC(=O)CCCCC(COC(=O)CCCCC)COC(=O)CCCCC)CCC1OC(=O)CCCN(C)C] | 9.44 |
| PNI 518 | 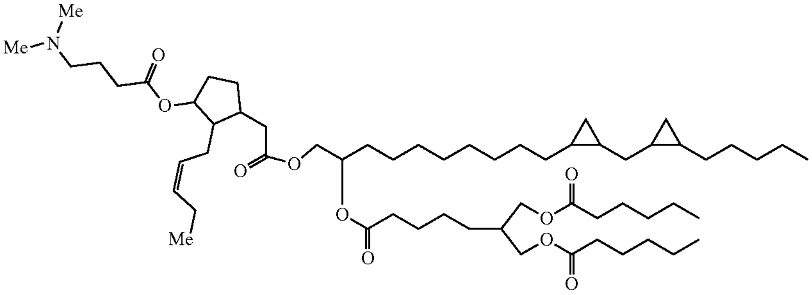 [SMILES: CC/C=C\CC1C(CC(=O)OCC(CCCCCCCCC2CC2CC2CC2CCCCC)OC(=O)CCCCC(COC(=O)CCCCC)COC(=O)CCCCC)CCC1OC(=O)CCCN(C)C] | 9.44 |

TABLE 2-continued
| ID | Representative Compounds | Theoretical pKa$_1$ |
|---|---|---|
| PNI 519 | 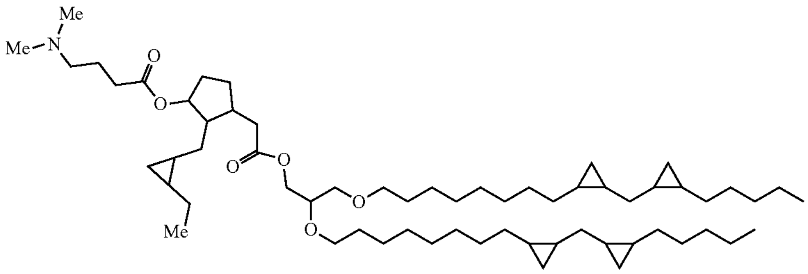 [SMILES: CCCCCC1CC1CC1CC1CCCCCCCCOCC(COC(=O)CC1CCC(OC(=O)CCCN(C)C)C1CC1CC1CC)OCCCCCCCCC1CC1CC1CC1CCCCC] | 9.44 |
| PNI 520 | 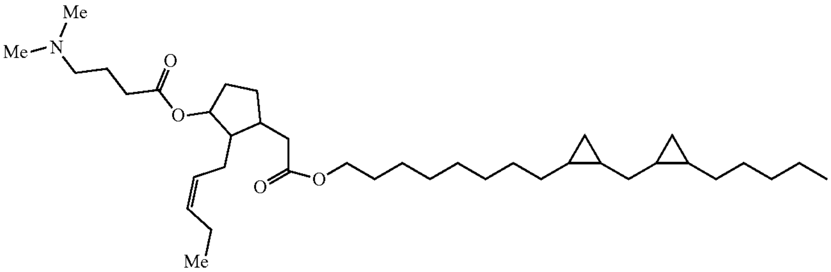 [SMILES: CC/C=C\CC1C(CC(=O)OCCCCCCCCC2CC2CC2CC2CCCCC)CCC1OC(=O)CCCN(C)C] | 9.44 |
| PNI 317 | 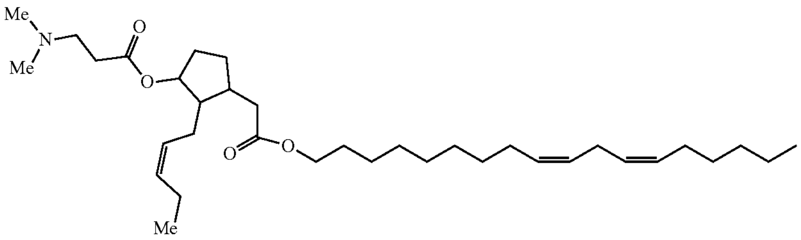 [SMILES: CC/C=C\CC1C(CC(=O)OCCCCCCCC/C=C\C/C=C\CCCCC)CCC1OC(=O)CCN(C)C] | 8.67 |
| PNI 318 | 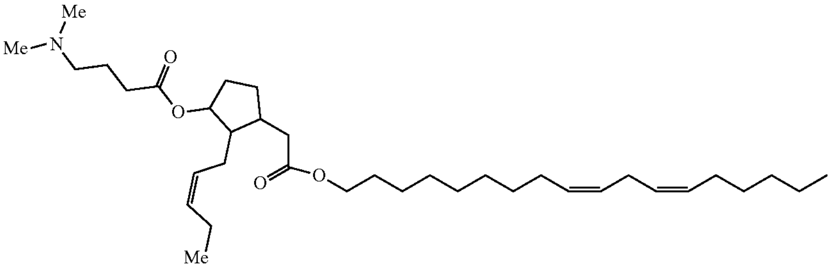 [SMILES: CC/C=C\CC1C(CC(=O)OCCCCCCCC/C=C\C/C=C\CCCCC)CCC1OC(=O)CCCN(C)C] | 9.44 |
| PNI 320 | 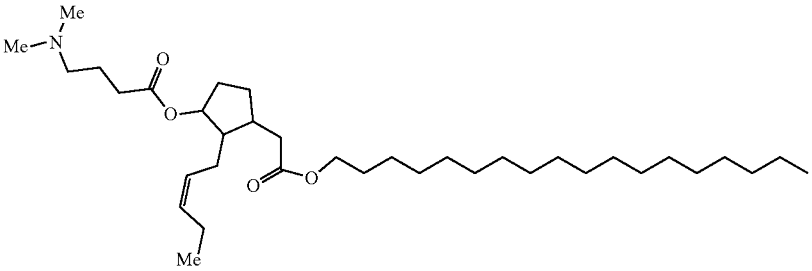 [SMILES: CC/C=C\CC1C(CC(=O)OCCCCCCCCCCCCCCCCCC)CCC1OC(=O)CCCN(C)C] | 9.44 |

TABLE 2-continued

| ID | Representative Compounds | Theoretical pKa[1] |
|---|---|---|
| PNI 521 | 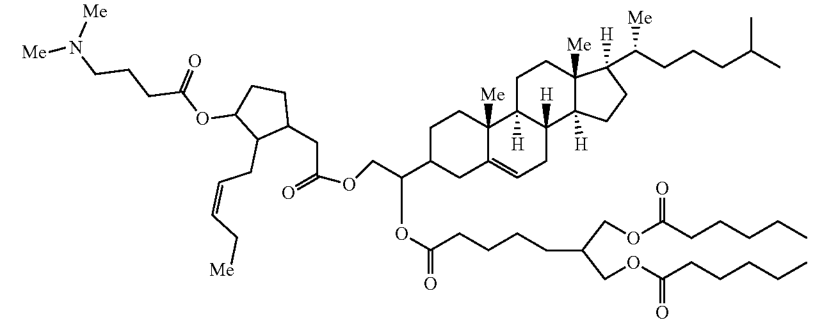 | 9.44 |
| PNI 522 | 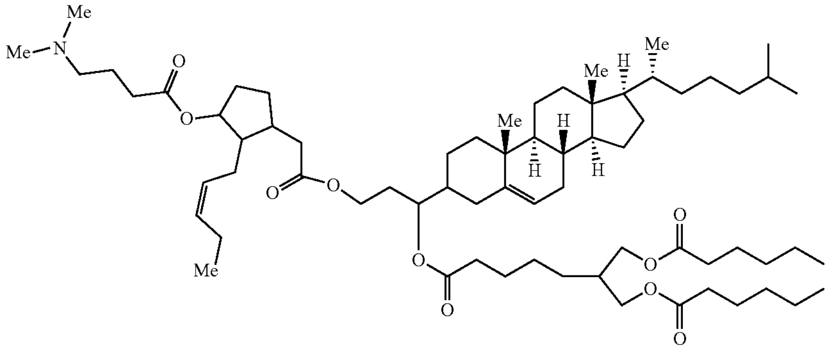 | 9.44 |

[1]Predicted through ChemDraw.

The ionizable lipids of the present invention have asymmetric centers, and occur as racemates, racemic mixtures, individual enantiomers, enantiomeric mixtures, individual diastereomers and as diastereomeric mixtures, with all possible isomers and mixtures thereof.

In embodiments of the invention, the theoretical pKa of lipids in Table 2 is predicted using ChemDraw™ Professional. The experimental pKa of formulated lipid nanoparticles comprising lipids in Table 1 is calculated using a TNS assay. The procedure for TNS assay is described in Example 25.

There is provided according to embodiments of the invention a lipid mix composition including any of the compounds supra combined with a structural lipid, a steroid, and a stabilizing agent as well as at least one therapeutic agent.

In embodiments, the structural lipid includes one or more structural lipids selected from the group consisting of DSPC, DSPE, DPPC, DMPC, DOPC, POPC, DOPE and SM. In preferred embodiments, the structural lipid is DSPC. In other preferred embodiments, the structural lipid is DOPE.

In embodiments, the stabilizing agent includes one or more surfactants and/or polymer conjugated lipids.

In embodiments, the molar ratio of the compound to the rest of the components is 30 Mol % to 70 Mol %. In embodiments, the sterol is cholesterol. In embodiments, the therapeutic agent includes one or more nucleic acid. In embodiments, the therapeutic agent includes one or more polypeptides. In some embodiments, the therapeutic agent includes both a nucleic acid and a polypeptide component.

There is provided according to the invention a compound as appears above, or a pharmaceutically acceptable salt thereof, wherein the experimental pKa of nanoparticles is in the range 5.6-7.1.

There is provided according to the invention a pharmaceutical composition comprising a compound as defined above, and at least one pharmaceutically acceptable carrier or excipient.

There is provided according to the invention a lipid mix composition wherein the compound is present at about 40 Mol %-49 Mol %, structural lipid is present at about 11-30 Mol %, cholesterol is present at about 35 to 39 Mol %, and stabilizing agent is present at about 0.5-3 Mol %. In embodiments, the compound is present at 37.5 Mol %. In embodiments, the compound is present at 38.5 Mol %. In embodiments, the structural lipid is present at about 20 Mol %. In embodiments, the stabilizing agent is present at about 1.5 Mol %. In embodiments, the stabilizing agent is present at about 2.5 Mol %.

There is provided according to the invention a lipid mix composition wherein the the stabilizing agent is selected from the group consisting of PEG-DMG 2000, Polyoxyethylene (10) stearyl ether, polyoxyethylene (40) stearate, Polysorbate 80, Polyoxyethylene (4) lauryl ether, Polyoxyethylene (20) stearyl ether, Polyoxyethylene (23) lauryl ether, and D-α-Tocopherol polyethylene glycol 1000 succinate;

There is provided, according to the invention, the use of a compound described above to prepare a therapeutic agent for administering a therapeutic agent to an ex vivo cell.

There is provided, according to the invention, the use of a compound described above in the preparation of a pharmaceutical formulation.

In embodiments, the therapeutic agent further includes a nucleic acid therapeutic.

In embodiments, the nucleic acid therapeutic is an mRNA, siRNA, miRNA, guide RNA, synthetic guide RNA, an artificial chromosome, circular or linearized DNA, DNA minicircles, or msDNA. In embodiments, the use of the composition is for use in the preparation of a vaccine. In embodiments, the vaccine is directed to the prevention of coronavirus infection. According to embodiments of the invention, the mRNA is a self assembling viral RNA.

There is provided according to the invention the use of any one of the compositions described above for the treatment of disease. In further embodiments, the use is for the preparation or administration of a prophylactic vaccine.

In embodiments, the compounds or compositions are for use in a therapeutic or cancer vaccine. In embodiments, the vaccine is directed to the prevention of coronavirus infection. In embodiments, There is provided according to the invention the compounds described above wherein one of the hydrogens is substituted with a halogen. In embodiments, the halogen is Iodine or fluorine.

There is provided according to the invention the use of the lipid mix composition described above in the preparation of a pharmaceutical for modulating Human T cells; CAR-T, TCR, gene-editing, or allogenic T cells. In embodiments, the pharmaceutical is used for modulating T cells, wherein the T cells are isolated from patients, or T cells that have been engineered specifically to T cells or allogenic T cells. In embodiments, the pharmaceutical is used for modifying NKT cells and iNKT cells.

In embodiments, the pharmaceutical further includes a polypeptide. In embodiments, the pharmaceutical further includes a ribonucleoprotein. In further embodiments, the compositions are in the form of lipid particles.

Also provided according to still other embodiments of the invention are pharmaceutical compositions comprising a compound and at least one pharmaceutically acceptable carrier or excipient. In embodiments, the compositions take the form of lipid particles.

BRIEF DESCRIPTION OF THE DRAWINGS

Further features and advantages of the present disclosure will become apparent from the following detailed description, taken in combination with the appended drawings, in which.

It will be noted that throughout the appended drawings, like features are identified by like reference numerals.

DETAILED DESCRIPTION

Figure 1:
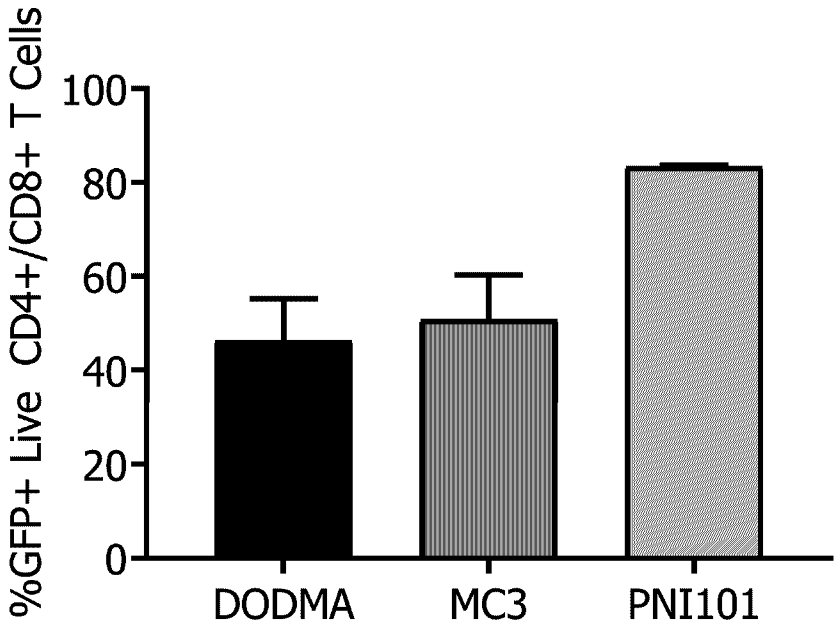
FIG. 1 is a bar graph illustrating relative GFP expression levels in live CD4+/CD8+ T cells mediated by mRNA Lipid Nanoparticles (LNP) comprising DODMA, DLin-MC3-DMA or PNI 101 using CT10 composition at an N/P ratio of 10, and analyzed for gene expression by flow cytometry 48 hours after treatment.

In this disclosure, the word "comprising" is used in a non-limiting sense to mean that items following the word are included, but items not specifically mentioned are not excluded. It will be understood that in embodiments which comprise or may comprise a specified feature or variable or parameter, alternative embodiments may consist, or consist essentially of such features, or variables or parameters. A reference to an element by the indefinite article "a" does not exclude the possibility that more than one of the elements is present, unless the context clearly requires that there be one and only one of the elements.

In this disclosure the recitation of numerical ranges by endpoints includes all numbers subsumed within that range including all whole numbers, all integers and all fractional intermediates (e.g., 1 to 5 includes 1, 1.5, 2, 2.75, 3, 3.80, 4, and 5 etc.). In this disclosure the singular forms an "an", and "the" include plural referents unless the content clearly dictates otherwise. Thus, for example, reference to a composition containing "a compound" includes a mixture of two or more compounds.

In this disclosure term "or" is generally employed in its sense including "and/or" unless the content clearly dictates otherwise.

"Lipid" refers to a structurally diverse group of organic compounds that are fatty acid derivatives or sterols or could be lipid like materials as in lipidoids (example C12-200) and are characterized by being insoluble in water but soluble in many organic solvents.

"Lipid Mix Compositions". Lipid mix compositions refers to the types of components, ratios of components, and the ratio of the total components to the nucleic acid payloads. For example, a lipid mix composition of 40 Mol % ionizable lipid, 20 Mol % structural lipid, 17 Mol % sterol, and 2.5 Mol % stabilizing agent would be a lipid mix composition. PNI123/DSPC/Cholesterol/PEG-DMG (50:10:38.5:1.5 mol %) would be a more specific composition. PNI123/DOPE/Cholesterol/PEG-DMG (47.5:10:38.5:1.5) would be yet another specific composition.

As used herein, "N/P" is the ratio of moles of the amine groups of ionizable lipids to those of the phosphate groups of nucleic acid. In embodiments of the invention, N/P ratios are from 6 to 10, and most preferred ratios are from N/P 4-12. In one embodiment the N/P ratio is 6, 8, or 10. The nucleic acid component is associated with this lipid mix composition to form a lipid nucleic acid particle, or LNP, in a premeditated ratio such as ionizable lipid amine (N) to nucleic acid phosphate ratio (P) of N/P 4, N/P 6, N/P 8, N/P 10, N/P 12 or another relevant particular N/P ratio.

"Lipid Particles". The invention provides lipid particles manufactured from the lipid mix compositions described above. The lipid particle represents the physical organization of the lipid mix composition with the therapeutic agent and among the components. A lipid nanoparticle is a lipid particle. Lipid particles are generally spherical assemblies of lipids, nucleic acid, cholesterol and stabilizing agents. Positive and negative charges, ratios, as well as hydrophilicity and hydrophobicity dictate the physical structure of the lipid particles in terms of size and orientation of components. The structural organization of these lipid particles may lead to an aqueous interior with a minimum bilayer as in liposomes or it may have a solid interior as in a solid nucleic acid lipid nanoparticle. There may be phospholipid monolayers or bilayers in single or multiple forms. Lipid particles are between 1 and 1000 μm in size.

"Viability" when referring to cells in vitro, means the ability to continue to grow, divide, and continue to grow and divide, as is normal for the cell type or tissue culture strain. Cell viability is affected by harsh conditions or treatments. Cell viability is critical in ex vivo therapy or parenteral administration.

"Ionizable lipid." The compositions of the invention comprise ionizable lipids. As used herein, the term "ionizable lipid" refers to a lipid that is cationic or becomes ionizable (protonated) as the pH is lowered below the pKa of the ionizable group of the lipid, but is more neutral at higher pH values. At pH values below the pKa, the lipid is then able to associate with negatively charged nucleic acids (e.g., oligonucleotides). As used herein, the term "ionizable lipid" includes lipids that assume a positive charge on pH decrease from physiological pH, and any of a number of lipid species that carry a net positive charge at a selective pH, such as physiological pH. Permanently cationic lipids such as DOTMA have proven too toxic. for clinical use. The ionizable lipid is present in lipid formulations according to other embodiments of the invention, preferably in a ratio of about 30 to about 70 Mol %, in some embodiments, about 30 Mol %, in other embodiments, about 40 Mol %, in other embodiments, about 45 Mol % in other embodiments, about 47.5 Mol % in other embodiments, about 50 Mol %, in still other embodiments, and about 60 Mol % in yet others ("Mol %" means the percentage of the total moles that is of a particular component). The term "about" in this paragraph signifies a plus or minus range of 5 Mol %. DODMA, or 1,2-dioleyloxy-3-dimethylaminopropane, is an ionizable lipid, as is DLin-MC3-DMA or O-(Z,Z,Z,Z-heptatriaconta-6,9,26,29-tetraen-19-yl)-4-(N,N-dimethylamino) ("MC3").

Lipid particles may be generated from the lipid formulations including the ionizable lipids of the invention.

Structural lipids, also known as "helper lipids" or "neutral lipids" are incorporated into lipid formulations and lipid particles of the invention in some embodiments. The lipid formulations and lipid particles of the invention include one or more structural lipids at about 10 to 40 Mol % of the composition. Suitable structural lipids support the formation of particles during manufacture. Structural lipids refer to any one of a number of lipid species that exist in either in an anionic, uncharged or neutral zwitterionic form at physiological pH. Representative structural lipids include diacylphosphatidylcholines, diacylphosphatidylethanolamines, diacylphosphatidylglycerols, ceramides, sphingomyelins, dihydrosphingomyelins, cephalins, and cerebrosides.

Exemplary structural lipids include zwitterionic lipids, for example, distearoylphosphatidylcholine (DSPC), dioleoylphosphatidylcholine (DOPC), dipalmitoylphosphatidylcholine (DPPC), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearoyl-2-oleoyl-phosphatidyethanol amine (SOPE), and 1,2-dielaidoyl-sn-glycero-3-phophoethanolamine (trans DOPE). In one preferred embodiment, the structural lipid is distearoylphosphatidylcholine (DSPC).

In another embodiment, the structural lipid is any lipid that is negatively charged at physiological pH. These lipids include phosphatidylglycerols such as dioleoylphosphatidylglycerol (DOPG), dipalmitoylphosphatidylglycerol (DPPG), palmitoylolеyolphosphatidylglycerol (POPG), cardiolipin, phosphatidylinositol, diacylphosphatidylserine, diacylphosphatidic acid, and other anionic modifying groups joined to neutral lipids. Other suitable structural lipids include glycolipids (e.g., monosialoganglioside GM1).

Stabilizers or Stabilizing agents are included in lipid formulations embodiments to ensure integrity of the mixtures upon self assembly. Stabilizing agents are a class of molecules which disrupt or help form the hydrophobic-hydrophilic interactions among molecules. Suitable stabilizing agent include, but are not limited to, polysorbate 80 (also known as Tween 80, IUPAC name 2-[2-[3,4-bis(2-hydroxyethoxy)oxolan-2-yl]-2-(2-hydroxyethoxy)ethoxy]ethyl octadec-9-enoate), Myrj52 (Polyoxyethylene (40) stearate), Brij™ S10 (Polyoxyethylene (10) stearyl ether), BRIJ™ L4=Polyoxyethylene (4) lauryl ether; BRIJ™ S20=Polyoxyethylene (20) stearyl ether; BRIJ™ S35=Polyoxyethylene (23) lauryl ether; TPGS 1000=D-α-Tocopherol polyethylene glycol 1000 succinate; Tween 20/Polysorbate 80/Tridecyl-D-maltoside in equal ratios. In other preferred embodiments, the stabilizing agent includes PEGylated lipids including PEG-DMG 2000. Polyethylene glycol conjugated lipids may also be used. The stabilizing agent may be used alone or in combinations with each other.

In some embodiments, the stabilizing agent includes about 0.1 to 3 Mol % of the overall lipid mixture. In some embodiments, the stabilizing agent includes about 0.5 to 2.5 Mol % of the overall lipid mixture. In some embodiments, the stabilizing agent is present at greater than 2.5 Mol %. In some embodiments the stabilizing agent is present at 5 Mol %. In some embodiments the stabilizing agent is present at 10 Mol %. In some embodiments, the stabilizing agent is about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, and so forth. In other embodiments, the stabilizing agent is 2.6-10 Mol % of the lipid mixture. In other embodiments, the stabilizing agent is present at greater than 10 Mol % of the lipid mixture.

Sterols are included in the preferred lipid mix compositions for certain applications, and lipid particles made therefrom include cholesterol and phytosterol. In the lipid mixes of the invention, cholesterol is present at about 30 to 50 Mol % of the final lipid mix in some embodiments. Alternately cholesterol is present at about 35 to 41 Mol % of the final lipid mix. In some embodiments cholesterol is present at 17% to 38.5% In other embodiments, sterol is absent. In some embodiments a modified sterol or synthetically derived sterol is present.

Nucleic Acids. The lipid mix compositions and lipid particles of the present invention are useful for the systemic or local delivery of nucleic acids. As used herein, the term "nucleic acid therapeutic" (NAT) is meant to include any oligonucleotide or polynucleotide whose delivery into a cell causes a desirable effect. The definition includes diagnostic agents and research reagents which follow the same physical principles afforded by the invention. Fragments containing up to 50 nucleotides are generally termed oligonucleotides, and longer fragments are called polynucleotides. In particular embodiments, oligonucleotides of the present invention are 20-50 nucleotides in length. In embodiments of the invention, oligonucleotides are 996 to 4500 nucleotides in length, as in the case of messenger RNA. In particular embodiments oligonucleotides of the invention include up to 14,000 nucleotides The term "nucleic acid" also refers to ribonucleotides, deoxynucleotides, modified ribonucleotides, modified deoxyribonucleotides, modified phosphate-sugar-backbone oligonucleotides, other nucleotides, nucleotide analogs, and combinations thereof, and can be single stranded, double stranded, or contain portions of both double stranded and single stranded sequence, as appropriate. mRNA can be modified or unmodified, base modified, and may include different type of capping structures, such as Cap1. In some embodiments nucleic acid refers to self amplifying RNA ("saRNA"). Lundstrom, K. Nanoparticle-based delivery of self-amplifying RNA. Gene Ther 27, 183-185 (2020).

As used herein, the terms "polynucleotide" and "oligonucleotide" are used interchangeably and mean single-stranded and double-stranded polymers of nucleotide monomers, including 2'-deoxyribonucleotides (DNA) and ribonucleotides (RNA) linked by internucleotide phosphodiester bond linkages, e.g., 3'-5' and 2'-5', inverted linkages, e.g., 3'-3' and 5'-5', branched structures, or internucleotide analogs. Polynucleotides have associated counter ions, such as H+, NH4+, trialkylammonium, Mg2+, Na+, and the like. A polynucleotide may be composed entirely of deoxyribonucleotides, entirely of ribonucleotides, or chimeric mixtures thereof. Polynucleotides may include internucleotide, nucleobase and/or sugar analogs.

The term "polypeptides" herein encompasses "oligopeptides" and "proteins" and tertiary and quaternary structures thereof, that are therapeutic agents in some embodiments. An oligopeptide generally consists of from two to twenty amino acids. A polypeptide is a single linear chain of many amino acids of any length held together by amide bonds. A protein consists of one or more and may include structural proteins, energy catalysts, albumin, hemoglobin, immunoglobulins, and enzymes.

A "ribonucleoprotein" is a complex of Cas9 protein and guide RNA in some embodiments. In some embodiments, a ribonucleoprotein is the therapeutic agent referred to in aspects of the invention.

Currently, nucleic acid therapeutics include deoxyribonucleic acid, complementary deoxyribonucleic acid, complete genes, ribonucleic acid, oligonucleotides and ribozymes for gene therapies targeting a variety of diseases, such as cancer, infectious diseases, genetic disorders and neurodegenerative diseases. As described herein, the nucleic acid therapeutic (NAT) is incorporated into lipid particle during its formation with compounds of the invention. More than one nucleic acid therapeutic may be incorporated in this way. They may be derived from natural sources, or more commonly, synthesized or grown in culture. Examples of nucleic acid therapeutics include but are not limited to antisense oligonucleotides, ribozymes, microRNA, mRNA, ribozyme, tRNA, tracrRNA, sgRNA, snRNA, siRNA, shRNA, ncRNA, miRNA, mRNA, pre-condensed DNA, pDNA or an aptamer. Nucleic acid Reagents are used to silence genes (with for example siRNA), express genes (with for example mRNA), edit genomes (with for example CRISPR/Cas9), and reprogram cells for return to the originating organism (for example ex vivo cell therapy to reprogram immune cells for cancer therapy; autologous transfer or allogenic transfer).

The nucleic acid that is present in a lipid particle according to this invention includes any form of nucleic acid that is known. The nucleic acids used herein can be single-stranded DNA or RNA, or double-stranded DNA or RNA, or DNA-RNA hybrids. Examples of double-stranded DNA include structural genes, genes including control and termination regions, and self-replicating systems such as viral or plasmid DNA. Examples of double-stranded RNA include siRNA and other RNA interference reagents. Single-stranded nucleic acids include antisense oligonucleotides, guide RNA, including CRISPR-Cas9 gRNA, ribozymes, microRNA, mRNA, and triplex-forming oligonucleotides. More than one nucleic acid may be incorporated into the lipid particle, for example mRNA and guide RNA together, or different types of each, or in combination with protein.

Plasmid DNA is a preferred nucleic acid to be formulated in embodiments of the invention. A plasmid is a DNA molecule that is separate from chromosomal DNA in a cell, and can replicate independently. Plasmids range from less than 1000 nucleotides to tens of thousands of nucleotides in size. The most common form is small circular, double-stranded DNA. Plasmids can be synthesized and delivered to mammalian cells for therapeutic purposes. Synthetic plasmids are used as vectors in molecular cloning, serving to drive the replication of recombinant DNA sequences within host organisms. Plasmids may be introduced into cells via transformation using physical methods such as electroporation, or chemical means as in the present invention, via lipid particle-enhanced transfection. These lipid mix compositions of the invention have several advantages over physical techniques, including i) high biocompatibility and low toxicity in cell and tissue systems ii) relative ease of manufacture iii) lipophilic matrices are less susceptible to the erosion phenomena observed in polymeric systems iv) an increased circulatory half-life in vivo due to their invisibility from the immune system.

In some cases, a nucleic acid encodes a genetically engineered receptor that specifically binds to a ligand, such as a recombinant receptor, and a molecule involved in a metabolic pathway, or functional portion thereof. Alternately, the molecule involved in a metabolic pathway is a recombinant molecule, including an exogenous entity. A genetically engineered receptor and the molecule involved in a metabolic pathway may be encoded by one nucleic acid or two or more different nucleic acids. In some examples, a first nucleic acid might encode a genetically engineered receptor that specifically binds to a ligand and a second nucleic acid might encode the molecule involved in a metabolic pathway.

"Therapeutic agents" as used herein include nucleic acid therapeutics as herein described, polypeptides as herein described, and polysaccharides, salts, small molecules, inorganic ions and radionuclides.

The lipid particles according to some embodiments of the invention can be characterized by electron microscopy. The particles of the invention having a substantially solid core have an electron dense core as seen by electron microscopy. One such structure is disclosed in U.S. Pat. No. 9,758,795 by Cullis et al. Electron dense is defined such that area-averaged electron density of the interior 50% of the projected area of a solid core particle (as seen in a 2-D cryo EM image) is not less than x % (x=20%, 40%, 60%) of the maximum electron density at the periphery of the particle. Electron density is calculated as the absolute value of the difference in image intensity of the region of interest from the background intensity in a region containing no nanoparticle.

The lipid particles of the invention can be assessed for size using devices that size particles in solution, such as the Malvern™ Zetasizer™. The particles generally have a mean particle diameter of from 30 nm to 1000 nm. A subgroup of lipid particles is "lipid nanoparticles" or LNP with a mean diameter of from about 15 to about 300 nm. In some embodiments, the mean particle diameter is greater than 300 nm. In some embodiments, the lipid particle has a diameter of about 300 nm or less, 250 nm or less, 200 nm or less, 150 nm or less, 100 nm or less, or 50 nm or less. In one embodiment, the lipid particle has a diameter of from about 50 to about 150 nm. Smaller particles generally exhibit increased circulatory lifetime in vivo compared to larger particles. Smaller particles have an increased ability to reach tumor sites than larger nanoparticles. In one embodiment, the lipid particle has a diameter from about 15 to about 50 nm.

Mixing. The lipid particles according to embodiments of the invention can be prepared by standard T-tube mixing techniques, turbulent mixing, trituration mixing, agitation promoting orders self-assembly, or passive mixing of all the elements with self-assembly of elements into nanoparticles. A variety of methods have been developed to formulate lipid nanoparticles (LNP) containing genetic drugs. Suitable methods are disclosed in U.S. Pat. No. 5,753,613 by Ansell, Mui and Hope and U.S. Pat. No. 6,734,171 by Saravolac et al., by way of example. These methods include mixing preformed lipid particles with nucleic acid therapeutic (NAT) in the presence of ethanol or mixing lipid dissolved in ethanol with an aqueous media containing NAT and result in lipid particles with NAT encapsulation efficiencies of 65-99%. Both of these methods rely on the presence of ionizable lipid to achieve encapsulation of NAT and a stabilizing agent to inhibit aggregation and the formation of large structures. The properties of the lipid particle systems produced, including size and NAT encapsulation efficiency, are sensitive to a variety of lipid mix composition parameters such as ionic strength, lipid and ethanol concentration, pH, NAT concentration and mixing rates.1

Microfluidic two-phase droplet techniques have been applied to produce monodisperse polymeric microparticles for drug delivery or to produce large vesicles for the encapsulation of cells, proteins, or other biomolecules. The use of hydrodynamic flow focusing, a common microfluidic technique to provide rapid mixing of reagents, to create monodisperse liposomes of controlled size has been demonstrated.

In general, parameters such as the relative lipid and NAT concentrations at the time of mixing, as well as the mixing rates are difficult to control using current formulation procedures, resulting in variability in the characteristics of NAT produced, both within and between preparations. Automatic micro-mixing instruments such as the NanoAssemblr® instruments (Precision NanoSystems Inc, Vancouver, Canada) enable the rapid and controlled manufacture of nanomedicines (liposomes, lipid nanoparticles, and polymeric nanoparticles). NanoAssemblr® instruments accomplish controlled molecular self-assembly of nanoparticles via microfluidic mixing cartridges that allow millisecond mixing of nanoparticle components at the nanoliter, microlitre, or larger scale with customization or parallelization. Rapid mixing on a small scale allows reproducible control over particle synthesis and quality that is not possible in larger instruments.

Preferred methods incorporate instruments such as the microfluidic mixing devices like the NanoAssemblr® Spark™, Ignite™, Benchtop™ and NanoAssemblr® Blaze™ in order to achieve nearly 100% of the nucleic acid used in the formation process is encapsulated in the particles in one step. In one embodiment, the lipid particles are prepared by a process by which from about 90 to about 100% of the nucleic acid used in the formation process is encapsulated in the particles.

U.S. Pat. Nos. 9,758,795 and 9,943,846, by Cullis et al. describe methods of using small volume mixing technology and novel formulations derived thereby. U.S. Application Pub. No. 20160022580 by Ramsay et al. describes more advanced methods of using small volume mixing technology and products to formulate different materials. U.S. Pat. No. 9,943,846 by Walsh, et al. discloses microfluidic mixers with different paths and wells to elements to be mixed. PCT Publication WO2017117647 by Wild, Leaver and Taylor discloses microfluidic mixers with disposable sterile paths. U.S. Pat. No. 10,076,730 by Wild, Leaver and Taylor discloses bifurcating toroidal micromixing geometries and their application to micromixing. PCT Publication No. WO2018006166 by Chang, Klaassen, Leaver et al. discloses a programmable automated micromixer and mixing chips therefore. US Design Nos. D771834, D771833, D772427, and D803416 by Wild and Leaver, and D800335, D800336 and D812242 by Chang et al., disclose mixing cartridges having microchannels and mixing geometries for mixer instruments sold by Precision NanoSystems Inc.

In embodiments of the invention, devices for biological microfluidic mixing are used to prepare the lipid particles according to embodiments of the invention. The devices include a first and second stream of reagents, which feed into the microfluidic mixer, and lipid particles are collected from the outlet, or emerge into a sterile environment.

The first stream includes a therapeutic agent in a first solvent. Suitable first solvents include solvents in which the therapeutic agents are soluble and that are miscible with the second solvent. Suitable first solvents include aqueous buffers. Representative first solvents include citrate and acetate buffers or other low pH buffers.

The second stream includes lipid mix materials in a second solvent. Suitable second solvents include solvents in which the ionizable lipids according to embodiments of the invention are soluble, and that are miscible with the first solvent. Suitable second solvents include 1,4-dioxane, tetrahydrofuran, acetone, acetonitrile, dimethyl sulfoxide, dimethylformamide, acids, and alcohols. Representative second solvents include aqueous ethanol 90%, or anhydrous ethanol.

In one embodiment of the invention, a suitable device includes one or more microchannels (i.e., a channel having its greatest dimension less than 1 millimeter). In one example, the microchannel has a diameter from about 20 to about 300 μm. In examples, at least one region of the microchannel has a principal flow direction and one or more surfaces having at least one groove or protrusion defined therein, the groove or protrusion having an orientation that forms an angle with the principal direction (e.g., a staggered herringbone mixer), as described in U.S. Pat. No. 9,943,846, or a bifurcating toroidal flow as described in U.S. Pat. No. 10,076,730. To achieve maximal mixing rates, it is advantageous to avoid undue fluidic resistance prior to the mixing region. Thus, one example of a device has non-microfluidic channels having dimensions greater than 1000 μm, to deliver the fluids to a single mixing channel.

Less automated mixing methods and instruments such as those disclosed in Zhang, S-h et al.,[2] and Stroock A et al., U.S. Published Patent Application US20040262223, and Jeffs, L B et al.[3], are also useful in creating lipid particle compositions of the invention.

The ionizable lipids of the present invention may be used to deliver a therapeutic agent to a cell, in vitro or in vivo. In particular embodiments, the therapeutic agent is a nucleic acid, which is delivered to a cell using nucleic acid-lipid particles of the present invention. The nucleic acid can be an siRNA, miRNA, an LNA, a plasmid, replicon, an mRNA, a guide RNA, a transposon, or a single gene. In other embodiments, the therapeutic agent to be delivered to a cell or cells is a gene editing technology. Gene editing technologies are a group of technologies that change an organism's DNA, and enable addition, removal, or alteration of genetic material at particular locations in the genome. There are several methods for genome editing including CRISPR-Cas9, (clustered regularly interspaced short palindromic repeats and CRISPR-associated protein 9), TALEN and ZFN[4].

In other embodiments, the therapeutic agent is an oligopeptide, polypeptide, or protein which is delivered to a cell using peptide-lipid particles of the present invention. In other embodiments, the therapeutic agent is a mixture of nucleic acid and protein components, such as Cas9. The methods and lipid mix compositions may be readily adapted for the delivery of any suitable therapeutic agent for the treatment of any disease or disorder that would benefit from such treatment.

In certain embodiments, the present invention provides methods for introducing a nucleic acid into a cell (i.e. transfection). Transfection is a technique commonly used in molecular biology for the introduction of nucleic acid therapeutics (or NATs) from the extracellular to the intracellular space for the purpose of transcription, translation and expression of the delivered gene(s) or for down regulating the expression of a disease-related gene. Transfection efficiency is commonly defined as either the i) percentage of cells in the total treated population showing positive expression of the delivered gene, as measured by live or fixed cell imaging (for detection of fluorescent protein), and flow cytometry or ii) the intensity or amount of protein expressed by treated cell(s) as analyzed by live or fixed cell imaging or flow cytometry or iii) using protein quantification techniques such as ELISA, or western blot. These methods may be carried out by contacting the particles or lipid mix compositions of the present invention with the cells for a period of time sufficient for intracellular delivery to occur.

Typical applications include using well known procedures to provide intracellular delivery of siRNA to knock down or silence specific cellular targets in vitro and in vivo. Alternatively, applications include delivery of DNA or mRNA sequences that code for therapeutically useful polypeptides. In this manner, therapy is provided for genetic diseases by supplying deficient or absent gene products. Methods of the present invention may be practiced in vitro, ex vivo, or in vivo. For example, the lipid mix compositions of the present invention can also be used for delivery of nucleic acids to cells in vivo, using methods which are known to those of skill in the art. In another example, the lipid mix compositions of the invention can be used for delivery of nucleic acids to a sample of patient cells that are ex vivo, then are returned to the patient.

The delivery of nucleic acid therapeutics by a lipid particle of the invention is described below.

For in vivo administration, the pharmaceutical compositions are preferably administered parenterally (e.g., intraarticularly, intravenously, intraperitoneally, subcutaneously, intrathecally, intradermally, intratracheally, intraosseous, intramuscularly or intratumorally). In particular embodiments, the pharmaceutical compositions are administered intravenously, intrathecally, or intraperitoneally by a bolus injection. Other routes of administration include topical (skin, eyes, mucus membranes), oral, pulmonary, intranasal, sublingual, rectal, and vaginal.

For ex vivo applications, the pharmaceutical compositions are preferably administered to biological samples that have been removed from the organism, then the cells are washed and restored to the organism. The organism may be a mammal, and in particular may be human. This process is used for cell reprogramming, genetic restoration, immunotherapy, for example.

In one embodiment, the present invention provides a method of modulating the expression of a target polynucleotide or polypeptide. These methods generally comprise contacting a cell with a lipid particle of the present invention that is associated with a nucleic acid capable of modulating the expression of a target polynucleotide or polypeptide. As used herein, the term "modulating" refers to altering the expression of a target polynucleotide or polypeptide. Modulating can mean increasing or enhancing, or it can mean decreasing or reducing.

In related embodiments, the present invention provides a method of treating a disease or disorder characterized by overexpression of a polypeptide in a subject, comprising providing to the subject a pharmaceutical composition of the present invention, wherein the therapeutic agent is selected from an siRNA, a microRNA, an antisense oligonucleotide, and a plasmid capable of expressing an siRNA, a microRNA, or an antisense oligonucleotide, and wherein the siRNA, microRNA, or antisense RNA includes a polynucleotide that specifically binds to a polynucleotide that encodes the polypeptide, or a complement thereof.

In related embodiments, the present invention provides a method of treating a disease or disorder characterized by under-expression of a polypeptide in a subject, comprising providing to the subject a pharmaceutical composition of the present invention, wherein the therapeutic agent is selected from an mRNA, a self amplifying RNA (SAM or saRNA), a self-replicating DNA, or a plasmid, includes a nucleic acid therapeutic that specifically encodes or expresses the under-expressed polypeptide, or a complement thereof.

Methods of delivery of biological active agents for treatment of disease include, in one embodiment, the compounds, compositions, methods and uses of the invention are for delivering a biologically active agent to liver cells (e.g. hepatocytes). In one embodiment, the compounds, compositions, methods and uses of the invention are for delivering a biologically active agent to a tumor or to tumor cells (e.g. a primary tumor or metastatic cancer cells). In another embodiment, the compounds, compositions, methods and uses are for delivering a biologically active agent to the skin adipose, muscle and lymph nodes (subcutaneous dosing).

For delivery of a biologically active agent to the liver or liver cells, in one embodiment a composition of the invention is contacted with the liver or liver cells of the via parenteral administration (e.g. intravenous, intramuscular, subcutaneous administration) or local administration (e.g. direct injection, portal vein injection, catheterization, stenting), to facilitate delivery. For delivery of a biologically active agent to the kidney or kidney cells, in one embodiment a composition of the invention is contacted with the kidney or kidney cells of the patient via parenteral administration (e.g. intravenous, intramuscular, subcutaneous administration) or local administration (e.g. direct injection, catheterization, stenting), to facilitate delivery. For delivery of a biologically active agent to a tumor or tumor cells, in one embodiment, a composition of the invention is contacted with the tumor or tumor cells of the patient via parenteral administration (e.g. intravenous, intramuscular, subcutaneous administration) or local administration (e.g. direct injection, catheterization, stenting), to facilitate delivery.

For delivery of a biologically active agent to the CNS or CNS cells), in one embodiment, a composition of the invention is contacted with the CNS or CNS cells (e.g. brain cells and/or spinal cord cells) of the patient via parenteral administration (e.g. intravenous, intramuscular, subcutaneous administration) or local administration (e.g. direct injection, catheterization, stenting, osmotic pump administration (e.g. intrathecal or ventricular)), to facilitate delivery. For delivery of a biologically active agent to the Peripheral Nervous System (PNS) or PNS cells, in one embodiment a composition of the invention is contacted with the PNS or PNS cells of the patient via parenteral administration (e.g. intravenous, intramuscular, subcutaneous administration) or local administration (e.g. direct injection), to facilitate delivery. For delivery of a biologically active agent to a lung or lung cells, in one embodiment a composition of the invention is contacted with the lung or lung cells of the patient via parenteral administration (e.g. intravenous, intramuscular, subcutaneous administration) or local administration (e.g. pulmonary administration directly to lung tissues and cells), to facilitate delivery.

For delivery of a biologically active agent to the vasculature or vascular cells, in one embodiment, a composition of the invention is contacted with the vasculature or vascular cells of the patient via parenteral administration (e.g. intravenous, intramuscular, subcutaneous administration) or local administration (e.g. clamping, catheterization, stenting), to facilitate delivery.

For delivery of a biologically active agent to the skin or skin cells (e.g. dermis cells and/or follicular cells), in one embodiment, a composition of the invention is contacted with the skin or skin cells (e.g. dermis cells and/or follicular cells) of the patient via parenteral administration (e.g. intravenous, intramuscular, subcutaneous administration) or local administration (e.g. direct dermal application, iontophoresis), to facilitate delivery. For delivery of a biologically active agent to an eye or ocular cells (e.g. macula, fovea, cornea, retina), in one embodiment a composition of the invention is contacted with the eye or ocular cells (e.g. macula, fovea, cornea, retina) of the patient via parenteral administration (e.g. intravenous, intramuscular, subcutaneous administration) or local administration (e.g. direct injection, intraocular injection, periocular injection, subretinal, iontophoresis, use of eyedrops, implants), to facilitate delivery. For delivery of a biologically active agent to an ear or cells of the ear (e.g. cells of the inner ear, middle ear and/or outer ear), in one embodiment composition of the invention is contacted with the ear or cells of the ear (e.g. cells of the inner ear, middle ear and/or outer ear) of the patient as is generally known in the art, such as via parenteral administration (e.g. intravenous, intramuscular, subcutaneous administration) or local administration (e.g. direct injection), to facilitate delivery. For delivery of a biologically active agent (e.g. RNA encoding an immunogen) to cells of the immune system (e.g. antigen-presenting cells, including professional antigen presenting cells), in one embodiment composition of the invention is delivered intramuscularly, after which immune cells can infiltrate the delivery site and process delivered RNA and/or process encoded antigen produced by non-immune cells, such as muscle cells. Such immune cells can include macrophages (e.g. bone marrow derived macrophages), dendritic cells (e.g. bone marrow derived plasmacytoid dendritic cells and/or bone marrow derived myeloid dendritic cells), monocytes (e.g. human peripheral blood monocytes), etc. (for example, see WO2012/006372 by Geall, Andy et al.).

Immunization. For immunization purposes, a composition of the invention will generally be prepared as an injectable, a pulmonary or nasal aerosol, or in a delivery device (e.g. syringe, nebulizer, sprayer, inhaler, dermal patch, etc.). This delivery device can be used to administer a pharmaceutical composition to a subject, e.g. to a human, for immunization.

According to the invention, for immunization purposes, in some embodiments, the invention encompasses delivering an RNA that encodes an immunogen. This immunogen elicits an immune response which recognizes the immunogen, to provide immunity against a pathogen, or against an allergen, or against a tumor antigen. Immunizing against disease and/or infection caused by a pathogen is preferred.

The RNA is delivered with a lipid composition of the invention (e.g. formulated as a liposome or LNP). In some embodiments, the invention utilizes LNPs within which immunogen-encoding RNA is encapsulated. Encapsulation within LNPs can protect RNA from RNase digestion. The encapsulation efficiency does not have to be 100%. Presence of external RNA molecules (e.g. on the exterior surface of a liposome or LNP) or "naked" RNA molecules (RNA molecules not associated with a liposome or LNP) is acceptable. Preferably, for a composition comprising lipids and RNA molecules, at least half of the RNA molecules (e.g., at least 50%, at least 60%, at least 65%, at least 70%, at least 75%, at least 80%, at least 85%, at least 90%, at least 95%, at least about 96%, at least about 97%, at least about 98%, or at least 99% of the RNA molecules) are encapsulated in LNPs or complexed LNPs.

Some lipid nanoparticles may comprise a lipid core (e.g., the composition may comprise a mixture of LNPs and nanoparticles with a lipid core). In such cases, the RNA molecules may be encapsulated by LNPs that have an aqueous core, and complexed with the LNPs that have a lipid core by noncovalent interactions (e.g., ionic interactions between negatively charged RNA and cationic lipid). Encapsulation and complexation with LNPs (whether with a lipid or aqueous core) can protect RNA from RNase digestion. The encapsulation/complexation efficiency does not have to be 100%. Presence of "naked" RNA molecules (RNA molecules not associated with a liposome) is acceptable. Preferably, for a composition comprising a population of LNPs and a population of RNA molecules, at least half of the population of RNA molecules (e.g., at least e.g., at least 50%, at least 55%, at least 60%, at least 65%, at least 70%, at least 75%, at least 80%, at least 85%, at least 90%, or at least 95% of the RNA molecules) are either encapsulated in LNPs, or complexed with LNPs.

For delivery of immunogen-coding RNA, the preferred range of LNP diameters is in the range of 60-180 nm, and in more particular embodiments, in the range of 80-160 nm. An LNP can be part of a composition comprising a population of LNPS, and the LNPS within the population can have a range of diameters. For a composition comprising a population of LNPS with different diameters, it is preferred that (1) at least 80% by number of the LNPS have diameters in the range of 60-180 nm, e.g., in the range of 80-160 nm, (ii) the average diameter (by intensity, e.g. Z-average) of the population is ideally in the range of 60-180 nm, e.g., in the range of 80-160 nm; and/or the diameters within the plurality have a polydispersity index <0.2. To obtain LNPS with the desired diameter(s), mixing can be performed using a process in which two feed streams of aqueous RNA solution are combined in a single mixing zone with one stream of an ethanolic lipid solution, all at the same flow rate e.g. in a microfluidic channel. See other description relating to NanoAssemblr® microfluidic mixers sold by Precision NanoSystems Inc., Vancouver, Canada.

Useful mixtures of lipids, for forming lipid compositions (e.g., LNPS) for immunization uses, comprise: a lipid of formula (I); a structural lipid, cholesterol; and a stabilizing agent, such as PEG-DMG. The structural lipid is a neutral zwitterionic lipid, such as DSPC (1,2-diastearoyl-sn-glycero-3-phosphocholine) or DSPE in some embodiments. In certain embodiments, the lipid compositions provided by the invention (such as LNPS) have adjuvant activity, i.e., in the absence of an immunogen, such as protein antigen or a nucleic acid (DNA or RNA), such as a nucleic acid encoding such an antigen.

RNA Molecules. After in vivo administration of an immunization composition, the delivered RNA is released and is translated inside a cell to provide the immunogen in situ. In certain embodiments, the RNA is plus ("+") stranded, so it can be translated by cells without needing any intervening replication steps such as reverse transcription. In certain embodiments, the RNA is a self-replicating RNA. A self-replicating RNA molecule (replicon) can, when delivered to a vertebrate cell even without any proteins, lead to the production of multiple daughter RNAs by transcription from itself (via an antisense copy which it generates from itself). A self-replicating RNA molecule is thus in certain embodiments: a (+) strand molecule that can be directly translated after delivery to a cell, and this translation provides an RNA-dependent RNA polymerase which then produces both antisense and sense transcripts from the delivered RNA. Thus the delivered RNA leads to the production of multiple daughter RNAs. These daughter RNAs, as well as collinear subgenomic transcripts, may be translated themselves to provide in situ expression of an encoded immunogen, or may be transcribed to provide further transcripts with the same sense as the delivered RNA which are translated to provide in situ expression of the immunogen. The overall result of this sequence of transcriptions is an amplification in the number of the introduced replicon RNAs and so the encoded immunogen becomes a major polypeptide product of the host cells.

One suitable system for achieving self-replication is to use an alphavirus-based RNA replicon. These (+) stranded replicons are translated after delivery to a cell to yield a replicase (or replicase-transcriptase). The replicase is translated as a polyprotein which auto cleaves to provide a replication complex which creates genomic (−) strand copies of the (+) strand delivered RNA. These (−) strand transcripts can themselves be transcribed to give further copies of the (+) stranded parent RNA, and also to give a subgenomic transcript which encodes the immunogen. Translation of the subgenomic transcript thus leads to in situ expression of the immunogen by the infected cell. Suitable alphavirus replicons can use a replicase from a sindbis virus, a semliki forest virus, an eastern equine encephalitis virus, a Venezuelan equine encephalitis virus, etc.

Mutant or wild-type virus sequences such as the attenuated TC83 mutant of VEEV can be used in replicons. A preferred self-replicating RNA molecule thus encodes (I) an RNA-dependent RNA polymerase which can transcribe RNA from the self-replicating RNA molecule and (ii) an immunogen. The polymerase can be an alphavirus replicase e.g. comprising one or more of alphavirus proteins nsP1, nsP2, nsP3 and nsP4. Whereas natural alphavirus genomes encode structural virion proteins in addition to the non-structural replicase polyprotein in particular embodiments, a self-replicating RNA molecule of the invention does not encode alphavirus structural proteins. Thus a particular self-replicating RNA can lead to the production of genomic RNA copies of itself in a cell, but not to the production of RNA-containing virions. The alphavirus structural proteins which are necessary for perpetuation in wild-type viruses are absent from self-replicating RNAs of the invention and their place is taken by gene(s) encoding the immunogen of interest, such that the subgenomic transcript encodes the immunogen rather than the structural alphavirus virion proteins. Thus, a self-replicating RNA molecule useful with the invention may have two open reading frames: one encodes a replicase e.g., the first, (5') open reading frame; the other open reading frame encodes an immunogen, e.g., the second, (3') open reading frame. In some embodiments, the RNA may have additional (e.g. downstream) open reading frames e.g. to encode further immunogens or to encode accessory polypeptides. A self-replicating RNA molecule can have a 5' sequence which is compatible with the encoded replicase. Self-replicating RNA molecules can have various lengths, but they are typically about 5000-25000 nucleotides long e.g. 8000-15000 nucleotides, or 9000-12000 nucleotides. Thus, the RNA is longer than seen in conventional mRNA delivery. In some embodiments, the self-replicating RNA is greater than about 2000 nucleotides, such as greater than about: 9000, 12000, 15000, 18000, 21000, 24000, or more nucleotides long.

An RNA molecule may have a 5' cap (e.g. a 7-methylguanosine). This cap can enhance in vivo translation of the RNA. The 5' nucleotide of an RNA molecule useful with the invention may have a 5' triphosphate group. In a capped RNA, this may be linked to a 7-methylguanosine via a 5'-to-5' bridge. A 5' triphosphate can enhance RIG-1 binding and thus promote adjuvant effects. An RNA molecule may have a 3' poly A tail. It may also include a poly A polymerase recognition sequence (e.g. AAUAAA) near its 3' end. An RNA molecule useful with the invention for immunization purposes will typically be single-stranded. Single-stranded RNAs can generally initiate an adjuvant effect by binding to TLR7, TLR8, RNA helicases and/or PKR. RNA delivered in double-stranded form (dsRNA) can bind to TLR3, and this receptor can also be triggered by dsRNA which is formed either during replication of a single-stranded RNA or within the secondary structure of a single-stranded RNA.

RNA molecules for immunization purposes can conveniently be prepared by in vitro transcription (IVT). IVT can use a (cDNA) template created and propagated in plasmid form in bacteria, or created synthetically (for example by gene synthesis and/or polymerase chain-reaction (PCR) engineering methods). As discussed in WO2011/005799 by Hekele, Armin et al., the self-replicating RNA can include (in addition to any 5' cap structure) one or more nucleotides having a modified nucleobase. For instance, a self-replicating RNA can include one or more modified pyrimidine nucleobases, such as pseudouridine and/or 5 methylcytosine residues. In some embodiments, however, the RNA includes no modified nucleobases, and may include no modified nucleotides i.e. all of the nucleotides in the RNA are standard A, C, G and U ribonucleotides (except for any 5' cap structure, which may include a 7' methylguanosine). In other embodiments, the RNA may include a 5' cap comprising a 7' methylguanosine, and the first 1, 2 or 3 5' ribonucleotides may be methylated at the 2' position of the ribose. An RNA used with the invention for immunization purposes ideally includes only phosphodiester linkages between nucleosides, but in some embodiments, it contains phosphoramidate, phosphorothioate, and/or methylphosphonate linkages. The invention includes embodiments in which multiple species of RNAs are formulated with a lipid composition provided by the invention, such as two, three, four or more species of RNA, including different classes of RNA (such as mRNA, siRNA, self-replicating RNAs, and combinations thereof).

Immunogen RNA molecules used with the invention for immunization purposes, in some embodiments, encode a polypeptide immunogen. In these embodiments, after administration, the RNA is translated in vivo and the immunogen can elicit an immune response in the recipient. The immunogen may elicit an immune response against a pathogen (e.g. a bacterium, a virus, a fungus or a parasite) but, in some embodiments, it elicits an immune response against an allergen or a tumor antigen. The immune response may comprise an antibody response (usually including IgG) and/or a cell mediated immune response. The polypeptide immunogen will typically elicit an immune response which recognizes the corresponding pathogen (or allergen or tumor) polypeptide, but in some embodiments the polypeptide may act as a mimotope to elicit an immune response which recognizes a saccharide. The immunogen will typically be a surface polypeptide e.g. an adhesin, a hemagglutinin, an envelope glycoprotein, a spike glycoprotein, etc. The RNA molecule can encode a single polypeptide immunogen or multiple polypeptides. Multiple immunogens can be presented as a single polypeptide immunogen (fusion polypeptide) or as separate polypeptides. If immunogens are expressed as separate polypeptides from a replicon, then one or more of these may be provided with an upstream IRES or an additional viral promoter element. Alternatively, multiple immunogens may be expressed from a polyprotein that encodes individual immunogens fused to a short autocatalytic protease (e.g. foot-and-mouth disease virus 2A protein), or as inteins. In certain embodiments, polypeptide immunogens (e.g., 1, 2, 3, 4, 5, 6, 7, 8, 9, 10, or more immunogens) may be used, either alone or together with a RNA molecule, such as a self-replicating RNA, encoding one or more immunogens (either the same or different as the polypeptide immunogens).

In some embodiments the immunogen elicits an immune response against Coronavirus, whose immunogens include, but are not limited to, those derived from a SARS CoV-1, SARS-CoV-2 (Roujian Lu 1, Xiang Zhao 1, Juan Li 2, et al. "Genomic Characterisation and Epidemiology of 2019 Novel Coronavirus: Implications for Virus Origins and Receptor Binding" Lancet 2020 Feb 22; 395(10224):565-574. doi: 10.1016/S0140-6736(20)30251-8. Epub 2020 Jan 30.); *Neisseria meningitidis* for which useful immunogens include, but are not limited to, membrane proteins such as adhesins, autotransporters, toxins, iron acquisition proteins, and factor H binding protein. A combination of three useful polypeptides is disclosed in Giuliani et al. (2006) Proc Natl Head Sci USA 103(29):10834-9; *Streptococcus pneumoniae*, for which useful polypeptide immunogens are disclosed in WO2009/016515 by Veja, Masignani et al. including the RrgB pilus subunit, the beta-N-acetyl-hexosaminidase precursor (spr0057), spr0096, general stress protein GSP-781 (spr2021, SP2216), serine/threonine kinase StkP (SP1732), and pneumococcal surface adhesin PsaA;

Hepatitis viruses, whose immunogens can include hepatitis B virus surface antigen (HBsAg), hepatitis C virus, delta hepatitis virus, hepatitis E virus, or hepatitis G virus antigens; Rhabdovirus: immunogens include, but are not limited to, those derived from a Rhabdovirus, such as a Lyssavirus (e.g. a Rabies virus) and Vesiculovirus (VSV); Caliciviridae, whose immunogens include, but are not limited to, those derived from Calciviridae, such as Norwalk virus (Norovirus), and Norwalk-like Viruses, such as Hawaii Virus and Snow Mountain Virus; avian infectious bronchitis (IBV), Mouse hepatitis virus (MHV), and Porcine transmissible gastroenteritis virus (TGEV); Retrovirus, whose immunogens include those derived from an Oncovirus, a Lentivirus (e.g. HIV-1 or HIV-2) or a Spumavirus; Reovirus: immunogens include, but are not limited to, those derived from an Orthoreovirus, a Rotavirus, an Orbivirus, or a Coltivirus; Parvovirus, whose immunogens include those derived from Parvovirus B119; Herpesvirus, whose immunogens include those derived from a human herpesvirus, such as Herpes Simplex Viruses (HSV) (e.g. HSV types I and 2), Varicella-zoster virus (VZV), EpsteinBarr virus (EBV), Cytomegalovirus (CMV), Human Herpesvirus 6 (HHV6), Human Herpesvirus 7 (HHV7), and Human Herpesvirus 8 (HHV8); Papovaviruses, whose immunogens include those derived from Papillomaviruses and Adenovirus.

In some embodiments, the immunogen elicits an immune response to Chikungunya virus; in other embodiments, the immunogen elicits an immune response to Zika virus.

In some embodiments, the immunogen elicits an immune response against a virus which infects fish.

Fungal immunogens may be derived from Dermatophytres and other opportunistic organisms.

In some embodiments, the immunogen elicits an immune response against a parasite from the *Plasmodium* genus, such as *P. falciparum, P. vivax, P. malariae* or *P. ovale*. Thus the invention may be used for immunising against malaria.

In some embodiments the immunogen elicits an immune response against a parasite from the Caligidae family, particularly those from the Lepeophtheirus and *Caligus* genera e.g. sea lice such as Lepeophtheirus *salmonis* or *Caligus rogercresseyi*.

In some embodiments, the immunogen is an mRNA specific to neoantigens in cancer cells or solid tumours. Peng, M., Mo, Y., Wang, Y. et al. Neoantigen vaccine: an emerging tumor immunotherapy. Mol Cancer 18, 128 (2019).

In some embodiments the immunogen is a tumor antigen selected from: (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors; (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUMI (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLRFUT; (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT I (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), mammaglobin, alpha-fetoprotein (associated with, e.g., hepatoma), KSA (associated with, e.g., colorectal cancer), gastrin (associated with, e.g., pancreatic and gastric cancer), telomerase catalytic protein, MUC-I (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer); (d) shared antigens, for example, melanoma-melanocyte antigens such as MART-1/Melan A, gp100, MCIR, melanocyte-stimulating hormone receptor, tyrosinase, tyrosinase related protein-I/TRPI and tyrosinase related protein-2/TRP2 (associated with, e.g., melanoma); (e) prostate associated antigens such as PAP, PSA, PSMA, PSH-PI, PSM-PI, PSM-P2, associated with e.g., prostate cancer; (f) immunoglobulin idiotypes (associated with myeloma and B cell lymphomas, for example). In certain embodiments, tumor immunogens include, but are not limited to, p15, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29&BCAA), CA 195, CA 242, CA-50, CAM43, CD68&KPI, CO-029, FGF-5, Ga733 (EpCAM), HTgp-175, M344, MA-50, MG7-Ag, MOV18, NB/70K, NY-CO-I, RCASI, SDCCAG16, TA-90 (Mac-2 binding protein/cyclophilin C-associated protein), TAAL6, TAG72, TLP, TPS, and the like.

Pharmaceutical Compositions for Vaccines. A pharmaceutical composition of the invention, particularly one useful for immunization, may include one or more small molecule immunopotentiators. Pharmaceutical compositions of the invention may include one or more preservatives, such as thiomersal or 2 phenoxyethanol. Mercury-free and preservative-free vaccines can be prepared.

Compositions comprise an immunologically effective amount of the lipid compositions described herein (e.g., LNPS), as well as any other components, as needed. Immunologically effective amount refers to the amount administered to an individual, either in a single dose or as part of a series, is effective for treatment (e.g., prophylactic immune response against a pathogen). This amount varies depending upon the health and physical condition of the individual to be treated, age, the taxonomic group of individual to be treated (e.g. non-human primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials.

The compositions of the invention will generally be expressed in terms of the amount of RNA per dose. A preferred dose has ~100 pg RNA (e.g. from 10-100 pg, such as about 10 μg, 25 pg, 50 μg, 75 μg or 100 pg), but expression can be seen at much lower levels e.g. ~1 μg/dose, ~100 ng/dose, ~10 ng/dose, ~1 ng/dose, etc. In some embodiments, the preferred dose is 100 pg. In other embodiments, the preferred dose is up to 250 pg. The invention also provides a delivery device (e.g. syringe, nebulizer, sprayer, inhaler, dermal patch, etc.) containing a pharmaceutical composition of the invention. This device can be used to administer the composition to a vertebrate subject The LNP-formulated RNA and pharmaceutical compositions described herein are for in vivo use for inducing an immune response against an immunogen of interest. The invention provides a method for inducing an immune response in a vertebrate comprising administering an effective amount of the LNP formulated RNA, or pharmaceutical composition, as described herein. The immune response is preferably protective and preferably involves antibodies and/or cell-mediated immunity. The compositions may be used for both priming and boosting purposes. Alternatively, a prime-boost immunization schedule can be a mix of RNA and the corresponding polypeptide immunogen (e.g., RNA prime, protein boost).

The invention also provides an LNP or pharmaceutical composition for use in inducing an immune response in a vertebrate. The invention also provides the use of a LNP or pharmaceutical composition in the manufacture of a medicament for inducing an immune response in a vertebrate. By inducing an immune response in the vertebrate by these uses and methods, the vertebrate can be protected against various diseases and/or infections e.g. against bacterial and/or viral diseases as discussed above. Vaccines according to the invention may either be prophylactic (i.e. to prevent infection) or therapeutic (i.e. to treat infection), but will typically be prophylactic. The vertebrate is preferably a mammal, such as a human or a large veterinary mammal (e.g. horses, cattle, deer, goats, pigs).

Compositions of the invention will generally be administered directly to a patient. Direct delivery may be accomplished by parenteral injection (e.g. subcutaneously, intraperitoneally, intravenously, intramuscularly, intradermally, or to the interstitial space of a tissue. Alternative delivery routes include rectal, oral (e.g. tablet, spray), buccal, sublingual, vaginal, topical, transdermal or transcutaneous, intranasal, ocular, aural, pulmonary or other mucosal administration. Intradermal and intramuscular administration are two preferred routes. Injection may be via a needle (e.g. a hypodermic needle), but needle-free injection may alternatively be used. A typical intramuscular dose is 0.5 ml. The invention may be used to induce systemic and/or mucosal immunity, preferably to elicit an enhanced systemic and/or mucosal immunity. Dosage can be by a single dose schedule or a multiple dose schedule. Multiple doses may be used in a primary immunization schedule and/or in a booster immunization schedule.

In a multiple dose schedule the various doses may be given by the same or different routes e.g. a parenteral prime and mucosal boost, a mucosal prime and parenteral boost, etc. Multiple doses will typically be administered at least one week apart (e.g. about two weeks, about three weeks, about four weeks, about six weeks, about eight weeks, about ten weeks, about 12 weeks, about 16 weeks, etc.). In one embodiment, multiple doses may be administered approximately six weeks, ten weeks and 14 weeks after birth, e.g. at an age of six weeks, ten weeks and 14 weeks, as often used in the World Health Organization's Expanded Program on Immunization ("EPI"). In an alternative embodiment, two primary doses are administered about two months apart, e.g. about seven, eight or nine weeks apart, followed by one or more booster doses about six months to one year after the second primary dose, e.g. about six, eight, ten or 12 months after the second primary dose. In a further embodiment, three primary doses are administered about two months apart, e.g. about seven, eight or nine weeks apart, followed by one or more booster doses about six months to one year after the third primary dose.

Gene Editing. Gene editing is a group of technologies that can be used to change an organism's DNA by adding, removing, or modifying the genetic sequence at particular locations in the genome. Several approaches to genome editing have been developed, including CRISPR-Cas9, (clustered regularly interspaced short palindromic repeats) and CRISPR-associated protein 9. CRISPR-Cas9 was adapted from a genome editing system in bacteria which capture snippets of DNA from invading viruses and creates DNA segments known as CRISPR arrays. The CRISPR arrays allow the bacteria to "remember" the viruses, so if the viruses attack again, the bacteria produce RNA segments from the CRISPR arrays to target the viruses' DNA. The bacteria then use Cas9 or a similar enzyme to cut the DNA apart, which disables the virus.

The CRISPR-Cas9 system adapted for gene editing works similarly. A small piece of RNA with a short "guide" sequence that attaches (binds) to a specific target sequence of DNA in a genome is generated. The RNA also binds to the Cas9 enzyme. As in bacteria, the modified RNA is used to recognize the DNA sequence, and the Cas9 enzyme cuts the DNA at the targeted location. Although Cas9 is the enzyme that is used most often, other enzymes (for example Cpf1) can also be used. Once the DNA is cut, researchers use the cell's own DNA repair machinery to add or delete pieces of genetic material, or to make changes to the DNA by replacing an existing segment with a customized DNA sequence.

In embodiments of the invention, the new ionizable lipids find use as part of the delivery of, for example, a CRISPR-Cas system chimeric RNA polynucleotide sequence for modifying an organism by manipulation of a target sequence in a genomic locus of interest. Other nucleic acid components might include a guide sequence capable of hybridizing to a target sequence in a eukaryotic cell, a tracr mate sequence and tracr sequence such as that described in WO14204726 A1 by CHZHAN Fen et al.

CRISPR~Cas9 systems are used in embodiments to target genes in live cells through delivery of the CRISPR-Cas9 system to the appropriate location (i.e. to cells within the organs or tissues of interest). Preferred tissues are within the following organs: kidney; digestive system including the stomach, pancreas, duodenum, ileum and/or colon; lung; brain, in particular neurons, and/or cns in general; eye, including retinal tissue; ear, including the inner ear; skin; muscle; bone; and/or liver in general.

Genes subject to editing using ionizable lipids and compositions according to embodiments of the invention will be those associated with disease.

In embodiments, the pharmaceutical compositions described herein may be prepared by any method known or hereafter developed in the art of pharmacology. In general, such preparatory methods include the step of associating the active ingredient with an excipient and/or one or more other accessory ingredients.

A pharmaceutical composition in accordance with the present disclosure may be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient may generally be equal to the dosage of the active ingredient which would be administered to a subject and/or a convenient fraction of such a dosage including, but not limited to, one-half or one-third of such a dosage.

Relative amounts of the active ingredient, the pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered. For example, the composition may comprise between 0.1 percent and 99 percent (w/w) of the active ingredient.

Pharmaceutical formulations may additionally comprise a pharmaceutically acceptable excipient, which, as used herein, includes, but is not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparing the composition are known in the art (see Remington: The Science and Practice of Pharmacy, 21st Edition, A. R. Gennaro, Lippincott, Williams and Wilkins, Baltimore, MD, 2006). The use of a conventional excipient medium is contemplated herein, except insofar as any conventional excipient medium may be incompatible with a substance or its derivatives, such as by producing any undesirable biological effect or otherwise interacting in a deleterious manner with any other component(s) of the pharmaceutical composition.

In some embodiments, the particle size of the lipid particles may be increased and/or decreased. The change in particle size may be able to help counter biological reaction such as, but not limited to, inflammation or may increase the biological effect of the NAT delivered to mammals by changing biodistribution. Size may also be used to determine target tissue, with larger particles being cleared quickly and smaller one reaching different organ systems.

Pharmaceutically acceptable excipients used in the manufacture of pharmaceutical compositions include, but are not limited to, inert diluents, surface active agents and/or emulsifiers, preservatives, buffering agents, lubricating agents, and/or oils. Such excipients may optionally be included in the pharmaceutical formulations of the invention.

In some embodiments, exemplary mRNA, plasmid or other NAT encodes the protein or enzyme selected from human growth hormone, erythropoietin, ATP-binding cassette (ABC) transporter, alpha-1-antitrypsin, acid alpha glucosidase, arylsulfatase A, carboxypeptidase N, a-galactosidase A, alpha-L-iduronidase, iduronate-2-sulfatase, iduronate sulfatase, N-acetylglucosamine-1-phosphate transferase, N-acetylglucosaminidase, alpha-glucosaminide acetyltransferase, N-acetylglucosamine 6-sulfatase, N-acetylgalactosamine-4-sulfatase, beta-glucosidase, galactose-6-sulfate sulfatase, beta-galactosidase, beta-glucuronidase, BMPER-2, glucocerebrosidase, heparan sulfamidase, heparin-N-sulfatase, lysosomal acid lipase, hyaluronidase, galactocerebrosidase, ornithine transcarbamylase (OTC), carbamoyl-phosphate synthetase 1 (CPS 1), argininosuccinate synthetase (ASS 1), argininosuccinate lyase (ASL), arginase 1 (ARGI), cystic fibrosis transmembrane conductance regulator (CFTR), survival motor neuron (SMN), Factor VIII, Factor IX, transcription activator-like effector nucleases like TALENS, zinc-finger nucleases (ZFNs), (CRISPR)-associated protein 9 (Cas9), and self-replicating RNA, and low density lipoprotein receptors (LDLR).

Other plasmid or nucleic acids can be applied to cell-based system using this invention in the context of a research or screening platform. These include the introduction of genetic material for the purpose of inducing specific physiological or functional changes in cells, such as in the process of reprogramming for the generation of induced pluripotent stem cells. In this case, specific genes (known as Yamanaka factors) are introduced to patient-derived somatic cells, which trigger a reversal of the cell to a stem cell-like state. These enable the cells to divide indefinitely and become pluripotent (able to differentiate to many other downstream cell types) which can be used for both research and clinical applications. These and similar genetic manipulation steps can be enhanced by the lipid particles of the invention to improve the efficiency of processes commonly used when working with induced stem cells.

The following is a description of representative lipid particles prepared with nucleic acid (LNP), how they are made, evidence of their advantages, and methods for using them to deliver therapeutic benefits.

Lipid mix composition of lipid particles were generated by rapidly mixing lipid-ethanol solution with an aqueous buffer inside a microfluidic mixer designed to induce chaotic advection and provide a controlled mixing environment at intermediate Reynolds number (24<Re<1000). The microfluidic channels have herringbone features or are configured in a manner as shown in PCT Publication WO2017117647 by Wild, Leaver and Taylor.

Particle sizes and "polydispersity index" (PDI) of the lipid particle were measured by dynamic light scattering (DLS). PDI indicates the width of the particle distribution. This is a parameter calculated from a cumulative analysis of the (DLS)-measured intensity autocorrelation function assuming a single particle size mode and a single exponential fit to the autocorrelation function. From a biophysical point of view, a PDI below 0.1 indicates that the sample is monodisperse. The particles produced by mechanical micromixers such as the NanoAssemblr® Spark™ and NanoAssemblr® Benchtop (Precision NanoSystems Inc.) are substantially homogeneous in size assuming all other variables are neutral. A lower PDI indicates a more homogenous population of lipid particles. The Spark™ instrument is used in a screening setting to identify the lead compositions. Once the composition is selected, the lipid particle can be fine-tuned using the NanoAssemblr® Benchtop. Once the process parameters Flow Rate Ratio and Total Flow Rate is identified for the specific nanoparticle composition, the nanoparticle technology can be scaled up using the same process parameter values.

In preferred embodiments, the nucleic acid is a plasmid composed of double stranded deoxyribonucleic acid. A plasmid is a genetic structure that resides in a cell's cytoplasm (as opposed to the nucleic where the traditional cellular genetics reside) cell that can replicate independently of the chromosomes, typically a small circular DNA strand. Plasmids can also be used to create novel cellular or animal models for medical research. Plasmids are an important tool in molecular biology and as an emerging therapeutic due to their i) ease of manipulation and isolation ii) ability to self-replicate for scaled-up manufacturing iii) long term stability iv) functionality in a range of organisms and applications. An engineered plasmid will have, in addition to a replication origin (or not, depending on the intended use), restriction enzyme recognition sites to allow breaking the circle to introduce new genetic material, and a selective marker such as an antibiotic resistance gene. A plasmid may be from about 1000 bp to about 20 kilobase pairs (bp).

As used herein, the term "about" is defined as meaning 10% plus or minus the recited number. It is used to signify that the desired target concentration might be, for example, 40 Mol %, but that through mixing inconsistencies, the actual percentage might differ by +/−5 Mol %.

As used herein, the term "substantially" is defined as being 5% plus or minus the recited number. It is used to signify that the desired target concentration might be, for example, 40 Mol %, but that through mixing inconsistencies, the actual percentage might differ by +/−5 Mol %.

As used herein, the term "nucleic acid" is defined as a substance intended to have a direct effect in the diagnosis, cure, mitigation, treatment or prevention of disease, or to have direct effect in restoring, correcting or modifying physiological functions, or to act as a research reagent. In preferred embodiments, the nucleic acid is an oligonucleotide. In preferred embodiments, the therapeutic agent is a nucleic acid therapeutic, such as an RNA polynucleotide. In preferred embodiments, the therapeutic agent is double stranded circular DNA (plasmid), linearized plasmid DNA, minicircles or msDNA (multicopy single stranded DNA).

In this disclosure, the word "comprising" is used in a non-limiting sense to mean that items following the word are included, but items not specifically mentioned are not excluded. It will be understood that in embodiments which comprise or may comprise a specified feature or variable or parameter, alternative embodiments may consist, or consist essentially of such features, or variables or parameters. A reference to an element by the indefinite article "a" does not exclude the possibility that more than one of the elements is present, unless the context clearly requires that there be one and only one of the elements.

In this disclosure, "transfection" means the transfer of nucleic acid into cells for the purpose of inducing the expression of a specific gene(s) of interest in both laboratory and clinical settings. It typically includes an ionizable lipid to associate with nucleic acid, and structural lipids. LIPO- FECTIN™ and LIPOFECTAMINE™ are established commercial transfecting reagents sold by ThermoFisher Scientific. These research reagents contain permanently cationic lipid/s and are not suitable for use in or ex vivo.

In this disclosure the recitation of numerical ranges by endpoints includes all numbers subsumed within that range including all whole numbers, all integers and all fractional intermediates (e.g., 1 to 5 includes 1, 1.5, 2, 2.75, 3, 3.80, 4, and 5 etc.). In this disclosure the singular forms an "an", and "the" include plural referents unless the content clearly dictates otherwise. Thus, for example, reference to a composition containing "a compound" includes a mixture of two or more compounds. In this disclosure term "or" is generally employed in its sense including "and/or" unless the content clearly dictates otherwise.

"Stabilizer" or stabilizing agent is a term used to identify the agent that is added to the ionizable lipid, the structural lipid, and the sterol that form the lipid composition according to the invention. Stabilizers are non-ionic as herein described. Examples of non-ionic stabilizing agents include: Polysorbates (Tweens), Brij™ S20 (polyoxyethylene (20) stearyl ether), Brij™35 (Polyoxyethylene lauryl ether, Polyethyleneglycol lauryl ether), Brij™ S10 (Polyethylene glycol octadecyl ether, Polyoxyethylene (10) stearyl ether), Myrj™52 (polyoxyethylene (40) stearate). stabilizing agent combinations are also used in some embodiments, including polysorbate and maltoside, Alkyl polyglycosides (TBD), PEG-conjugated lipids or other polymer conjugated lipids.

"Alkyl" means a straight chain or branched, noncyclic or cyclic, saturated aliphatic hydrocarbon containing from 1 to 24 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like.

"Alkenyl" means an alkyl, as defined above, containing at least one double bond between adjacent carbon atoms. Alkenyls include both cis and trans isomers. Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

"Alkynyl" means any alkyl or alkenyl, as defined above, which additionally contains at least one triple bond between adjacent carbons. Representative straight chain and branched alkynyls include acetylenyl, propynyl, 1-butynyl, 2-butynyl, 1-pentynyl, 2-pentynyl, 3-methyl-1 butynyl, and the like.

The term "acyl" refers to hydrogen, alkyl, partially saturated or fully saturated cycloalkyl, partially saturated or fully saturated heterocycle, aryl, and heteroaryl substituted carbonyl groups. For example, acyl includes groups such as $(C_1-C_{20})$alkanoyl (e.g., formyl, acetyl, propionyl, butyryl, valeryl, caproyl, t-butylacetyl, etc.), $(C_3-C_{20})$cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl,1H-pyrroyl-2-carbonyl, 1H-pyrroyl-3-carbonyl, benzo[b]thiophenyl-2-carbonyl, etc.).

The term "aryl" refers to an aromatic monocyclic, bicyclic, or tricyclic hydrocarbon ring system, wherein any ring atom can be substituted. Examples of aryl moieties include, but are not limited to, phenyl, naphthyl, anthracenyl, and pyrenyl.

"Heterocycle" means a 3- to 7-membered monocyclic, or 7- to 10-membered bicyclic, heterocyclic ring which is either saturated, unsaturated, or aromatic, and which contains from 1 or 2 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined below. Heterocycles include morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom can be substituted. The heteroaryl groups herein described may also contain fused rings that share a common carbon-carbon bond. The term "alkylheterocycle" refers to a heteroaryl wherein at least one of the ring atoms is substituted with alkyl, alkenyl or alkynyl The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, oxo, thioxy, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted. Exemplary substituents include amino, alkylamino, dialkylamino, and cyclic amino compounds.

"Halogen" means fluoro, chloro, bromo and iodo.

The terms "alkylamine" and "dialkylamine" refer to —NH(alkyl) and —N(alkyl)$_2$ radicals respectively.

The term "hydroxyalkyl" means —O-alkyl radical.

The term "alkylheterocycle" refers to an alkyl where at least one methylene has been replaced by a heterocycle.

In some embodiments, the methods of the invention may require the use of protecting groups. Protecting group methodology is well known to those skilled in the art (see, for example, Protective Groups in Organic Synthesis, Green, T. W. et. al., Wiley-Interscience, New York City, 1999). Briefly, protecting groups within the context of this invention are any group that reduces or eliminates unwanted reactivity of a functional group. A protecting group can be added to a functional group to mask its reactivity during certain reactions and then removed to reveal the original functional group. In some embodiments an "alcohol protecting group" is used. An "alcohol protecting group" is any group which decreases or eliminates unwanted reactivity of an alcohol functional group. Protecting groups can be added and removed using techniques well known in the art.

Additionally, the invention may be described as in formula (I), (II) or, (Ill); A compound, or a pharmaceutically acceptable salt thereof, as shown in formula (I), (II), or (Ill), wherein the experimental pKa of nanoparticles is in the range 5.6-7.1.

According to the invention, there is provided a compound, or a pharmaceutically (I)

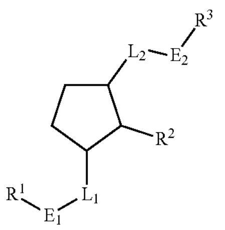

acceptable salt thereof, of formula (I)

wherein:

$L_1$ is a direct bond;

$E_1$ is selected from —OC(O)-$\delta^1$; $\delta^1$ designates the bond linked to the $R^1$ group;

$R^1$ is selected from:

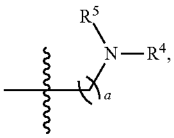

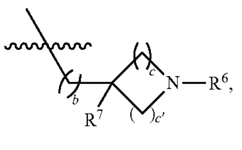

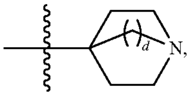

and

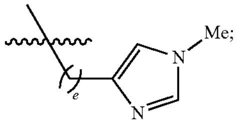

wherein:

$R^4$ and $R^5$ are each, independently selected from $C_1$-$C_6$ alkyl; alternatively, $R^4$ and $R^5$ may join to form 5-6 membered heterocyclic ring containing up to 2 nitrogen (N), optionally substituted with 1-2 substituents each independently selected from a $C_1$-$C_6$ alkyl;

$R^6$ is selected from $C_1$-$C_6$ alkyl, and cyclopropyl group;

$R^7$ is selected from H, and $C_1$-$C_6$ alkyl group;

a is 1, 2, or 3;

b is 0, or 1;

c is 0, 1, or 2;

c' is 2, 3, or 4;

d is 2;

e is 1;

$R^2$ is selected from H, $C_1$-$C_5$ alkyl, $C_2$-$C_5$ alkenyl, and

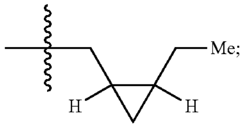 [SMILES: *CC1CC1CC]

$L_2$ is $\delta^2$—$(CR^8R^{8'})_k$-$\delta^3$ wherein $R^8$ and $R^{8'}$ are each H; $\delta^2$ designates the bond linked to $E_2$ group and $\delta^3$ designates the bond linked to cyclopentyl scaffold described in formula (I);

k is 1;

$E_2$ is —C(O)O-$\delta^4$; where $\delta^4$ designates the bond linked to $R^3$ group; $R^3$ is selected from:

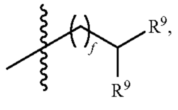

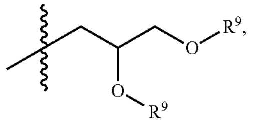

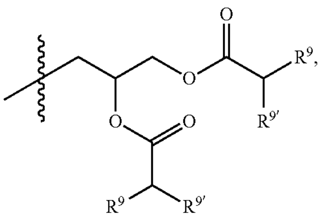

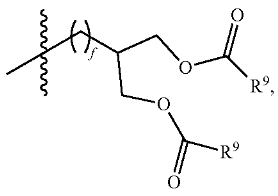

and

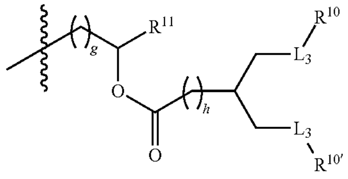

wherein:

f and h are 0;

g is 1, or 2;

$R^9$ is a $C_6$-$C_{20}$ chain having the formula —$(CH_2)_i$-[$L_4$-$(CH_2)$]— $R^{12}$, wherein:

$L_4$ is selected from

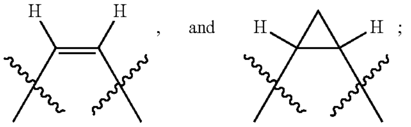

i is an integer in the range 6-20;

j is 0, 1, or 2;

$R^{12}$ is selected from H and $C_4$-$C_8$ alkyl group; $R^{9'}$ is selected from H, and $C_4$-$C_{10}$ alkyl; $R^{10}$ and $R^{10'}$ are each, independently selected from $C_4$-$C_{10}$ alkyl; $L_3$ is a direct bond; $R^{11}$ is the same as $R^9$.

The compounds of the present invention may be prepared by known organic synthesis techniques, including the methods described in more detail in the Examples.

Scope of the invention may include various salts, hydrates, and solvates of the compound.

Compounds of the invention can also include various pharmaceutically acceptable isotopes.

Compounds of the invention include various pharmaceutically acceptable substitutions, such as fluorinated or iodinated derivatives.

Compounds of this invention can be synthesized using various possible synthetic routes, which can be readily selected by one of skill in the art of organic synthesis.

The phrase 'pharmaceutically acceptable' is employed to describe compounds, materials, compositions, nanoparticle suspensions in solutions or any other form such as lyophilized, powder form, aerosol, or other dosage forms within the scope of sound medical judgement suitable for use in contact with human and animal tissues or cells with a reasonable benefit/risk ratio. Benefit/risk ratio may come from protecting the therapeutic entities such as small molecules, nucleic acids, peptides, or proteins from degradation in biological milieu in vivo or ex vivo.

Compounds may also be evaluated in one or more preclinical models known for those schooled in the art to show the therapeutic validation of a pharmaceutically viable cargo such as NAT, peptides and proteins. These include, but are not limited to rodent models and non-human primates.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

EXAMPLES

General considerations: All solvents and reagents were commercial products and used as such unless noted otherwise. Temperatures are given in degrees Celsius. The structure of final starting materials, intermediates and final products is confirmed by standard analytical methods, e.g., MS or NMR. Unless otherwise stated, $^1H$ NMR spectra were recorded in $CDCl_3$ solutions, at 298 K using AVANCE NEO NanoBay Bruker 400 MHz NMR spectrometer. Chemical shifts are reported in parts per million (ppm) relative to TMS (0.00) and coupling constants, J, are in Hertz (Hz) for $^1H$. The following abbreviations are used to denote signal patterns: s=singlet, d=doublet, t=triplet, q=quartet, p=pentet, m=multiplet, dd=doublet of doublets, br s=broad singlet, dt=doublet of triplets. Unless otherwise stated, column purification was carried out using Isolera™ Prime using an appropriate eluent of isocratic or gradient composition.

All final compounds were determined to be greater than 85% pure via analysis by reverse phase UHPLC-MS (Retention times RT in minutes) using Shimadzu Nexera UHPLC instrument with DAD and ELSD and Acquity Peptide BEH C18 2.1 mm×50 mm, 1.7 μm column and a gradient with 10 mM ammonium bicarbonate in water (A) and Acetonitrile: Methanol 80:20 ratio (B). The gradient study ran at linearly 80 to 100% B over 12 minutes at 0.8 mL/min. Injection volume was 2 μL and the column temperature was ambient. Detection was based on multimode with electrospray and atmospheric pressure chemical ionization (ESI and APCI) in positive and negative mode using Shimadzu 2020 Single Quad mass spectrometer (Science Park, Singapore) and evaporative light scattering detector (ELSD) except PNI 101 and PNI 123. Low resolution MS data of PNI 101 and PNI 123 were recorded using a Bruker micrOTOF™ Time-of-Flight mass spectrometer with a positive electrospray ionization source on an Agilent™ 1200 HPLC. Sodium formate was used as a reference. Samples were introduced by flow injection via HPLC with acetonitrile/water (0.1% formic acid) as mobile phase.

Abbreviations

ACD-A=Anticoagulant Citrate Dextrose Solution
AcOH=acetic acid
aq.=aqueous
DCM=dichloromethane
DMAP=4-dimethylaminopyridine
DMF=N,N-dimethylformamide
EDCl=1-ethyl-3-(3-dimethylaminopropyl)carbodiimide
EPO=erythropoietin
ESI=electrospray ionization
EtOAc=ethyl acetate
g=gram
G=gravity
h=hour(s)
HPLC=High performance liquid chromatography
MC3=DLin-MC3-DMA
MFI=Median Fluorescence Intensity
min=minute(s)
mL=milliliter(s)
mmol=millimole(s)
MS=mass spectroscopy
MTBE=methyl-t-butyl ether
NaH=sodium hydride
NaOH=sodium hydroxide
NMR=nuclear magnetic resonance
Pet.=petroleum
ppm=parts per million
Red AI®=sodium bis-(2-methoxyethoxy)aluminum dihydride
satd.=saturated
THE=tetrahydrofuran
TLC=thin layer chromatography
TNS=6-(p-Toluidino)-2-naphthalenesulfonic acid sodium salt
wt=weight
° C.=Degree Celsius

Example 1
Synthesis of PNI 101, 123, 128, 132, 135, 143, 542, 557, 558, 559, 567
Scheme 1
Synthesis of compound 3
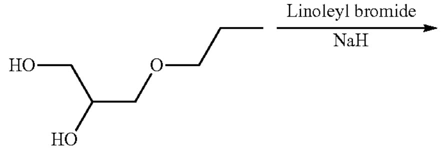
1
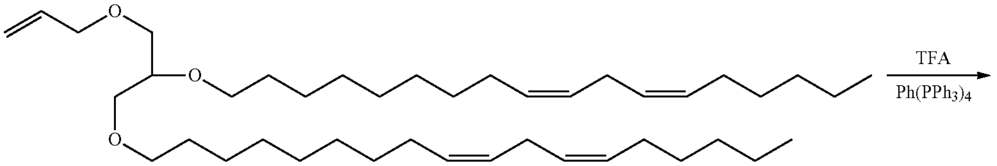
2
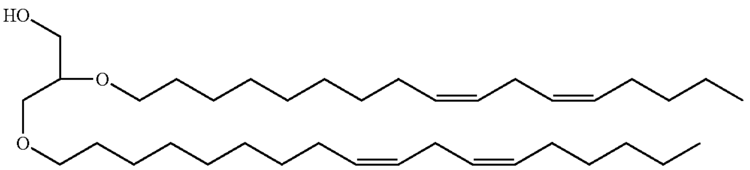
3
Scheme 2.
General route for synthesis of PNI 101, 123, 128, 132, 135, 143, 542, 557, 558, 559, and 587
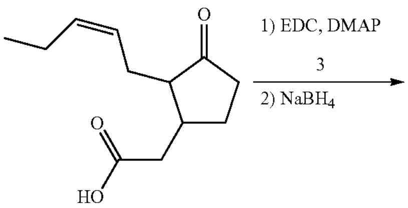
4
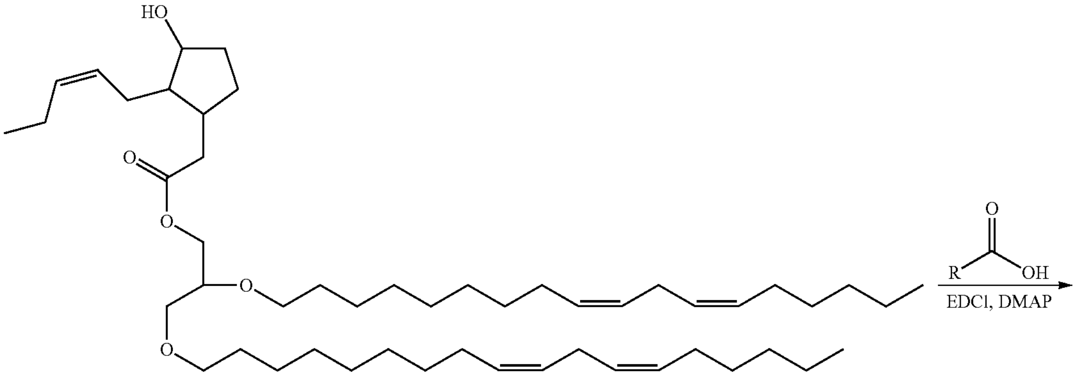
6

-continued

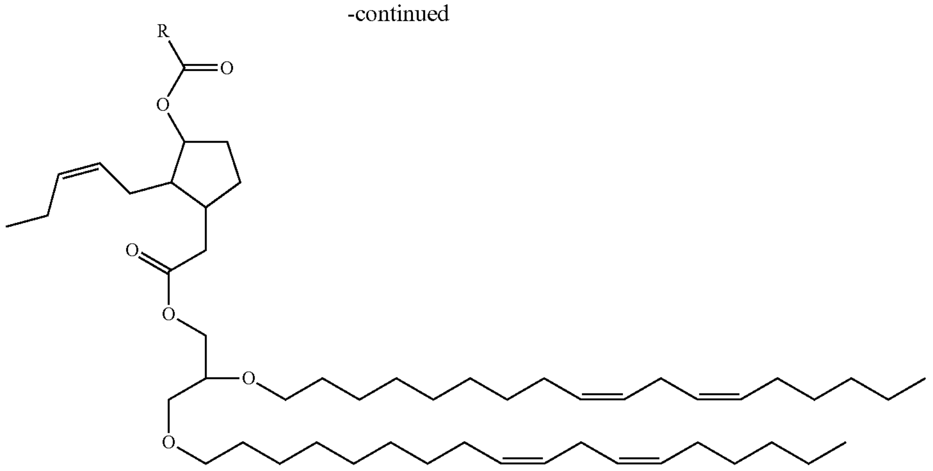

Compound 2: To a well-stirred solution of 3-(allyloxy) propane-1,2-diol (1, 2.25 g, 17.02 mmol) in dry THF (95 mL), sodium hydride (3.00 g, 74.9 mmol, 60% dispersion in mineral oil) was added portionwise at room temperature under nitrogen atmosphere. After stirring for 30 min, a solution of linoleyl bromide (13.46 g, 40.9 mmol) and 15-crown-5 (0.762 g, 3.46 mmol) in dry THE (20 mL) were added. The reaction mixture was refluxed for 2 h and then stirred at room temperature overnight. After completion of the reaction as indicated by TLC, the reaction mixture was quenched with satd. aq. $NH_4Cl$ solution (30 mL), then EtOAc (150 mL) and water (150 mL) were added to it. The organic layer was separated, and aqueous layer was extracted with EtOAc (3×75 mL). The combined organic layers were washed with brine, dried over anhydrous $Na_2SO_4$, and concentrated under reduced pressure. The crude product was purified by Isolera™ silica gel (100-200 mesh) column chromatography using 2% ethyl acetate in Pet. ether as the eluent to afford 2 (4.01 g, 6.25 mmol, 36.7% yield) as colourless oil. $^1H$ NMR (500 MHz, CDCl3) δ 5.97-5.87 (m, 1H), 5.42-5.31 (m, 8H), 5.28 (d, 1H, J=15.0), 5.18 (d, 1H, J=10.0), 4.02 (d, 2H, J=5.0), 3.61-3.38 (m, 9H), 2.78 (t, 4H, J=7.5), 2.06 (q, 8H, J=15.0, 5.0), 1.60-1.54 (m, 4H), 1.40-1.27 (m, 32H), 0.90 (app t, 6H, J=5.0). RT=4.96 min. 98.5% purity. ESI-MS: m/z=652 [M+Na]+ for $C_{42}H_{76}O_3Na$.

Compound 3: To a solution of 2 (2.70 g, 4.29 mmol) in anhydrous EtOH (45 mL), TFA (4.5 mL) and $Pd(PPh_3)_4$ (495 mg, 0.428 mmol) were added under $N_2$ atmosphere and the reaction mixture was refluxed for 16 h. TLC analysis showed some amount of unreacted 2. 100 mg of ($Pd(PPh_3)_4$) was further added to the reaction mixture further and reflux was continued for another 2 h resulting in complete consumption of 2. The reaction mixture was evaporated to dryness, dissolved in EtOAc (100 mL) and filtered through celite. The solvent was removed over rotary evaporator to provide crude as pale-yellow oil which was purified by silica gel column chromatography using 5% Methanol/DCM as the eluent. Compound 3 (2.15 g, 3.65 mmol) was obtained as a colorless oil in 85% yield. $^1H$ NMR (500 MHz, $CDCl_3$) δ 5.42-5.31 (m, 8H), 3.74 (dd, 1H, J=10.0, 5.0), 3.64-3.59 (m, 2H), 3.56-3.43 (m, 7H), 2.78 (t, 4H, J=7.5), 2.06 (q, 8H, J=15.0, 5.0), 1.60-1.54 (m, 4H), 1.40-1.27 (m, 32H), 0.90 (app t, 6H, J=5.0). RT=3.58 min. 97.4% purity. ESI-MS: m/z=590 $[M+H]^+$ for $C_{39}H_{73}O_3$.

Compound 5: To a stirred solution of 3 (1.5 g, 2.55 mmol) in dry DCM (15 mL), DMAP (0.031 g, 0.255 mmol) was added followed by addition of a solution of 4 (1.071 g, 5.09 mmol) in dry DCM (15 mL) at room temperature under nitrogen atmosphere. EDCl hydrochloride (0.976 g, 5.09 mmol) was added to the reaction mixture and was stirred at room temperature for 16 hours. Upon completion of reaction as indicated by TLC, the solvent was evaporated under reduced pressure and the residue was dissolved in EtOAc (100 mL). The organic layer was washed with water (2×35 mL), brine (2×35 mL), dried over anhydrous $Na_2SO_4$, filtered and concentrated. The crude ketone, 2,3-bis(((9Z, 12Z)-octadeca-9,12-dien-1-yl)oxy)propyl 2-(3-oxo-2-((Z)-pent-2-en-1-yl)cyclopentyl)acetate was obtained as thick yellow oil, which was taken as such for next step without further purification. RT=4.77 min. 95.2% purity. ESI-MS: m/z=804 $[M+Na]^+$ for $C_{51}H_{33}O_5Na$.

A stirred solution of 2,3-bis(((9Z,12Z)-octadeca-9,12-dien-1-yl)oxy)propyl 2-(3-oxo-2-((Z)-pent-2-en-1-yl)cyclopentyl)acetate (2.4 g, 3.07 mmol) in dry MeOH (20 ml) and dry THE (5 ml) was cooled to −10° C. and sodium borohydride (0.465 g, 12.29 mmol) was added slowly under nitrogen atmosphere. The reaction mixture was stirred for 30 minutes and TLC analysis showed the complete consumption of ketone. The solvent was evaporated under reduced pressure and the residue was dissolved in EtOAc (75 mL). The organic layer was washed with water (150 ml) and the aqueous layer was extracted with EtOAc (2×50 mL). The combined organic layers were washed with brine (2×75 mL), dried over anhydrous $Na_2SO_4$, filtered and concentrated. The crude product was purified by Isolera™ silica gel (100-200 mesh) column chromatography using 10% EtOAc in Pet. ether to give 5 (1.7 g, 2.170 mmol, 85.1% yield over 2 steps from ketone) as light-yellow oil. $^1H$ NMR (500 MHz, $CDCl_3$) δ 5.52-5.31 (m, 10H), 4.26-4.23 (m, 1H), 4.12-4.08 (m, 1H), 3.91 (br s, 1H), 3.62 (p, 1H, J=5.0), 3.56 (app t, 2H, J=7.5), 3.51-3.47 (m, 2H), 3.44 (app t, 2H, J=5.0), 2.78 (t, 4H, J=5.0), 2.60-2.56 (m, 1H), 2.32 (dd, 1H, J=15.0, 5.0), 2.24-2.17 (m, 2H), 2.13-2.04 (m, 10H), 2.01-1.85 (m, 3H), 1.66-1.61 (m, 1H), 1.59-1.53 (m, 6H), 1.51-1.44 (m, 1H), 1.39-1.30 (m, 32H), 0.98 (t, 3H, J=7.5), 0.90 (t, 6H, J=5.0). RT=4.71 min. 93.5% purity. ESI-MS: m/z=806 $[M+Na]^+$ for $C_{51}H_{90}O_5Na$.

PNI 101

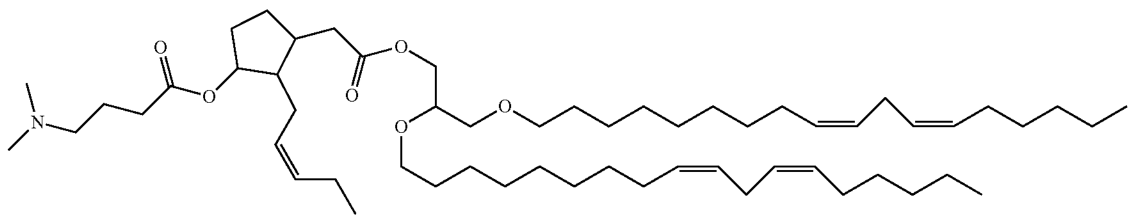

To a solution of 5 (313 mg, 0.40 mmol) in dry DCM (6 mL), DMAP (cat.) was added followed by addition of a solution of 4-(dimethylamino)butanoic acid hydrochloride (67 mg, 0.40 mmol) in dry DMF (2 mL) under $N_2$ atmosphere at room temperature. Finally, solid EDCl hydrochloride (115 mg, 0.60 mmol) was added to the reaction mixture and was stirred for 1 h. TLC analysis of the reaction mixture showed complete consumption of 5. The reaction mixture was evaporated to dryness, dissolved in ethyl acetate (10 mL), washed with water (3×5 mL). Organic layer was washed with brine, dried over anhydrous $Na_2SO_4$, concentrated over a rotary evaporator to provide a crude reaction mixture which was purified by silica gel column chromatography using 5% Methanol/$CH_2Cl_2$ as the eluent. PNI 101 (250 mg, 0.28 mmol) was obtained as thick colorless oil in a 70% yield. $^1$H NMR (500 MHz, $CDCl_3$) δ 5.46-5.28 (m, 10H), 4.26-4.22 (m, 1H), 4.13-4.06 (m, 1H), 3.63-3.60 (m, 1H), 3.57-3.54 (m, 2H), 3.50-3.47 (m, 2H), 3.45-3.42 (m, 2H), 2.78 (t, 4H, J=5.0), 2.62-2.57 (m, 1H), 2.31 (p, 4H, J=7.5), 2.24 (s, 6H), 2.15-2.09 (m, 2H), 2.08-2.01 (m, 10H), 1.98-1.92 (m, 2H), 1.79 (p, 2H, J=7.5), 1.70-1.63 (m, 2H), 1.56 (p, 4H, J=7.5), 1.39-1.26 (m, 36H), 0.97-0.93 (m, 3H), 0.90 (apparent t, 6H, J=7.5). Molecular weight for $C_{57}H_{102}NO_6$ $[M+H]^+$ Calculated 896.7707. Found 896.7670.

PNI 123

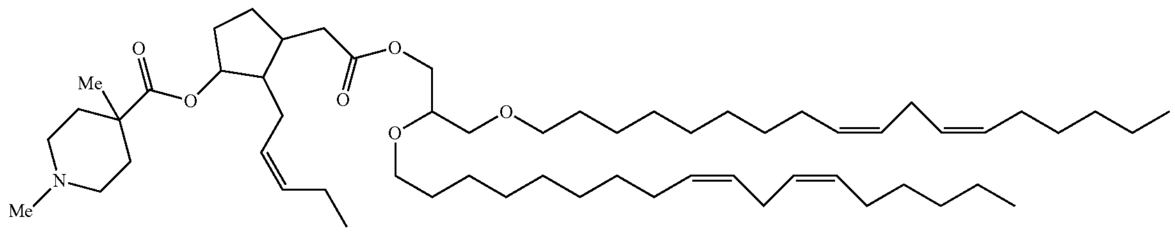

To a solution of 5 (250 mg, 0.32 mmol) in dry $CH_2Cl_2$ (6 mL), DMAP (cat.) was added followed by addition of a solution of 1,4-dimethylpiperidine-4-carboxylic acid hydrochloride (62 mg, 0.32 mmol) in dry DMF (5 mL) under $N_2$ atmosphere at room temperature. Finally, solid EDCl hydrochloride (92 mg, 0.48 mmol) was added to the reaction mixture and it was heated at 65° C. for 3 h. TLC analysis indicated that some of 5 was still unreacted. The reaction mixture was cooled to room temperature and to it, 1,4-dimethylpiperidine-4-carboxylic acid hydrochloride (62 mg, 0.32 mmol), dissolved in dry DMF (5 mL), DMAP (cat.) and EDCl hydrochloride (92 mg, 0.48 mmol) were further added sequentially and the reaction mixture was stirred at 65° C. for one additional hour. TLC analysis showed consumption of the majority of 5. The reaction mixture was concentrated over a rotary evaporator to remove most of DMF, dissolved in EtOAc (20 mL), washed with water (3×10 mL). Organic layer was washed with brine, dried over anhydrous $Na_2SO_4$, concentrated over a rotary evaporator to provide a crude reaction mixture which was purified by silica gel column chromatography using 5% Methanol/$CH_2Cl_2$ as the eluent. PNI 123 (90 mg, 0.0978 mmol) was obtained as thick pale-yellow oil in 30% yield. $^1$H NMR (500 MHz, $CDCl_3$) δ 5.45-5.29 (m, 10H), 4.89-4.86 (m, 1H), 4.27-4.23 (m, 1H), 4.11-4.08 (m, 1H), 3.64-3.60 (m, 1H), 3.55 (app t, 2H, J=5.0), 3.51-3.42 (m, 4H), 2.78 (t, 4H, J=5.0), 2.58 (dd, 1H, J=15.0, 5.0), 2.49 (brs, 4H), 2.30 (dd, 1H, J=15.0, 5.0), 2.23-2.11 (m, 5H), 2.08-2.04 (m, 10H), 2.01-1.97 (m, 4H), 1.72-1.69 (m, 2H), 1.64-1.53 (m, 8H), 1.39-1.26 (m, 32H), 1.23 (s, 3H), 0.97 (app t, 3H, J=7.5), 0.90 (app t, 6H, J=7.5). Molecular weight for $C_{59}H_{104}NO_6$ $[M+H]^+$ Calculated 922.7864. Found 922.7837.

PNI 128

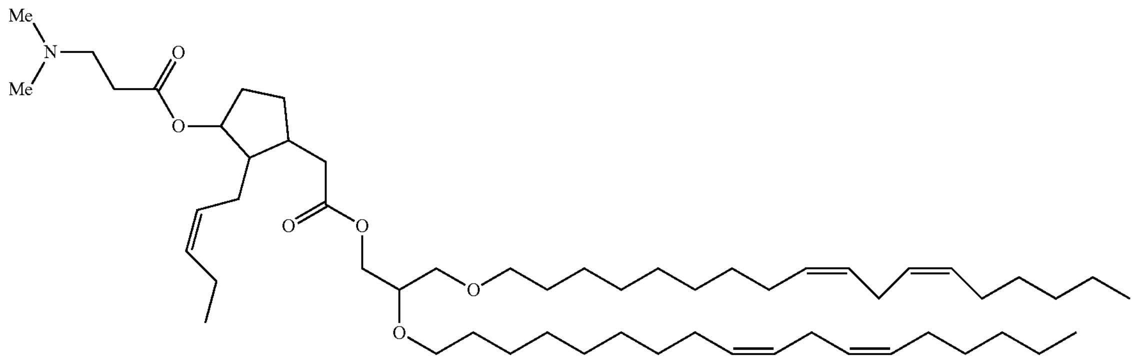

To a stirred solution of 3-(dimethylamino)propanoic acid hydrochloride (0.078 g, 0.511 mmol) in dry DMF (2 mL), a solution of 5 (0.4 g, 0.511 mmol) in dry DCM (8 mL) and DMAP (6.24 mg, 0.051 mmol) were added at room temperature under nitrogen atmosphere. Then, EDCl hydrochloride (0.147 g, 0.766 mmol) was added and the reaction mixture was stirred for 16 hours. TLC analysis showed alcohol 5 was not consumed completely. So, a solution of 3-(dimethylamino)propanoic acid hydrochloride (0.031 g, 0.204 mmol) in DMF (2 mL) was added, followed by EDCl hydrochloride (0.098 g, 0.511 mmol), DIPEA (0.312 ml, 1.787 mmol) and dry DCM (4 mL). The reaction mixture was stirred at room temperature for 16 hours. The solvent was evaporated under reduced pressure and the residue was dissolved in EtOAc (60 mL). The organic layer was washed with water (150 mL) and the aq. layer was extracted with EtOAc (2x30 mL). The combined organic layers were washed with brine (2x75 mL), dried over anhydrous $Na_2SO_4$, filtered and concentrated. The crude purified by Isolera™ silica gel (100-200 mesh) column chromatography using 5% MeOH in EtOAc to afford PNI 128 (0.195 g, 0.220 mmol, 43.0% yield) as light-yellow oil. 150 mg of alcohol 5 was also recovered. $^1H$ (400 MHz, $CDCl_3$) δ 5.47-5.30 (m, 10H), 4.88-4.84 (m, 1H), 4.24 (dd, 1H, J=12.0, 4.0), 4.10 (dd, 1H, J=12.0, 8.0), 3.63-3.42 (m, 7H), 2.78 (app t, 4H, J=6.0), 2.70-2.56 (m, 3H), 2.52-2.44 (m, 2H), 2.35-2.21 (m, 7H), 2.14-1.92 (m, 14H), 1.71-1.52 (m, 6H), 1.38-1.26 (m, 34H), 0.98-0.93 (m, 3H), 0.90 (app t, 6H, J=6.0). RT=5.09 min. 97.7% purity. ESI-MS: m/z=883 $[M+H]^+$ for $C_{56}H_{100}NO_6$.

To a stirred solution of 1-methylpiperidine-4-carboxylic acid hydrochloride (0.110 g, 0.613 mmol) in dry DMF (2 mL), a solution of 5 (0.4 g, 0.511 mmol) in dry DCM (8 mL) and DMAP (0.012 g, 0.102 mmol) were added at room temperature under nitrogen atmosphere. Then, EDCl hydrochloride (0.147 g, 0.766 mmol) and dry DCM (2 mL) was added and the reaction mixture was stirred at room temperature for 16 hours. After completion of the reaction as indicated by TLC, the solvent was evaporated under reduced pressure and the residue was dissolved in EtOAc (60 mL). The organic layer was washed with water (150 mL) and the aqueous layer was extracted with EtOAc (2x30 mL). The combined organic layers were washed with brine (2x75 mL), dried over anhydrous $Na_2SO_4$, filtered and concentrated. The crude product was purified by silica gel (100-200 mesh) column chromatography (Isolera™) using 8% MeOH in EtOAc to give PNI 132 (0.27 g, 0.295 mmol, 57.8% yield) as yellow oil. 120 mg of alcohol 5 was also recovered. $^1H$ (400 MHz, $CDCl_3$) δ 5.46-5.28 (m, 10H), 4.86-4.83 (m, 1H), 4.26-4.22 (m, 1H), 4.10 (dd, 1H, J=12.0, 8.0), 3.65-3.42 (m, 7H), 2.85-2.76 (m, 6H), 2.58 (dd, 1H, J=12.0, 8.0), 2.31-1.89 (m, 23H), 1.82-1.76 (m, 2H), 1.59-1.52 (m, 6H), 1.38-1.26 (m, 34H), 0.97-0.93 (m, 3H), 0.90 (t, 6H, J=6.0). RT=5.20 min. 99.3% purity. ESI-MS: m/z=909 $[M+H]^+$ for $C_{58}H_{102}NO_6$.

PNI 132

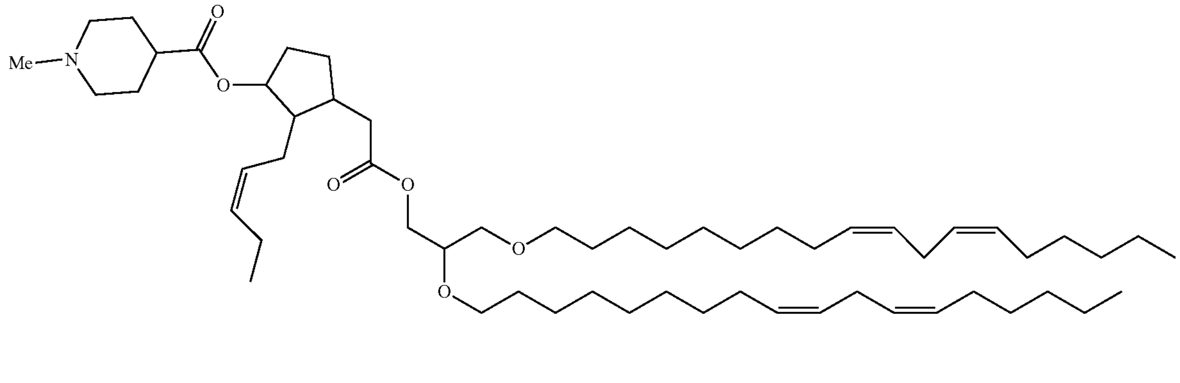

PNI 135

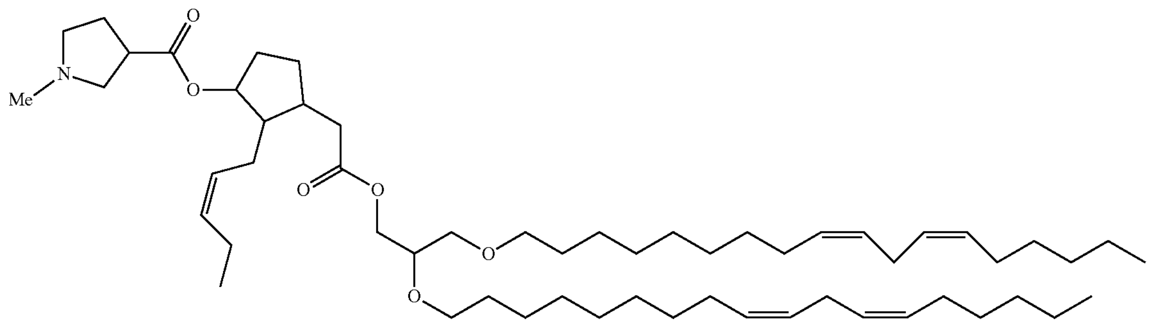

PNI 135 was synthesized using the method similar to the one used for synthesis of PNI 132. Synthesis of PNI 135 was performed using 1-methylpyrrolidine-3-carboxylic acid (0.074 g, 0.575 mmol) in DCM (20 mL), 5 (0.3 g, 0.383 mmol) in dry DCM (5 ml), DMAP (0.023 g, 0.192 mmol) and EDCl hydrochloride (0.147 g, 0.766 mmol). The crude product was purified by Isolera™ silica gel (100-200 mesh) column chromatography using 5% MeOH in DCM as eluent to afford PNI 135 (0.170 g, 0.185 mmol, 48.4% yield) as thick colorless oil. $^1H$ (400 MHz, $CDCl_3$) δ 5.45-5.30 (m, 10H), 4.87-4.83 (m, 1H), 4.26-4.22 (m, 1H), 4.10 (dd, 1H, J=12.0, 8.0), 3.61 (p, 1H, J=4.0), 3.55 (t, 2H, J=6.0), 3.49-3.42 (m, 4H), 3.07-3.00 (m, 1H), 2.97-2.88 (m, 1H), 2.78 (app t, 4H, J=6.0), 2.68-2.48 (m, 3H), 2.41 (s, 3H), 2.29 (dd, 1H, J=16.0, 8.0), 2.22-1.91 (m, 18H), 1.73-1.63 (m, 3H), 1.56 (p, 4H, J=8.0), 1.38-1.26 (m, 32H), 0.96 (t, 3H, J=6.0), 0.90 (app t, 6H, J=6.0). RT=3.55 min. 97.6% purity. ESI-MS: m/z=895 $[M+H]^+$ for $C_{57}H_{100}NO_6$.

PNI 143 was synthesized using the method similar to the one used for synthesis of PNI 132. Synthesis of PNI 143 was performed using 2-(1-methyl-1H-imidazol-4-yl)acetic acid (0.079 g, 0.562 mmol) in dry DMF (2 mL), 5 (0.400 g, 0.511 mmol) in dry DCM (8 mL), DMAP (6.24 mg, 0.051 mmol) and EDCl hydrochloride (0.196 g, 1.021 mmol). The crude product was purified by Isolera™ silica gel (100-200 mesh) column chromatography using 5% MeOH in EtOAc to afford PNI 143 (0.208 g, 0.230 mmol, 45.0% yield) as yellow oil. $^1H$ (400 MHz, $CDCl_3$) δ 7.35 (s, 1H), 6.85 (s, 1H), 5.45-5.20 (m, 10H), 4.89-4.86 (m, 1H), 4.27-4.21 (m, 1H), 4.10 (dd, 1H, J=12.0, 8.0), 3.65 (s, 3H), 3.64-3.59 (m, 3H), 3.55 (t, 2H, J=8.0), 3.49-3.42 (m, 4H), 2.78 (t, 4H, J=6.0), 2.62-2.53 (m, 1H), 2.29-1.87 (m, 15H), 1.75-1.66 (m, 2H), 1.56-1.49 (m, 4H), 1.40-1.24 (m, 34H), 0.96-0.92 (m, 3H), 0.89 (t, 6H, J=6.0). RT=4.63 min. 99.4% purity. ESI-MS: m/z=906 $[M+H]^+$ for $C_{57}H_{97}N_2O_6$.

PNI 143

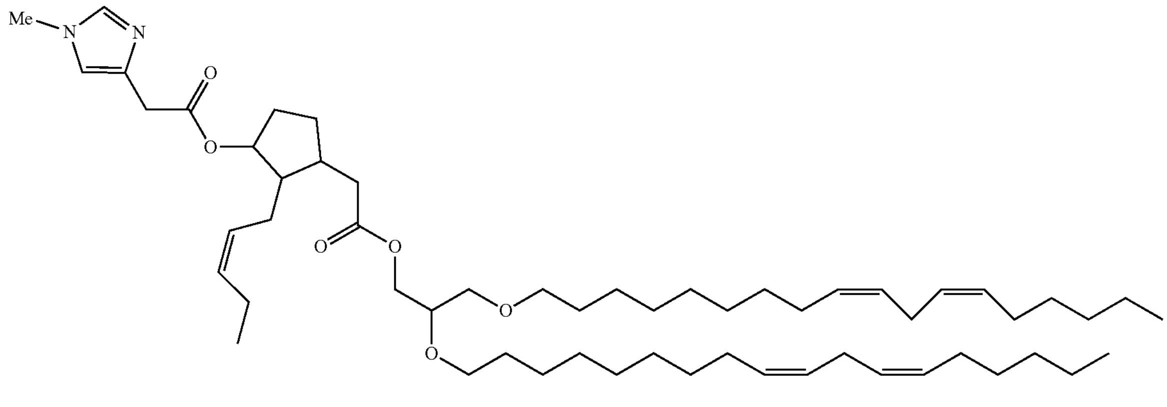

PNI 542

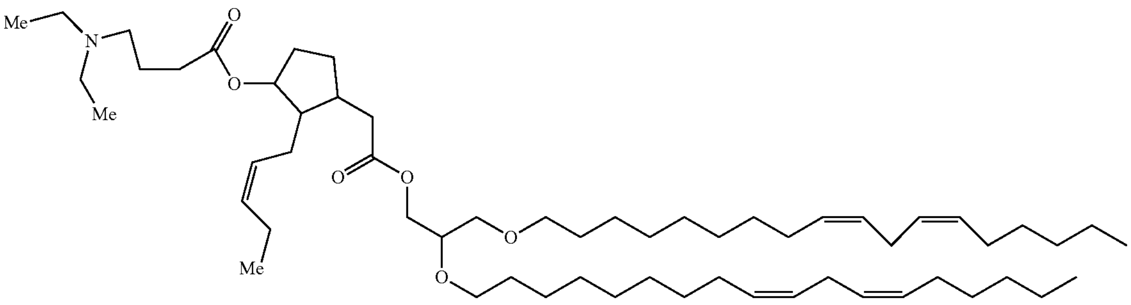

PNI 542 was synthesized using the method similar to the one used for synthesis of PNI 132. Synthesis of PNI 542 was performed using 4-(diethylamino)butanoic acid hydrochloride (0.094 g, 0.479 mmol) in dry DCM (6 mL), 5 (0.25 g, 0.319 mmol) in dry DCM (4 mL), DMAP (0.078 g, 0.638 mmol) and EDCl hydrochloride (0.122 g, 0.638 mmol). The crude product was purified by silica gel (100-200 mesh) column chromatography (Isolera™) using 5% MeOH in EtOAc to give PNI 542 (0.125 g, 0.135 mmol, 42.4% yield) as yellow oil. $^{1}$H (400 MHz, $CDCl_3$) δ 5.47-5.30 (m, 10H), 4.87-4.84 (m, 1H), 4.26-4.22 (m, 1H), 4.10 (dd, 1H, J=12.0, 8.0), 3.66-3.42 (m, 7H), 2.78 (t, 4H, J=6.0), 2.62-2.40 (m, 6H), 2.33-2.25 (m, 2H), 2.22-1.90 (m, 18H), 1.76 (p, 2H, J=8.0), 1.70-1.52 (m, 6H), 1.38-1.26 (m, 32H), 1.02 (t, 6H, J=8.0), 0.98-0.93 (m, 3H), 0.90 (app t, 6H, J=6.0). RT=3.75 min. 98% purity. ESI-MS: m/z=925 $[M+H]^+$ for $C_{59}H_{106}NO_6$.

PNI 557 was synthesized using the method similar to the one used for synthesis of PNI 132. Synthesis of PNI 557 was performed using 2-(1-methylpyrrolidin-3-yl)acetic acid hydrochloride (0.110 g, 0.613 mmol) in dry DMF (2 mL), 5 (0.4 g, 0.511 mmol) in dry DCM (8 mL), DMAP (6.24 mg, 0.051 mmol), EDCl (0.196 g, 1.021 mmol) and dry DCM (2.0 mL). The crude product was purified by Isolera™ silica gel (100-200 mesh) column chromatography using 7% MeOH in EtOAc to provide PNI 557 (0.275 g, 0.297 mmol, 58.1% yield) as yellow oil. 120 mg of alcohol 5 was also recovered. $^{1}$H (400 MHz, $CDCl_3$) δ 5.46-5.28 (m, 10H), 4.86-4.83 (m, 1H), 4.26-4.22 (m, 1H), 4.10 (dd, 1H, J=12.0, 8.0), 3.62 (p, 1H, J=4.0), 3.55 (t, 2H, J=8.0), 3.49-3.37 (m, 4H), 2.89-2.71 (m, 6H), 2.64-2.49 (m, 3H), 2.40-2.13 (m, 5H), 2.09-1.87 (m, 17H), 1.61-1.50 (m, 6H), 1.40-1.26 (m, 35H), 0.98-0.94 (m, 3H), 0.90 (t, 6H, J=6.0). RT=5.00 min. 98.0% purity. ESI-MS: m/z=909 $[M+H]^+$ for $C_{58}H_{10}NO_6$.

PNI 557

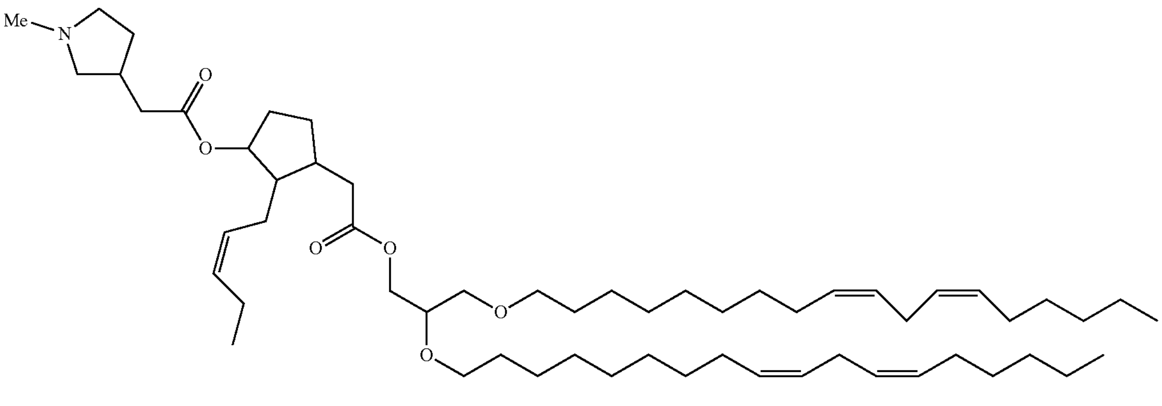

PNI 558

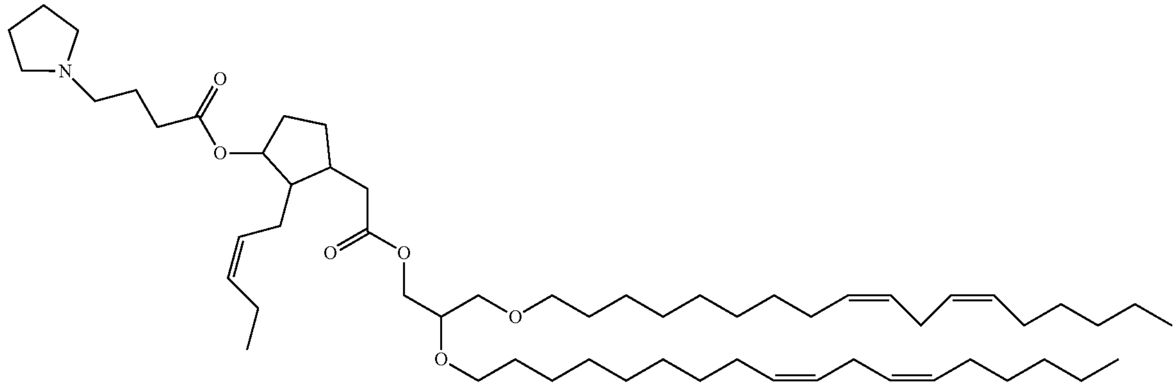

PNI 558 was synthesized using the method similar to the one used for synthesis of PNI 132. Synthesis of PNI 558 was performed using 4-(pyrrolidin-1-yl)butanoic acid hydrochloride (0.093 g, 0.479 mmol) in dry DCM (6 mL), 5 (0.25 g, 0.319 mmol) in dry DCM (4 mL), DMAP (0.078 g, 0.638 mmol) and EDCl (0.122 g, 0.638 mmol). The crude product was purified by Isolera™ silica gel (100-200 mesh) column chromatography using 5% MeOH in EtOAc to give PNI 558 (0.165 g, 0.179 mmol, 56.0% yield) as yellow oil. $^1$H (400 MHz, $CDCl_3$) δ 5.42-5.30 (m, 10H), 4.86-4.83 (m, 1H), 4.26-4.22 (m, 1H), 4.10 (dd, 1H, J=12.0, 8.0), 3.62 (p, 1H, J=4.0), 3.55 (t, 2H, J=8.0), 3.49-3.42 (m, 4H), 2.78 (t, 4H, J=6.0), 2.68-2.45 (m, 7H), 2.36-2.29 (m, 3H), 2.22-2.12 (m, 2H), 2.08-1.89 (m, 14H), 1.87-1.75 (m, 6H), 1.72-1.66 (m, 2H), 1.57-1.50 (m, 4H), 1.40-1.22 (m, 32H), 0.97-0.94 (m, 3H), 0.90 (t, 6H, J=6.0). RT=3.82 min. 97.8% purity. ESI-MS: m/z=923 $[M+H]^+$ for $C_{59}H_{104}NO_6$.

PNI 559 was synthesized using the method similar to the one used for synthesis of PNI 132. Synthesis of PNI 559 was performed using 2-(1-methylpiperidin-2-yl)acetic acid hydrochloride (0.093 g, 0.479 mmol) in dry DCM (6 mL), 5 (0.25 g, 0.319 mmol) in dry DCM (4 mL), DMAP (0.078 g, 0.638 mmol) and EDCl (0.122 g, 0.638 mmol). The crude product was purified by Isolera™ silica gel (100-200 mesh) column chromatography using 6% MeOH in EtOAc to provide PNI 559 (0.245 g, 0.266 mmol, 83% yield) as light-yellow oil. $^1$H (400 MHz, $CDCl_3$) δ 5.42-5.30 (m, 10H), 4.87-4.82 (m, 1H), 4.24 (dd, 1H, J=12.0, 4.0), 4.10 (dd, 1H, J=12.0, 8.0), 3.62 (p, 1H, J=4.0), 3.55 (t, 2H, J=8.0), 3.50-3.42 (m, 4H), 2.82-2.74 (m, 5H), 2.65-2.56 (m, 2H), 2.50-2.40 (m, 1H), 2.32-1.92 (m, 21H), 1.75-1.48 (m, 11H), 1.40-1.26 (m, 34H), 0.97-0.94 (m, 3H), 0.90 (t, 6H, J=6.0). RT=4.05 min. 98.0% purity. ES-MS: m/z=923 $[M+H]^+$ for $C_{59}H_{104}NO_6$

PNI 559

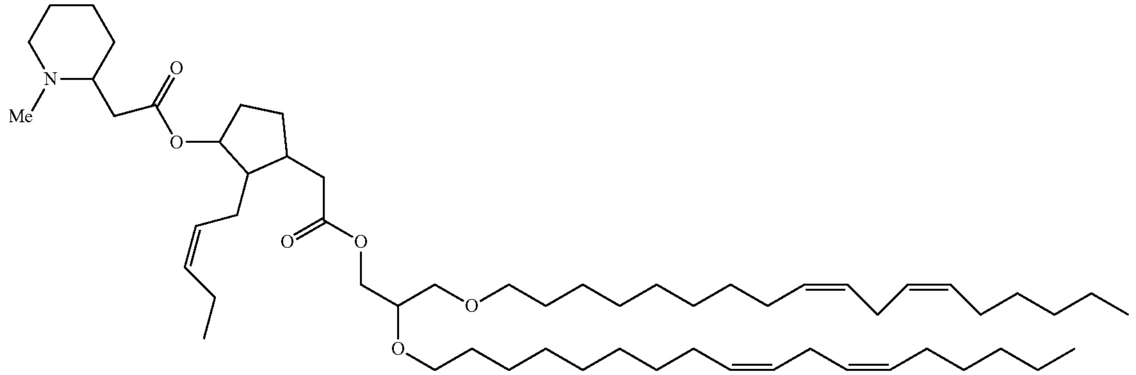

PNI 567

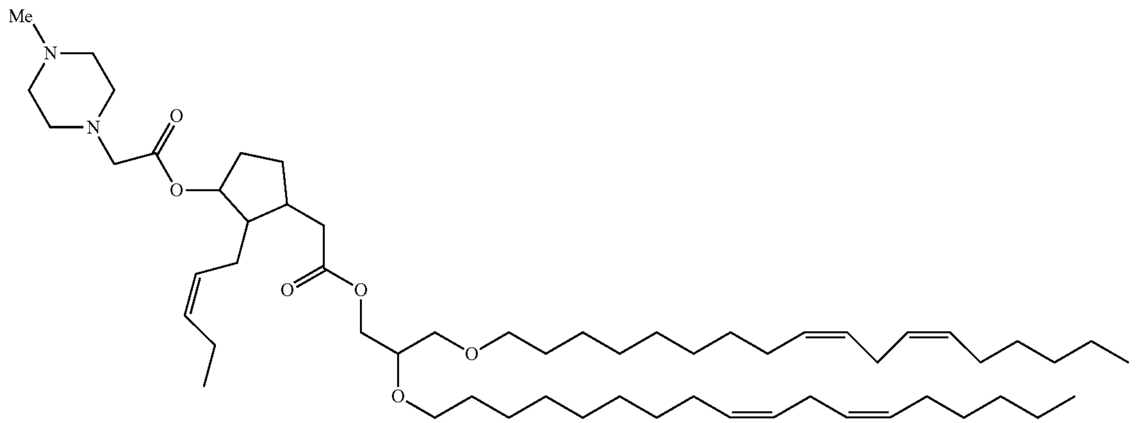

PNI 567 was synthesized using the method similar to the one used for synthesis of PNI 132. Synthesis of PNI 567 was performed using 2-(4-methylpiperazin-1-yl)acetic acid (0.105 g, 0.664 mmol) in dry DCM (25 mL), 5 (0.4 g, 0.511 mmol) in dry DCM (5 mL), DMAP (0.086 g, 0.664 mmol) and EDCl hydrochloride (0.293 g, 1.532 mmol). The crude product was purified by silica gel (100-200 mesh) column chromatography (Isolera™) using 5% MeOH in DCM to give PNI 567 (0.43 g, 0.466 mmol, 91% yield) as thick pale-yellow oil. $^1$H (400 MHz, $CDCl_3$) δ 5.46-5.21 (m, 10H), 4.90-4.87 (m, 1H), 4.26-4.21 (m, 1H), 4.09 (dd, 1H, J=12.0, 4.0), 3.64-3.58 (m, 1H), 3.54 (t, 2H, J=6.0), 3.48-3.41 (m, 4H), 3.17 (s, 2H), 2.77 (t, 4H, J=6.0), 2.69-2.44 (m, 9H), 2.31 (s, 3H), 2.28-1.90 (m, 16H), 1.73-1.63 (m, 1H), 1.59-1.52 (m 5H), 1.43-1.26 (m, 33H), 0.97-0.93 (m, 3H), 0.89 (app t, 6H, J=8.0). RT=3.21 min. 95.5% purity. ESI-MS: m/z=924 [M+H]$^+$ for $C_{58}H_{103}N_{206}$.

Example 2

Synthesis of PNI 516, 549, 560, 568, 569, 570, 571, and 573

Scheme 3.
Synthesis of compound 10

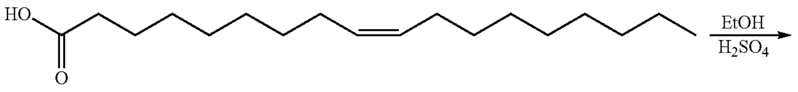

Oleic acid

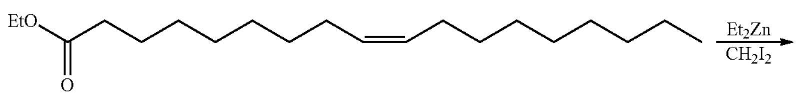

6

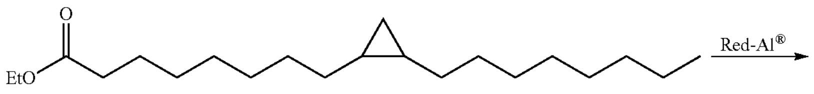

7

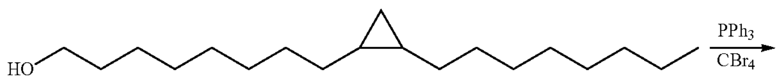

8

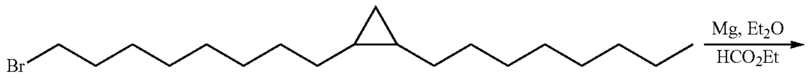

9

-continued

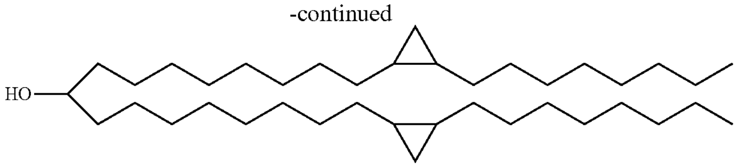

10

Scheme 4

General route for synthesis of PNI 516, 549, 560, 568, 569, 570, 571 and 573

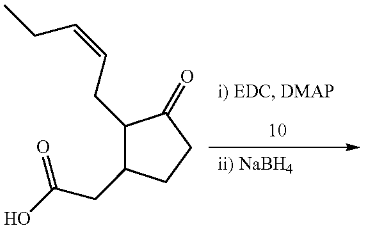

4

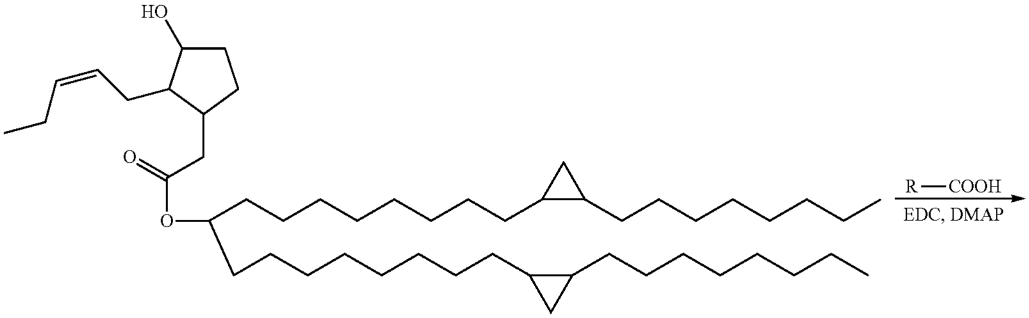

11

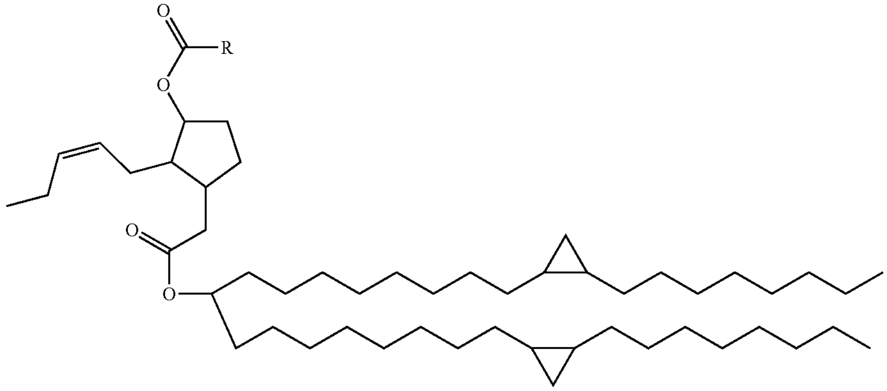

Compound 6: To a stirred solution of oleic acid (58 g, 205 mmol) in dry ethanol (580 mL), conc. $H_2SO_4$ (1.094 mL, 20.53 mmol) was added slowly and the reaction mixture was refluxed for 16 h. Upon completion of the reaction as indicated by TLC, the solvent was evaporated under reduced pressure. The residue was cooled to 0° C., neutralised with satd. aq. $NaHCO_3$ solution and extracted with DCM (3×250 mL). The combined organic layers were dried over anhydrous $Na_2SO_4$, filtered and concentrated to obtain ethyl oleate (6, 61.6 g, 198 mmol, 97% yield) as colorless oil. The ester was taken as such for the next step without further purification. $^1H$ (400 MHz, $CDCl_3$) δ 5.39-5.31 (m, 2H), 4.13 (q, 2H, J=8.0), 2.29 (t, 2H, J=8.0), 2.02 (app q, 4H, J=8.0), 1.62 (p, 2H, J=8.0), 1.35-1.24 (m, 23H), 0.89 (t, 3H, J=6.0). RT=3.73 min. 99.5% purity. ESI-MS: m/z=311 $[M+H]^+$ for $C_{20}H_{39}O_2$.

Compound 7: A solution diiodomethane (31.2 mL, 386 mmol) in toluene (120 mL) was stirred at −15° C. under nitrogen atmosphere. Diethylzinc (129 mL, 193 mmol, 1.5 M solution in toluene) was added dropwise to the reaction mixture at −15° C. for 30 mins. Note: The internal temperature of the reaction mixture should be maintained less than 0° C. Then, a solution of 6 (30 g, 97 mmol) in toluene (30 mL) was added dropwise to above reaction mixture so that internal temperature is maintained less than 0° C. The reaction mixture was stirred at same temperature for 15 mins and gradually allowed to warm to room temperature over 30 mins. After stirring for 7 h at room temperature, TLC analysis showed the completion of reaction. The reaction mixture was cooled to 0° C. and quenched with satd. aq. $NH_4Cl$ solution (100 mL). The organic layer was separated, and the aqueous layer was extracted with toluene (2×75 mL). The combined organic layers were dried over anhydrous $Na_2SO_4$, filtered and concentrated. The crude product was purified by Isolera™ silica gel (100-200 mesh) column chromatography using 6% EtOAc in Pet. ether to afford 7 (28.05 g, 86 mmol, 89% yield) as pale-yellow oil. $^1H$ (400 MHz, $CDCl_3$) δ 4.13 (q, 2H, J=8.0), 2.29 (t, 2H, J=8.0), 1.63 (p, 2H, J=8.0), 1.38-1.24 (m, 25H), 1.19-1.08 (m, 2H), 0.89 (t, 3H, J=6.0), 0.68-0.62 (m, 2H), 0.59-0.54 (m, 1H), −0.34 (app q, 1H, J=4.0). RT=4.01 min. 98.7% purity. ESI-MS: m/z=325 $[M+H]^+$ for $C_{21}H_{41}O_2$.

Compound 8: To a stirred solution of 7 (26 g, 80 mmol) in dry THE (250 ml) was added dropwise a solution of Red-Al® (54.1 mL, 160 mmol, 60 wt. % in toluene) under nitrogen atmosphere at −10° C. The reaction mixture was allowed to stir at 20° C. for 1 h. After completion of the reaction as indicated by TLC, the mixture was cooled to −10° C. and quenched with satd. aq. $Na_2SO_4$ solution (70 mL). The solid formation was observed in the reaction flask and it was diluted with EtOAc (260 mL). The content of the flask was filtered through a Celite™ $SiO_2$ bed and washed with EtOAc, until there was no compound observed in the filtrate. The combined filtrates were concentrated, and the residue was dissolved in EtOAc (700 mL). The organic layer was washed with water (2×200 mL) and brine (2×200 mL). The organic layer was separated, dried over anhydrous $Na_2SO_4$, filtered and concentrated to obtain 8 (22 g, 77 mmol, 96% yield) as yellow oil. $^1H$ (400 MHz, $CDCl_3$) δ 4.76 (s, 1H), 3.65 (t, 2H, J=6.0), 1.57 (p, 2H, J=8.0), 1.38-1.28 (m, 24H), 1.20-1.10 (m, 2H), 0.89 (t, 3H, J=6.0), 0.68-0.62 (m, 2H), 0.59-0.54 (m, 1H), −0.33 (app q, 1H, J=4.0). RT=2.88 min. 99.1% purity. ESI-MS: m/z=283 $[M+H]^+$ for $C_{19}H_{39}O$.

Compound 9: To a stirred solution of 8 (21.5 g, 76 mmol) in dry DCM (350 mL), triphenylphosphine (39.9 g, 152 mmol) was added at room temperature under nitrogen atmosphere. Carbon tetrabromide (50.5 g, 152 mmol) was added slowly to the reaction mixture and the mixture was stirred at room temperature for 4 h. After completion of the reaction as indicated by TLC, the solvent was evaporated under reduced pressure. The crude product was purified by (Isolera™, silica gel, 100-200 mesh) using 1% EtOAc in Pet. ether to provide 9 (25.5 g, 73.8 mmol, 97% yield) as colorless oil. $^1H$ (400 MHz, $CDCl_3$) δ 3.41 (t, 2H, J=6.0), 1.86 (p, 2H, J=8.0), 1.47-1.30 (m, 24H), 1.20-1.10 (m, 2H), 0.89 (t, 3H, J=8.0), 0.69-0.62 (m, 2H), 0.59-0.54 (m, 1H), −0.33 (app q, 1H, J=4.0). RT=3.22 min. 99.9% purity.

Compound 10: 1,2-Dibromoethane (0.025 ml, 0.290 mmol) was added to a stirred suspension of freshly activated Mg turnings (0.106 g, 4.34 mmol) in dry THE (3 mL) at room temperature under nitrogen atmosphere. The mixture was stirred for 5 minutes and a solution of 9 (1.0 g, 2.90 mmol) in dry THE (3 mL) was added. The reaction mixture was refluxed for 1 hr and TLC analysis showed the complete consumption of 9. The mixture was cooled to 20° C. and a solution of ethyl formate (0.106 mL, 1.303 mmol) in dry THE (2 mL) was added. After stirring at 30° C. for 1 hour, the reaction mixture was cooled to 0° C. and acetone (1 mL) was added dropwise followed by ice cold water (1 mL). The suspension was slowly poured into an ice cold solution of aq. 10% $H_2SO_4$ (10 mL) with slow stirring and the aq. layer was extracted with MTBE (3×25 mL). The combined organic layers were washed with brine (2×25 mL), dried over anhydrous $Na_2SO_4$, filtered and concentrated. The residue was dissolved in THE (3 mL) and a solution of NaOH (1.158 g, 29.0 mmol) in water (7 mL) was added. The reaction mixture was heated to 65° C. for 18 hours and TLC analysis showed the complete consumption of starting material. The reaction mixture was cooled to room temperature and extracted with MTBE (2×25 mL). The combined organic layers were washed with brine (2×20 mL), dried over anhydrous $Na_2SO_4$, filtered and concentrated. The crude product was purified by silica gel (100-200 mesh) column chromatography (Isolera™) using 6% EtOAc in Pet. ether to afford 10 (0.185 g, 0.330 mmol, 11.39% yield) as yellow oil. $^1H$ (400 MHz, $CDCl_3$) δ 3.64-3.54 (m, 1H), 1.45-1.27 (m, 56H), 1.19-1.11 (m, 4H), 0.89 (t, 6H, J=6.0), 0.68-0.63 (m, 4H), 0.59-0.54 (m, 2H), −0.33 (app q, 2H, J=4.0).

Compound 11: 1,17-bis(2-octylcyclopropyl)heptadecan-9-yl (Z)-2-(3-oxo-2-(pent-2-en-1-yl)cyclopentyl)acetate was synthesized using the method similar to the one used for synthesis of 2,3-bis(((9Z,12Z)-octadeca-9,12-dien-1-yl)oxy)propyl 2-(3-oxo-2-((Z)-pent-2-en-1-yl)cyclopentyl)acetate. Synthesis of this crude ketone was performed using 10 (1.25 g, 2.228 mmol) in dry DCM (12 mL), DMAP (0.408 g, 3.34 mmol), 4 (0.937 g, 4.46 mmol) in dry DCM (8 mL) and EDCl hydrochloride (0.854 g, 4.46 mmol). The crude product (1.62 g, 2.151 mmol, 97% crude yield) was obtained as thick yellow oil and was taken for the next step without further purification.

Compound 11 was synthesized using the method similar to the one used for synthesis of 5. Synthesis of 11 was performed using 1,17-bis(2-octylcyclopropyl)heptadecan-9-yl (Z)-2-(3-oxo-2-(pent-2-en-1-yl)cyclopentyl)acetate (1.6 g, 2.124 mmol) in dry MeOH (16 mL) and THE (4 mL) and sodium borohydride (0.321 g, 8.50 mmol). The crude product was purified by Isolera™ silica gel (100-200 mesh) column chromatography using 10% EtOAc in Pet. ether to provide 11 (1.51 g, 1.999 mmol, 94% yield) as light-yellow oil. $^1H$ (400 MHz, $CDCl_3$) δ 5.50-5.43 (m, 1H), 5.29-5.26 (m, 1H), 4.90 (p, 1H, J=6.0), 3.89-3.78 (m, 1H), 2.72 (dd, 1H, J=16.0, 4.0), 2.42-1.87 (m, 9H), 1.55-1.48 (m, 6H), 1.37-1.25 (m, 52H), 1.20-1.07 (m, 4H), 0.97 (t, 3H, J=8.0), 0.89 (app t, 6H, J=6.0), 0.69-0.60 (m, 4H), 0.59-0.54 (m, 2H), −0.33 (q, 2H, J=8.0). RT=5.20 min. 56.2% purity. ESI-MS: m/z=778 $[M+Na]^+$ for $C_{51}H_{94}O_3Na$.

PNI 516

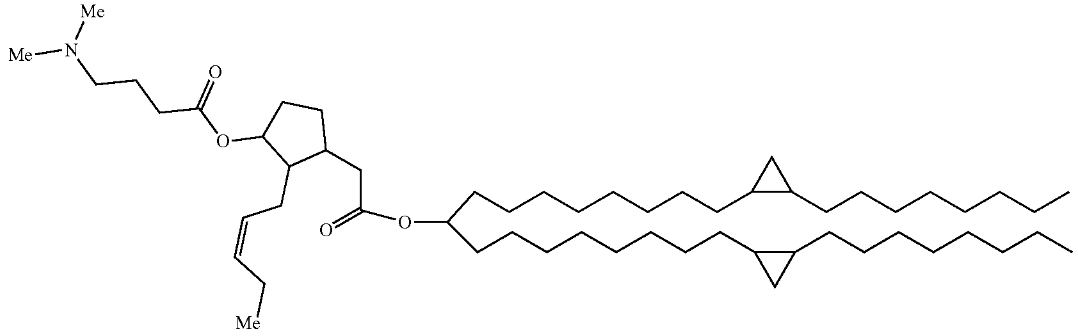

PNI 516 was synthesized using the method similar to the one used for synthesis of PNI 132. Synthesis of PNI 516 was performed using 4-(dimethylamino)butanoic acid hydrochloride (0.133 g, 0.794 mmol) in dry DMF (2 mL), 11 (0.5 g, 0.662 mmol) in dry DCM (8 mL), DMAP (0.162 g, 1.324 mmol) and EDCl hydrochloride (0.254 g, 1.324 mmol). The crude product was purified by Isolera™ silica gel (100-200 mesh) column chromatography using 8% MeOH in EtOAc to afford PNI 516 (0.305 g, 0.349 mmol, 52.7% yield) as light-yellow oil. $^1$H (400 MHz, $CDCl_3$) δ 5.48-5.25 (m, 2H), 4.90-4.84 (m, 2H), 2.78-2.44 (m, 8H), 2.40-2.36 (m, 2H), 2.26-1.90 (m, 11H), 1.72-1.52 (m, 7H), 1.43-1.22 (m, 52H), 1.20-1.06 (m, 4H), 0.98-0.93 (m, 3H), 0.89 (t, 6H, J=6.0), 0.69-0.54 (m, 6H), −0.31–−0.35 (m, 2H). RT=9.64 min. 99.3% purity. ESI-MS: m/z=869 $[M+H]^+$ for $C_{57}H_{106}NO_4$.

PNI 549

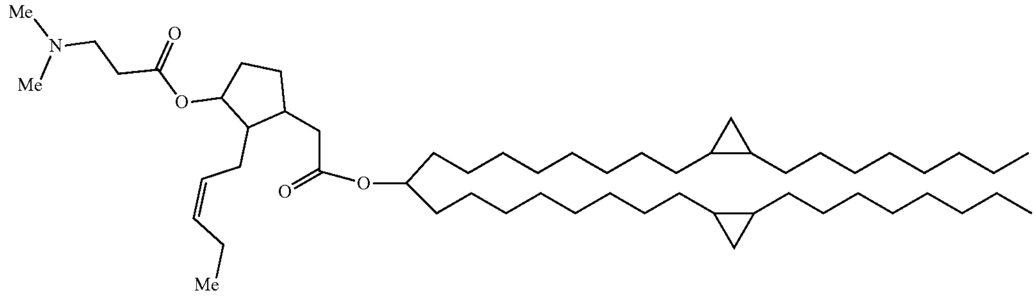

PNI 549 was synthesized using the method similar to the one used for synthesis of PNI 132. Synthesis of PNI 549 was performed using 3-(dimethylamino)propanoic acid hydrochloride (0.122 g, 0.794 mmol) in dry DCM (8 mL), 11 (0.4 g, 0.530 mmol) in dry DCM (4 mL), DMAP (0.129 g, 1.059 mmol) and EDCl (0.203 g, 1.059 mmol). The crude product was purified by Ilsolera™ silica gel (100-200 mesh) column chromatography using 10% MeOH in EtOAc to give PNI 549 (0.17 g, 0.197 mmol, 37.2% yield) as light-yellow oil. Note: 140 mg of 11 was also recovered. $^1$H (400 MHz, $CDCl_3$) δ 5.47-5.40 (m, 1H), 5.37-5.27 (m, 1H), 4.90-4.84 (m, 2H), 2.67-2.54 (m, 3H), 2.51-2.40 (m, 2H), 2.32-1.89 (m, 15H), 1.74-1.64 (m, 2H), 1.55-1.48 (m, 4H), 1.42-1.24 (m, 52H), 1.20-1.07 (m, 4H), 0.98-0.93 (m, 3H), 0.89 (t, 6H, J=8.0), 0.71-0.54 (m, 6H), −0.33 (q, 2H, J=4.0). RT=10.16 min. 98.9% purity. ESI-MS: m/z=877 $[M+Na]^+$ for $C_{56}H_{103}NO_4Na$.

PNI 560

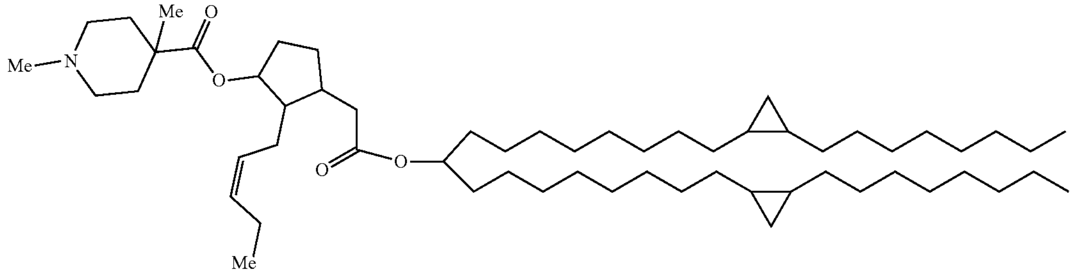

PNI 560 was synthesized using the method similar to the one used for synthesis of PNI 132. Synthesis of PNI 560 was performed using 1,4-dimethylpiperidine-4-carboxylic acid hydrochloride (0.092 g, 0.477 mmol) in dry DMF (2 ml), 11 (0.3 g, 0.397 mmol) in dry DCM (8 mL), DMAP (0.097 g, 0.794 mmol) and EDCl hydrochloride (0.152 g, 0.794 mmol). The crude product was purified by Isolera™ silica gel (100-200 mesh) column chromatography using 10% MeOH in EtOAc to afford PNI 560 (0.172 g, 0.191 mmol, 48.1% yield) as light-yellow oil. Note: 50 mg of 11 was recovered. $^1$H (400 MHz, $CDCl_3$) δ 5.43-5.37 (m, 1H), 5.31-5.22 (m, 1H), 4.86-4.81 (m, 2H), 2.63-2.48 (m, 5H), 2.23-1.87 (m, 13H), 1.72-1.43 (m, 7H), 1.38-1.19 (m, 57H), 1.15-1.04 (m, 4H), 0.94-0.91 (m, 3H), 0.85 (t, 6H, J=6.0), 0.66-0.50 (m, 6H), −0.38 (app q, 2H, J=4.0). RT=11.40 min. 99.3% purity. ESI-MS: m/z=895 $[M+H]^+$ for $C_{59}H_{108}NO_4$.

PNI 569 was synthesized using the method similar to the one used for synthesis of PNI 132. Synthesis of PNI 569 was performed using 1-methylpiperidine-3-carboxylic acid (0.083 g, 0.583 mmol) in dry DCM (20 mL), 11 (0.4 g, 0.530 mmol) in dry DCM (5 mL), DMAP (0.071 g, 0.583 mmol) and EDCl hydrochloride (0.234 g, 1.218 mmol). The crude product was purified by silica gel (100-200 mesh) column chromatography (Isolera™) using 3% MeOH in DCM to give PNI 569 (0.38 g, 0.432 mmol, 81% yield) as pale-yellow oil. $^1$H (400 MHz, $CDCl_3$) δ 5.48-5.29 (m, 2H), 4.97-4.85 (m, 2H), 2.61-2.30 (m, 5H), 2.26-1.73 (m, 14H), 1.71-1.46 (m, 8H), 1.42-1.20 (m, 53H), 1.19-1.04 (m, 4H), 0.96 (t, 3H, J=8.0), 0.89 (t, 6H, J=6.0), 0.69-0.61 (m, 4H), 0.59-0.54 (m, 2H), −0.33 (q, 2H, J=4.0). RT=8.18 min. 99.6% purity. ESI-MS: m/z=881 $[M+H]^+$ for $C_{58}H_{106}NO_4$.

PNI 568

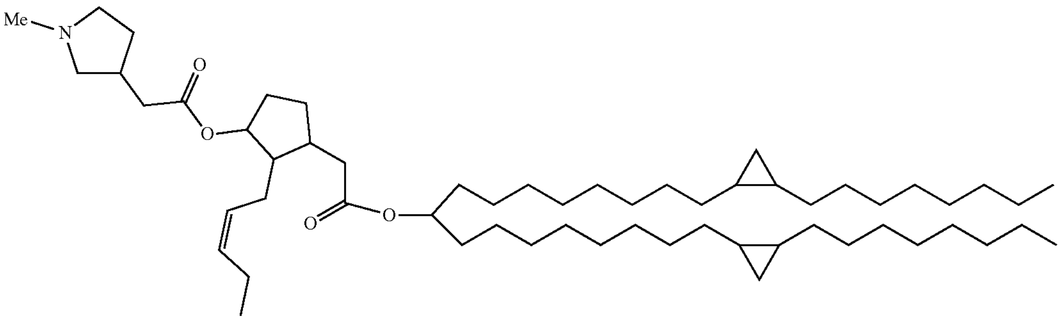

PNI 568 was synthesized using the method similar to the one used for synthesis of PNI 132. Synthesis of PNI 568 was performed using 2-(1-methylpyrrolidin-3-yl)acetic acid hydrochloride (0.114 g, 0.636 mmol) in dry DCM (20 mL), 11 (0.4 g, 0.530 mmol) in dry DCM (5 mL), DMAP (0.078 g, 0.636 mmol) and EDCl hydrochloride (0.244 g, 1.271 mmol). The crude product was purified by silica gel (100-200 mesh) column chromatography (Isolera™) using 3% MeOH in DCM to provide PNI 568 (0.375 g, 0.426 mmol, 80% yield) as pale-yellow oil. $^1$H (400 MHz, $CDCl_3$) δ 5.46-5.26 (m, 2H), 4.90-4.83 (m, 2H), 2.86-2.75 (m, 4H), 2.61-2.52 (m, 3H), 2.39-1.85 (m, 12H), 1.69-1.62 (m, 3H), 1.58-1.46 (m, 5H), 1.44-1.26 (m, 53H), 1.19-1.07 (m, 4H), 0.98-0.94 (m, 3H), 0.89 (t, 6H, J=8.0), 0.69-0.60 (m, 4H), 0.59-0.54 (m, 2H), −0.33 (q, 2H, J=4.0). RT=9.19 min. 99.7% purity. ESI-MS: m/z=881 $[M+H]^+$ for $C_{58}H_{106}NO_4$.

PNI 569

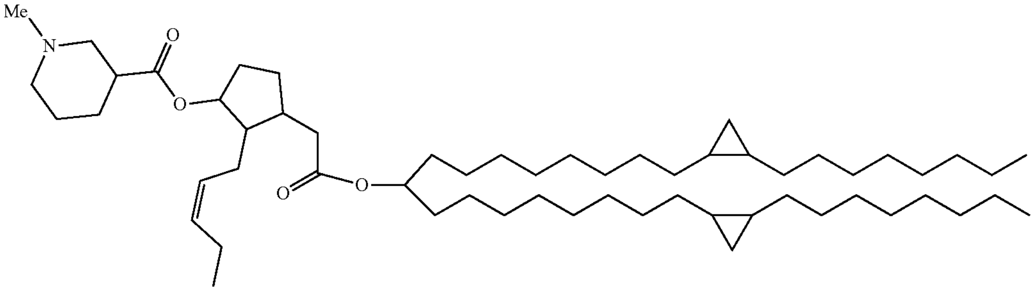

PNI 570

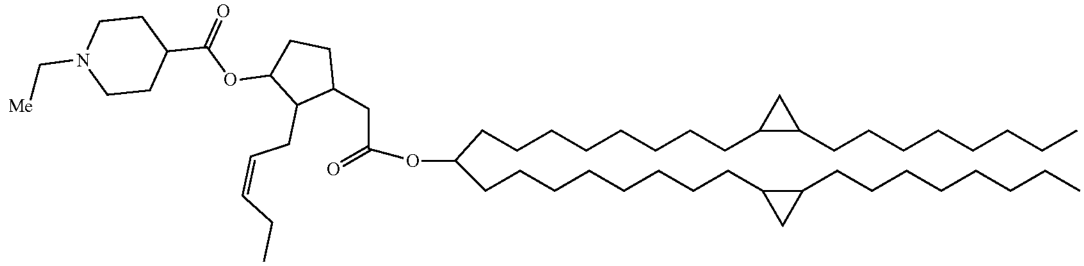

PNI 570 was synthesized using the method similar to the one used for synthesis of PNI 132. Synthesis of PNI 570 was performed using 1-ethylpiperidine-4-carboxylic acid (0.100 g, 0.636 mmol) in dry DCM (20 mL), 11 (0.4 g, 0.530 mmol) in dry DCM (5 mL), DMAP (0.078 g, 0.636 mmol) and EDCl hydrochloride (0.244 g, 1.271 mmol). The crude product was purified by silica gel (100-200 mesh) column chromatography (Isolera™) using 4% MeOH in DCM to give PNI 570 (0.3 g, 0.335 mmol, 63.3% yield) as light brown oil. $^1H$ (400 MHz, $CDCl_3$) δ 5.47-5.28 (m, 2H), 4.97-4.85 (m, 2H), 3.27-2.66 (m, 5H), 2.60-2.52 (m, 2H), 2.26-1.92 (m, 12H), 1.70-1.50 (m, 8H), 1.42-1.26 (m, 55H), 1.19-1.03 (m, 4H), 0.98-0.93 (m, 3H), 0.89 (t, 6H, J=6.0), 0.68-0.62 (m, 4H), 0.59-0.54 (m, 2H), −0.33 (q, 2H, J=4.0). RT=9.25 min. 99.9% purity. ESI-MS: m/z=895 $[M+H]^+$ for $C_{59}H_{108}NO_4$.

PNI 571

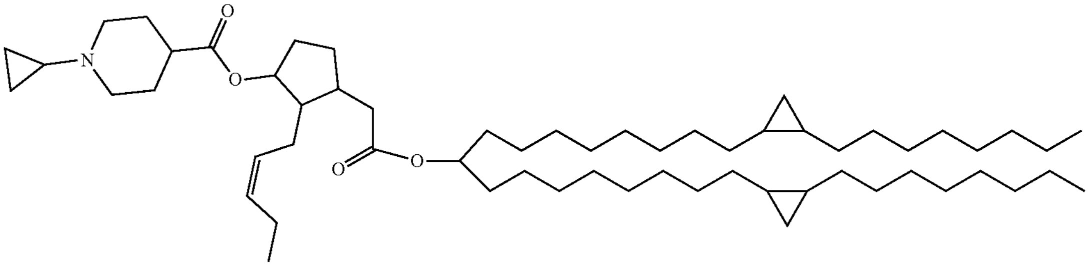

PNI 571 was synthesized using the method similar to the one used for synthesis of PNI 132. Synthesis of PNI 571 was performed using 1-cyclopropylpiperidine-4-carboxylic acid (0.099 g, 0.583 mmol) in dry DCM (20 mL), 11 (0.4 g, 0.530 mmol) in dry DCM (5 mL), DMAP (0.071 g, 0.583 mmol) and EDCl hydrochloride (0.234 g, 1.218 mmol). The crude product was purified by silica gel (100-200 mesh) column chromatography (Isolera™) using 4% MeOH in DCM to provide PNI 571 (0.335 g, 0.370 mmol, 69.8% yield) as pale-yellow oil. $^1H$ (400 MHz, $CDCl_3$) δ 5.47-5.31 (m, 2H), 5.02-4.85 (m, 2H), 3.01-2.98 (m, 2H), 2.60-2.53 (m, 2H), 2.25-1.88 (m, 14H), 1.75-1.47 (m, 8H), 1.43-1.26 (m, 52H), 1.17-1.11 (m, 4H), 0.97-0.93 (m, 3H), 0.89 (t, 6H, J=6.0), 0.69-0.61 (m, 4H), 0.59-0.54 (m, 2H), 0.50-0.34 (m, 4H), −0.33 (q, 2H, J=4.0). RT=10.63 min. 94.6% purity. ESI-MS: m/z=929 $[M+Na]^+$ for $C_{60}H_{107}NO_4Na$.

PNI 573

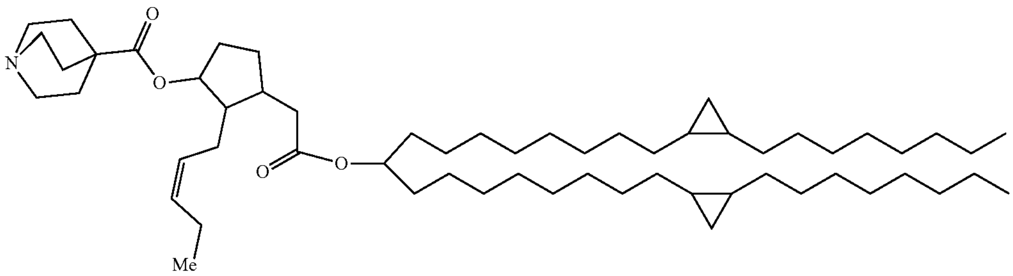

PNI 573 was synthesized using the method similar to the one used for synthesis of PNI 132. Synthesis of PNI 573 was performed using quinuclidine-4-carboxylic acid hydrochloride (5, 0.101 g, 0.530 mmol) in dry DCM (20 mL), 11 (0.4 g, 0.530 mmol) in dry DCM (5 mL), DMAP (0.065 g, 0.530 mmol) and EDCl hydrochloride (0.234 g, 1.218 mmol). The crude product was purified by silica gel (100-200 mesh) column chromatography (Isolera™) using 5% MeOH in DCM to give PNI 573 (0.155 g, 0.174 mmol, 32.8% yield) as yellow oil. $^1$H (400 MHz, $CDCl_3$) δ 5.48-5.22 (m, 2H), 5.02-4.86 (m, 2H), 3.29 (t, 6H, J=8.0), 2.57-2.52 (m, 1H), 2.29-1.96 (m, 15H), 1.74-1.46 (m, 6H), 1.59-1.26 (m, 52H), 1.19-1.06 (m, 4H), 0.96 (t, 3H, J=8.0), 0.89 (t, 6H, J=6.0), 0.69-0.61 (m, 4H), 0.59-0.54 (m, 2H), −0.33 (q, 2H, J=4.0). RT=7.65 min. 97.8% purity. ESI-MS: m/z=893 $[M+H]^+$ for $C_{59}H_{106}NO_4$.

Example 3. Synthesis of PNI 543 and 544

Scheme 5.
Synthesis of Compound 13

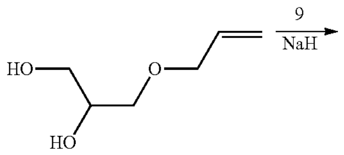

1

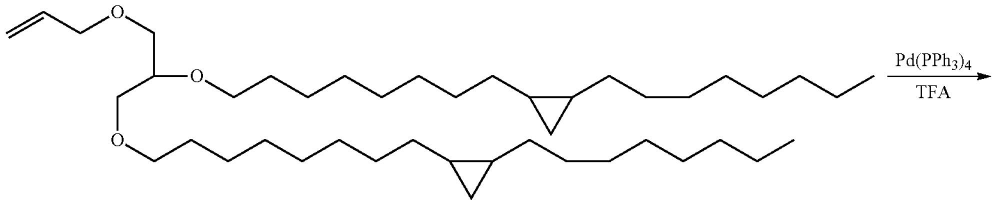

12

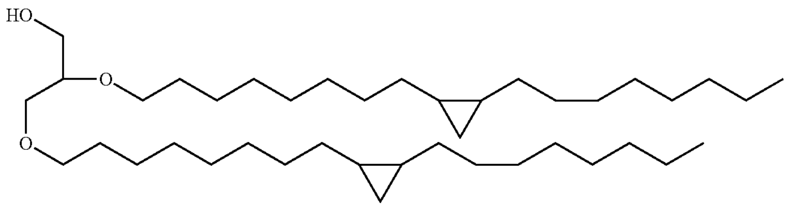

13

Scheme 6. General route for synthesis of PNI 543 and 544

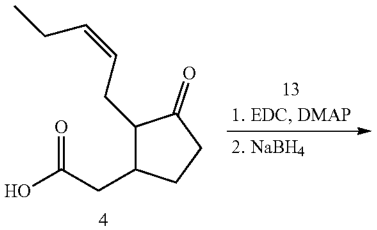

4

-continued

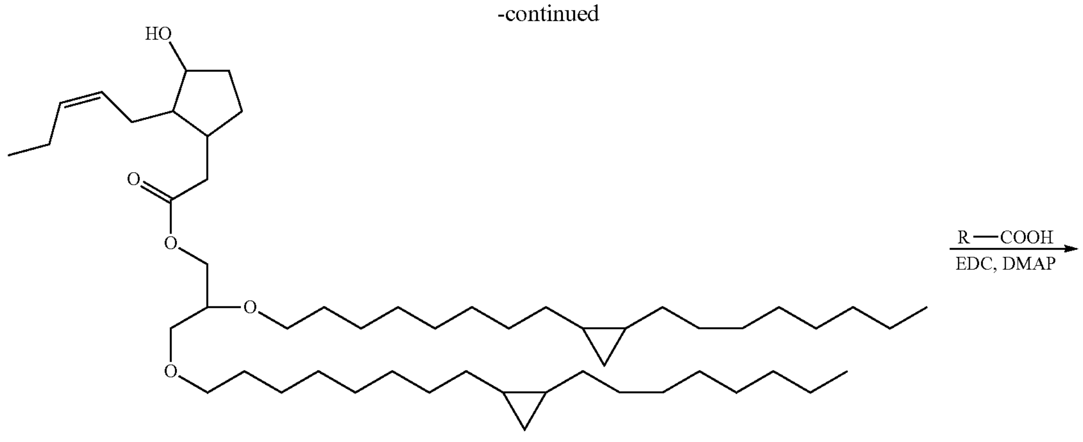

14

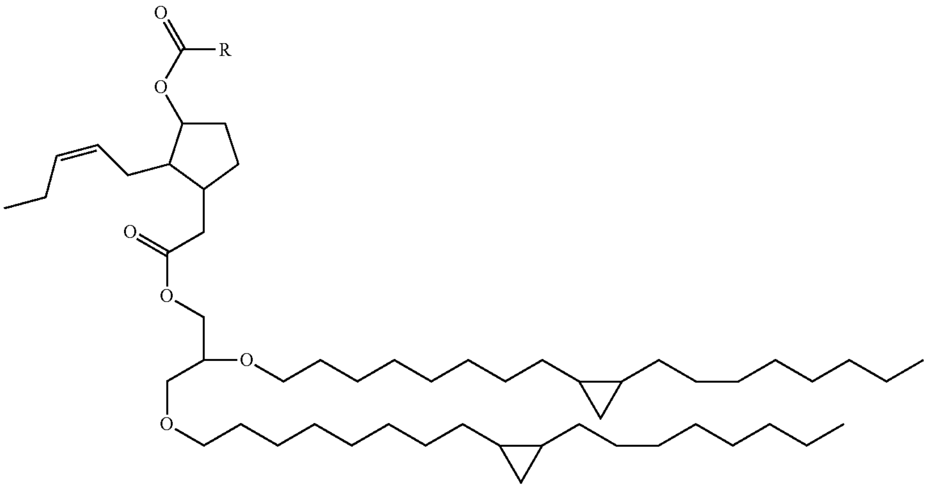

Compound 12: Compound 12 was synthesized using the method similar to the one used for synthesis of compound 2. Synthesis of 12 was performed using sodium hydride (0.666 g, 16.65 mmol, 60% dispersion in mineral oil), 3-(allyloxy) propane-1,2-diol (1, 0.5 g, 3.78 mmol) in dry THE (40 mL), 9 (3.14 g, 9.08 mmol) in dry THE (10 mL) and 15-crown-5 (0.175 g, 0.794 mmol). The crude product was purified by Isolera™ silica gel (100-200 mesh) column chromatography using 2% EtOAc in Pet. ether as eluent to afford 12 (0.53 g, 0.787 mmol, 20.81% yield) as yellow oil. $^1H$ (400 MHz, $CDCl_3$) δ 5.96-5.86 (m, 1H), 5.28 (dd, 1H, J=16.0, 4.0), 5.17 (dd, 1H, J=12.0, 4.0), 4.02 (d, 2H, J=4.0), 3.60-3.43 (m, 9H), 1.59-1.51 (m, 4H), 1.38-1.28 (m, 48H), 1.20-1.06 (m, 4H), 0.89 (t, 6H, J=6.0), 0.70-0.61 (m, 4H), 0.59-0.54 (m, 2H), −0.33 (q, 2H, J=8.0). RT=3.12 min. 98.3% purity. ESI-MS: m/z=663 $[M+H]^+$ for $C_{44}H_{85}O_3$.

Compound 13: Compound 13 was synthesized using the method similar to the one used for synthesis of compound 3. Synthesis of 13 was performed using TFA (0.848 mL, 11.01 mmol), $Pd(PPh_3)_4$ (0.091 g, 0.079 mmol), 12 (0.52 g, 0.787 mmol) in dry EtOH (10 mL) and additional $Pd(PPh_3)_4$ (0.045 g, 0.039 mmol). The crude product was purified by Isolera™ silica gel (100-200 mesh) column chromatography using 6% EtOAc in Pet·ether to provide 13 (0.305 g, 0.491 mmol, 62.4% yield) as light-yellow oil. $^1H$ (400 MHz, $CDCl_3$) δ 3.75-3.43 (m, 9H), 1.74-1.53 (m, 4H), 1.38-1.28 (m, 48H), 1.19-1.10 (m, 4H), 0.89 (t, 6H, J=6.0), 0.68-0.62 (m, 4H), 0.59-0.54 (m, 2H), −0.33 (q, 2H, J=4.0). RT=2.27 min. 94.6% purity.

Compound 14: Compound 2,3-bis((8-(2-octylcyclopropyl)octyl)oxy)propyl (Z)-2-(3-oxo-2-(pent-2-en-1-yl)cyclopentyl)acetate was synthesized using the method similar to the one used for synthesis of 2,3-bis(((9Z,12Z)-octadeca-9,12-dien-1-yl)oxy)propyl 2-(3-oxo-2-((Z)-pent-2-en-1-yl)cyclopentyl)acetate. Synthesis of this ketone was performed using 13 (3.5 g, 5.64 mmol) in dry DCM (20 mL), DMAP (1.033 g, 8.45 mmol), 4 (1.777 g, 8.45 mmol) in dry DCM (10 mL) and EDCl hydrochloride (1.620 g, 8.45 mmol). The crude product was used for the next step without further purification. $^1H$ (400 MHz, $CDCl_3$) δ 5.49-5.43 (m, 1H), 5.30-5.23 (m, 1H), 4.28 (dd, 1H, J=12.0, 4.0), 4.14-4.10 (m, 1H), 3.63 (p, 1H, J=4.0), 3.55 (t, 2H, J=8.0), 3.50-3.42 (m, 4H), 2.79-2.69 (m, 1H), 2.40-2.02 (m, 7H), 1.93-1.87 (m, 2H), 1.65-1.48 (m, 6H), 1.38-1.28 (m, 48H), 1.19-1.06 (m, 4H), 0.96 (t, 3H, J=6.0), 0.89 (t, 6H, J=6.0), 0.68-0.62 (m, 4H), 0.59-0.54 (m, 2H), −0.34 (q, 2H, J=4.0). RT=6.00 min. 73.6% purity. ESI-MS: m/z=836 $[M+Na]^+$ for $C_{53}H_{96}O_5Na$.

Compound 14 was synthesized using the method similar to the one used for synthesis of compound 5. Synthesis of 14 was performed using 2,3-bis((8-(2-octylcyclopropyl)octyl)oxy)propyl (Z)-2-(3-oxo-2-(pent-2-en-1-yl)cyclopentyl)acetate (4.8 g, 6.01 mmol) in dry Ethanol:THE (15 mL, 2:1) and sodium borohydride (0.795 g, 21.02 mmol). The crude product was purified by silica gel (100-200 mesh) column chromatography (Isolera™) using 10% EtOAc in pet. ether as the eluent to give 14 (2.357 g, 2.5 mmol, 41.6% yield) as a thick colourless oil. $^1H$ (400 MHz, $CDCl_3$) δ 5.50-5.36 (m, 2H), 4.26-4.20 (m, 1H), 4.12-4.04 (m, 1H), 3.94-3.86 (m, 1H), 3.62 (p, 1H, J=6.0), 3.55 (t, 2H, J=6.0), 3.49-3.42 (m, 4H), 2.61-2.52 (m, 1H), 2.29-2.04 (m, 7H), 1.95-1.84 (m, 2H), 1.67-1.53 (m, 6H), 1.38-1.28 (m, 48H), 1.19-1.11 (m, 4H), 0.98 (t, 3H, J=8.0), 0.89 (t, 6H, J=6.0), 0.68-0.62 (m, 4H), 0.59-0.54 (m, 2H), −0.33 (q, 2H, J=4.0). RT=5.78 min. 85.0% purity. ESI-MS: m/z=838 $[M+Na]^+$ for $C_{53}H_{98}O_5Na$.

PNI 543

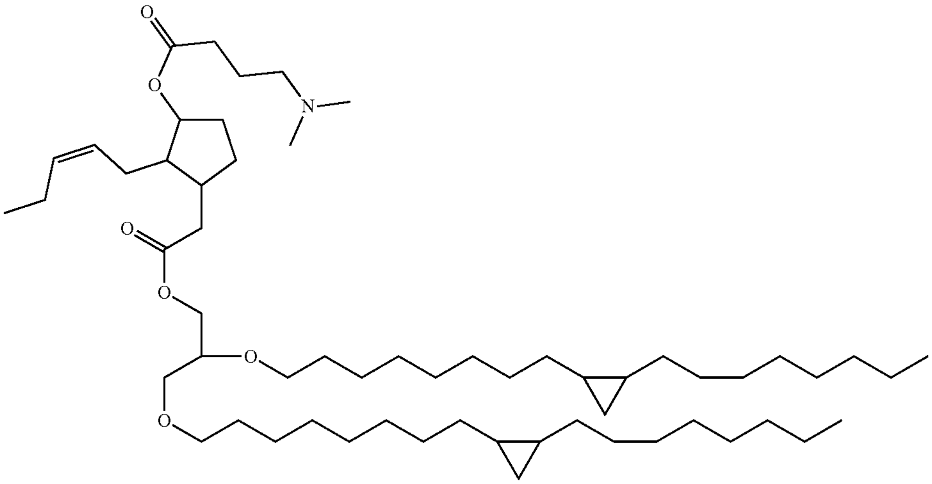

PNI 543 was synthesized using the method similar to the one used for synthesis of PNI 132. Synthesis of PNI 543 was performed using 4-(dimethylamino)butanoic acid hydrochloride (0.097 g, 0.578 mmol) in dry DCM (10 mL), 14 (0.4 g, 0.511 mmol) in dry DCM (8 mL), DMAP (6.24 mg, 0.051 mmol) and EDCl hydrochloride (0.147 g, 0.766 mmol). The crude product was purified by Isolera™ silica gel (100-200 mesh) column chromatography using 5% MeOH in EtOAc to afford PNI 543 (0.240 g, 0.258 mmol, 52.7% yield) as a colourless liquid. $^1$H (400 MHz, $CDCl_3$) δ 5.45-5.41 (m, 1H), 5.36-5.31 (m, 1H), 4.86-4.83 (m, 1H), 4.24 (dd, 1H, J=12.0, 4.0), 4.10 (dd, 1H, J=12.0, 8.0), 3.62 (p, 1H, J=4.0), 3.55 (t, 2H, J=8.0), 3.49-3.42 (m, 4H), 2.59 (dd, 1H, J=16.0, 4.0), 2.32-2.26 (m, 4H), 2.22 (s, 6H), 2.20-1.88 (m, 9H), 1.78 (p, 2H, J=8.0), 1.72-1.65 (m, 2H), 1.56 (p, 4H, J=8.0), 1.40-1.28 (m, 48H), 1.17-1.11 (m, 4H), 0.96 (t, 3H, J=6.0), 0.89 (t, 6H, J=6.0), 0.68-0.62 (m, 4H), 0.59-0.54 (m, 2H), −0.33 (q, 2H, J=4.0). RT=6.67 min. 99.9% purity. ESI-MS: m/z=929 $[M+H]^+$ for $C_5H_{110}NO_6$.

PNI 544

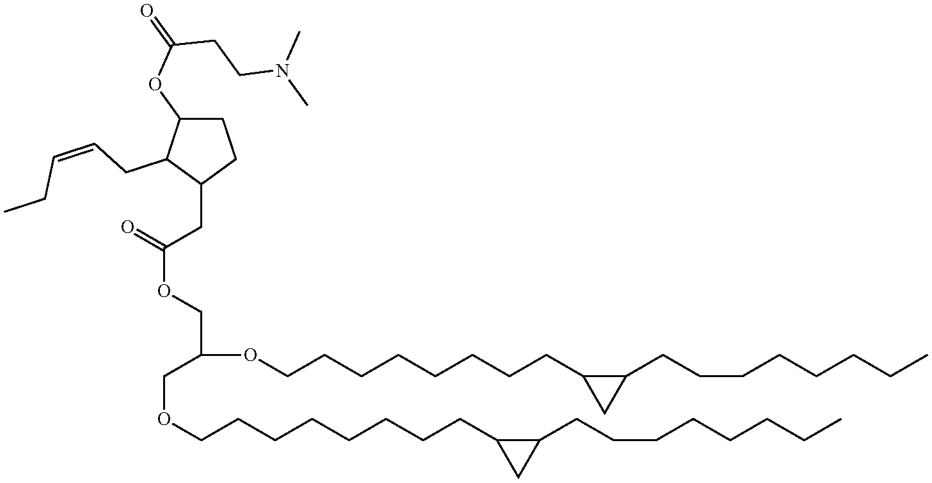

PNI 544 was synthesized using the method similar to the one used for synthesis of PNI 132. Synthesis of PNI 544 was performed using 3-(dimethylamino)propanoic acid hydrochloride (0.115 g, 0.748 mmol) in dry DCM (10 mL), 14 (0.400 g, 0.491 mmol) in dry DCM (10 mL), DMAP (0.018 g, 0.147 mmol) and EDCl (0.141 g, 0.736 mmol). The crude product was purified by silica gel (100-200 mesh) column chromatography (Isolera™) using 60-100% ethyl acetate in petroleum ether to afford PNI 544 (0.096 g, 0.105 mmol, 21.40% yield) as a colourless liquid. $^1$H (400 MHz, $CDCl_3$) δ 5.47-5.41 (m, 1H), 5.36-5.30 (m, 1H), 4.88-4.84 (m, 1H), 4.24 (dd, 1H, J=12.0, 4.0), 4.10 (dd, 1H, J=12.0, 8.0), 3.62 (p, 1H, J=4.0), 3.55 (t, 2H, J=8.0), 3.49-3.42 (m, 4H), 2.62-2.56 (m, 3H), 2.46-2.42 (m, 2H), 2.32-2.09 (m, 9H), 2.07-1.88 (m, 6H), 1.74-1.67 (m, 2H), 1.56-1.50 (m, 4H), 1.40-1.26 (m, 48H), 1.19-1.12 (m, 4H), 0.96 (t, 3H, J=8.0), 0.89 (t, 6H, J=6.0), 0.69-0.62 (m, 4H), 0.59-0.54 (m, 2H), −0.33 (q, 2H, J=4.0). RT=6.68 min. 98.5% purity. ESI-MS: m/z=915 $[M+H]^+$ for $C_{58}H_{108}NO_6$.

Example 4

Synthesis of PNI 545 and 546

Scheme 7.

General route for synthesis of PNI 545 and 546

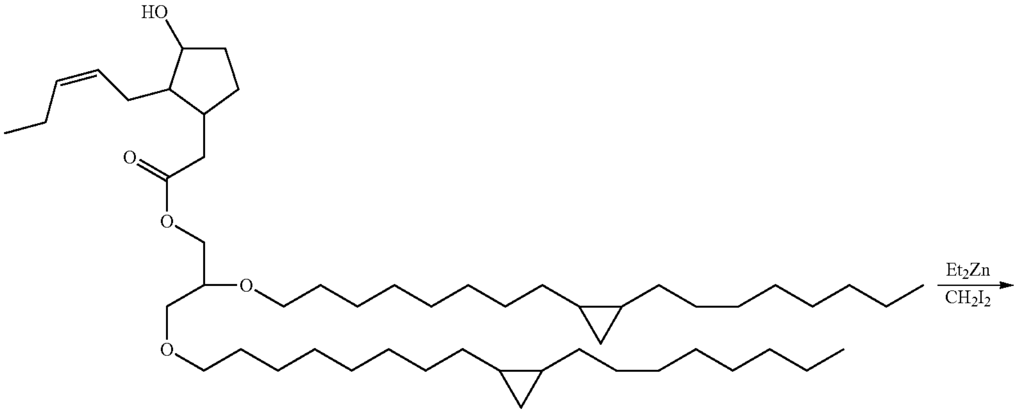

14

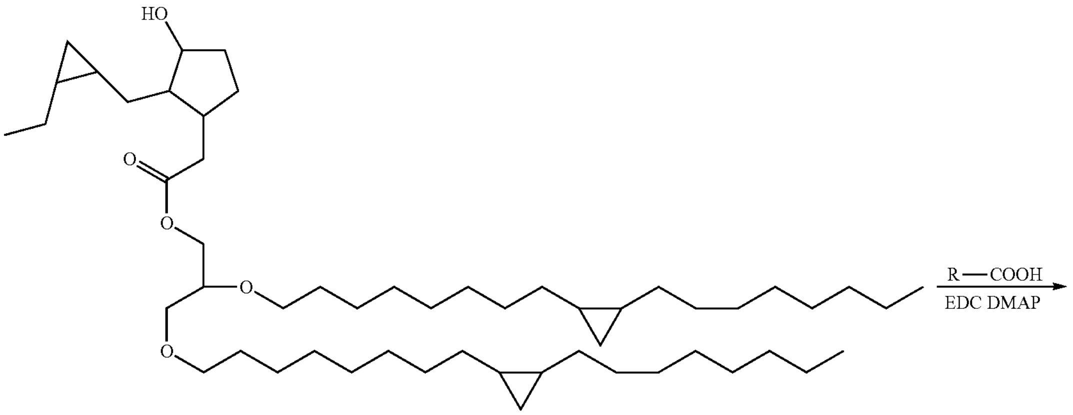

15

-continued

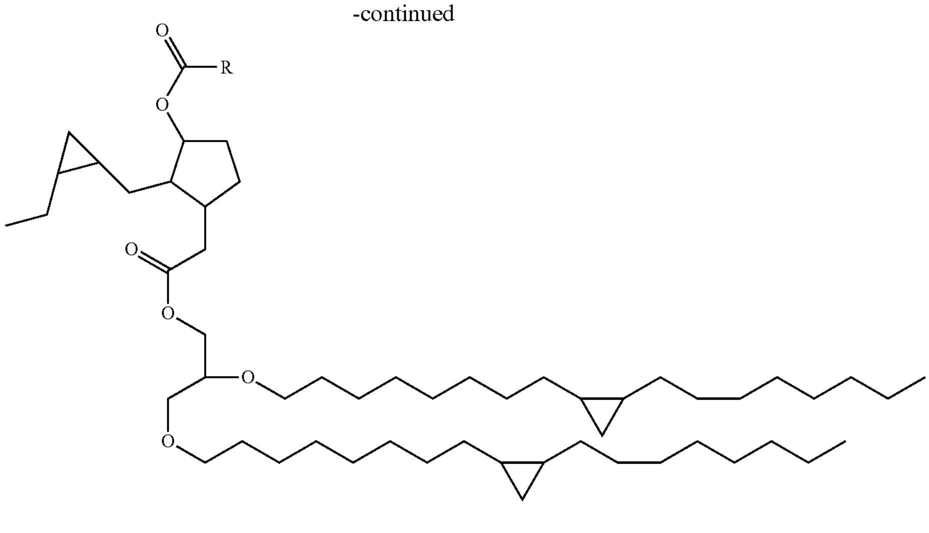

Compound 15: Into a 500 mL three-neck round bottomed flask containing a well-stirred solution of 14 (1.5 g, 1.840 mmol) in dry toluene (30 mL) was added diiodomethane (0.712 ml, 8.83 mmol) under nitrogen atmosphere. The reaction mixture was cooled to −40° C. and Diethylzinc (4.42 mL, 4.42 mmol, 1 M solution in toluene) was added dropwise via additional funnel by maintaining temperature at −40° C. Then the reaction temperature was slowly raised to −10° C. over a period of 45 mins and the temperature was maintained for 2 h. The mixture was allowed to warm to room temperature and the stirring was continued for 18 h. After completion of the reaction as indicated by TLC, the reaction mixture was quenched with satd. aq. $NH_4Cl$ solution (20 mL). The organic layer was separated, and the aqueous layer was extracted with toluene (2×30 mL). The combined organic layers were washed with brine (50 mL), dried over anhydrous $Na_2SO_4$ and concentrated under reduced pressure. The crude product was purified by Isolera™ silica gel (100-200 mesh) column chromatography using 10% EtOAc in Pet. ether to give 15 (0.995 g, 1.2 mmol, 79% yield) as a colourless liquid. $^1H$ (400 MHz, $CDCl_3$) δ 4.39-4.37 (m, 1H), 4.23 (dd, 1H, J=12.0, 4.0), 4.12-4.04 (m, 2H), 3.65-3.59 (m, 1H), 3.55 (t, 2H, J=6.0), 3.52-3.42 (m, 4H), 2.54 (dd, 1H, J=16.0, 12.0), 2.19-2.10 (m, 4H), 1.95-1.86 (m, 1H), 1.67-1.48 (m, 6H), 1.43-1.28 (m, 50H), 1.19-1.10 (m, 6H), 1.00 (t, 3H, J=8.0), 0.89 (t, 6H, J=6.0), 0.70-0.63 (m, 7H), 0.59-0.54 (m, 2H), −0.19-0.24 (m, 1H), −0.33 (q, 2H, J=4.0). RT=7.06 min. 70.6% purity. ESI-MS: m/z=852 $[M+Na]^+$ for $C_{54}H_{100}O_5Na$.

PNI 545

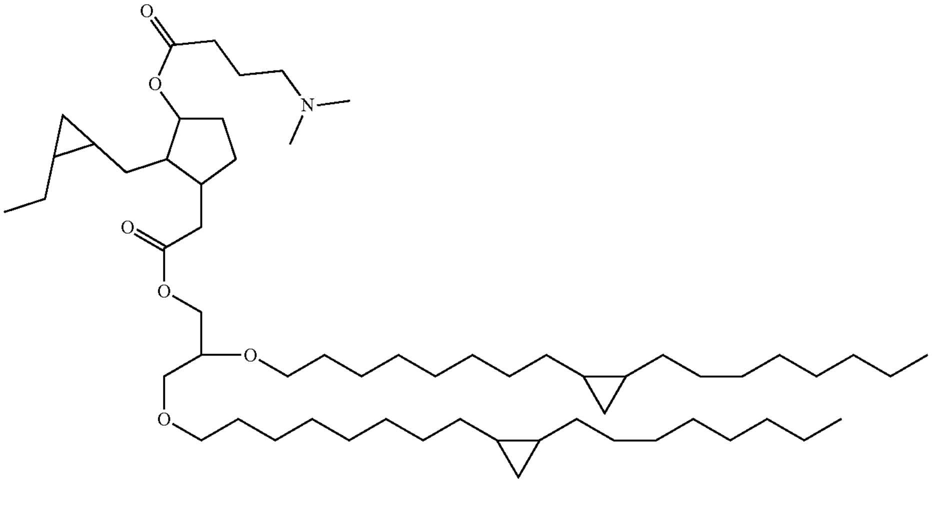

PNI 545 was synthesized using the method similar to the one used for synthesis of PNI 132. Synthesis of PNI 545 was performed using 4-(dimethylamino)butanoic acid hydrochloride (0.067 g, 0.398 mmol) in dry DCM (10 mL), 15 (0.220 g, 0.265 mmol) in dry DCM (10 mL), DMAP (0.016 g, 0.133 mmol) and EDCl hydrochloride (0.127 g, 0.663 mmol). The crude product was purified by silica gel (100-200 mesh) column chromatography (Isolera™) using 2% MeOH in EtOAc to give PNI 545 (0.115 g, 0.122 mmol, 46.0% yield) as light-yellow oil. $^1H$ (400 MHz, $CDCl_3$) δ 5.36-5.34 (m, 1H), 4.27-4.22 (m, 1H), 4.14-4.07 (m, 1H), 3.62 (p, 1H, J=4.0), 3.56 (t, 2H, J=6.0), 3.49-3.52 (m, 4H), 2.58 (d, 1H, J=12.0), 2.45-2.23 (m, 9H), 2.20-2.13 (m, 2H), 2.09-1.93 (m, 4H), 1.89-1.78 (m, 2H), 1.75-1.48 (m, 6H), 1.40-1.22 (m, 50H), 1.17-1.13 (m, 6H), 0.98 (t, 3H, J=6.0), 0.89 (t, 6H, J=6.0), 0.69-0.54 (m, 9H), −0.31-−0.37 (m, 3H). RT=7.38 min. 98.4% purity. ESI-MS: m/z=965 $[M+Na]^+$ for $C_{60}H_{111}NO_6Na$.

PNI 546

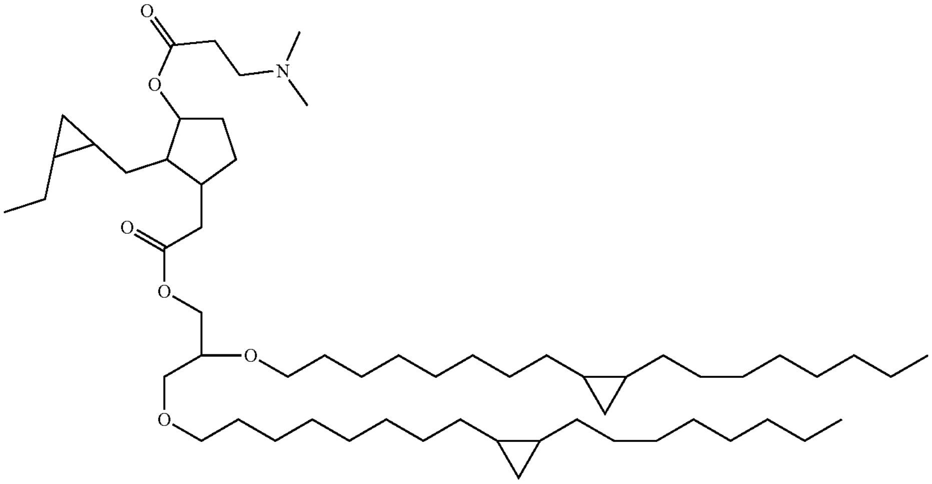

PNI 546 was synthesized using the method similar to the one used for synthesis of PNI 132. Synthesis of PNI 546 was performed using 3-(dimethylamino)propanoic acid hydrochloride (0.102 g, 0.663 mmol) in dry DCM (10 mL), 15 (0.22 g, 0.265 mmol) in dry DCM (5 mL), DMAP (0.049 g, 0.398 mmol) and EDCl (0.153 g, 0.796 mmol). The crude product was purified by silica gel (100-200 mesh) column chromatography (Isolera™) using 2% MeOH in EtOAc to afford PNI 546 (0.055 g, 0.059 mmol, 22.33% yield) as a light-yellow oil. $^1H$ (400 MHz, $CDCl_3$) δ 5.37-5.33 (m, 1H), 4.27-4.21 (m, 1H), 4.13-4.08 (m, 1H), 3.62 (p, 1H, J=4.0), 3.56 (t, 2H, J=6.0), 3.49-3.42 (m, 4H), 2.68 (br s, 2H), 2.60-2.50 (m, 3H), 2.30 (s, 6H), 2.21-1.92 (m, 5H), 1.74-1.66 (m, 6H), 1.38-1.26 (m, 50H), 1.17-1.10 (m, 6H), 0.98 (t, 3H, J=6.0), 0.89 (t, 6H, J=6.0), 0.70-0.54 (m, 9H), −0.31-−0.35 (m, 3H). RT=7.38 min. 98.2% purity. ESI-MS: m/z=951 $[M+Na]^+$ for $C_{59}H_{109}NO_6Na$.

Example 5

Synthesis of PNI 547 and 548

Scheme 8
Synthesis of PNI 547 and 548

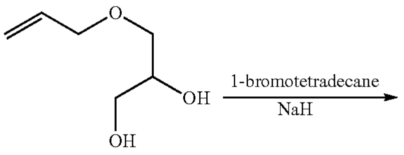

1

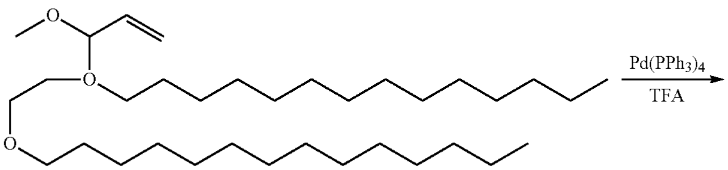

16

-continued
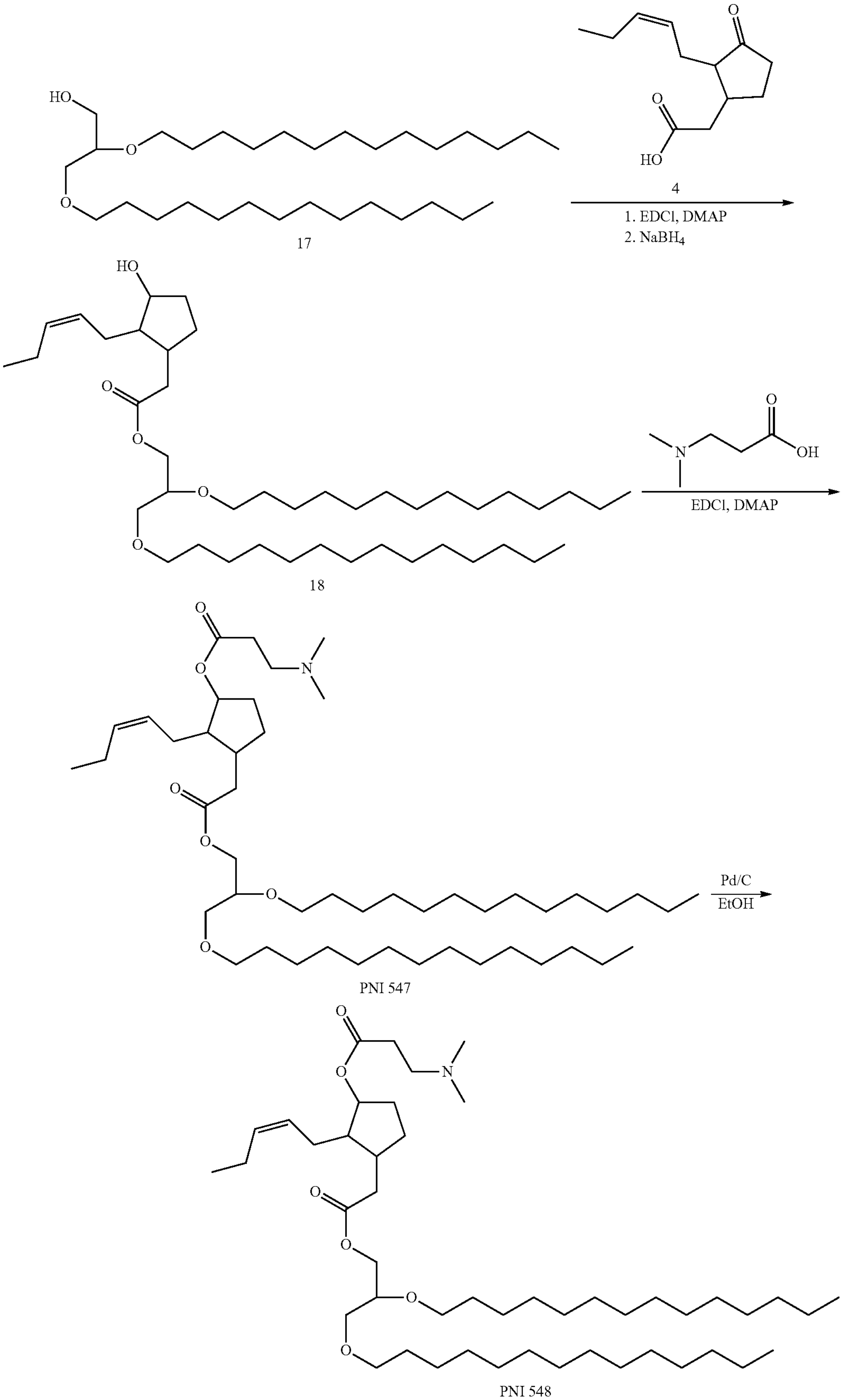
17
18
PNI 547
PNI 548

Compound 16: Compound 16 was synthesized using the method similar to the one used for synthesis of compound 2. Synthesis of 16 was performed using sodium hydride (2.179 g, 91 mmol, 60% dispersion in mineral oil), 3-(allyloxy) propane-1,2-diol (1, 3.0 g, 22.70 mmol) in dry THF (30 mL), 1-bromotetradecane (15.74 g, 56.7 mmol) in THF (30 mL) and 15-crown-5 (1.50 g, 6.81 mmol). The crude product was purified by column chromatography (Isolera™) using silica gel (100-200 mesh) by using 10% EtOAc in Pet. ether as an eluent to get 16 (5.0 g, 9.53 mmol, 42.0% yield). $^1$H (400 MHz, $CDCl_3$) δ 5.96-5.86 (m, 1H), 5.28 (dd, 1H, J=16.0, 4.0), 5.18 (dd, 1H, J=12.0, 4.0), 4.02 (d, 2H, J=4.0), 3.59-3.43 (m, 9H), 1.61-1.53 (m, 4H), 1.34-1.17 (m, 44H), 0.89 (t, 6H, J=6.0). RT=4.27 min. 99.9% purity. ESI-MS: m/z=547 $[M+Na]^+$ for $C_{34}H_{68}O_3Na$.

Compound 17: To a stirred solution of 16 (3.0 g, 5.72 mmol) in dry EtOH (50 mL) were added TFA (4.5 mL) and $Pd(PPh_3)_4$ (0.660 g, 0.572 mmol) at under nitrogen atmosphere. The reaction mixture was stirred at 85° C. for 16 h and the consumption of starting material was confirmed by TLC analysis. The reaction mixture was concentrated under reduced pressure and filtered through a celite bed. The celite bed was washed with EtOAc (3×200 mL) and the combined filtrates were concentrated. The crude material was purified by silica gel (100-200 mesh) column chromatography using 30% EtOAc in Pet. ether as the eluent to give 17 (2.5 g, 5.16 mmol, 90% yield) as colorless oil. $^1$H (400 MHz, $CDCl_3$) δ 3.74 (dd, 1H, J=12.0, 4.0), 3.66-3.43 (m, 8H), 2.14 (br s, 1H), 1.61-1.53 (m, 4H), 1.35-1.22 (m, 44H), 0.89 (t, 6H, J=6.0). RT=2.60 min. 99.4% purity. ESI-MS: m/z=485 $[M+H]^+$ for $C_{31}H_{65}O_3$.

Compound 18: 2,3-bis(tetradecyloxy)propyl (Z)-2-(3-oxo-2-(pent-2-en-1-yl)cyclopentyl)acetate was synthesized using the method similar to the one used for synthesis of 2,3-bis(((9Z,12Z)-octadeca-9,12-dien-1-yl)oxy)propyl 2-(3-oxo-2-((Z)-pent-2-en-1-yl)cyclopentyl)acetate. Synthesis of this ketone was performed using 17 (3.0 g, 6.19 mmol) in dry DCM (20 mL), DMAP (0.378 g, 3.09 mmol), 4 (1.952 g, 9.28 mmol) in dry DCM (30 mL) and EDCl hydrochloride (2.97 g, 15.47 mmol). The crude product (pale orange liquid) was used as such for the next step without further purification. $^1$H (400 MHz, $CDCl_3$) δ 5.49-5.43 (m, 1H), 5.30-5.23 (m, 1H), 4.28 (dd, 1H, J=12.0, 4.0), 4.14-4.09 (m, 1H), 3.62 (p, 1H, J=4.0), 3.55 (t, 2H, J=8.0), 3.49-3.42 (m, 4H), 2.77-2.70 (m, 1H), 2.40-1.98 (m, 9H), 1.59-1.48 (m, 6H), 1.33-1.20 (m, 44H), 0.96 (t, 3H, J=8.0), 0.88 (t, 6H, J=6.0). RT=3.09 min. 59.4% purity. ESI-MS: m/z=700 $[M+Na]^+$ for $C_{43}H_{80}O_5Na$.

Compound 18 was synthesized using the method similar to the one used for synthesis of 5. Synthesis of 18 was performed using 2,3-bis(tetradecyloxy)propyl (Z)-2-(3-oxo-2-(pent-2-en-1-yl)cyclopentyl)acetate (2.5 g, 3.69 mmol) in 25 mL of dry MeOH:THE (4:1) and sodium borohydride (0.489 g, 12.92 mmol). The crude product was purified by Isolera™ silica gel (100-200 mesh) column chromatography 10% EtOAc in Pet. ether as eluent to afford 18 (1.5 g, 2.209 mmol, 59.8% yield) as thick colorless oil. $^1$H (400 MHz, $CDCl_3$) δ 5.52-5.36 (m, 2H), 4.24 (dd, 1H, J=12.0, 4.0), 4.09 (dd, 1H, J=12.0, 4.0), 3.94-3.86 (m, 1H), 3.62 (p, 1H, J=4.0), 3.55 (t, 2H, J=8.0), 3.49-3.42 (m, 4H), 2.60-2.54 (m, 1H), 2.35-2.29 (m, 1H), 2.23-1.83 (m, 8H), 1.65-1.47 (m, 6H), 1.34-1.21 (m, 44H), 0.98 (t, 3H, J=8.0), 0.89 (t, 6H, J=6.0).

PNI 547

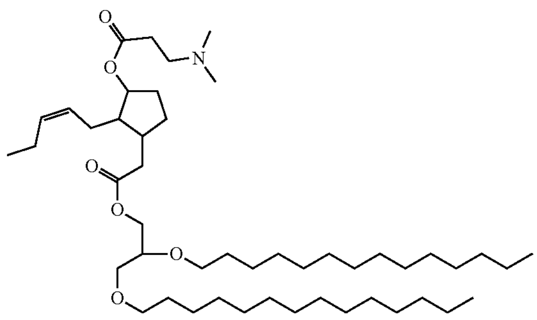

PNI 547 was synthesized using the method similar to the one used for synthesis of PNI 132. Synthesis of PNI 547 was performed using 3-(dimethylamino)propanoic acid hydrochloride (0.424 g, 2.76 mmol) in dry DCM (30 mL), 18 (0.75 g, 1.104 mmol) in dry DCM (5 mL), DMAP (0.067 g, 0.552 mmol) and EDCl hydrochloride (0.423 g, 2.209 mmol). The crude product was purified by Isolera™ silica gel (100-200 mesh) column chromatography using 5% MeOH in EtOAc to give PNI 547 (0.51 g, 0.655 mmol, 59.3% yield) as colourless oil. $^1$H (400 MHz, $CDCl_3$) δ 5.45-5.28 (m, 2H), 4.89-4.85 (m, 1H), 4.26-4.21 (m, 1H), 4.10 (dd, 1H, J=12.0, 8.0), 3.62 (p, 1H, J=4.0), 3.55 (t, 2H, J=6.0), 3.49-3.42 (m, 4H), 3.09-2.92 (m, 2H), 2.78-2.67 (m, 2H), 2.62-2.55 (m, 7H), 2.32-1.89 (m, 9H), 1.73-1.63 (m, 2H), 1.55 (p, 4H, J=8.0), 1.37-1.16 (m, 44H), 0.97-0.93 (m, 3H), 0.88 (t, 6H, J=6.0). RT=3.48 min. 99.5% purity. ESI-MS: m/z=779 $[M+H]^+$ for $C_{48}H_{92}NO_6$.

PNI 548

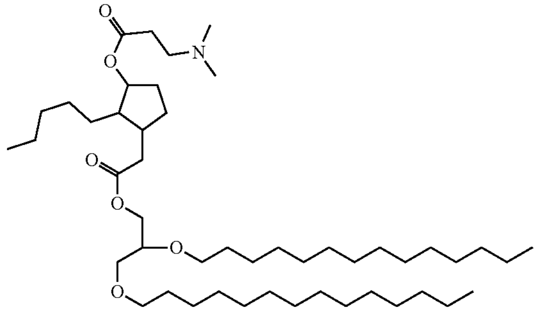

Palladium on carbon (0.041 g, 0.385 mmol, 10% by wt.) was added to a stirred solution of PNI 547 (0.150 g, 0.193 mmol) in dry EtOH (20 mL) under nitrogen atmosphere. The reaction mixture was stirred at room temperature under $H_2$ atmosphere (bladder) for 6 h. After completion of the reaction as indicated by TLC, the reaction mixture was filtered through a celite bed and washed with EtOH until no compound was observed in the washings. The combined filtrates were concentrated, and the residue was dissolved in EtOAc (30 mL). The organic layer was washed with water (2×20 mL) and brine (2×20 mL). The organic layer was separated, dried over anhydrous $Na_2SO_4$, filtered and concentrated. The crude product was purified by silica gel (100-200 mesh) column chromatography (Isolera™) using 5% MeOH in DCM as the eluent to give PNI 548 (0.12 g, 0.154 mmol, 80% yield) as thick light-yellow oil. $^1$H (400 MHz, $CDCl_3$) δ 4.89-4.86 (m, 1H), 4.26-4.22 (m, 1H), 4.10

(dd, 1H, J=12.0, 8.0), 3.62 (p, 1H, J=4.0), 3.55 (t, 2H, J=6.0), 3.49-3.42 (m, 4H), 2.65-2.44 (m, 5H), 2.37-1.79 (m, 11H), 1.69-1.49 (m, 6H), 1.44-1.22 (m, 52H), 0.89 (app t, 9H, J=6.0). RT=3.87 min. 89.4% purity. ESI-MS: m/z=781 $[M+H]^+$ for $C_{48}H_{94}NO_6$.
Example 6
Synthesis of PNI 554, 562 and 565
Scheme 9.
Synthesis of compound 23
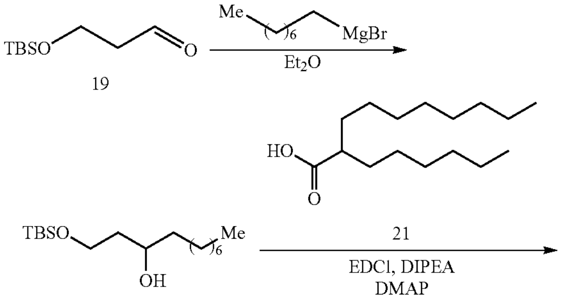
19
21
20
-continued
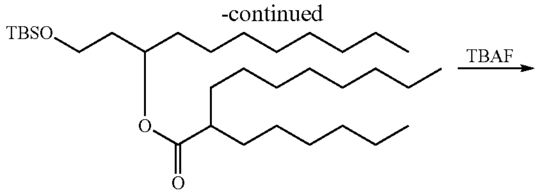
22
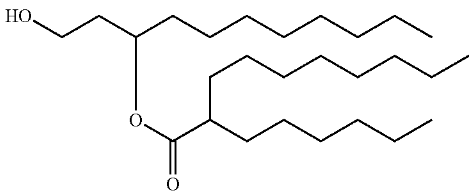
23
Scheme 10.
Synthesis of PNI 554, 562 and 565
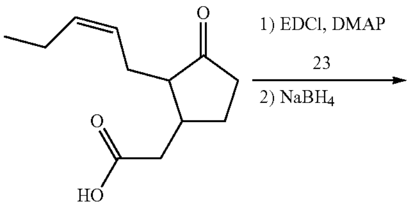
4
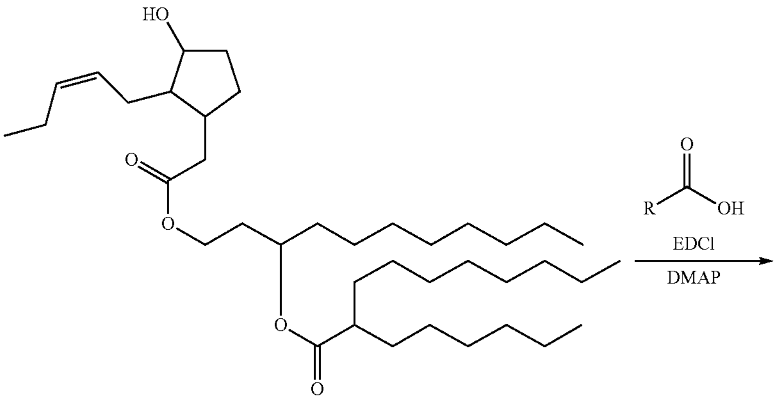
24

-continued

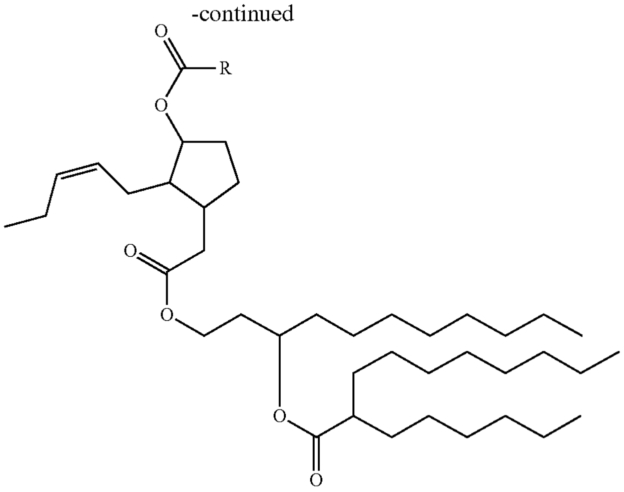

Compound 20: n-Octylmagnesium bromide (7.96 mL, 15.93 mmol) was added dropwise to a stirred solution of 19 (2.5 g, 13.27 mmol) in dry THE at 0° C. under nitrogen atmosphere and the reaction mixture was allowed to warm to room temperature. After stirring for 4 hours, the reaction mixture was quenched with satd. aq. $NH_4Cl$ (50 mL) and extracted with EtOAc (3×50 mL). The combined organic layers were washed with brine (2×50 mL), dried over anhydrous $Na_2SO_4$, filtered and concentrated. The crude product was purified by silica gel column (100-200 mesh) chromatography (Isolera™) using 5% EtOAc in Pet. ether to give 20 (1.05 g, 3.47 mmol, 26.1% yield) as light-yellow oil. $^1H$ (400 MHz, $CDCl_3$) δ 3.93-3.89 (m, 1H), 3.85-3.79 (m, 2H), 3.39 (d, 1H, J=4.0), 1.65 (q, 2H, J=4.0), 1.52-1.42 (m, 2H), 1.34-1.21 (m, 12H), 0.91-0.87 (m, 12H), 0.09 (s, 6H). RT=1.13 min. 97.1% purity. ESI-MS: m/z=303 $[M+H]^+$ for $C_{17}H_{39}O_2Si$.

Compound 22: To a stirred solution of 2-hexyldecanoic acid (21, 1.271 g, 4.96 mmol) in dry DCM (8 mL), DMAP (0.686 g, 5.62 mmol) and EDCl hydrochloride (1.077 g, 5.62 mmol) were added at room temperature under nitrogen atmosphere. The reaction mixture was stirred for 10 minutes and a solution of 20 (1.0 g, 3.30 mmol) in dry DCM (4 mL). The reaction mixture was stirred at room temperature for 16 hours and TLC analysis showed the complete consumption of 20. The solvent was evaporated under reduced pressure and the residue was dissolved in EtOAc (100 mL). The organic layer was washed with water (2×50 mL), brine (2×50 mL), dried over anhydrous $Na_2SO_4$, filtered and concentrated. The crude product was purified by Isolera™ silica gel (100-200 mesh) column chromatography using 5% EtOAc in Pet. ether to give 22 (1.76 g, 3.25 mmol, 98% yield) as light-yellow oil. $^1H$ (400 MHz, $CDCl_3$) δ 4.97 (p, 1H, J=6.0), 3.68-3.58 (m, 2H), 2.32-2.25 (m, 1H), 1.81-1.74 (m, 2H), 1.62-1.42 (m, 6H), 1.34-1.21 (m, 32H), 0.90-0.86 (m, 18H), 0.04 (s, 6H). RT=4.26 min. 87.5% purity.

Compound 23: TBAF (1 M solution in THF, 3.88 mL, 3.88 mmol) was added dropwise to a stirred solution of 22 (1.75 g, 3.23 mmol) in dry THE (20 mL) at room temperature under nitrogen atmosphere. The reaction mixture was stirred for 16 hours and TLC analysis showed the complete consumption of 22. The reaction mixture was quenched with 1 N HCl (50 mL) and extracted with EtOAc (2×75 mL). The combined organic layers were washed with brine (2×50 mL), dried over anhydrous $Na_2SO_4$, filtered and concentrated. The crude product was purified by Isolera™ silica gel (100-200 mesh) column chromatography using 5% EtOAc in Pet. ether to give 23 (1.36 g, 3.19 mmol, 99% yield) as light-yellow oil. $^1H$ (400 MHz, $CDCl_3$) δ 5.06-4.99 (m, 1H), 3.66-3.61 (m, 1H), 3.55-3.49 (m, 1H), 2.38-2.31 (m, 1H), 1.89-1.81 (m, 1H), 1.69-1.40 (m, 7H), 1.37-1.22 (m, 32H), 0.92-0.87 (m, 9H). RT=1.85 min. 99.2% purity. ESI-MS: m/z=449 $[M+Na]^+$ for $C_{27}H_{54}O_3Na$.

Compound 24: (Z)-1-(2-(3-oxo-2-(pent-2-en-1-yl)cyclopentyl)acetoxy)undecan-3-yl 2-hexyldecanoate was synthesized using the method similar to the one used for synthesis of 2,3-bis(((9Z,12Z)-octadeca-9,12-dien-1-yl)oxy)propyl 2-(3-oxo-2-((Z)-pent-2-en-1-yl)cyclopentyl)acetate. Synthesis of this ketone was performed using 23 (1.35 g, 3.16 mmol) in dry DCM (5 mL), DMAP (0.773 g, 6.33 mmol), 4 (1.330 g, 6.33 mmol) in dry DCM (15 mL) and EDCl hydrochloride (1.213 g, 6.33 mmol). The crude (2.01 g, 3.25 mmol, 100% crude yield) was obtained as yellow oil and was used for the next step without further purification.

Compound 24 was synthesized using the method similar to the one used for synthesis of 5. Synthesis of 24 was performed using (Z)-1-(2-(3-oxo-2-(pent-2-en-1-yl)cyclopentyl)acetoxy)undecan-3-yl 2-hexyldecanoate (2.0 g, 3.23 mmol) in dry MeOH (20 mL) and dry THE (5 mL) and sodium borohydride (0.489 g, 12.92 mmol). The crude product was purified by Isolera™ silica gel (100-200 mesh) column chromatography using 10% EtOAc in Pet. ether to afford 24 (1.82 g, 2.91 mmol, 90% yield) as light-yellow oil. $^1H$ (400 MHz, $CDCl_3$) δ 5.52-5.38 (m, 2H), 4.99 (p, 1H, J=8.0), 4.25-4.19 (m, 1H), 4.17-4.10 (m, 1H), 4.07-4.01 (m, 1H), 3.93-3.86 (m, 1H), 2.58-2.52 (m, 1H), 2.34-2.26 (m, 2H), 2.23-1.81 (m, 8H), 1.67-1.40 (m, 10H), 1.34-1.20 (m, 32H), 0.98 (t, 3H, J=8.0), 0.88 (t, 9H, J=8.0). RT=2.26 min. 99.5% purity. ESI-MS: m/z=622 $[M+H]^+$ for $C_{39}H_{73}O_5$.

PNI 554

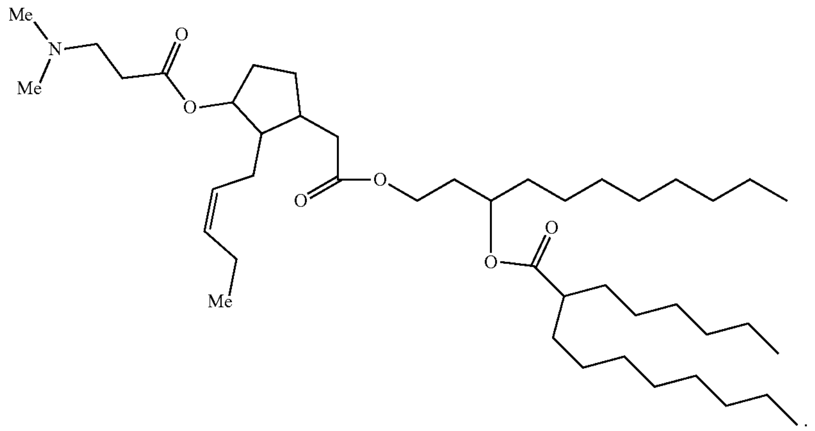

To a stirred solution of 3-(dimethylamino)propanoic acid hydrochloride (0.148 g, 0.966 mmol) in dry DCM (10 mL), DMAP (0.157 g, 1.288 mmol) and EDCl hydrochloride (0.247 g, 1.288 mmol) were added at room temperature under nitrogen atmosphere. After stirring for 10 minutes, a solution of 24 (0.4 g, 0.644 mmol) in dry DCM (5 mL) was added and reaction mixture was stirred at room temperature for 16 hours. TLC analysis showed that 24 was not consumed completely. A pre-stirred mixture of 3-(dimethylamino)propanoic acid hydrochloride (0.198 g, 1.288 mmol), DMAP (0.157 g, 1.288 mmol) and EDCl (0.370 g, 1.932 mmol) in DCM (10 mL) was added to the reaction mixture and the stirring was continued for 16 h. TLC analysis showed the completion of 24 and the solvent was evaporated under reduced pressure. The residue was dissolved in EtOAc (120 mL) and washed with water (2×50 mL), brine (2×50 mL), dried over anhydrous $Na_2SO_4$, filtered and concentrated. The crude product was purified by Isolera™ silica gel (100-200 mesh) column chromatography using 3% MeOH in DCM to give PNI 554 (0.325 g, 0.451 mmol, 70.1% yield) as light-yellow oil. $^1H$ (400 MHz, $CDCl_3$) δ 5.47-5.26 (m, 2H), 5.02-4.84 (m, 2H), 4.17-4.11 (m, 1H), 4.07-4.03 (m, 1H), 2.66-2.46 (m, 5H), 2.34-1.85 (m, 18H), 1.72-1.65 (m, 2H), 1.46-1.38 (m, 4H), 1.34-1.17 (m, 34H), 0.97-0.93 (m, 3H), 0.88 (t, 9H, J=8.0). RT=2.40 min. 99.3% purity. ESI-MS: m/z=721 $[M+H]^+$ for $C_{44}H_{32}NO_6$.

PNI 562

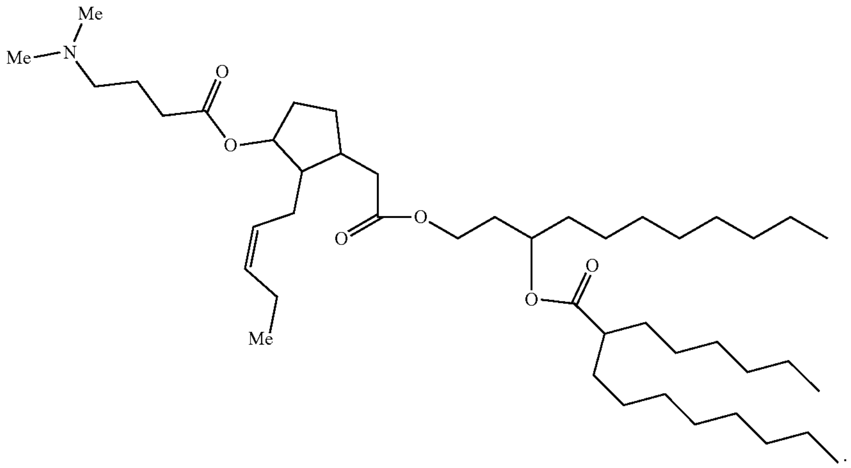

PNI 562 was synthesized using the method similar to the one used for synthesis of PNI 132. Synthesis of PNI 562 was performed using 4-(dimethylamino)butanoic acid hydrochloride (0.121 g, 0.725 mmol) in dry DCM (8 mL), DMAP (0.118 g, 0.966 mmol), EDCl hydrochloride (0.185 g, 0.966 mmol) and 24 (0.3 g, 0.483 mmol) in dry DCM (4 mL). The crude product was purified by Isolera™ silica gel (100-200 mesh) column chromatography using 4% MeOH in DCM to afford PNI 562 (0.195 g, 0.260 mmol, 53.9% yield) as light-yellow oil. $^1H$ (400 MHz, $CDCl_3$) δ 5.47-5.29 (m, 2H), 5.03-4.83 (m, 2H), 4.17-4.11 (m, 1H), 4.07-4.01 (m, 1H), 2.59-2.53 (m, 1H), 2.43-1.81 (m, 23H), 1.73-1.65 (m, 3H), 1.48-1.39 (m, 4H), 1.36-1.16 (m, 34H), 0.97-0.93 (m, 3H), 0.88 (t, 9H, J=8.0). RT=2.46 min. 98.0% purity. ESI-MS: m/z=735 $[M+H]^+$ for $C_{45}H_{84}NO_6$.

PNI 565

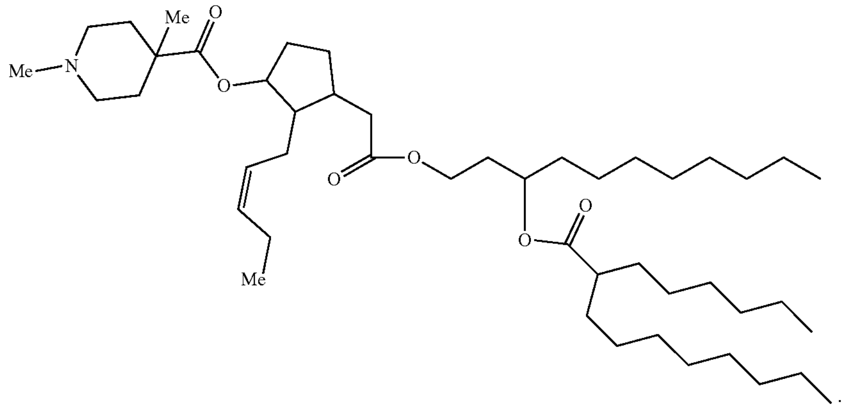

PNI 565 was synthesized using the method similar to the one used for synthesis of PNI 132. Synthesis of PNI 565 was performed using 1,4-dimethylpiperidine-4-carboxylic acid hydrochloride (0.150 g, 0.773 mmol) in dry DCM (10 mL), DMAP (0.126 g, 1.031 mmol), EDCl hydrochloride (0.198 g, 1.031 mmol) and 24 (0.32 g, 0.515 mmol) in dry DCM (5 mL). The crude product was purified by Isolera™ silica gel (100-200 mesh) column chromatography using 5% MeOH in DCM to give PNI 565 (0.27 g, 0.353 mmol, 68.5% yield) as light-yellow oil. $^1H$ (400 MHz, $CDCl_3$) δ 5.47-5.29 (m, 2H), 5.03-4.95 (m, 1H), 4.88-4.84 (m, 1H), 4.17-4.11 (m, 1H), 4.08-4.01 (m, 1H), 2.76 (br s, 2H), 2.56 (dd, 1H, J=16.0, 4.0), 2.42-1.87 (m, 21H), 1.58-1.51 (m, 2H), 1.45-1.40 (m, 4H), 1.32-1.19 (m, 37H), 0.98-0.94 (m, 3H), 0.88 (t, 9H, J=8.0). RT=2.56 min. 99.4% purity. ESI-MS: m/z=761 $[M+H]^+$ for $C_{47}H_{86}NO_6$.

Example 7

Synthesis of PNI 510, 552 and 563

Scheme 11. Synthesis of compound 27

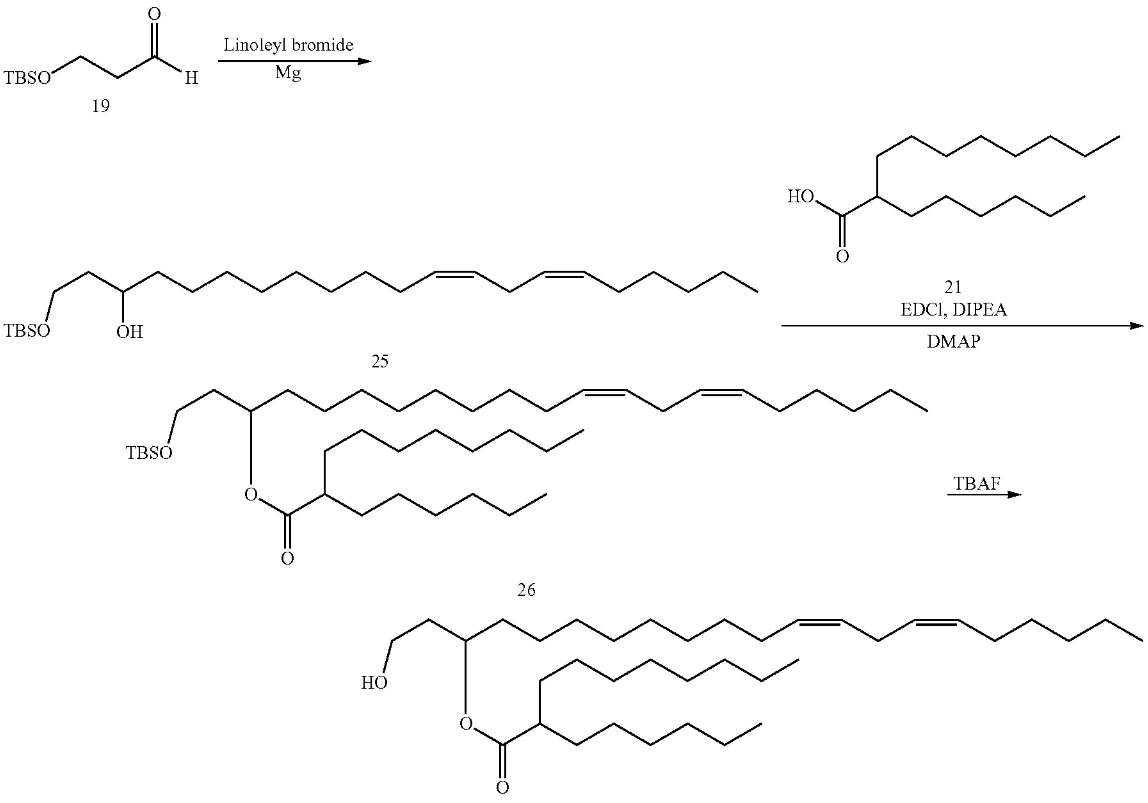

19

21

25

26

27

Scheme 12. General route for synthesis of PNI 510, 562 and 563

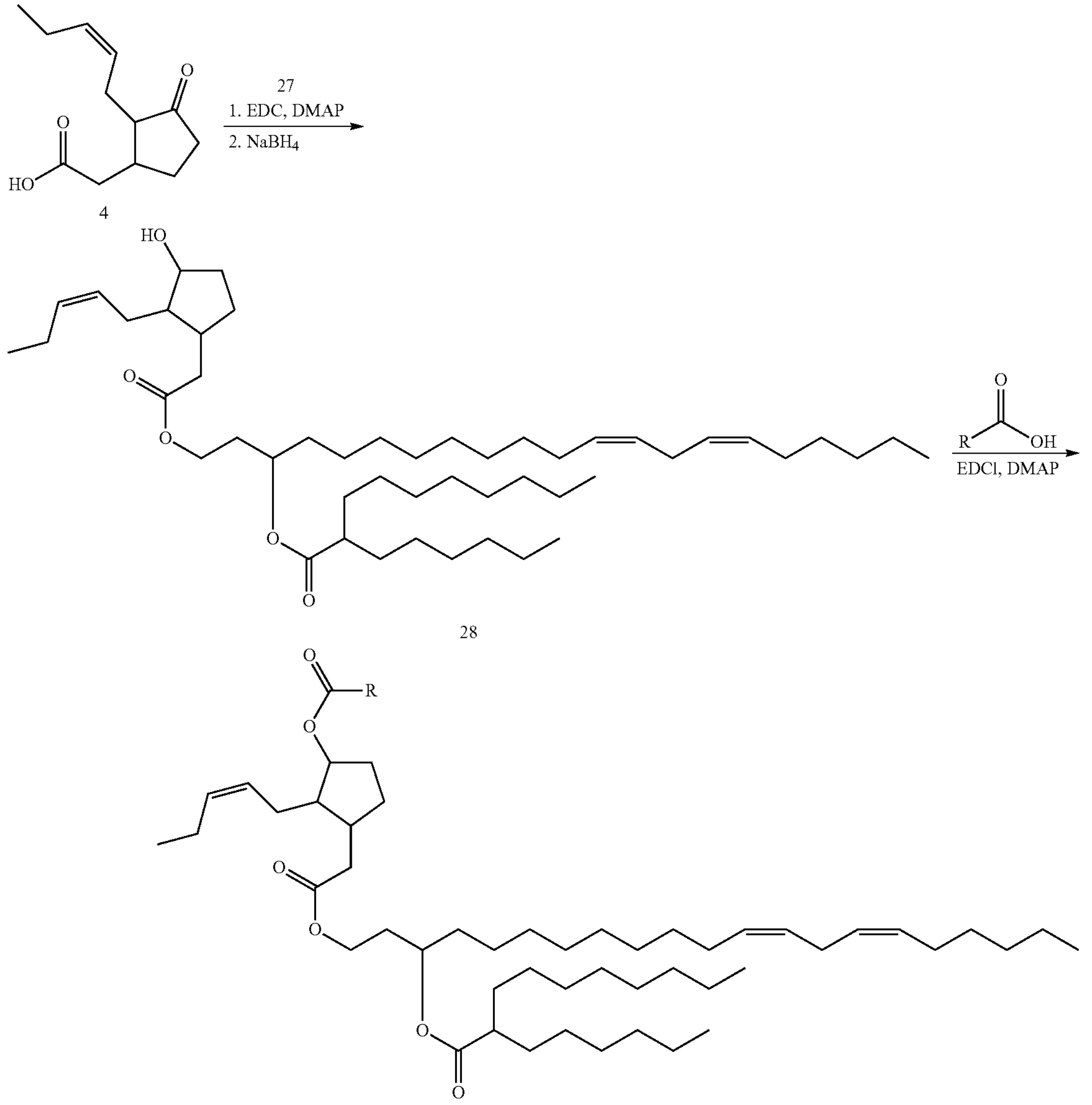

4

28

Compound 25:1,2-dibromoethane (0.114 mL, 1.327 mmol) was added to a well-stirred suspension of activated Mg turnings (0.484 g, 19.91 mmol) in dry THF (5 mL) under nitrogen atmosphere and the mixture was stirred for 5 minutes at room temperature. A solution of linoleyl bromide (5.68 g, 17.26 mmol) in dry THF (8 mL) was added and the reaction mixture was refluxed for 1 h. After completion of the reaction as indicated by TLC, the reaction mixture was cooled to 20° C. and a solution of 19 (2.5 g, 13.27 mmol) in dry THF (7 mL) was added. The mixture was stirred at room temperature for 3 hours and TLC analysis showed the complete consumption of 19. The reaction mixture was cooled to 0° C. and quenched with aqueous 1 N HCl (50 mL) with slow stirring. The organic layer was separated, and the aqueous layer was extracted with EtOAc (2×75 mL). The combined organic layer was washed with brine (2×50 mL), dried over anhydrous $Na_2SO_4$, filtered, concentrated. The crude material was purified by Isolera™ silica gel (100-200 mesh) column chromatography using 5% EtOAc in Pet. ether to give 25 (2.25 g, 5.13 mmol, 38.6% yield) as yellow oil. $^1H$ (400 MHz, $CDCl_3$) δ 5.42-5.30 (m, 4H), 3.93-3.89 (m, 1H), 3.85-3.79 (m, 2H), 3.40 (d, 1H, J=4.0), 2.78 (t, 2H, J=8.0), 2.06 (q, 4H, J=8.0), 1.65 (q, 2H, J=4.0), 1.42-1.29 (m, 20H), 0.91 (s, 12H), 0.09 (s, 6H). RT=1.96 min. 99.1% purity. ESI-MS: m/z=439 $[M+H]^+$ for $C_{27}H_{55}O_2Si$.

Compound 26: Compound 26 was synthesized using the method similar to the one used for synthesis of 22. Synthesis of 26 was performed using 2-hexyldecanoic acid (21, 1.800 g, 7.02 mmol) in dry DCM (10 mL), DMAP (1.225 g, 10.03 mmol), EDCl hydrochloride (1.922 g, 10.03 mmol) and 25 (2.2 g, 5.01 mmol) in DCM (10 mL). The crude product was purified by silica gel (100-200 mesh) column chromatography (Isolera™) using 5% EtOAc in Pet. ether to give 26 (3.25 g, 4.80 mmol, 96% yield) as yellow oil. $^1H$ (400 MHz, $CDCl_3$) δ 5.42-5.30 (m, 4H), 5.00-4.94 (m, 1H), 3.68-3.58 (m, 2H), 2.78 (t, 2H, J=6.0), 2.32-2.25 (m, 1H), 2.08-2.00 (m, 4H), 1.77 (p, 2H, J=8.0), 1.68-1.47 (m, 4H), 1.38-1.20

(m, 40H), 0.91-0.86 (m, 18H), 0.04 (s, 6H). RT=4.26 min. 87.5% purity. ESI-MS: m/z=700 $[M+Na]^+$ for $C_{43}H_{34}O_3SiNa$.

Compound 27: Compound 27 was synthesized using the method similar to the one used for synthesis of 23. Synthesis of 27 was performed using TBAF (3.88 mL, 3.88 mmol, 1 M solution in THF) and 26 (1.75 g, 3.23 mmol) in THF (20 mL) at room temperature under nitrogen atmosphere. The crude product was purified by Isolera™ silica gel (100-200 mesh) column chromatography using 5% EtOAc in Pet. ether to afford 27 (1.36 g, 3.19 mmol, 99% yield) as light-yellow oil. $^1H$ (400 MHz, $CDCl_3$) δ 5.42-5.32 (m, 4H), 5.06-4.99 (m, 1H), 3.67-3.61 (m, 1H), 3.55-3.49 (m, 1H), 2.78 (t, 2H, J=6.0), 2.40-2.31 (m, 2H), 2.06 (q, 4H, J=8.0), 1.89-1.81 (m, 2H), 1.51-1.42 (m, 4H), 1.38-1.26 (m, 40H), 0.92-0.87 (m, 9H). RT=2.77 min. 92.2% purity. ESI-MS: m/z=585 $[M+Na]^+$ for $C_{37}H_{70}O_3Na$.

Compound 28: (12Z,15Z)-1-(2-(3-oxo-2-((Z)-pent-2-en-1-yl)cyclopentyl)acetoxy)henicosa-12,15-dien-3-yl 2-hexyldecanoate was synthesized using the method similar to the one used for synthesis of 2,3-bis(((9Z,12Z)-octadeca-9,12-dien-1-yl)oxy)propyl 2-(3-oxo-2-((Z)-pent-2-en-1-yl)cyclopentyl)acetate. Synthesis of this ketone was performed using 4 (1.330 g, 6.33 mmol) in DCM (15 mL), DMAP (0.773 g, 6.33 mmol), EDCl hydrochloride (1.213 g, 6.33 mmol) and 27 (1.35 g, 3.16 mmol) in DCM (5 mL). The crude product (2.01 g, 3.25 mmol, yellow oil) was taken as such for the next step without further purification. $^1H$ (400 MHz, $CDCl_3$) δ 5.50-5.24 (m, 6H), 4.99 (p, 1H, J=6.0), 4.20-4.03 (m, 2H), 2.83-2.69 (m, 3H), 2.42-1.86 (m, 16H), 1.52-1.41 (m, 6H), 1.38-1.21 (m, 40H), 0.98-0.94 (m, 3H), 0.91-0.86 (m, 9H). RT=3.34 min. 99.5% purity. ESI-MS: m/z=778 $[M+Na]^+$ for $C_{49}H_{86}O_5Na$.

Compound 28 was synthesized using the method similar to the one used for synthesis of 5. Synthesis of 28 was performed using (12Z,15Z)-1-(2-(3-oxo-2-((Z)-pent-2-en-1-yl)cyclopentyl)acetoxy)henicosa-12,15-dien-3-yl 2-hexyldecanoate (2.0 g, 3.23 mmol) in MeOH (20 mL) and THE (5 mL) and sodium borohydride (0.489 g, 12.92 mmol). The crude product was purified by Isolera™ silica gel (100-200 mesh) column chromatography using 10% EtOAc in Pet. ether to give 28 (1.82 g, 2.91 mmol, 90% yield) as light-yellow oil. $^1H$ (400 MHz, $CDCl_3$) δ 5.50-5.30 (m, 6H), 4.99 (p, 1H, J=8.0), 4.17-4.10 (m, 1H), 4.07-4.01 (m, 1H), 3.93-3.88 (m, 1H), 2.78 (t, 2H, J=6.0), 2.58-2.52 (m, 1H), 2.39-1.83 (m, 16H), 1.50-1.40 (m, 6H), 1.38-1.26 (m, 40H), 0.98 (t, 3H, J=8.0), 0.91-0.86 (m, 9H). RT=3.38 min. 99.3% purity. ESI-MS: m/z=780 $[M+Na]^+$ for $C_{49}H_{88}O_5Na$.

PNI 510

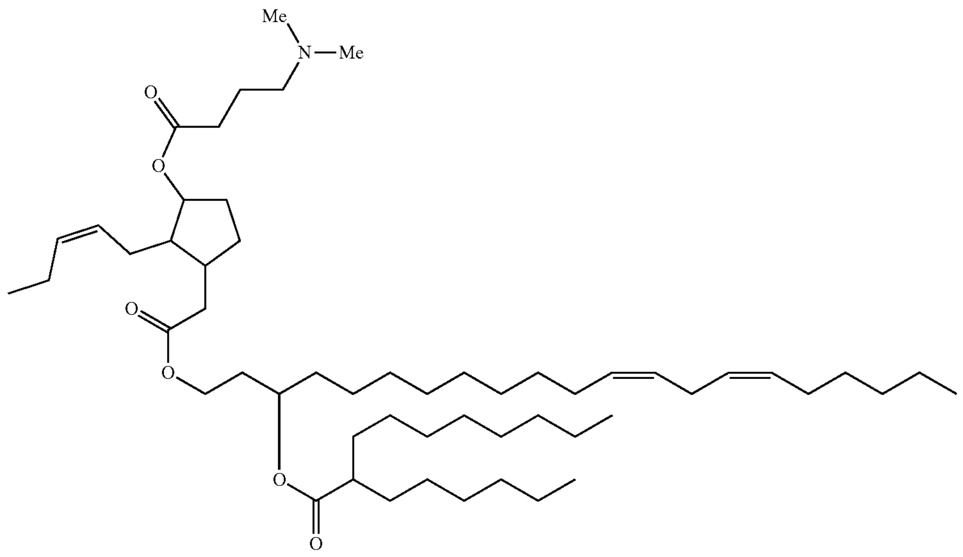

PNI 510 was synthesized using the method similar to the one used for synthesis of PNI 132. Synthesis of PNI 510 was performed using 4-(dimethylamino)butanoic acid hydrochloride (0.194 g, 1.156 mmol) in dry DCM (10 mL), 28 (0.35 g, 0.462 mmol) in DCM (5 mL), DMAP (0.141 g, 1.156 mmol) and EDCl hydrochloride (0.310 g, 1.618 mmol). The crude product was purified by silica gel (100-200 mesh) column chromatography using 5% MeOH in DCM to give PNI 510 (0.385 g, 0.439 mmol, 95% yield) as a blue oil. $^1H$ (400 MHz, $CDCl_3$) δ 5.47-5.27 (m, 6H), 5.02-4.82 (m, 2H), 4.16-4.09 (m, 1H), 4.07-4.01 (m, 1H), 2.77 (t, 2H, J=6.0), 2.57-2.52 (m, 1H), 2.41-2.19 (m, 11H), 2.18-1.79 (m, 14H), 1.71-1.55 (m, 5H), 1.48-1.39 (m, 4H), 1.38-1.17 (m, 40H), 0.97-0.93 (m, 3H), 0.91-0.86 (m, 9H). RT=3.65 min. 99.3% purity. ESI-MS: m/z=871 $[M+H]^+$ for $C_{55}H_{100}NO_6$.

PNI 552

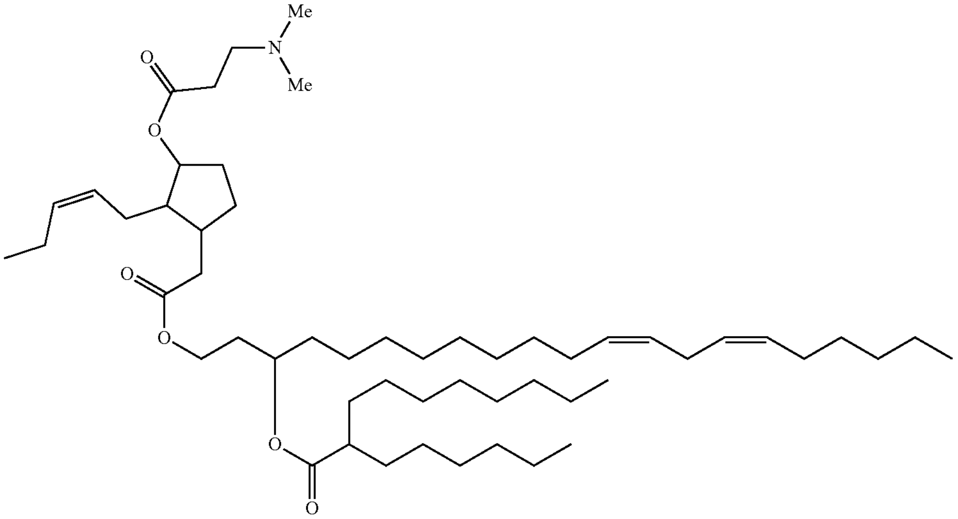

PNI 552 was synthesized using the method similar to the one used for synthesis of PNI 132. Synthesis of PNI 552 was performed using 3-(dimethylamino)propanoic acid hydrochloride (0.243 g, 1.585 mmol) in dry DCM (10 mL), 28 (0.4 g, 0.528 mmol) in DCM (5 mL), DMAP (0.194 g, 1.585 mmol) and EDCl hydrochloride (0.405 g, 2.113 mmol). The crude product was purified by Isolera™ silica gel (100-200 mesh) column chromatography using 4% MeOH in DCM to afford PNI 552 (0.405 g, 0.468 mmol, 89% yield) as light blue oil. $^{1}H$ (400 MHz, $CDCl_3$) δ 5.47-5.30 (m, 6H), 5.02-4.82 (m, 2H), 4.16-4.11 (m, 1H), 4.07-4.01 (m, 1H), 2.78 (t, 2H, J=6.0), 2.74-2.62 (m, 2H), 2.60-2.43 (m, 3H), 2.40-2.23 (m, 7H), 2.21-1.85 (m, 14H), 1.75-1.67 (m, 3H), 1.49-1.40 (m, 4H), 1.38-1.17 (m, 40H), 0.97-0.93 (m, 3H), 0.91-0.86 (m, 9H). RT=3.62 min. 98.9% purity. ESI-MS: m/z=857 $[M+H]^+$ for $C_{54}H_{98}NO_6$.

PNI 563 was synthesized using the method similar to the one used for synthesis of PNI 132. Synthesis of PNI 563 was performed using 1,4-dimethylpiperidine-4-carboxylic acid (0.189 g, 0.977 mmol) in dry DCM (10 mL), 28 (0.37 g, 0.489 mmol) in dry DCM (5 mL), DMAP (0.119 g, 0.977 mmol) and EDCl hydrochloride (0.281 g, 1.466 mmol). The crude product was purified by silica gel (100-200 mesh) column chromatography (Isolera™) using 5% MeOH in DCM to afford PNI 563 (0.335 g, 0.372 mmol, 76% yield) as light blue oil. $^{1}H$ (400 MHz, $CDCl_3$) δ 5.47-5.21 (m, 6H), 5.02-4.84 (m, 2H), 4.17-4.11 (m, 1H), 4.09-4.01 (m, 1H), 2.79-2.64 (m, 4H), 2.61-2.53 (m, 1H), 2.34-1.85 (m, 22H), 1.69-1.49 (m, 3H), 1.46-1.18 (m, 49H), 0.98-0.94 (m, 3H), 0.91-0.86 (m, 9H). RT=4.03 min. 99.6% purity. ESI-MS: m/z=897 $[M+H]^+$ for $C_{57}H_{102}NO_6$.

PNI 563

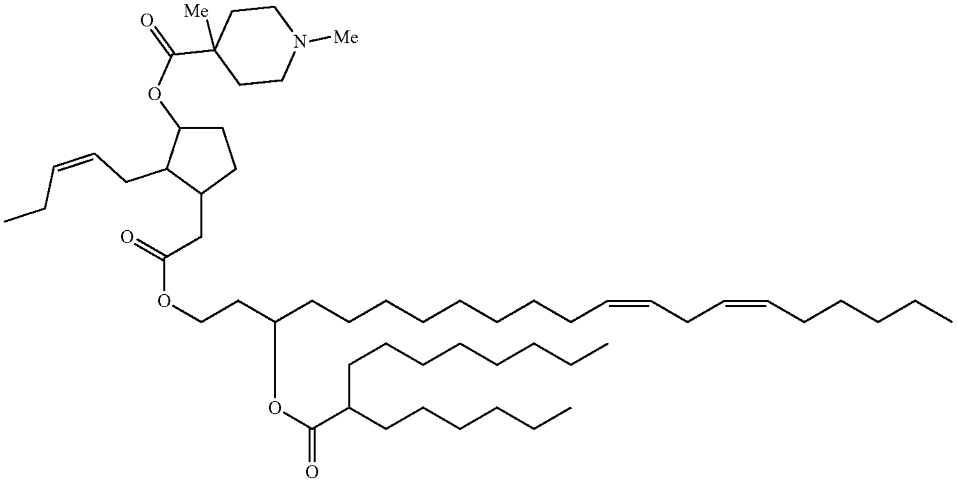

Example 8
Synthesis of PNI 515 and 551
Scheme 13. Synthesis of compound 31
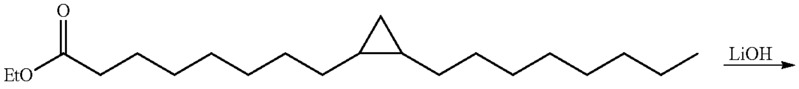
7
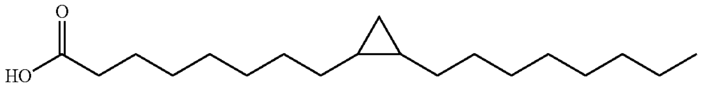
29
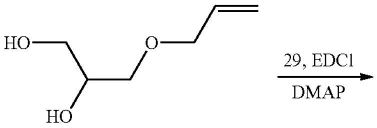
1
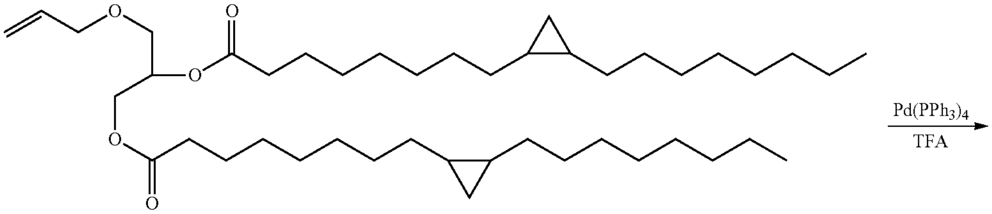
30
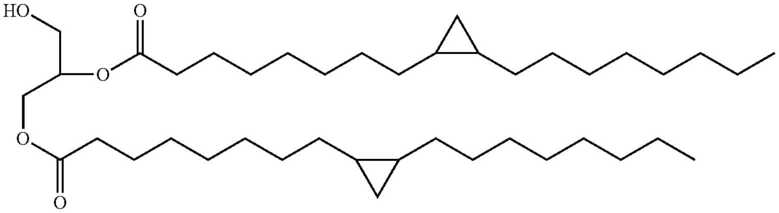
31
Scheme 14. General route for synthesis of PNI 515 and 551
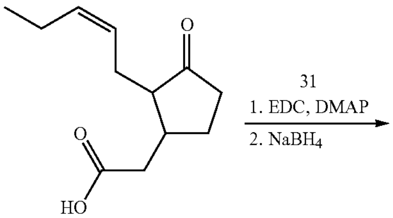
4

-continued

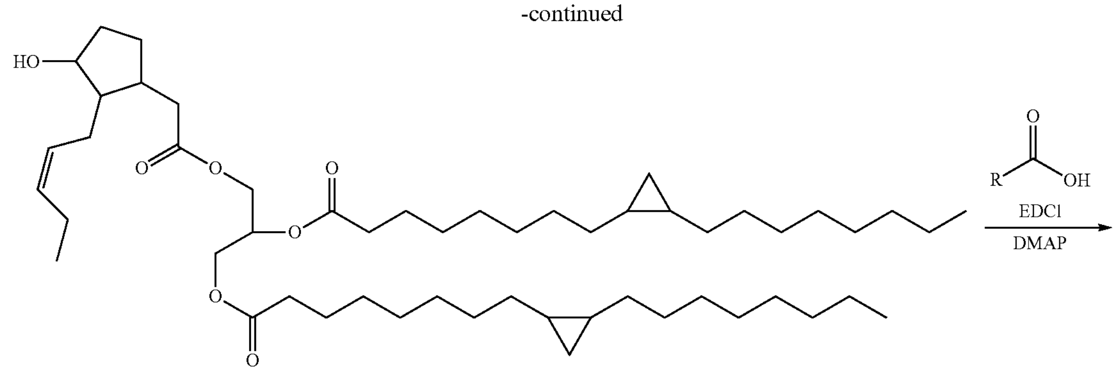

32

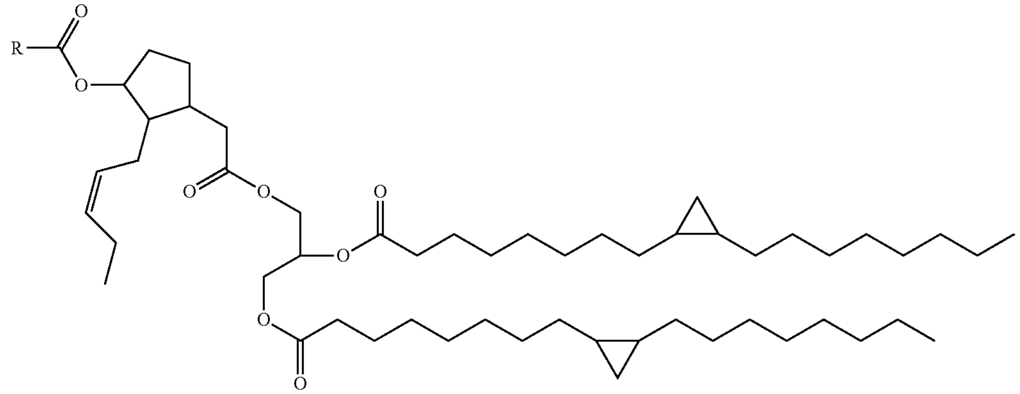

Compound 29: LiOH (1.660 g, 69.3 mmol) was added to a stirred solution of 7 (15 g, 46.2 mmol) in EtOH (105 mL) and water (45 mL) and the reaction mixture was stirred at ambient temperature for 16 hours. Upon the completion of the reaction as indicated by TLC, the reaction mixture was concentrated in vacuo to obtain the residue. The residue was diluted with water (100 mL) and washed with MTBE (2x100 mL). The aq. layer was cooled to 0° C., acidified with 6N HCl and extracted with EtOAc (3x300 mL). The combined organic layers were dried over anhydrous $Na_2SO_4$, filtered and concentrated to obtain 29 (13.05 g, 43.0 mmol, 93% yield) as white solid. $^1$H (400 MHz, $CDCl_3$) δ 2.36 (t, 2H, J=6.0), 1.64 (p, 2H, J=8.0), 1.39-1.28 (m, 22H), 1.19-1.10 (m, 2H), 0.89 (t, 3H, J=6.0), 0.68-0.62 (m, 2H), 0.59-0.54 (m, 1H), −0.33 (app q, 1H, J=4.0). RT=2.91 min. 97.7% purity. ESI-MS: m/z=295 $[M-H]^-$ for $C_{19}H_{35}O_2$.

Compound 30: To a stirred solution of 29 (5.3 g, 17.88 mmol) in dry DCM (25 mL), DMAP (3.28 g, 26.8 mmol) and EDCl hydrochloride (5.14 g, 26.8 mmol) were added at room temperature under nitrogen atmosphere. The mixture was stirred for 10 minutes and a solution of 3-(allyloxy) propane-1,2-diol (1, 1.039 g, 7.87 mmol) in dry DCM (5 mL) was added. The reaction mixture was stirred at room temperature for 16 hours and the consumption of starting material was confirmed by TLC analysis. The solvent was evaporated to dryness under reduced pressure and the residue was dissolved in EtOAc (200 mL). The organic layer was washed with water (2x100 mL), brine (2x100 mL), dried over anhydrous $Na_2SO_4$, filtered and concentrated. The crude product was purified by Isolera™ silica gel (100-200 mesh) column chromatography using 5% EtOAc in Pet. ether to give 30 (4.25 g, 6.15 mmol, 34.4% yield) as yellow oil. $^1$H (400 MHz, $CDCl_3$) δ 5.92-5.82 (m, 1H), 5.28 (dd, 1H, J=16.0, 4.0), 5.24-5.18 (m, 2H), 4.35 (dd, 1H, J=12.0, 4.0), 4.18 (dd, 1H, J=12.0, 4.0), 4.05-3.96 (m, 2H), 3.58 (d, 2H, J=4.0), 2.35-2.29 (m, 4H), 1.67-1.60 (m, 4H), 1.40-1.28 (m, 44H), 1.19-1.10 (m, 4H), 0.89 (t, 6H, J=6.0), 0.68-0.62 (m, 4H), 0.59-0.54 (m, 2H), −0.33 (q, 2H, J=4.0). RT=4.13 min. 99.8% purity. ESI-MS: m/z=712 $[M+Na]^+$ for $C_{44}H_{80}O_5Na$.

Compound 31: Intermediate 31 was synthesized using the method similar to the one used for synthesis of intermediate 3. Synthesis of 31 was performed using TFA (6.57 ml, 85 mmol), $Pd(PPh_3)_4$ (0.704 g, 0.609 mmol) and 30 (4.2 g, 6.09 mmol) in dry EtOH (80 mL). The crude product was purified by silica gel (100-200 mesh) column chromatography (Isolera™) using 10% EtOAc in Pet. ether to give 31 (1.12 g, 1.726 mmol, 28.3% yield) as yellow oil. $^1$H (400 MHz, $CDCl_3$) δ 4.32-4.08 (m, 5H), 2.36 (t, 4H, J=8.0), 1.68-1.60 (m, 4H), 1.40-1.26 (m, 44H), 1.16-1.11 (m, 4H), 0.89 (t, 6H, J=6.0), 0.68-0.62 (m, 4H), 0.59-0.54 (m, 2H), −0.33 (q, 2H, J=4.0). RT=3.45 min. 68.9% purity. ESI-MS: m/z=671 $[M+Na]^+$ for $C_{41}H_{76}O_5Na$.

Compound 32: (Z)-3-(2-(3-hydroxy-2-(pent-2-en-1-yl) cyclopentyl) acetoxy) propane-1,2-diyl bis(8-(2-octylcyclopropyl)octanoate) was synthesized using the method similar to the one used for synthesis of 2,3-bis(((9Z,12Z)-octadeca-9,12-dien-1-yl)oxy)propyl 2-(3-oxo-2-((Z)-pent-2-en-1-yl) cyclopentyl)acetate. Synthesis of this ketone was performed using 31 (1.1 g, 1.695 mmol) in dry DCM (10 mL), DMAP (0.414 g, 3.39 mmol), 4 (0.713 g, 3.39 mmol) in dry DCM (15 mL) and EDCl hydrochloride (0.650 g, 3.39 mmol). The crude ketone product (1.72 g) was obtained as yellow oil and was taken as such for the next step without further purification. $^1$H (400 MHz, $CDCl_3$) δ 5.50-5.43 (m, 1H), 5.31-5.26 (m, 2H), 4.33 (dd, 2H, J=12.0, 4.0), 4.16 (dd, 2H, J=12.0, 8.0), 2.80-2.71 (m, 1H), 2.41-1.89 (m, 13H), 1.64-1.58 (m, 4H), 1.53-1.48 (m, 2H), 1.38-1.26 (m, 44H), 1.19-1.10 (m, 4H), 0.97 (t, 3H, J=6.0), 0.89 (t, 6H, J=6.0), 0.68-0.62 (m, 4H), 0.59-0.54 (m, 2H), −0.33 (q, 2H, J=4.0). RT=3.98 min. 74.8% purity.

Compound 32 was synthesized using the method similar to the one used for synthesis of 5. Synthesis of 32 was performed using (Z)-3-(2-(3-hydroxy-2-(pent-2-en-1-yl)cyclopentyl)acetoxy)propane-1,2-diyl bis(8-(2-octylcyclopropyl)octanoate) (1.7 g, 2.021 mmol) in dry MeOH (20 mL) and dry THE (5 mL) and sodium borohydride (0.306 g, 8.08 mmol). The crude product was purified by Isolera™ silica gel (100-200 mesh) column chromatography using 12% EtOAc in Pet. ether to give 32 (1.01 g, 1.170 mmol, 57.9% yield) as yellow oil. $^1$H (400 MHz, $CDCl_3$) δ 5.53-5.36 (m, 2H), 5.29-5.24 (m, 1H), 4.31 (dt, 2H, J=12.0, 4.0), 4.23-4.20 (m, 1H), 4.15 (dd, 2H, J=12.0, 4.0), 3.91 (q, 1H, J=4.0), 2.62-2.53 (m, 1H), 2.38-2.28 (m, 5H), 2.23-1.82 (m, 8H), 1.67-1.60 (m, 4H), 1.51-1.45 (m, 2H), 1.38-1.28 (m, 44H), 1.19-1.10 (m, 4H), 0.98 (t, 3H, J=8.0), 0.89 (t, 6H, J=6.0), 0.68-0.62 (m, 4H), 0.59-0.54 (m, 2H), −0.33 (q, 2H, J=4.0). RT=3.72 min. 97.7% purity. ESI-MS: m/z=866 $[M+Na]^+$ for $C_{53}H_{94}O_7Na$.

PNI 515

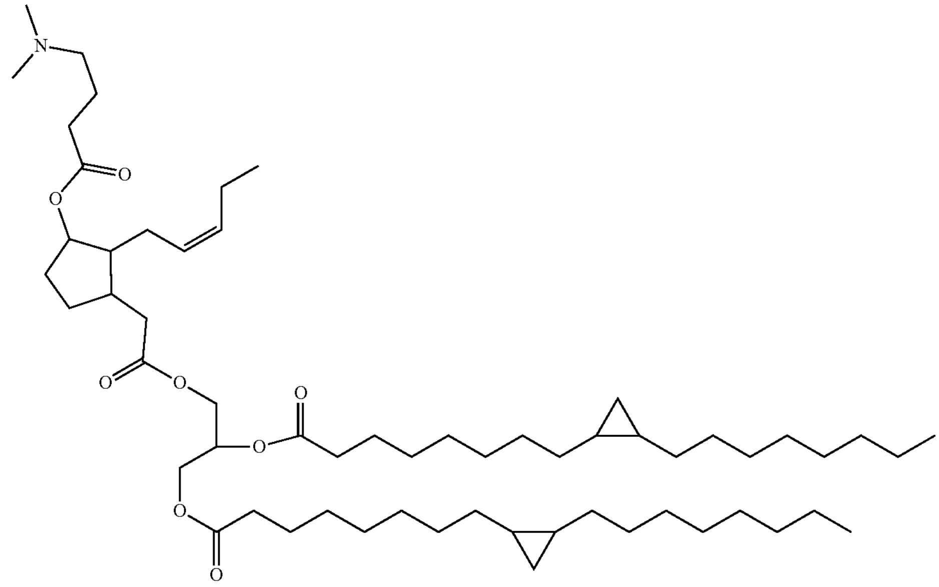

PNI 515 was synthesized using the method similar to the one used for synthesis of PNI 132. Synthesis of PNI 515 was performed using 4-(dimethylamino)butanoic acid hydrochloride (0.139 g, 0.830 mmol) in dry DCM (10 mL), DMAP (0.101 g, 0.830 mmol), EDCl hydrochloride (0.239 g, 1.245 mmol) and 32 (0.35 g, 0.415 mmol) in dry DCM (5 mL). The crude product was purified by Isolera™ silica gel (100-200 mesh) column chromatography using 5% MeOH in DCM to afford PNI 515 (0.35 g, 0.365 mmol, 88% yield) as pale-yellow oil. $^1$H (400 MHz, $CDCl_3$) δ 5.48-5.26 (m, 3H), 4.87-4.83 (m, 1H), 4.33-4.27 (m, 2H), 4.15 (dd, 2H, J=12.0, 4.0), 2.64-2.57 (m, 1H), 2.36-1.78 (m, 23H), 1.74-1.50 (m, 8H), 1.42-1.26 (m, 44H), 1.20-1.08 (m, 4H), 0.98-0.93 (m, 3H), 0.89 (app t, 6H, J=6.0), 0.68-0.61 (m, 4H), 0.59-0.54 (m, 2H), −0.34 (q, 2H, J=4.0). RT=2.64 min. 99.9% purity. ESI-MS: m/z=957 $[M+H]^+$ for $C_{59}H_{106}NO_3$.

PNI 551

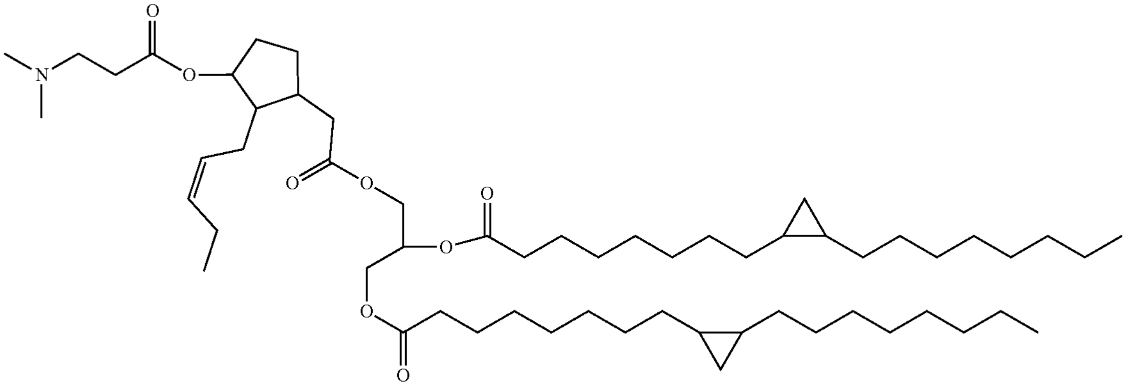

PNI 551 was synthesized using the method similar to the one used for synthesis of PNI 132. Synthesis of PNI 551 was performed using 3-(dimethylamino)propanoic acid hydrochloride (0.191 g, 1.245 mmol) in dry DCM (10 mL), DMAP (0.152 g, 1.245 mmol), EDCl hydrochloride (0.318 g, 1.660 mmol) and 32 (0.35 g, 0.415 mmol) in dry DCM (5 mL). The crude product was purified by Isolera™ silica gel (100-200 mesh) column chromatography using 4% MeOH in DCM to afford PNI 551 (0.37 g, 0.392 mmol, 94% yield) as pale-yellow oil. $^1H$ (400 MHz, $CDCl_3$) δ 5.48-5.27 (m, 3H), 4.89-4.82 (m, 1H), 4.32-4.28 (m, 2H), 4.15 (dd, 2H, J=12.0, 4.0), 2.74-2.57 (m, 3H), 2.54-2.43 (m, 2H), 2.37-2.24 (m, 10H), 2.20-1.89 (m, 9H), 1.75-1.62 (m, 6H), 1.38-1.26 (m, 44H), 1.19-1.07 (m, 4H), 0.98-0.93 (m, 3H), 0.89 (app t, 6H, J=6.0), 0.69-0.61 (m, 4H), 0.59-0.54 (m, 2H), −0.33 (q, 2H, J=4.0). RT=2.68 min. 99.8% purity. ESI-MS: m/z=943 $[M+H]^+$ for $C_{58}H_{104}NO_8$.

Example 9

Synthesis of PNI 269

Scheme 15. Synthesis of PNI 269

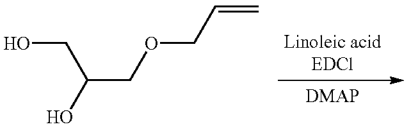

1

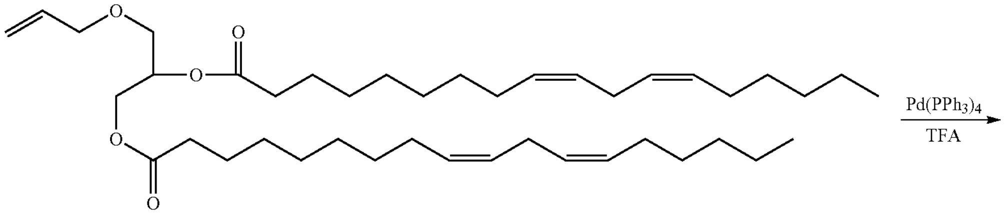

33

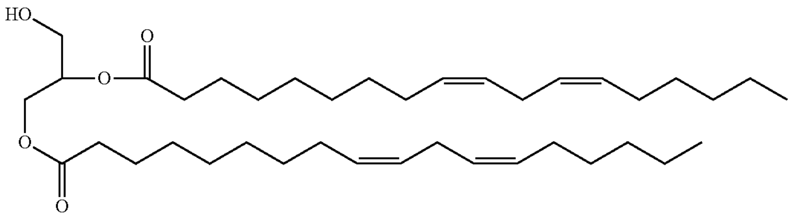

34

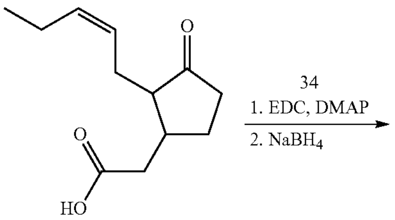

4

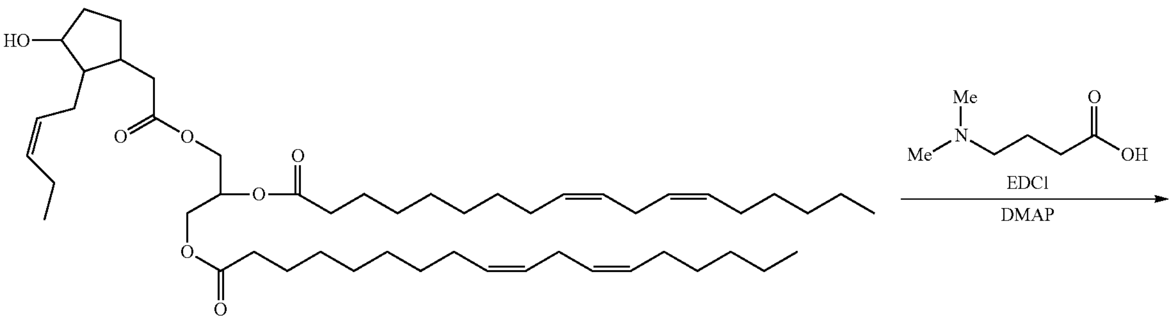

35

-continued

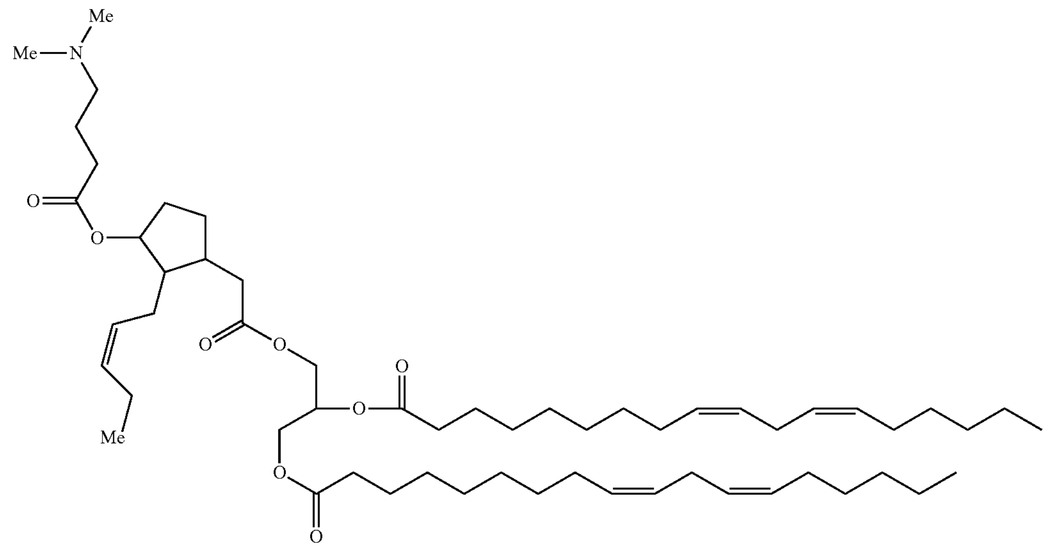

PNI 269

Compound 33: Compound 33 was synthesized using the method similar to the one used for synthesis of 30. Synthesis of 33 was performed using linoleic acid (2.0 g, 7.13 mmol) in dry DCM (10 mL), DMAP (1.305 g, 10.70 mmol), EDCl hydrochloride (2.043 g, 10.70 mmol) and 3-(allyloxy)propane-1,2-diol (1, 0.377 g, 2.85 mmol) in dry DCM (10 mL). The crude product was purified by silica gel (100-200 mesh) column chromatography (Isolera™) using 5% EtOAc in Pet. ether to give 33 (1.2 g, 1.826 mmol, 25.6% yield) as colorless oil. $^1$H (400 MHz, $CDCl_3$) δ 5.92-5.82 (m, 1H), 5.42-5.29 (m, 9H), 5.26-5.18 (m, 2H), 4.35 (dd, 1H, J=12.0, 4.0), 4.18 (dd, 1H, J=12.0, 8.0), 4.05-3.96 (m, 2H), 3.57 (d, 2H, J=8.0), 2.78 (t, 4H, J=6.0), 2.32 (app q, 4H, J=8.0), 2.06 (q, 8H, J=8.0), 1.66-1.58 (m, 4H), 1.40-1.25 (m, 28H), 0.90 (t, 6H, J=6.0). RT=2.63 min. 97.4% purity. ESI-MS: m/z=679 $[M+Na]^+$ for $C_{42}H_{72}O_5Na$.

Compound 34: Compound 34 was synthesized using the method similar to the one used for synthesis of compound 3. Synthesis of 34 was performed using TFA (4 mL), $Pd(PPh_3)_4$ (1.055 g, 0.913 mmol) and 33 (4.0 g, 6.09 mmol) in dry EtOH (40 mL). The crude product was purified by Isolera™ silica gel (100-200 mesh) column chromatography using 5% EtOAc in Pet. ether to give 34 (1.8 g, 2.92 mmol, 47.9% yield) as yellow oil. $^1$H (400 MHz, $CDCl_3$) δ 5.42-5.29 (m, 9H), 4.33-4.08 (m, 4H), 2.77 (t, 4H, J=6.0), 2.37-2.27 (m, 4H), 2.05 (q, 8H, J=6.0), 1.65-1.59 (m, 4H), 1.38-1.24 (m, 28H), 0.89 (t, 6H, J=6.0). RT=2.20 min. 76.1% purity. ESI-MS: m/z=617 $[M+H]^+$ for $C_{39}H_{69}O_5$.

Compound 35: 3-(2-(3-oxo-2-((Z)-pent-2-en-1-yl)cyclopentyl)acetoxy)propane-1,2-diyl (9Z,9'Z,12Z,12'Z)-bis(octadeca-9,12-dienoate) was synthesized using the method similar to the one used for synthesis of 2,3-bis(((9Z,12Z)-octadeca-9,12-dien-1-yl)oxy)propyl 2-(3-oxo-2-((Z)-pent-2-en-1-yl) cyclopentyl)acetate. Synthesis of this ketone was performed using 34 (0.8 g, 1.297 mmol) in DCM (20 mL), DMAP (0.237 g, 1.945 mmol), 4 (0.300 g, 1.426 mmol) in DCM (20 mL) and EDCl hydrochloride (0.371 g, 1.945 mmol). The crude product was obtained as a pale orange oil. This crude ketone was used for the next step without further purification. RT=2.67 min. 58.2% purity. ESI-MS: m/z=832 $[M+Na]^+$ for $C_{51}H_{84}O_7Na$.

Compound 35 was synthesized using the method similar to the one used for synthesis of 5. Synthesis of 35 was performed using 3-(2-(3-oxo-2-((Z)-pent-2-en-1-yl)cyclopentyl)acetoxy)propane-1,2-diyl(9Z,9'Z,12Z,12'Z)-bis(octadeca-9,12-dienoate) (0.8 g, 0.989 mmol) in 15 mL of dry MeOH:THE (2:1) and sodium borohydride (0.128 g, 3.46 mmol). The crude product was purified by Isolera™ silica gel (100-200 mesh) column chromatography using 10% EtOAc in Pet. ether as the eluent to provide 35 (0.31 g, 0.382 mmol, 38.7% yield) as thick colorless oil. $^1$H (400 MHz, $CDCl_3$) δ 5.52-5.24 (m, 11H), 4.33-4.28 (m, 2H), 4.22 (br s, 1H), 4.17-4.12 (m, 2H), 3.93-3.89 (m, 1H), 2.77 (t, 4H, J=6.0), 2.62-2.53 (m, 1H), 2.34-2.29 (m, 5H), 2.23-1.84 (m, 16H), 1.67-1.60 (m, 6H), 1.40-1.24 (m, 28H), 0.98 (t, 3H, J=8.0), 0.89 (t, 6H, J=6.0). RT=2.62 min. 82.8% purity. ESI-MS: m/z=834 $[M+Na]^+$ for $C_{51}H_{86}O_7Na$.

PNI 269

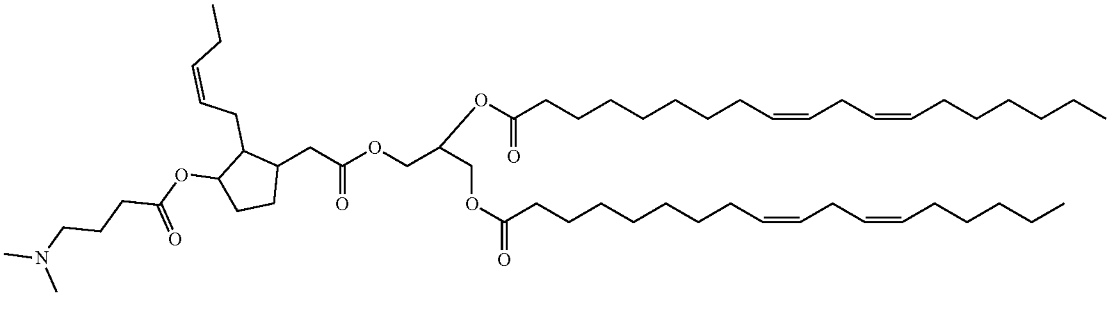

PNI 269 was synthesized using the method similar to the one used for synthesis of PNI 132. Synthesis of PNI 269 was performed using 4-(dimethylamino)butanoic acid hydrochloride (0.073 g, 0.435 mmol) in dry DCM (20 mL), DMAP (0.023 g, 0.185 mmol), EDCl hydrochloride (0.141 g, 0.740 mmol) and 35 (0.3 g, 0.370 mmol) in dry DCM (5 mL). The crude product was purified by Isolera™ silica gel (100-200 mesh) column chromatography using 5% MeOH in DCM as the eluent to afford PNI 269 (0.17 g, 0.147 mmol, 39.8% yield) was obtained as thick colorless oil. $^{1}H$ (400 MHz, $CDCl_3$) δ 5.46-5.18 (m, 11H), 4.86-4.83 (m, 1H), 4.32-4.28 (m, 2H), 4.15 (dd, 2H, J=12.0, 8.0), 2.77 (t, 4H, J=6.0), 2.63-2.52 (m, 3H), 2.45-2.25 (m, 13H), 2.20-1.86 (m, 16H), 1.73-1.51 (m, 8H), 1.37-1.26 (m, 28H), 0.97-0.93 (m, 3H), 0.91-0.87 (m, 6H). RT=2.88 min. 88.5% purity. ESI-MS: m/z=925 $[M+H]^+$ for $C_{57}H_{98}NO_8$.

Example 10

Synthesis of PNI 148

Scheme 16. synthesis of PNI 148

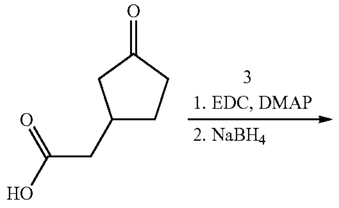

36

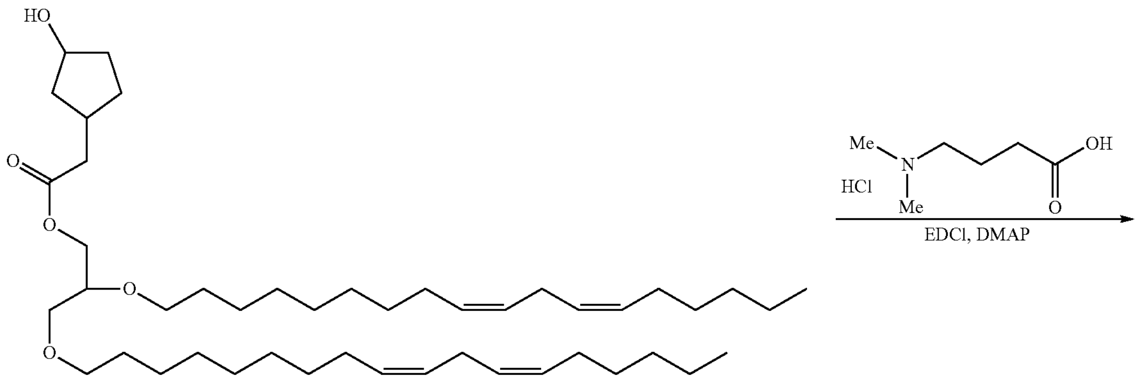

37

-continued

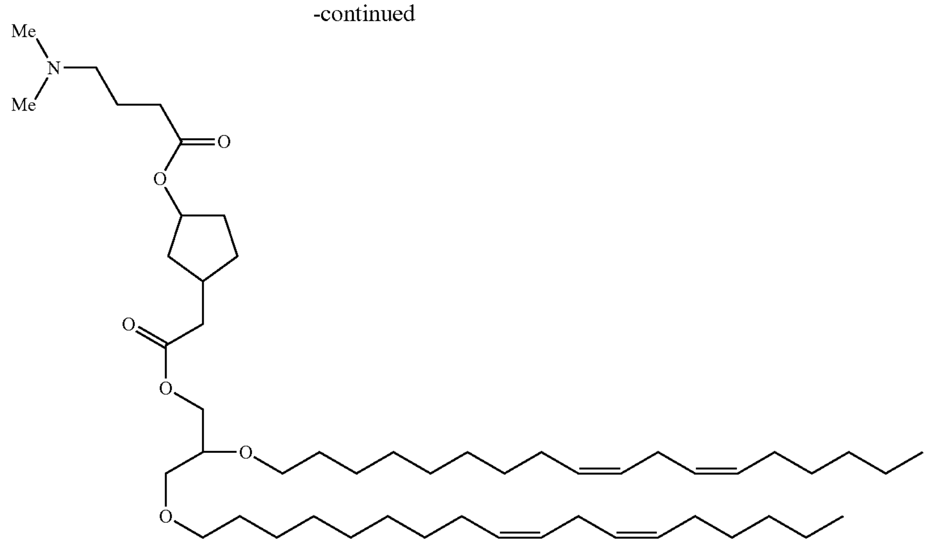

PNI 148

Compound 37: 2,3-bis(((9Z,12Z)-octadeca-9,12-dien-1-yl)oxy)propyl 2-(3-oxocyclopentyl) acetate was synthesized using the method similar to the one used for synthesis of 2,3-bis(((9Z,12Z)-octadeca-9,12-dien-1-yl) oxy) propyl 2-(3-oxo-2-((Z)-pent-2-en-1-yl)cyclopentyl)acetate. Synthesis of this ketone was performed using 3 (0.33 g, 0.560 mmol) in dry DCM (5 mL), DMAP (0.034 g, 0.280 mmol), 36 (0.119 g, 0.840 mmol) in DCM (20 mL) and EDCl hydrochloride (0.215 g, 1.121 mmol). The crude product to give 37 (0.34 g, 0.361 mmol, 62.8% yield) as thick colorless oil. $^1$H (400 MHz, $CDCl_3$) δ 5.41-5.30 (m, 8H), 4.39-4.32 (m, 2H), 4.26-4.22 (m, 1H), 4.10 (dd, 1H, J=12.0, 4.0), 3.62 (p, 1H, J=4.0), 3.55 (t, 2H, J=8.0), 3.49-3.42 (m, 4H), 2.78 (t, 4H, J=6.0), 2.63-2.15 (m, 4H), 2.08-2.03 (m, 8H), 1.90-1.65 (m, 3H), 1.59-1.47 (m, 6H), 1.38-1.26 (m, 32H), 0.90 (t, 6H, J=6.0). RT=2.79 min. 97.2% purity. ESI-MS: m/z=738 $[M+Na]^+$ for $C_{46}H_{82}O_5Na$.

PNI 148

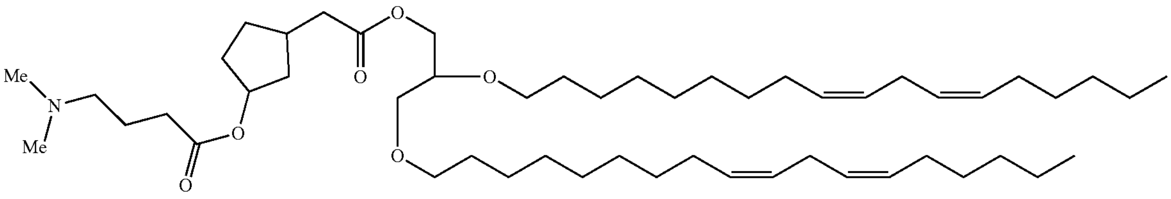

(0.43 g, 0.482 mmol, 86% yield) was obtained as a pale orange liquid, which was taken as such for the next step without further purification. $^1$H (400 MHz, $CDCl_3$) δ 5.42-5.30 (m, 8H), 4.29 (dt, 1H, J=12.0, 4.0), 4.16-4.09 (m, 1H), 3.63 (p, 1H, J=4.0), 3.55 (t, 2H, J=8.0), 3.50-3.42 (m, 4H), 2.78 (t, 4H, J=6.0), 2.67-2.15 (m, 7H), 2.08-2.03 (m, 8H), 1.90 (dd, 1H, J=16.0. 8.0), 1.65-1.52 (m, 5H), 1.40-1.25 (m, 32H), 0.89 (t, 6H, J=6.0). RT=2.77 min. 80.0% purity. ESI-MS: m/z=712 $[M+H]^+$ for $C_{46}H_{81}O_5$.

Compound 37 was synthesized using the method similar to the one used for synthesis of 5. Synthesis of 37 was performed using 2,3-bis(((9Z,12Z)-octadeca-9,12-dien-1-yl)oxy)propyl 2-(3-oxocyclopentyl)acetate (0.41 g, 0.575 mmol) in 25 mL of dry MeOH:THE (2:1) and sodium borohydride (0.076 g, 2.012 mmol). The crude product was purified by Isolera™ silica gel (100-200 mesh) column chromatography using 10% EtOAc in Pet. ether as the eluent PNI 148 was synthesized using the method similar to the one used for synthesis of PNI 132. Synthesis of PNI 148 was performed using 4-(dimethylamino)butanoic acid hydrochloride (0.147 g, 0.876 mmol) in dry DCM (30 mL), DMAP (0.109 g, 0.895 mmol), EDCl hydrochloride (0.300 g, 1.566 mmol) and 36 (0.320 g, 0.447 mmol) in dry DCM (5 mL). The crude product was purified by Isolera™ silica gel (100-200 mesh) column chromatography using 5% MeOH in DCM as the eluent to afford PNI 148 (0.16 g, 0.191 mmol, 42.7% yield) as thick colorless oil. $^1$H (400 MHz, $CDCl_3$) δ 5.42-5.30 (m, 8H), 5.20-5.13 (m, 1H), 4.24 (dt, 1H, J=12.0, 4.0), 4.12-4.07 (m 1H), 3.61 (p, 1H, J=4.0), 3.55 (t, 2H, J=6.0), 3.48-3.42 (m, 4H), 2.77 (t, 4H, J=6.0), 2.54-2.25 (m, 12H), 2.12-1.76 (m, 15H), 1.55 (p, 4H, J=8.0), 1.43-1.20 (m, 34H), 0.89 (t, 6H, J=6.0). RT=3.03 min. 98.8% purity. ESI-MS: m/z=829 $[M+H]^+$ for $C_{52}H_{94}NO_6$.

Example 11

Synthesis of PNI 147

Scheme 17. Synthesis of PNI 147

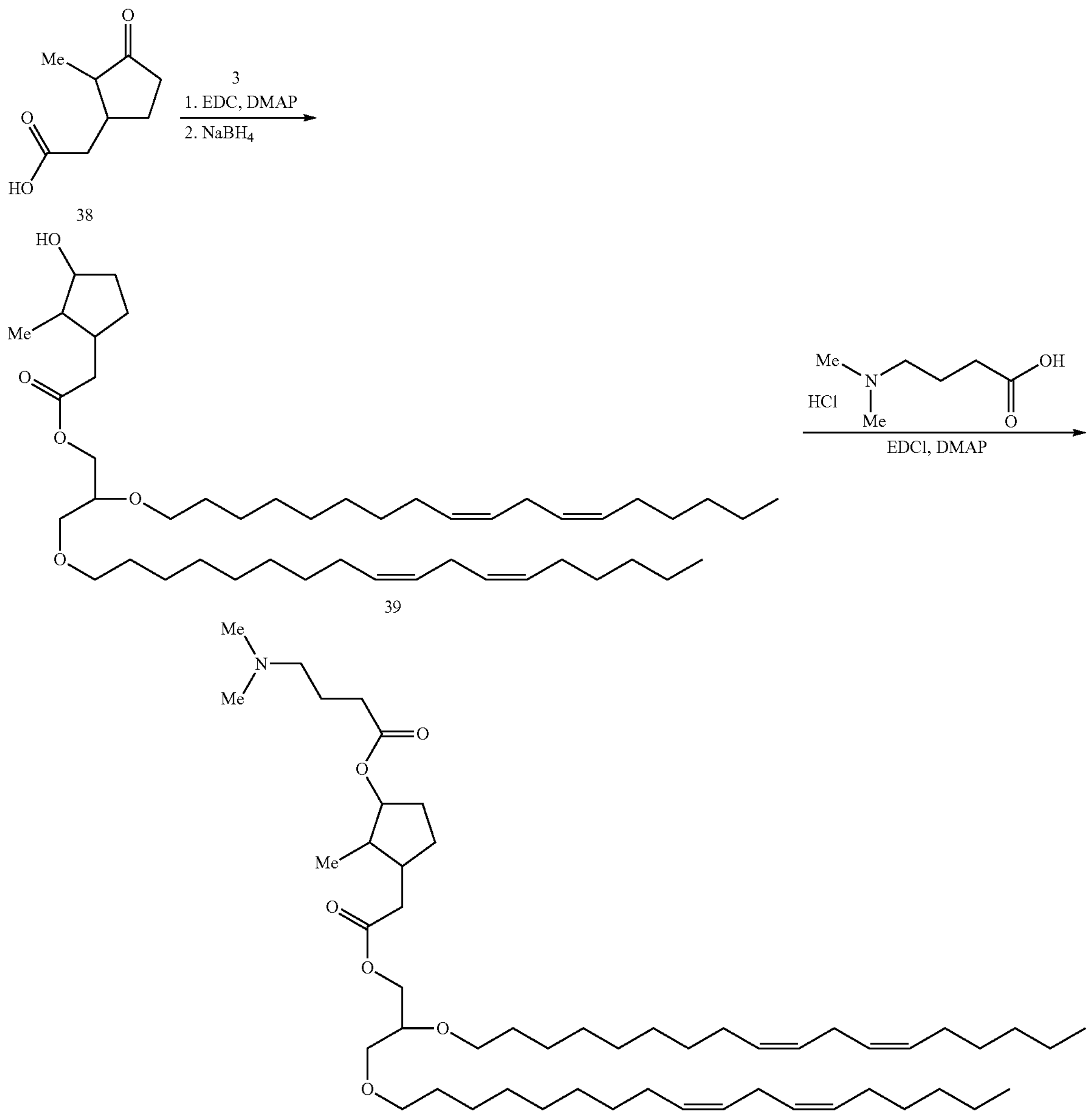

38

39

PNI 147

Compound 39

2,3-bis(((9Z,12Z)-octadeca-9,12-dien-1-yl)oxy)propyl 2-(2-methyl-3-oxocyclopentyl)acetate was synthesized using the method similar to the one used for synthesis of 2,3-bis(((9Z,12Z)-octadeca-9,12-dien-1-yl)oxy)propyl 2-(3-oxo-2-((Z)-pent-2-en-1-yl)cyclopentyl)acetate. Synthesis of this ketone was performed using 3 (0.4 g, 0.679 mmol) in dry DCM (5 mL), DMAP (0.114 g, 0.883 mmol), 38 (0.138 g, 0.883 mmol) in dry DCM (25 mL) and EDCl hydrochloride (0.389 g, 2.037 mmol). The crude product, 2,3-bis(((9Z,12Z)-octadeca-9,12-dien-1-yl)oxy)propyl 2-(3-hydroxy-2-methylcyclopentyl)acetate (0.56 g, 0.770 mmol, 113% yield) was obtained as pale yellow oil, which was used for next step without purification. $^1$H (400 MHz, $CDCl_3$) δ 5.40-5.30 (m, 8H), 4.29 (dd, 1H, J=12.0, 4.0), 4.15-4.10 (m, 1H), 3.63 (p, 1H, J=4.0), 3.55 (t, 2H, J=8.0), 3.51-3.42 (m, 4H), 2.77 (t, 4H, J=6.0), 2.67 (dd, 1H, J=16.0, 4.0), 2.42-2.10 (m, 6H), 2.08-2.02 (m, 8H), 1.85-1.73 (m, 1H), 1.59-1.50 (m, 4H), 1.39-1.24 (m, 32H), 1.09 (d, 3H, J=8.0), 0.89 (t, 6H, J=8.0). RT=2.78 min. 96.5% purity. ESI-MS: m/z=749 $[M+Na]^+$ for $C_{47}H_{82}O_5Na$.

Compound 39 was synthesized using the method similar to the one used for synthesis of 5. Synthesis of 39 was performed using 2,3-bis(((9Z,12Z)-octadeca-9,12-dien-1-yl)oxy)propyl 2-(2-methyl-3-oxocyclopentyl)acetate (0.55 g, 0.756 mmol) in dry MeOH:THF (25 mL, 4:1) and sodium borohydride (0.100 g, 2.65 mmol). The crude product was purified by silica gel (100-200 mesh) column chromatography (Isolera™) using 10% EtOAc in Pet. ether to give 39 (0.33 g, 0.453 mmol, 59.8% yield) as thick colorless oil. $^1H$ (400 MHz, $CDCl_3$) δ $^1H$ (400 MHz, $CDCl_3$) δ 5.42-5.30 (m, 8H), 4.24 (dd, 1H, J=12.0, 4.0), 4.14-4.05 (m, 1H), 3.75 (q, 1H, J=8.0), 3.62 (p, 1H, J=4.0), 3.55 (t, 2H, J=8.0), 3.49-3.42 (m, 4H), 2.78 (t, 4H, J=6.0), 2.54 (dd, 1H, J=16.0, 6.0), 2.28 (dd, 1H, J=12.0, 8.0), 2.20-1.80 (m, 13H), 1.64-1.52 (m, 5H), 1.40-1.24 (m, 32H), 1.04 (d, 3H, J=8.0), 0.90 (t, 6H, J=6.0). RT=2.80 min. 96.6% purity. ESI-MS: m/z=751 $[M+Na]^+$ for $C_{47}H_{84}O_5Na$.

PNI 147

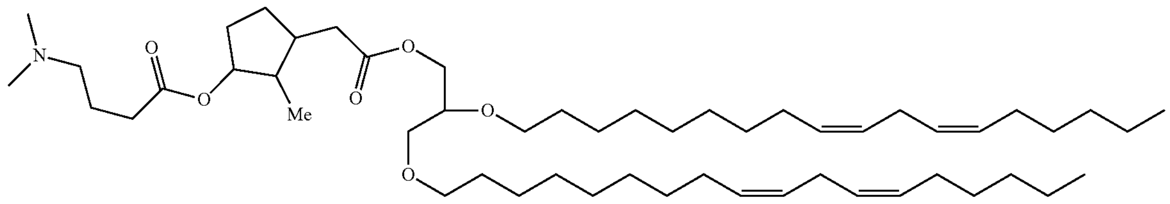

PNI 147 was synthesized using the method similar to the one used for synthesis of PNI 132. Synthesis of PNI 147 was performed using 4-(dimethylamino)butanoic acid hydrochloride (0.090 g, 0.535 mmol) in dry DCM (25 mL), DMAP (0.065 g, 0.535 mmol), EDCl hydrochloride (0.276 g, 1.440 mmol) and 39 (0.3 g, 0.411 mmol) in dry DCM (5 mL). The crude product was purified by silica gel (100-200 mesh) column chromatography (Isolera™) using 5% MeOH in DCM to afford PNI 147 (0.21 g, 0.249 mmol, 60.6% yield) as yellow oil. $^1H$ (400 MHz, $CDCl_3$) δ 5.42-5.30 (m, 8H), 4.71 (q, 1H, J=4.0), 4.24 (dd, 1H, J=12.0, 4.0), 4.13-4.05 (m, 1H), 3.62 (p, 1H, J=4.0), 3.55 (t, 2H, J=8.0), 3.49-3.42 (m, 4H), 2.78 (t, 4H, J=6.0), 2.53 (dd, 1H, J=12.0, 4.0), 2.48-2.40 (m, 2H), 2.36 (s, 6H), 2.27 (dd, 1H, J=12.0, 8.0), 2.05 (q, 8H, J=6.0), 2.00-1.80 (m, 7H), 1.67-1.52 (m, 7H), 1.42-1.26 (m, 32H), 1.03 (d, 3H, J=8.0), 0.89 (t, 6H, J=6.0). RT=3.03 min. 95.6% purity. ESI-MS: m/z=865 $[M+Na]^+$ for $C_{53}H_{95}NO_6Na$.

Example 12

Synthesis of PNI 584, 585 and 586

Scheme 18. Scheme for synthesis of PNI 584, 585 and 586

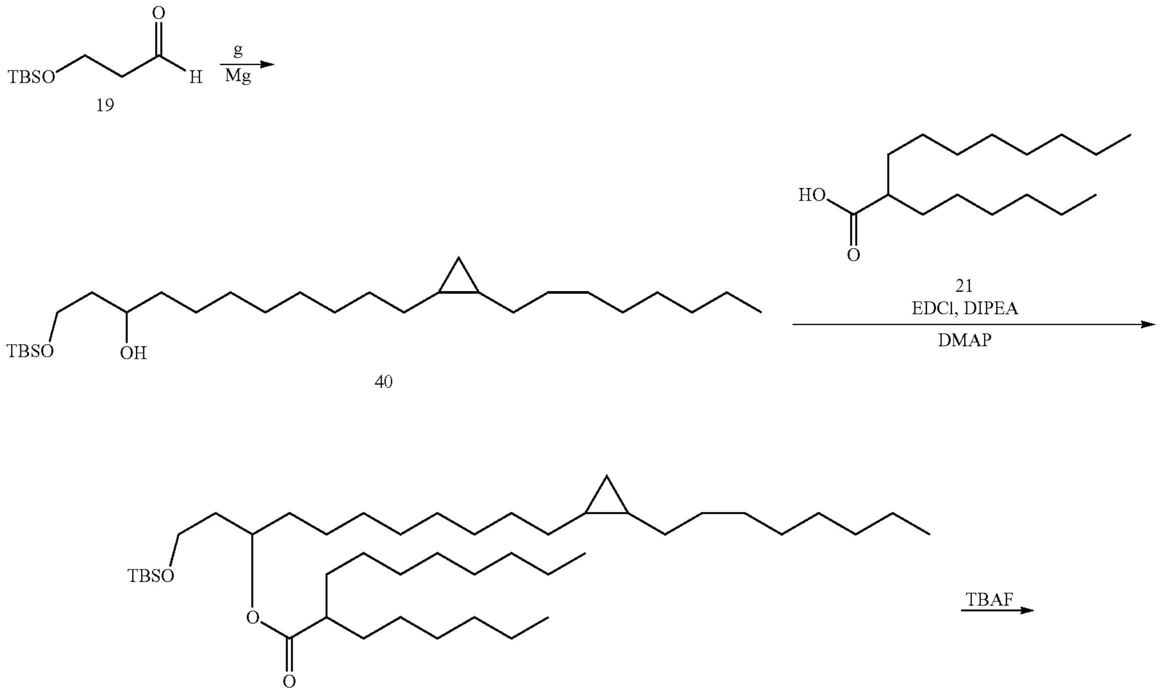

19

21

40

41

-continued

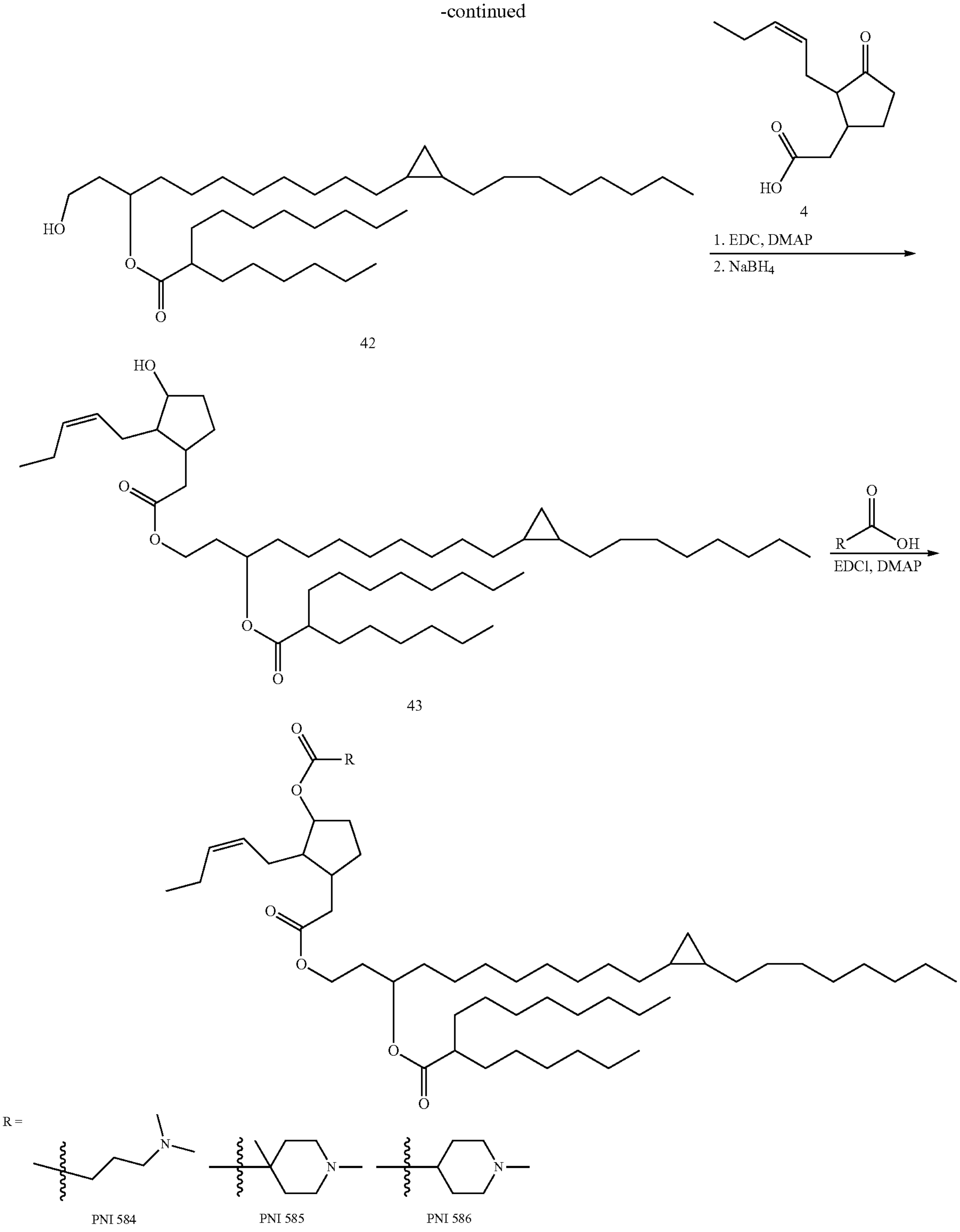

Compound 40

To a stirred suspension of freshly activated Mg turnings (0.528 g, 21.71 mmol) in dry THF (10 mL), 1,2-dibromoethane (0.136 g, 0.724 mmol) was added and stirred for 5 minutes at 25° C. under the nitrogen atmosphere. A solution of 9 (5.0 g, 14.48 mmol) in dry THF (15 mL) was added and the reaction mixture was refluxed for 1 h. The completion of the reaction was confirmed by TLC analysis. The reaction mixture was cooled to 20° C. and a solution 19 (2.73 g, 14.48 mmol) in dry THF (15 mL) was added. The reaction mixture was stirred at 25° C. for 3 h and the progress of the reaction was monitored by the TLC. The mixture was cooled to 0° C. and the excess reagent was quenched with satd. aq. $NH_4Cl$ solution (50 mL) with slow stirring. The aq. layer was extracted with EtOAc (2×75 mL) and the combined organic layers were washed with brine (2×50 mL), dried over anhyd. $Na_2SO_4$, filtered and concentrated. The crude product was purified by silica gel (100-200 mesh) column chromatography (Isolera™) using 5% EtOAc in Pet. ether to give 40 (1.0 g, 1.583 mmol, 10.94% yield) as yellow oil. $^1$H (400 MHz, $CDCl_3$) δ 3.93-3.63 (m, 3H), 1.94-1.52 (m, 4H), 1.43-1.28 (m, 26H), 1.20-1.07 (m, 2H), 0.93-0.87 (m, 12H), 0.69-0.61 (m, 2H), 0.59-0.54 (m, 1H), 0.05 (s, 6H), −0.33 (q, 1H, J=4.0). RT=2.22 min. 72.7% purity. ESI-MS: m/z=455 $[M+H]^+$ for $C_{28}H_{59}O_2Si$.

Compound 41 was synthesized using the method similar to the one used for synthesis of 22. Synthesis of 41 was performed using 21 (0.846 g, 3.30 mmol) in dry DCM (25 mL), DMAP (0.425 g, 3.30 mmol), EDCl hydrochloride (1.475 g, 7.69 mmol) and 40 (1.0 g, 2.199 mmol) in dry DCM (5 mL). The crude product was purified by silica gel (100-200 mesh) column chromatography (Isolera™) using 5% EtOAc in Pet. ether to give 41 (0.75 g, 0.603 mmol, 27.4% yield) as pale-yellow oil and was taken as such next step without further purification. $^1$H (400 MHz, $CDCl_3$) δ 5.16-5.13 (m, 1H), 3.75-3.62 (m, 2H), 2.36-2.27 (m, 1H), 1.90-1.74 (m, 2H), 1.65-1.51 (m, 6H), 1.45-1.11 (m, 48H), 0.92-0.84 (m, 18H), 0.68-0.62 (m, 2H), 0.59-0.54 (m, 1H), 0.05 (s, 6H), −0.33 (q, 1H, J=4.0). RT=6.01 min. 55.8% purity. ESI-MS: m/z=694 $[M+H]^+$ for $C_{44}H_{89}O_3Si$.

Compound 42 was synthesized using the method similar to the one used for synthesis of 23. Synthesis of 42 was performed using TBAF (1.515 mL, 1.515 mmol, 1 M solution in THF) and 41 (0.7 g, 1.010 mmol) in dry THE (20 mL). The crude product was purified by silica gel (100-200 mesh) column chromatography using 10% EtOAc in Pet. ether to give 42 (0.32 g, 0.421 mmol, 41.7% yield) as light-yellow oil. $^1$H (400 MHz, $CDCl_3$) δ 5.06-4.99 (m, 1H), 3.67-3.61 (m, 1H), 3.57-3.49 (m, 1H), 2.39-2.32 (m, 3H), 1.93-1.43 (m, 6H), 1.39-1.10 (m, 48H), 0.92-0.87 (m, 9H), 0.68-0.62 (m, 2H), 0.59-0.54 (m, 1H), −0.33 (q, 1H, J=4.0). RT=3.18 min. 76.2% purity. ESI-MS: m/z=601.5 $[M+Na]^+$ for $C_{38}H_{74}O_3Na$.

Compound 43

(Z)-11-(2-octylcyclopropyl)-1-(2-(3-oxo-2-(pent-2-en-1-yl)cyclopentyl)acetoxy)undecan-3-yl 2-hexyldecanoate was synthesized using the method similar to the one used for synthesis of 2,3-bis(((9Z,12Z)-octadeca-9,12-dien-1-yl)oxy)propyl 2-(3-oxo-2-((Z)-pent-2-en-1-yl)cyclopentyl)acetate. Synthesis of this ketone was performed using 4 (0.142 g, 0.674 mmol) in dry DCM (15 mL), DMAP (0.083 g, 0.674 mmol), EDCl hydrochloride (0.346 g, 1.813 mmol) and 42 (0.3 g, 0.518 mmol) in dry DCM (5 mL). The crude was purified by silica gel (100-200 mesh) column chromatography (Isolera™) using 10% EtOAc in Pet. ether to give product (0.15 g, 0.193 mmol, 37.2% yield) as colorless oil. $^1$H (400 MHz, $CDCl_3$) δ 5.49-5.43 (m, 1H), 5.30-5.23 (m, 1H), 5.02-4.96 (m, 1H), 4.19-4.01 (m, 2H), 2.73-2.67 (m, 1H), 2.40-1.86 (m, 12H), 1.63-1.49 (m, 8H), 1.46-1.12 (m, 48H), 0.96 (t, 3H, J=8.0), 0.90-0.86 (m, 9H), 0.69-0.62 (m, 2H), 0.59-0.54 (m, 1H), −0.34 (q, 1H, J=4.0). RT=3.88 min. 99.8% purity. ESI-MS: m/z=793.6 $[M+Na]^+$ for $C_{50}H_{90}O_5Na$.

Compound 43 was synthesized using the method similar to the one used for synthesis of 5. Synthesis of 43 was performed using (Z)-11-(2-octylcyclopropyl)-1-(2-(3-oxo-2-(pent-2-en-1-yl)cyclopentyl)acetoxy)undecan-3-yl 2-hexyldecanoate (0.15 g, 0.194 mmol) in 10 mL of dry MeOH and 4 mL of dry THE and sodium borohydride (0.026 g, 0.681 mmol). The crude product was purified by silica gel (100-200 mesh) column chromatography (Isolera™) using 15% EtOAc in Pet. ether to provide 43 (0.09 g, 0.114 mmol, 58.7% yield) as viscous colorless oil. $^1$H (400 MHz, $CDCl_3$) δ 5.52-5.36 (m, 2H), 5.01-4.97 (m, 1H), 4.23-3.89 (m, 4H), 2.58-2.50 (m, 1H), 2.32-1.82 (m, 12H), 1.64-1.55 (m, 8H), 1.51-1.06 (m, 48H), 0.98 (t, 3H, J=8.0), 0.90-0.83 (m, 9H), 0.69-0.61 (m, 2H), 0.59-0.54 (m, 1H), −0.34 (q, 1H, J=4.0). RT=4.17 min. 98.3% purity. ESI-MS: m/z=795.6 $[M+Na]^+$ for $C_{50}H_{92}O_5Na$.

PNI 584

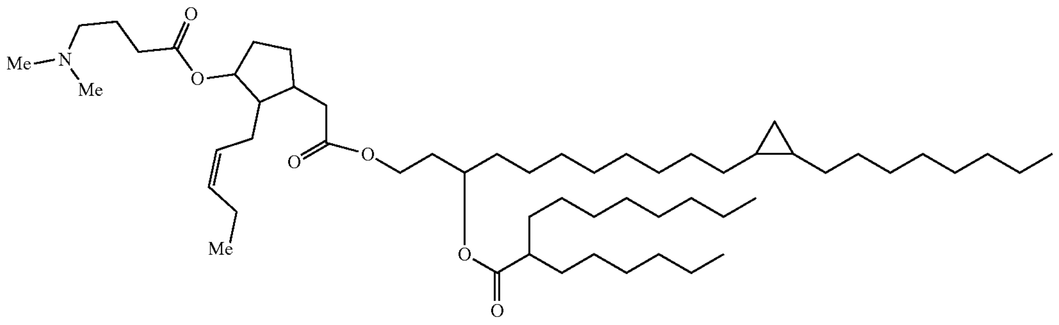

PNI 584 was synthesized using the method similar to the one used for synthesis of PNI 132. Synthesis of PNI 584 was performed using 4-(dimethylamino)butanoic acid hydrochloride (0.194 g, 1.156 mmol) in dry DCM (10 mL), 43 (0.36 g, 0.462 mmol) in DCM (5 mL), DMAP (0.141 g, 1.156 mmol) and EDCl hydrochloride (0.310 g, 1.618 mmol). The crude product was purified by silica gel (100-200 mesh) column chromatography using 5% MeOH in DCM to give PNI 584 (0.371 g, 0.419 mmol, 91% yield) as pale-yellow oil.

PNI 585

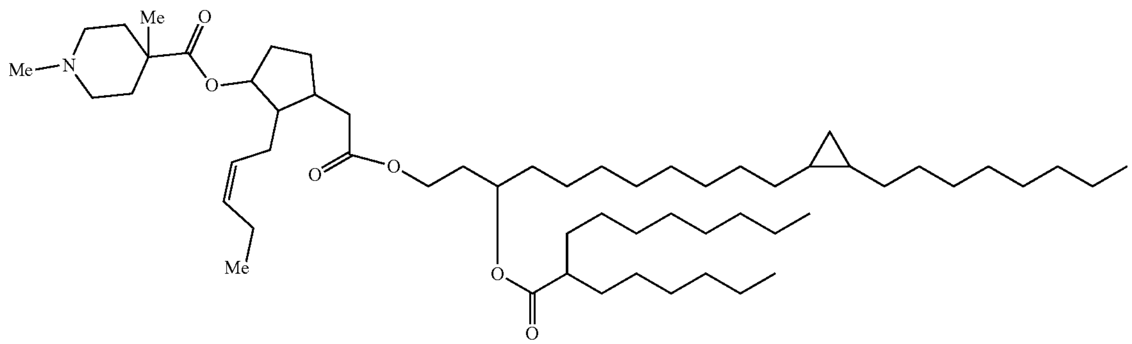

PNI 585 was synthesized using the method similar to the one used for synthesis of PNI 132. Synthesis of PNI 585 was performed using 1,4-dimethylpiperidine-4-carboxylic acid hydrochloride (0.189 g, 0.977 mmol) in dry DCM (10 mL), 43 (0.38 g, 0.489 mmol) in dry DCM (5 mL), DMAP (0.119 g, 0.977 mmol) and EDCl hydrochloride (0.281 g, 1.466 mmol). The crude product was purified by silica gel (100-200 mesh) column chromatography (Isolera™) using 4% MeOH in DCM to afford PNI 585 (0.385 g, 0.422 mmol, 86% yield) as light-yellow oil.

PNI 586

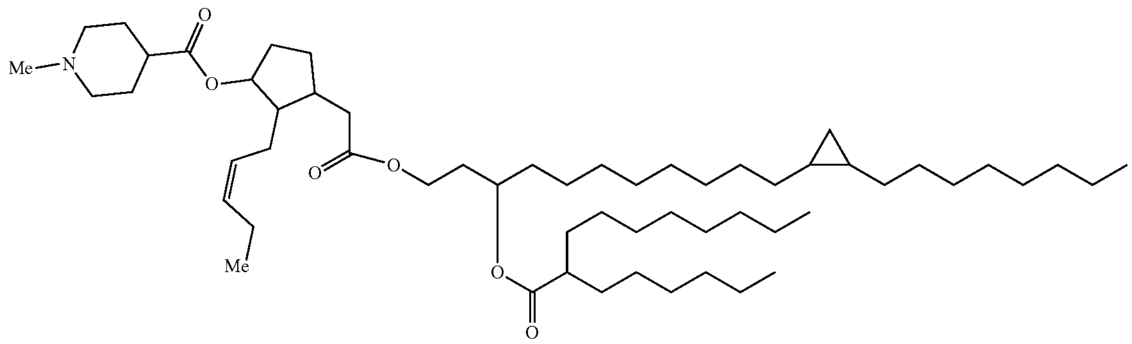

PNI 586 was synthesized using the method similar to the one used for synthesis of PNI 132. Synthesis of PNI 586 was performed using 1-methylpiperidine-4-carboxylic acid hydrochloride (0.176 g, 0.977 mmol) in dry DCM (10 mL), 43 (0.38 g, 0.489 mmol) in dry DCM (5 mL), DMAP (0.119 g, 0.977 mmol) and EDCl hydrochloride (0.281 g, 1.466 mmol). The crude product was purified by silica gel (100-200 mesh) column chromatography (Isolera™) using 5% MeOH in DCM to afford PNI 586 (0.345 g, 0.384 mmol, 79% yield) as light-yellow oil.

Example 13

Schemes for Synthesis of Representative Compounds

Scheme 19. Scheme for synthesis of PNI 572, 597 and 598

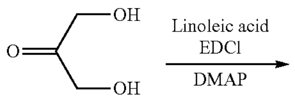

44

-continued
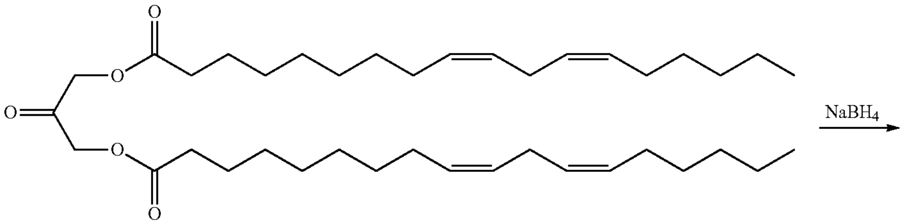
45
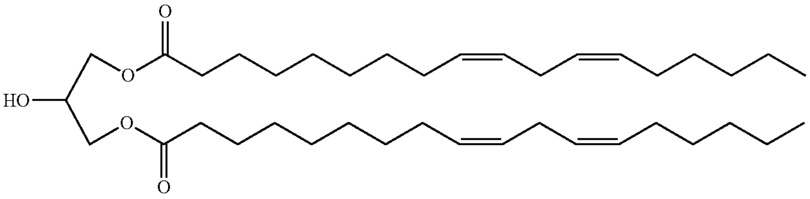
46
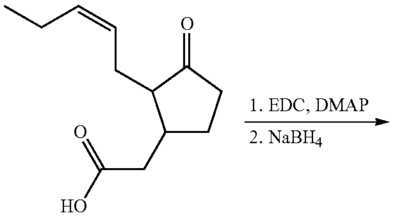
4
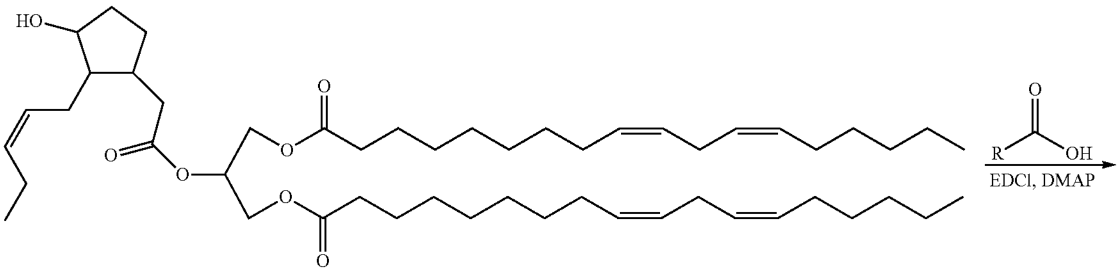
47
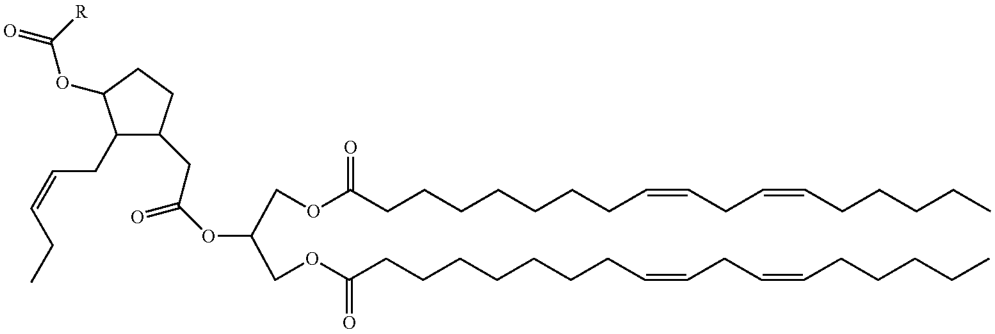
R =
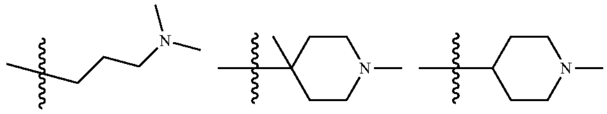
PNI 598 PNI 597 PNI 572

Scheme 20. Scheme for synthesis of PNI 588 and 589
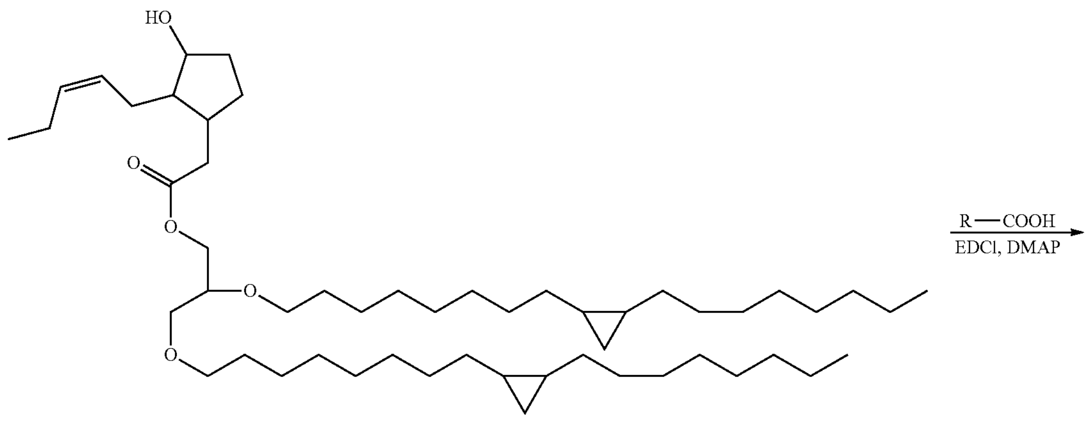
14
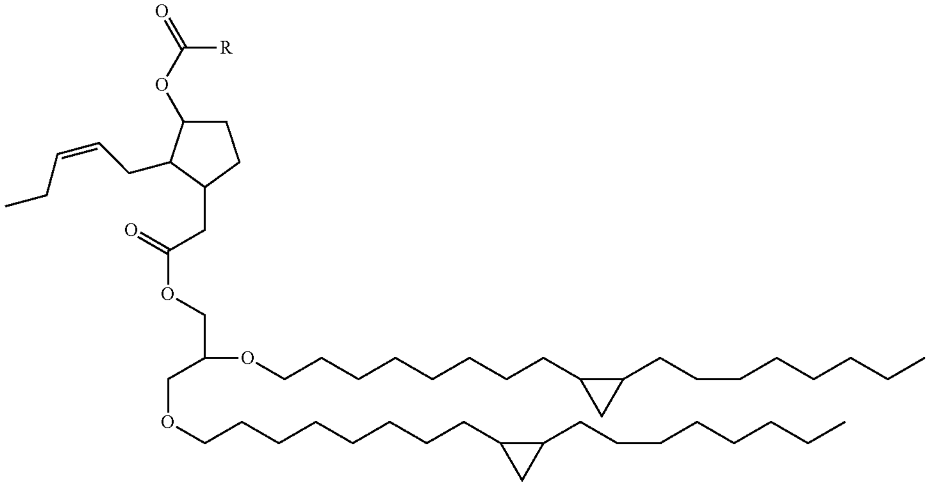
R =
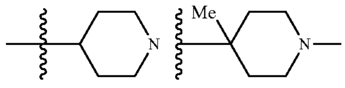
PNI 588 PNI 589
Scheme 21. Scheme for synthesis of PNI 150, 151, 154, 155, 156, 158, 159, and 166.
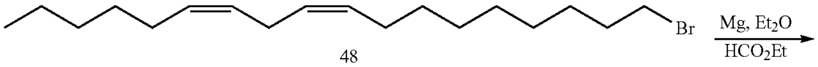
48
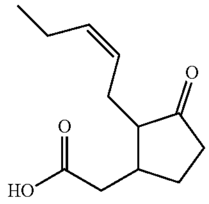
4
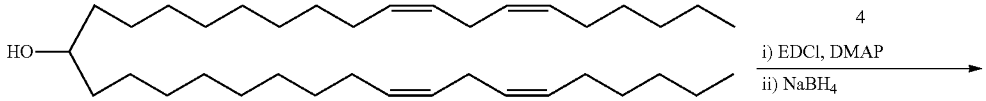
49

-continued
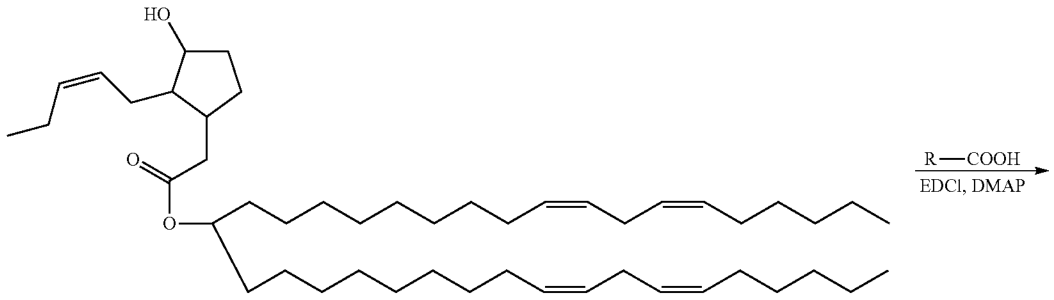
50
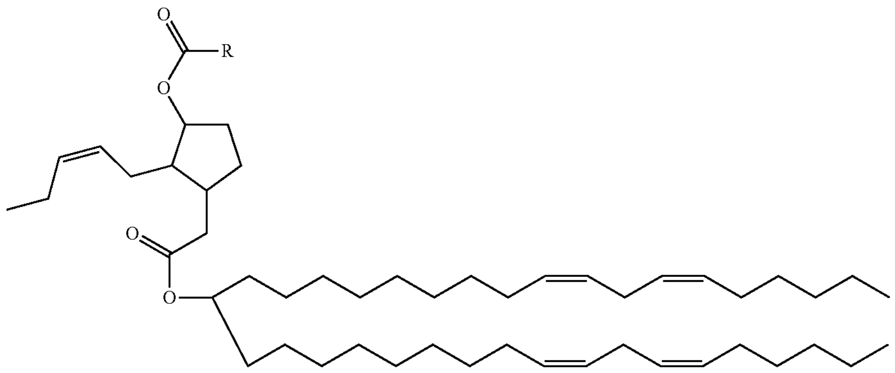
R =
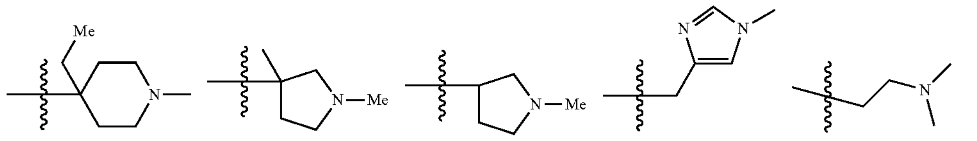
PNI 156 PNI 158 PNI 159 PNI 166 PNI 151
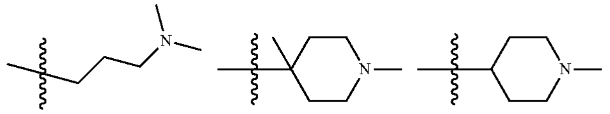
PNI 584 PNI 585 PNI 586
Scheme 22. Scheme for synthesis of PNI 133, 134, 136, 590 and 566
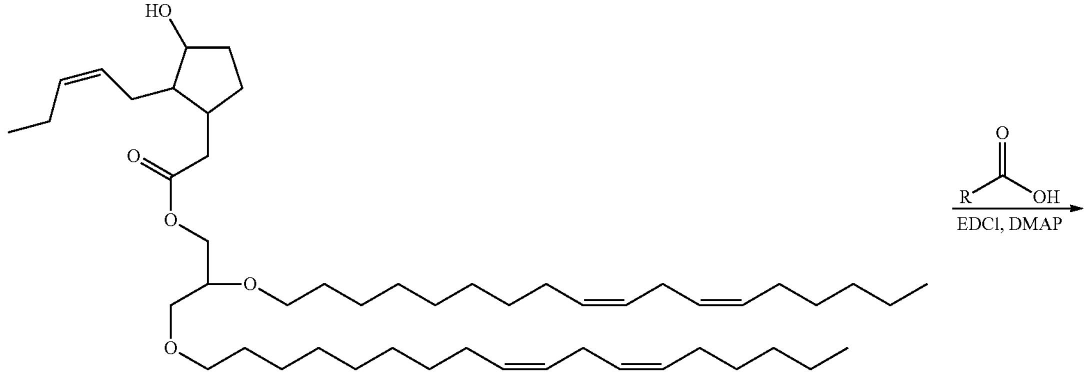
5

-continued
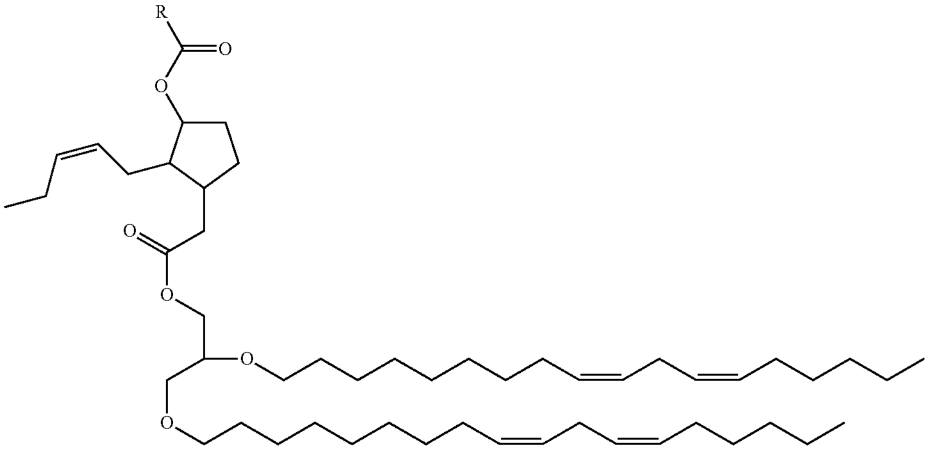
R =
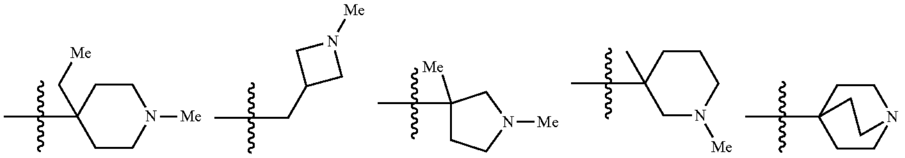
PNI 133 PNI 134 PNI 136 PNI 590 PNI 566
Scheme 23. Scheme for synthesis of PNI 599 and 600
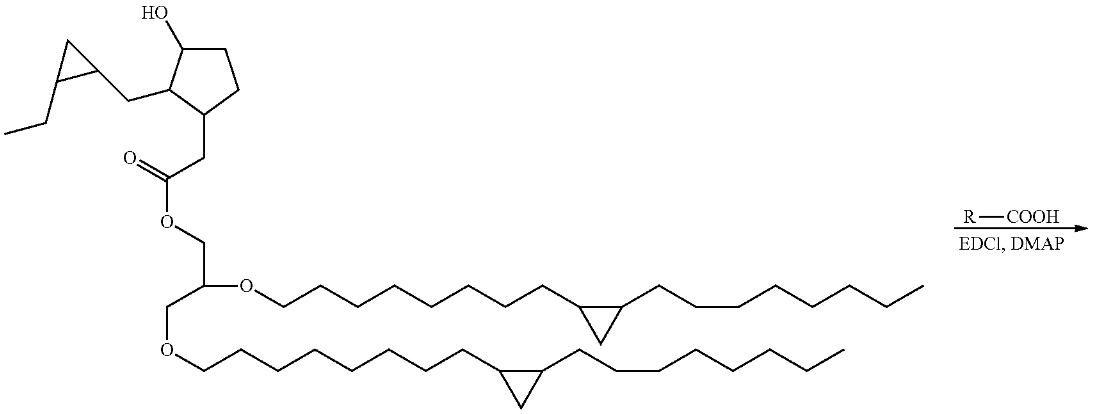
15
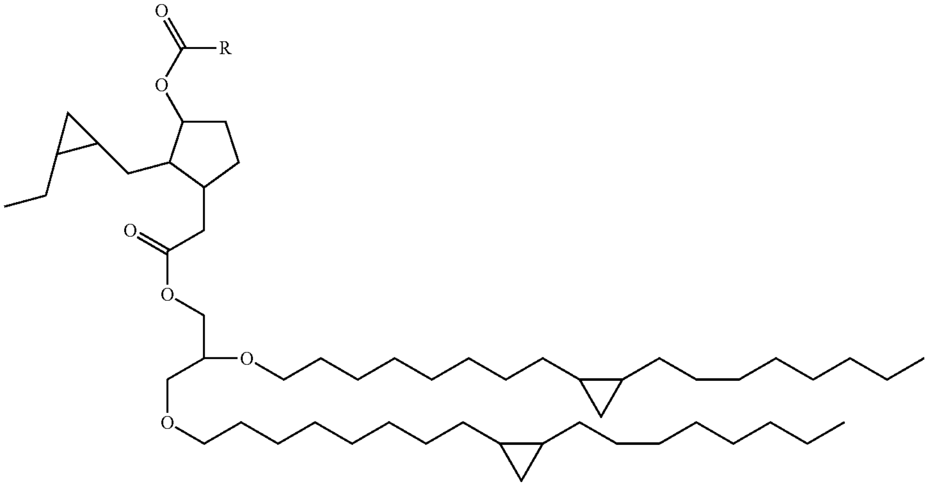

-continued

R =

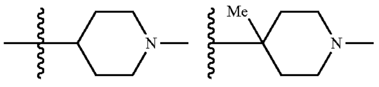

PNI 600 PNI 599

Scheme 24. Scheme for synthesis of PNI 587, 605 and 606

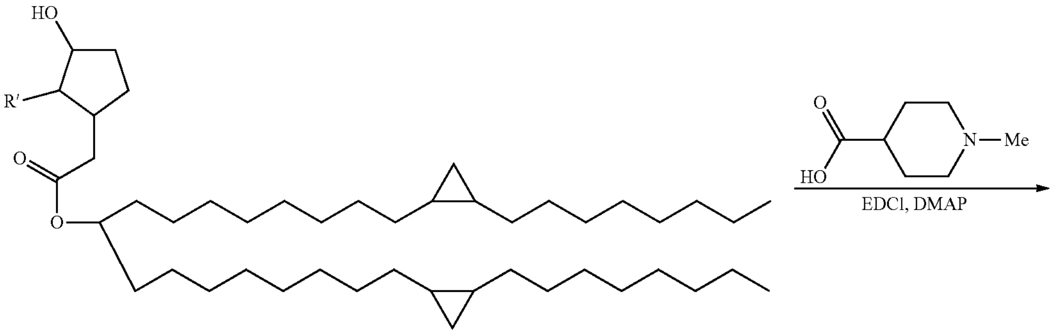

51

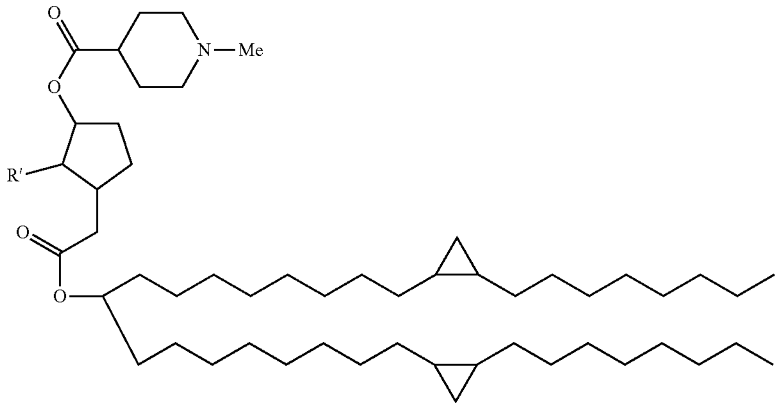

R =

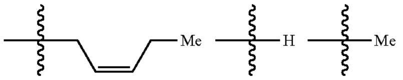

PNI 587 PNI 605 PNI 606

Example 14

Isolation of Primary T Cells From Human Whole Blood And Expansion

Unless otherwise noted, all reagents were purchased from STEMCELL Technologies, Vancouver, Canada.

Lyophilized human IL-2 was reconstituted to a concentration of 0.1 mg/mi in sterile 1× PBS without calcium or magnesium in a biological safety cabinet. Adding 50 μl of this human IL-2 to 50 mL of ImmunoCult-XF™ T Cell Expansion Medium generated the medium for T cells. 7-30 mL of Human Whole Peripheral Blood with ACD-A anticoagulant was placed in a sterile 50 mL polypropylene conical tube in a biological safety cabinet.

Negative Selection Protocol. Blood was drawn from healthy human donors and combined with ACD-A, an anticoagulant. A pan T cell negative selection kit, EasySep™ direct human T cell isolation kit was used to isolate both CD4+ and CD8+ T cells. The cells were maintained in ImmunoCult-XF™ T Cell Exp Medium supplemented with human recombinant IL2 (Peprotech). On the day of isolation, the cells were activated with a triple activator, ImmunoCult™ Human CD3/CD28/CD2 T Cell Activator.

Positive selection Protocol. Blood was drawn from healthy human donors and combined with ACD-A, an anticoagulant. A PBMC suspension was prepared using density gradient centrifugation through the use of Lymphoprep™. T cells were then positively selected from the PBMC suspension using EasySep™ Human CD3 Pos Selection Kit II. The cells were maintained in ImmunoCult-XF™ T Cell Exp Medium supplemented with human recombinant IL2 (Peprotech). On the day of isolation, the cells were activated with a triple activator, ImmunoCult™ Human CD3/CD28/CD2 T Cell Activator.

T cells were isolated from the blood using an EasySep™ Direct Human T Cell Isolation Kit. First 50 μl/mL of Isolation Cocktail™ and then 50 μl/mL of the EasySep™ RapidSpheres™ were added to the tube of blood. Blood was mixed gently and incubated at room temperature (RT) for 5 minutes. The tube was placed into an EasySep™ 50 Magnet™ apparatus and incubated at RT for 10 minutes. The enriched cell suspension was pipetted into a new sterile 50 mL polypropylene tube, and the RapidSpheres™ process repeated.

This doubly enriched cell suspension was pipetted into a new sterile 50 mL polypropylene conical tube and centrifuged for 10 min at 300 g at RT.

Supernatant was removed and the cell pellet was resuspended in 10 mL of PBS and respun at 300 g for 10 min to wash any remaining supernatant from the cells. The supernatant was again removed and the cells resuspended in pre-warmed complete T cell media. A sample was drawn, and a Trypan blue exclusion test of cell viability was performed (Thermo Fisher).

Example 15

Activation/Expansion of T Cells

The scientific background for activating T cells may be found in the 2003 paper by Trickett A. et al.[6] The cell suspension of Example 8 was diluted in Complete T Cell media (ThermoFisher) to 1E6 cells/ml, and the T cells activated by adding 25 μl of either ImmunoCult™ Human CD3/CD28/CD2 triple T Cell Activator™ or ImmunoCult™ Human CD3/CD28 dual T Cell Activator™ per mL of T cell media. Cell growth was monitored by a daily cell count under magnification. Cells were diluted with Complete T Cell media to maintain concentrations of about 1E6 cells/mL. On about day 5, 6 or 7, the T cells entered log phase of growth, and a rapid expansion occurred.

To confirm that the T cells were in log phase, CD25 expression was assessed and needed to be greater than 80% by flow cytometry (BD Biosciences) and the expansion of the cells were monitored by graphing the total number of T cells over time.

Downstream processing and analysis of treated T cells were done with flow cytometry and ELISA. Reagents were from Stemcell Technologies, Vancouver, Canada unless otherwise stated. T cells were isolated from a single donor. At 48H following LNP-mediated mRNA exposure, the treated T cells were harvested by transferring the cell suspensions to pre-labeled 1.5 mL tubes and centrifuged 300×G at 4 degrees C. for 10 minutes. Supernatant was removed and the pellet resuspended in PBS. An amount of 0.5 ul of BD Horizon™ Fixable Viability Stain 575V™ (BD Biosciences), was added, and the mixture incubated in the dark for 10 minutes at RT. This stain binds to intracellular amines of a permeable plasma cell membrane of a necrotic cell and can be used to differentiate a viable cell and a non-viable cell during a flow cytometry assay.

The cells were centrifuged again as before, then washed twice with 1 mL of Stain buffer (BSA, BD Pharminigen), and the washed pellet was placed in 100 μl BSA. The following antibodies were added to each tube of treated cells in 2 μl volumes: CD25, CD8, CD4, (PerCP-Cy™ 5.5 Mouse Anti Human CD25, BV786 Mouse Anti-Human CD8 Clone RPA-T8, and APC-Cy™7 Mouse Anti-Human CD4 Clone SK3, all from BD Pharmingen™) with the exception of the controls: in the eGFP only sample and viability control, no antibody was added. In the single stain compensation tubes, only one antibody per tube was added.

The tubes were incubated at 4 degrees C. for 30 min, whereupon 400 μl of stain buffer (BSA) was added, and the cells were centrifuged again. Cells were washed once with 1 mL of stain buffer and spun down again. Cell pellets were resuspended in 1 mL of stain buffer and added to pre-labeled flow tubes with cell strainer caps (Corning Falcon).

After transfection, flow cytometry was used to generate eGFP or EPO expression levels as well as MFI values for the studies.

Cryopreservation: If cells were cryopreserved for later use, blood was drawn from healthy human donors and combined with ACD-A, an anticoagulant. A pan T cell negative selection kit, EasySep Direct human T cell isolation kit was used to isolate both CD4+ and CD8+ T cells. Cells were cryopreserved using CryoStor® CS10 and stored in liquid nitrogen. At the time of thaw, cells were maintained in ImmunoCult-XF™ T Cell Exp Medium supplemented with human recombinant L2 (Peprotech). On the day of thaw, the cells were activated with a triple activator, ImmunoCUlt™ Human CD3/CD28/CD2 T Cell Activator.

Example 16

Microfluidic Mixing of Nucleic Acid Therapeutics (NAT) into Lipid Nanoparticles (LNP)

N/P 8 or 10 was used for all experiments unless otherwise noted. Lipid Mix composition (ionizable lipid/structural lipid/cholesterol/stabilizing agent) solutions were prepared in ethanol by combining prescribed amounts of lipids (see Table 3) from individual lipid stocks in ethanol. For the NanoAssemblr SPARK™, a lipid mix solution concentration of 37.5 mM was used, and for the NanoAssemblr® Benchtop or Ignite™, a lipid mix solution of 12.5 or 25 mM was typically used.

TABLE 3

Lipid Mix Compositions for Use with the IL of the Invention

| Identifier | Lipid Mix Compositions for Use with the IL of the Invention |
|---|---|
| Lipid mix A | 50 mol % IL/10 mol % DSPC/37.5 mol % Cholesterol/2.5 mol % Polyoxyethylene (40) stearate) |
| Lipid mix D | 40 mol % IL/40 mol % DOPE/17.5 mol % Cholesterol/2.5 mol % polyoxyethylene (40) stearate |
| Lipid mix G | 40 mol % IL/30 mol % DOPE/17 mol % Cholesterol/10 mol % Triglyceride/2.5 mol % polyoxyethylene (40) stearate |
| Lipid mix H | 40 mol % IL/20 mol % DOPE/17.5 mol % Cholesterol/20 mol % Triglyceride/2.5 mol % polyoxyethylene (40) stearate |
| Lipid mix J | 40 mol % IL/40 mol % DOPE/0 mol % Cholesterol/17.4 mol % Triglyceride/2.5 mol % polyoxyethylene (40) stearate |
| LM TBD | 40 mol % IL/20 mol % DOPE/37.5 mol % Cholesterol/2.5 mol % Tridecyl-D-maltoside |
| LM T20 | 40 mol % IL/20 mol % DOPE/37.5 mol % Cholesterol/2.5 mol % Tween 20 |
| LM T80 | 40 mol % IL/20 mol % DOPE/37.5 mol % Cholesterol/2.5 mol % Polysorbate 80 |
| Lipid Mix K | 40 mol % IL/20 mol % DOPE/37.5 mol % Cholesterol/2.5 mol % Lipid H |
| Lipid Mix L | 40 mol % IL/20 mol % DOPE/35.9 mol % Cholesterol/4 mol % Lipid H |
| LM02 | 50 mol % IL/10 mol % DSPC/38.5 mol % Cholesterol/1.5 mol % PEG-DMG |
| LM02b | 50 mol % IL/10 mol % DOPE/38.5 mol % Cholesterol/1.5 mol % PEG-DMG 2000 |
| LM02c | 50 mol % IL/10 mol % DSPC/38.5 mol % Cholesterol/1.5 mol % PEG-DMG 2000 |
| LMV1 | 47.5 mol % IL/12.5 mol % DOPE/38.5 mol % Cholesterol/1.5 mol % PEG-DMG 2000 |
| LMV2 | 47.5 mol % IL/12.5 mol % DSPC/38.5 mol % Cholesterol/1.5 mol % PEG-DMG 2000 |
| S9 | 50 mol % IL/10 mol % DSPC/37.5 mol % Cholesterol/2.5 mol % BRIJ ™ S20 |
| S10 | 50 mol % IL/10 mol % DSPC/40 mol % Cholesterol/2.5 mol % TPGS1000 |

TABLE 3-continued

| Lipid Mix Compositions for Use with the IL of the Invention | |
|---|---|
| Identifier | Lipid Mix Compositions for Use with the IL of the Invention |
| S11 | 50 mol % IL/10 mol % DSPC/37.5 mol % Cholesterol/2.5 mol % BRIJ ™S10 |
| S11C | 50 mol % IL/10 mol % DSPC/38.5 mol % Cholesterol/1.5 mol % BRIJ ™S10 |
| S12 | 50 mol % IL/10 mol % DSPC/37.5 mol % Cholesterol/2.5 mol % BRIJ ™ L4 |
| CT7 | 50 mol % IL/10 mol % DSPC/38.5 mol % Cholesterol/1.5 mol % Polysorbate 80 |
| CT7C | 50 mol % IL/10 mol % DSPC /37.5 mol % Cholesterol/2.5 mol % Polysorbate 80 |
| CT7B | 50 mol % IL/10 mol % DSPC/39.5 mol % Cholesterol/0.5 mol % Polysorbate 80 |
| CT10 | 40 mol % IL/20 mol % DSPC/37.5 mol % Cholesterol/2.5 mol % BRIJ ™ S10 |
| CT14 | 40 mol % IL/20 mol % DSPC/39.5 mol % Cholesterol/0.5 mol % TPGS1000 |
| CT15 | 40 mol % IL/20 mol % DSPC/39.5 mol % Cholesterol/0.5 mol % BRIJ ™S10 |
| CT22 | 40 mol % IL/20 mol % DSPC/38.5 mol % Cholesterol/1.5 mol % Polysorbate 80 |
| CT34 | 40 mol % IL/20 mol % DSPC/39.5 mol % Cholesterol/0.5 mol % BRIJ ™ S20 |
| C12-200 | 50 mol % C12-200/10 mol % DSPC/38.5 mol % Cholesterol/1.5 mol % PEG-DMG |

IL = ionizable lipid;
Tween80 = Polysorbate 80;
BRIJ ™ L4 = Polyoxyethylene (4) lauryl ether;
BRIJ ™ S10 = Polyoxyethylene (10) stearyl ether;
BRIJ ™ S20= Polyoxyethylene (20) stearyl ether;
BRIJ ™ S35 = Polyoxyethylene (23) lauryl ether;
TPGS 1000 = D-α-Tocopherol polyethylene glycol 1000 succinate;
Lipid H =Tween 20/Polysorbate 80/Tridecyl-D-maltoside in equal ratios;
Stabilizing Agent = any stabilizing agent including PEG-DMG or as defined in the Description supra under that category.

Components of the Lipid Mixes include the ionizable lipid, structural lipid, cholesterol and stabilizing agent. Low pH buffers (3-6) may be used. For ionizable aminolipids, the pH of the buffer is typically below the pKa of the lipid.

siRNA, Messenger RNA or plasmid NAT preparation is described below. Observed particle attributes were generally sized from 50-200 nm for mRNA, depending on lipid composition.

Lipid particles were also manufactured by a larger microfluidic mixer instrument, the NanoAssemblr® Ignite™ for testing. Briefly, 350 μL of mRNA was diluted using 100 mM sodium acetate buffer to the required concentration of 0.2 to 0.3 mg/mL. Lipid particle samples were then prepared by running both fluids, namely, nucleic acids in aqueous solvent and Lipid Mix in ethanol at a flow ratio of 3:1 and at a total flow rate of 12 ml/min in the microfluidic mixer. Following mixing in the microfluidic device, the post cartridge lipid nucleic acid particle sample was diluted into RNAse free tubes containing three to 40 volumes of phosphate buffered saline (PBS), pH 7.4. Ethanol was finally removed through dialysis in PBS, pH 7, or using Amicon™ centrifugal filters (Millipore, USA) at 3000 RPM, or using TFF systems. Once the required concentration was achieved, the lipid nucleic acid particles were filter sterilized using 0.2 μm filters in aseptic conditions. Final encapsulation efficiency was measured by the Ribogreen™ assay. Quant-iT™ RiboGreen® RNA Reagent and Kit (Invitrogen) following manufacturer directions.

Nucleic Acid Reagents

Messenger RNA or plasmid nucleic acid therapeutic (NAT) as described below, was diluted using sodium acetate buffer to the required concentration. Lipid nucleic acid particle (LNAP) samples were then prepared by running both fluids using the NanoAssemblr® Spark instrument. Briefly, 10-20 pg of nucleic acids in 100 mM sodium acetate buffer in a total volume of 32 μL was mixed with 16 μL of 37.5 mM lipid mix solution as required by the N/P ratios (4, 6, or 10 in illustrated examples). The microfluidically mixed lipid nucleic acid particles (LNAP) made in the instrument were immediately diluted down with 48 μL Ca++ and Mg++ free 1× PBS at pH 7.4 in the aqueous output well. These LNAP were immediately collected into microcentrifuge tubes containing 96 μL of the same buffer at pH 7.4. Encapsulation efficiency was measured by a modified Ribogreen™ assay (Quanti-iT RiboGreen™ RNA assay kit, Fisher). This information was used to establish the desired dosage.

The nucleic acid therapeutic model reagents used in the following experiments are described below. Trilink Cleancap® eGFP mRNA: Cat. L-7601 (Trilink Biotechnologies, San Diego, CA); Trilink Cleancap® EPO mRNA: Cat. L-7209 (Trilink); Millipore Sigma TagRFP Simplicon RNA Kit: Cat. SCR712 (contains both TagRFP RNA & B18R RNA) (Millipore Sigma Canada, Oakville Ontario); CD19 CAR plasmid with an EGFP reporter was purchased from Creative Biolabs (Shirley, NY) and contains a T7 promoter (Mut)-signal peptide-scFv-CD8 hinge transmembrane-4-1 BB-CD3zeta-T2A-eGFP reporter gene CAR cassette (2353 bp) within the pcDNA. The total size of this CD19 CAR plasmid DNA template is around 7649-7661 bp.

An unmodified CAR messenger RNA (mRNA) transcript encoding the CD19 scFv-h (BB±-eGFP reporter gene cassette was synthesized by in vitro transcription with wild-type bases and capped (Cap 1) using CleanCap® AG methodology by Trilink Biotechnologies Inc. This unmodified CAR mRNA transcript was enzymatically polyadenylated followed by a DNase and Phosphatase treatment. The final mRNA transcript product was silica membrane purified and packaged in a solution of 1 mM Sodium Citrate buffer (pH 6.4) at concentration of 1 mg/mL. This custom CD19 CAR plasmid vector and CD19 CAR encoding mRNA were purchased from Creative Biolab and Trilink Biotechnologies Inc respectively.

OVA antigen has utility in vaccine research as it has been used as a model antigen to stimulate immune response[9]. (Usually OVA antigen is used with a sensitizing agent such as Alum, but when OVA antigen is delivered in the mRNA form, the hypothesis is that sensitizing agents such as Alum are not needed, and mRNA itself is able to produce the response to the antigen by the immune cells. CleanCap® OVA mRNA L-7610 and CleanCap® OVA mRNA (5 moU) L-7210, both from TriLink Biotechnologies, were used in these studies.

Example 17

Lipid Nucleic Acid Particle or "LNP" Characterization and Encapsulation

After the lipid particles were made as described in Example 17, particle size (hydrodynamic diameter of the particles) was determined by Dynamic Light Scattering (DLS) using a ZetaSizer™ Nano ZS™ (Malvern Instruments, UK). He/Ne laser of 633 nm wavelength was used as the light source. Data were measured from the scattered intensity data conducted in backscattering detection mode (measurement angle=173). Measurements were an average of 10 runs of two cycles each per sample. Z-Average size was reported as the particle size, and is defined as the harmonic intensity averaged particle diameter. These LNP characteristics, as well as the results of the mRNA encapsulation efficiency for various Lipid Mixes are also described in the application are shown in Tables 4, 5 and 6. There was good encapsulation in all the formulations, with polydispersity (PDI) under 0.3.

TABLE 4

| PNI Lipid ID | Diameter (Z. ave, nm) | Polydispersity Index (PDI) | Encapsulation Efficiency (%) |
|---|---|---|---|
| MC3 | 77.2 | 0.07 | 88.6 |
| PNI101 | 74.10 | 0.156 | 93.0 |
| PNI123 | 124.7 | 0.054 | 60.1 |
| PNI 128 | 61.7 | 0.09 | 88.2 |
| PNI 132 | 74.5 | 0.06 | 98.2 |
| PNI 516 | 68.5 | 0.12 | 98.7 |
| PNI 542 | 79.4 | 0.04 | 98.8 |
| PNI 544 | 51.3 | 0.04 | 97.9 |
| PNI 545 | 63.9 | 0.07 | 98.4 |
| PNI 546 | 64.0 | 0.03 | 96.3 |
| PNI 549 | 71.2 | 0.05 | 96.4 |
| PNI 554 | 55.1 | 0.06 | 96.6 |
| PNI 557 | 95.4 | 0.02 | 98.7 |
| PNI 558 | 91.2 | 0.07 | 98.7 |
| PNI 559 | 59.4 | 0.07 | 95.9 |
| PNI 560 | 60.5 | 0.06 | 98.4 |
| PNI 565 | 69.9 | 0.03 | 97.4 |

TABLE 5

Size, PDI and encapsulation efficiency of 5-moU EPO encoded LNPs comprising various synthesized ionizable lipids manufactured using the NanoAssemblr ® platform. IL:DSPC:cholesterol:DMG-PEG (50:10:38.5:1.5) with an N/P ratio of 6 was used.

| Lipid ID | Payload | Diameter (Z. ave, nm) | Polydispersity Index (PDI) | Encapsulation Efficiency (%) |
|---|---|---|---|---|
| MC3 | 5-moU EPO | 65.1 | 0.04 | 98.8 |
| PNI 101 | 5-moU EPO | 97.7 | 0.08 | 93.4 |
| PNI 123 | 5-moU EPO | 76.6 | 0.04 | 97.3 |
| PNI 128 | 5-moU EPO | 64.8 | 0.04 | 97.1 |
| PNI 132 | 5-moU EPO | 70.3 | 0.04 | 98.2 |
| PNI 143 | 5-moU EPO | 88.0 | 0.87 | 98.7 |
| PNI 516 | 5-moU EPO | 69.0 | 0.02 | 98.7 |
| PNI 542 | 5-moU EPO | 68.5 | 0.02 | 98.7 |
| PNI 543 | 5-moU EPO | 73.6 | 0.14 | 98.7 |
| PNI 544 | 5-moU EPO | 62.3 | 0.05 | 97.6 |
| PNI 545 | 5-moU EPO | 59.0 | 0.04 | 98.6 |
| PNI 546 | 5-moU EPO | 56.9 | 0.09 | 96.3 |
| PNI 549 | 5-moU EPO | 62.5 | 0.06 | 97.4 |
| PNI 554 | 5-moU EPO | 55.4 | 0.09 | 97.5 |
| PNI 557 | 5-moU EPO | 71.8 | 0.08 | 98.9 |
| PNI 558 | 5-moU EPO | 73.2 | 0.03 | 98.9 |
| PNI 559 | 5-moU EPO | 64.6 | 0.03 | 97.3 |
| PNI 560 | 5-moU EPO | 63.1 | 0.06 | 98.7 |
| PNI 565 | 5-moU EPO | 60.8 | 0.03 | 97.9 |

TABLE 6

Size, PDI and encapsulation efficiency of OVA encoded LNPs comprising various synthesized ionizable lipids manufactured using NanoAssemblr ® platform. LM02 with N/P ratio of 8 was used.

| Lipid ID | Payload | Diameter (Z. ave, nm) | Polydispersity Index (PDI) | Encapsulation Efficiency (%) |
|---|---|---|---|---|
| MC3 | 5-moU OVA | 65.8 | 0.07 | 95.2 |
| ID 516 | 5-moU OVA | 76.5 | 0.04 | 98.2 |
| MC3 | WT OVA | 67.5 | 0.03 | 95.4 |
| ID 516 | WT OVA | 75.9 | 0.02 | 98.6 |
| ID 101 | WT OVA | 93.2 | 0.09 | 98.4 |
| ID 123 | WT OVA | 96.5 | 0.03 | 76.1 |
| ID 128 | WT OVA | 74.9 | 0.02 | 97.0 |

TABLE 6-continued

Size, PDI and encapsulation efficiency of OVA encoded LNPs comprising various synthesized ionizable lipids manufactured using NanoAssemblr ® platform. LM02 with N/P ratio of 8 was used.

| Lipid ID | Payload | Diameter (Z. ave, nm) | Polydispersity Index (PDI) | Encapsulation Efficiency (%) |
|---|---|---|---|---|
| ID 132 | WT OVA | 82.6 | 0.07 | 97.1 |
| ID 539 | WT OVA | 80.4 | 0.07 | 96.9 |
| ID 540 | WT OVA | 73.4 | 0.04 | 96.7 |
| ID 542 | WT OVA | 74.6 | 0.01 | 98.7 |
| ID 560 | WT OVA | 76.7 | 0.05 | 97.7 |

Example 18

Downstream Processing and Analysis of Treated T Cells with Flow Cytometry

Three isolations of T cells were taken from a single donor and divided into three groups: Pan T cells (all T cells), CD4+ T cells alone, CD8+ T cells alone. 48H following lipid particle mRNA exposure, the treated T cells were harvested by transferring the cell suspensions to pre-labeled 1.5 mL tubes and centrifuged 300×g at 4 degrees Celsius for 10 minutes. Supernatant was removed and the pellet resuspended in PBS. An amount of 0.5 ul of BD Horizon™ Fixable Viability Stain 575V™ (BD Biosciences), was added, and the mixture incubated in the dark for 10 minutes at RT. This stain binds to amines.

The cells were centrifuged again as before, then washed twice with 1 mL of Stain buffer (BSA, BD Pharminigen), and the washed pellet placed in 100 μl BSA. The following antibodies were added to each tube of treated cells in 2 μl volumes: CD25, CD8, CD4, (PerCP-Cy™ 5.5 Mouse Anti Human CD25, BV786 Mouse Anti-Human CD8 Clone RPA-T8, APC-Cy™7 Mouse Anti-Human CD4 Clone SK3, all from BD Pharmingen™) with the exception of the controls: in the GFP only sample and viability control, no antibody was added, while in the single stain compensation tubes, only one antibody per tube was added.

The tubes were incubated at 4 degrees C. for 30 min, whereupon 400 μl of stain buffer (BSA) was added, and the cells were centrifuged again. Cells were washed once with 1 mL of stain buffer and spun down again. Cell pellets were resuspended in 1 mL of stain buffer and added to pre-labeled flow tubes with cell strainer caps (Corning Falcon).

Negative Selection Protocol. Reagents are from Stemcell Technologies, Vancouver, Canada unless otherwise stated. Blood was drawn from healthy human donors and combined with ACD-A, an anticoagulant. A pan T cell negative selection kit, EasySep™ direct human T cell isolation kit was used to isolate both CD4+ and CD8+ T cells. The cells were maintained in ImmunoCult-XF™ T Cell Exp Medium supplemented with human recombinant IL2 (Peprotech). On the day of isolation, the cells were activated with a triple activator, ImmunoCult™ Human CD3/CD28/CD2 T Cell Activator.

Freezing and Thawing of Human T cells. Reagents are from Stemcell Technologies, Vancouver, Canada unless otherwise stated. Blood was drawn from healthy human donors and combined with ACD-A, an anticoagulant. A pan T cell negative selection kit, EasySep Direct human T cell isolation kit was used to isolate both CD4+ and CD8+ T cells. Cells were cryopreserved using CryoStor® CS10 (StemCell Technologies) and stored in liquid nitrogen. At the time of thaw, cells were maintained in ImmunoCult-XF™ T Cell Exp Medium supplemented with human recombinant IL2 (Peprotech). On the day of thaw, the cells were activated with a triple activator, ImmunoCult™ Human CD3/CD28/CD2 T Cell Activator.

Positive selection Protocol. Blood was drawn from healthy human donors and combined with ACD-A, an anticoagulant. A PBMC suspension was prepared using density gradient centrifugation through the use of Lymphoprep™ reagent. T cells were then positively selected from the PBMC suspension using EasySep™ Human CD3 Pos Selection Kit II. The cells were maintained in ImmunoCult-XF™ T Cell Exp Medium supplemented with human recombinant IL2 (Peprotech). On the day of isolation, the cells were activated with a triple activator, ImmunoCult™ Human CD3/CD28/CD2.

After transfection, flow cytometry was used to general GFP expression levels as well as MFI values for the studies.

Example 19

Comparative Data Showing Activity with GFP mRNA LNPs in Primary Human T Cells Ionizable lipids of the invention, and MC3, were compared in a composition of CT10 at an N/P ratio of 10 for their ability to induce transfection as measured by MFI of labeled mRNA in T cells (as measured by flow cytometry).

T Cells were prepared and treated as previously described using negative selection and the triple activation protocol.

In order to expose the isolated and activated T cells (Day 0) to the formulated mRNA, 2 ug of CleanCap™ EGFP (Trilink Biotechnologies, San Diego, CA), mRNA-containing LNP was added to 500,000 T cells in 1 mL of complete T cell media, with 1 μg/mL of Recombinant Human ApoE4 ("ApoE") (Peprotech Inc., Montreal, Canada).

The dose of mRNA LNP was calculated based upon Ribogreen™ assay results. T cells were counted through Trypan blue (Sigma) exclusion and diluted to 500,000 cells/mL. Briefly, in a 12 well plate, 1 mL was aliquoted into each well. ApoE was added to a final concentration of 1 μg/mL in each well. Based upon the calibration, the required amount of mRNA LNP was added (day 3 to 7), and the plate incubated for 48 hours.

The effect on transfection efficiency of mRNA LNP made with different ionizable lipids: DODMA, MC3 and PNI101, in CT10 composition (see Table 3) at an N/P ratio of 10 was assessed. Cells were treated with LNP 7 days post activation. Results are shown in FIG. 1. ID101 was found to have greater transfection efficiency than either DODMA or MC3.

Figure 2:
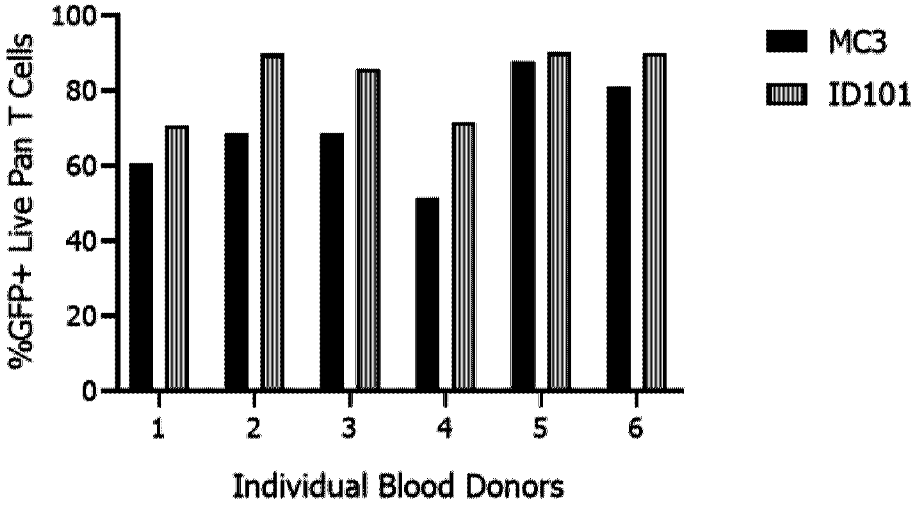
FIG. 2 is a graph illustrating GFP expression in isolated primary human T cells from six individual donors mediated by mRNA-LNPs containing ionizable lipid DLin-MC3-DMA or PNI lipid 101 in a CT10 composition, and with a N/P ratio of 10. Transfection efficiency and MFI were measured by flow cytometry 48 hours after T cells were dosed with 500 ng of encapsulated mRNA per 125,000 cells in LNPs 7 days after T cell activation.

In a related experiment using the same composition and NP ratio, gene expression was analyzed by flow cytometry 48 h after treatment in T cells from different donors, and the results are shown in FIG. 2. It was found that the transfection efficiency of LNPs containing ID101 was greater than those containing MC3 in six tested donors. Cell viability for the same experiment is not shown but was unaffected by treatment with ID101 as compared to untreated cells (control).

Figure 3:
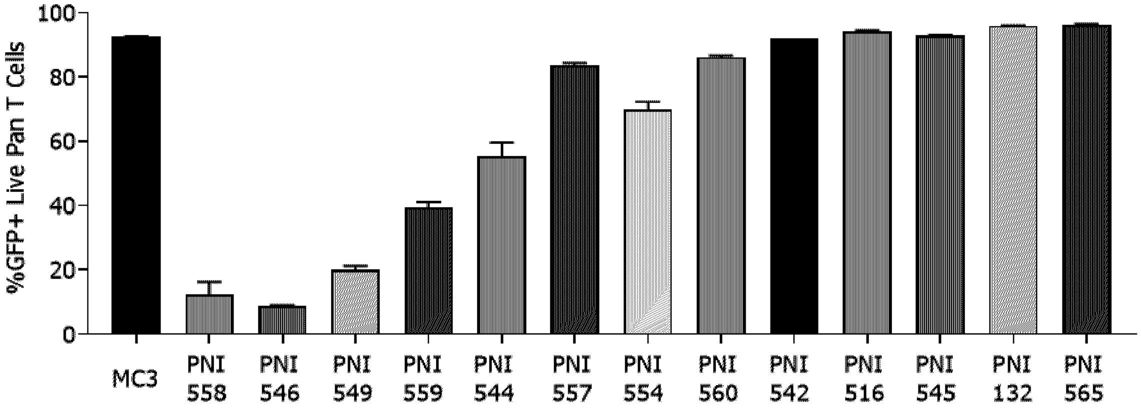
FIG. 3 shows two bar graphs illustrating GFP expression in isolated primary human T cells mediated by mRNA-LNPs containing ionizable lipid MC3, or each of several novel ionizable lipid PNI Lipids, using CT10 composition and an N/P ratio of 8, treatment 3 days post activation. Transfection efficiency (upper) and MFI (lower) were measured by flow cytometry 48 h after LNP addition.
Figure 3:
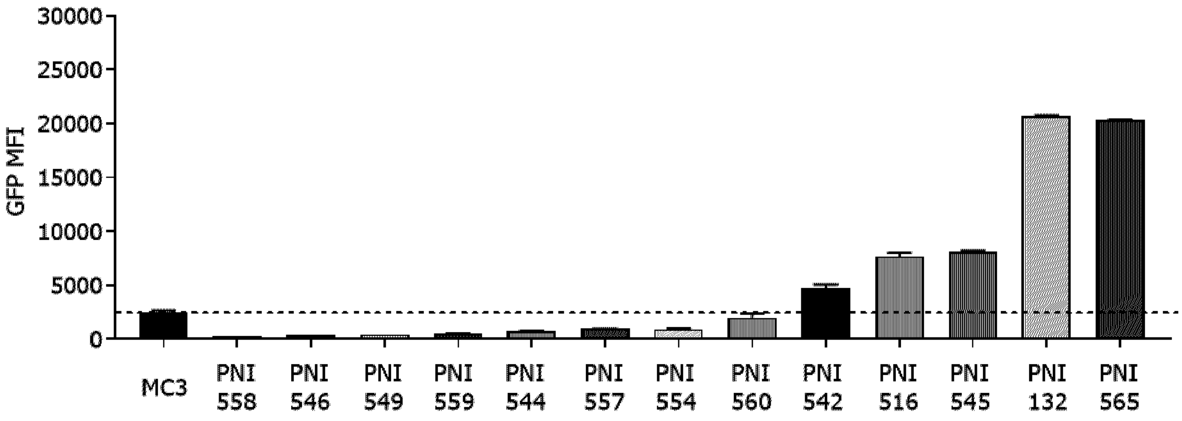

A wider variety of the ionizable lipids according to the invention were tested in live T cells at a dose of 500 ng, using MC3 as control. The CT10 composition was used. Percent positive for GFP live T cells were assayed as well as GFP MFI. Results are shown in the two tables in FIG. 3. A number of the new ionizable lipids were substantially as good or better than MC3 at transfecting T cells in vitro, particularly ID 132 and ID 565 in the more quantitative Mean Fluorescence Intensity (MFI) measurement.

Example 20

Prior Cryopreservation Has No Effect

Figure 4:
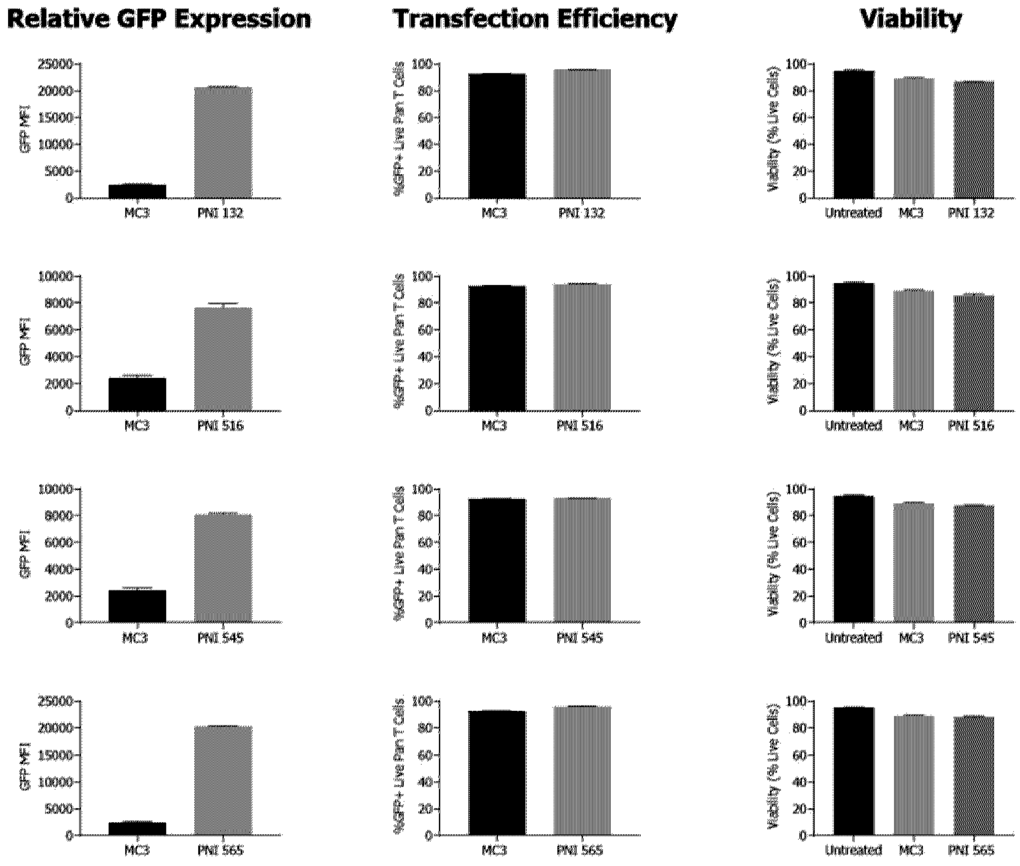
FIG. 4 is a bar graph showing GFP expression in isolated primary human previously cryopreserved T cells mediated 4 days after activation with 500 ng of encapsulated mRNA per 125,000 cells by mRNA-LNPs containing either DLin-MC3-DMA, PNI lipid 132, PNI lipid 516, PNI lipid 545, or PNI lipid 565, with CT10 composition, with N/P of 8. GFP MFI (first column), transfection efficiency (middle column), and viability (third column) were measured by flow cytometry 48 hours after LNP addition.

GFP expression in isolated primary human T cells subjected to freeze and thaw was investigated. Tested were mRNA-LNPs containing either MC3, PNI lipid 132, PNI lipid 516, PNI lipid 545, or PNI lipid 565, in a CT10 composition at N/P 8. T cells had been isolated from whole blood using the negative isolation procedure and cryopreserved in liquid nitrogen. Prior to addition of LNPs, these T cells were thawed and allowed to rest on ImmunoCult™ T Cell Expansion Media for 24 hours activation as elsewhere described. Transfection efficiency, viability and GFP MFI were measured by flow cytometry 48 hours after LNP addition. T cells were treated 4 days after activation with 500 ng of encapsulated mRNA per 125,000 cells. The results of the study are shown in FIG. 4, showing that all four ionizable lipids tested worked better than MC3 in total GFP expression (MFI), and generally equally in transfection efficiency, and in vitro toxicity (viability).

Example 21

Erythropoietin mRNA Delivery and Expression

Figure 5:
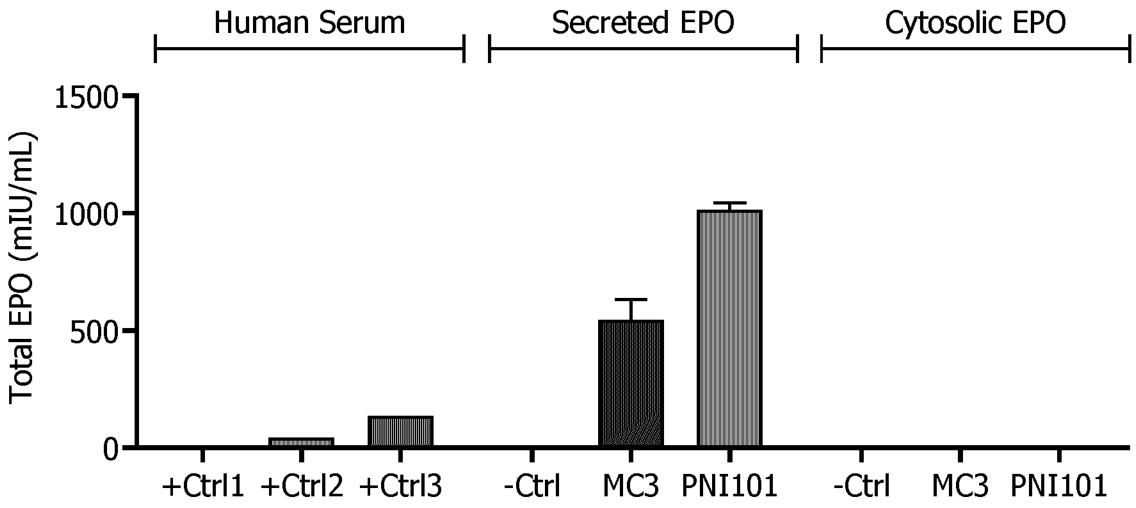
FIG. 5 is a bar graph illustrating expression levels of secreted and cytosolic recombinant human erythropoietin (EPO) determined by ELISA following mRNA LNP mediated transfection of CD4+/CD8+ T cells. Control was normal human sera standards provided by the manufacturer.

The Quantikine® IVD Human Epo ELISA double-antibody sandwich assay was used to demonstrate hEPO mRNA delivery and activity in vitro. Reagents were acquired from Quantikine, Minneapolis, MN. The assay was performed as directed on the Quantikine® IVD® ELISA Human Erythropoietin Immunoassay protocol in the package insert. Briefly; primary human T cells were isolated from fresh whole blood using a negative selection protocol and activated using a triple activator. Seven days post-activation, T cells were dosed with mRNA LNPs encoding EPO at 2 pg mRNA per 500,000 cells and N/P 10. After 48 h of exposure, the T cells were harvested and lysed for cytosolic EPO and media supernatant was sampled for secreted EPO. Quantikine® Human Serum Controls were used. The results are shown in FIG. 5 in mIU/mL. Control sera shows minimal or no EPO, MC3 EPO mRNA LNP treated T cells show about 545 mIU/mL secreted and no cytosolic EPO, and PNI 101 EPO mRNA LNP treated T cells show about 1016 mIU/mL secreted EPO and no cytosolic EPO.

Table 7 below includes the quantitative data for MC3 and PNI 101 for EPO concentration at 48 hours in primary human T cells, as well as the fold increase in EPO concentration relative for PNI 101 versus MC3 LNP. It was found that EPO expression mediated by LNPs containing PNI 101 was higher than those containing MC3.

TABLE 7
| Compound ID | EPO concentration (mIU/mL), 48 hours | Fold increase in EPO concentration relative to MC3 | Structure |
|---|---|---|---|
| MC3 | 545.2 | 1.0 | 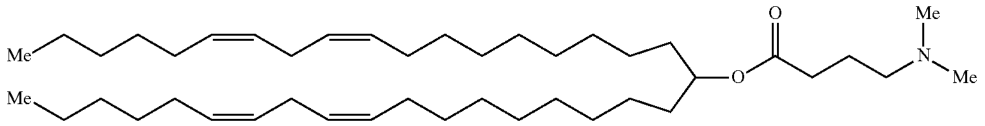 [SMILES: CCCCC/C=C\C/C=C\CCCCCCCCC(CCCCCCCC/C=C\C/C=C\CCCCC)OC(=O)CCCN(C)C] |
| PNI 101 | 1016.0 | 1.87 | 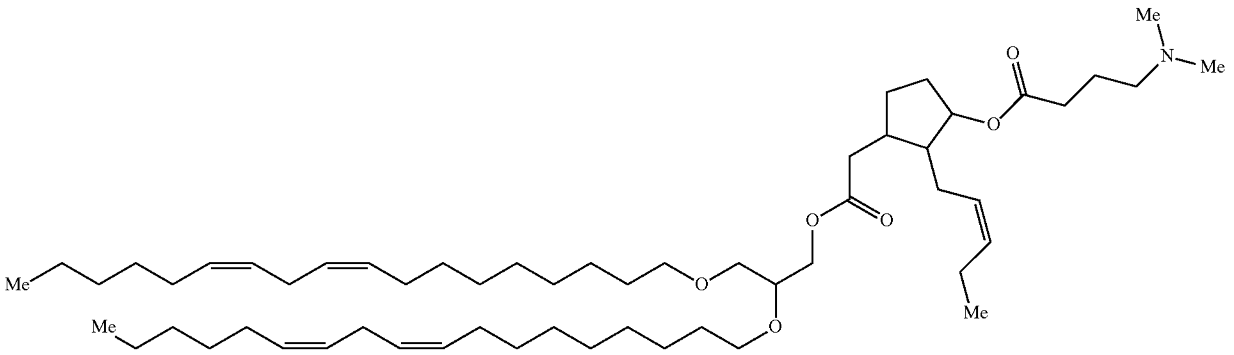 [SMILES: CC/C=C\CC1C(CC(=O)OCC(COCCCCCCCC/C=C\C/C=C\CCCCC)OCCCCCCCC/C=C\C/C=C\CCCCC)CCC1OC(=O)CCCN(C)C] |

Example 22

In Vivo Delivery Of EPO-Encoded mRNA LNP Via Intravenous Route

Lipid Nanoparticles with the composition IL/DSPC/Cholesterol/PEG-DMG2000 (LM 02—see Table 3) were used to encapsulate recombinant human erythropoietin (EPO) encoded mRNA with 5-moU modifications [TriLink CleanCapo 5-moU EPO mRNA L7201]. To create the LNP, lipid mix in ethanol was microfluidically mixed with a low PH buffered solution of 5-moU EPO mRNA mixer at an N/P ratio of 6 using a NanoAssemblr® Ignite™ microfluidic mixer. The microfluidically mixed particles were downstream processed using Amicon® ultra 15 10 kDa MWCO units (EMD Millipore) filtration technique. The RNA loaded lipid particles were then characterized for size, PDI and Encapsulation Efficiency (EE). Size and PDI were measured using dynamic light scattering techniques described above, and nucleic acid encapsulation efficiency was calculated using a Quant-iT RiboGreen RNA assay as described supra, modified to use hEPO mNA as the standard instead if the standard RNA in the kit. The hydrodynamic diameter of these mRNA-LNPs was ~70 nm with a PDI in the range of 0.02 to 0.1 and an encapsulation efficiency of ~97.8%.

Animals were handled according to the Institutional Animal Care and Use Committee ethics protocols. For experiments, 6-8 week old $C_{57}$BL/6 mice were purchased from Envigo (South Kent, WA, USA). For in vivo activity, female $C_{57}$BL/6 mice were treated intravenously with EPO mRNA LNPs at specified dosages of 0.5-3 mg/Kg. Samples of 50-75 μL of blood were collected 6 h post administration via saphenous vein, and at regular time intervals of 24 h or 48 h.

After harvest, blood was immediately prepared to produce serum samples using standard techniques, and stored at −80 degrees C. Briefly, after collection, the blood was allowed to clot at room temperature for 15-30 minutes. The clot was removed by centrifuging the tubes at 1000-2000×g for 10 min at 4 degrees Celsius. The clear golden-yellow color supernatant was carefully removed and transferred to sterile screw-capped clear polypropylene tubes on ice. The serum was then stored, if necessary, at −80° C. until analysis.

Samples were thawed, then analyzed at appropriate dilutions for EPO protein expression and for cytokine/chemokine levels. The total serum EPO levels were evaluated using Quantikine® IVD EPO ELISA kit (Bio-Techne, Minneapolis, MN, USA).

Figure 6:
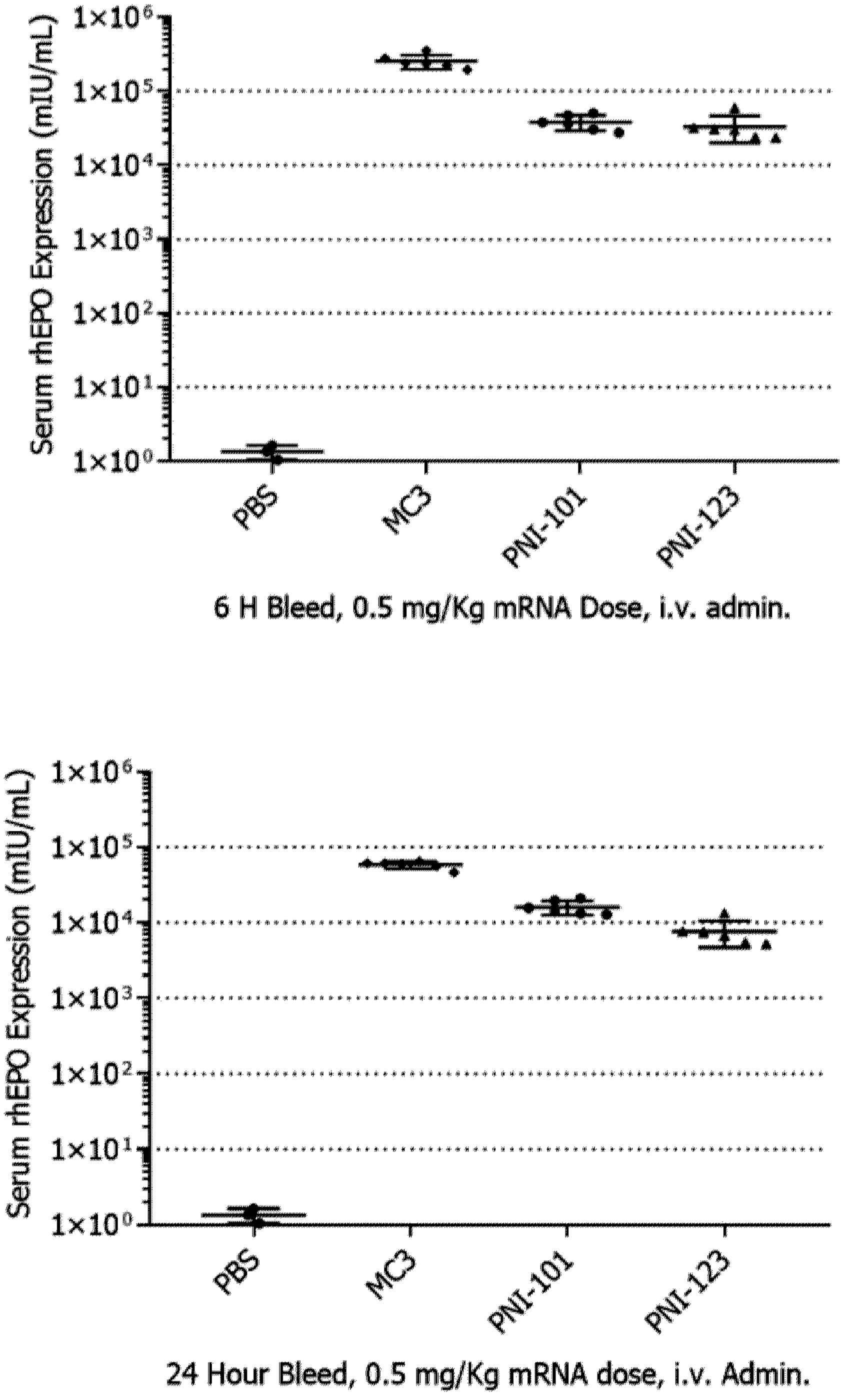
FIG. 6 shows EPO expression levels 6 h (upper) and 24 h (lower) in C56BL/6 mice following i.v administration of 0.5 mg/Kg dose of recombinant human EPO-encoded mRNA LNPs containing ionizable lipids MC3, PNI-101 and PNI 123 using the composition IL/DSPC/Cholesterol/PEG-DMG (50:10:38.5:1.5 mol %) at N/P 6.

Following i.v administration of a 0.5 mg/Kg dose of recombinant human EPO-encoded mRNA LNPs containing ionizable lipid MC3, PNI 121 or PNI 123 using the LM02 composition at N/P 6, EPO expression levels at 6 h (upper, FIG. 6) and at 24 h (lower, FIG. 6) in C56BL/6 mice were examined; hEPO protein was measured using Quantikine® IVD® ELISA Human Erythropoietin Immunoassay protocol.

Figure 7:
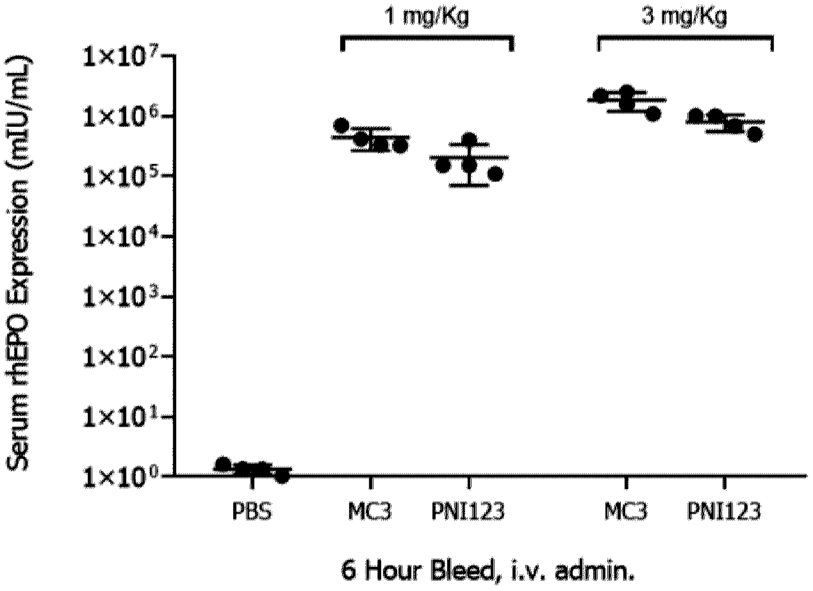
FIG. 7 shows EPO expression levels 6 h (upper) and 24 h (lower) in C56BL/6 mice following i.v administration of 1 or 3 mg/Kg dose of recombinant human EPO-encoded mRNA LNPs containing ionizable lipids DLin-MC3-DMA and PNI 123 using the composition IL/DSPC/Cholesterol/PEG-DMG (50:10:38.5:1.5 mol %) at N/P 6.
Figure 7:
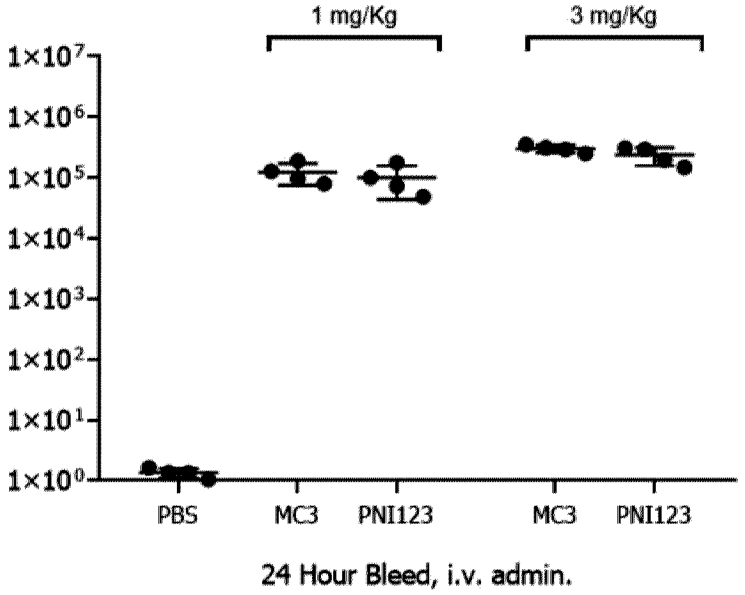

Results for the many of the same parameters except at 1 and 3 mg/Kg doses of recombinant human EPO-encoded mRNA LNPs are shown In FIG. 7. The different points on the graph represent different mice. In these tests, PNI 123 LNP performed very well against MC3 LNP for delivering hEPO and expressing hEPO in vivo.

Figure 8:
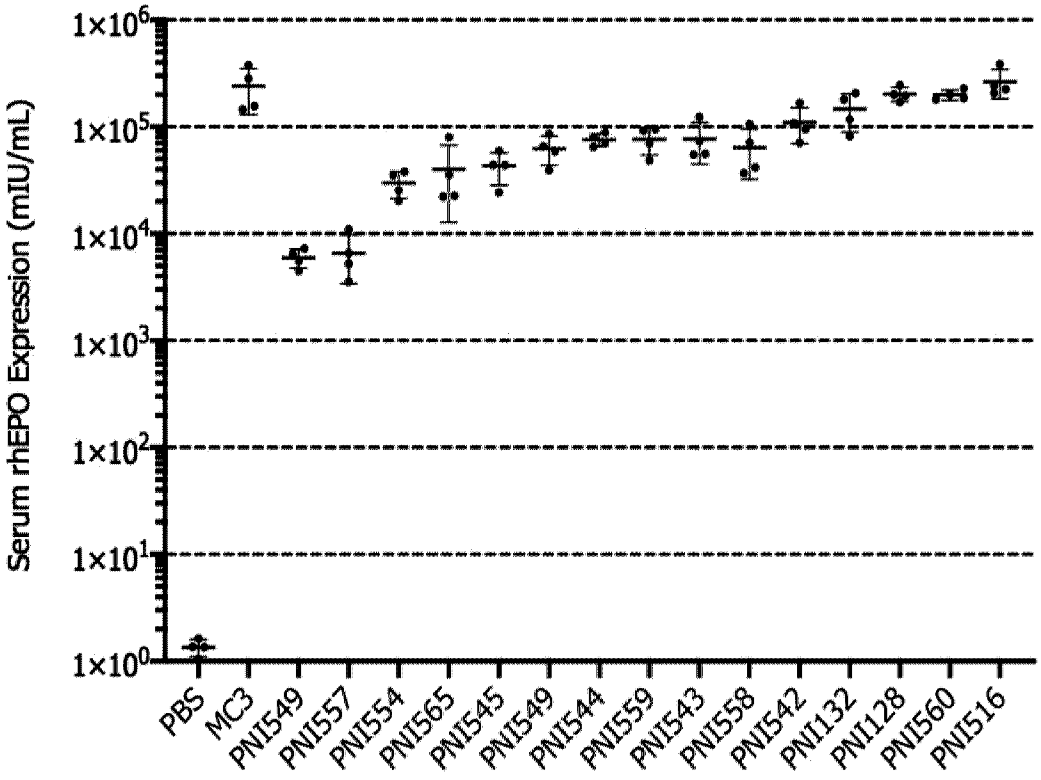
FIG. 8 is a scatter plot showing the EPO expression levels in mlU/mL 6 h after administration of 5-moU EPO mRNA encapsulated in LM02 LNAP comprising a variety of 15 ionizable lipids at an N/P ratio of 6 and a dose of 0.5 mg/Kg.

A broader number of ionizable lipids were tested under similar conditions. H-EPO-encoded mRNA LNPs containing various novel ionizable lipids were administered i.v. to mice, at a dose of the 0.5 mg/Kg. In this study, several of the ionizable lipids of the invention resulted in a higher serum rhEPO expression level as compared to PBS control, and were on par with MC3, especially ID 516. These results are shown in FIG. 8.

Example 23

CAR Expression

CD19 CAR expression in isolated primary human T cells mediated by mRNA-LNPs containing IL with CT10 composition at N/P 8 was assayed after in vitro exposure. The CAR vector pcDNA3.1 anti-CD19-h(BB Lambda)-EGFP-2nd-CAR (T7 Mut) 7661 bp was purchased from Creative BioLabs, NY, USA.

Figure 9:
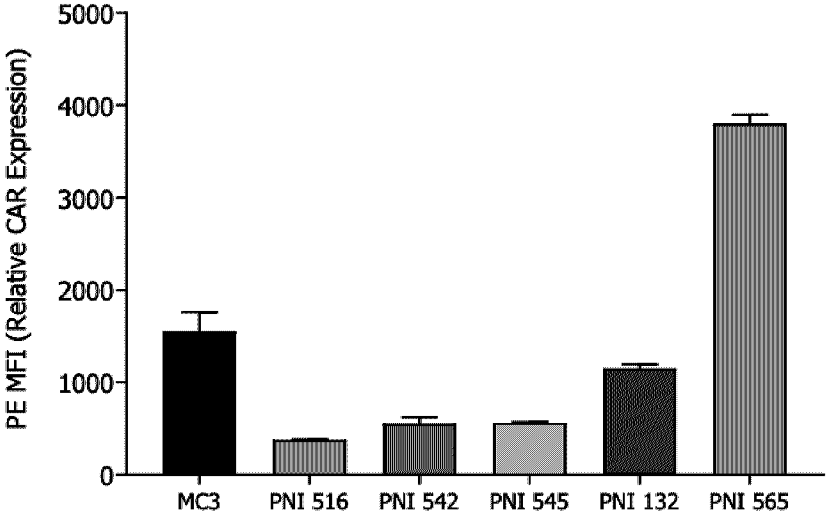
FIG. 9 are two illustrations of CD19 CAR expression levels in isolated primary human T cells mediated by mRNA CT10 N/P 8 LNPs containing PNI 545, PNI 516, PNI132, PNI 542, PNI 565 incorporating CD19 CAR (chimeric antigen receptor) mRNA. Geometric mean fluorescence intensity of anti-CD19-PE fluorophore (top bar graph) and CD19 CAR positive T cell population (bottom histogram) were measured by flow cytometry 24 hours following LNP addition with 500 ng of encapsulated mRNA per 125,000 T cells 3 days after triple activation.
Figure 9:
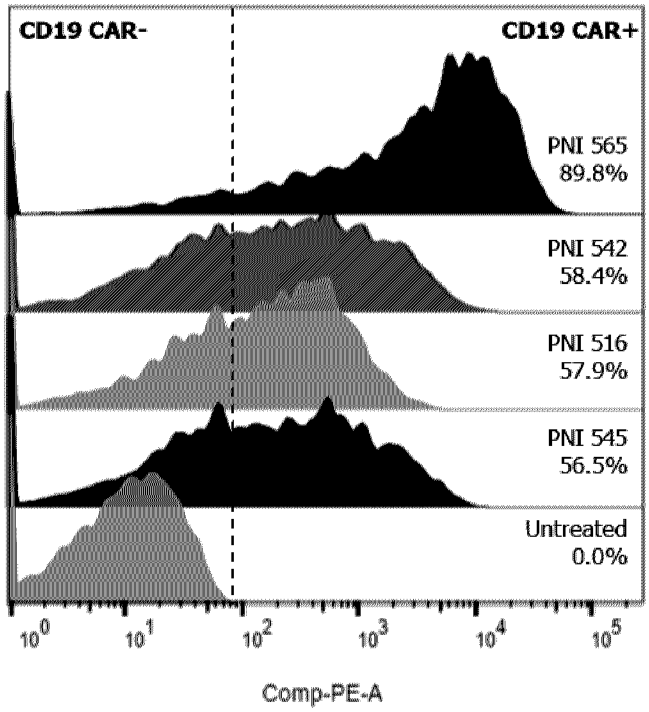

T cells were isolated from whole blood using a negative isolation procedure and T cell activation, and expansion was carried out by triple activation in ImmunoCult™ Human T Cell Expansion Media as described supra. As seen in FIG. 9, CD19 CAR expression was greater than MC3 LNP for PNI 565 LNP in transfected T cells in vitro.

Example 24

In Vivo Delivery of Ova-Encoded mRNA LNP Via Intramuscular Administration

Lipid Nanoparticles were used to encapsulate OVA antigen encoded CleanCap® OVA WT mRNA [TriLink L7610] or CleanCap® OVA 5-moU mRNA [TriLink L7210] to demonstrate vaccine utility. A lipid mixture of LM02b composition in ethanol was mixed with a low pH buffered solution of Ova mRNA at an N/P ratio of 8 using a NanoAssemblr® Ignite™ microfluidic mixer. The LNP were downstream processed using the Amicon™ ultra filtration technique and characterized for size, PDI and encapsulation efficiency. Size and PDI were measured using dynamic light scattering techniques, and nucleic acid encapsulation efficiency was calculated from a modified Quant-iT RiboGreen™ RNA assay. The hydrodynamic diameter of these mRNA-LNPs was ~76 nm with a polydispersity index of 0.01 to 0.12 and an encapsulation efficiency of ~95%

All animals were handled according to the Institutional Animal Care and Use Committee ethics protocols. For experiments, 6-8 week old $C_{57}$BL/6 mice (n=4) were purchased from Envigo. On Day 1 and Day 10, mice were intramuscularly immunized with 50 μL of various Ova LNPs. Each mouse was vaccinated with a dose of 5 ug OVA mRNA encapsulated in LNPs on Day 1 and 10. A dose of 50 ug OVA antigen was used as a positive control. At defined time intervals, 110-130 μL of blood was collected via saphenous bleeding technique, and processed into serum. At 2 weeks post second immunization, animals were euthanized, and blood was collected via cardiac puncture. Blood samples were processed immediately into serum (as described above) and stored at −80 degrees C. Aliquots of serum samples were thawed and analyzed at appropriate dilutions for Ova expression and for IgG measurements using standard ELISA techniques.

OVA ELISA of serum samples: Mouse sera at 6 h post vaccination was collected via saphenous bleed. OVA antigen was measured using standard sandwich ELISA using Ovalbumin (OVA)-ELISA Kit abx150365 (Abbexa Biologics, Inc., Arlingtom, TX, USA) components and according to the manufacturer's recommendations. Briefly, to an antibody pre-coated 96-well Abrexxa™ microplate, standards, appropriately diluted sera, and biotin-conjugated reagent were added to the wells and incubated for 1 h. Horseradish peroxidase (HRP)-conjugated reagent was added and incubated for 20 minutes. Stop solution was added to each well, and absorbance at 450 nm was measured using a plate reader, from which the concentration of OVA was calculated (results not shown).

Figure 10:
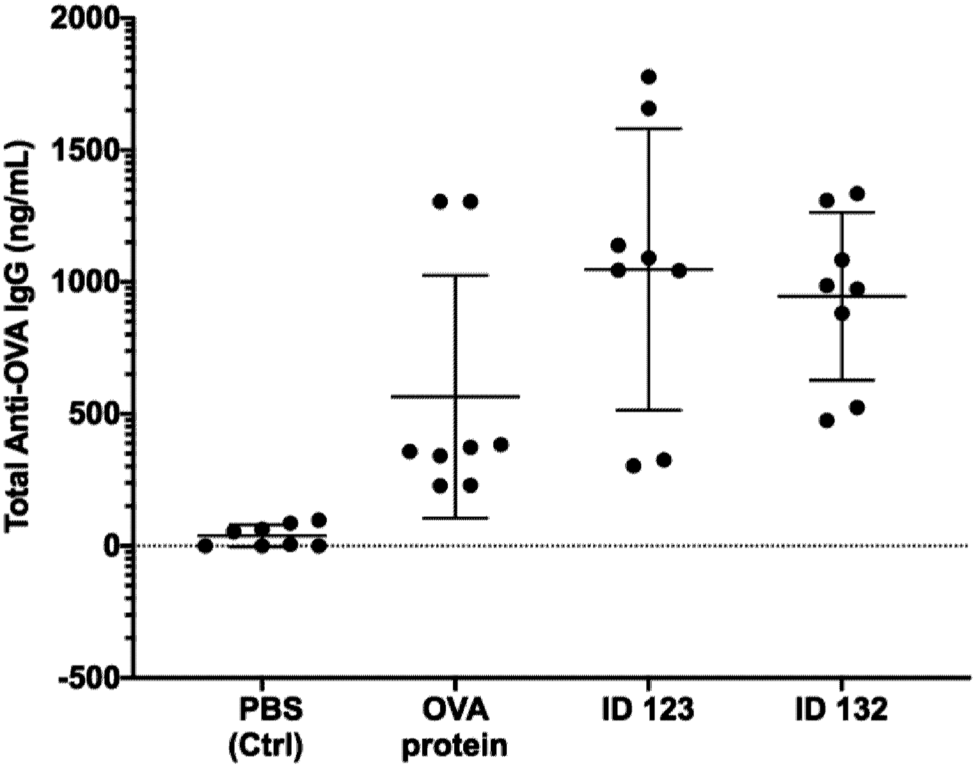
FIG. 10 is a scatter plot graph illustrating OVA-specific IgG antibody titres in the serum of mice immunized with 5 ug of OVA mRNA LNP vaccines. Two immunizations were done 10 days apart (day 1, day 10), followed by OVA specific IgG titre measurements were assessed by ELISA.

Anti-OVA-IgG ELISA of serum samples: Sera from the immunized mice were collected at 2 weeks post second immunization. OVA—specific production of IgG in response to OVA-encoded mRNA in various LNPs were measured by ELISA as described supra. Briefly, 96-well ELISA plates were precoated with OVA protein at a concentration of 2 pg protein per well in 100 mM in sodium bicarbonate buffer (pH 9.6) at 4 degrees C. overnight. Precoated plates were then blocked with 10% FBS (BSA) in 7.4 buffered PBS-Tween-20™ (0.05%) v/v and incubated at 37 degrees C. for 2 h. Serum samples and immunoglobulin standards were appropriately diluted (from 1:8 to 1:1000) in 1% BSA-PBS and added to the 96 well plate and incubated for 2 h at RT. (HRP)-conjugated goat anti-mouse IgG (#7076, Cell Signaling) was used at a dilution of 1:5,000 in PBS-Tween-10% FBS for labeling and incubated for 1 h. After the incubation period horseradish peroxidase substrate (3,3',5,5'-tetramethyl benzide—"TMB") was added. After 30 minutes of incubation, a stop solution of 2 N sulphuric acid was added and a plate reader was used to determine absorbance at 450 nm. The results of testing with PNI 123 and PNI 132 are shown in FIG. 10, as compared to negative control PBS and positive control 50 ug OVA protein. A dose of 5 μg of OVA encoded mRNA was able to generate the same or higher IgG response as that of a 10 fold higher dose of OVA protein, demonstrating the efficacy of the ionizable lipids of the invention for vaccine applications.

Example 25

Determination of Experimental pKa of Formulated Ionizable Lipids

The pKa of each cationic lipid was determined in lipid nanoparticles using an assay based on fluorescence of 6-(p-Toluidino)-2-naphthalenesulfonic acid sodium salt (TNS, Sigma Aldrich), which is a fluorescent probe for the conformational state of proteins[5]. Empty lipid nanoparticles comprising of cationic lipid/DSPC/cholesterol/PEG-lipid (50/10/38.5/1.5) in distilled water at a concentration of 3.125 mM total lipid are formulated using NanoAssemblr® Spark™, and were then was characterized for LNP quality on the Zetasizer™ using a 30× dilution with 1×PBS in the low volume cuvette. Lipid nanoparticles were further diluted 4× using distilled water to 0.781 mM total lipid. TNS was prepared as a 25 μM stock solution in distilled water. Then 6.4 μL of diluted LNP samples of 0.781 mM total lipid were mixed with 10 μL of diluted TNS to a final volume of 250 μL with buffer containing 10 mM HEPES, 10 mM MES, 10 mM $NH_4OAc$ and 130 mM NaCl where the pH ranged from 3 to 9 in 0.5 pH increments. Each well had a final concentration of 20 μM total lipid, 1 μM TNS, and 233.4 μL of buffer solution (to make up a total volume of 250 μL).

Figure 11:
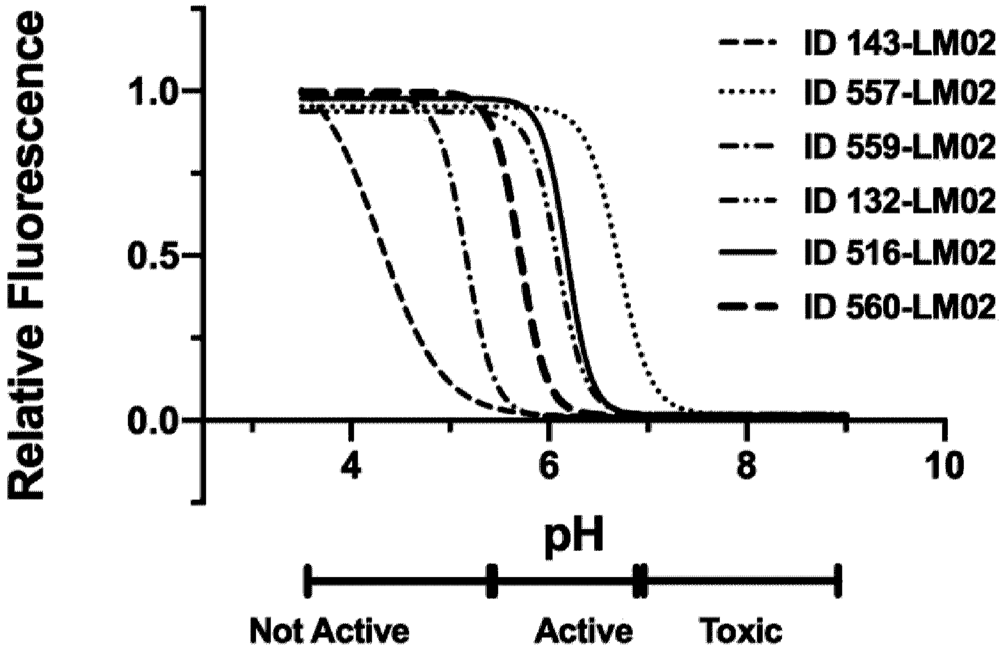
FIG. 11 is a graph illustrating TNS curves indicating surface pKa measurements of various ionizable lipids ID nos. PNI 143, PNI 557, PNI 559, PNI 132, PNI 516, and PNI 560 using the LNP composition LM02.

Samples were mixed thoroughly, and the fluorescence intensity was measured at room temperature in a BioTek™ Synergy™ $H_1$ Hybrid Multi-Mode Monochromator™ Fluorescence Microplate Reader using excitation and emission wavelengths of 321 nm and 445 nm respectively. A sigmoidal best fit analysis was applied to the fluorescence data using GraphPad Prism™ software, and the pKa was measured as the pH at half-maximal fluorescence intensity. Results are shown in FIG. 11.

Example 26

Ionizable Lipids Measured pka

The effect on transgene expression after LNP transfection exerted by surface pKa in the LNP resulting from different ionizable lipids was investigated. Lipids with lower pKa values were found to be inactive in transgene expression in T cells. Lipids with high pKa values were found to be toxic to T cells. Lipids in the pKa range of 5.5-6.9 were found to be active in promoting the transgene expression in T cells. Results of experimental pKa measurements and qualitative protein expression are in Table 8. The number of asterix symbols indicates protein expression levels interpreted by the inventors from quantitative data.

TABLE 8 pKa, EPO, & GFP measurements

| ID | Structure | pKa | EPO Protein expression: IV in mice | GFP Protein expression: Human T cell |
|---|---|---|---|---|
| PNI 101 | 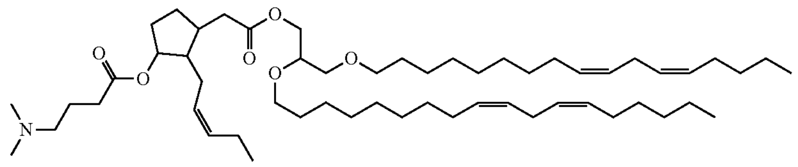 [SMILES: CC/C=C\CC1C(CC(=O)OCC(COCCCCCCCC/C=C\C/C=C\CCCC)OCCCCCCCC/C=C\C/C=C\CCCCC)CCC1OC(=O)CCCN(C)C] | 6.37 | ** | **** |
| PNI 123 | 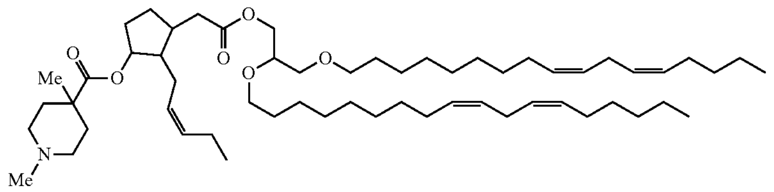 [SMILES: CC/C=C\CC1C(CC(=O)OCC(COCCCCCCCC/C=C\C/C=C\CCCC)OCCCCCCCC/C=C\C/C=C\CCCCC)CCC1OC(=O)C1(C)CCN(C)CC1] | 6.013 | *** | *** |

TABLE 8-continued
pKa, EPO, & GFP measurements
| ID | Structure | pKa | EPO Protein expression: IV in mice | GFP Protein expression: Human T cell |
|---|---|---|---|---|
| PNI 128 | 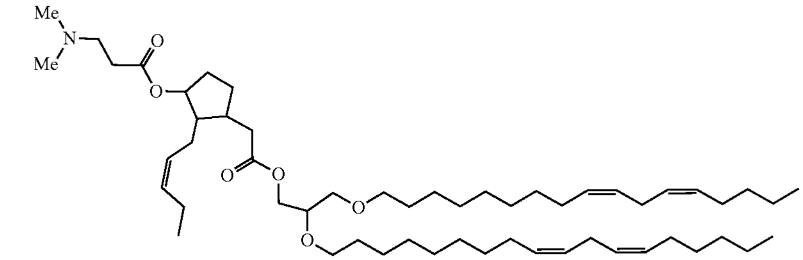 [SMILES: CC/C=C\CC1C(CC(=O)OCC(COCCCCCCCC/C=C\C/C=C\CCCC)OCCCCCCCC/C=C\C/C=C\CCCCC)CCC1OC(=O)CCN(C)C] | 5.56 | **** | — |
| PNI 132 | 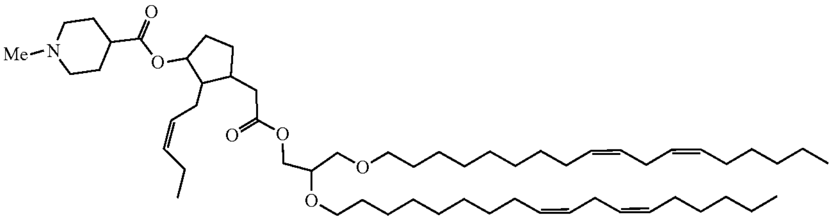 [SMILES: CC/C=C\CC1C(CC(=O)OCC(COCCCCCCCC/C=C\C/C=C\CCCCC)OCCCCCCCC/C=C\C/C=C\CCCCC)CCC1OC(=O)C1CCN(C)CC1] | 6.10 | *** | ******* |
| PNI 135 | 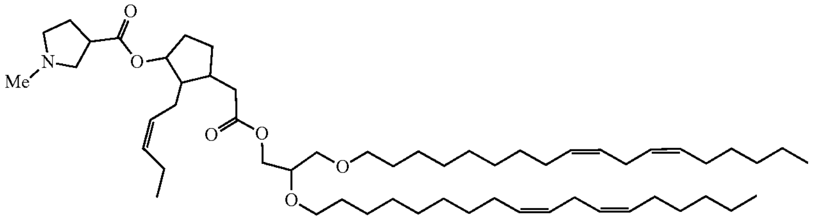 [SMILES: CC/C=C\CC1C(CC(=O)OCC(COCCCCCCCC/C=C\C/C=C\CCCCC)OCCCCCCCC/C=C\C/C=C\CCCCC)CCC1OC(=O)C1CCN(C)C1] | 5.48 | — | — |
| PNI 143 | 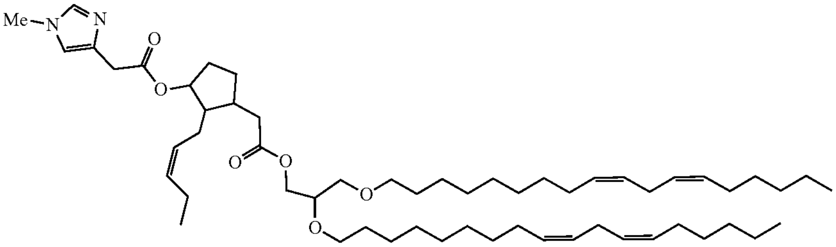 [SMILES: CC/C=C\CC1C(CC(=O)OCC(COCCCCCCCC/C=C\C/C=C\CCCCC)OCCCCCCCC/C=C\C/C=C\CCCCC)CCC1OC(=O)Cc1cn(C)cn1] | 4.31 | — | — |
| PNI 542 | 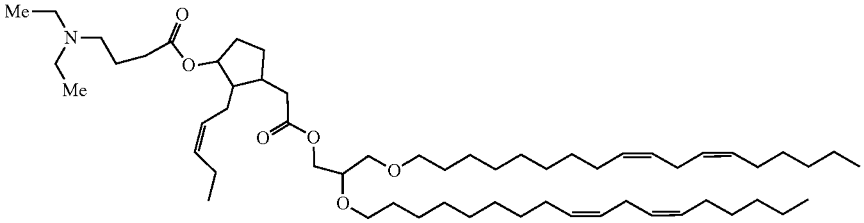 [SMILES: CC/C=C\CC1C(CC(=O)OCC(COCCCCCCCC/C=C\C/C=C\CCCCC)OCCCCCCCC/C=C\C/C=C\CCCCC)CCC1OC(=O)CCCN(CC)CC] | 6.11 | *** | ***** |
| PNI 557 | 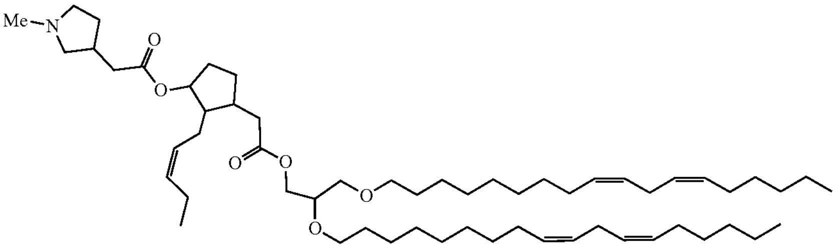 [SMILES: CC/C=C\CC1C(CC(=O)OCC(COCCCCCCCC/C=C\C/C=C\CCCCC)OCCCCCCCC/C=C\C/C=C\CCCCC)CCC1OC(=O)CC1CCN(C)C1] | 6.70 | ** | *** |

TABLE 8-continued
pKa, EPO, & GFP measurements
| ID | Structure | pKa | EPO Protein expression: IV in mice | GFP Protein expression: Human T cell |
|---|---|---|---|---|
| PNI 558 | 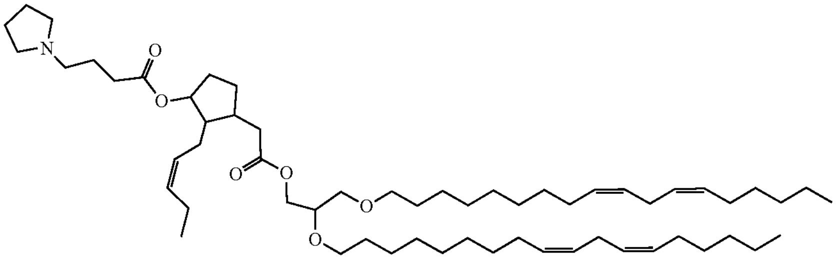 [SMILES: CC/C=C\CC1C(CC(=O)OCC(COCCCCCCCC/C=C\C/C=C\CCCCC)OCCCCCCCC/C=C\C/C=C\CCCCC)CCC1OC(=O)CCCN1CCCC1] | 6.28 | *** | * |
| PNI 559 | 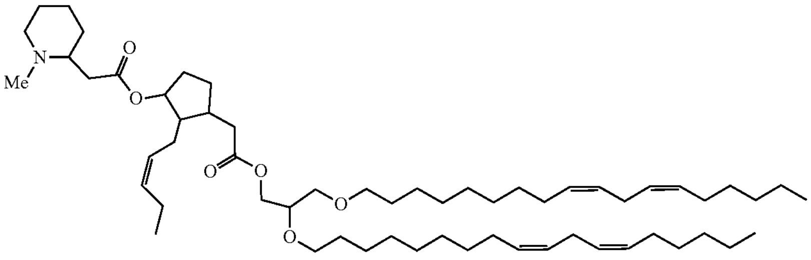 [SMILES: CC/C=C\CC1C(CC(=O)OCC(COCCCCCCCC/C=C\C/C=C\CCCCC)OCCCCCCCC/C=C\C/C=C\CCCCC)CCC1OC(=O)CC1CCCCN1C] | 5.16 | *** | ** |
| PNI 148 | 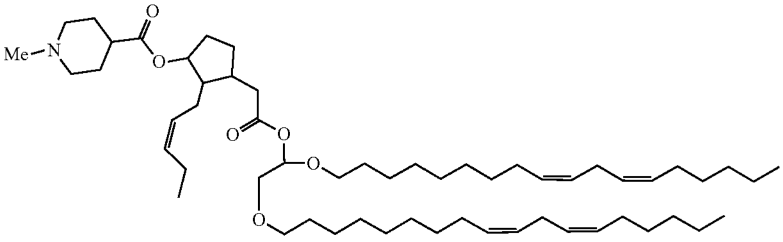 [SMILES: CC/C=C\CC1C(CC(=O)OC(COCCCCCCCC/C=C\C/C=C\CCCCC)OCCCCCCCC/C=C\C/C=C\CCCCC)CCC1OC(=O)C1CCN(C)CC1] | 6.77 | — | — |
| PNI 516 | 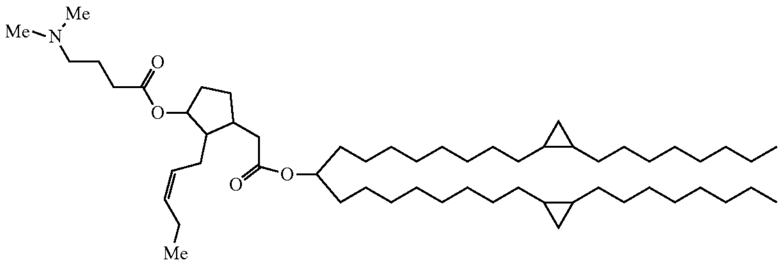 [SMILES: CC/C=C\CC1C(CC(=O)OC(CCCCCCCCC2CC2CCCCCCCC)CCCCCCCCC2CC2CCCCCCCC)CCC1OC(=O)CCCN(C)C] | 6.18 | **** | ***** |
| PNI 549 | 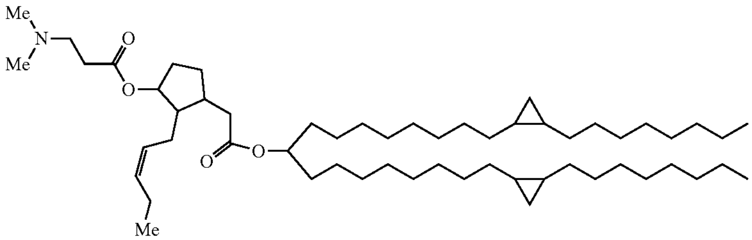 [SMILES: CC/C=C\CC1C(CC(=O)OC(CCCCCCCCC2CC2CCCCCCCC)CCCCCCCCC2CC2CCCCCCCC)CCC1OC(=O)CCN(C)C] | 5.27 | *** | ** |

TABLE 8-continued
| pKa, EPO, & GFP measurements | | | | |
|---|---|---|---|---|
| ID | Structure | pKa | EPO Protein ex-pression: IV in mice | GFP Protein expression: Human T cell |
| PNI 560 | 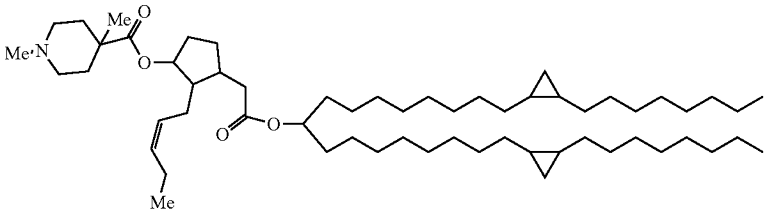 [SMILES: CC/C=C\CC1C(CC(=O)OC(CCCCCCCCC2CC2CCCCCCCC)CCCCCCCCC2CC2CCCCCCCC)CCC1OC(=O)C1(C)CCN(C)CC1] | 5.70 | **** | **** |
| PNI 543 | 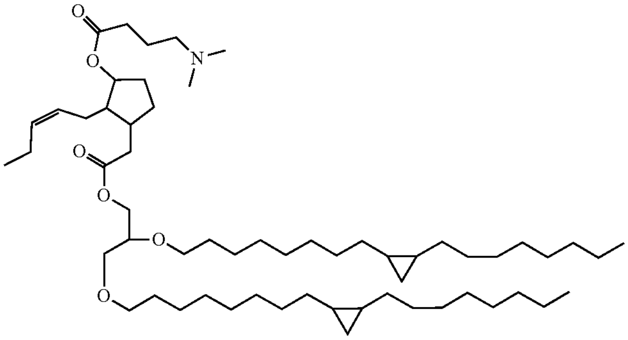 [SMILES: CC/C=C\CC1C(CC(=O)OCC(COCCCCCCCCC2CC2CCCCCCCC)OCCCCCCCCC2CC2CCCCCCCC)CCC1OC(=O)CCCN(C)C] | 6.31 | *** | — |
| PNI 544 | 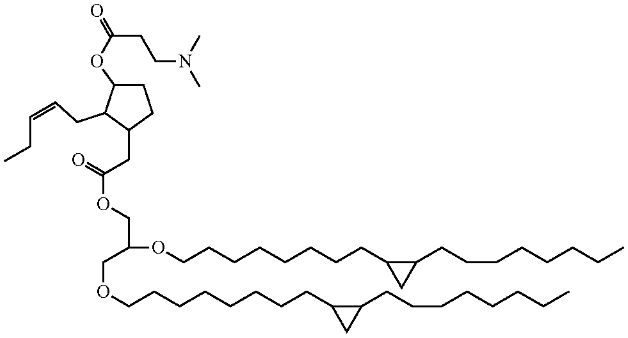 [SMILES: CC/C=C\CC1C(CC(=O)OCC(COCCCCCCCCC2CC2CCCCCCCC)OCCCCCCCCC2CC2CCCCCCCC)CCC1OC(=O)CCN(C)C] | 5.68 | *** | *** |
| PNI 545 | 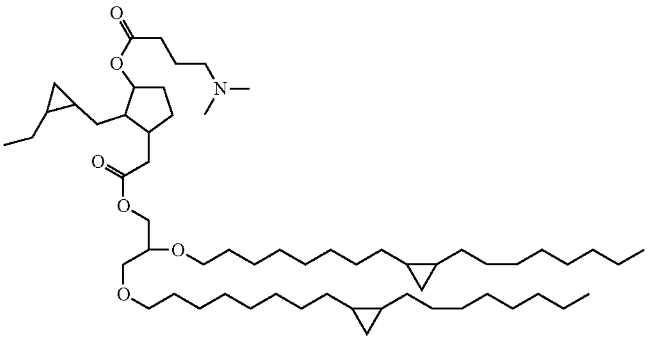 [SMILES: CCCCCCCCC1CC1CCCCCCCCOCC(COC(=O)CC1CCC(OC(=O)CCCN(C)C)C1CC1CC1CC)OCCCCCCCCC1CC1CCCCCCCC] | 5.91 | *** | ***** |

TABLE 8-continued
| pKa, EPO, & GFP measurements | | | | |
|---|---|---|---|---|
| ID | Structure | pKa | EPO Protein ex-pression: IV in mice | GFP Protein expression: Human T cell |
| PNI 546 | 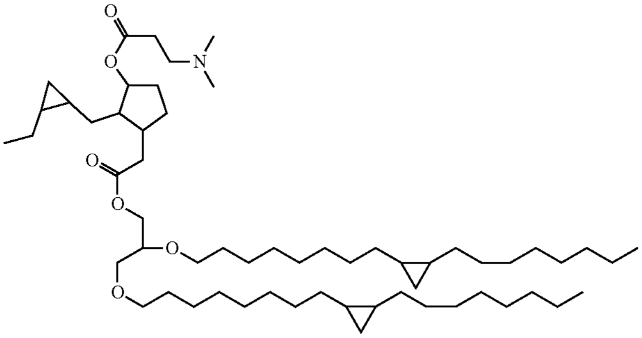 [SMILES: CCCCCCCCC1CC1CCCCCCCCOCC(COC(=O)CC1CCC(OC(=O)CCN(C)C)C1CC1CC1CC)OCCCCCCCCC1CC1CCCCCCCC] | 4.84 | * | * |
| PNI 547 | 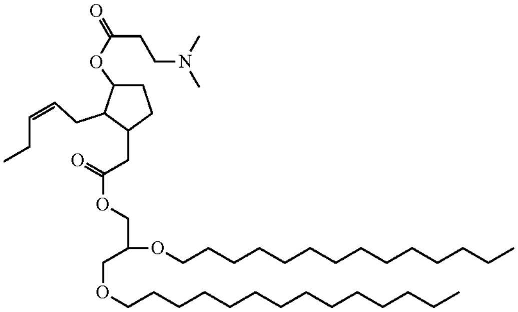 [SMILES: CC/C=C\CC1C(CC(=O)OCC(COCCCCCCCCCCCCCC)OCCCCCCCCCCCCCC)CCC1OC(=O)CCN(C)C] | 5.95 | — | — |
| PNI 548 | 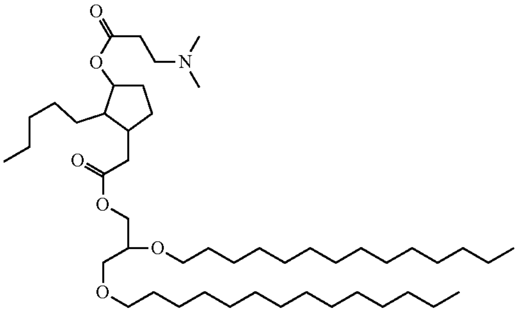 [SMILES: CCCCCCCCCCCCCCOCC(COC(=O)CC1CCC(OC(=O)CCN(C)C)C1CCCCC)OCCCCCCCCCCCCCC] | 5.50 | — | — |
| PNI 554 | 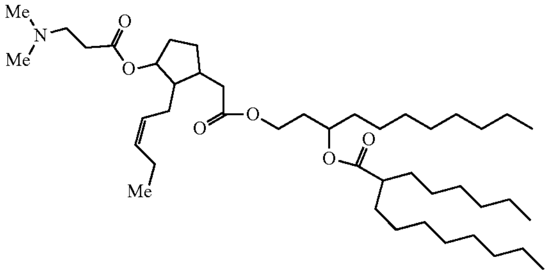 [SMILES: CC/C=C\CC1C(CC(=O)OCCC(CCCCCCCC)OC(=O)C(CCCCCC)CCCCCCCC)CCC1OC(=O)CCN(C)C] | 5.52 | *** | *** |

TABLE 8-continued
| pKa, EPO, & GFP measurements | | | | |
|---|---|---|---|---|
| ID | Structure | pKa | EPO Protein ex-pression: IV in mice | GFP Protein expression: Human T cell |
| PNI 562 | 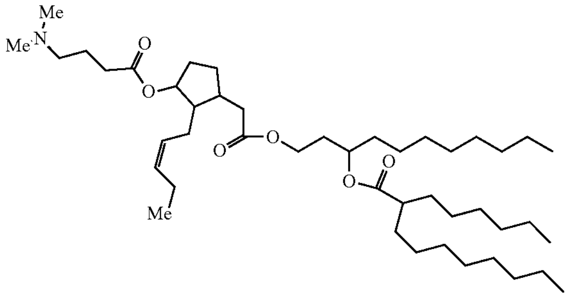 [SMILES: CC/C=C\CC1C(CC(=O)OCCC(CCCCCCCC)OC(=O)C(CCCCCC)CCCCCCCC)CCC1OC(=O)CCCN(C)C] | 6.36 | — | — |
| PNI 565 | 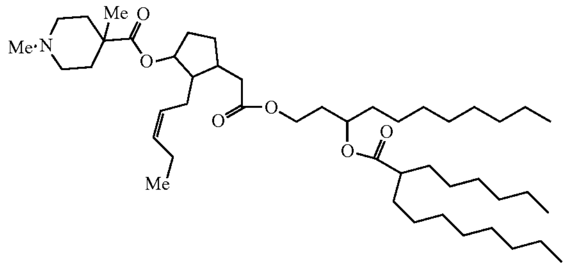 [SMILES: CC/C=C\CC1C(CC(=O)OCCC(CCCCCCCC)OC(=O)C(CCCCCC)CCCCCCCC)CCC1OC(=O)C1(C)CCN(C)CC1] | 5.99 | *** | ******* |
| PNI 510 | 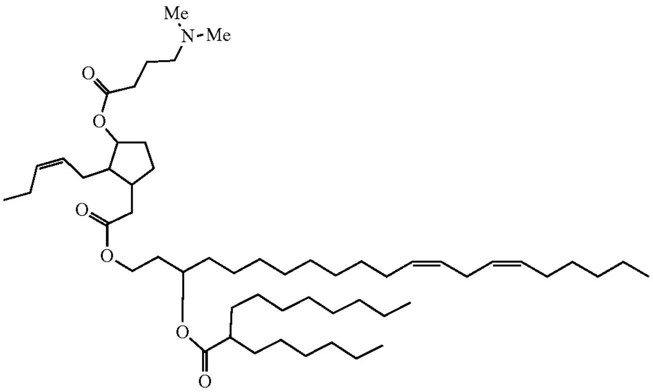 [SMILES: CC/C=C\CC1C(CC(=O)OCCC(CCCCCCCC/C=C\C/C=C\CCCCC)OC(=O)C(CCCCCC)CCCCCCCC)CCC1OC(=O)CCCN(C)C] | 6.20 | — | — |
| PNI 552 | 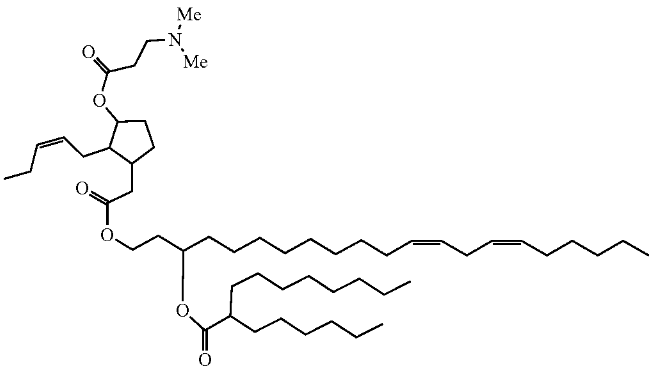 [SMILES: CC/C=C\CC1C(CC(=O)OCCC(CCCCCCCC/C=C\C/C=C\CCCCC)OC(=O)C(CCCCCC)CCCCCCCC)CCC1OC(=O)CCN(C)C] | 5.42 | — | — |

TABLE 8-continued
| pKa, EPO, & GFP measurements | | | | |
|---|---|---|---|---|
| ID | Structure | pKa | EPO Protein expression: IV in mice | GFP Protein expression: Human T cell |
| PNI 563 | 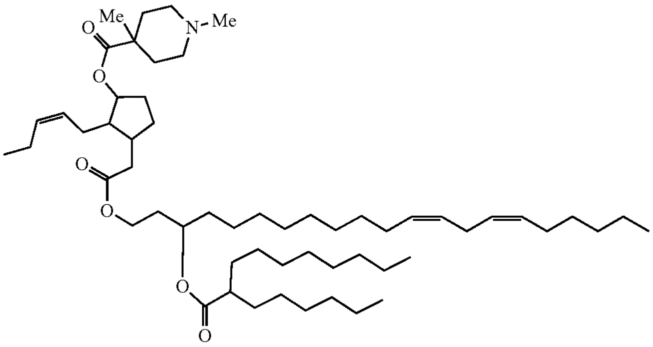 [SMILES: CC/C=C\CC1C(CC(=O)OCCC(CCCCCCCC/C=C\C/C=C\CCCCC)OC(=O)C(CCCCCC)CCCCCCCC)CCC1OC(=O)C1(C)CCN(C)CC1] | 5.96 | — | — |
| PNI 515 | 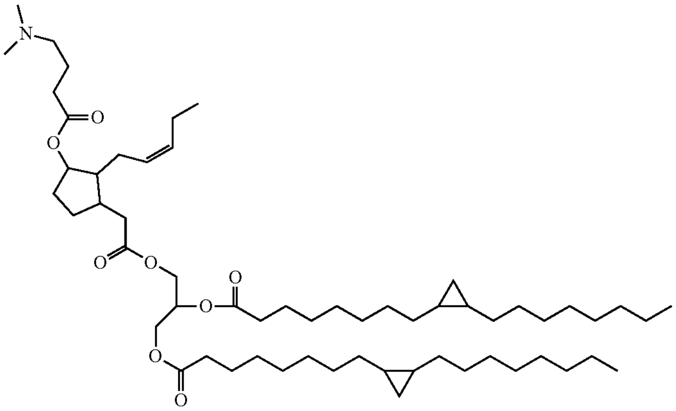 [SMILES: CC/C=C\CC1C(CC(=O)OCC(COC(=O)CCCCCCCC2CC2CCCCCCCC)OC(=O)CCCCCCCC2CC2CCCCCCCC)CCC1OC(=O)CCCN(C)C] | 6.27 | — | — |
| PNI 551 | 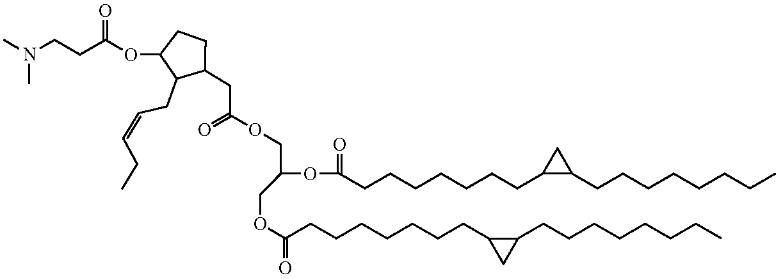 [SMILES: CC/C=C\CC1C(CC(=O)OCC(COC(=O)CCCCCCCC2CC2CCCCCCCC)OC(=O)CCCCCCCC2CC2CCCCCCCC)CCC1OC(=O)CCN(C)C] | 5.50 | — | — |
| PNI 269 | 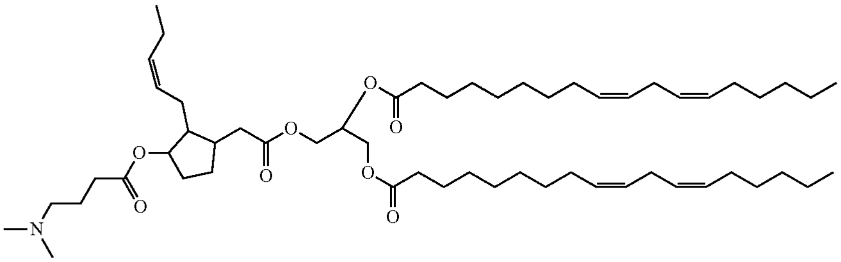 [SMILES: CC/C=C\CC1C(CC(=O)OCC(COC(=O)CCCCCCC/C=C\C/C=C\CCCCC)OC(=O)CCCCCCC/C=C\C/C=C\CCCCC)CCC1OC(=O)CCCN(C)C] | 6.28 | — | — |

TABLE 8-continued

| pKa, EPO, & GFP measurements | | | | |
|---|---|---|---|---|
| ID | Structure | pKa | EPO Protein expression: IV in mice | GFP Protein expression: Human T cell |
| PNI 567 | 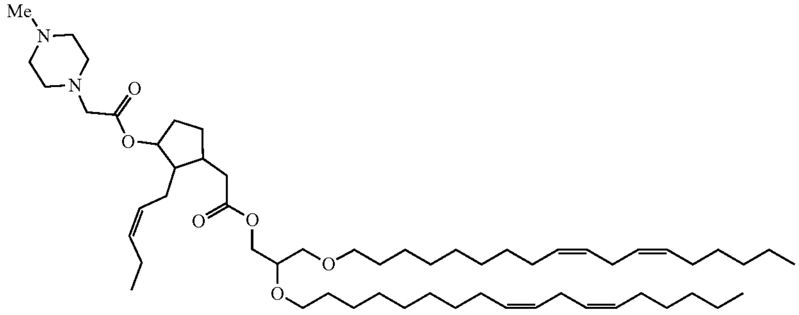 [SMILES: CC/C=C\CC1C(CC(=O)OCC(COCCCCCCCC/C=C\C/C=C\CCCCC)OCCCCCCCC/C=C\C/C=C\CCCCC)CCC1OC(=O)CN1CCN(C)CC1] | 6.23 | — | — |

While preferred embodiments have been described above and illustrated in the accompanying drawings, it will be evident to those skilled in the art that modifications may be made without departing from this disclosure. Such modifications are considered as possible variants encompassed in the scope of the disclosure.

BIBLIOGRAPHY

1. Garg, S.; Heuck, G.; Ip, S.; Ramsay, E., Microfluidics: a transformational tool for nanomedicine development and production. *J Drug Target* 2016, 24 (9), 821-835.
2. Zhang, S.-h.; Shen, S.-c.; Chen, Z.; Yun, J.-x.; Yao, K.-j.; Chen, B.-b.; Chen, J.-z., Preparation of solid lipid nanoparticles in co-flowing microchannels. *Chemical Engineering Journal* 2008, 144 (2), 324-328.
3. JEFFS, L. B., et al., A Scalable, Extrusion-Free Method for Efficient Liposomal Encapsulation of Plasmid DNA. *Pharmaceutical Research* 2005, 22 (3), 362-372.
4. Gaj, T.; Gersbach, C. A.; Barbas, C. F., 3rd, ZFN, TALEN, and CRISPR/Cas-based methods for genome engineering. *Trends in biotechnology* 2013, 31 (7), 397-405.
5. Trickett, A.; Kwan, Y. L., T cell stimulation and expansion using anti-CD3/CD28 beads. *J Immunol Methods* 2003, 275 (1-2), 251-5.

BIBLIOGRAPHY

6. Lundstrom, K. Nanoparticle-based delivery of self-amplifying RNA. Gene Ther 27, 183-185 (2020).
7. Peng, M., Mo, Y., Wang, Y. et al. Neoantigen vaccine: an emerging tumor immunotherapy. *Mol Cancer* 18, 128 (2019).
8. Roujian Lu 1, Xiang Zhao 1, Juan Li 2, et al. "Genomic Characterisation and Epidemiology of 2019 Novel Coronavirus: Implications for Virus Origins and Receptor Binding" Lancet 2020 Feb 22; 395(10224):565-574
9. Morokata T, et. al, Immunology (1999) 345-351

The invention claimed is:

1. A compound, or a pharmaceutically acceptable salt thereof, of formula (I):

(I)

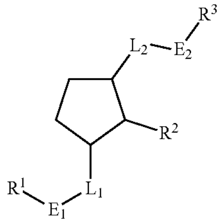

wherein:

$L_1$ is a direct bond or $C_1$-$C_5$ alkylene;

$E_1$ is —O—, —OC(O)O—, —OC(O)-$\delta^1$, —OC(O)N(Q)-$\delta^1$, —OC(O)S-$\delta^1$, —N(Q)C(O)-$\delta^1$, —N(Q)C(O)O-$\delta^1$, —C(O)O-$\delta^1$, or —C(O)N(Q)-$\delta^1$; Q is H or $C_1$-$C_5$ alkyl; $\delta^1$ designates the bond linked to the $R^1$ group;

$R^1$ is selected from:

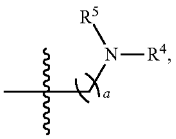

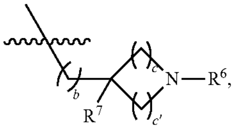

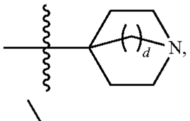

and

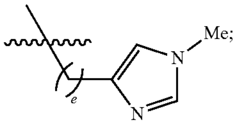

and wherein:

$R^4$ and $R^5$ are each independently $C_1$-$C_6$ alkyl, $C_2$-$C_6$ alkenyl, or $C_2$-$C_6$ alkynyl; alternatively $R^4$ and $R^5$ may join to form 4-6 membered heterocyclic ring containing oxygen (O) or up to 2 nitrogen (N), optionally substituted with 1 or 2 substituents that are each independently $C_1$-$C_6$ alkyl, cyclopropyl, OH, and $C_1$-$C_3$ alkoxy;

$R^6$ is $C_1$-$C_6$ alkyl, $C_2$-$C_6$ alkenyl, $C_2$-$C_6$ alkynyl, $C_3$-$C_6$ cycloalkyl or 2-hydroxyethyl;

$R^7$ is H, $C_1$-$C_6$ alkyl, $C_2$-$C_6$ alkenyl, or $C_2$-$C_6$ alkynyl;

a and c' are each independently 1, 2, 3, 4, or 5;

b, c and e are each independently 0, 1, or 2;

d is 1, or 2;

$R^2$ is H, $C_1$-$C_{12}$ alkyl, $C_2$-$C_{12}$ alkenyl, $C_2$-$C_{12}$ alkynyl, or

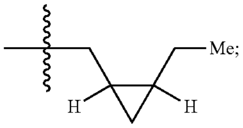 [SMILES: *CC1CC1CC]

$L_2$ is a direct bond or $\delta^2$—$(CR^8R^{8'})_k$-$\delta^3$ wherein $R^8$ and $R^{8'}$ are each independently H, $C_1$-$C_{12}$ alkyl, $C_2$-$C_{12}$ alkenyl or $C_2$-$C_{12}$ alkynyl; $\delta^2$ designates the bond linked to $E_2$ group, and $\delta^3$ designates the bond linked to cyclopentyl scaffold described in formula (I);

k is 1, 2, 3, 4, or 5;

$E_2$ is —O—, —OC(O)O—, —OC(O)-$\delta^4$, —OC(O)N(Q)-$\delta^4$, —N(Q)C(O)-$\delta^4$, —N(Q)C(O)O-$\delta^4$, —C(O)N(Q)-$\delta^4$ or —C(O)O-$\delta^4$; Q is H or $C_1$-$C_5$ alkyl; where $\delta^4$ designates the bond linked to $R^3$ group;

$R^3$ is $C_8$-$C_{20}$ alkyl, $C_8$-$C_{20}$ alkenyl, $C_8$-$C_{20}$ alkynyl,

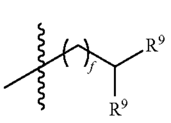
,
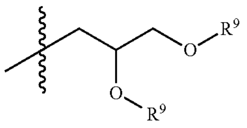
,
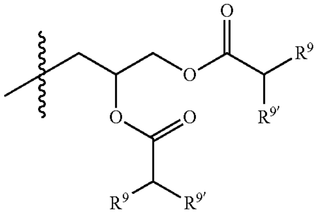
,
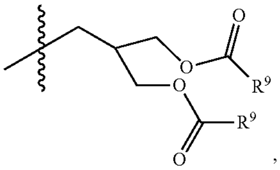
,
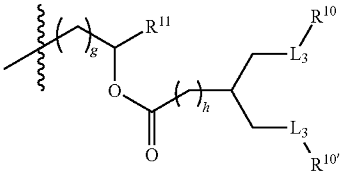
or
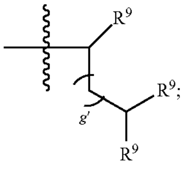

wherein:

f is 0 or 1;

g is 1 or 2;

g' is 1, 2, 3, 4, or 5;

h is 0, 1, 2, 3 or 4;

$R^9$ is a $C_6$-$C_{20}$ chain having the formula —$(CH_2)_i$-$[L_4$-$(CH_2)]_j$—$R^{12}$, wherein:

$L_4$ is selected from

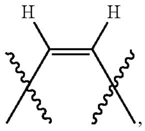
,
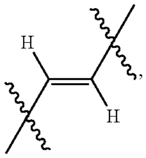
,
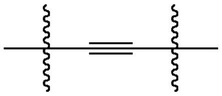
and
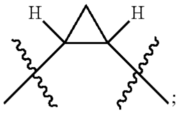
;

i is an integer in the range 6-20;

j is 0, 1, 2, or 3;

$R^{12}$ is H or $C_4$-$C_8$ alkyl;

$R^{9'}$ is H, $C_4$-$C_{10}$ alkyl, $C_4$-$C_{10}$ alkenyl, or $C_4$-$C_{10}$ alkynyl;

$R^{10}$ and $R^{10'}$ are each independently $C_4$-$C_{10}$ alkyl, $C_4$-$C_{10}$ alkenyl, or $C_4$-$C_{10}$ alkynyl;

$L_3$ is —OC(O)—$\delta^5$, —O-$\delta^5$, or a direct bond;

$\delta^5$ designates the bond linked to $R^{10}$ and $R^{10'}$; and $R^{11}$=$R^9$, or has the formula:

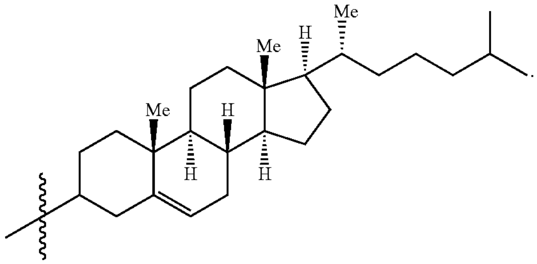

2. A compound or a pharmaceutically acceptable salt thereof, of formula (I):

(I)

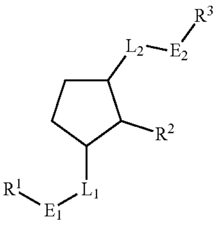

wherein:

$L_1$ is a direct bond or $C_1$-$C_5$ alkylene;

$E_1$ is —OC(O)O—, —OC(O)-$\delta^1$, —OC(O)N(Q)-$\delta^1$ or —OC(O)S-$\delta^1$; Q is H or $C_1$-$C_5$ alkyl; $\delta^1$ designates the bond linked to the $R^1$ group;

$R^1$ is selected from:

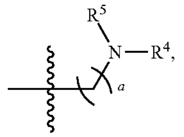

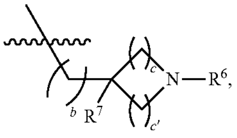

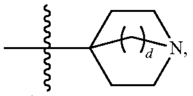

and

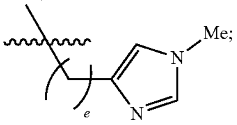

wherein:

$R^4$ and $R^5$ are each independently $C_1$-$C_6$ alkyl, $C_2$-$C_6$ alkenyl, $C_2$-$C_6$ alkynyl; alternatively $R^4$ and $R^5$ may join to form 5-6 membered heterocyclic ring containing up to 2 nitrogen (N), optionally substituted with 1 or 2 substituents that are each independently $C_1$-$C_6$ alkyl, or cyclopropyl;

$R^6$ is $C_1$-$C_6$ alkyl or $C_3$-$C_6$ cycloalkyl;

$R^7$ is H or $C_1$-$C_6$ alkyl;

a is 1, 2, or 3;

b and c are each independently 0, 1, or 2;

c' is 2, 3, or 4;

d is 1 or 2;

e is 0 or 1;

$R^2$ is H, $C_1$-$C_5$ alkyl, $C_2$-$C_5$ alkenyl, $C_2$-$C_5$ alkynyl, or

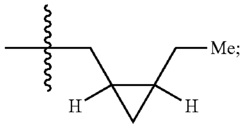 [SMILES: *CC1CC1CC]

$L_2$ is a direct bond or $\delta^2$—$(CR^8R^{8'})_k$-$\delta^3$ wherein $R^8$ and $R^{8'}$ are each independently H, $C_1$-$C_{12}$ alkyl, $C_2$-$C_{12}$ alkenyl or $C_2$-$C_{12}$ alkynyl;

$\delta^2$ designates the bond linked to $E_2$ group and $\delta^3$ designates the bond linked to cyclopentyl scaffold described in formula (I);

k is 1;

$E_2$ is selected from —O—, —OC(O)O—, —OC(O)-$\delta^4$, —OC(O)N(Q)-$\delta^4$, —C(O)N(Q)-$\delta^4$ or —C(O)O-$\delta^4$; Q is H or $C_1$-$C_5$ alkyl; where $\delta^4$ designates the bond linked to $R^3$ group;

$R^3$ is selected from $C_8$-$C_{20}$ alkyl, $C_8$-$C_{20}$ alkenyl, $C_8$-$C_{20}$ alkynyl,

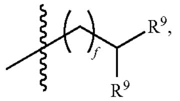

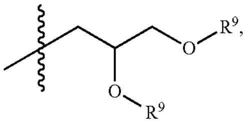

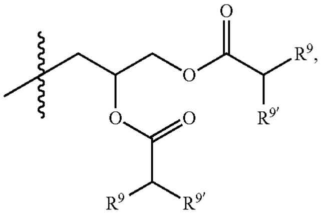

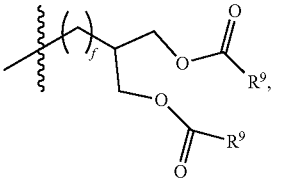

and

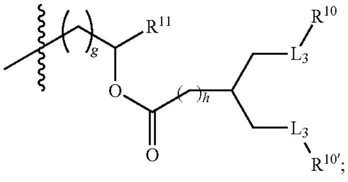

wherein:

f and h are each 0;

g is 1 or 2;

h is 0, 1, 2, 3 or 4;

$R^9$ is a $C_6$-$C_{20}$ chain having the formula —$(CH_2)_i$-$[L_4$-$(CH_2)]_j$—$R^{12}$, wherein:

$L_4$ is selected from

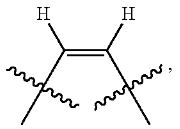

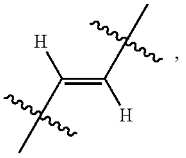

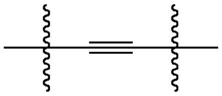

and

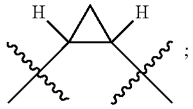

i is an integer from 6-20;

j is 0, 1, or 2;

$R^{12}$ is H or $C_4$-$C_8$ alkyl group;

$R^{9'}$ is H or $C_4$-$C_{10}$ alkyl;

$R^{10}$ and $R^{10'}$ are each independently $C_4$-$C_{10}$ alkyl, $C_4$-$C_{10}$ alkenyl, or $C_4$-$C_{10}$ alkynyl;

$L_3$ is —OC(O)-$\delta^5$ or a direct bond; $\delta^5$ designates the bond linked to $R^{10}$ and $R^{10'}$; and $R^{11}$ is the same as $R^9$.

3. The compound of claim 1, or a pharmaceutically acceptable salt thereof, of formula (I), wherein:

$L_1$ is a direct bond;

$E_1$ is —OC(O)O—, —OC(O)-$\delta^1$, —OC(O)N(Q)-$\delta^1$, or —OC(O)S-$\delta^1$; Q is H or $C_1$-$C_5$ alkyl; $\delta^1$ designates the bond linked to the $R^1$ group;

$R^1$ is selected from

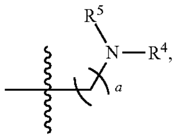

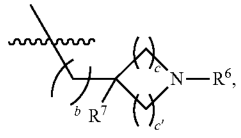

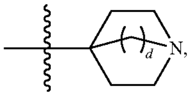

and

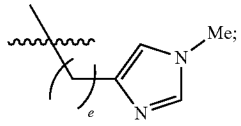

wherein:

$R^4$ and $R^5$ are each, independently $C_1$-$C_6$ alkyl; alternatively $R^4$ and $R^5$ may join to form 5-6 membered heterocyclic ring containing up to 2 nitrogen (N), optionally substituted with 1 or 2 substituents that are each independently a $C_1$-$C_6$ alkyl;

$R^6$ is $C_1$-$C_6$ alkyl or cyclopropyl;

$R^7$ is H or $C_1$-$C_6$ alkyl;

a is 1, 2, or 3;

b is 0 or 1;

c is 0, 1, or 2;

c' is 2, 3, or 4;

d is 2;

e is 1;

$R^2$ is H, $C_1$-$C_5$ alkyl, $C_2$-$C_5$ alkenyl,

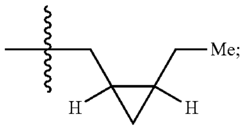 [SMILES: *CC1CC1CC]

$L_2$ is $\delta^2$—$(CH_2)_k$-$\delta^3$, wherein $\delta^2$ designates the bond linked to $E_2$ group, and $\delta^3$ designates the bond linked to cyclopentyl scaffold described in formula (I);

k is 1;

$E_2$ is —C(O)O-$\delta^4$, where $\delta^4$ designates the bond linked to $R^3$ group;

$R^3$ is selected from:

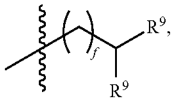

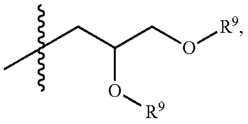

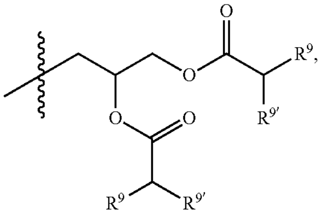

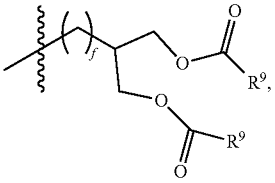

and

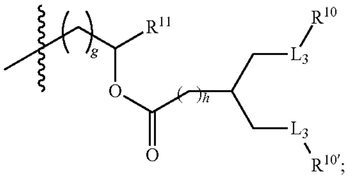

wherein:

f and h are each 0;

g is 1 or 2;

$R^9$ is a $C_6$-$C_{20}$ chain having the formula —$(CH_2)_i$-[$L_4$-$(CH_2)$]$_j$—$R^{12}$, wherein:

$L_4$ is selected from

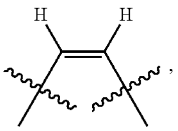

and

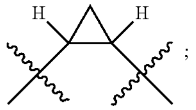

i is an integer in the range 6-20;

j is 0, 1, or 2;

$R^{12}$ is H or $C_4$-$C_8$ alkyl group;

$R^{9'}$ is H or $C_4$-$C_{10}$ alkyl;

$R^{10}$ and $R^{10'}$ are each independently $C_4$-$C_{10}$ alkyl;

$L_3$ is a direct bond;

$R^{11}$ is the same as $R^9$.

4. The compound of claim 1, or a pharmaceutically acceptable salt thereof, of formula (I), wherein:

$L_1$ is a direct bond;

$E_1$ is —OC(O)-$\delta^1$, wherein $\delta^1$ designates the bond linked to the $R^1$ group;

$R^1$ is selected from:

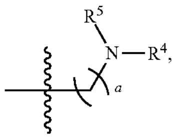

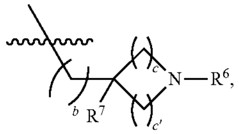

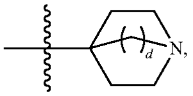

and

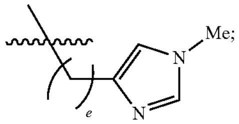

wherein:

$R^4$ and $R^5$ are each independently $C_1$-$C_6$ alkyl; alternatively, $R^4$ and $R^5$ may join to form a 5-6 membered heterocyclic ring containing up to 2 nitrogen (N), optionally substituted with 1 or 2 substituents that are each independently $C_1$-$C_6$ alkyl;

$R^6$ is a $C_1$-$C_6$ alkyl or cyclopropyl;

$R^7$ is H or $C_1$-$C_6$ alkyl;

a is 1, 2, or 3;

b is 0, or 1;

c is 0, 1, or 2;

c' is 2, 3, or 4;

d is 2;

e is 1;

$R^2$ is selected from H, $C_1$-$C_5$ alkyl, $C_2$-$C_5$ alkenyl, and

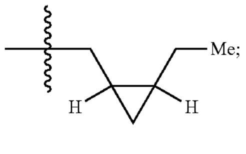 [SMILES: *CC1CC1CC]

$L_2$ is $\delta^2$—$(CH_2)_k$-$\delta^3$; $\delta^2$ designates the bond linked to $E_2$ group, and $\delta^3$ designates the bond linked to cyclopentyl scaffold described in formula (I);

k is 1;

$E_2$ is —C(O)O-$\delta^4$, where $\delta^4$ designates the bond linked to $R^3$ group;

$R^3$ is selected from:

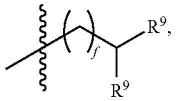

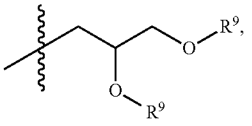

-continued

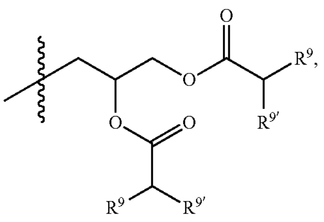

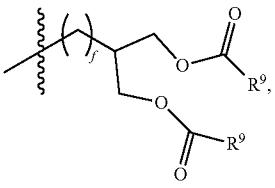

and

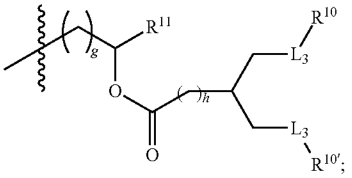

wherein:

f and h are 0;

g is 1 or 2;

$R^9$ is a $C_6$-$C_{20}$ chain having the formula —$(CH_2)_i[L_4$-$(CH_2)]_j$—$R^{12}$, wherein:

$L_4$ is selected from

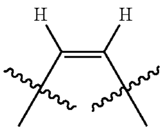

, and

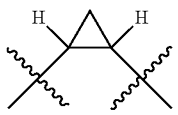

;

i is an integer in the range 6-20;

j is 0, 1, or 2;

$R^{12}$ is H or $C_4$-$C_8$ alkyl;

$R^{9'}$ is H or $C_4$-$C_{10}$ alkyl;

$R^{10}$ and $R^{10'}$ are each independently $C_4$-$C_{10}$ alkyl;

$L_3$ is a direct bond;

$R^{11}$ is the same as $R^9$.

5. The compound of claim 1, wherein the compound is selected from the group consisting of:

PNI 101
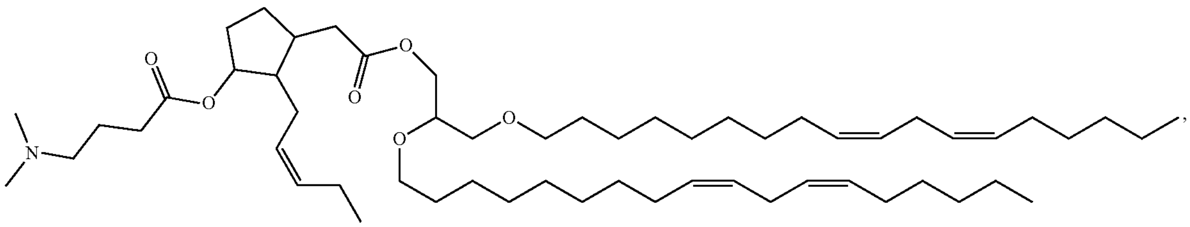
,
PNI 123
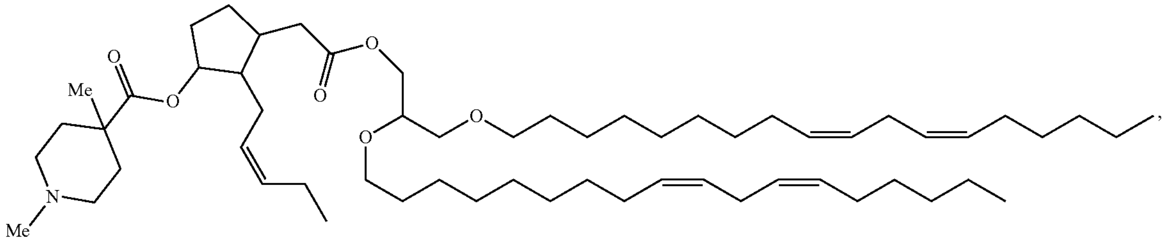
,
PNI 128
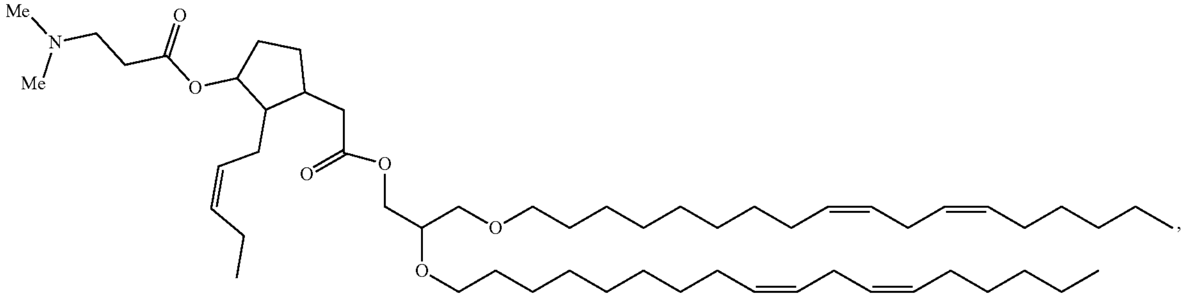
,
PNI 132
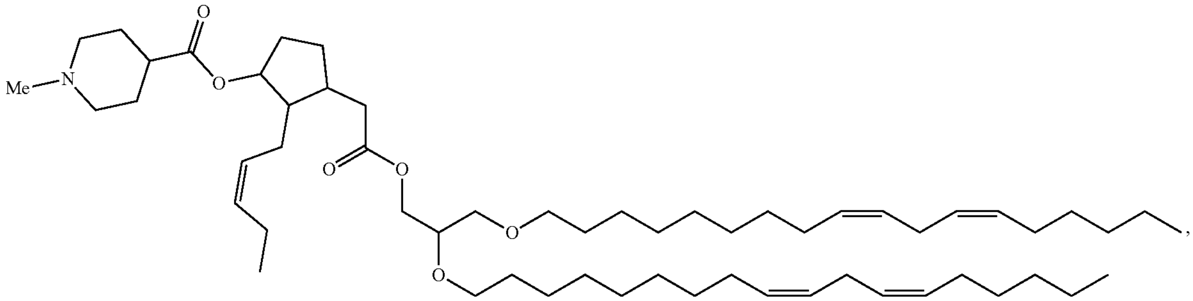
,
PNI 135
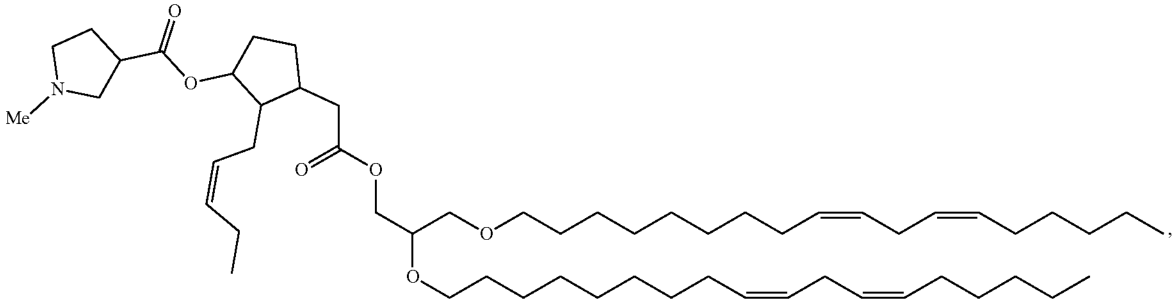
, -continued
PNI 143
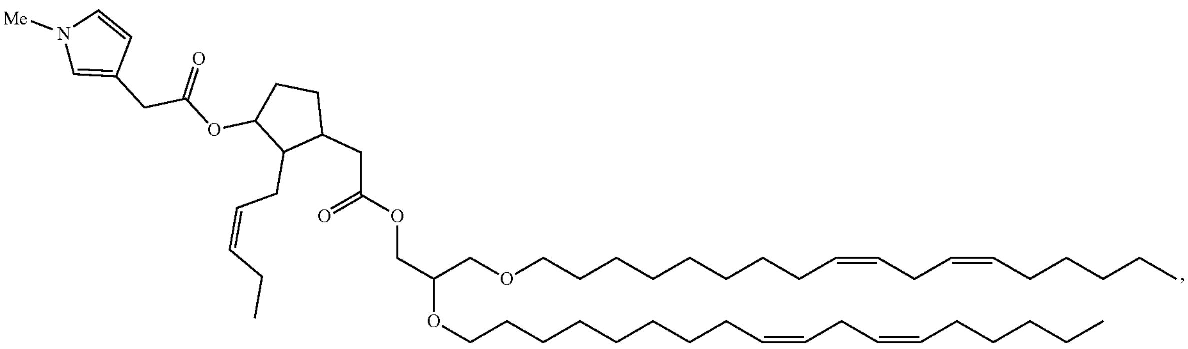
,
PNI 542
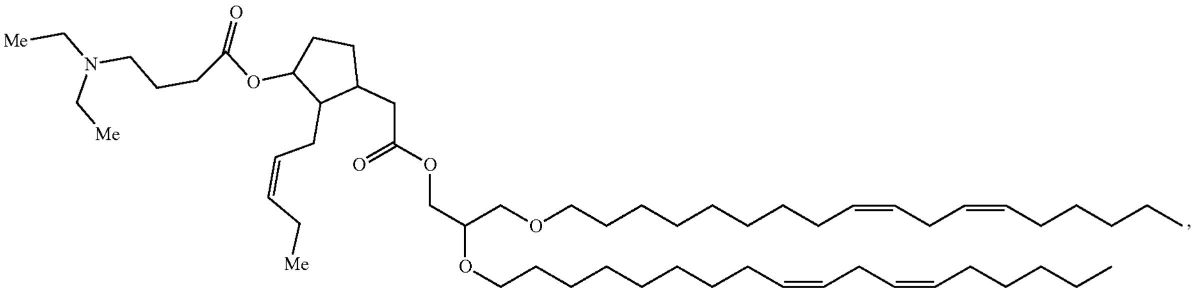
,
PNI 557
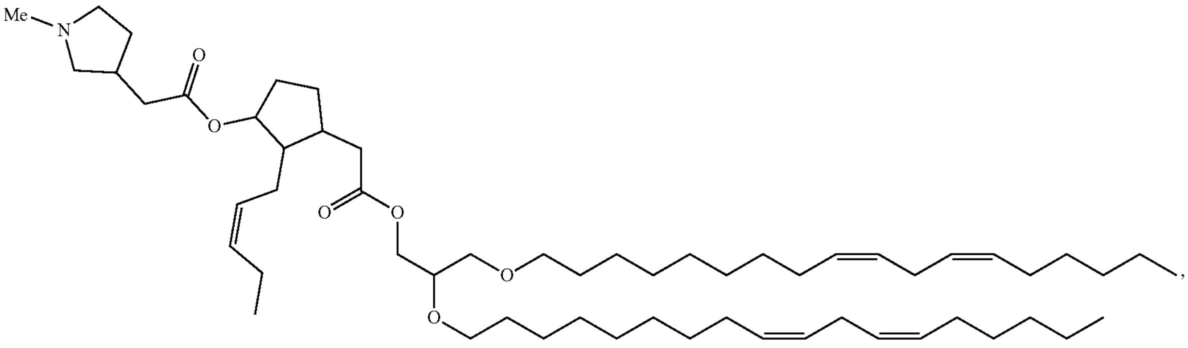
,
PNI 558
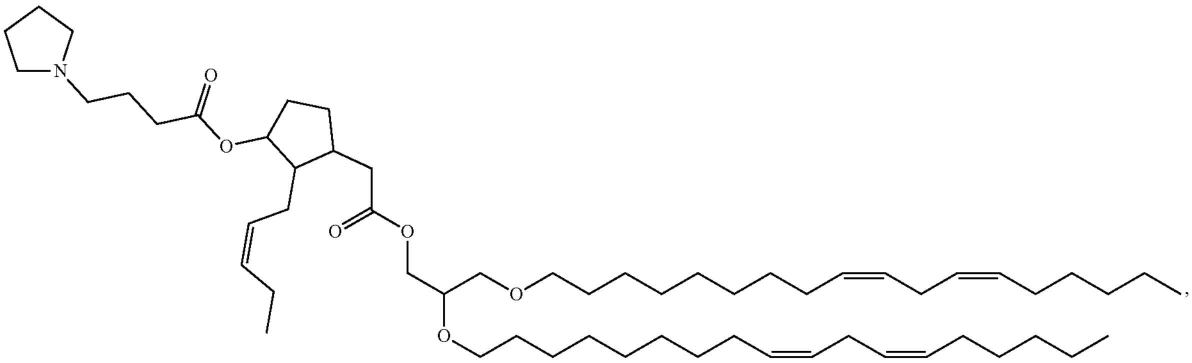
, -continued
PNI 559
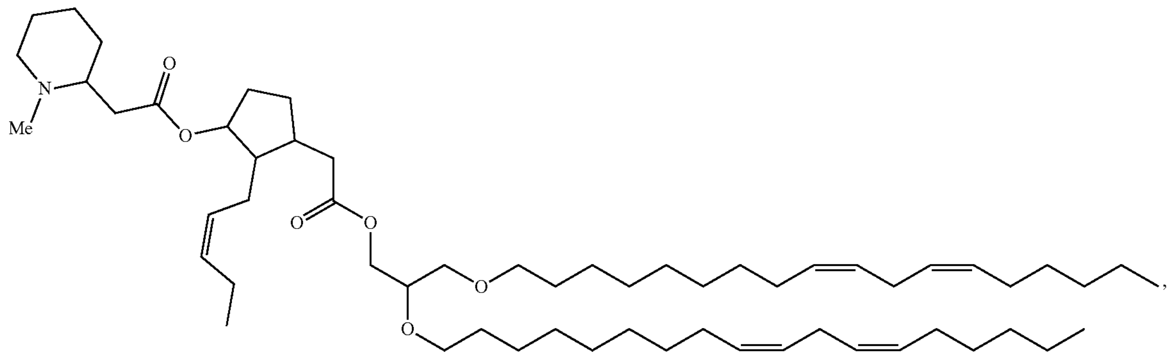
PNI 148
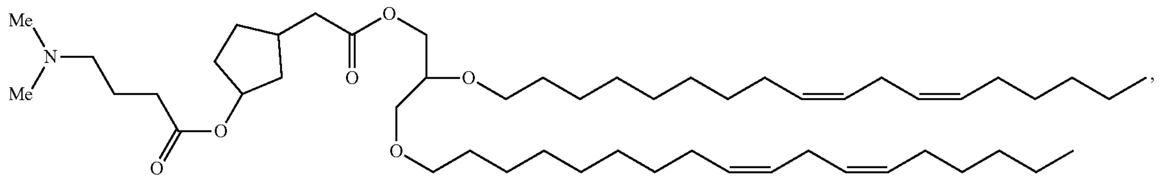
PNI 516
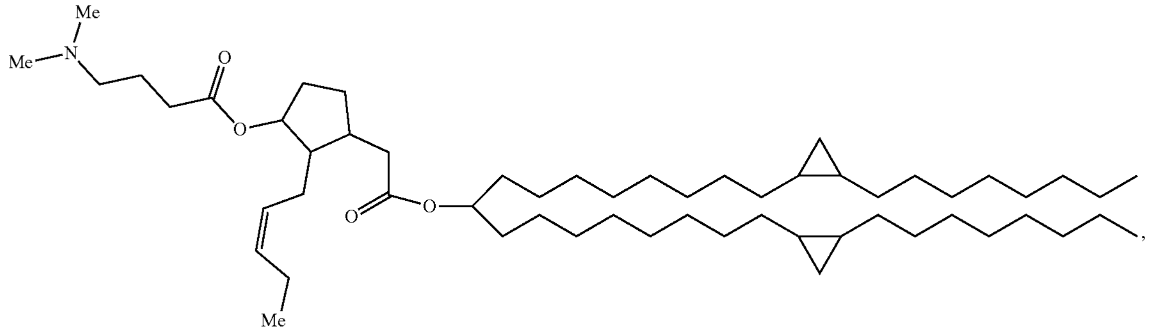
PNI 549
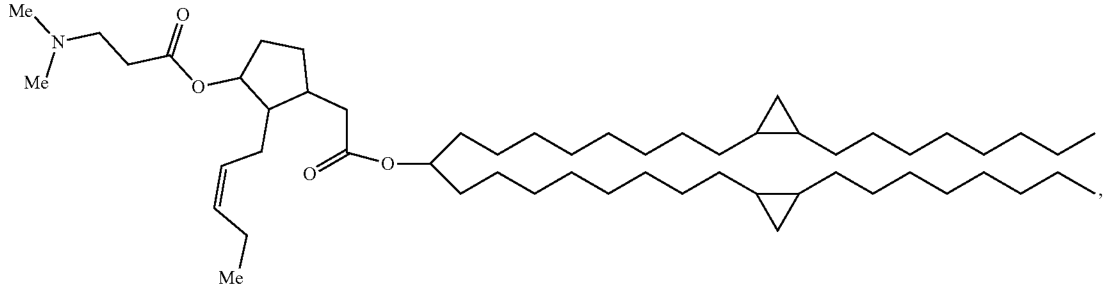
PNI 560
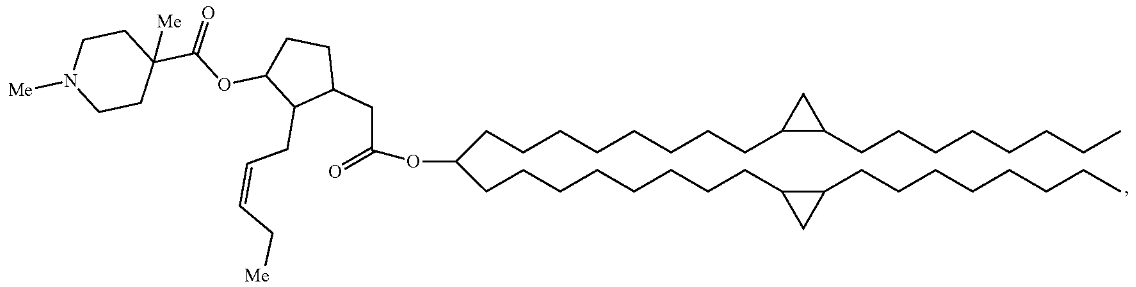

PNI 543
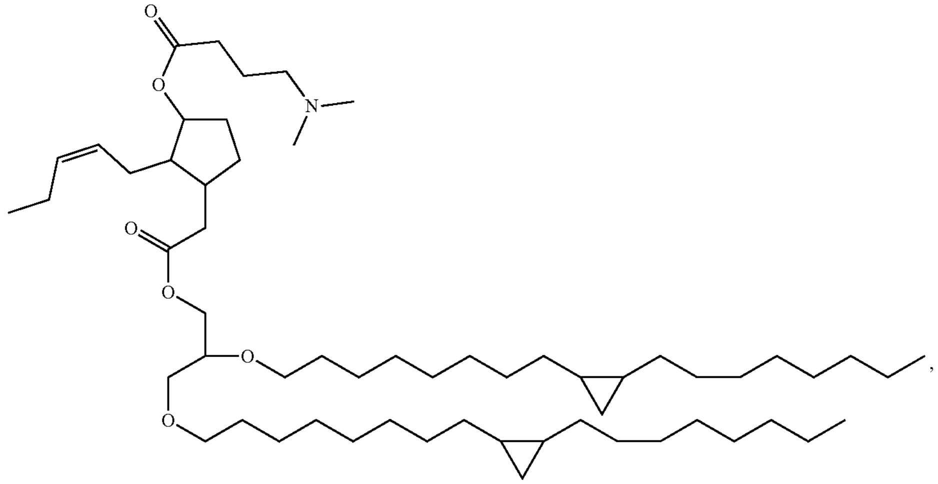
PNI 544
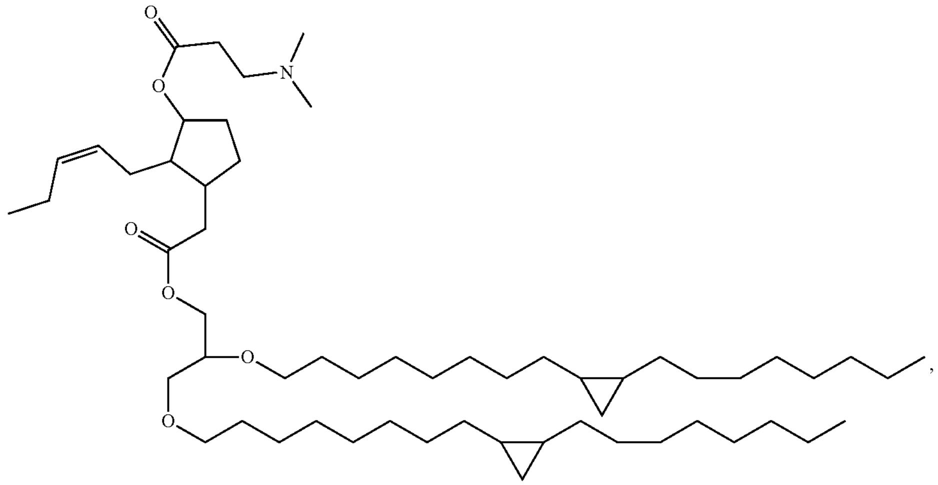
PNI 545
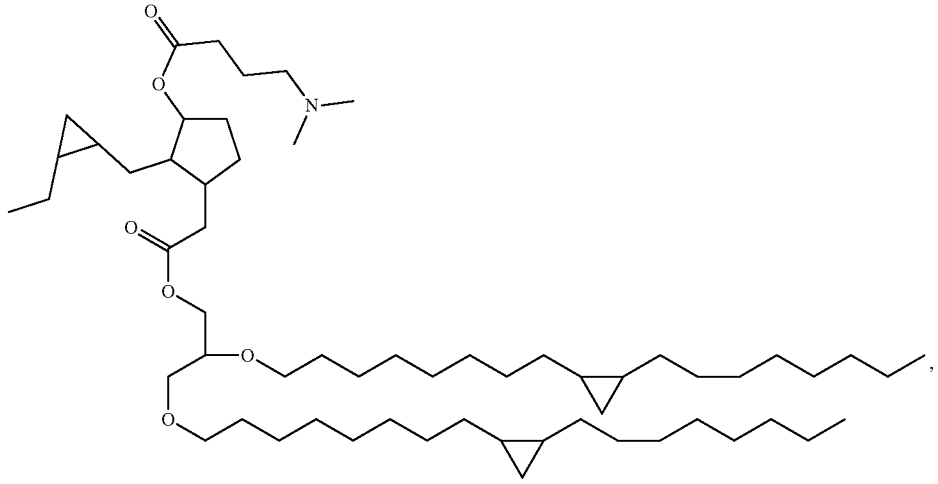

-continued
PNI 546
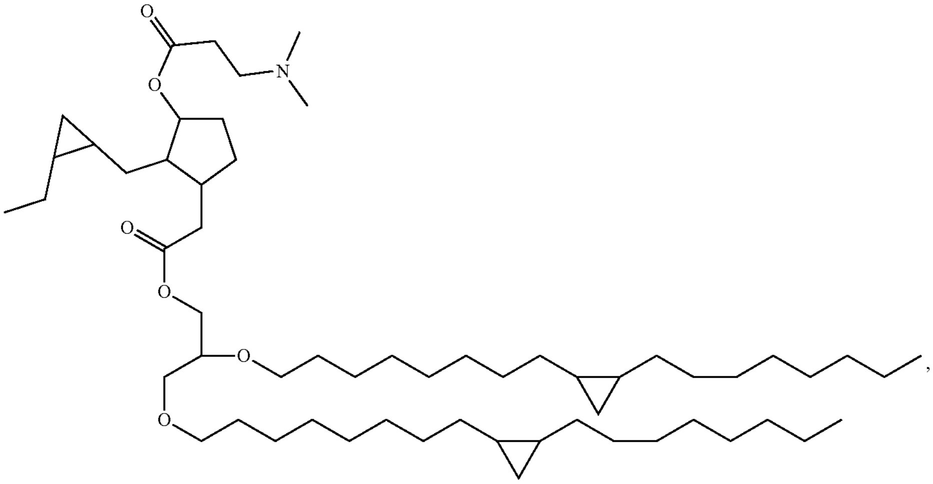
,
PNI 547
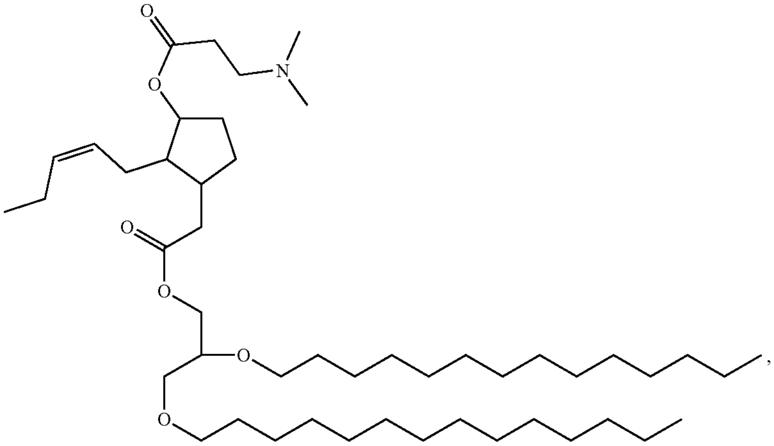
,
PNI 548
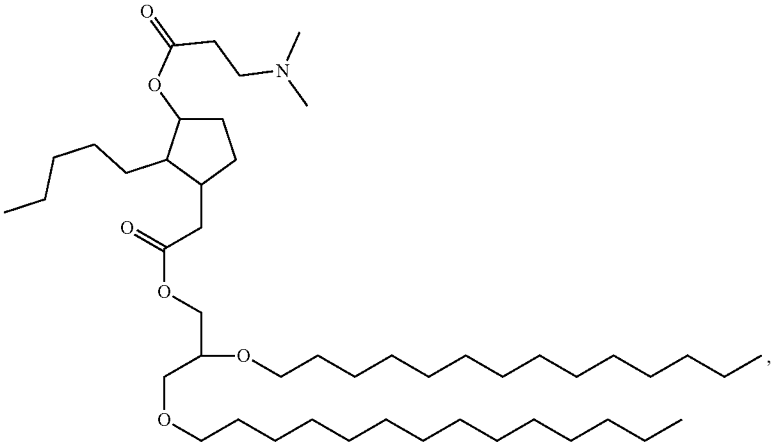
,

-continued
PNI 554
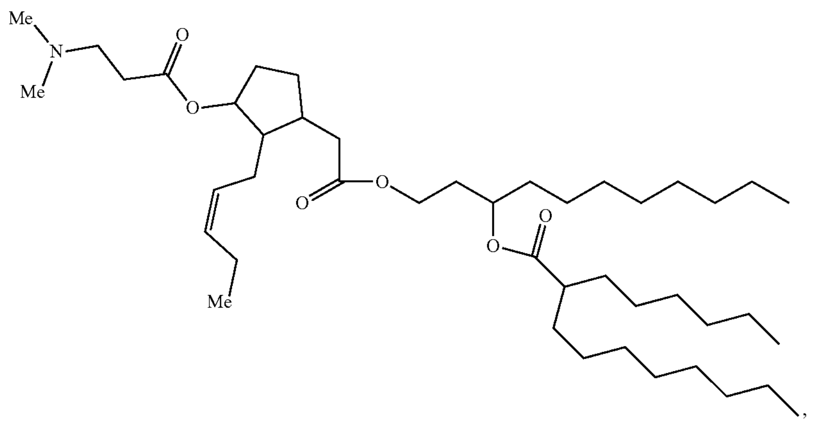
PNI 562
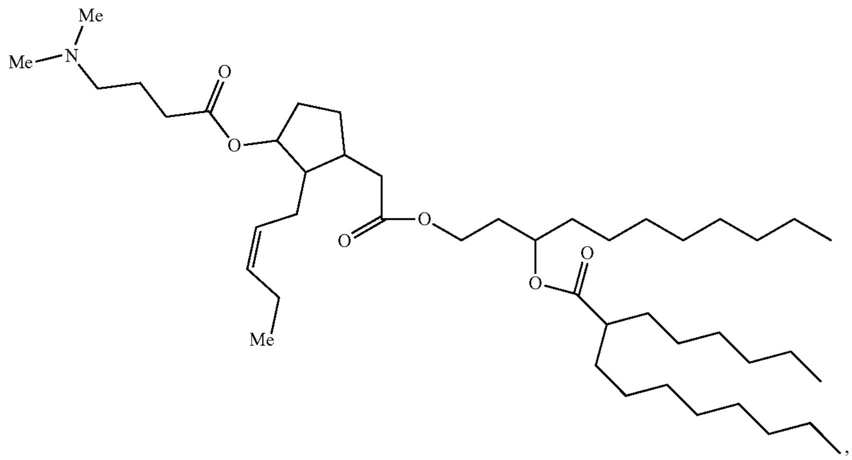
PNI 565
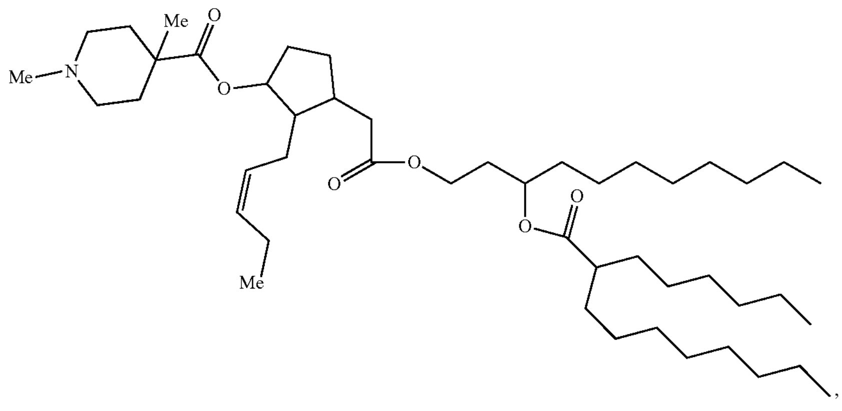

-continued
PNI 510
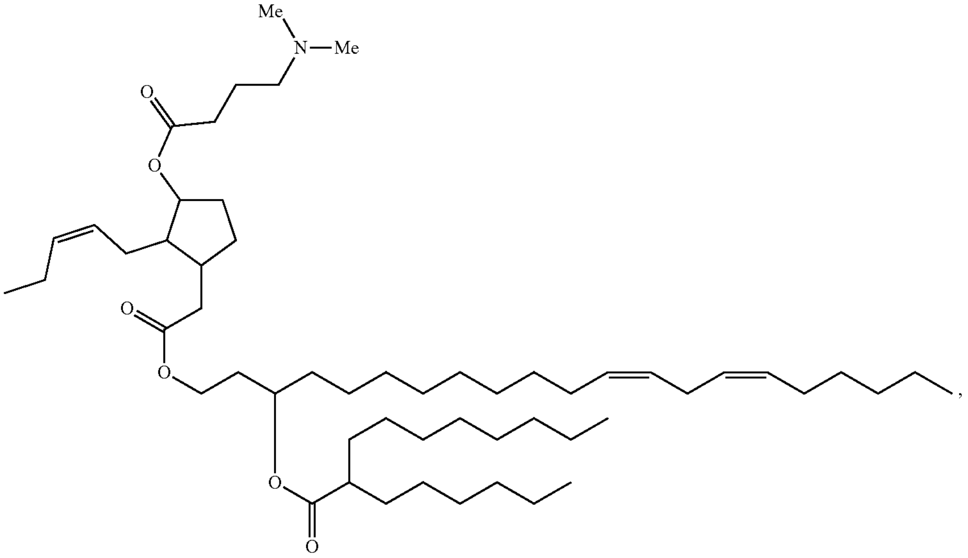
PNI 552
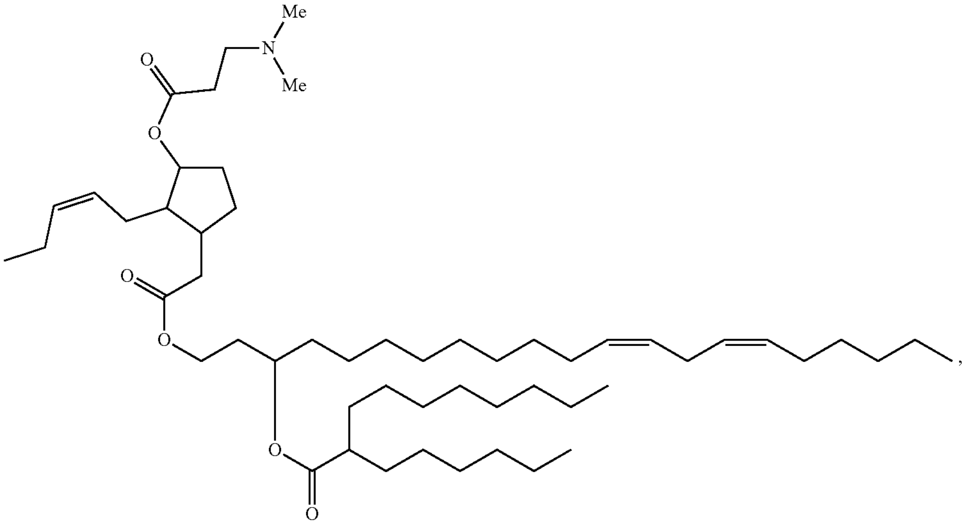
PNI 563
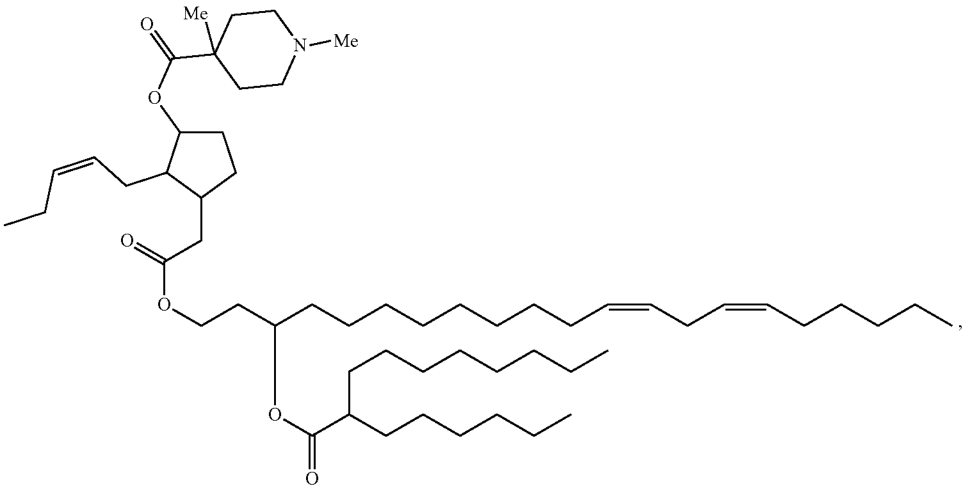

-continued
PNI 584
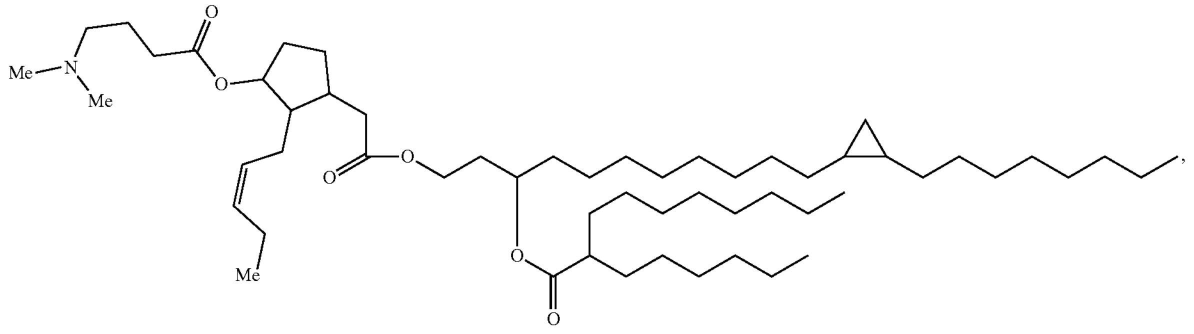
PNI 585
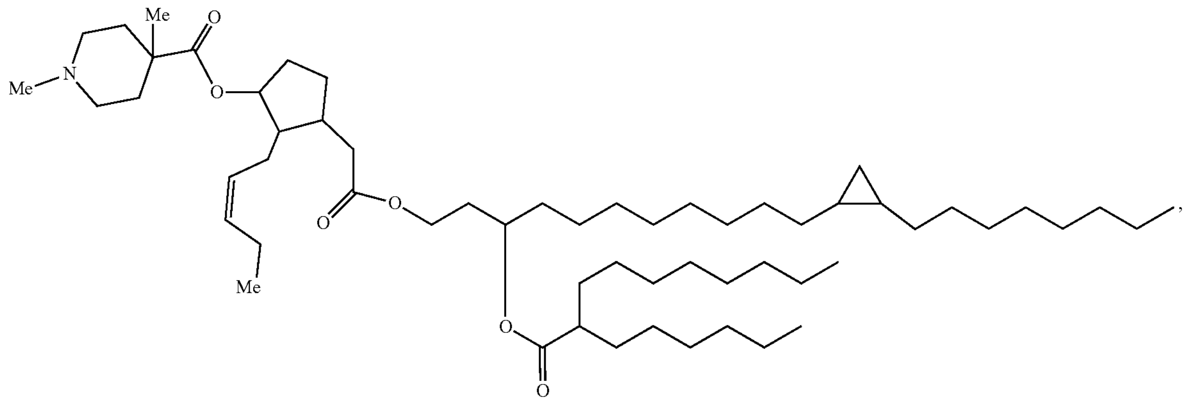
PNI 586
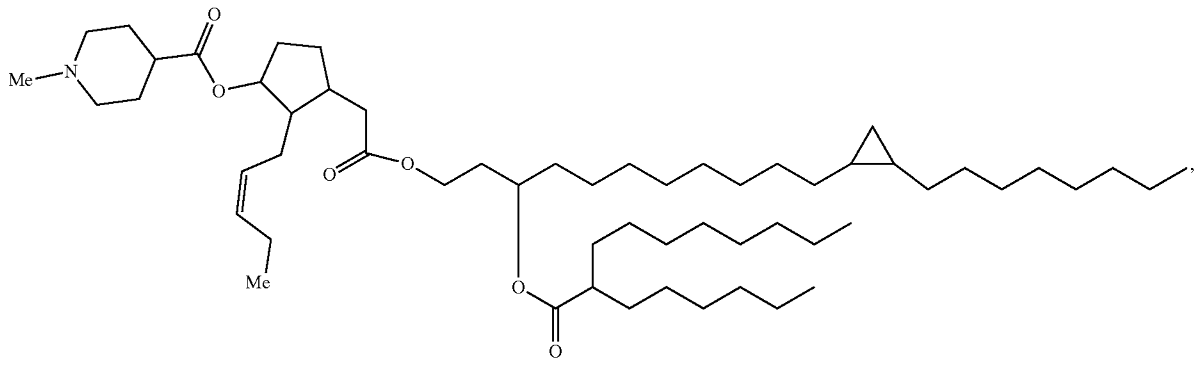

-continued
PNI 515
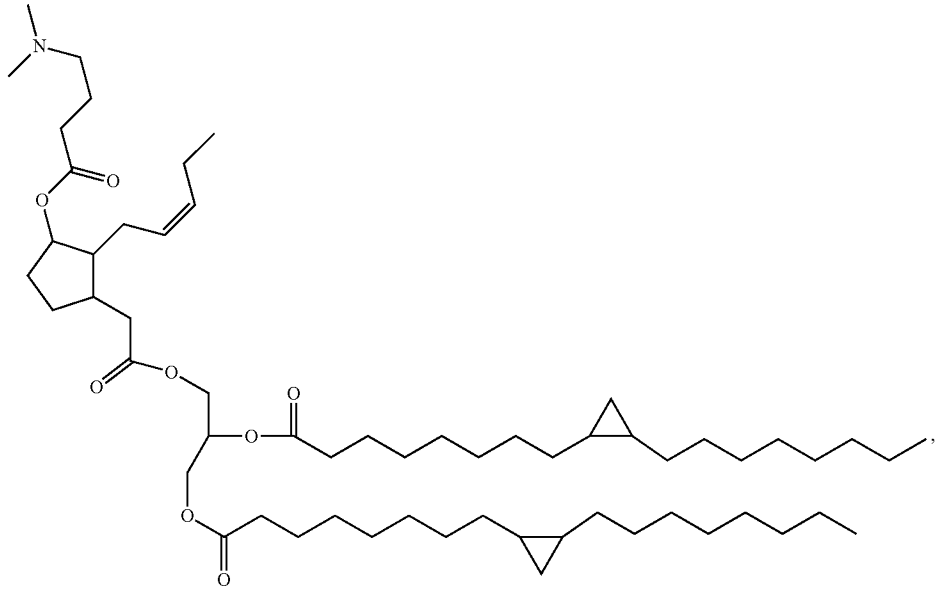
PNI 551
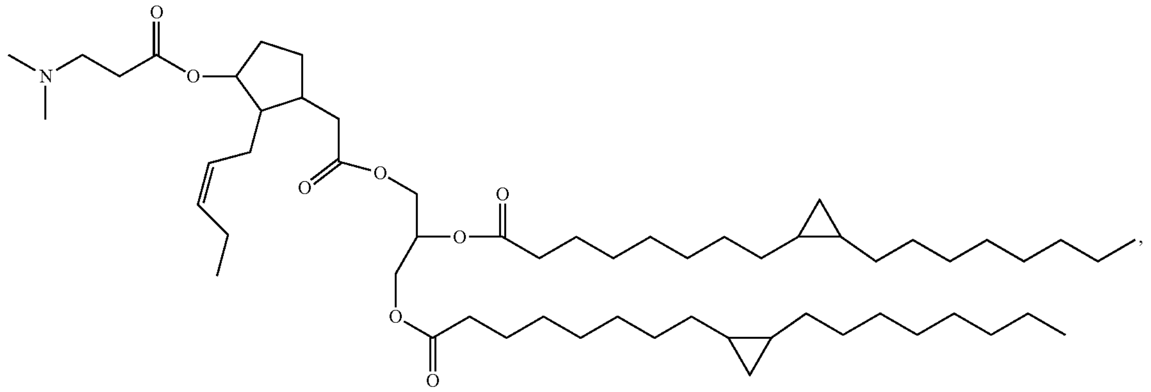
PNI 269
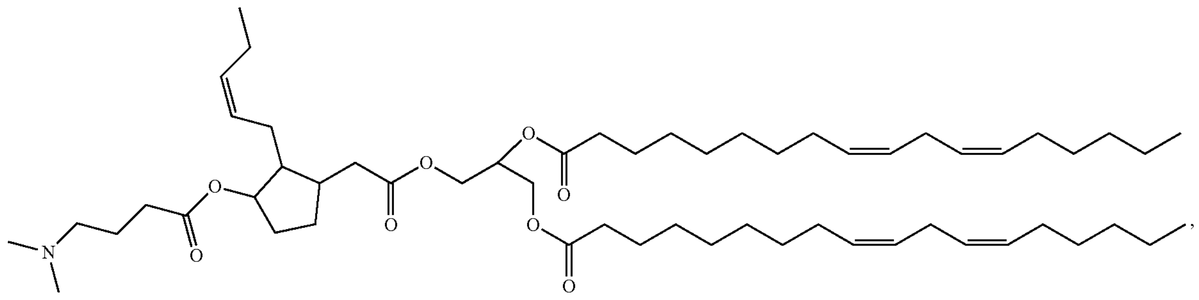
PNI 550
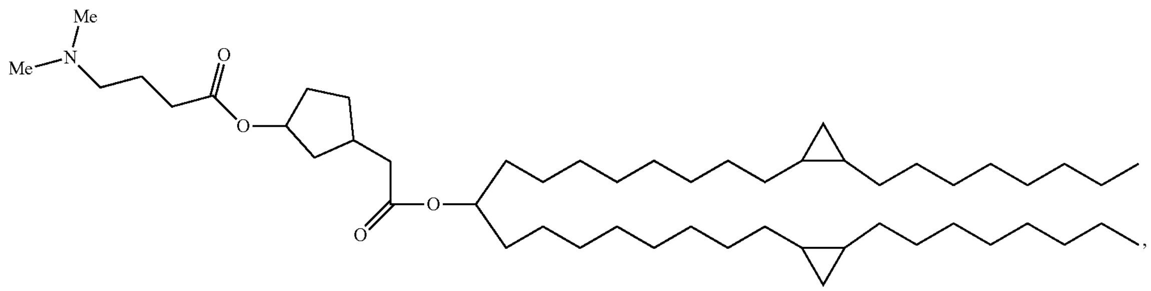

-continued
PNI 147
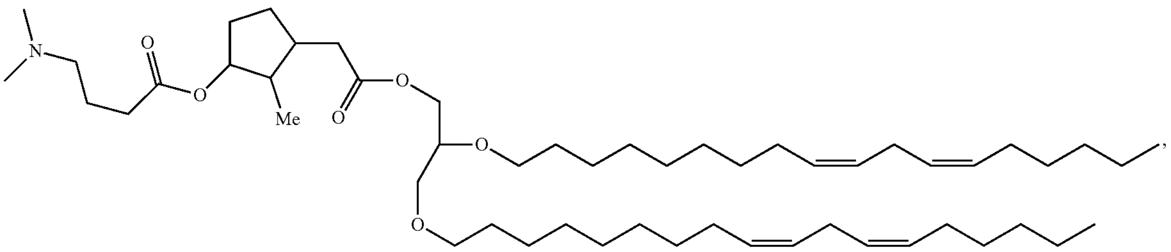
PNI 567
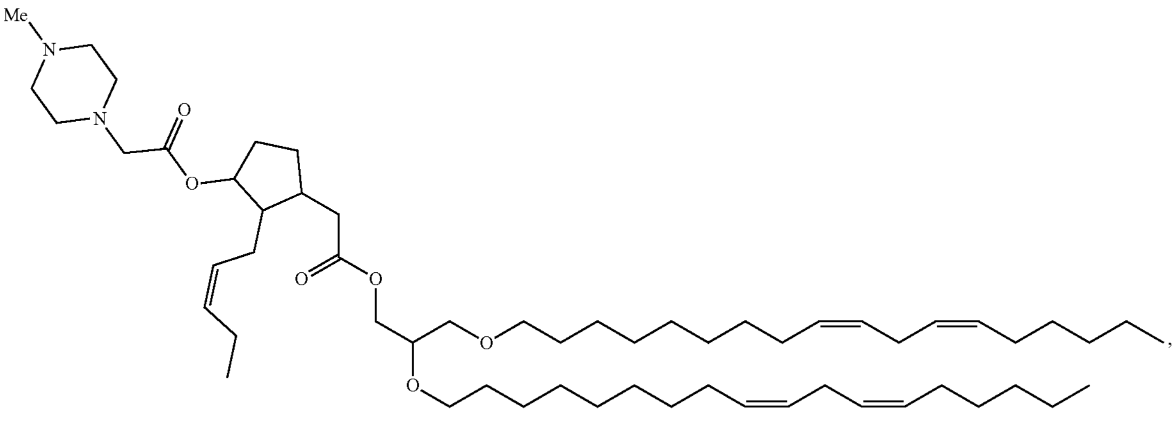
PNI 568
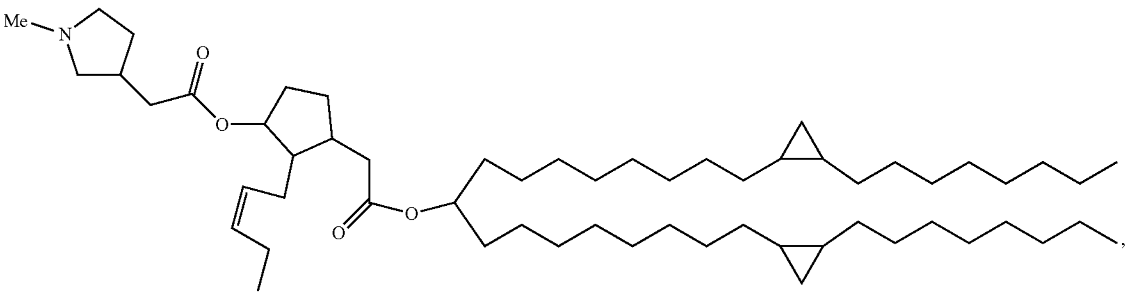
PNI 569
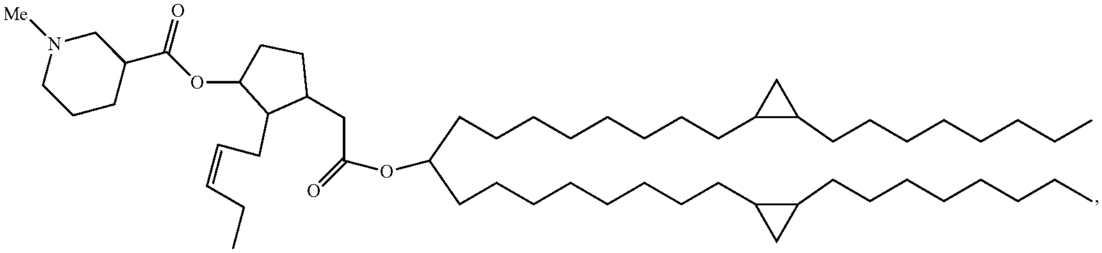
PNI 570
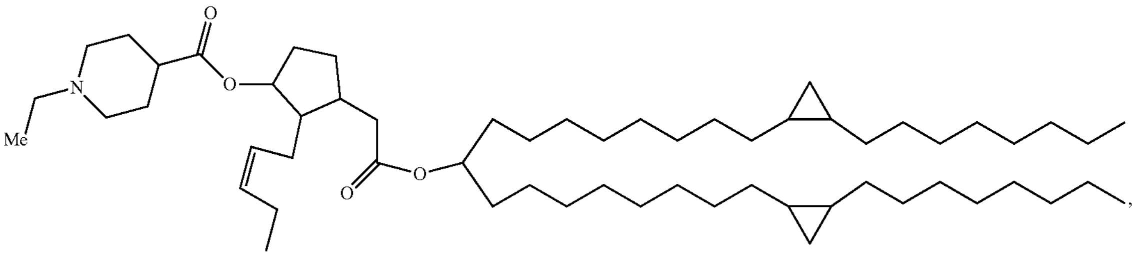

-continued
PNI 571
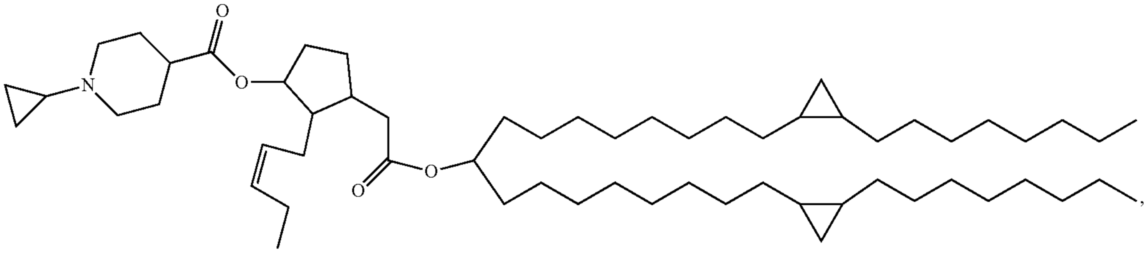
PNI 572
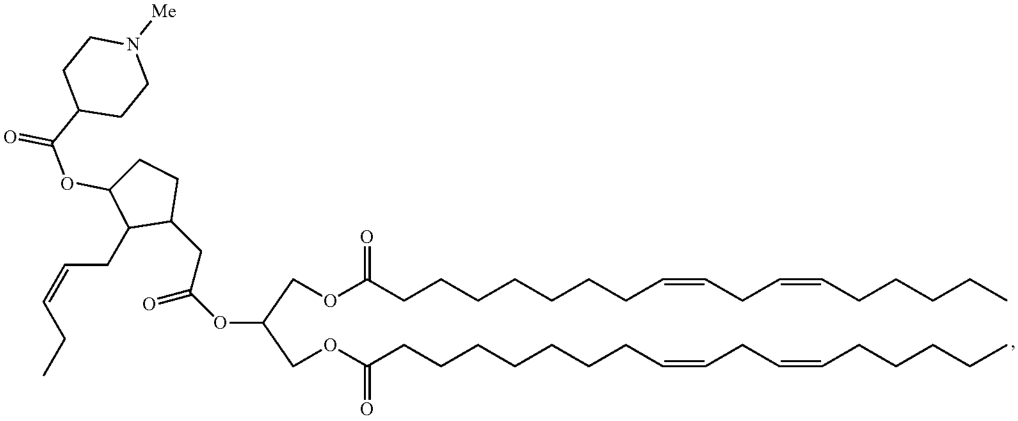
and
PNI 573
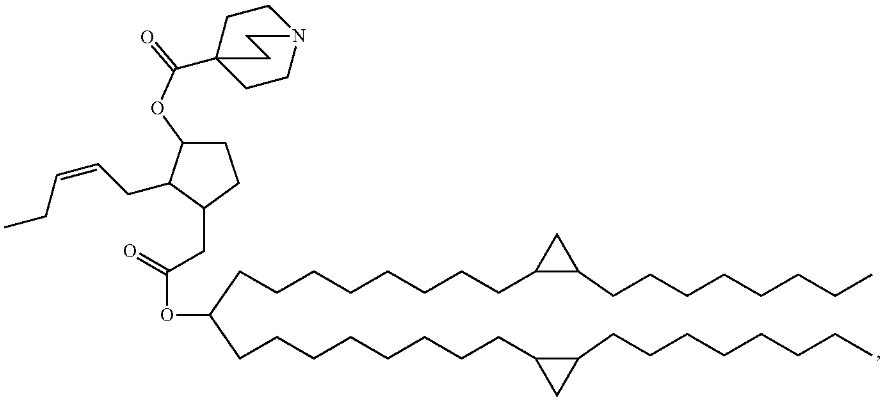
or a pharmaceutically acceptable salt thereof.
6. The compound of claim 1, wherein the compound is selected from the group consisting of:
PNI 587
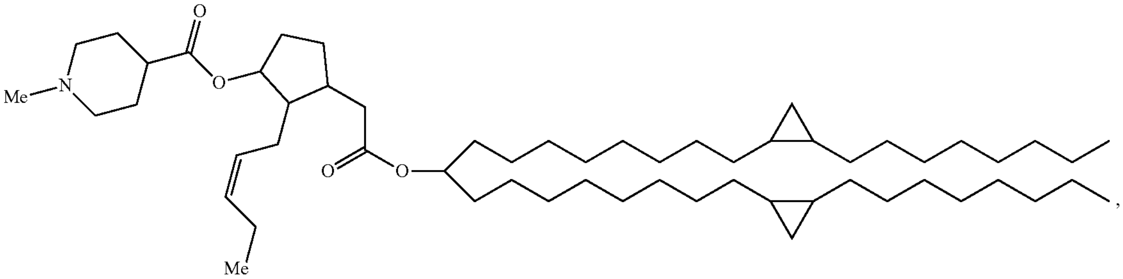

-continued
PNI 588
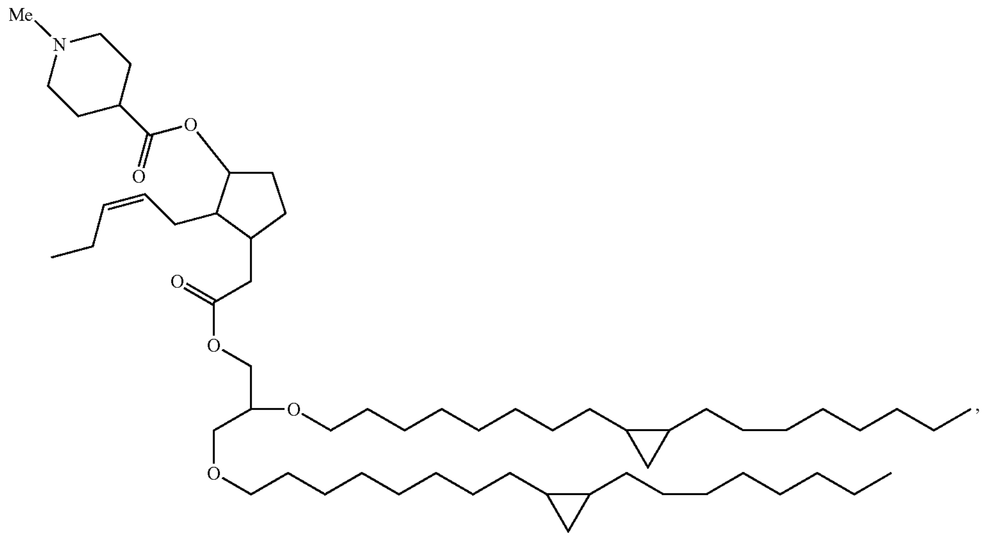
PNI 589
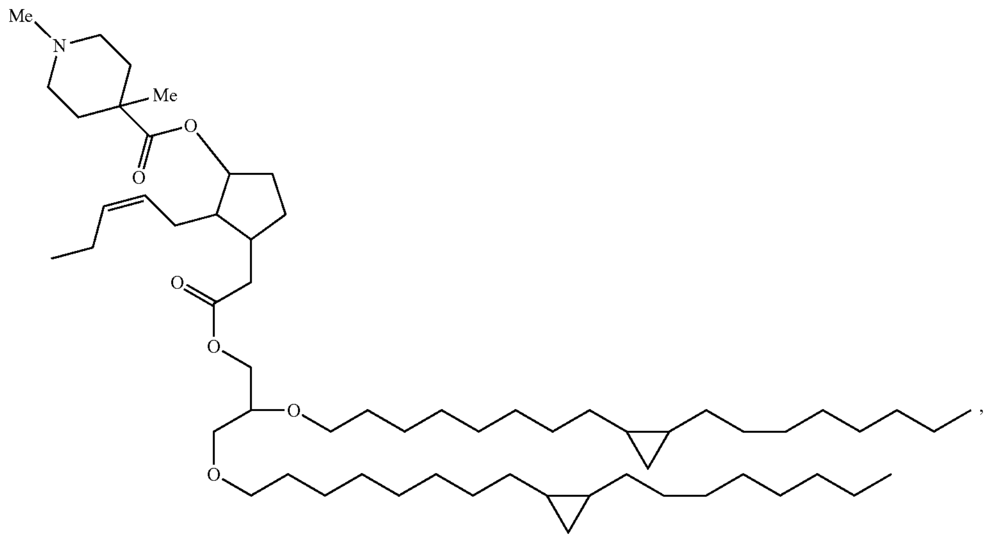
PNI 590
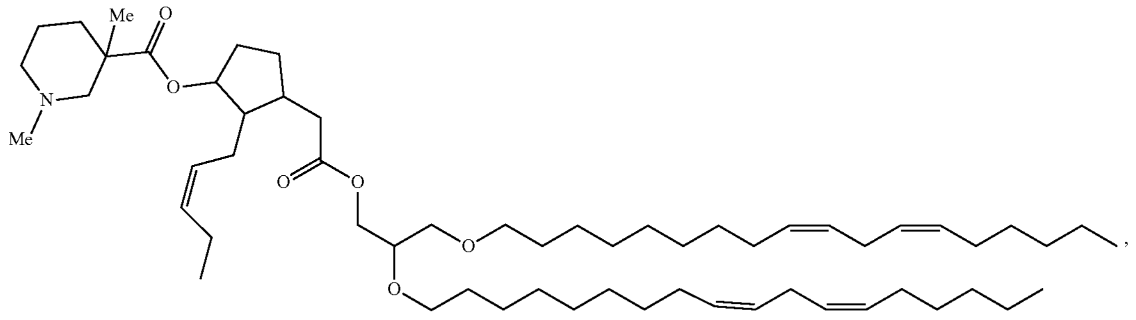

-continued
PNI 591
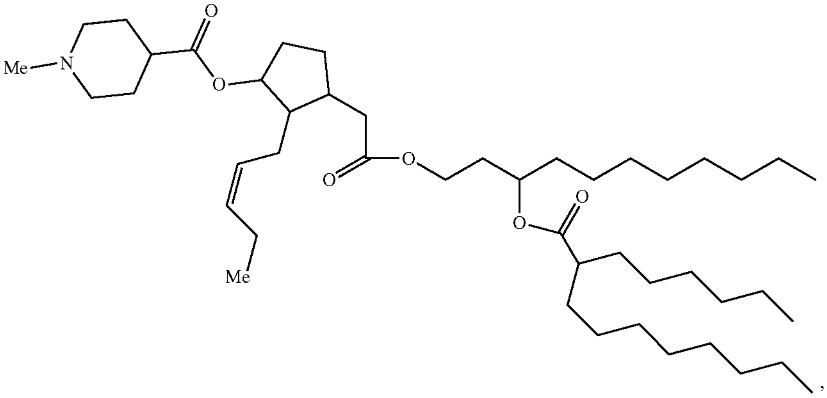
,
PNI 592
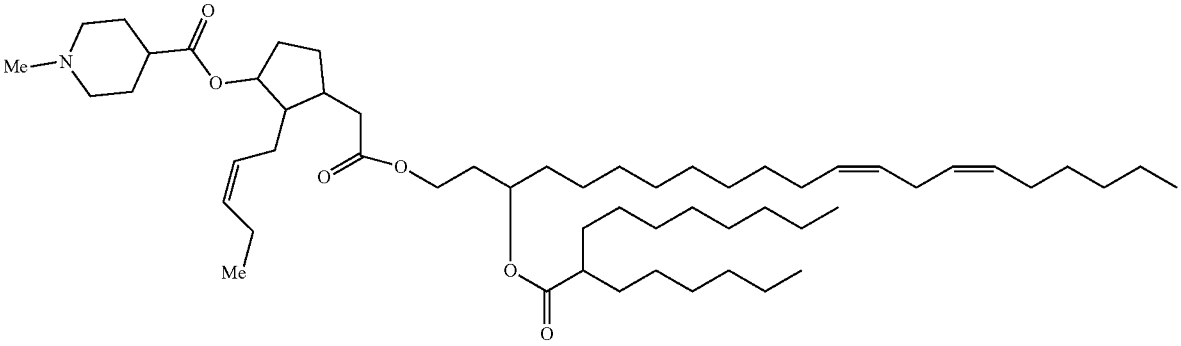
,
PNI 271
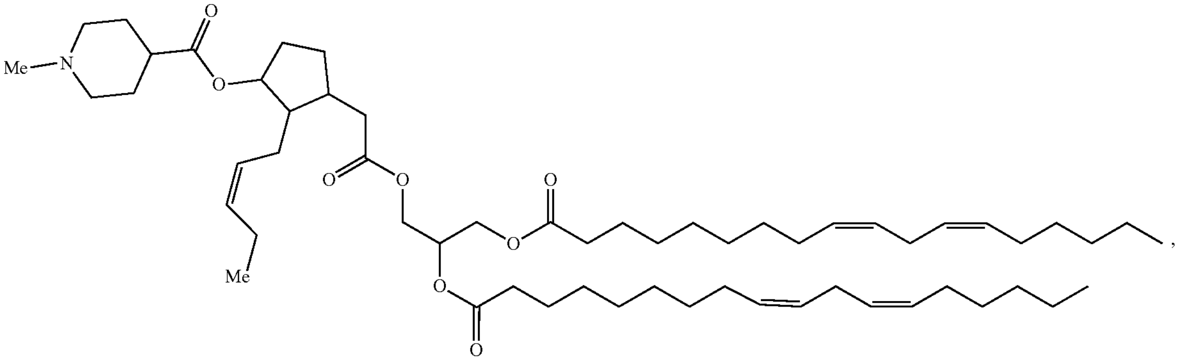
,
PNI 272
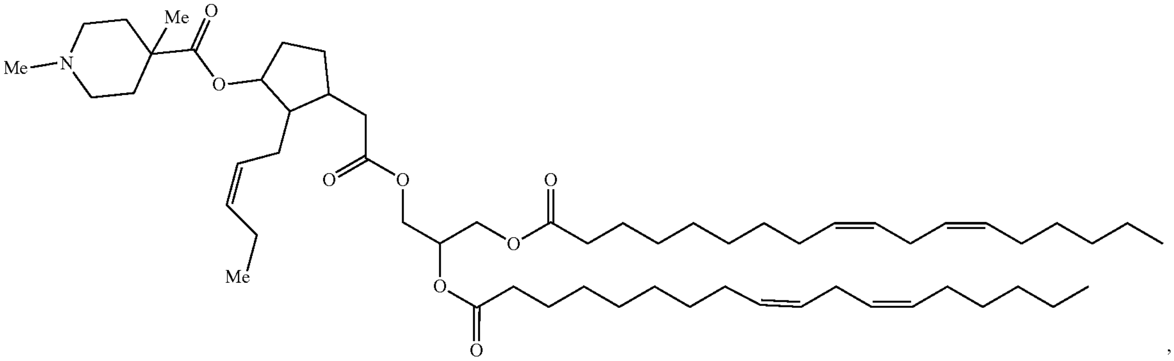
, -continued
PNI 593
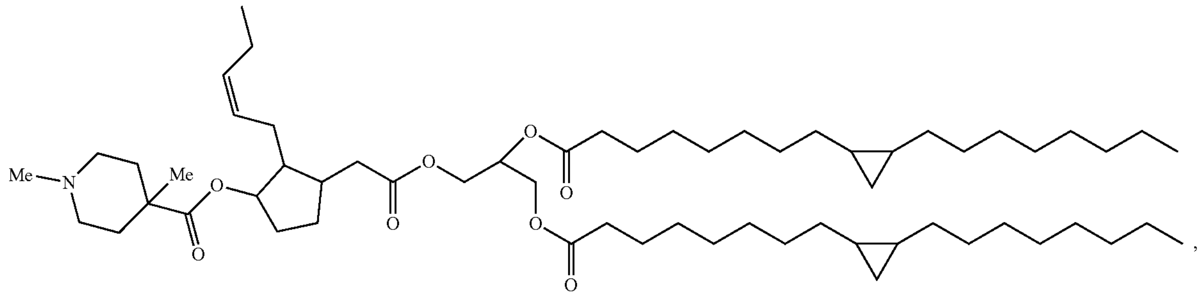
PNI 594
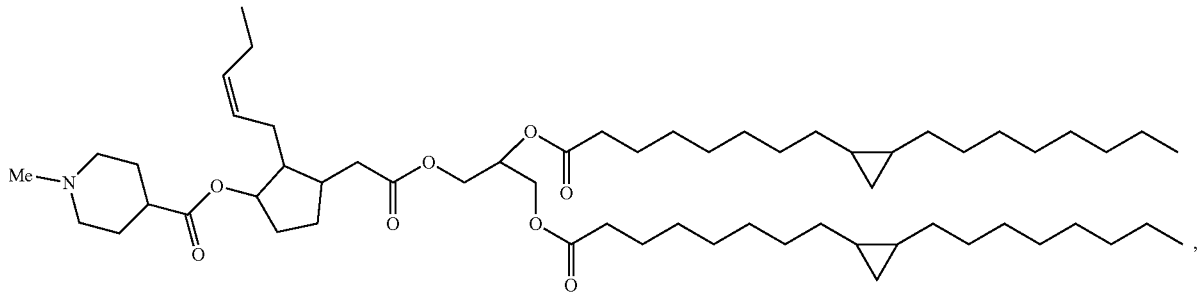
PNI 595
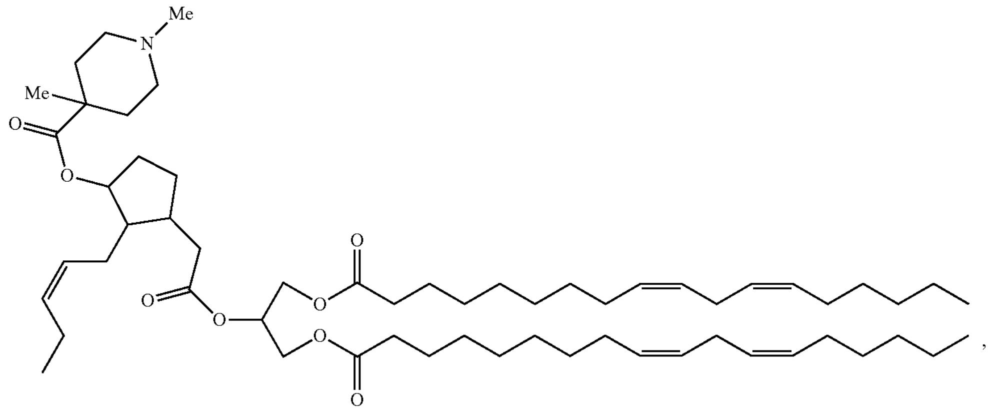
PNI 596
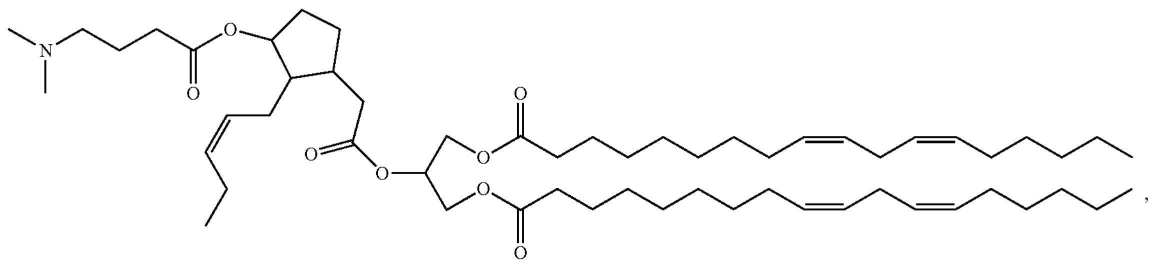

-continued
PNI 597
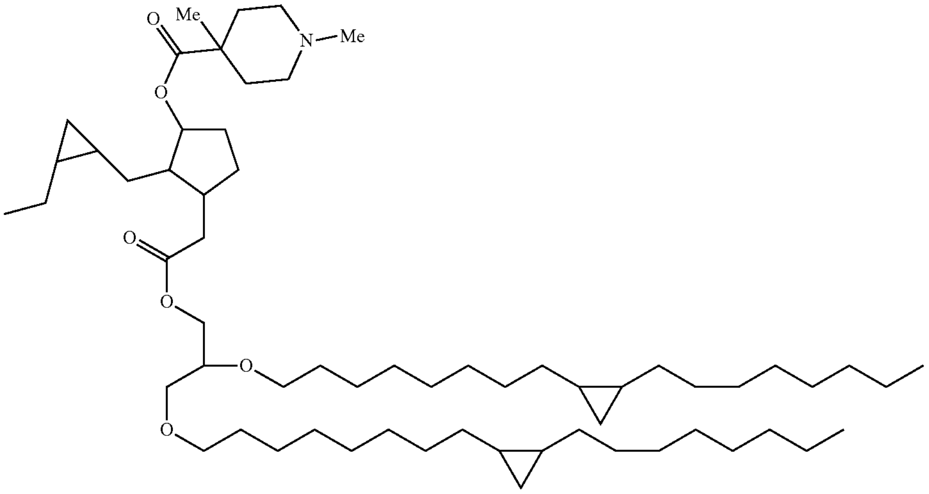
,
PNI 598
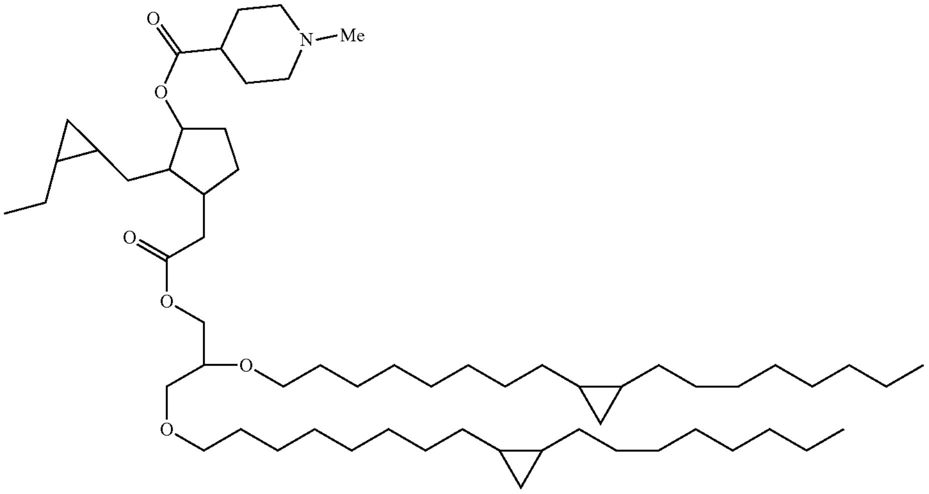
,
PNI 566
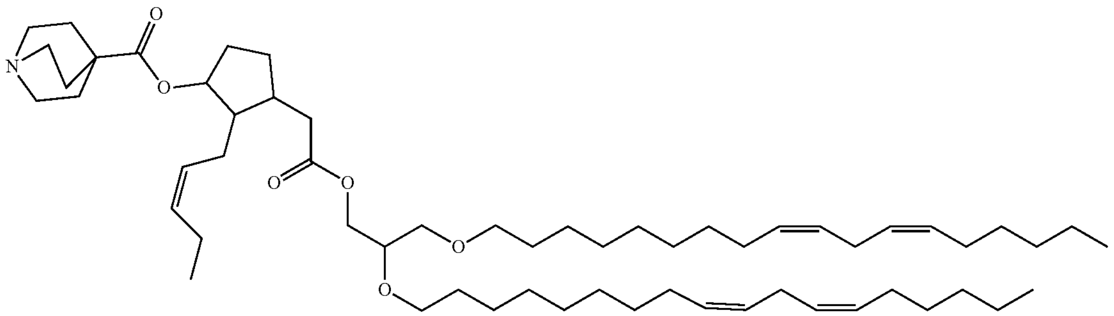
,

-continued
PNI 599
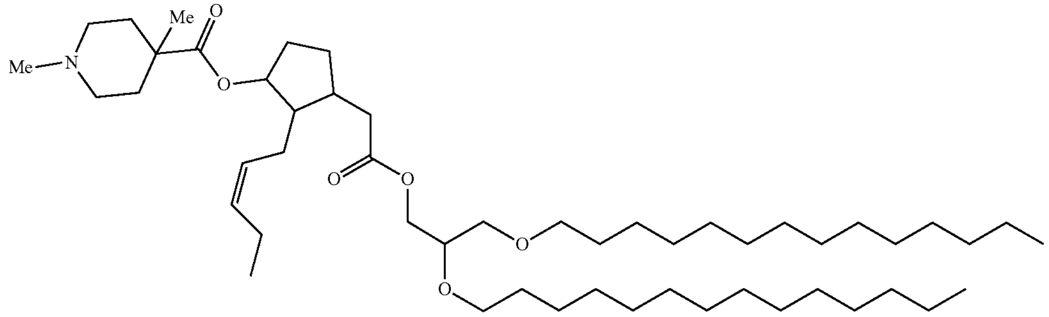
,
PNI 600
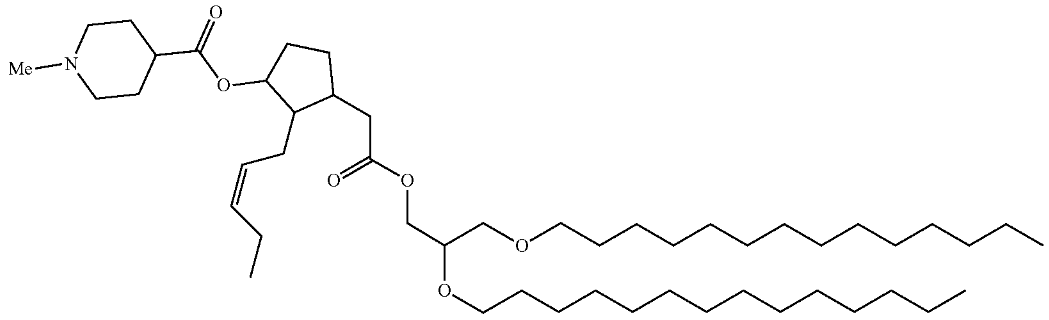
,
PNI 150
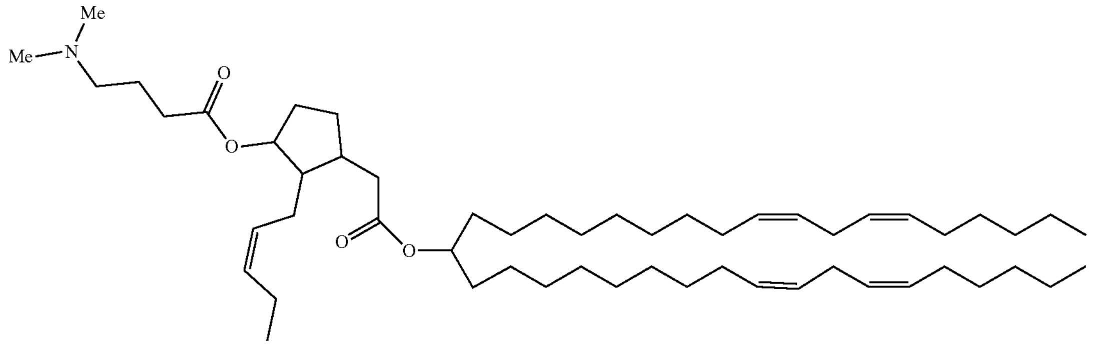
,
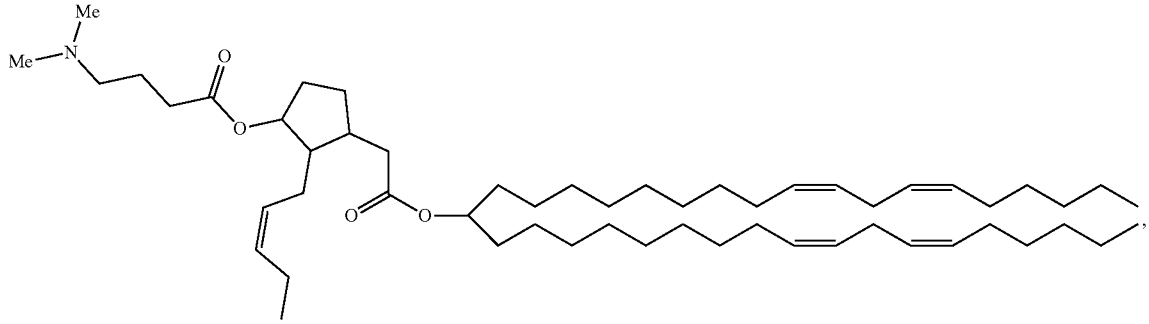
, -continued
PNI 154
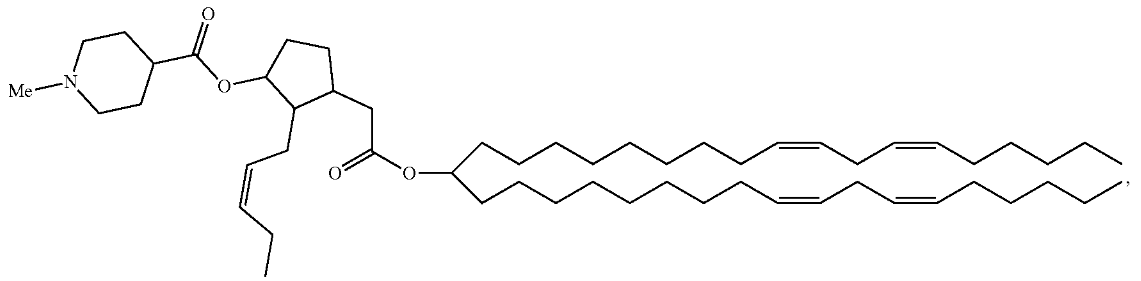
PNI 155
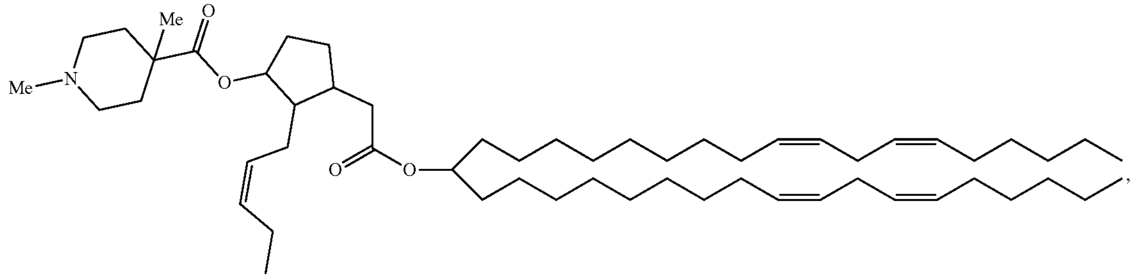
PNI 308
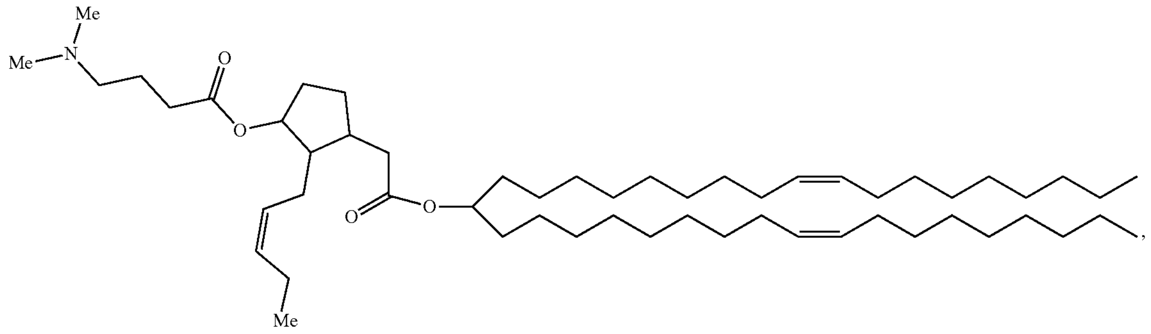
PNI 309
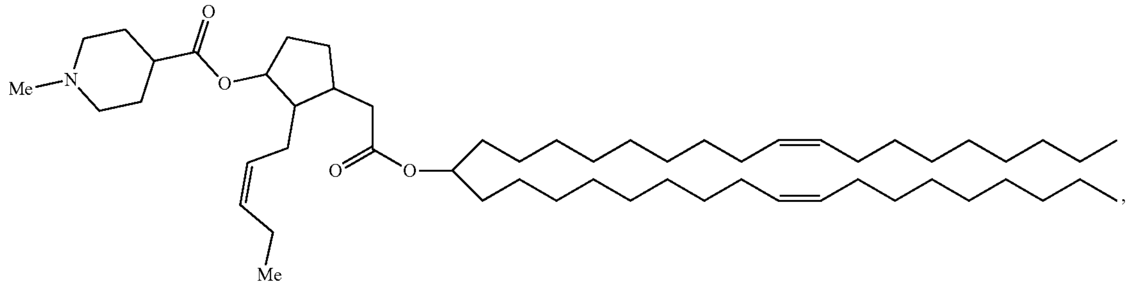
PNI 310
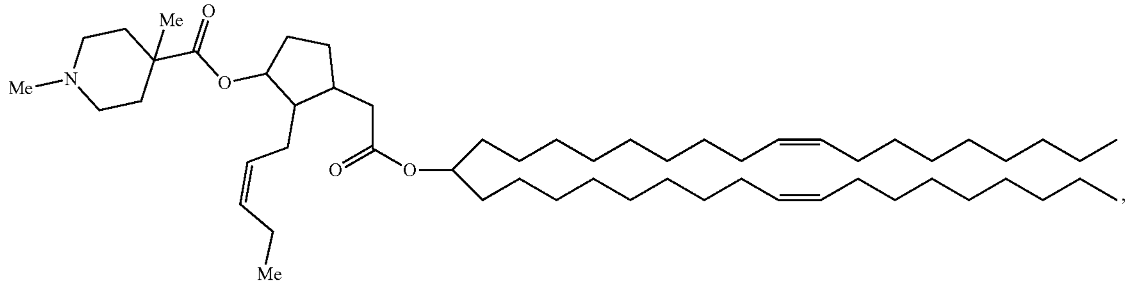

-continued
PNI 173
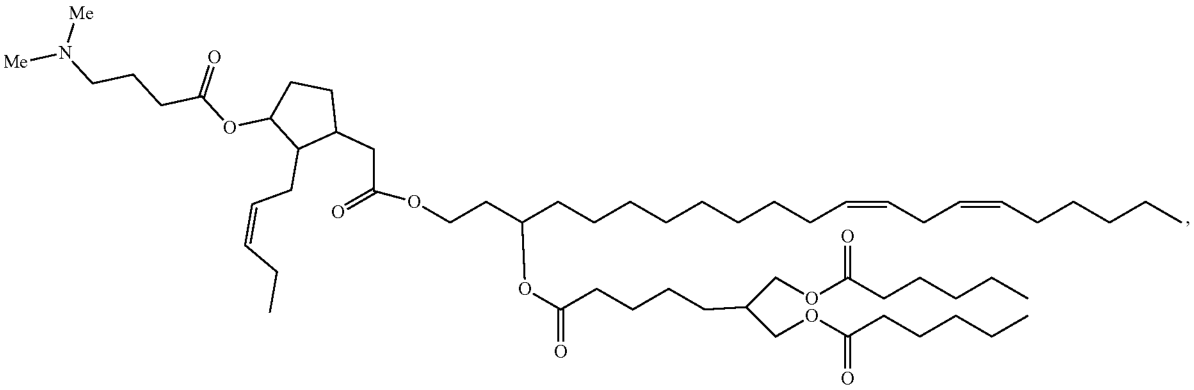
PNI 176
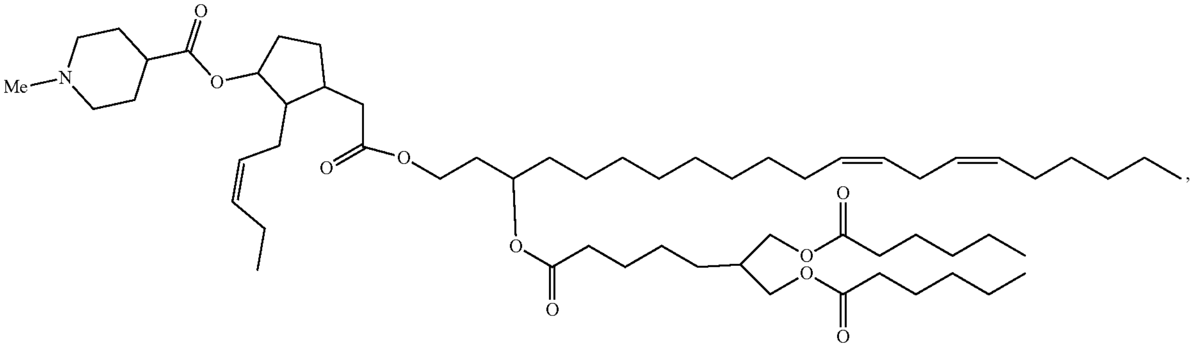
PNI 177
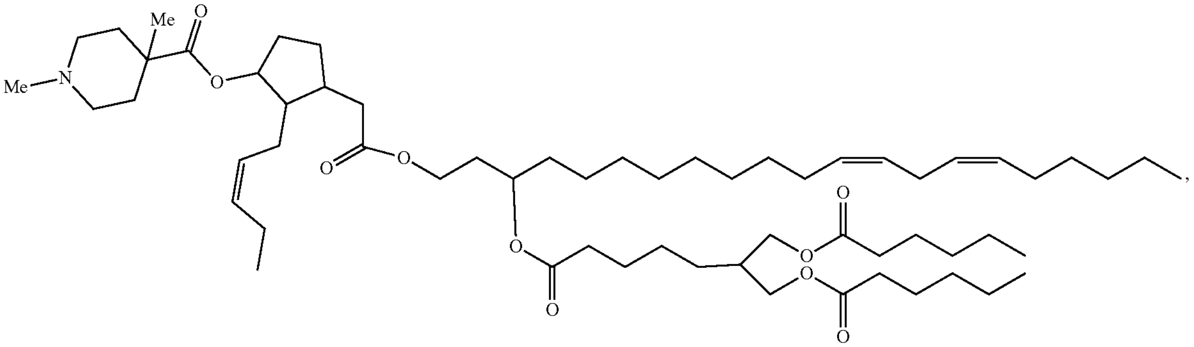
PNI 189
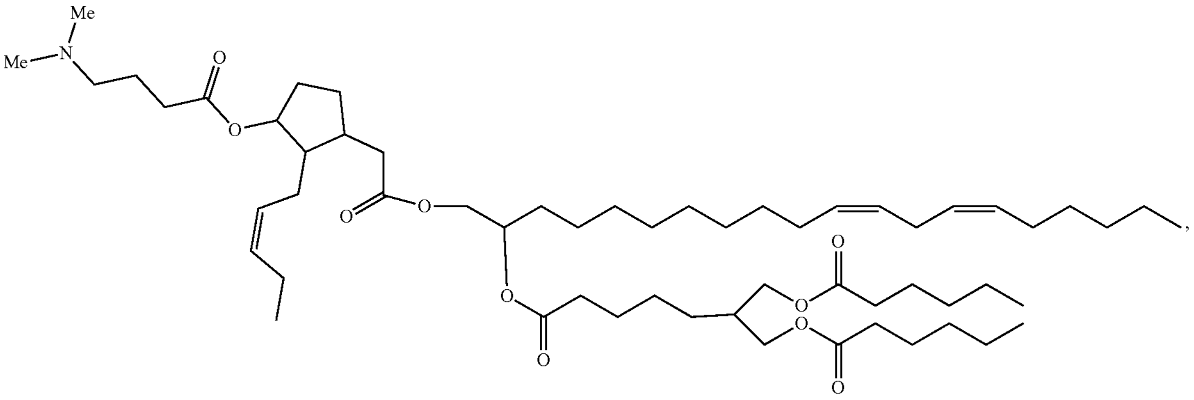

-continued
PNI 190
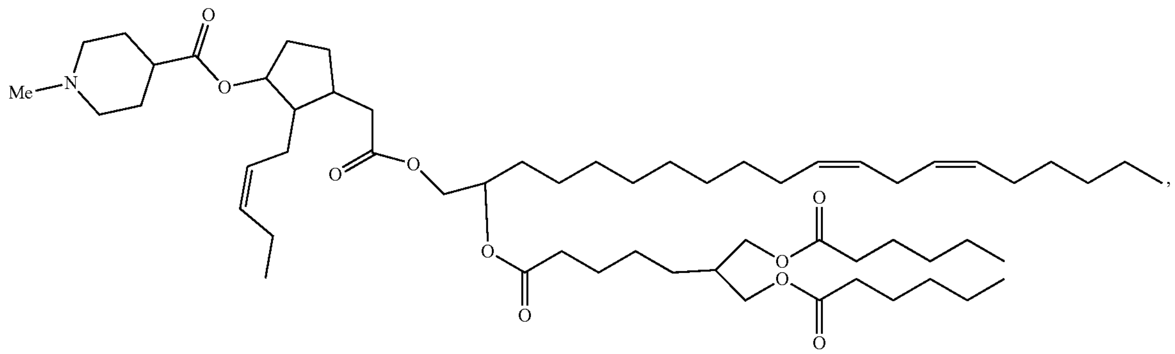
PNI 191
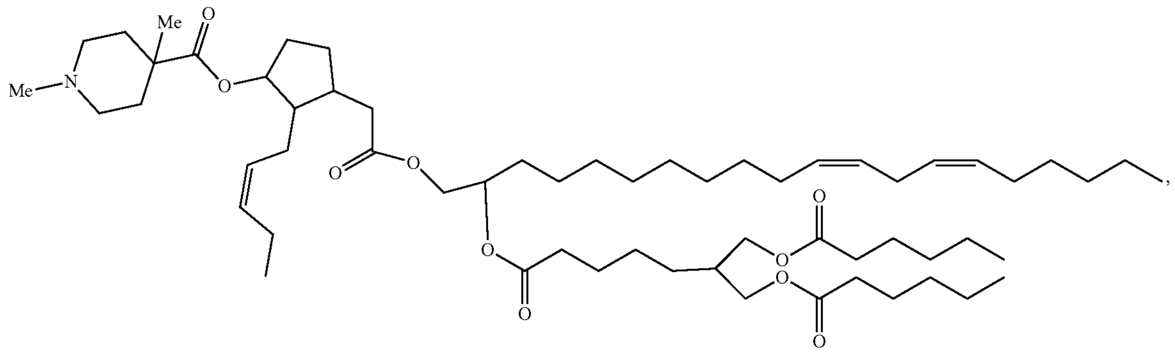
PNI 199
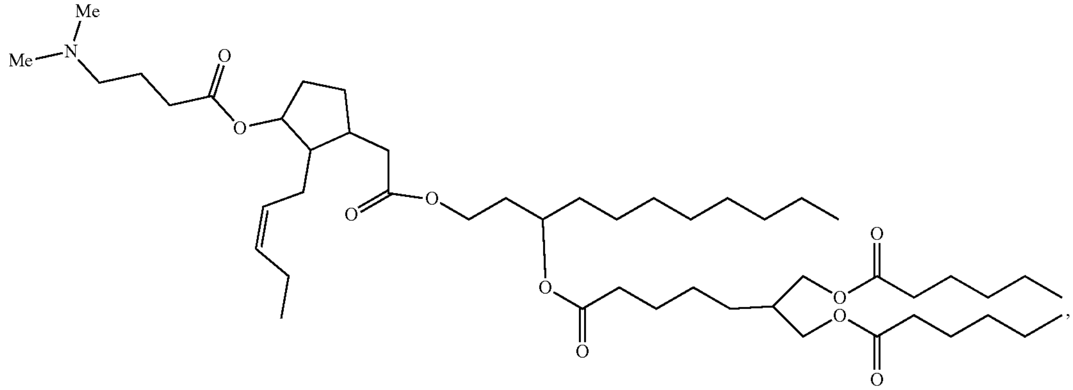
PNI 201
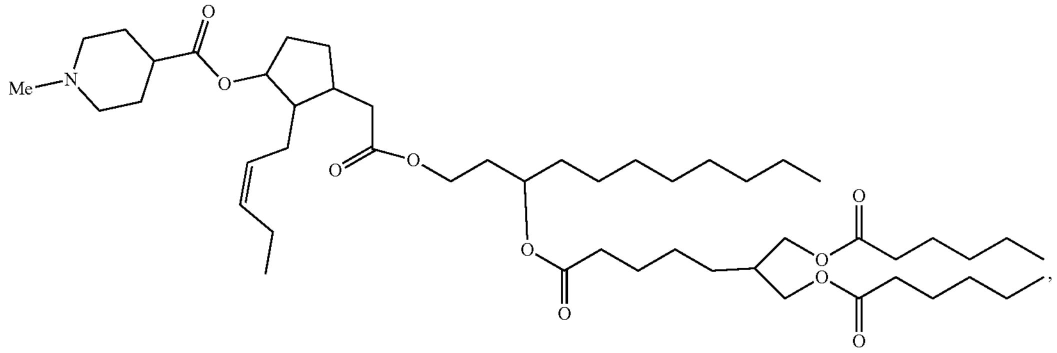

-continued
PNI 202
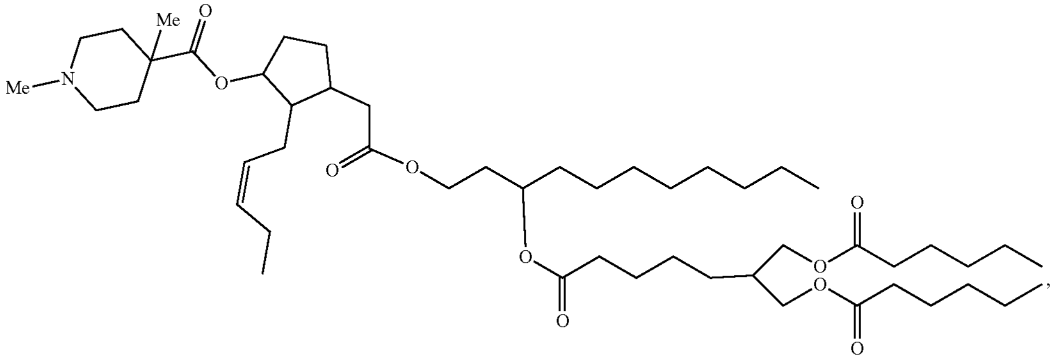
PNI 213
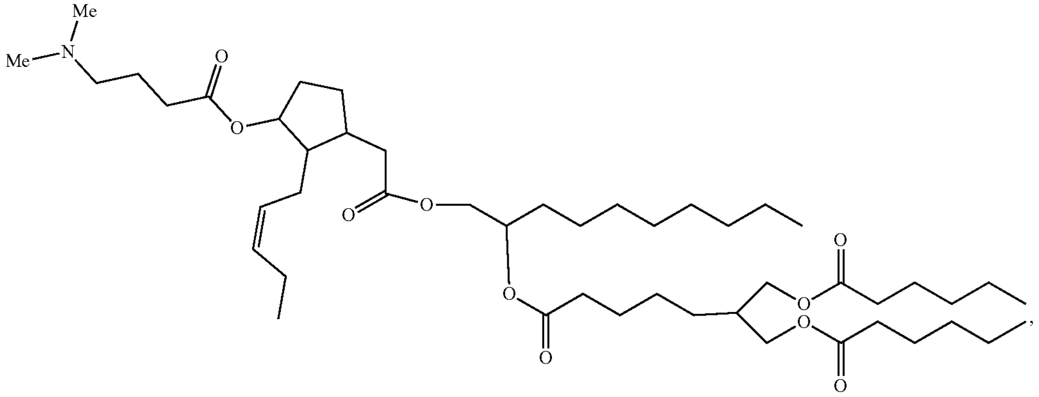
PNI 214
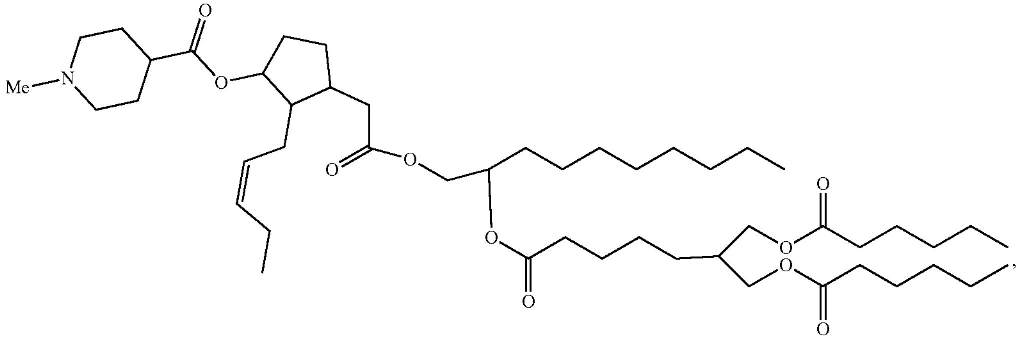
PNI 215
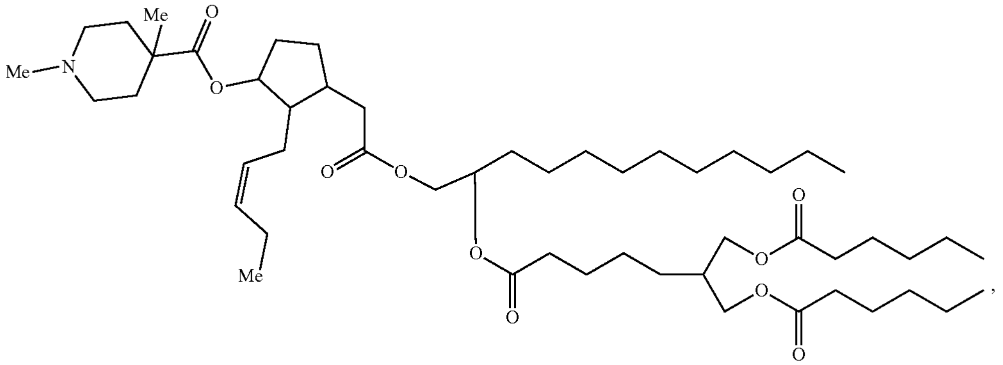

-continued
PNI 223
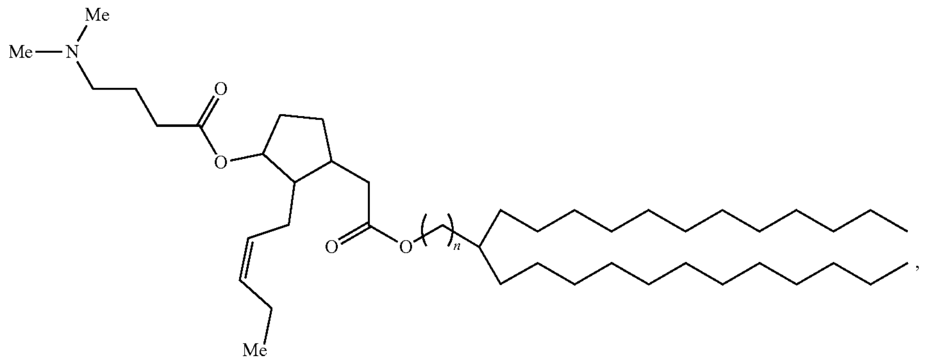
n = 0-1
PNI 225
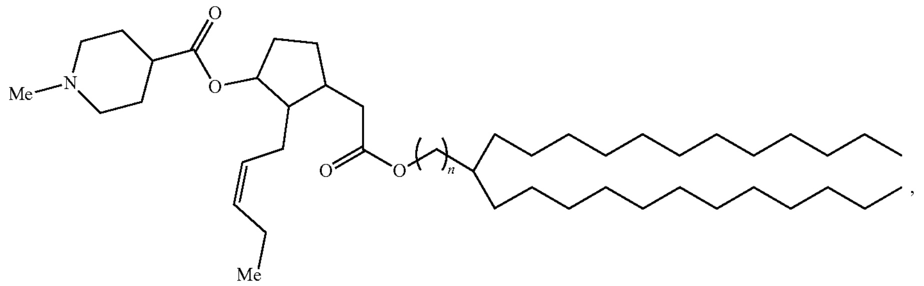
n = 0-1
PNI 226
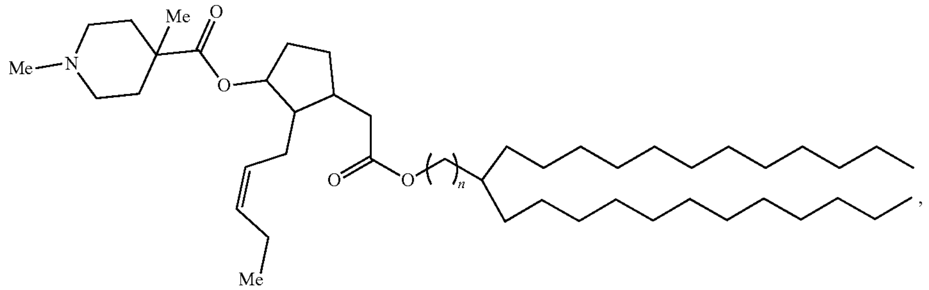
n = 0-1
PNI 238
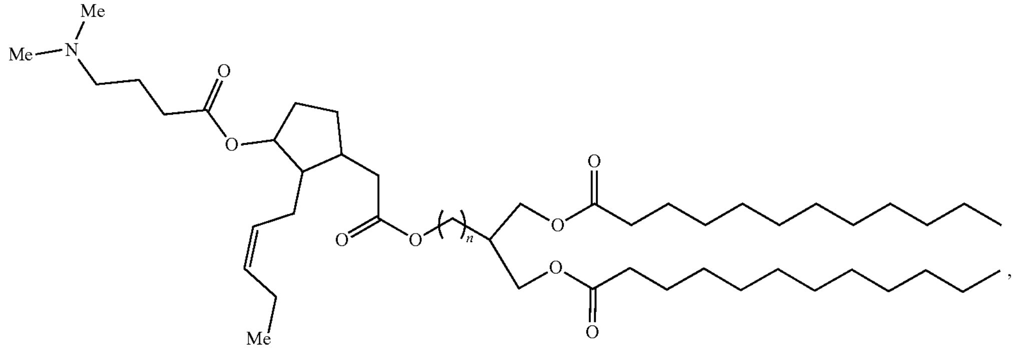
n = 0-1

-continued
PNI 241
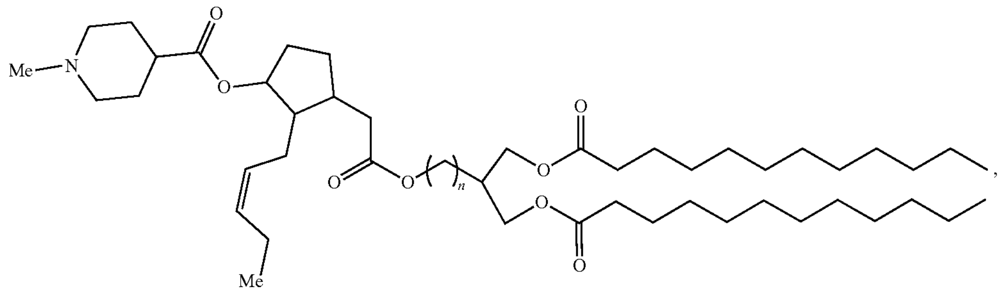
n = 0-1
PNI 242
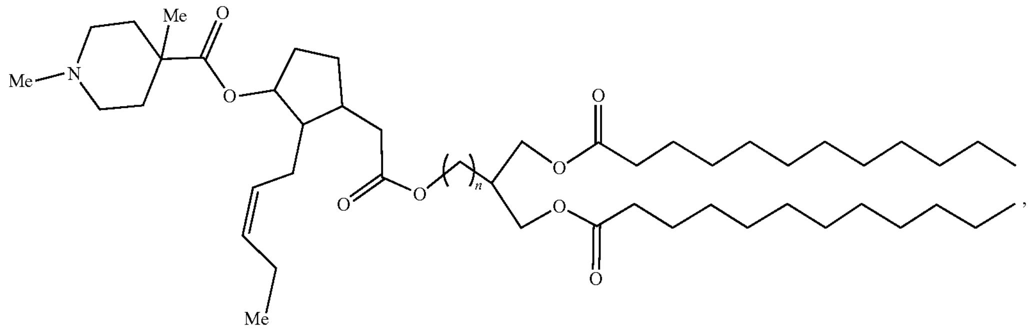
n = 0-1
PNI 254
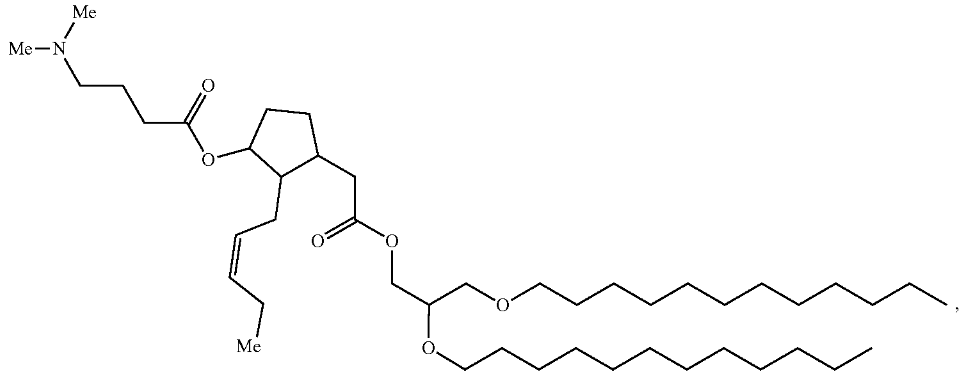
PNI 256
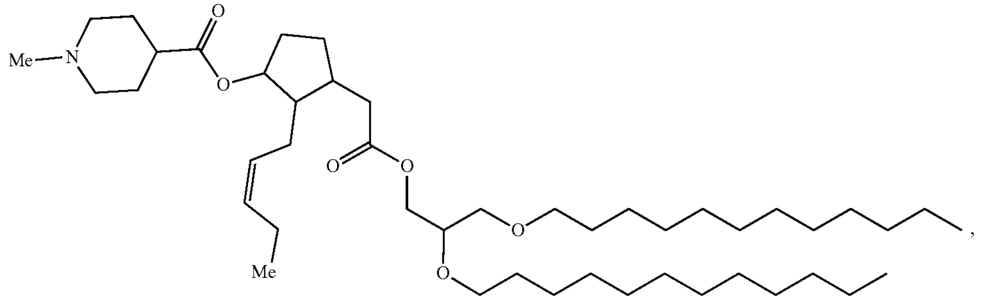

-continued
PNI 257
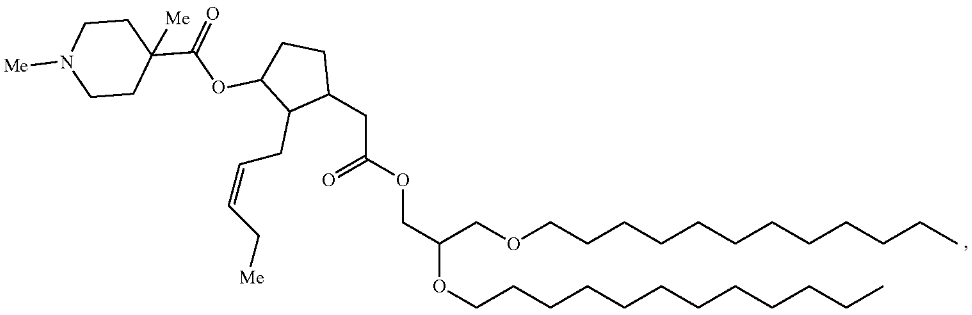
PNI 283
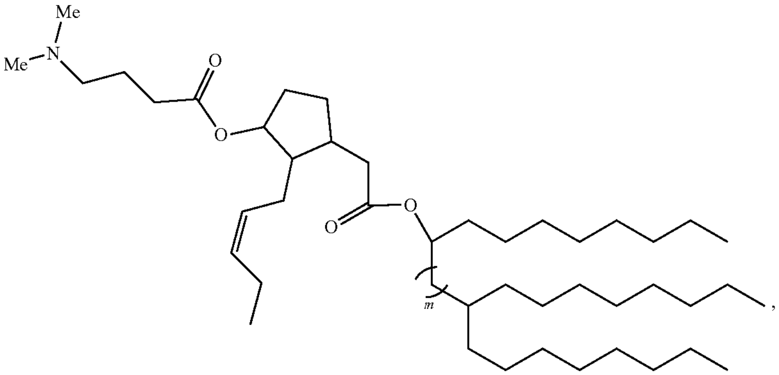
m = 1-5
PNI 285
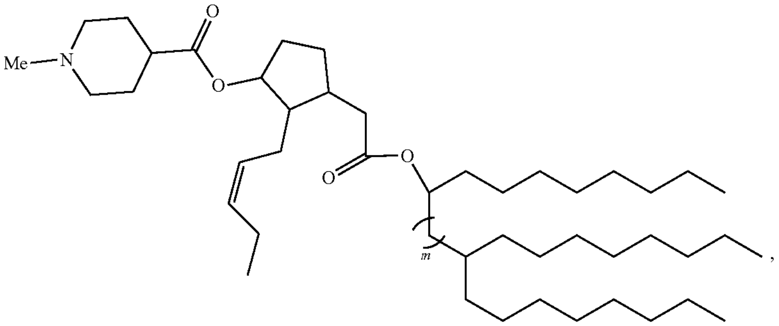
m = 1-5
PNI 286
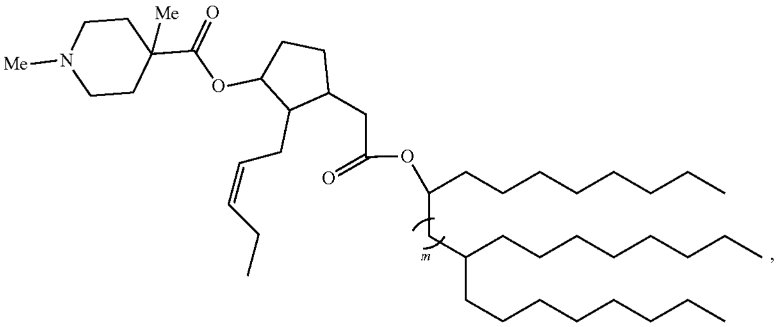
m = 1-5

-continued
PNI 297
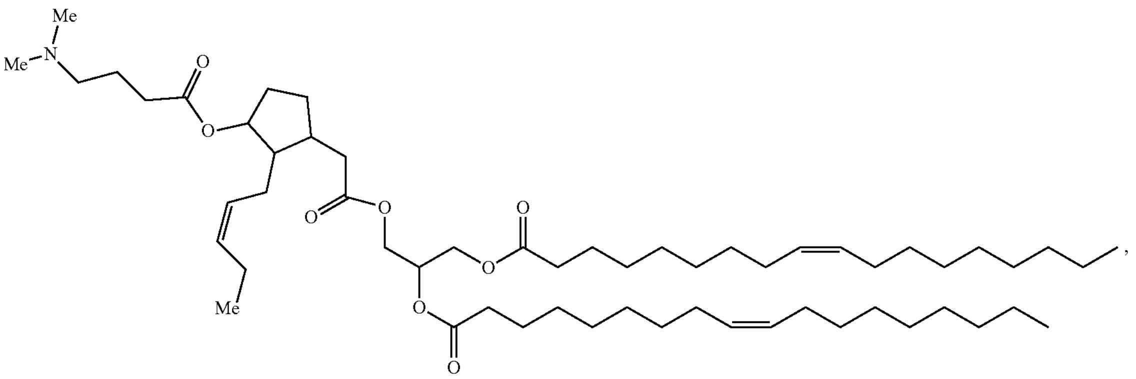
PNI 299
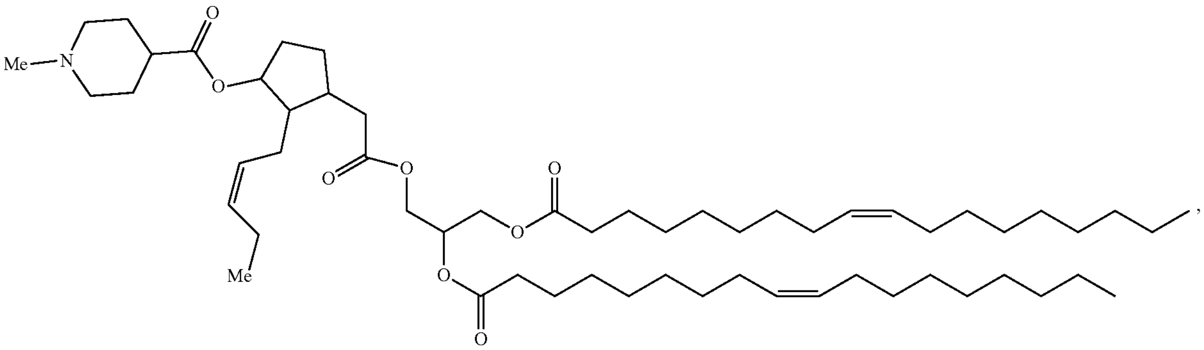
PNI 300
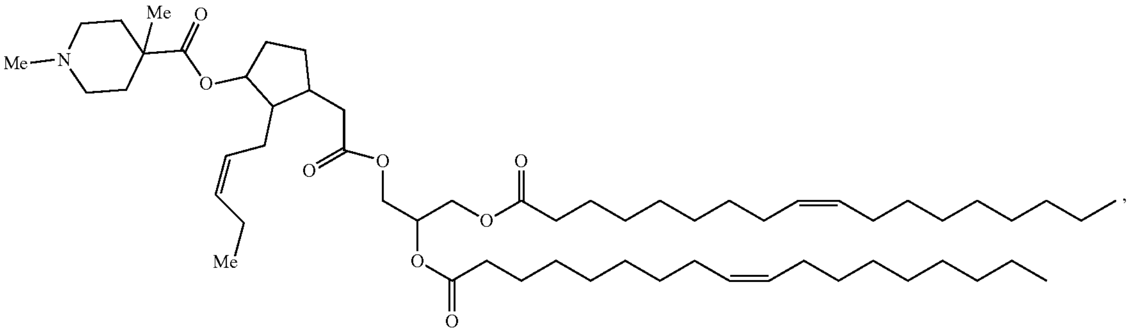
PNI 512
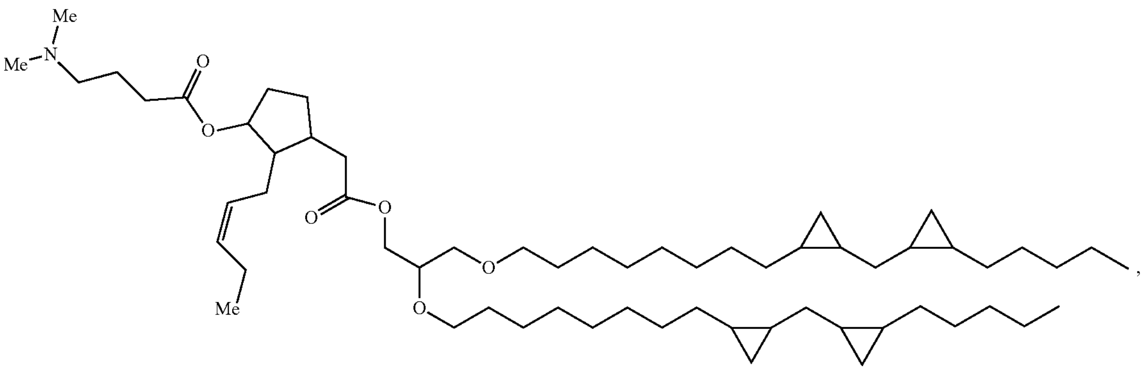

-continued
PNI 601
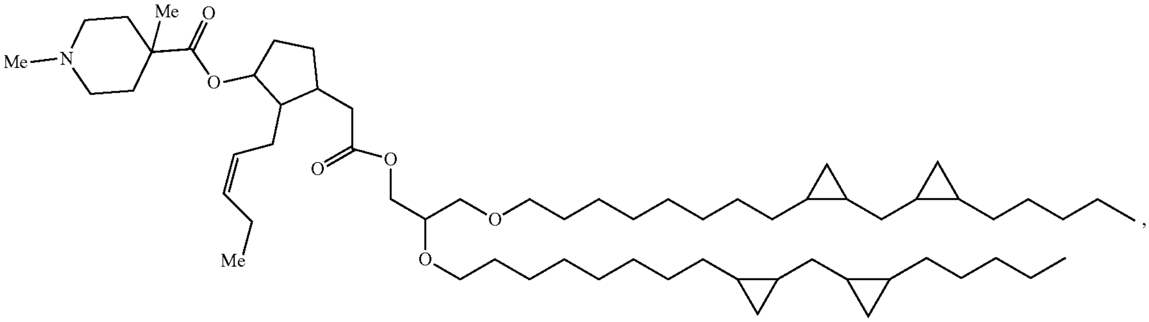
,
PNI 602
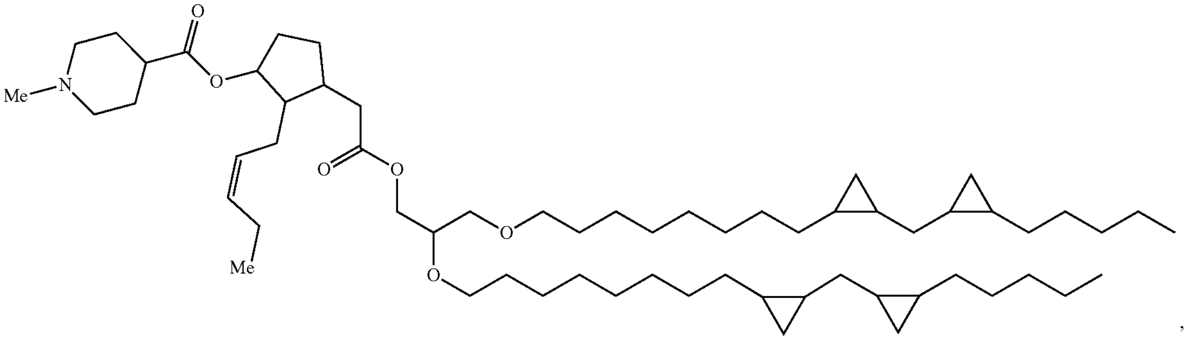
,
PNI 513
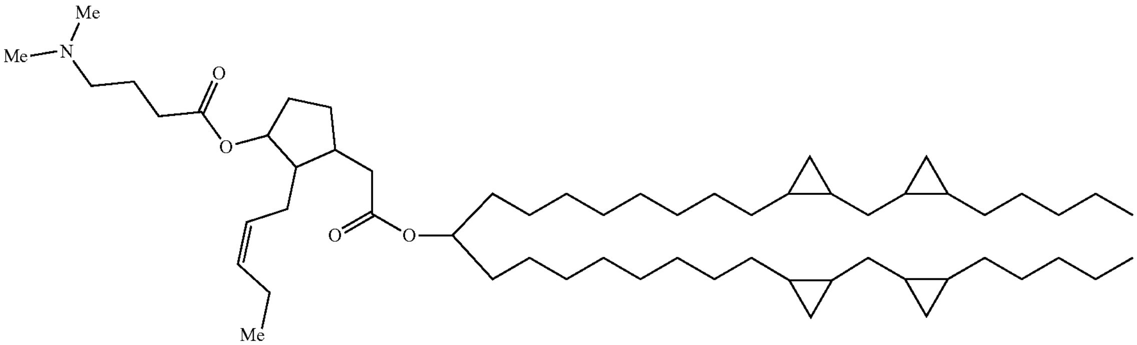
,
PNI 603
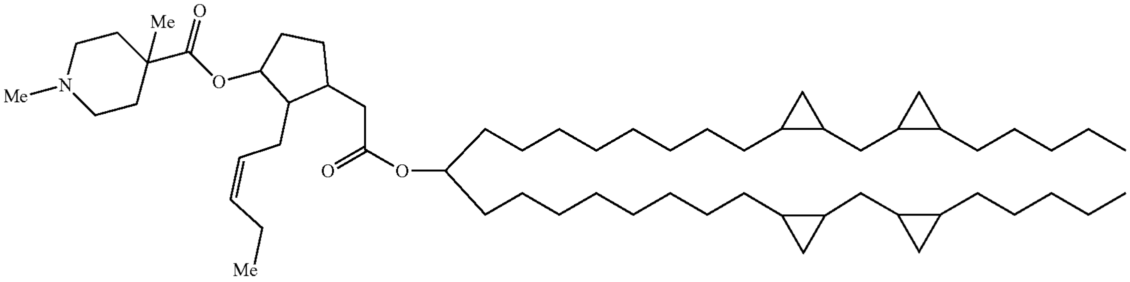
, -continued
PNI 604
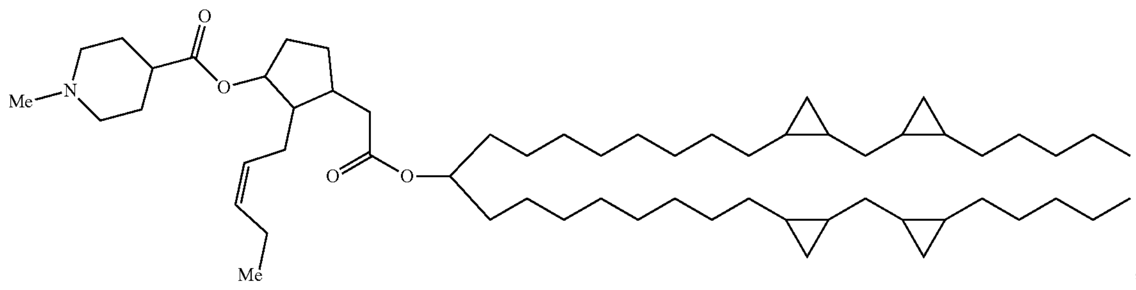
,
PNI 605
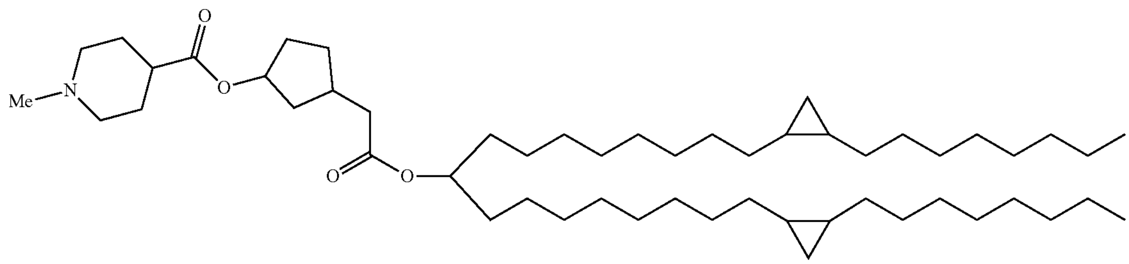
,
PNI 606
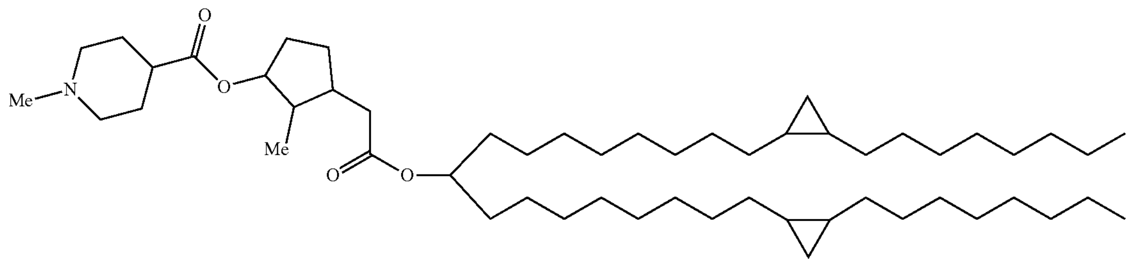
,
PNI 607
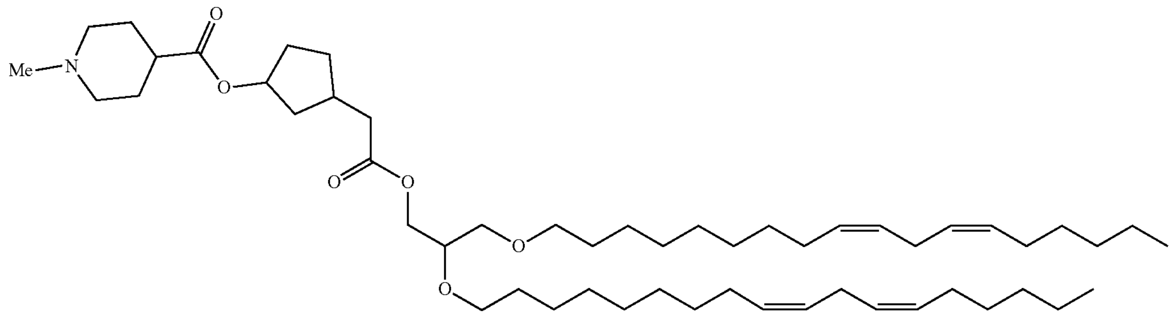
,
PNI 608
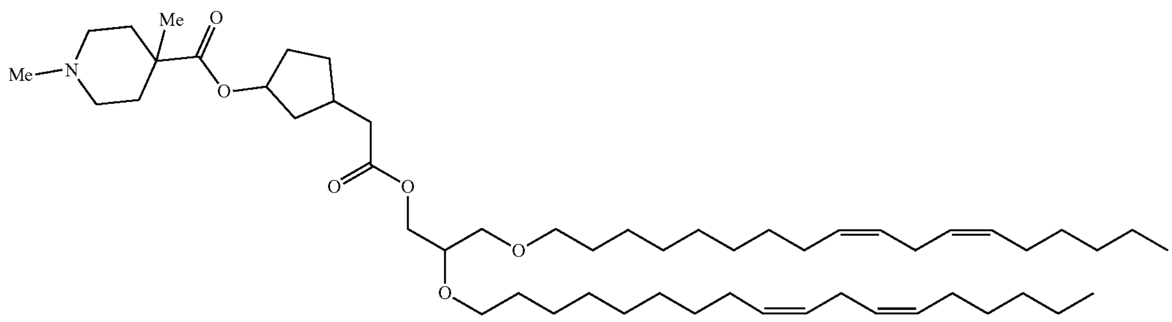
, -continued
PNI 609
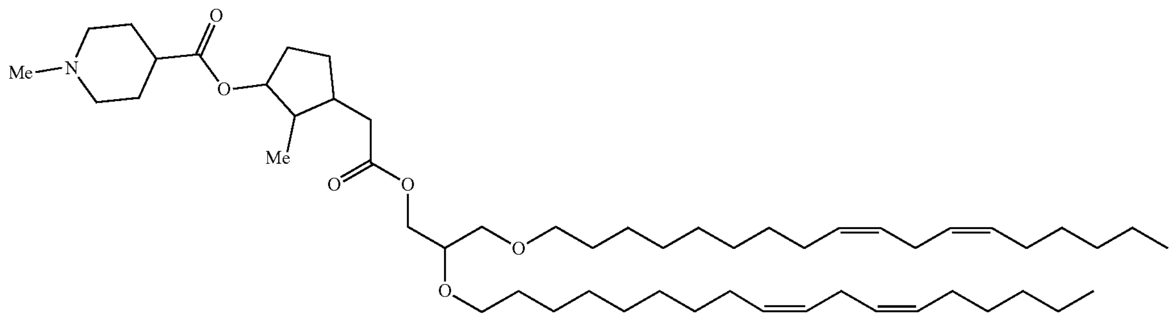
,
PNI 610
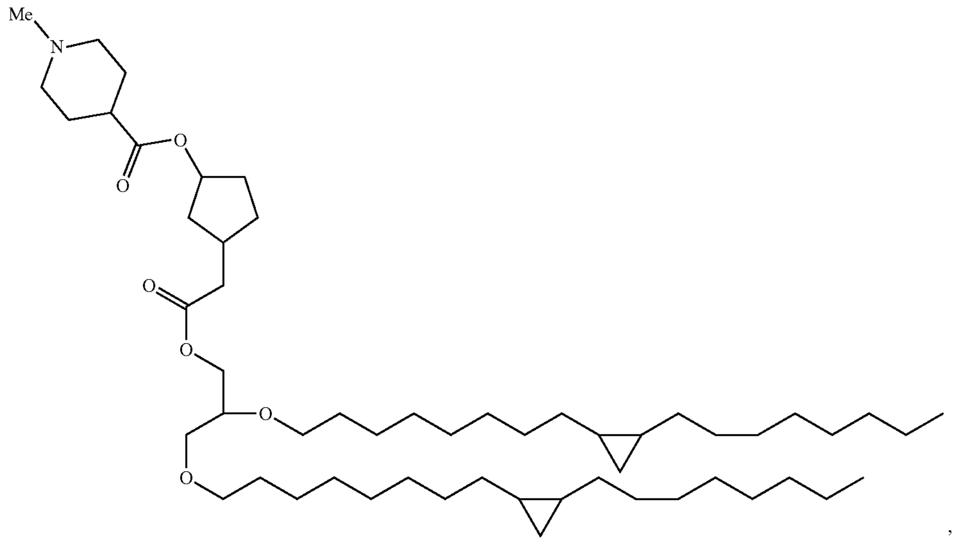
,
PNI 611
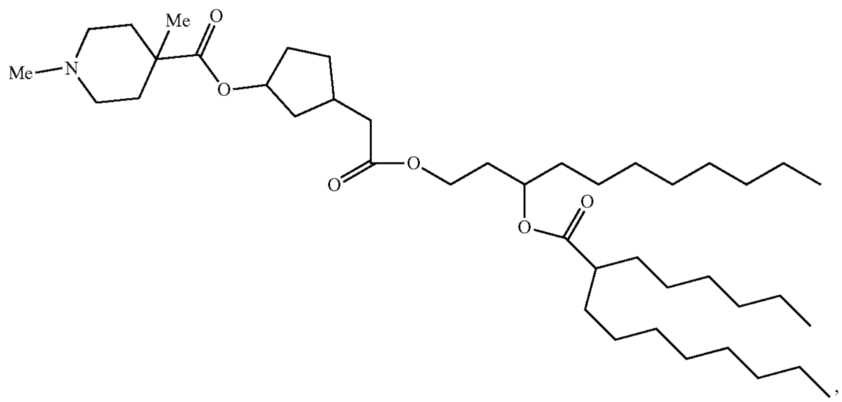
, -continued
PNI 612
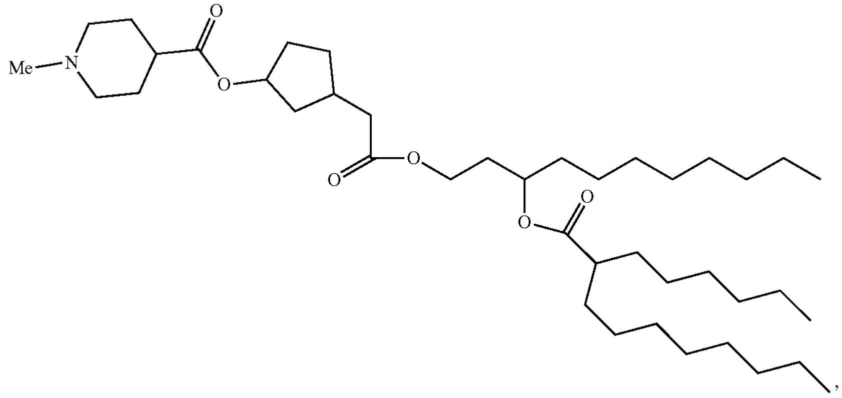
PNI 613
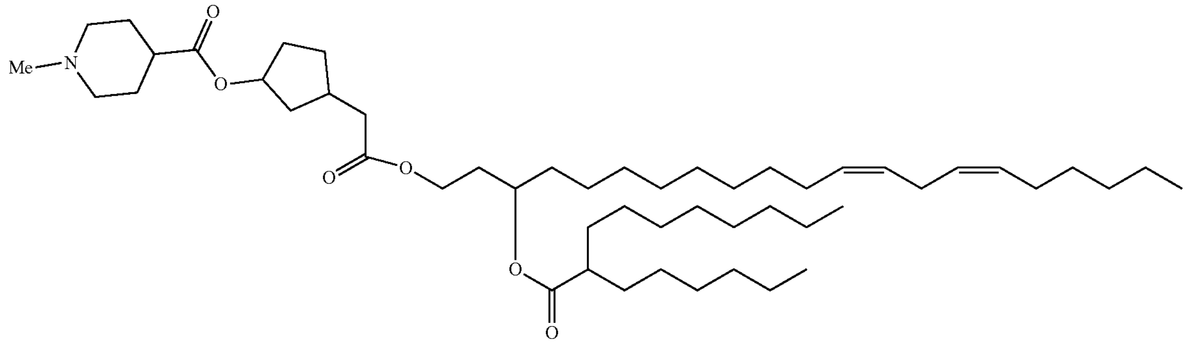
,
PNI 614
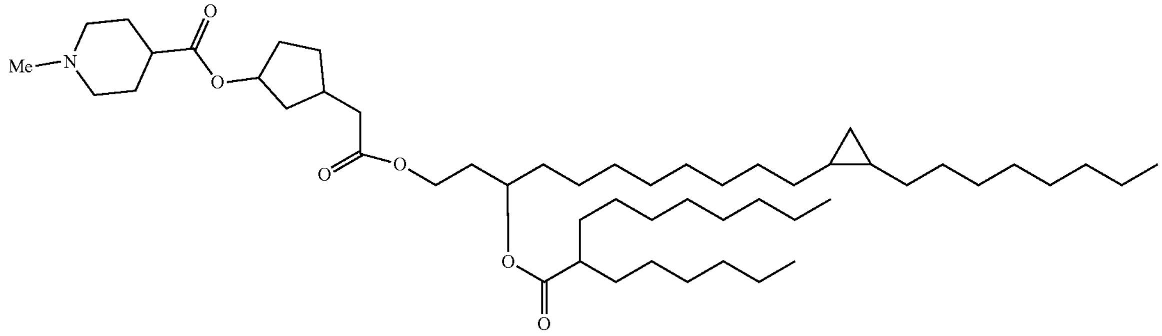
,
PNI 171
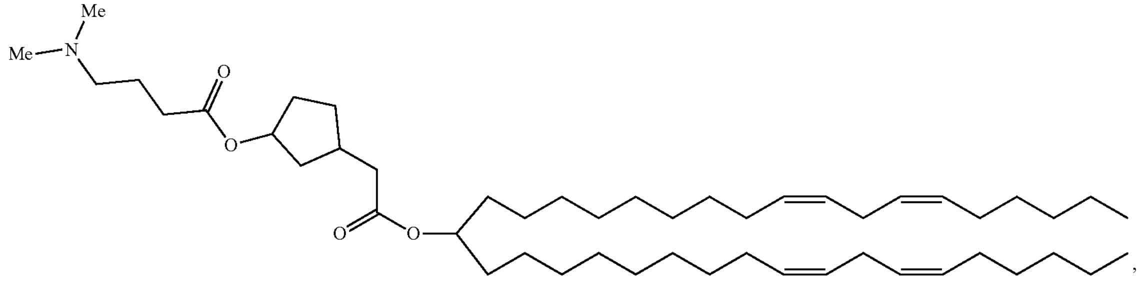

-continued
PNI 615
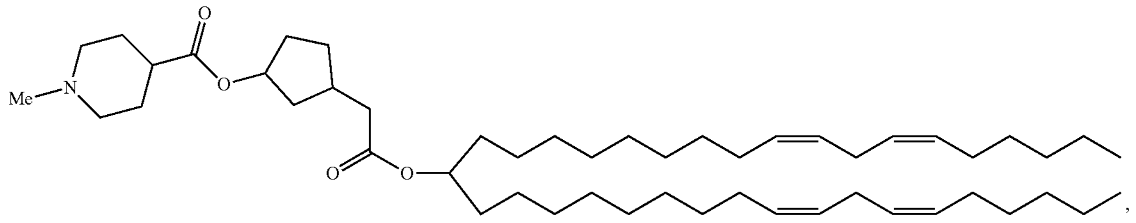
PNI 616
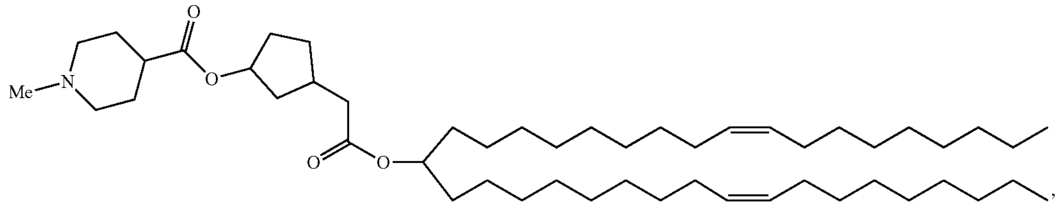
PNI 617
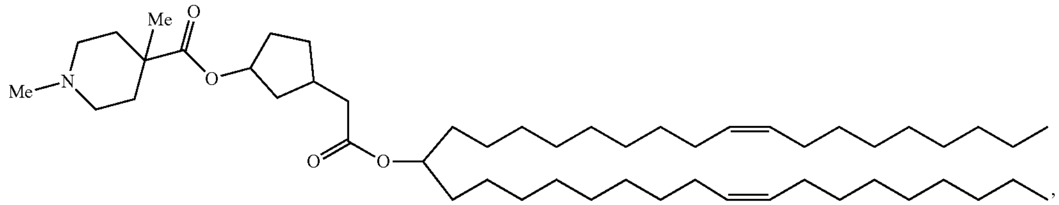
PNI 187
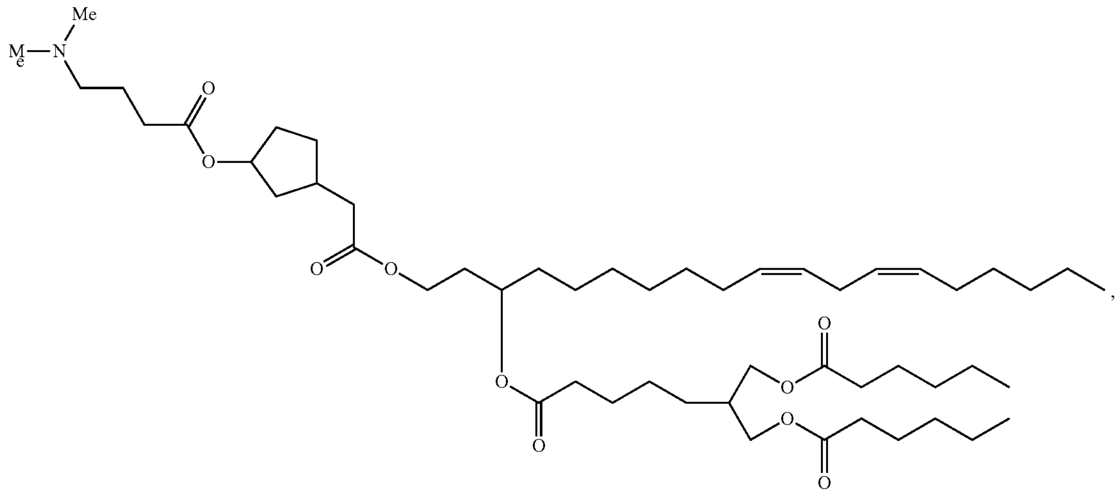

-continued
PNI 618
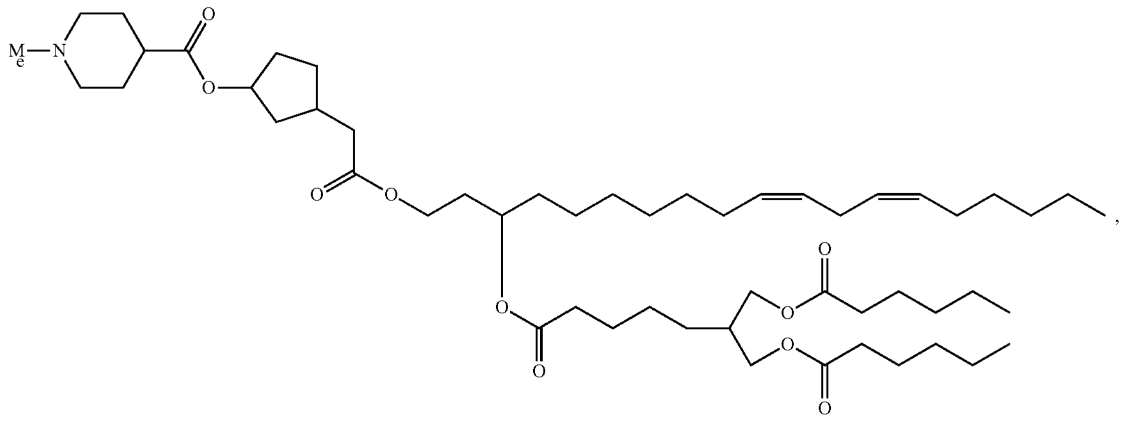
PNI 212
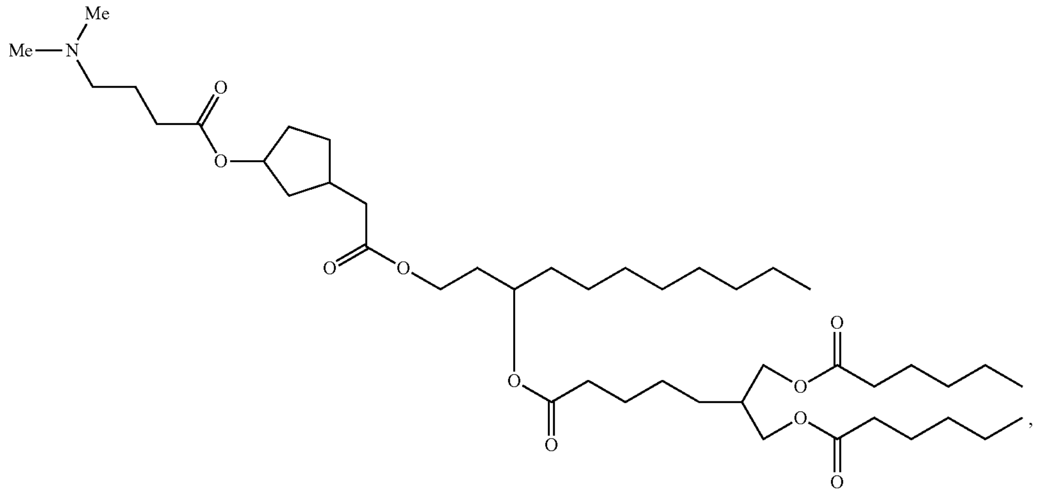
PNI 619
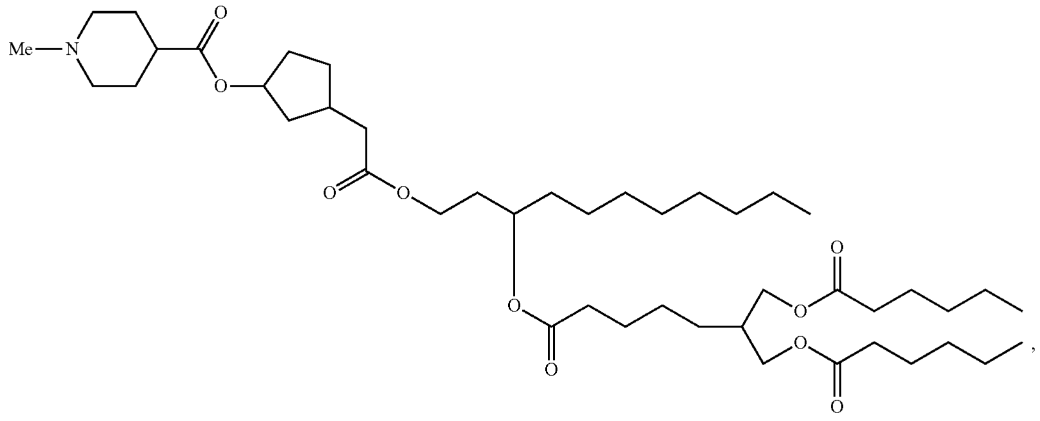

-continued
PNI 620
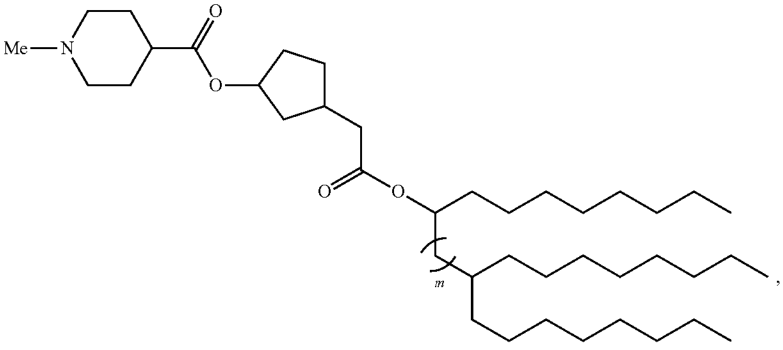
m = 1-5
PNI 621
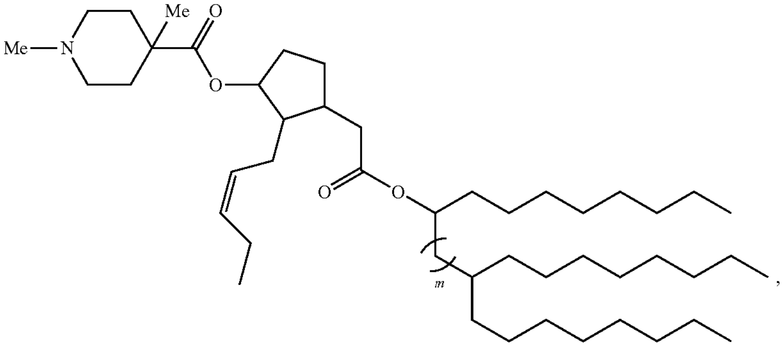
m = 1-5
PNI 622
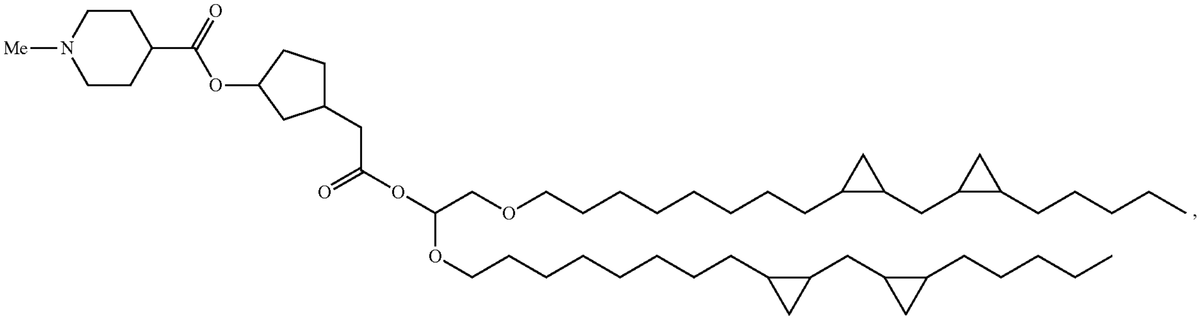
PNI 623
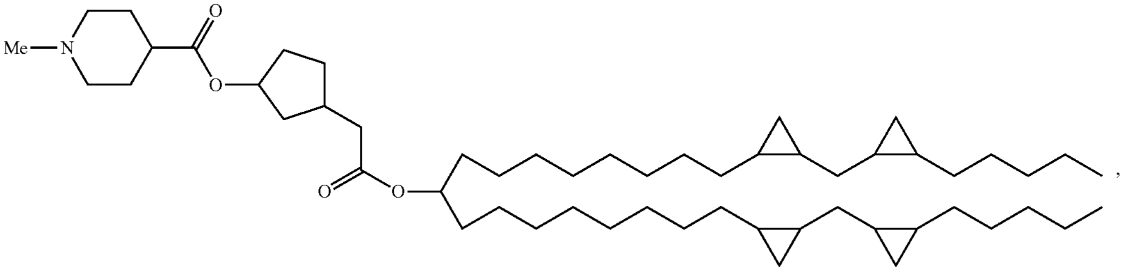

-continued
PNI 146
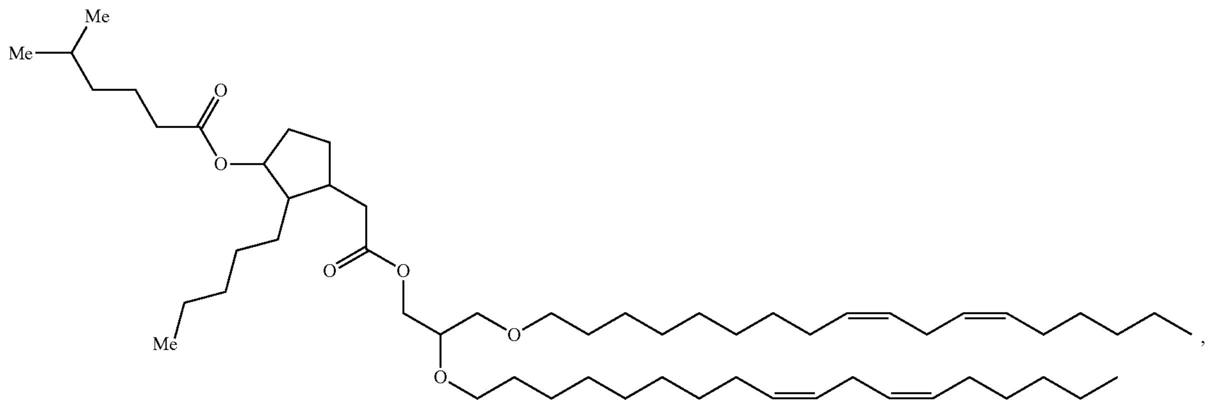
PNI 145
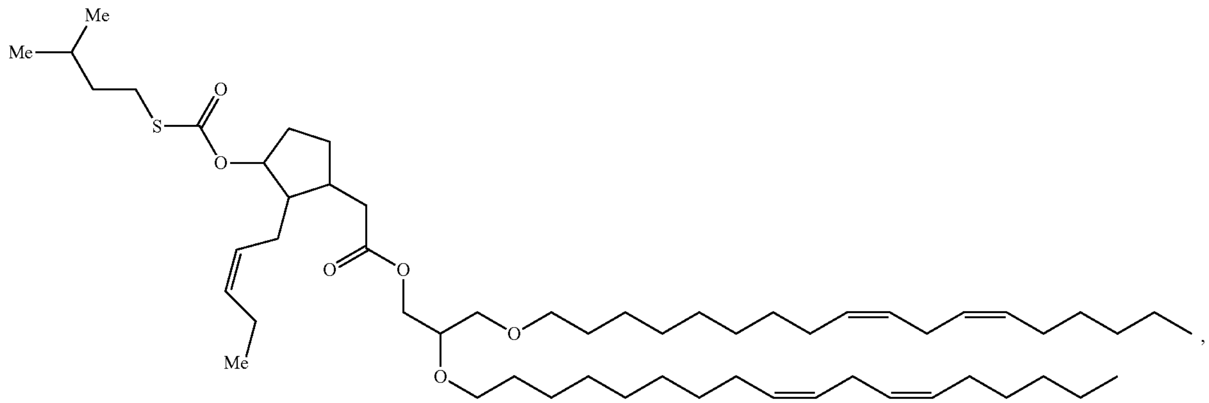
PNI 129
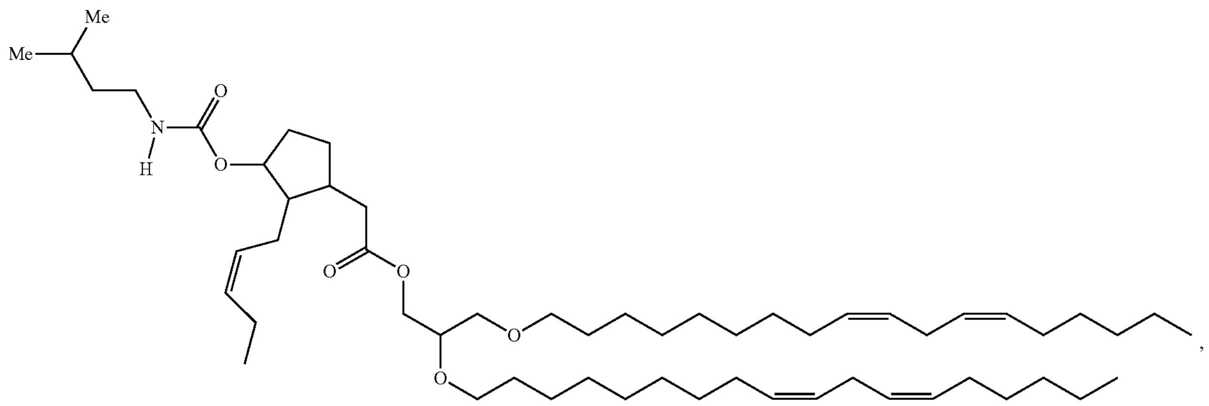

-continued
PNI 130
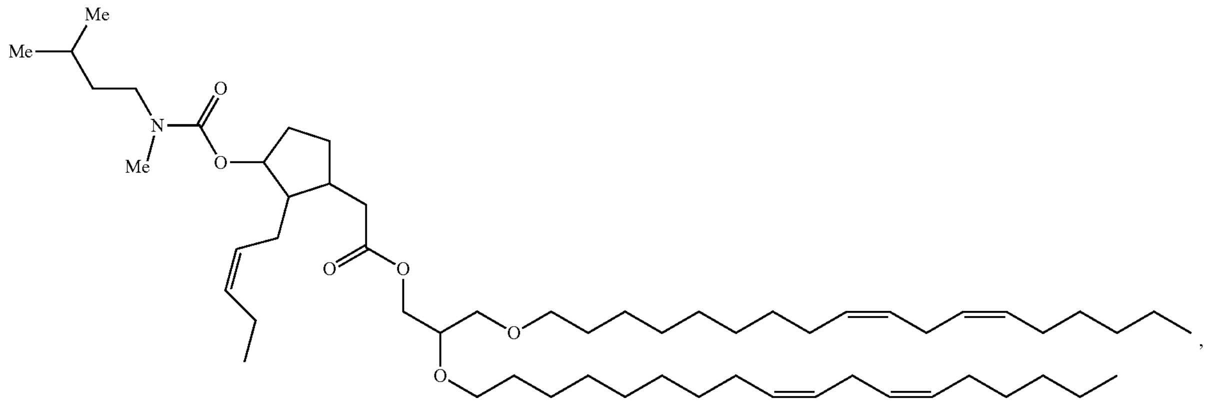
,
PNI 131
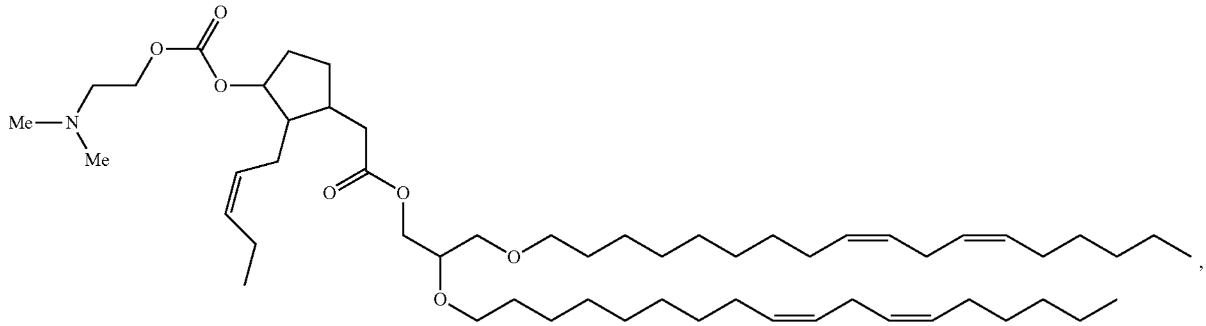
,
PNI 133
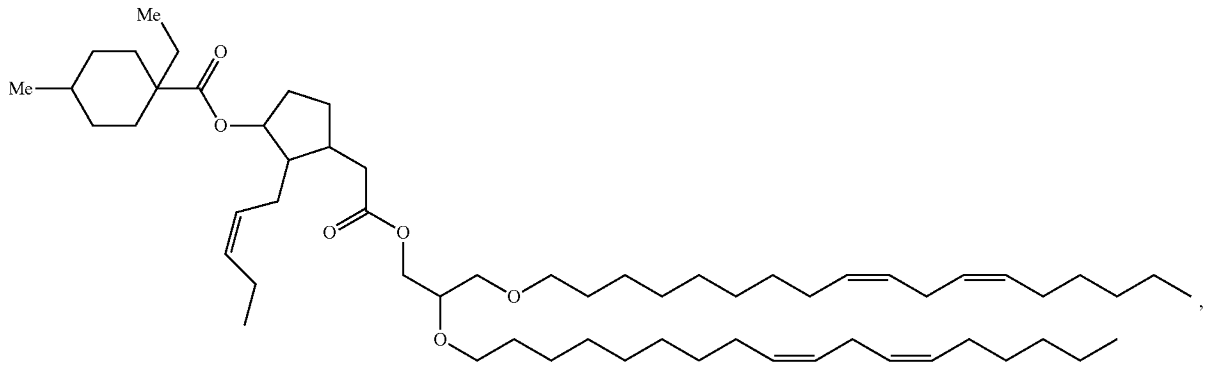
,
PNI 134
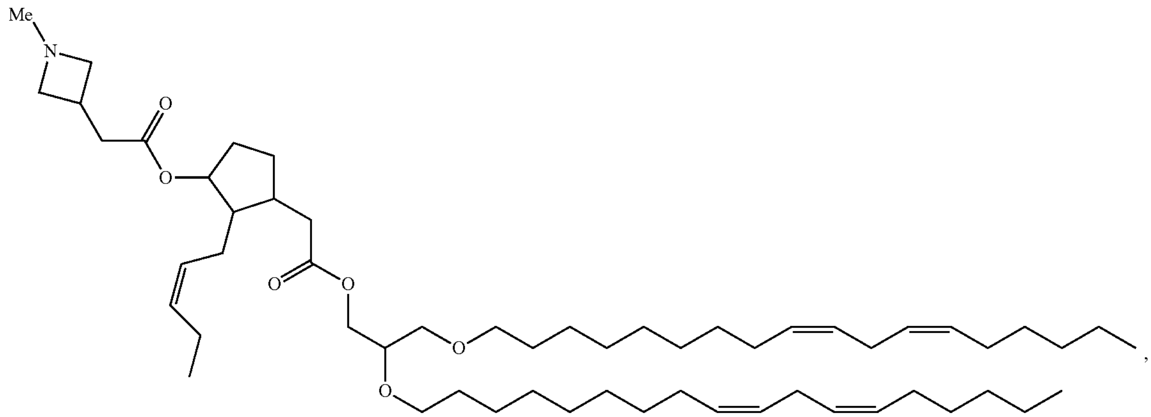
, PNI 136
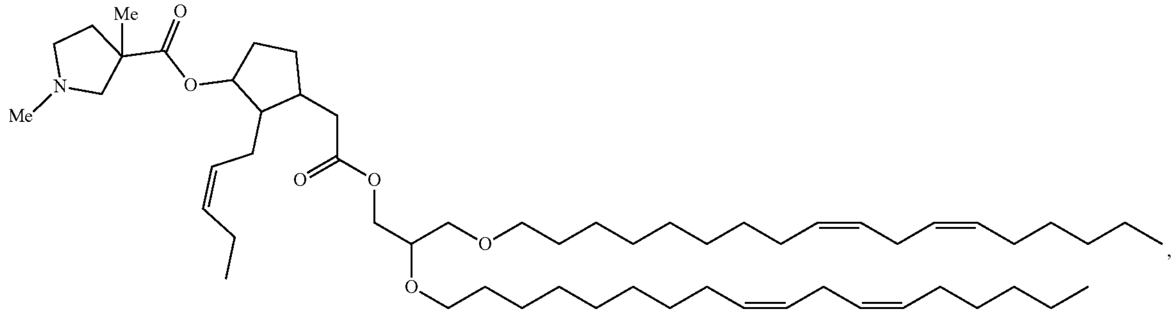
,
PNI 138
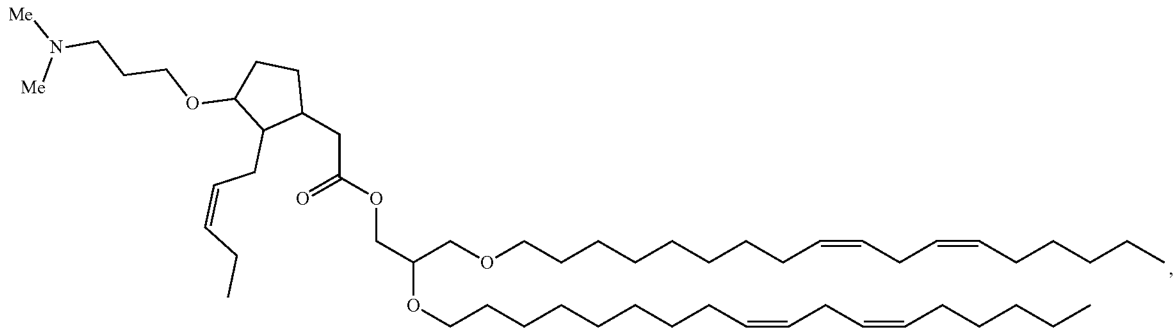
,
PNI 139
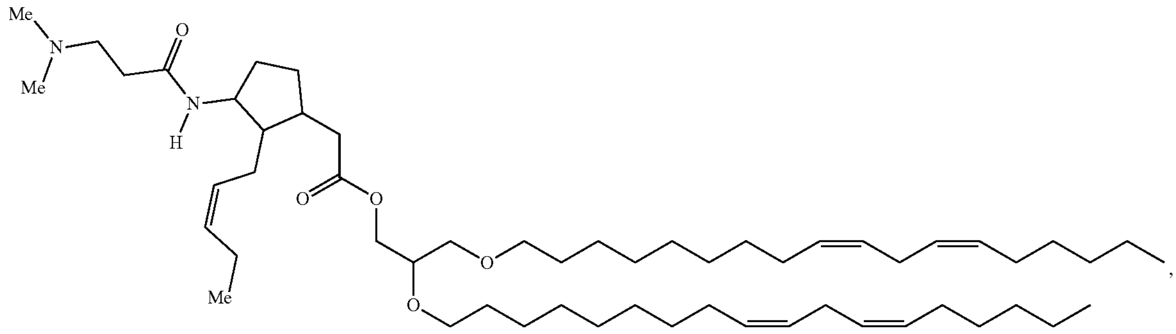
,
PNI 140
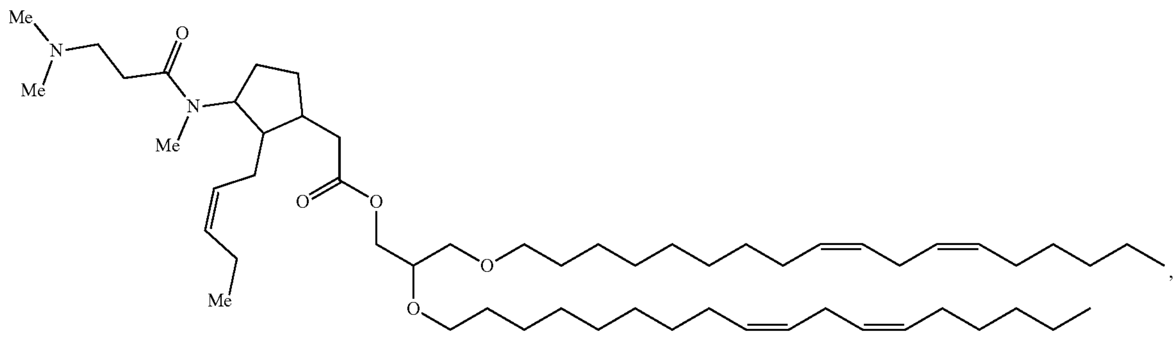
, -continued
PNI 141
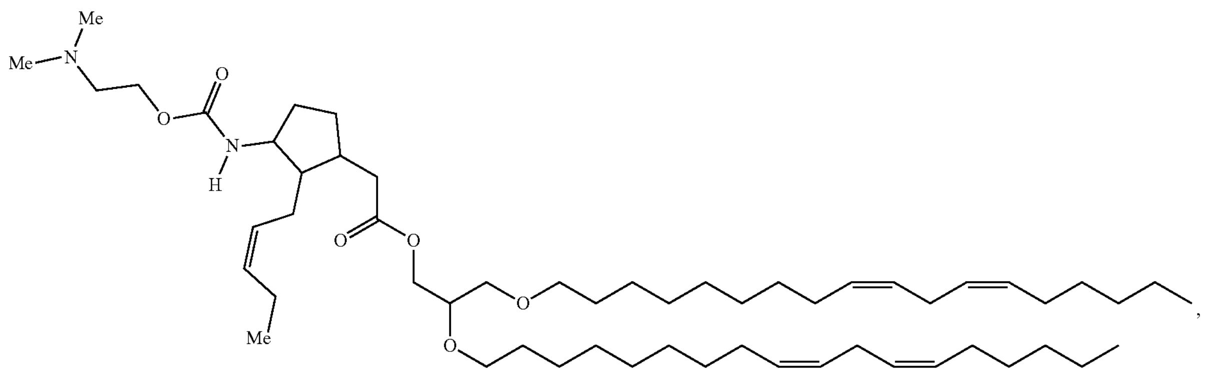
PNI 142
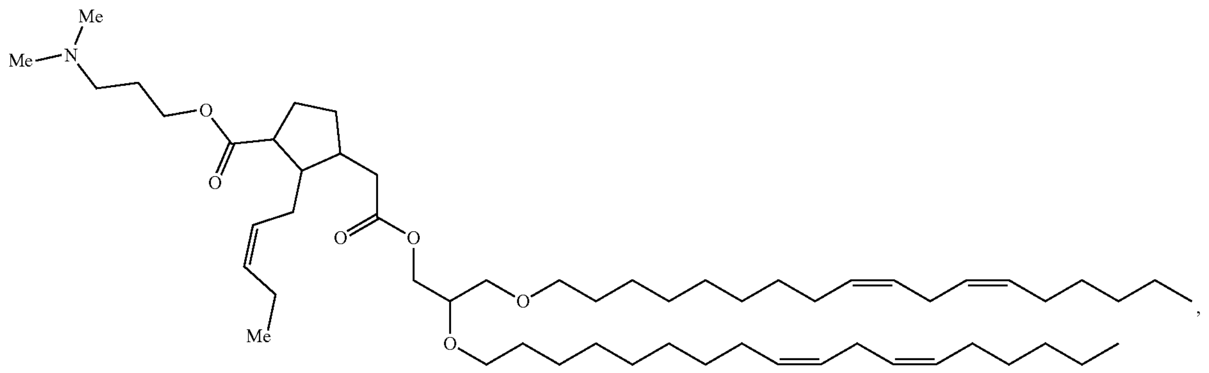
PNI 149
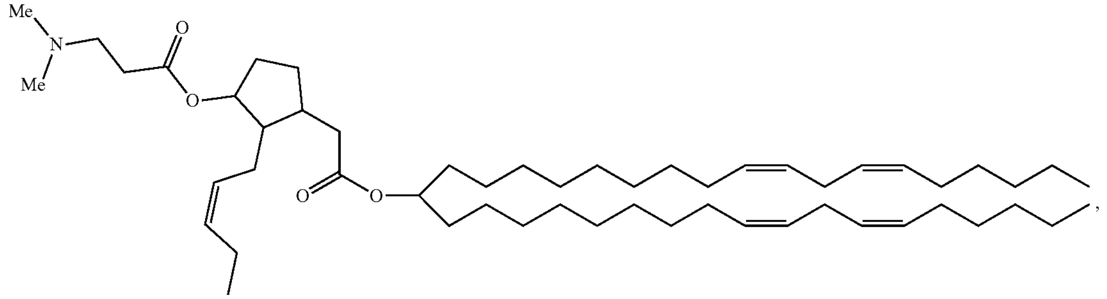
PNI 151
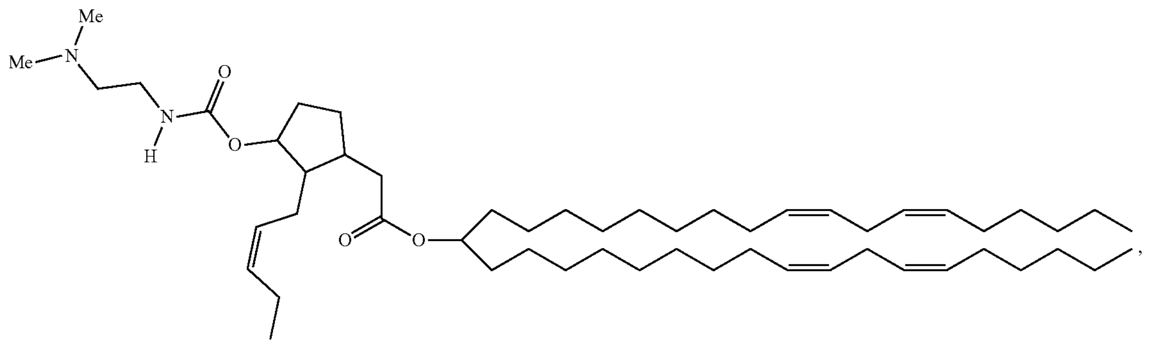

-continued
PNI 152
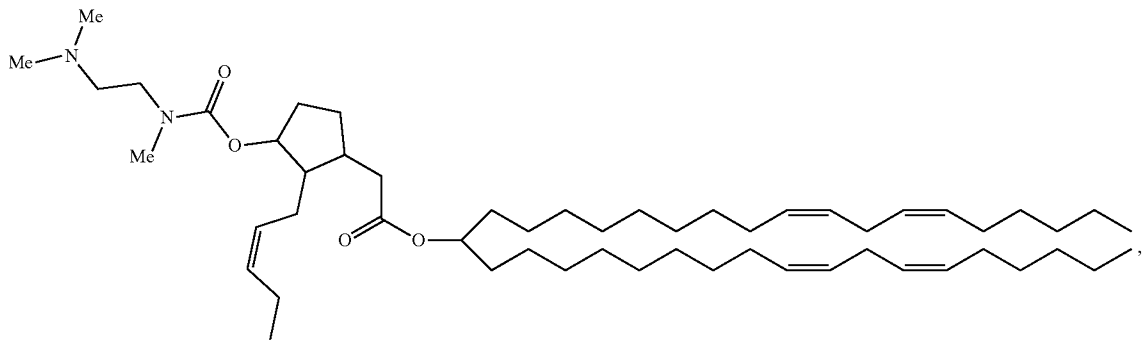
PNI 153
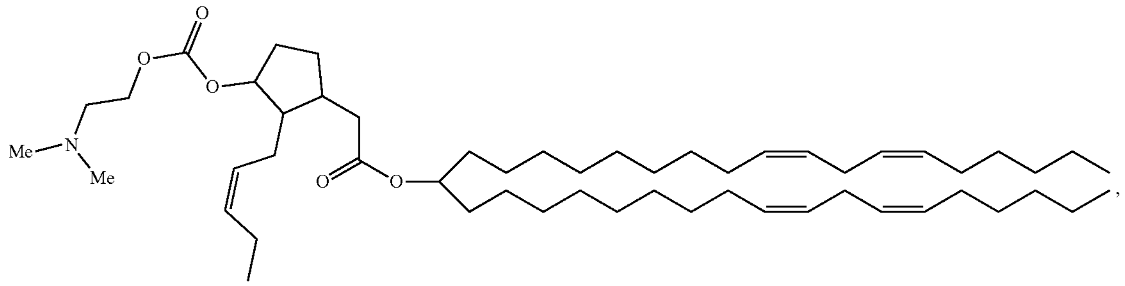
PNI 156
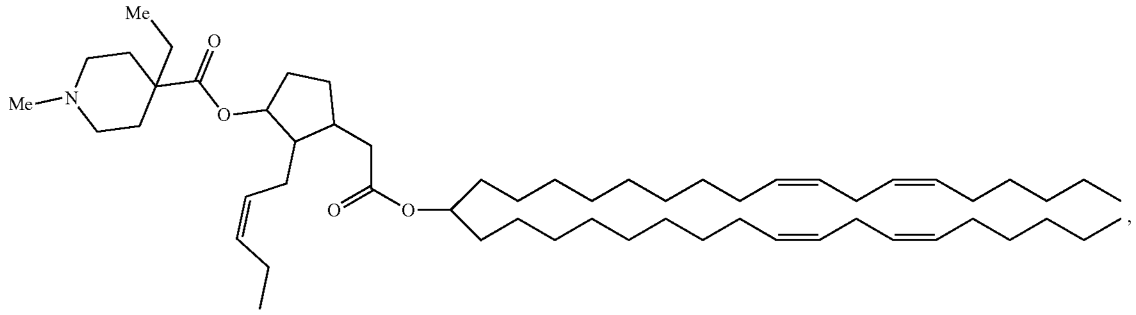
PNI 158
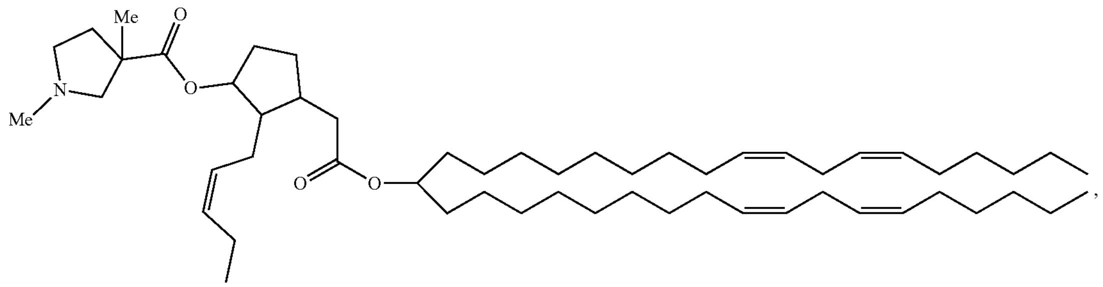
PNI 159
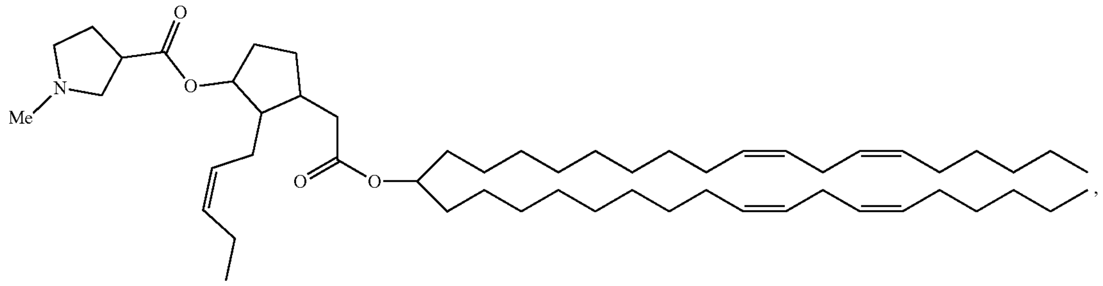

-continued
PNI 161
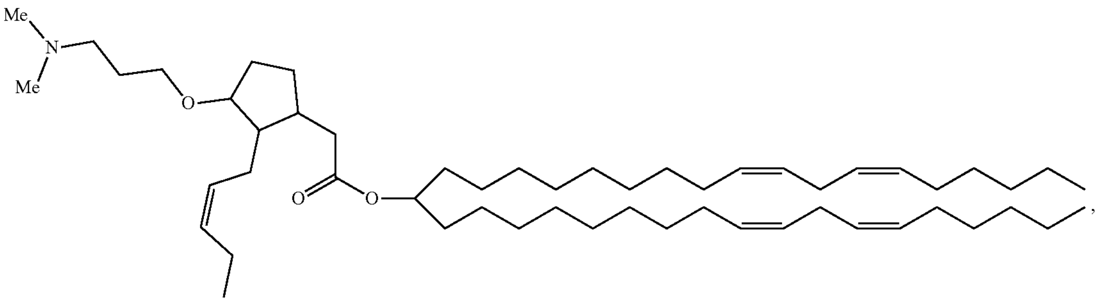
PNI 162
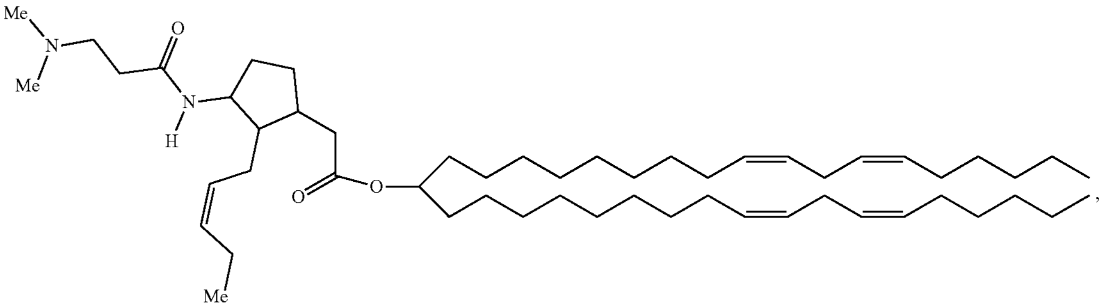
PNI 163
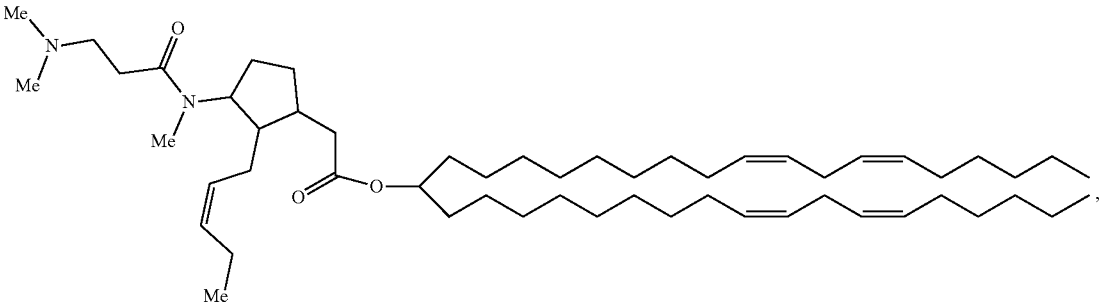
PNI 164
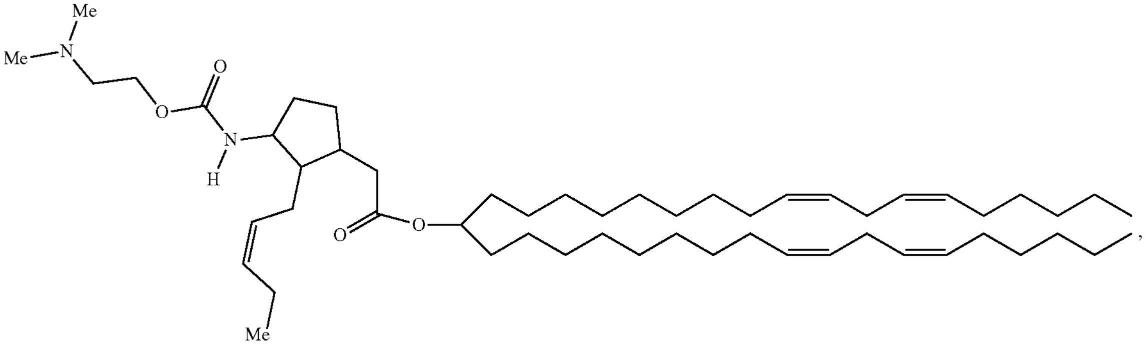

-continued
PNI 165
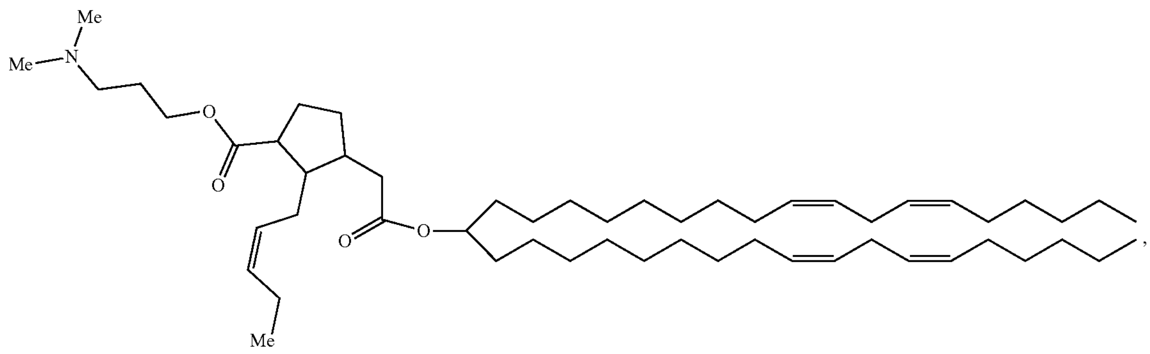
,
PNI 166
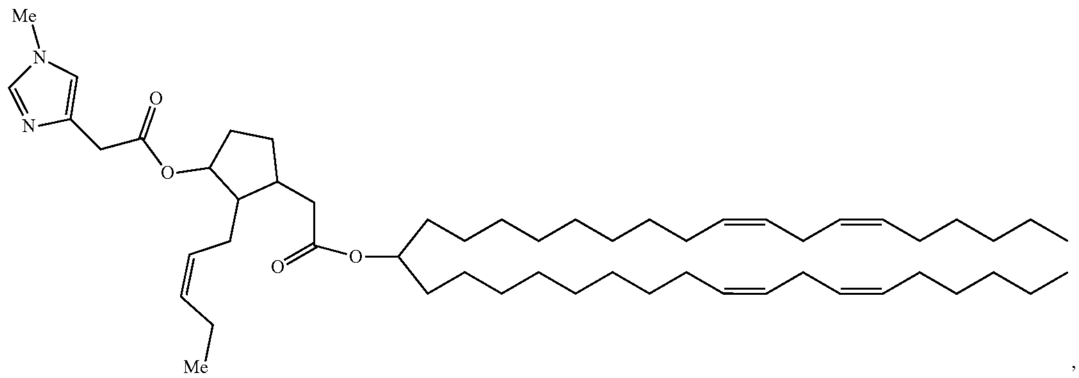
,
PNI 168
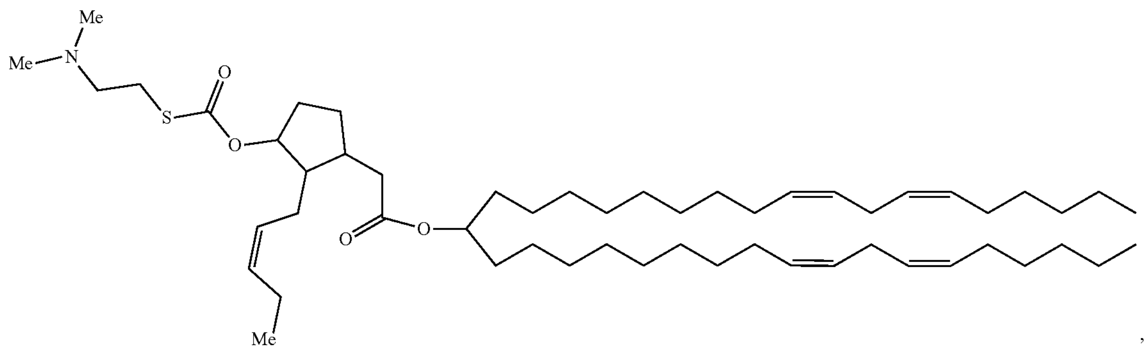
,
PNI 169
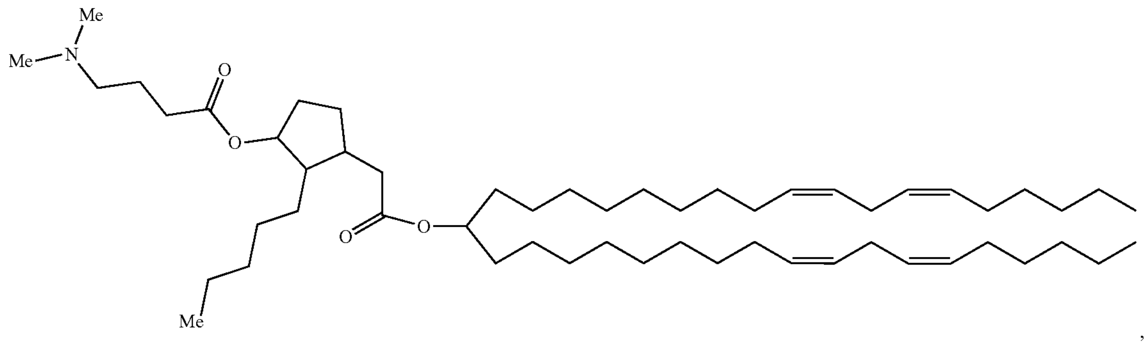
, -continued
PNI 170
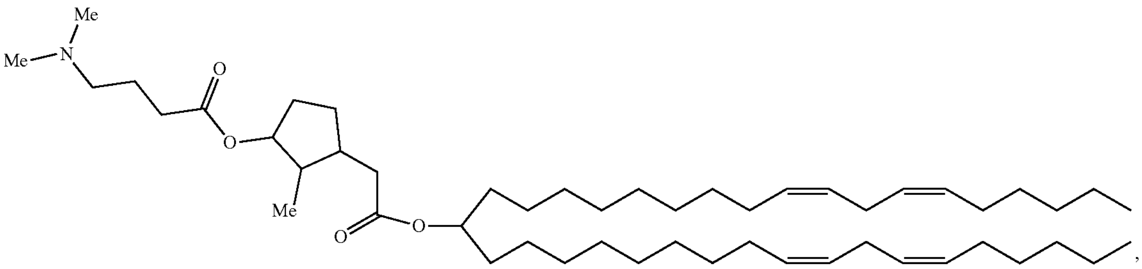
,
PNI 172
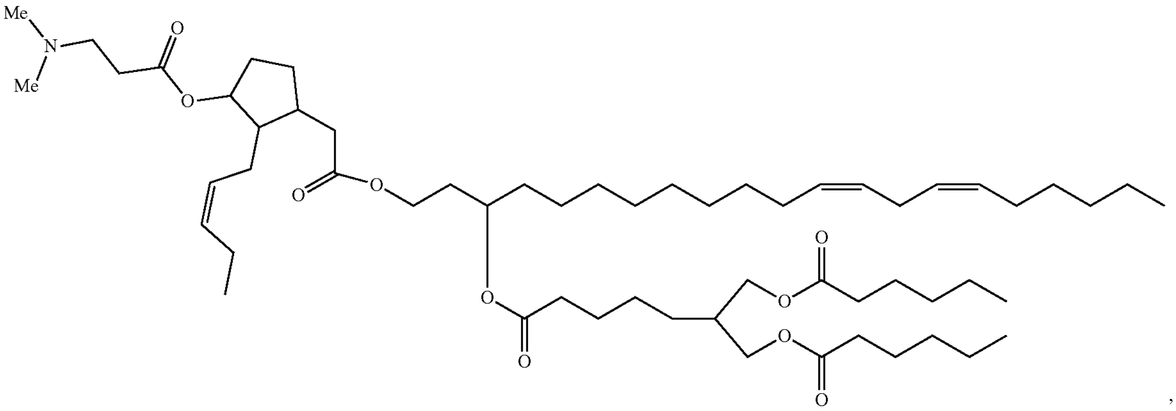
,
PNI 174
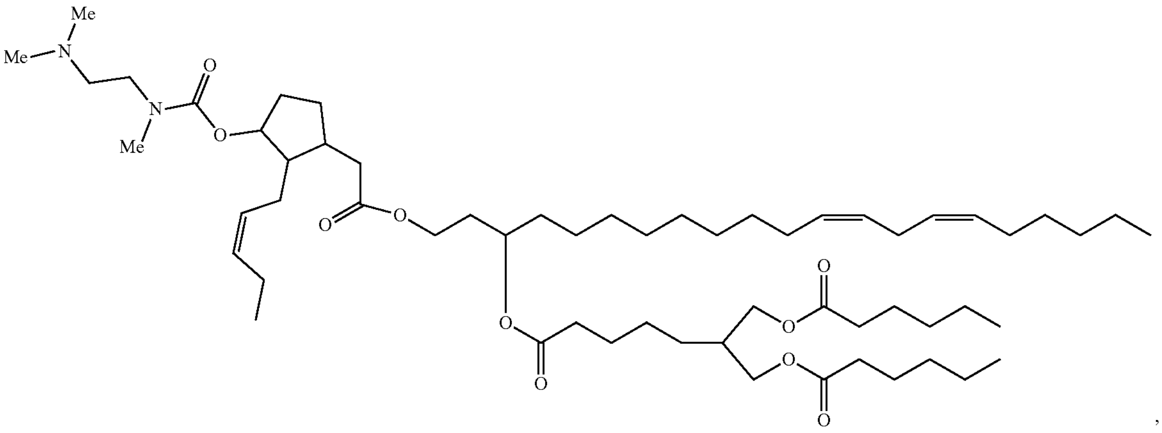
,
PNI 175
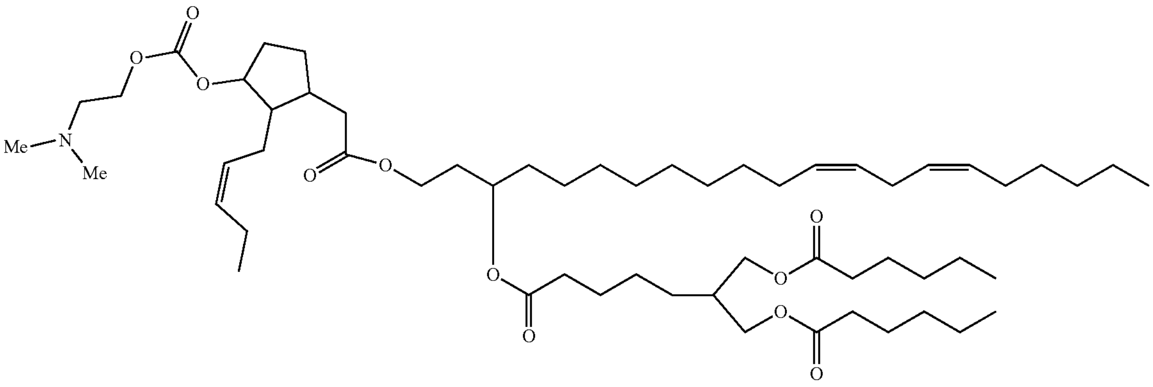
, -continued
PNI 180
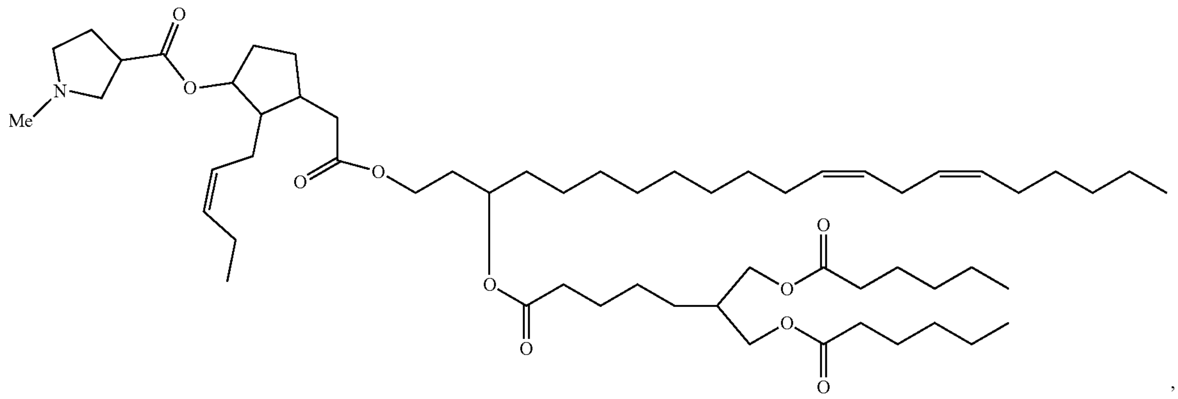
,
PNI 181
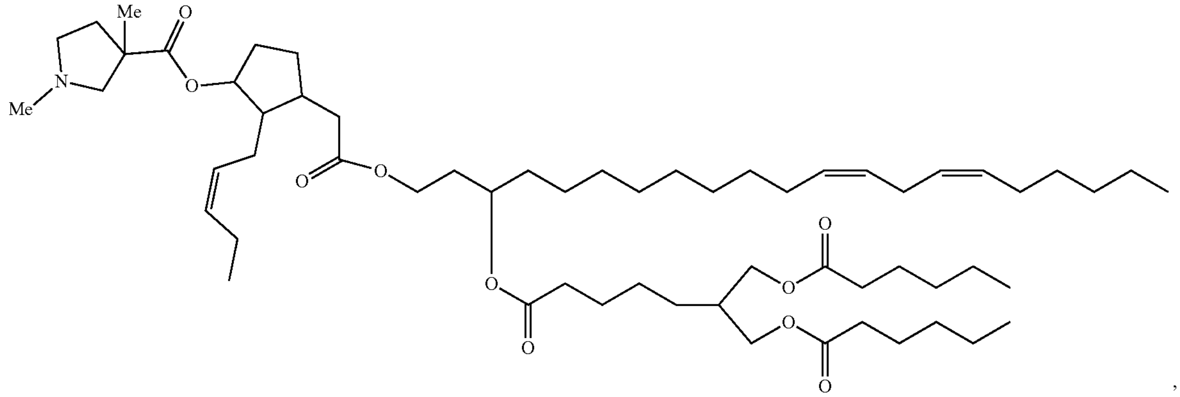
,
PNI 185
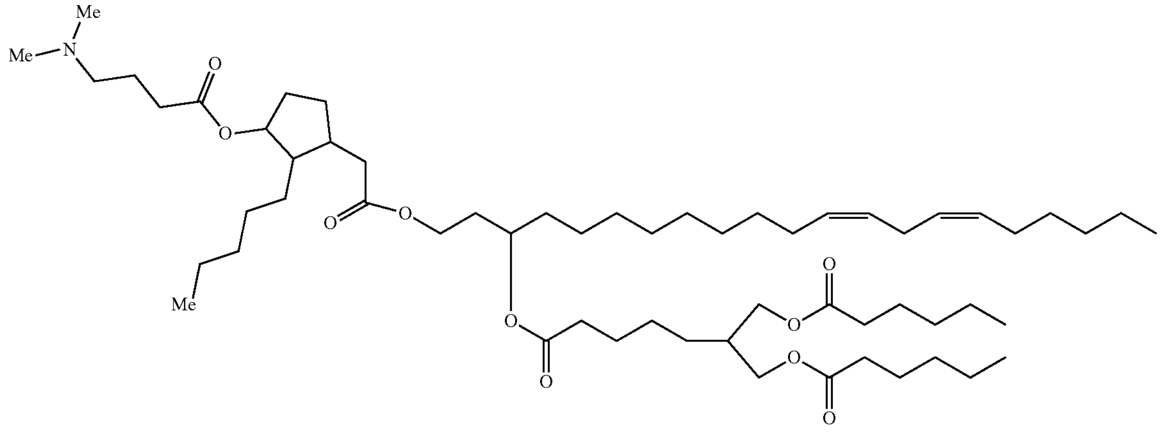
, -continued
PNI 186
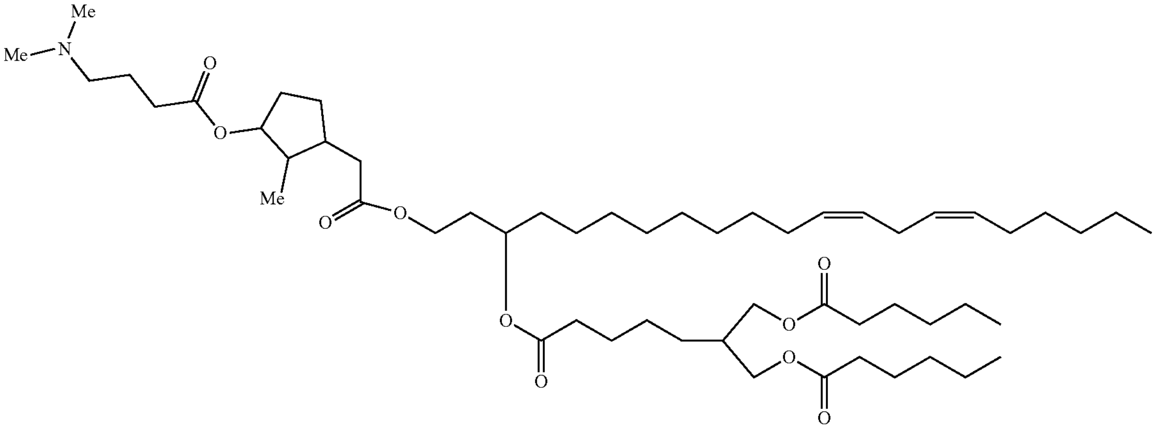
,
PNI 188
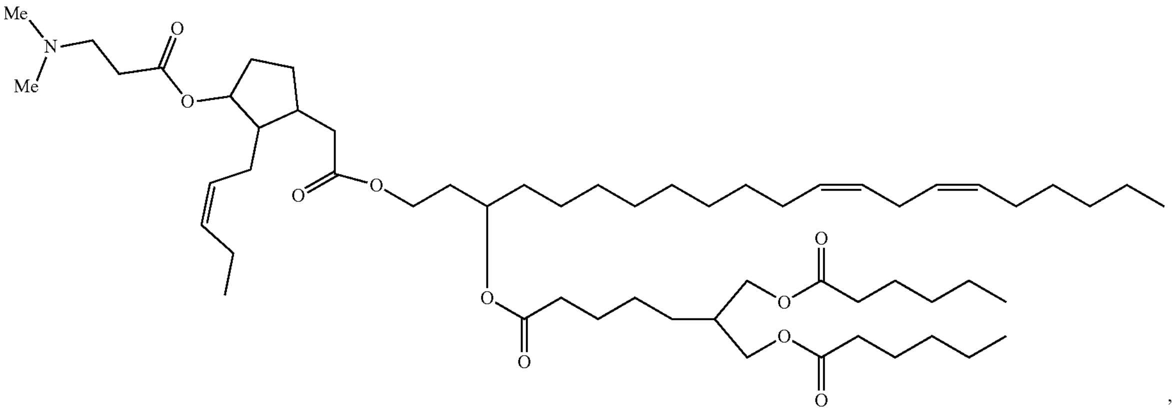
,
PNI 193
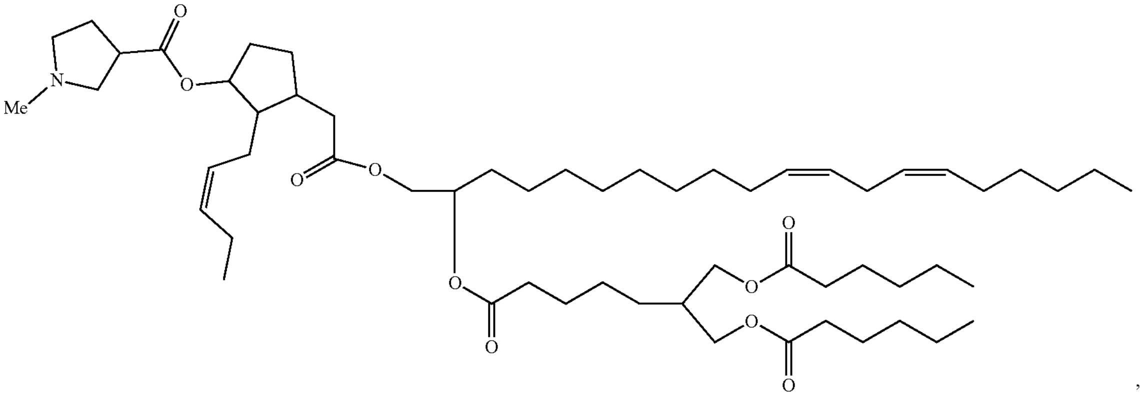
, -continued
PNI 194
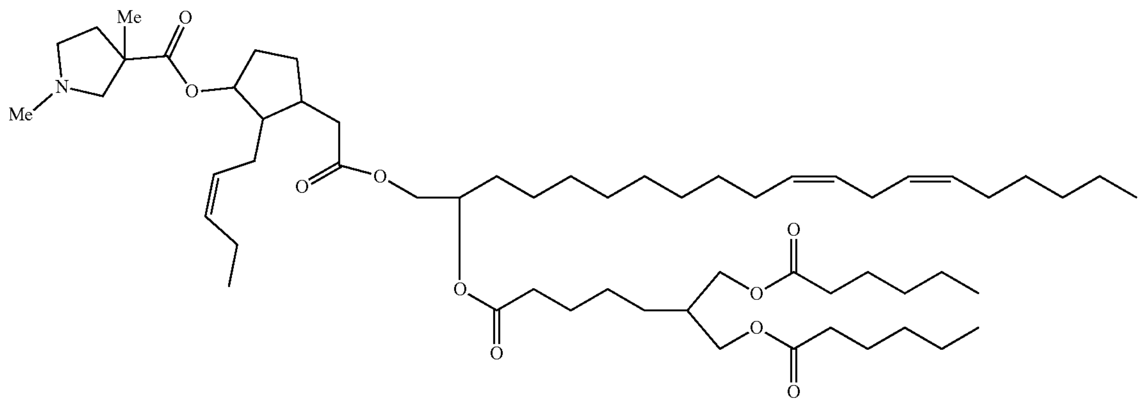
,
PNI 195
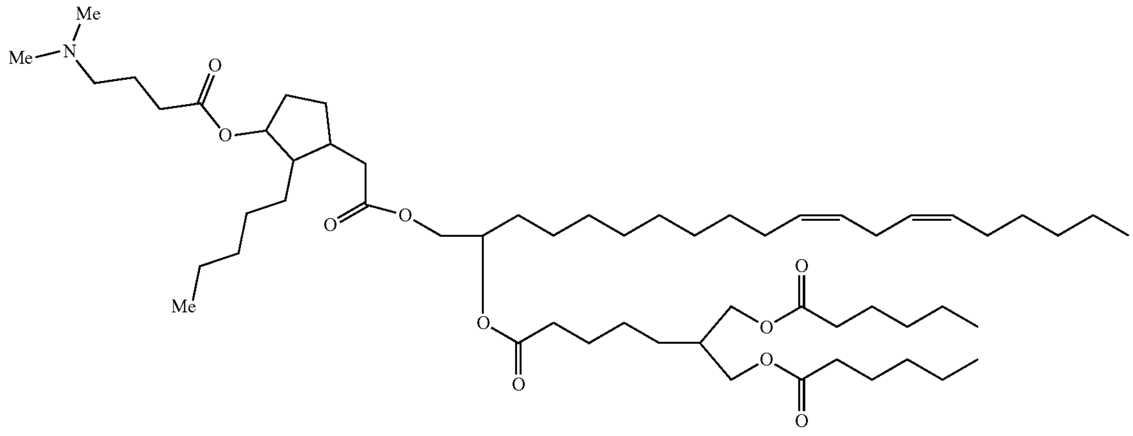
,
PNI 196
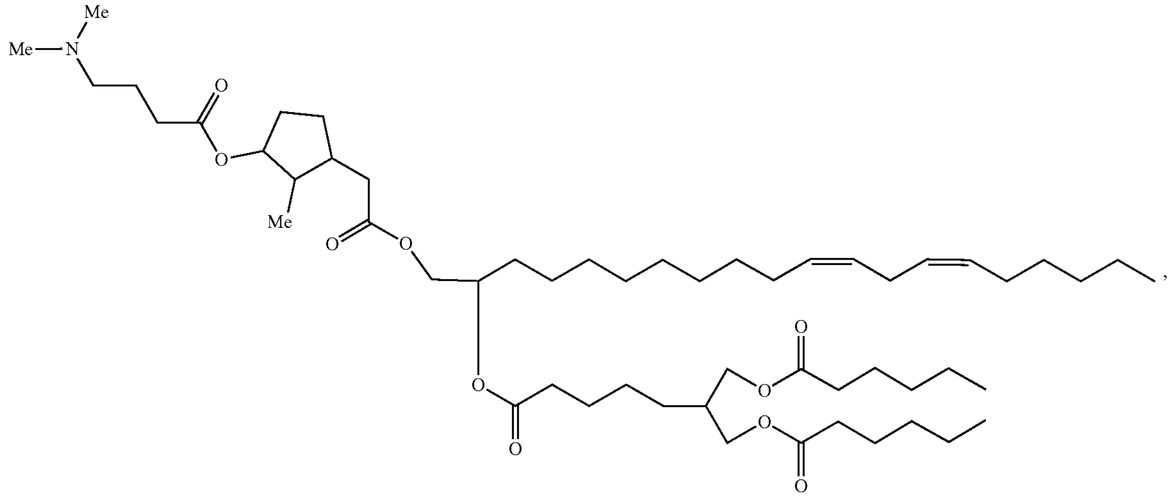
, -continued
PNI 198
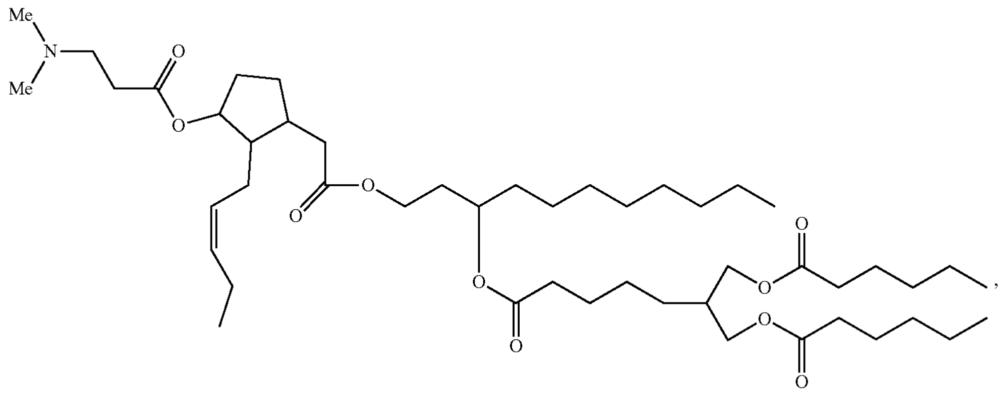
PNI 200
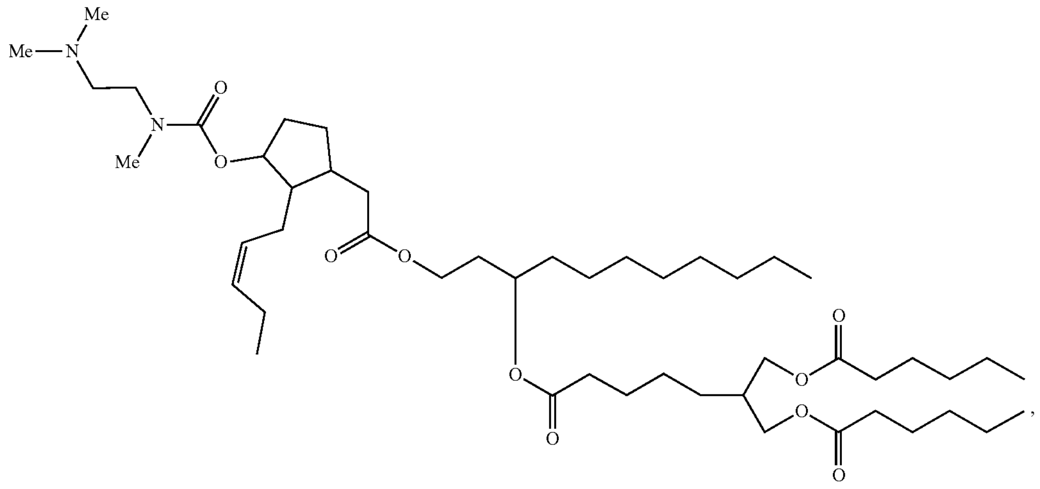
PNI 205
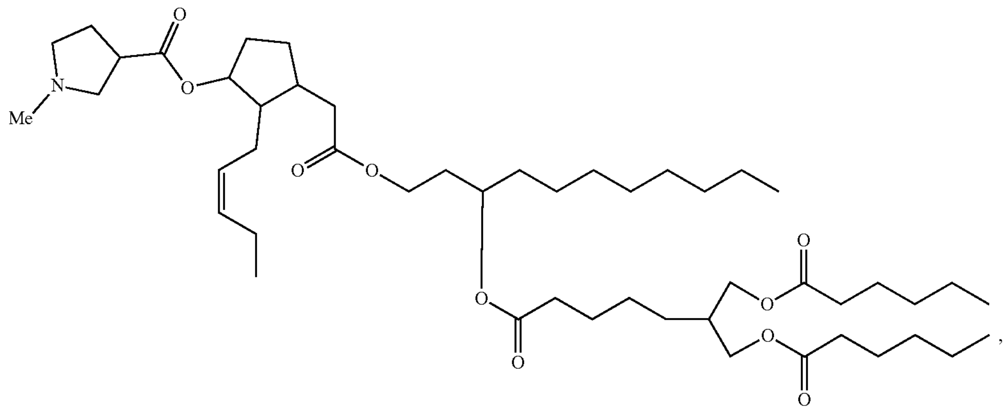

-continued
PNI 206
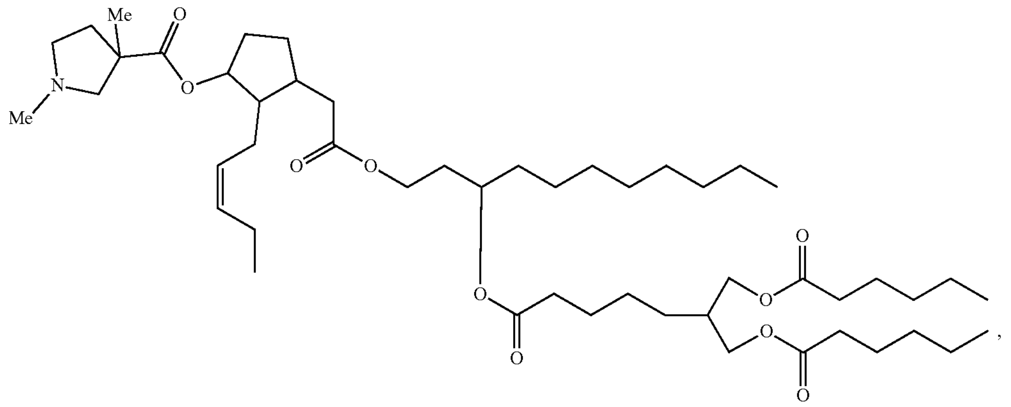
PNI 210
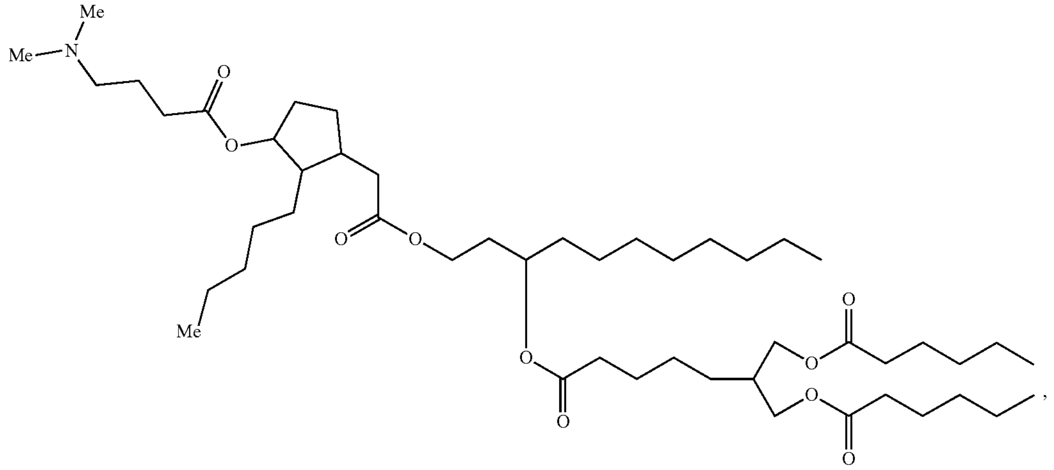
PNI 211
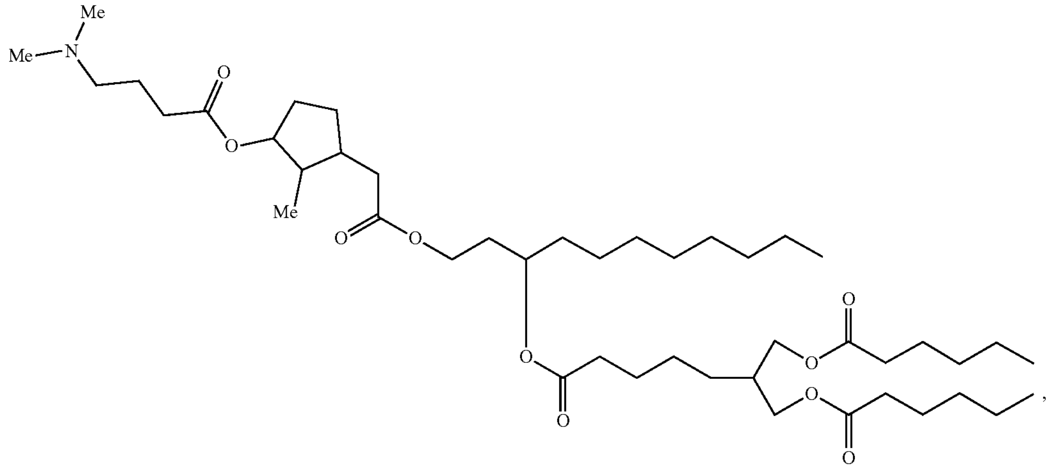

-continued
PNI 217
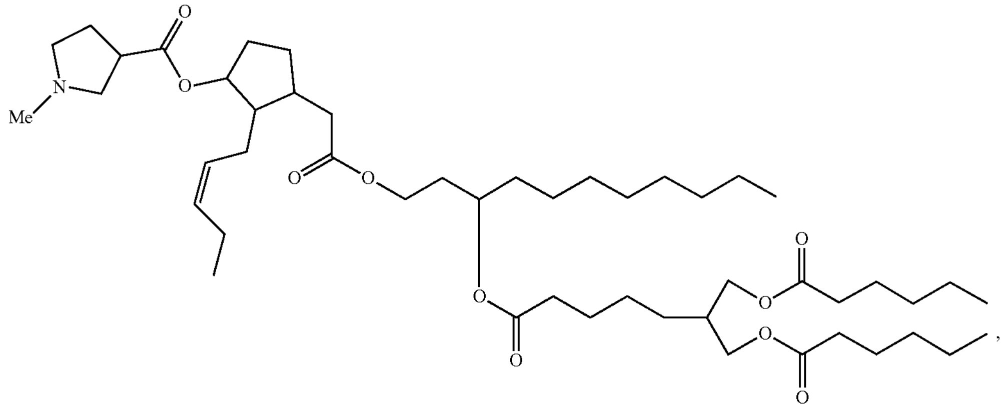
,
PNI 218
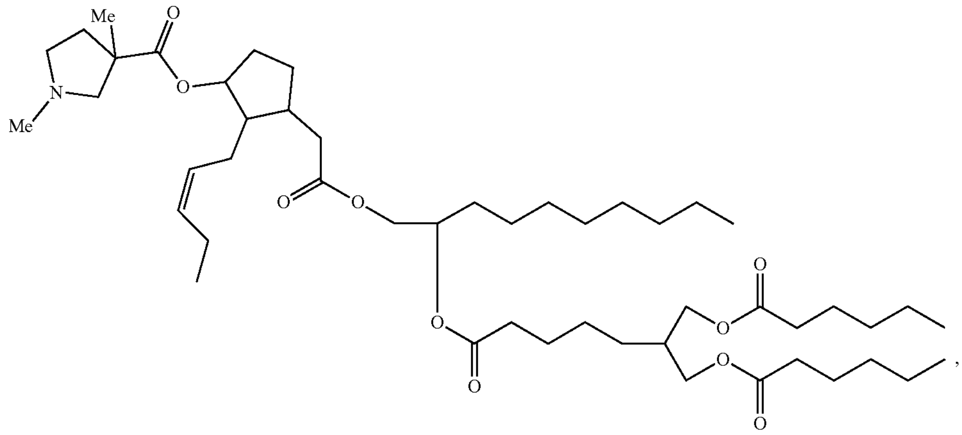
,
PNI 219
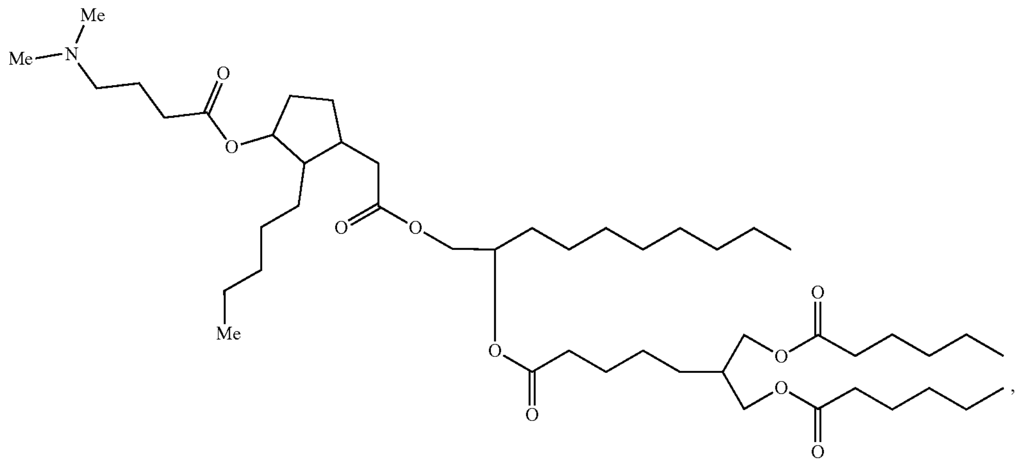
,

-continued
PNI 220
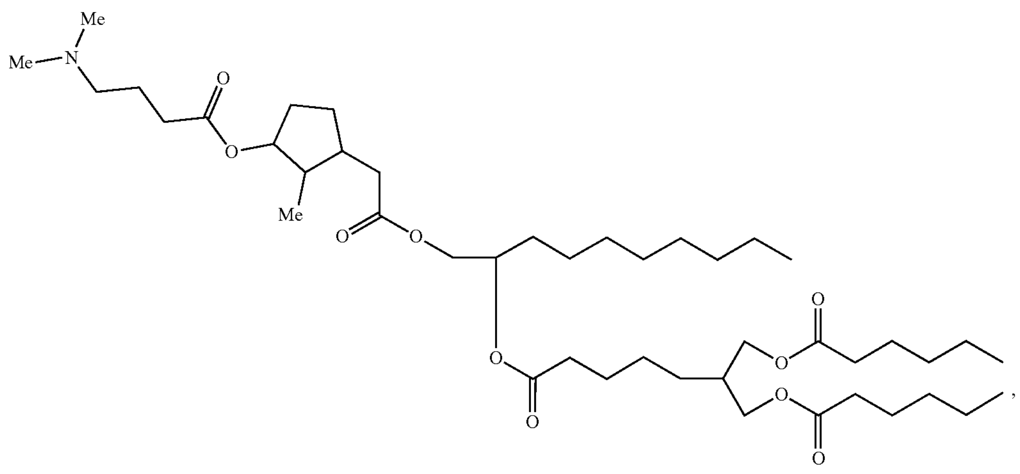
PNI 229
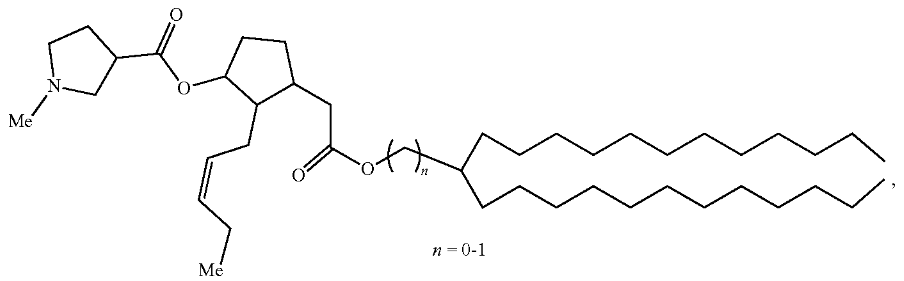
n = 0-1
PNI 230
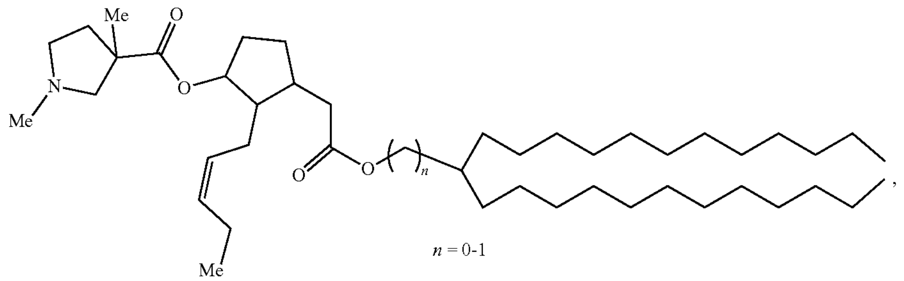
n = 0-1
PNI 234
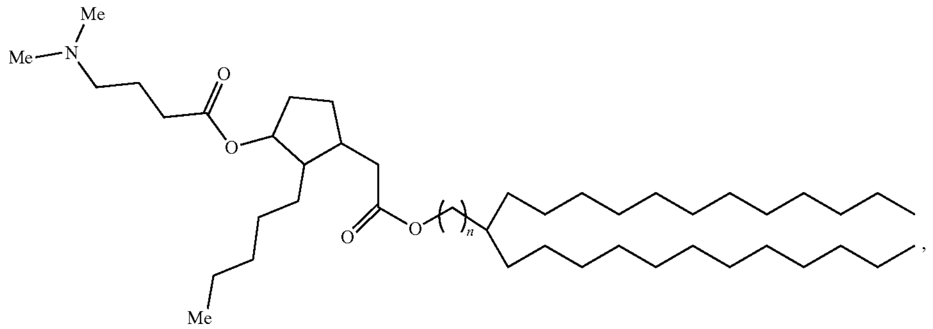
n = 0-1

-continued
PNI 235
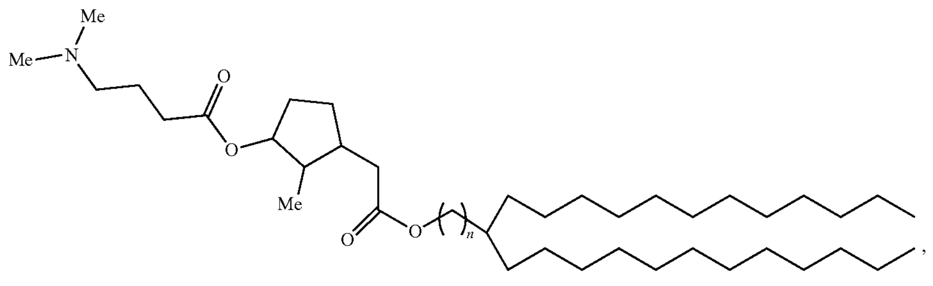
$n$ = 0-1
PNI 236
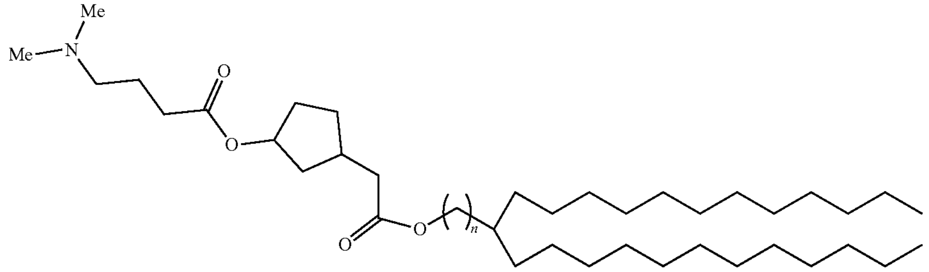
$n$ = 0-1
,
PNI 239
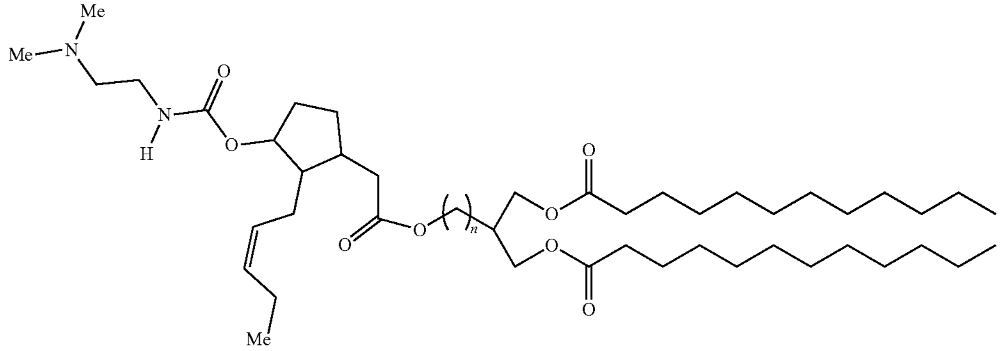
$n$ = 0-1
,
PNI 240
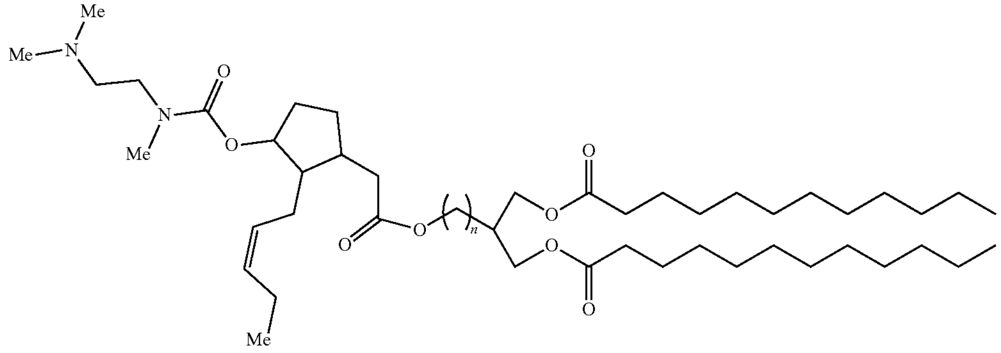
$n$ = 0-1
, -continued
PNI 245
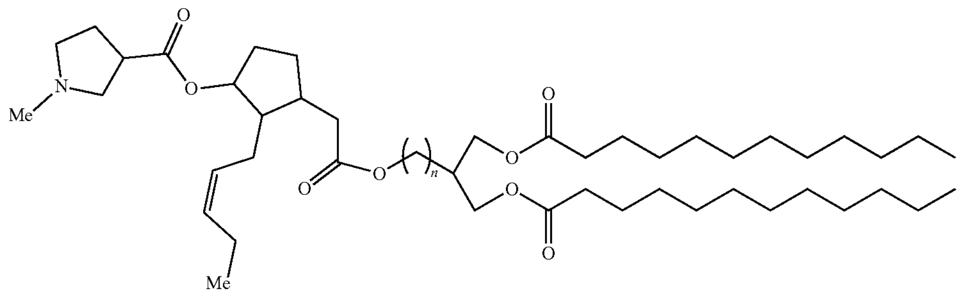
$n$ = 0-1
,
PNI 246
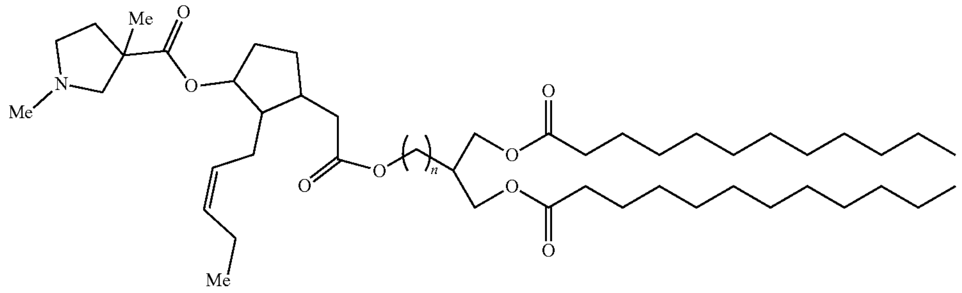
$n$ = 0-1
,
PNI 250
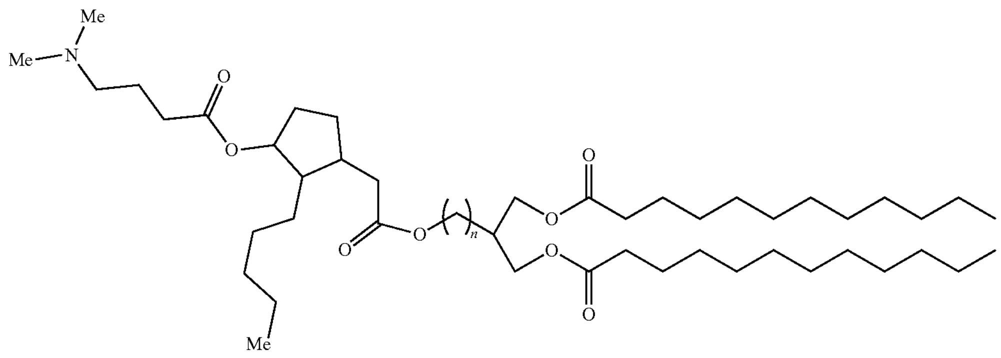
$n$ = 0-1
,
PNI 251
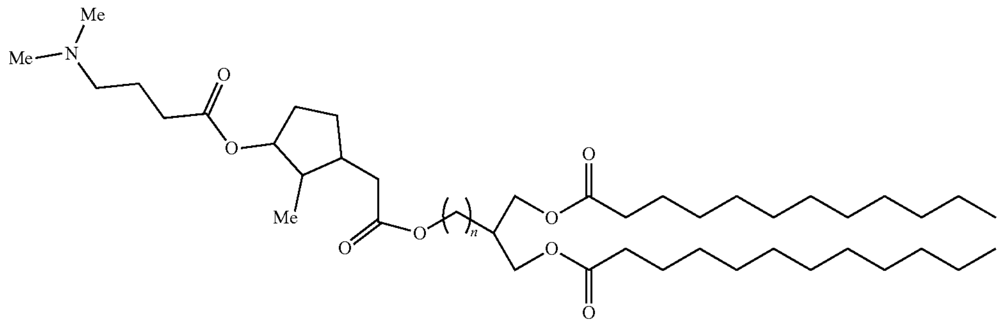
$n$ = 0-1
, -continued
PNI 252
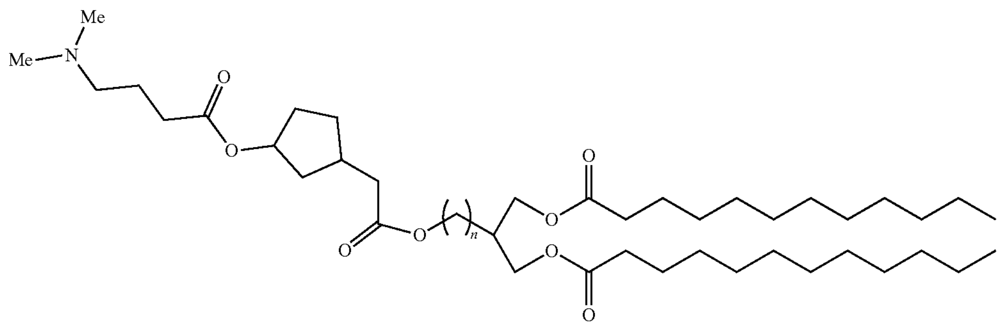
$n$ = 0-1
,
PNI 255
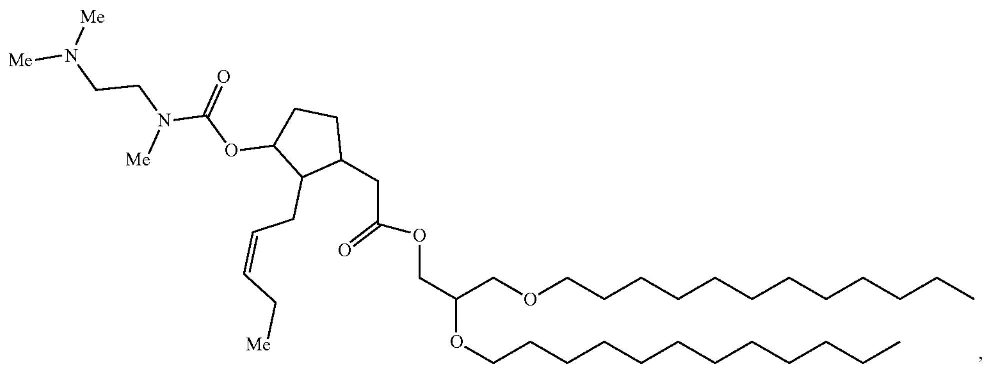
,
PNI 260
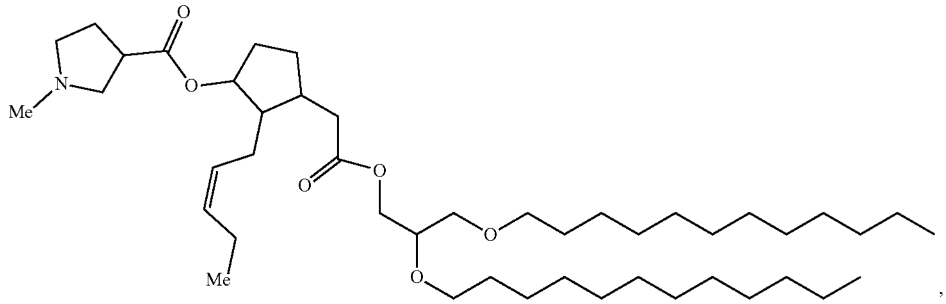
,
PNI 261
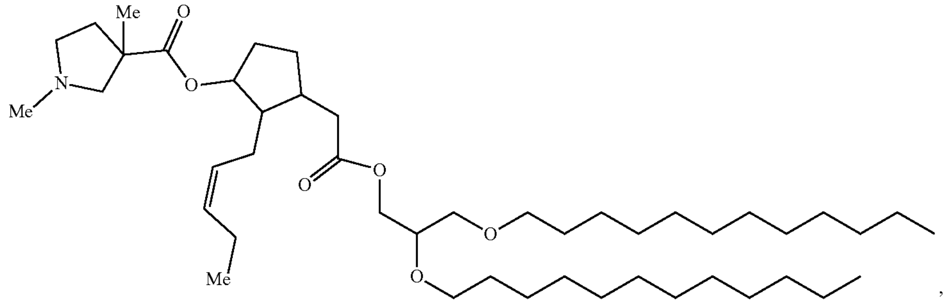
, -continued
PNI 265
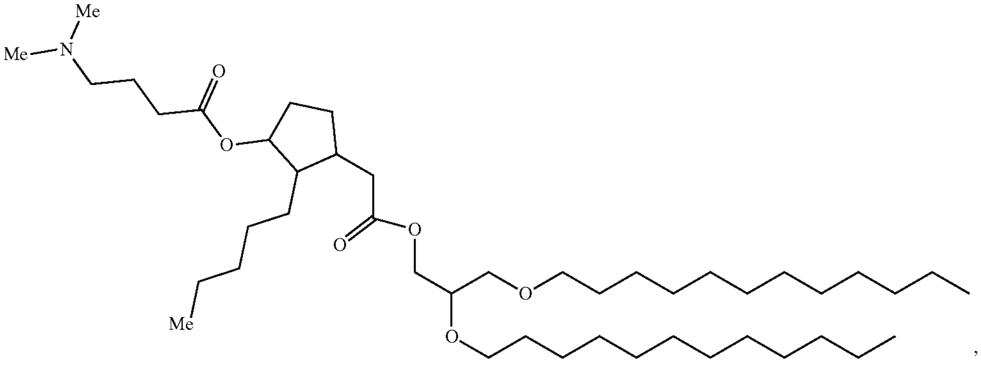
,
PNI 266
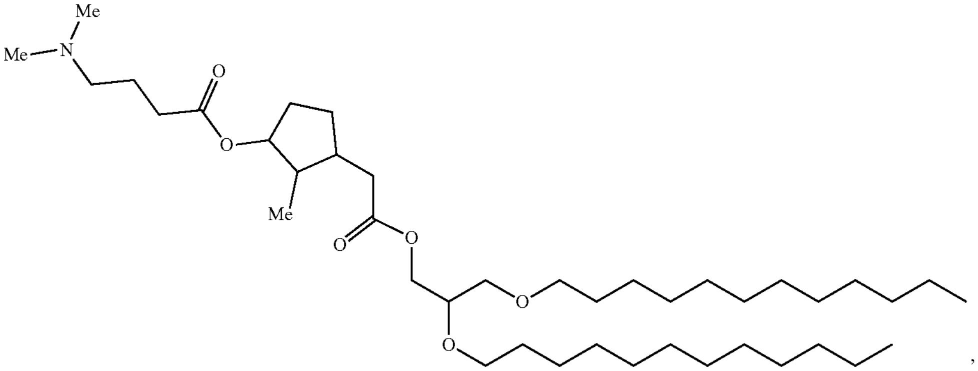
,
PNI 267
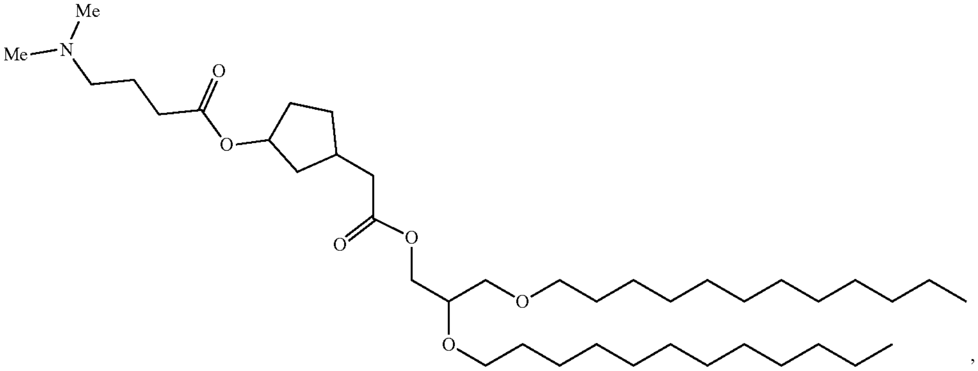
,
PNI 268
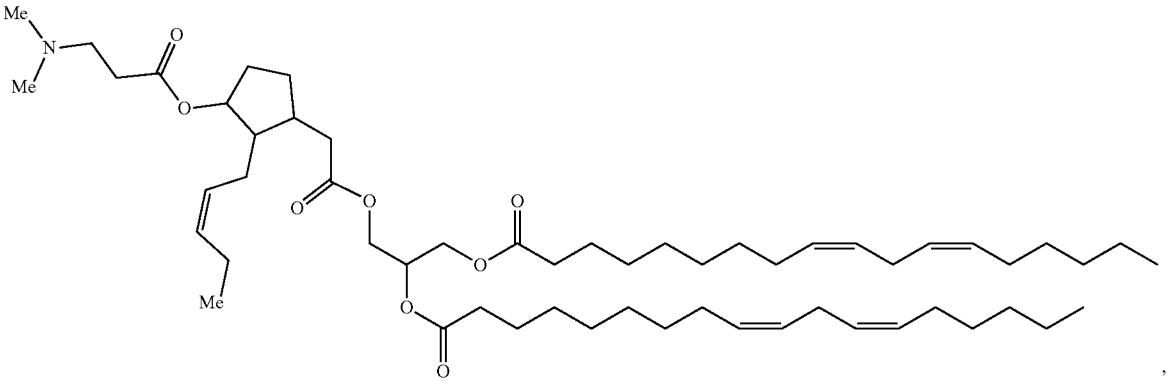
, -continued
PNI 274
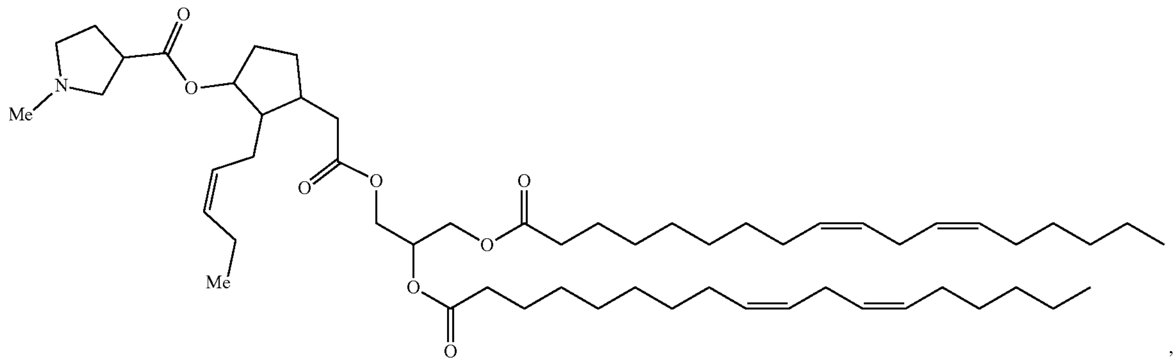
,
PNI 275
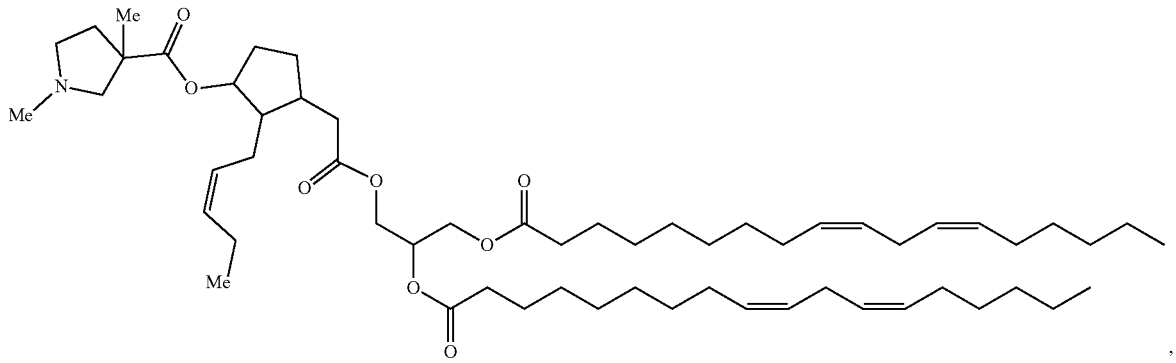
,
PNI 279
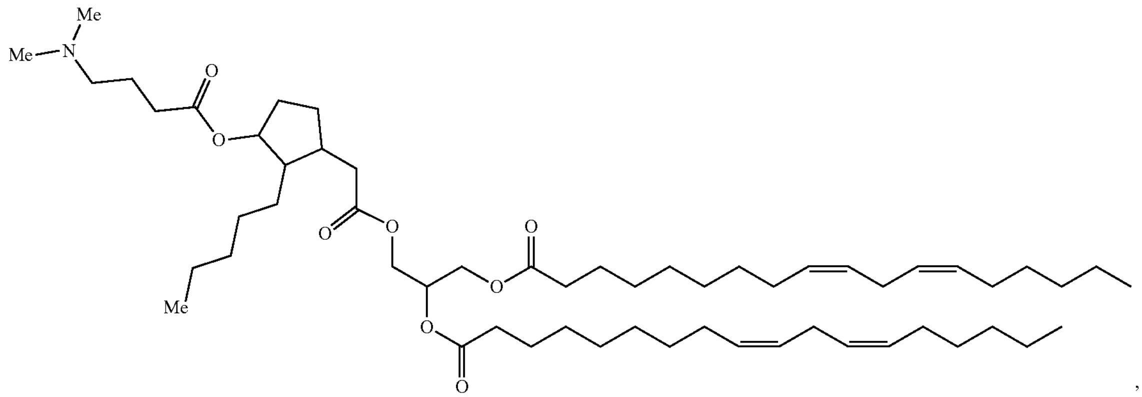
, PNI 280
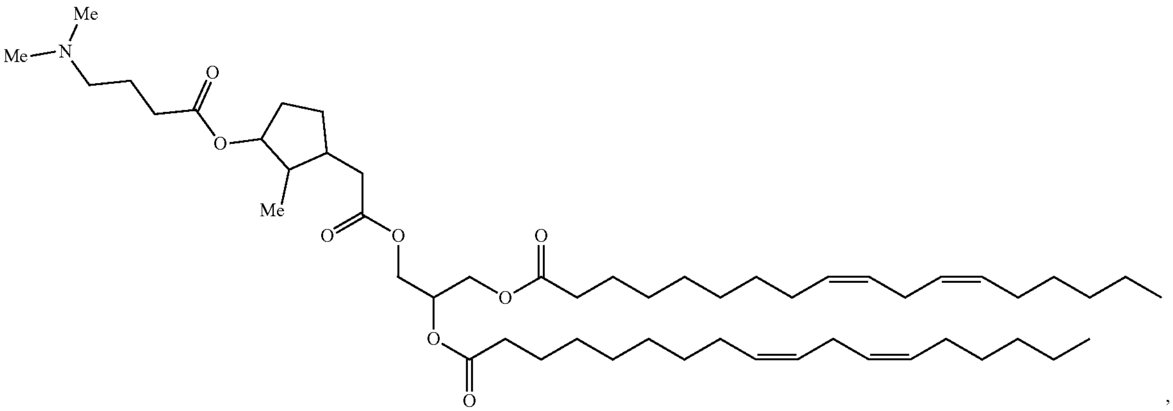
,
PNI 281
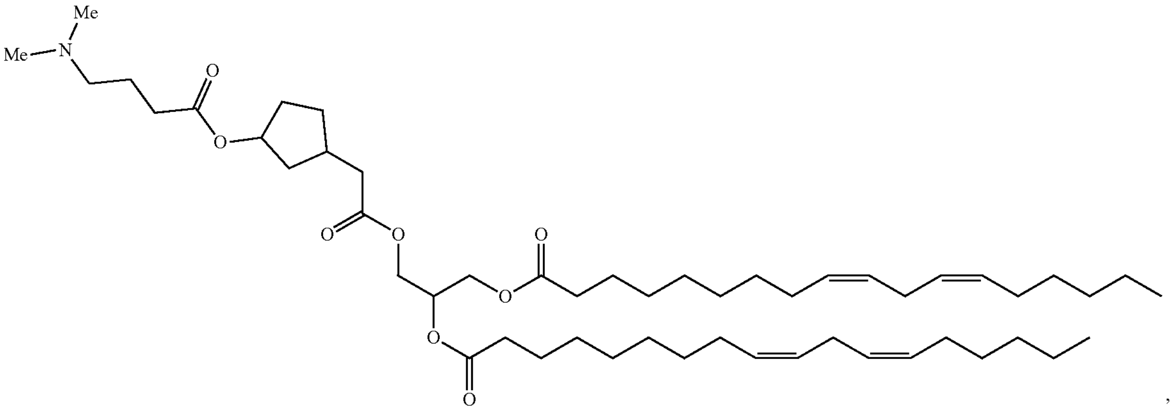
,
PNI 282
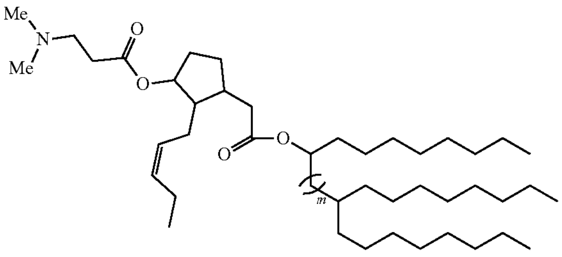
*m* = 1-5
,
PNI 284
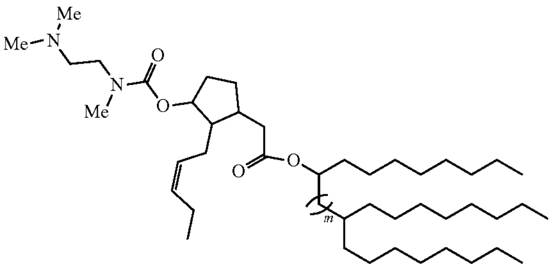
*m* = 1-5
,
PNI 288
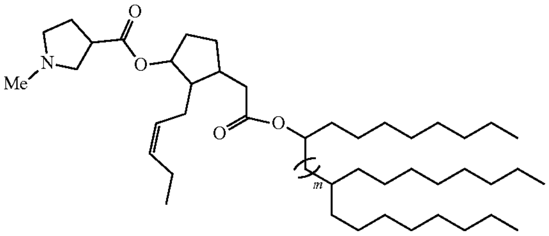
*m* = 1-5
,
PNI 289
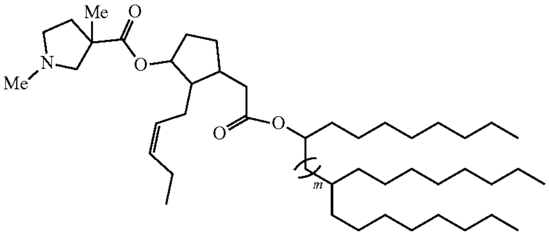
*m* = 1-5
, -continued
PNI 293
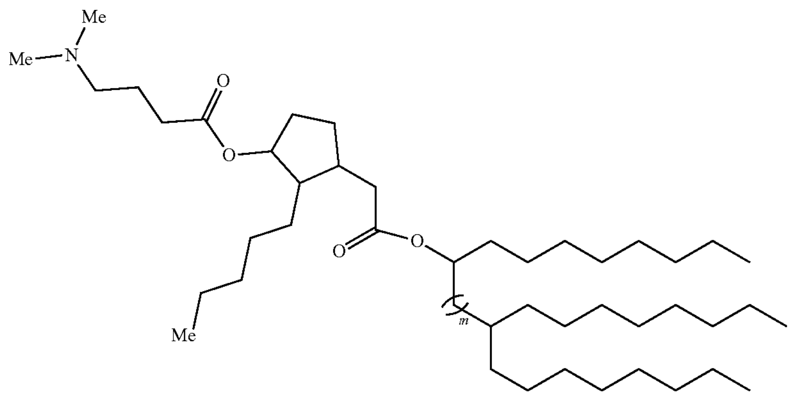
m = 1-5
,
PNI 294
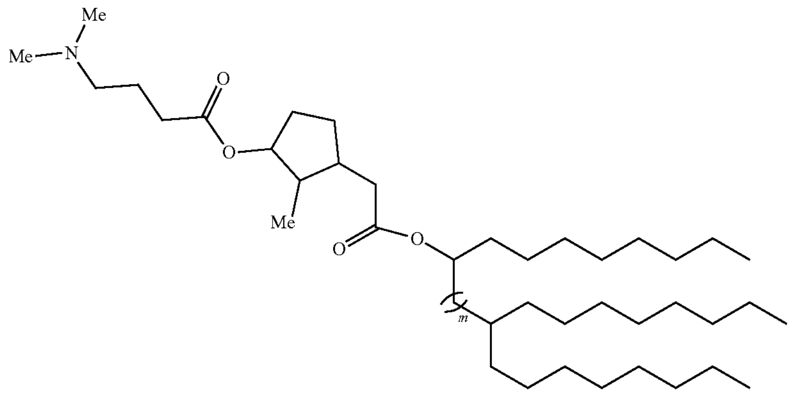
m = 1-5
,
PNI 295
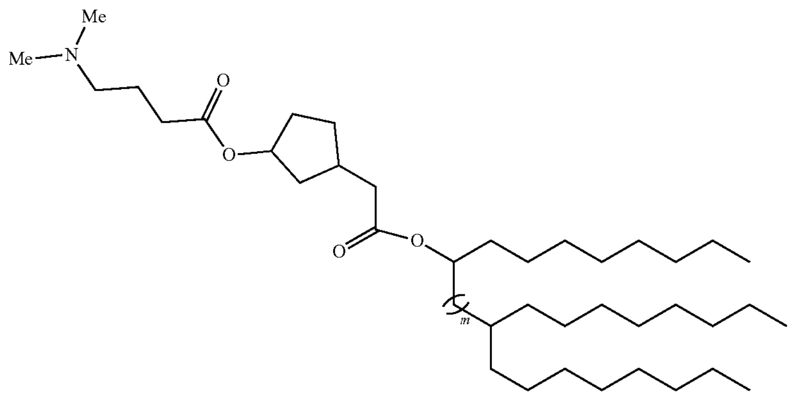
m = 1-5
, -continued
PNI 296
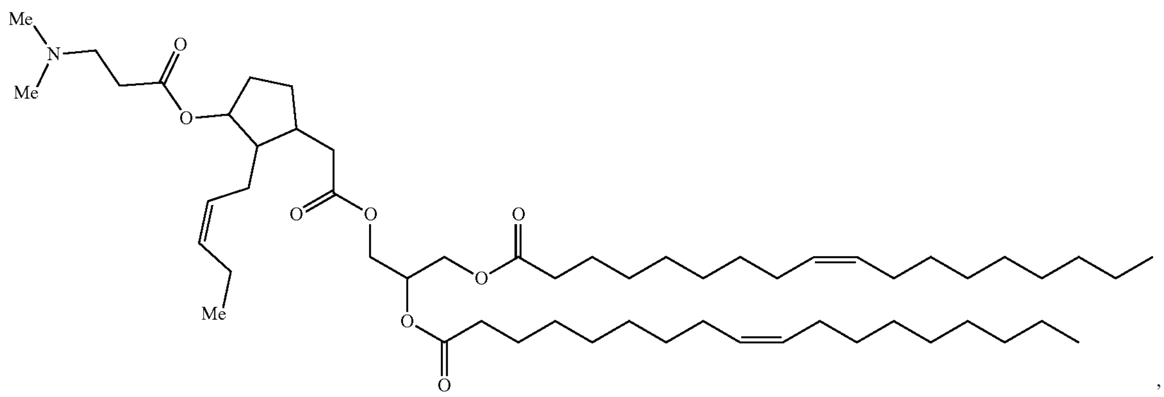
,
PNI 302
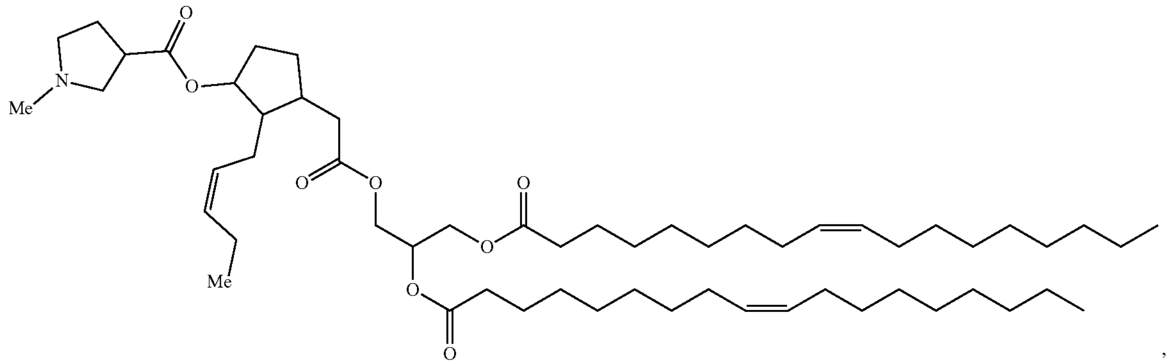
,
PNI 303
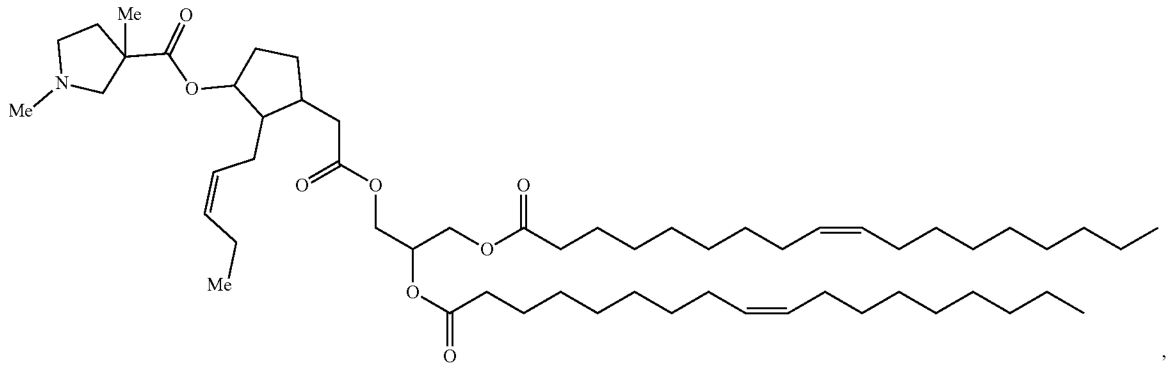
,
PNI 304
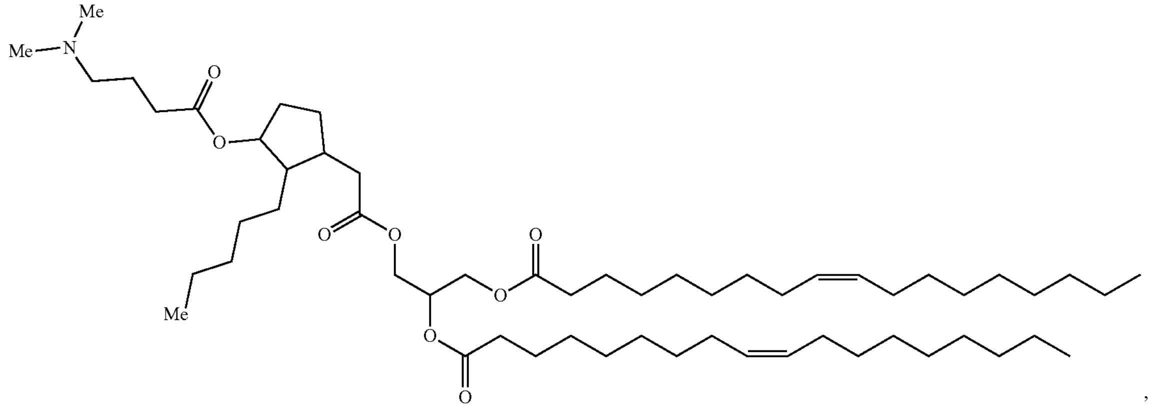
, -continued
PMI 307
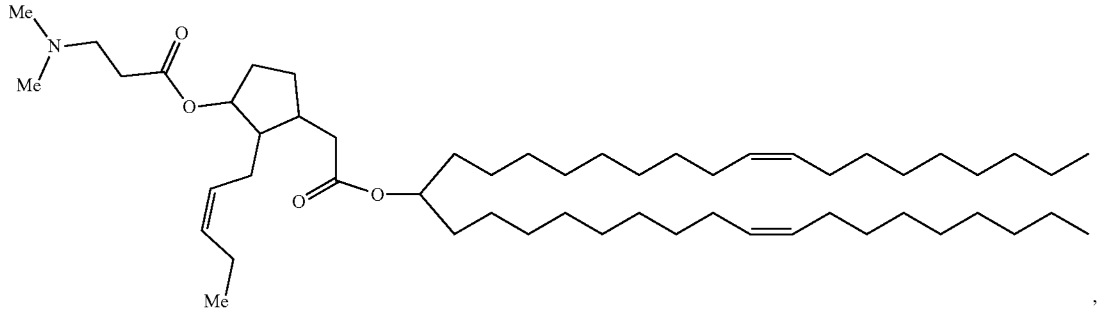
,
PNI 312
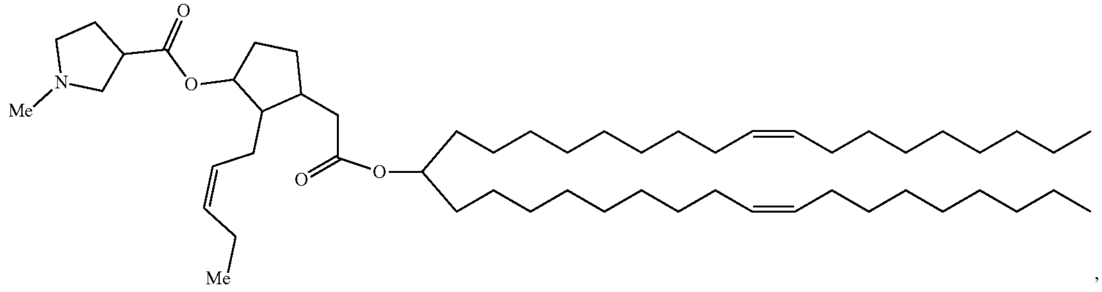
,
PNI 313
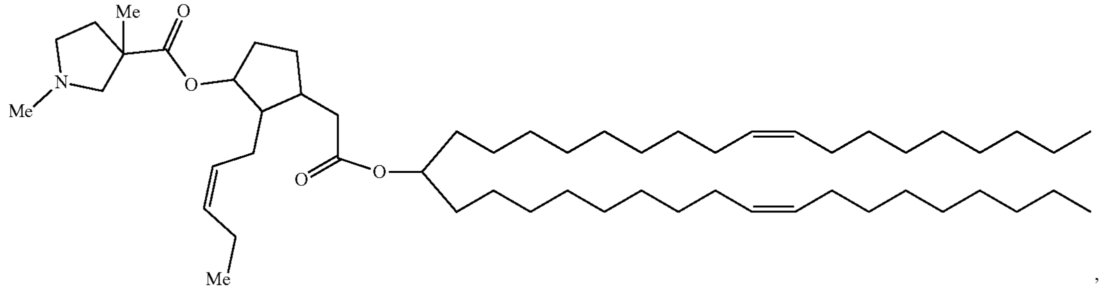
,
PNI 314
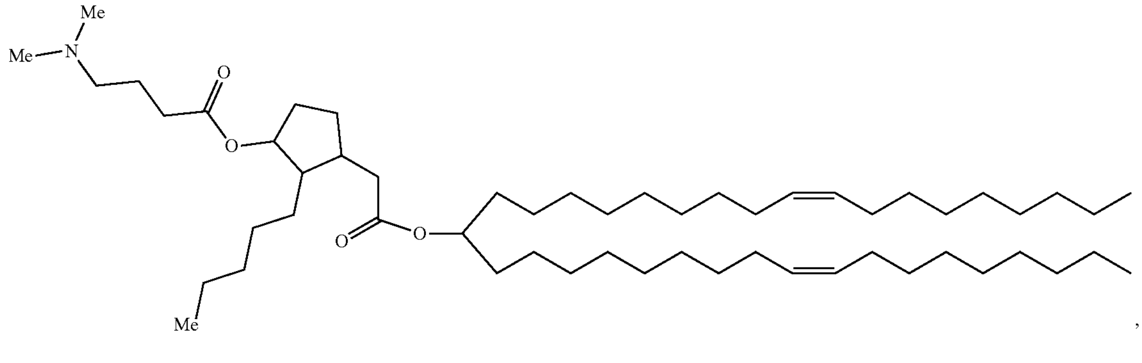
, PNI 508
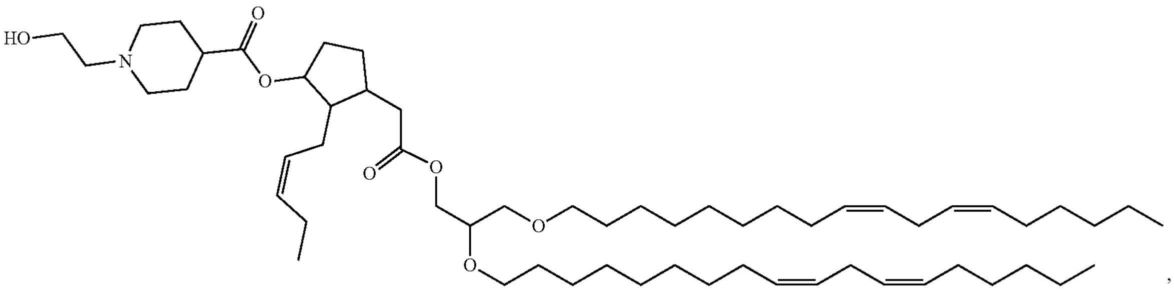
,
PNI 509
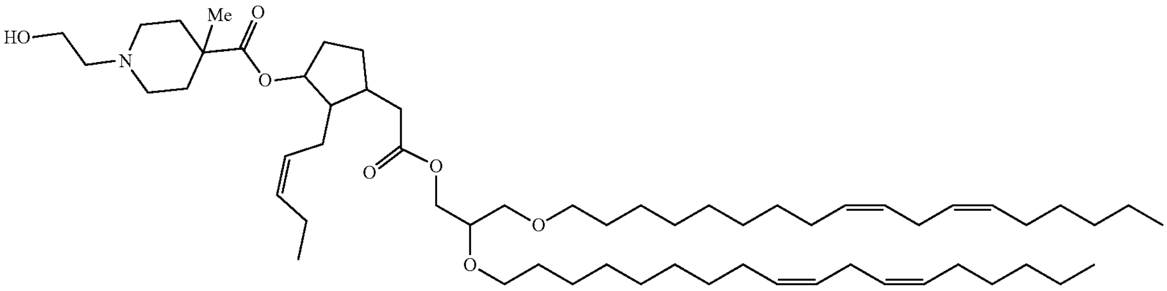
,
PNI 511
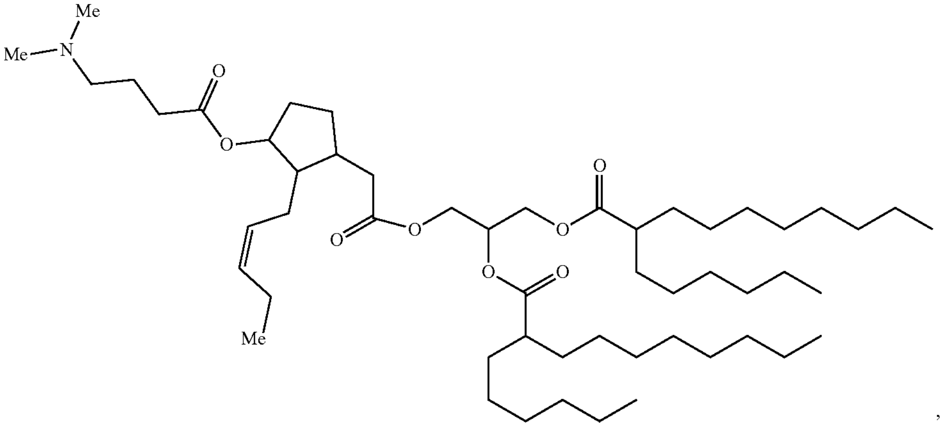
,
PNI 514
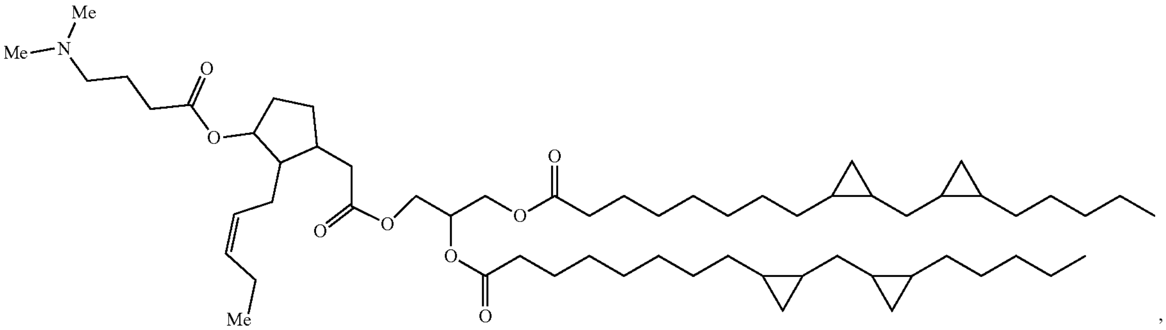
, -continued
PNI 517
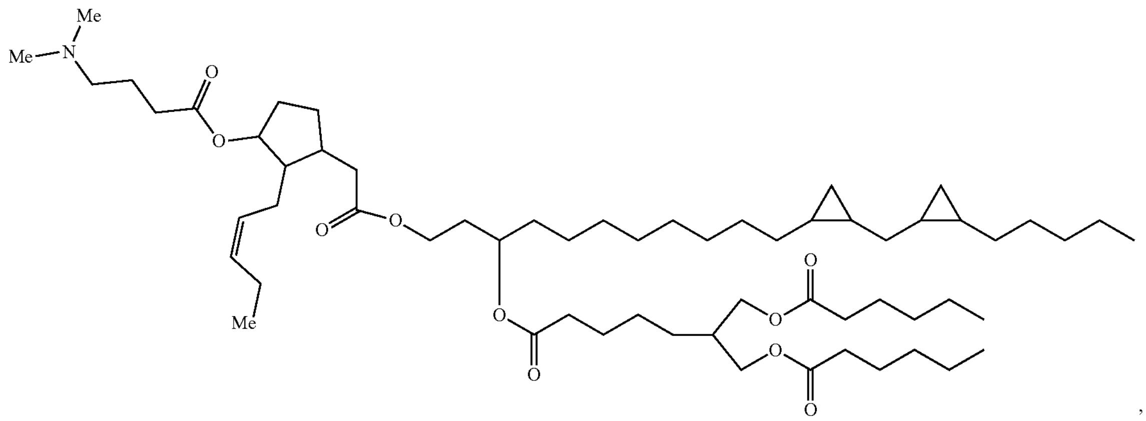
,
PNI 518
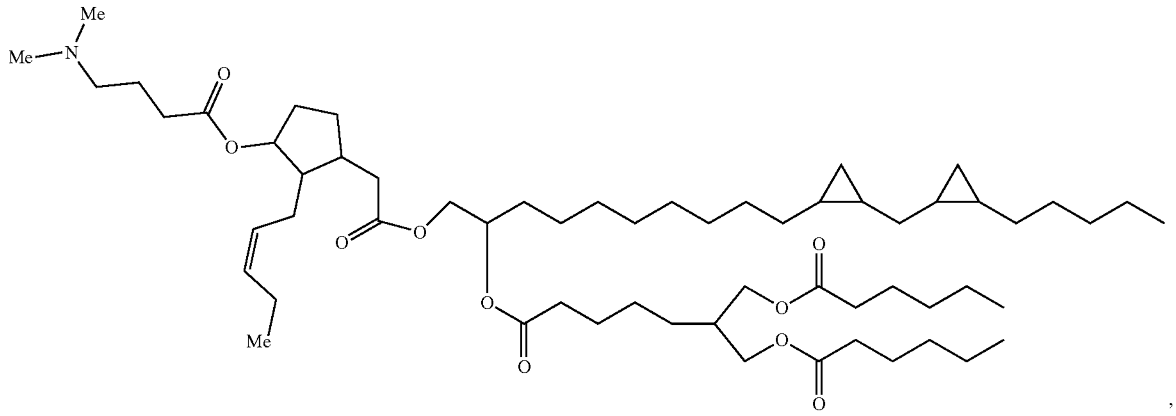
,
PNI 519
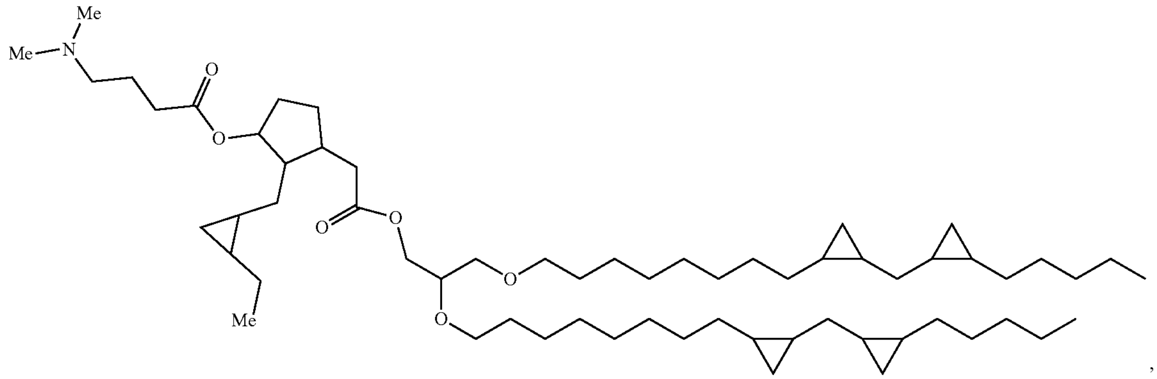
,
PNI 520
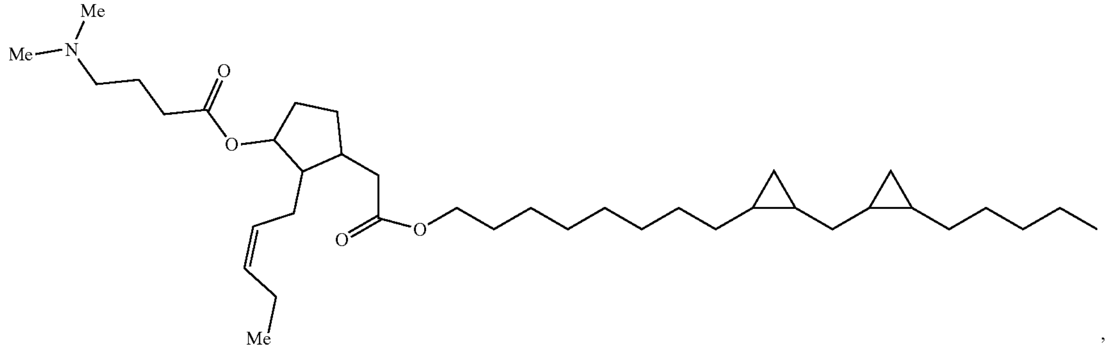
, -continued
PNI 317
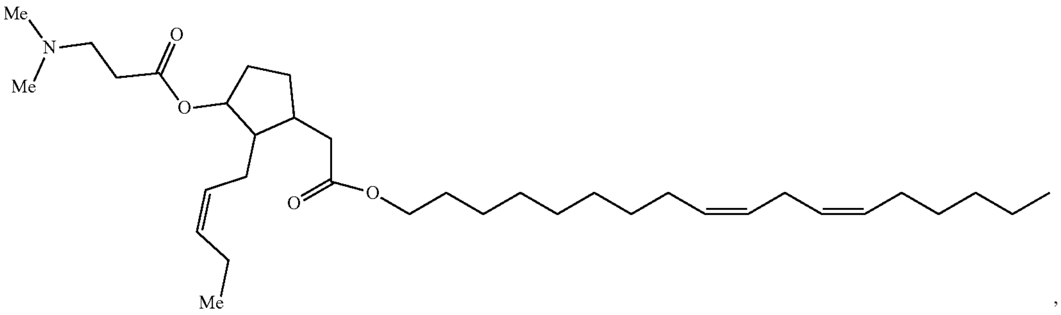
,
PNI 318
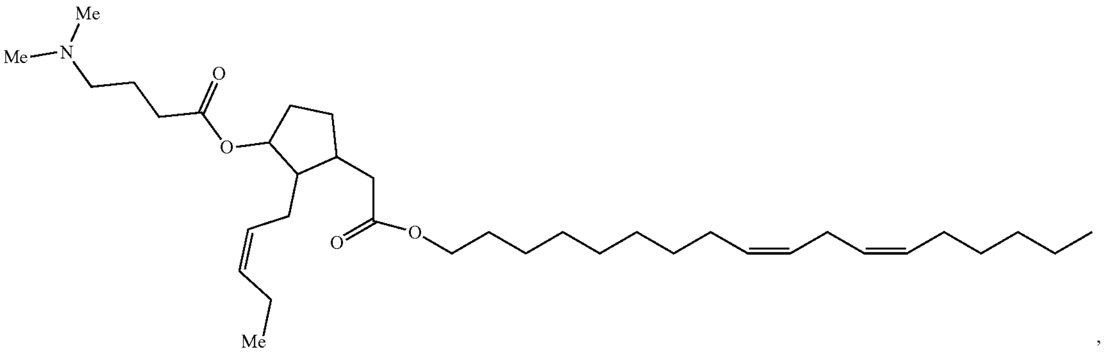
,
PNI 320
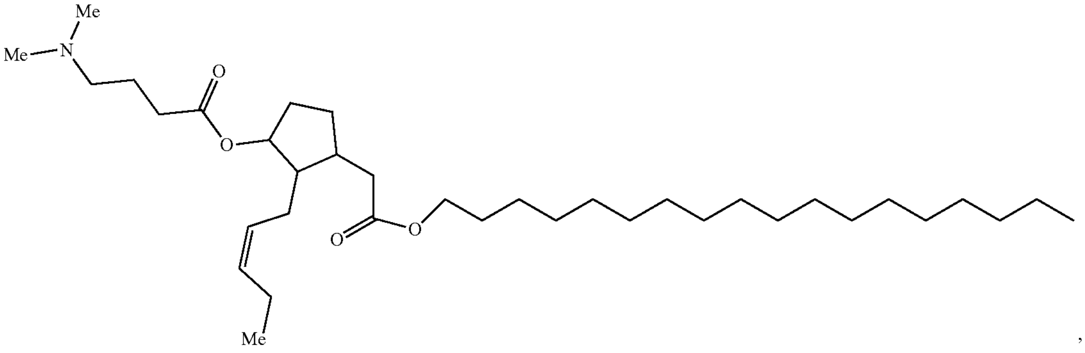
,
PNI 521
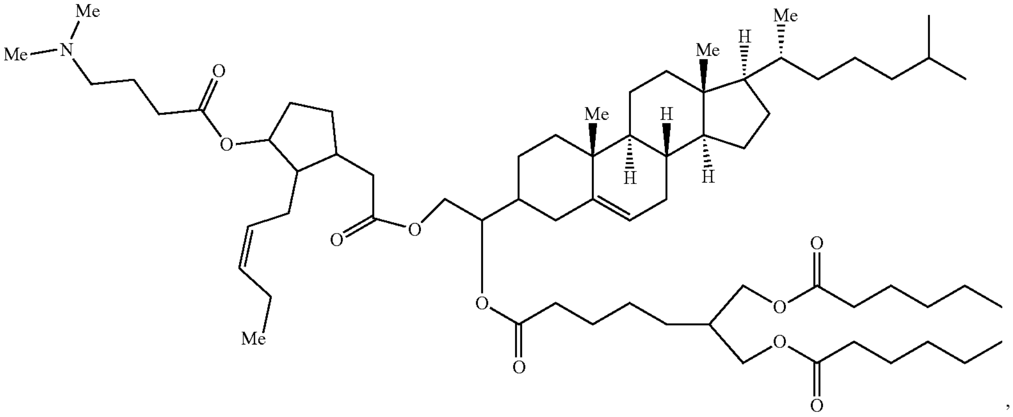
, and -continued

PNI 522

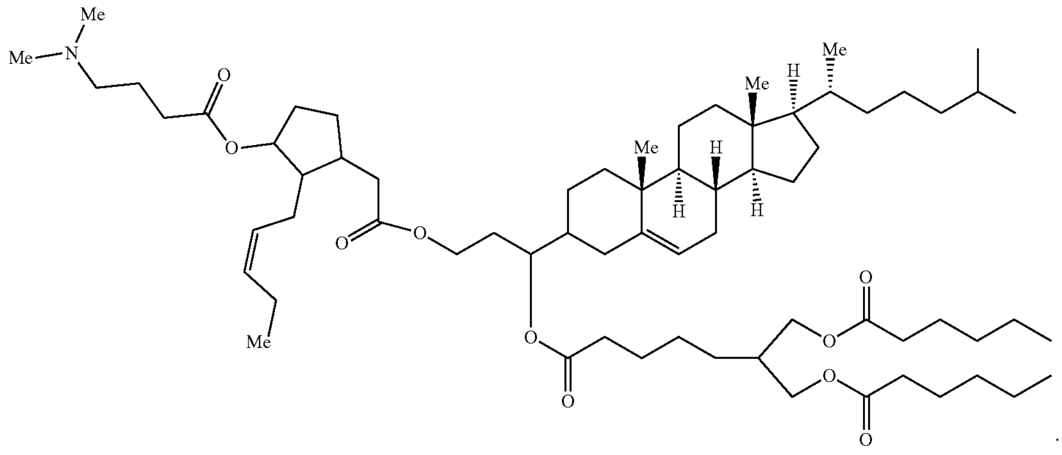

7. A lipid mix composition comprising the compound of claim 1 and a structural lipid.

8. The lipid mix composition of claim 7, wherein the structural lipid comprises DSPC, DSPE, DPPC, DMPC, DOPC, POPC, DOPE, SM, or a combination thereof.

9. The lipid mix composition of claim 7, further comprising a stabilizing agent.

10. The lipid mix composition of claim 9, further comprising a sterol, wherein the molar ratio of the compound to the rest of the components in the lipid mix composition is 30 Mol % to 70 Mol %.

11. The lipid mix composition of claim 7, wherein the experimental pKa of the lipid mix composition is in the range 5.6-7.1.

12. A pharmaceutical composition comprising a compound of claim 1 and at least one pharmaceutically acceptable carrier or excipient.

13. The lipid mix composition of claim 9, further comprising a sterol, wherein the compound is present at about 40 Mol %-49 Mol %, the structural lipid is present at about 11-20 Mol %, the sterol is present at about 37.5 Mol %, and the stabilizing agent is present at about 2.5 Mol %.

14. The lipid mix composition of claim 9, wherein the stabilizing agent includes PEG-DMG 2000, Polyoxyethylene (10) stearyl ether, polyoxyethylene (40) stearate, Polysorbate 80, Polyoxyethylene (4) lauryl ether, Polyoxyethylene (20) stearyl ether, Polyoxyethylene (23) lauryl ether, or D-α-Tocopherol polyethylene glycol 1000 succinate.

15. The compound of claim 5, wherein one of the hydrogens is substituted with a halogen.

16. The composition of claim 9, wherein the stabilizing agent comprises a surfactant and a polymer conjugated lipid.

* * * * *